(12) United States Patent
Ha et al.

(10) Patent No.: US 10,686,138 B2
(45) Date of Patent: Jun. 16, 2020

(54) COMPOUND AND ORGANIC LIGHT EMITTING DIODE COMPRISING SAME

(71) Applicant: LG Chem, Ltd., Seoul (KR)

(72) Inventors: Jae Seung Ha, Daejeon (KR); Wanpyo Hong, Daejeon (KR); Sang Duk Suh, Daejeon (KR)

(73) Assignee: LG Chem, Ltd. (KR)

( * ) Notice: Subject to any disclaimer, the term of this patent is extended or adjusted under 35 U.S.C. 154(b) by 311 days.

(21) Appl. No.: 15/765,740

(22) PCT Filed: Oct. 7, 2016

(86) PCT No.: PCT/KR2016/011278
§ 371 (c)(1),
(2) Date: Apr. 4, 2018

(87) PCT Pub. No.: WO2017/061832
PCT Pub. Date: Apr. 13, 2017

(65) Prior Publication Data
US 2018/0287068 A1 Oct. 4, 2018

(30) Foreign Application Priority Data

Oct. 7, 2015 (KR) .................... 10-2015-0141230
Mar. 28, 2016 (KR) .................... 10-2016-0037179

(51) Int. Cl.
| | | |
|---|---|---|
| *H01L 51/00* | (2006.01) | |
| *H01L 51/50* | (2006.01) | |
| *C07D 311/96* | (2006.01) | |
| *C09K 11/06* | (2006.01) | |
| *C07D 417/04* | (2006.01) | |
| *C07D 405/04* | (2006.01) | |
| *C07D 405/10* | (2006.01) | |
| *C07D 409/12* | (2006.01) | |
| *C07D 405/12* | (2006.01) | |
| *C07D 413/04* | (2006.01) | |
| *C07D 407/12* | (2006.01) | |

(52) U.S. Cl.
CPC ........ *H01L 51/0061* (2013.01); *C07D 311/96* (2013.01); *C07D 405/04* (2013.01); *C07D 405/10* (2013.01); *C07D 405/12* (2013.01); *C07D 407/12* (2013.01); *C07D 409/12* (2013.01); *C07D 413/04* (2013.01); *C07D 417/04* (2013.01); *C09K 11/06* (2013.01); *H01L 51/006* (2013.01); *H01L 51/0073* (2013.01); *C09K 2211/1018* (2013.01); *H01L 51/0052* (2013.01); *H01L 51/5012* (2013.01); *H01L 51/5064* (2013.01); *H01L 51/5072* (2013.01); *H01L 51/5088* (2013.01); *H01L 51/5092* (2013.01); *H01L 51/5096* (2013.01)

(58) Field of Classification Search
CPC ........................ C07D 311/96; H01L 51/0061
See application file for complete search history.

(56) References Cited

U.S. PATENT DOCUMENTS

| | | |
|---|---|---|
| 2014/0319097 A1 | 10/2014 | Kim et al. |
| 2015/0115241 A1 | 4/2015 | Zoellner et al. |
| 2015/0197592 A1 | 7/2015 | Someya et al. |
| 2015/0295181 A1 | 10/2015 | Mujica-Fernaud et al. |
| 2016/0322568 A1 | 11/2016 | Fadhel et al. |

FOREIGN PATENT DOCUMENTS

| | | | | |
|---|---|---|---|---|
| JP | 2015518653 A | | 7/2015 | |
| KR | 20130048307 A | | 5/2013 | |
| KR | 20150002740 A | * | 1/2015 | ......... H01L 51/5072 |
| KR | 20150002740 A | | 1/2015 | |
| KR | 20170041612 A | * | 4/2017 | .......... H01L 51/006 |
| WO | 2014050690 A1 | | 4/2014 | |
| WO | 2014072017 A1 | | 5/2014 | |
| WO | 2015097232 A1 | | 7/2015 | |
| WO | WO-2016001097 A1 | * | 1/2016 | .......... C07D 405/14 |

OTHER PUBLICATIONS

Liu et al., Organic Letters 2009, 11(17), 3850-3853.*
International Search Report for Application No. PCT/KR2016/011278, dated Jan. 20, 2017.
Wang, H. Y., et al., "Stable and Good Color Purity White Light-emitting Devices Based on Random Fluorene/spirofluorene Copolymers Doped with Iridium Complex." Journal of Polymer Science: Part B: Polymer Physics, vol. 50, No. 3, Feb. 2012, pp. 180-188.

* cited by examiner

*Primary Examiner* — Vu A Nguyen
(74) *Attorney, Agent, or Firm* — Lerner, David, Littenberg, Krumholz & Mentlik, LLP

(57) ABSTRACT

The present specification provides the compound represented by Chemical Formula 1 and an organic light emitting device including the same.

12 Claims, No Drawings

COMPOUND AND ORGANIC LIGHT EMITTING DIODE COMPRISING SAME

CROSS-REFERENCE TO RELATED APPLICATIONS

The present application is a national phase entry under 35 U.S.C. § 371 of International Application No. PCT/KR2016/011278 filed Oct. 7, 2016, which claims priority from Korean Patent Application No. 10-2015-0141230 filed Oct. 7, 2015 and Korean Patent Application No. 10-2016-0037179 filed Mar. 28, 2016, all of which are incorporated herein by reference.

TECHNICAL FIELD

This application claims priority to and the benefit of Korean Patent Application No. 10-2015-0141230 filed in the Korean Intellectual Property Office on Oct. 7, 2015, the entire contents of which are incorporated herein by reference.

The present specification relates to a new compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

Korean Patent Application Laid-Open No. 10-2013-048307

DISCLOSURE

Technical Problem

The present invention has been made in an effort to provide a compound having a low driving voltage and a long lifetime.

Further, the present invention has been made in an effort to provide an organic light emitting device including the compound.

Technical Solution

An exemplary embodiment of the present specification may provide a compound represented by the following Chemical Formula 1.

[Chemical Formula 1]

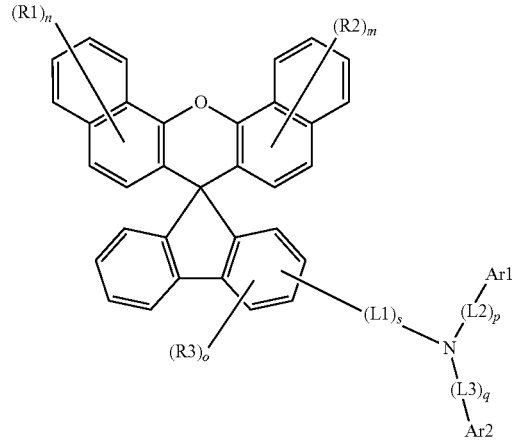

R1 to R3 are each independently any one selected from the group consisting of hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted aralkylamine group; a substituted or unsubstituted arylamine group; a substituted or unsubstituted arylphosphine group; a substituted or unsubstituted phosphine oxide group; a substituted or unsubstituted aryl group; and a substituted or unsubstituted heterocyclic group, L1 to L3 are a direct bond; or a divalent linking group, Ar1 and Ar2 are each independently any one selected from the group consisting of hydrogen; deuterium; a halogen group; a nitrile group; a nitro group; a substituted or unsubstituted amine group; a substituted or unsubstituted alkyl group; a substituted or unsubstituted alkoxy group; a substituted or unsubstituted aryl group; a substituted or unsubstituted fluorene group; and a substituted or unsubstituted heterocyclic group, L1 to L3, Ar1, and Ar2 may combine with an adjacent group to form a substituted or unsubstituted ring, n and m are each an integer of 0 to 6, o+s is an integer of 1 to 4, and s, p, and q are an integer of 1 to 4.

Further, an exemplary embodiment of the present specification may provide an organic light emitting device including: a first electrode; a second electrode provided to face the first electrode; and one or more organic material layers provided between the first electrode and the second electrode, in which one or more layers of the organic material layers include the compound of Chemical Formula 1.

Advantageous Effects

The compound according to an exemplary embodiment of the present specification may be used as a material for an organic material layer of an organic light emitting device, and thus may bring effects of improving the efficiency, achieving a low driving voltage, and improving lifetime characteristics in the organic light emitting device. Further, the compound according to an exemplary embodiment of the present specification may be used as a material for hole injection, hole transport, electron transport and electron injection, or light emission.

MODE FOR INVENTION

When one part "includes" one constituent element in the present specification, unless otherwise specifically described, this does not mean that another constituent element is excluded, but means that another constituent element may be further included.

Hereinafter, the present specification will be described in more detail.

An exemplary embodiment of the present specification provides the compound represented by Chemical Formula 1.

Examples of the substituents will be described below, but are not limited thereto.

In the present specification, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylamine group; an aralkylamine group; an arylamine group; and an arylphosphine group; or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, examples of a halogen group include fluorine, chlorine, bromine or iodine.

In the present specification, the number of carbon atoms of a carbonyl group is not particularly limited, but is preferably 1 to 40. Specifically, the carbonyl group may be a compound having the following structures, but is not limited thereto.

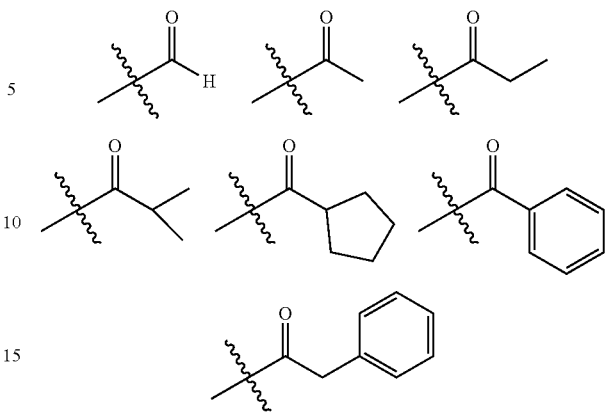

In the present specification, for an ester group, the oxygen of the ester group may be substituted with a straight-chained, branch-chained, or cyclic alkyl group having 1 to 25 carbon atoms, or an aryl group having 6 to 25 carbon atoms. Specifically, the ester group may be a compound having the following structural formulae, but is not limited thereto.

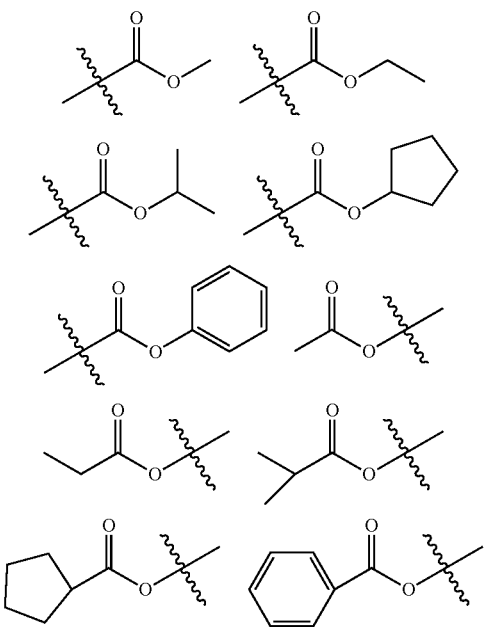

In the present specification, the number of carbon atoms of an imide group is not particularly limited, but is preferably 1 to 25. Specifically, the imide group may be a compound having the following structures, but is not limited thereto.

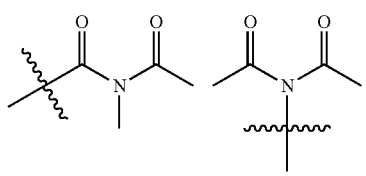

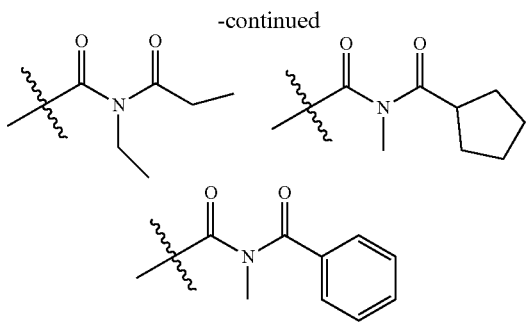

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, specific examples of a boron group include a trimethylboron group, a triethylboron group, a t-butyldimethylboron group, a triphenylboron group, a phenylboron group, and the like, but are not limited thereto.

In the present specification, the alkyl group may be straight-chained or branch-chained, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present specification, the alkenyl group may be straight-chained or branch-chained, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to still another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, examples of an arylamine group mean a substituted or unsubstituted monocyclic diarylamine group, a substituted or unsubstituted polycyclic diarylamine group, or a substituted or unsubstituted monocyclic and polycyclic diarylamine group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. Examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, a fluorenyl group may be substituted, and two substituents may combine with each other to form a spiro structure.

When the fluorenyl group is substituted, the group may be

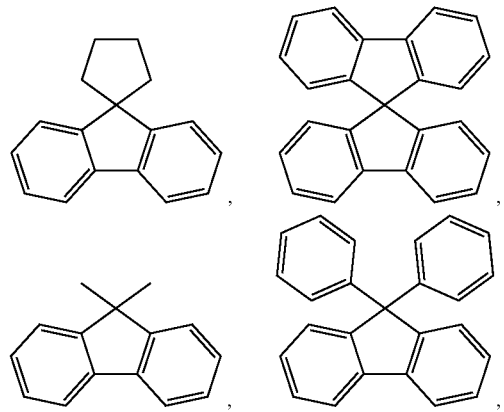

and the like. However, the fluorenyl group is not limited thereto.

In the present specification, a heterocyclic group is a heterocyclic group including one or more of N, O, S, Si, and Se as a heteroatom, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the above-described description on the aryl group may be applied to an aromatic hydrocarbon ring except for a divalent aromatic hydrocarbon ring.

In the present specification, the above-described description on the heterocyclic group may be applied to a hetero ring except for a divalent hetero ring.

In the present specification, the above-described description on the heterocyclic group may be applied to a heteroaryl group except for an aromatic heteroaryl group.

In the present specification, the above-described description on the aryl group may be applied to an aryl group in an aryloxy group, an arylthioxy group, an arylsulfoxy group, an arylphosphine group, an aralkyl group, an aralkylamine group, an aralkenyl group, and an arylamine group.

In the present specification, the above-described description on the alkyl group may be applied to an alkyl group in an alkylthioxy group, an alkylsulfoxy group, an aralkyl group, an aralkylamine group, and an alkylamine group.

In the present specification, the above-described description on the heterocyclic group may be applied to a heteroaryl group in a heteroaryl group and a heteroarylamine group.

In the present specification, the above-described description on the alkenyl group may be applied to an alkenyl group in an aralkenyl group.

In the present specification, the above-described description on the aryl group may be applied to an arylene except for a divalent arylene group.

In the present specification, the above-described description on the heterocyclic group may be applied to a heteroarylene except for a divalent heteroarylene group.

In the present specification, combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; or a substituted or unsubstituted aromatic hetero ring.

In the present specification, the aliphatic hydrocarbon ring means a ring composed of only carbon and hydrogen atoms as a ring which is not an aromatic group.

In the present specification, examples of an aromatic hydrocarbon ring include a phenyl group, a naphthyl group, an anthracenyl group, and the like, but are not limited thereto.

In the present specification, an aliphatic hetero ring means an aliphatic ring including one or more of hetero atoms.

In the present specification, an aromatic hetero ring means an aromatic ring including one or more of hetero atoms.

In the present specification, the aliphatic hydrocarbon ring, the aromatic hydrocarbon ring, the aliphatic hetero ring, and the aromatic hetero ring may be monocyclic or polycyclic.

According to an exemplary embodiment of the present specification, R1 to R3 are each independently any one selected from the group consisting of hydrogen; deuterium; a substituted or unsubstituted alkyl group; a substituted or unsubstituted cycloalkyl group; a substituted or unsubstituted alkenyl group; a substituted or unsubstituted aralkyl group; a substituted or unsubstituted aralkenyl group; a substituted or unsubstituted alkylaryl group; a substituted or unsubstituted aralkylamine group; a substituted or unsubstituted arylamine group; a substituted or unsubstituted aryl group; and a substituted or unsubstituted heterocyclic group.

Further, according to an exemplary embodiment of the present specification, R1 to R3 are each independently any one selected from the group consisting of hydrogen; deuterium; a substituted or unsubstituted alkyl group; a substituted or unsubstituted aralkyl group; a substituted or unsubstituted alkylaryl group; a substituted or unsubstituted aryl group; and a substituted or unsubstituted heterocyclic group.

In addition, according to an exemplary embodiment of the present specification, R1 to R3 are each independently any one selected from the group consisting of hydrogen; a substituted or unsubstituted alkyl group; a substituted or unsubstituted aryl group; and a substituted or unsubstituted heterocyclic group.

Furthermore, according to an exemplary embodiment of the present specification, R1 to R3 are each independently any one selected from the group consisting of hydrogen; an alkyl group; an aryl group; and a heterocyclic group.

According to an exemplary embodiment of the present specification, L is a direct bond; or a divalent linking group.

Further, according to an exemplary embodiment of the present specification, L is any one selected from the group consisting of a direct bond; a substituted or unsubstituted alkylene group; a substituted or unsubstituted cycloalkylene group; a substituted or unsubstituted alkenylene group; a substituted or unsubstituted aralkylene group; a substituted or unsubstituted aralkenylene group; a substituted or unsubstituted alkylarylene group; a substituted or unsubstituted divalent amine group; a substituted or unsubstituted divalent aralkylamine group; a substituted or unsubstituted divalent arylamine group; a substituted or unsubstituted arylene group; and a substituted or unsubstituted heterocyclic group.

In addition, according to an exemplary embodiment of the present specification, L is any one selected from the group consisting of a direct bond; a substituted or unsubstituted alkylene group; a substituted or unsubstituted aralkylene group; a substituted or unsubstituted aralkenylene group; a substituted or unsubstituted alkylarylene group; a substituted or unsubstituted divalent amine group; a substituted or unsubstituted divalent aralkylamine group; a substituted or unsubstituted divalent arylamine group; a substituted or unsubstituted arylene group; and a substituted or unsubstituted heterocyclic group.

Furthermore, according to an exemplary embodiment of the present specification, L is any one selected from the group consisting of a direct bond; a substituted or unsubstituted divalent amine group; a substituted or unsubstituted divalent arylamine group; a substituted or unsubstituted arylene group; and a substituted or unsubstituted heterocyclic group.

Further, according to an exemplary embodiment of the present specification, L is any one selected from the group consisting of a direct bond; a divalent amine group substituted with an aryl group; a divalent arylamine group; an arylene group substituted with an amine group or an alkyl group; and a heterocyclic group.

In addition, according to an exemplary embodiment of the present specification, L is any one of the following chemical formulae.

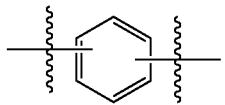

-continued

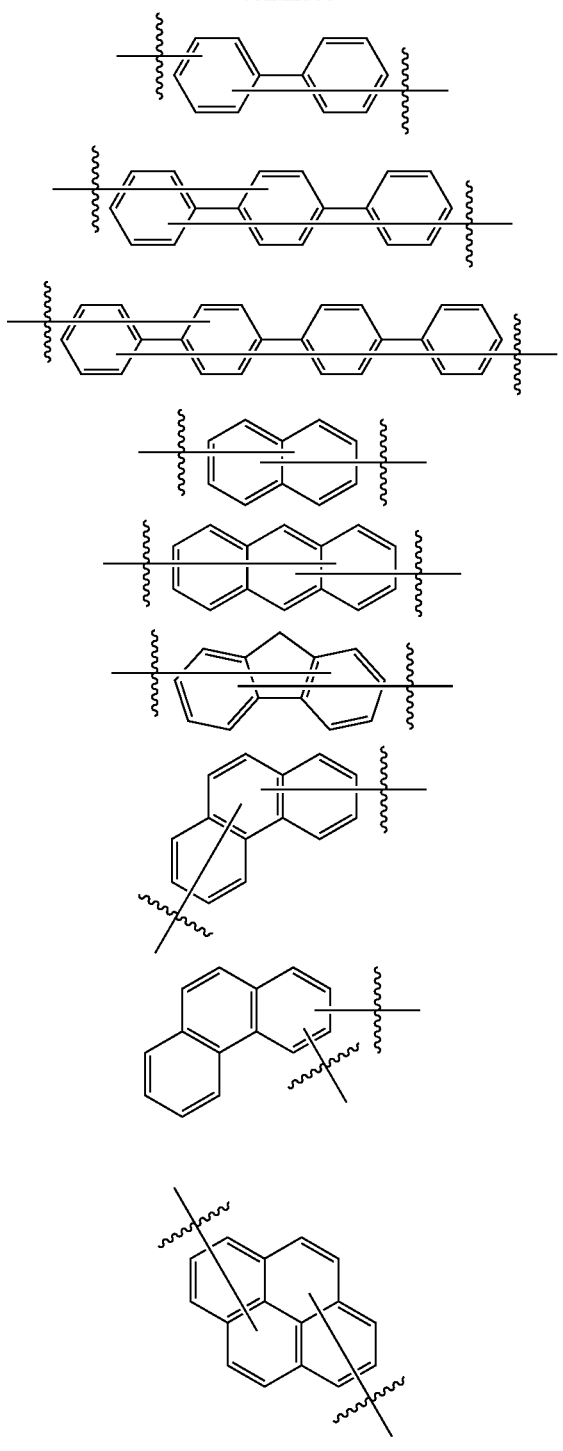

-continued

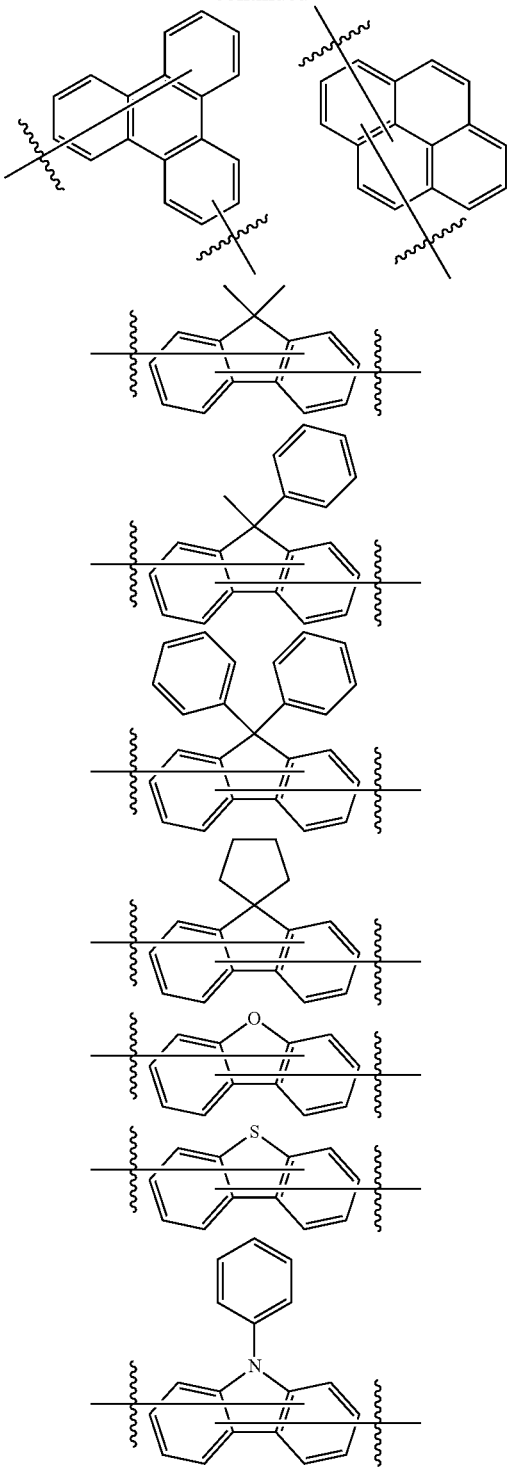

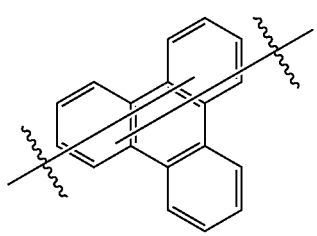

According to an exemplary embodiment of the present specification, A1 and Ar2 are each independently any one selected from the group consisting of hydrogen; deuterium; a halogen group; a nitrile group; a nitro group; a substituted or unsubstituted amine group; a substituted or unsubstituted alkyl group; a substituted or unsubstituted alkoxy group; a substituted or unsubstituted aryl group; a substituted or unsubstituted fluorene group; and a substituted or unsubstituted heterocyclic group.

Furthermore, according to an exemplary embodiment of the present specification, A1 and Ar2 are each independently any one selected from the group consisting of hydrogen; deuterium; a substituted or unsubstituted amine group; a substituted or unsubstituted alkyl group; a substituted or unsubstituted aryl group; a substituted or unsubstituted fluorene group; and a substituted or unsubstituted heterocyclic group.

Further, according to an exemplary embodiment of the present specification, A1 and Ar2 are each independently any one selected from the group consisting of hydrogen; a substituted or unsubstituted amine group; a substituted or unsubstituted aryl group; a substituted or unsubstituted fluorene group; and a substituted or unsubstituted heterocyclic group.

In addition, according to an exemplary embodiment of the present specification, A1 and Ar2 are each independently any one selected from the group consisting of hydrogen; an amine group substituted with an aryl group; an aryl group; a fluorene group substituted with an aryl group; and a heterocyclic group substituted with an aryl group.

According to an exemplary embodiment of the present specification, L, Ar1, and Ar2 may combine with an adjacent group to form a substituted or unsubstituted ring.

More specifically, Ar1 and Ar2 may combine with each other to form a substituted or unsubstituted ring.

Furthermore, according to an exemplary embodiment of the present specification, the substituted or unsubstituted ring formed by combining Ar1 and Ar2 with each other is any one of the following chemical formulae.

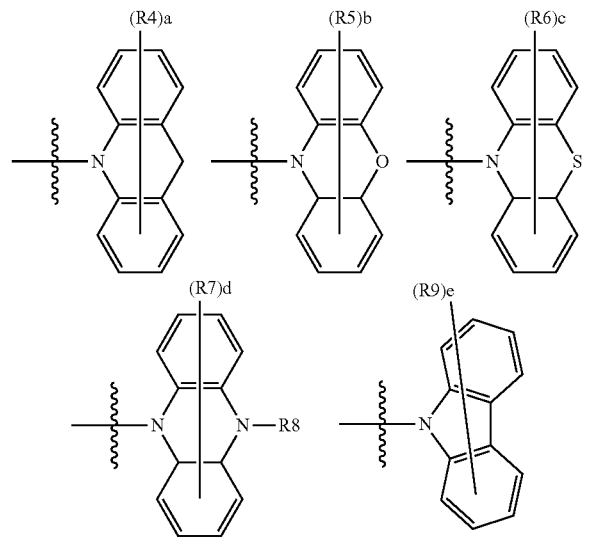

R4 to R9 are each independently selected from the group consisting of a substituted or unsubstituted alkyl group; a substituted or unsubstituted aryl group; a substituted or unsubstituted fluorene group; and a substituted or unsubstituted heterocyclic group.

a is an integer of 1 to 10, and
b to e are each an integer of 1 to 8.

Further, according to an exemplary embodiment of the present specification, R4 to R9 are each independently selected from the group consisting of a substituted or unsubstituted alkyl group; and a substituted or unsubstituted aryl group.

In addition, according to an exemplary embodiment of the present specification, R4 to R9 are each independently selected from the group consisting of an alkyl group; and an aryl group.

Furthermore, L and Ar1 or Ar2 may combine with each other to form a substituted or unsubstituted ring. In this case, the substituted or unsubstituted ring formed by combining L and Ar1 or Ar2 with each other is any one of the following chemical formulae.

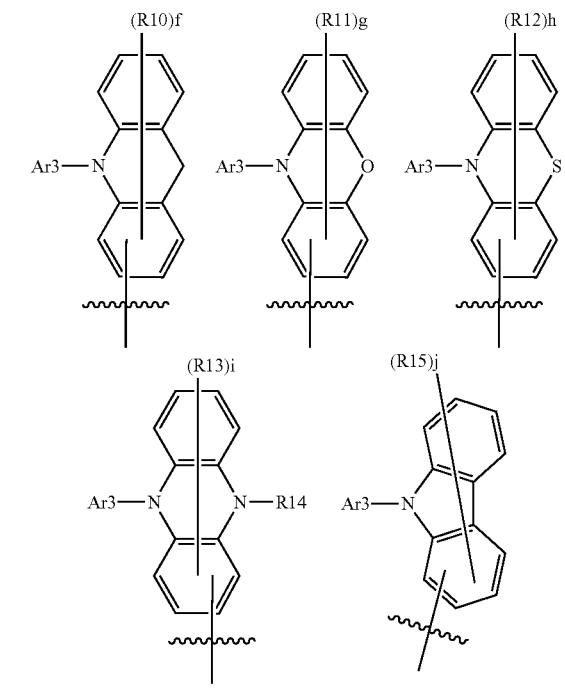

R10 to R15 are each independently selected from the group consisting of a substituted or unsubstituted alkyl group; a substituted or unsubstituted aryl group; a substituted or unsubstituted fluorene group; and a substituted or unsubstituted heterocyclic group, Ar3 is Ar1 or Ar2,
f is an integer of 1 to 9, and
g to j are each an integer of 1 to 7.

Further, according to an exemplary embodiment of the present specification, R10 to R15 are each independently selected from the group consisting of a substituted or unsubstituted alkyl group; and a substituted or unsubstituted aryl group.

In addition, according to an exemplary embodiment of the present specification, R10 to R15 are each independently selected from the group consisting of an alkyl group; and an aryl group.

According to an exemplary embodiment of the present specification, n and m in Chemical Formula 1 are each an integer of 0 to 6, o+s is an integer of 1 to 4, and s is an integer of 1 to 4.

When n or m is 0, a substituent of R1 or R2 is not present, and the case where n or m is 0 means being substituted with only hydrogen. Furthermore, in the right bottom benzene ring of a core structure, R3 and L may be substituted, and the number of substituents thereof may not exceed 4. Further, L means that at least one or more substituents are substituted, and the case where s is 4 or more means that L is substituted at all the positions in which the substituent may be positioned, and R3 is not present.

According to an exemplary embodiment of the present specification, the compound of the present invention is any one of the following chemical formulae.

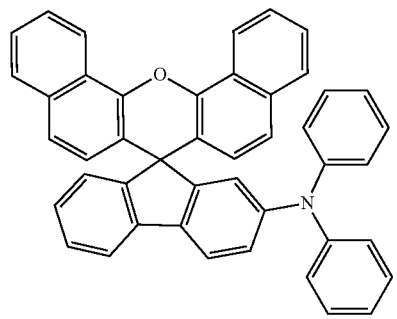
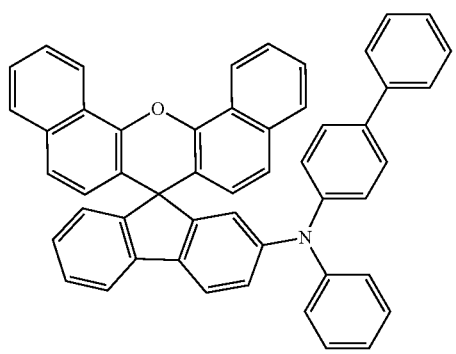
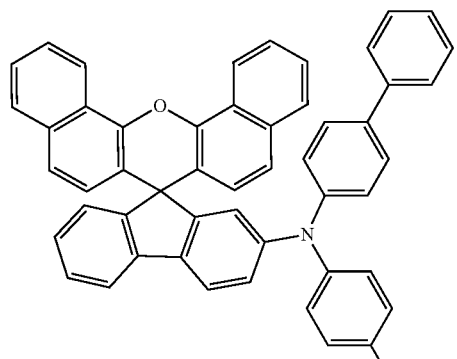
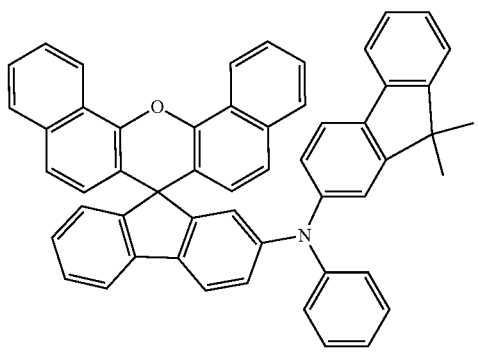
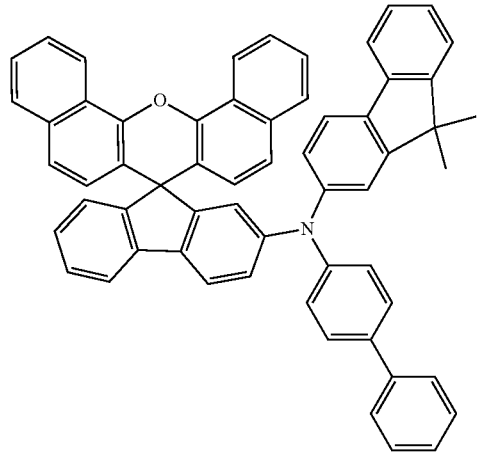
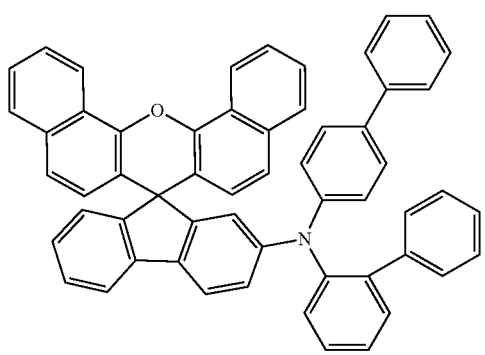
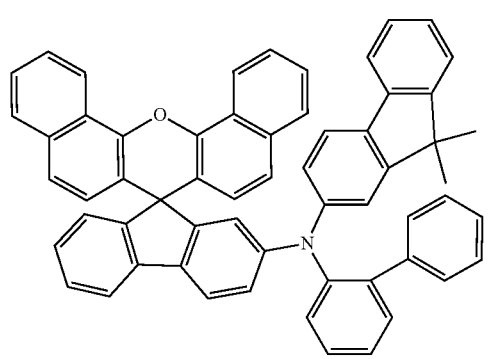
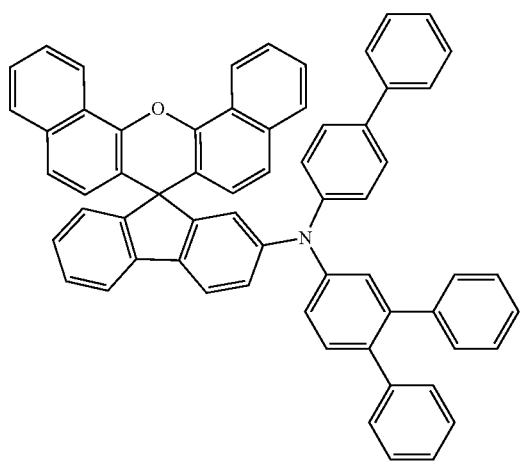

-continued
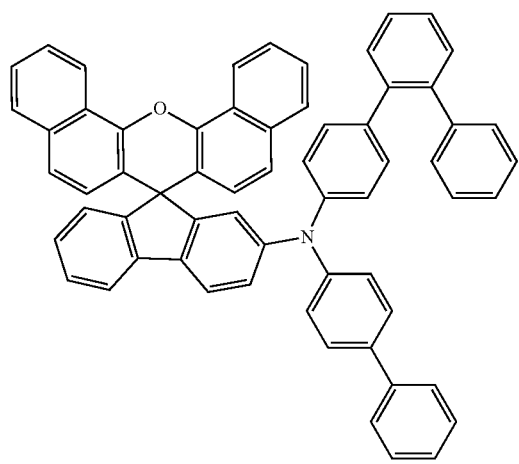
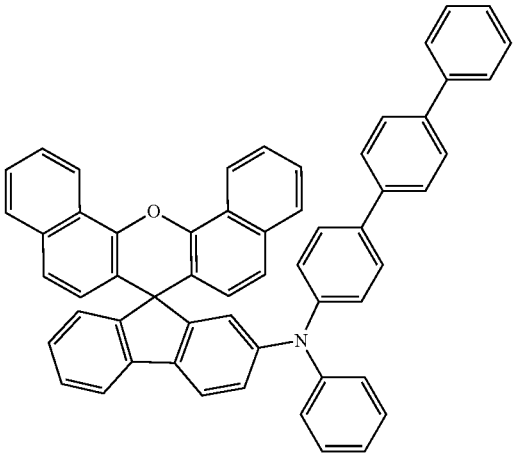
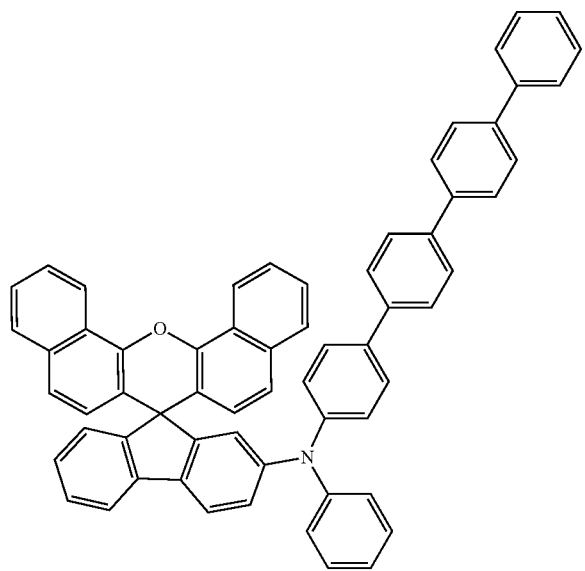
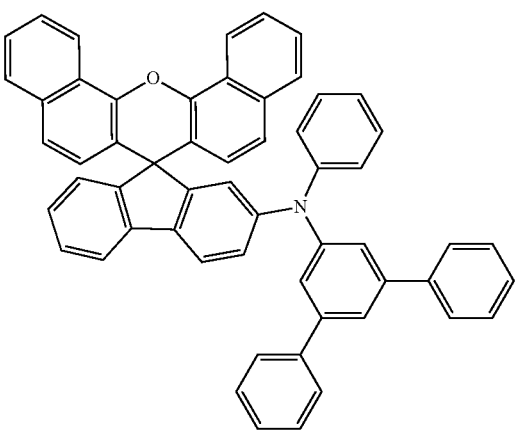
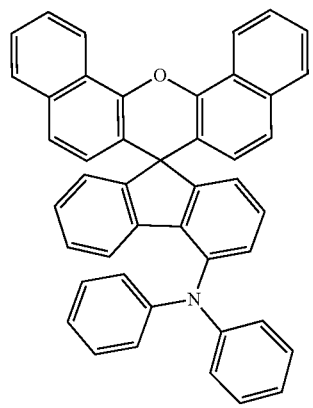
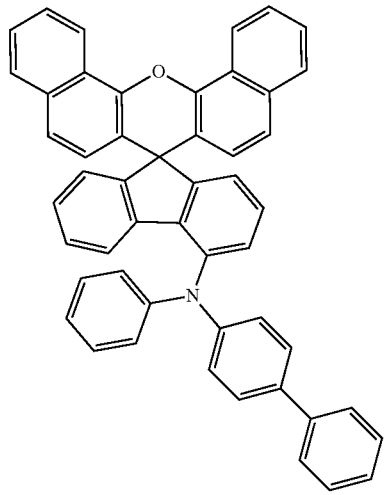

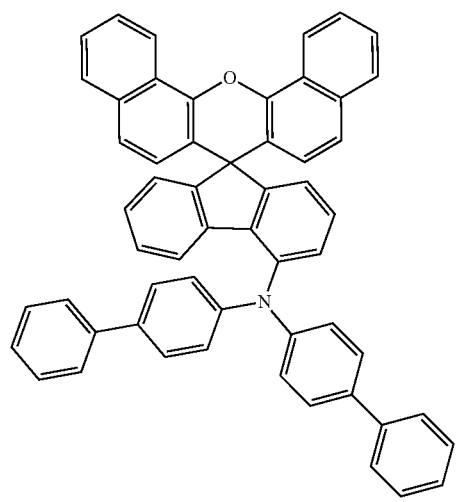
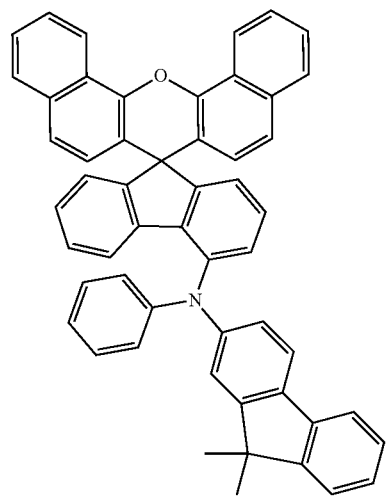
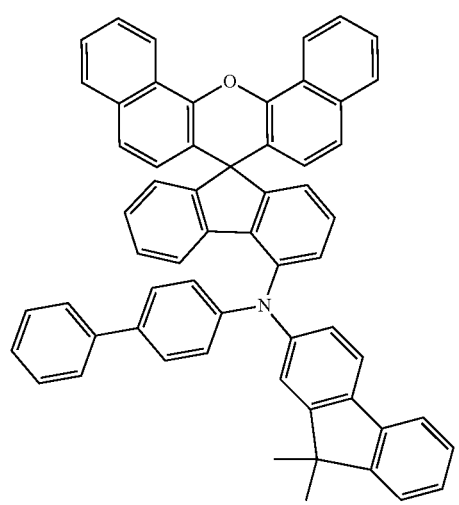
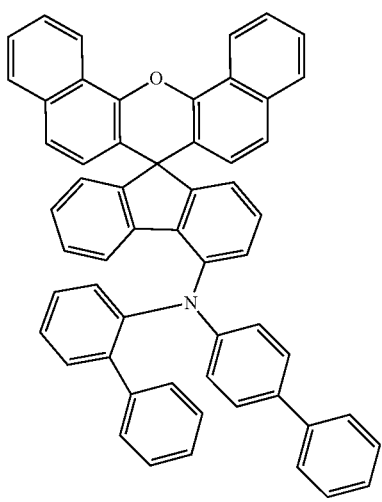
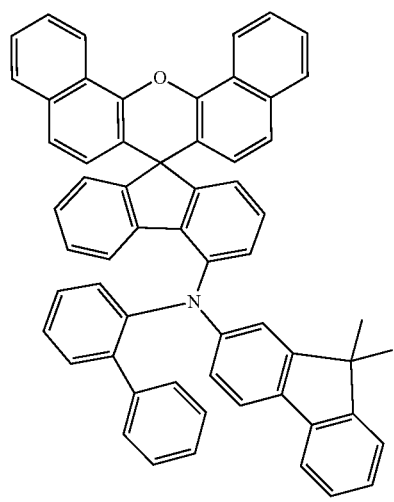
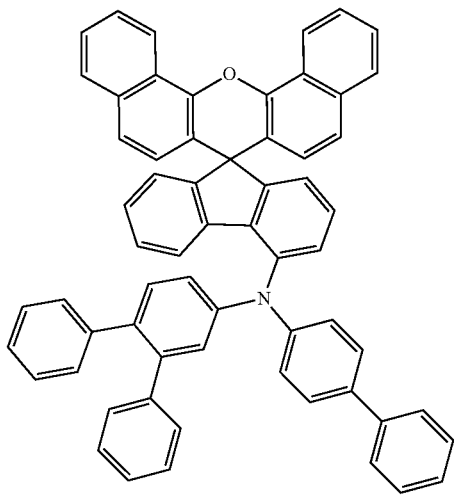

-continued
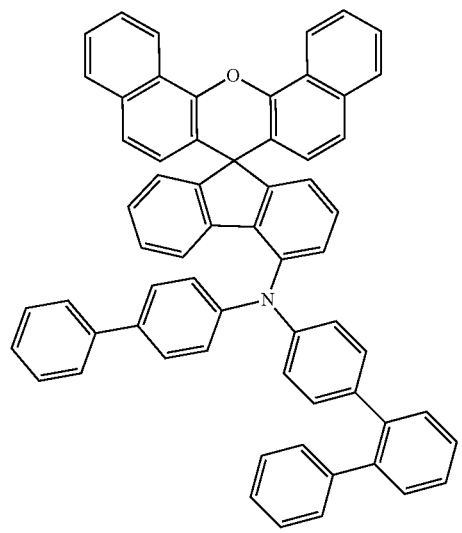
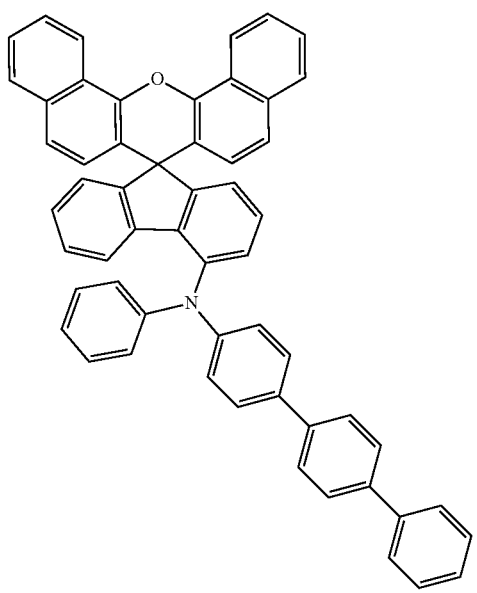
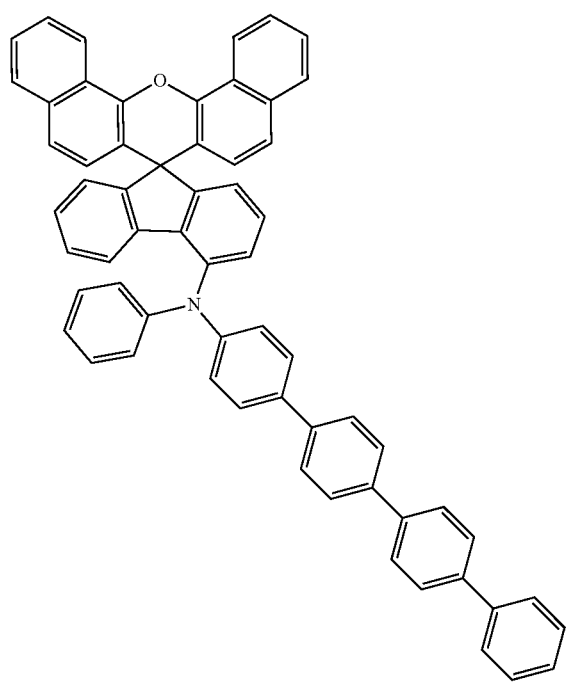
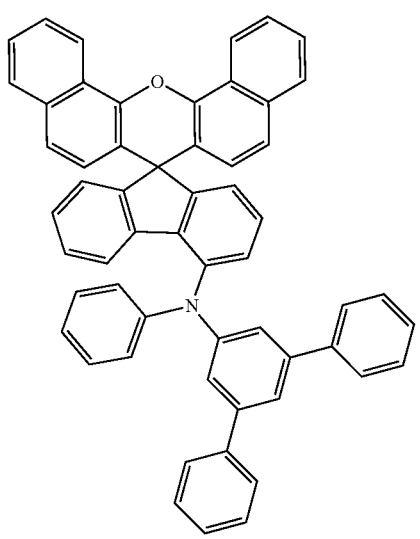
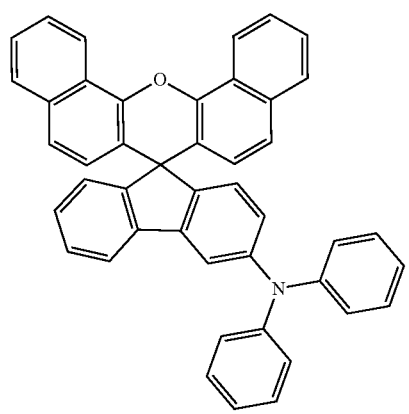

-continued
| 21 | 22 |
|---|---|
| 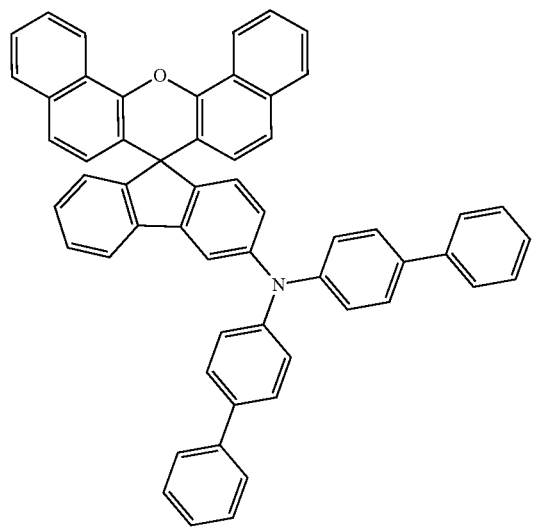 | 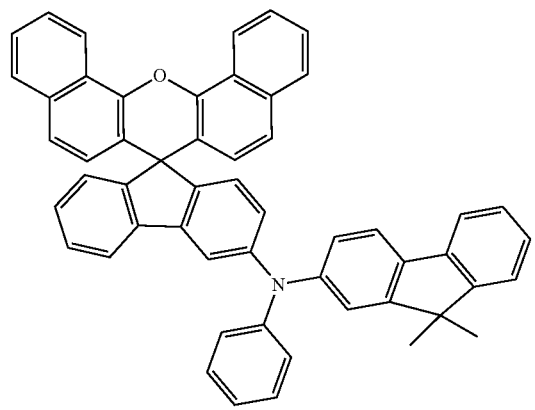 |
| 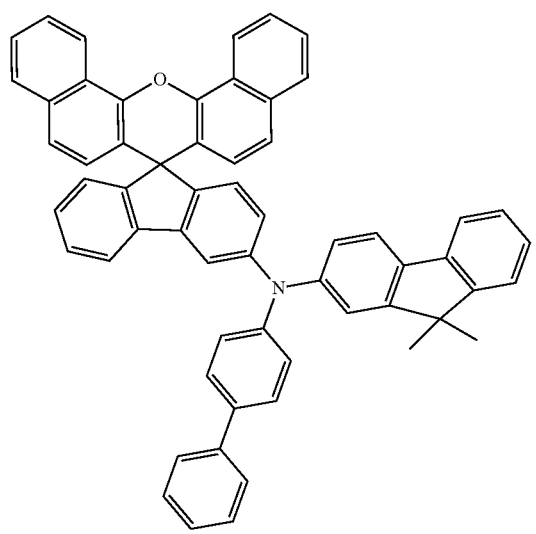 | 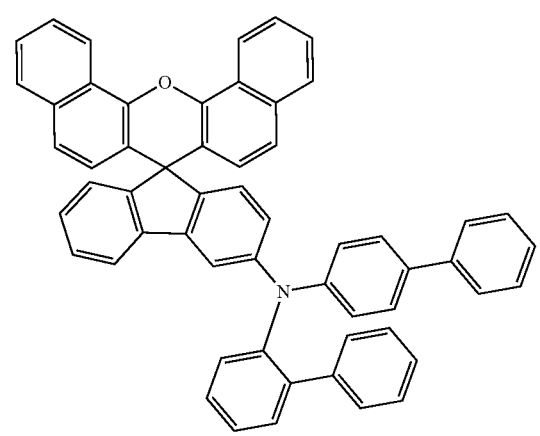 |
| 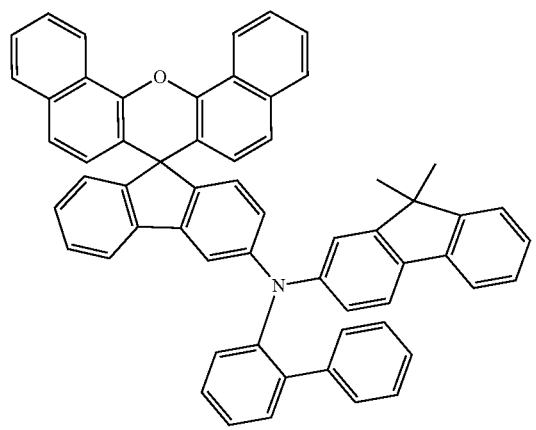 | 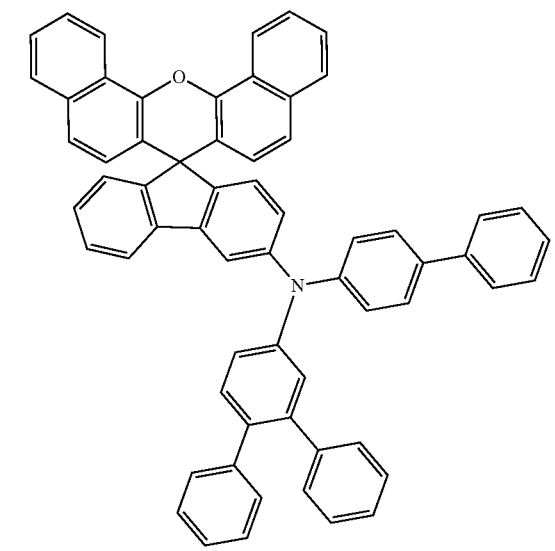 |

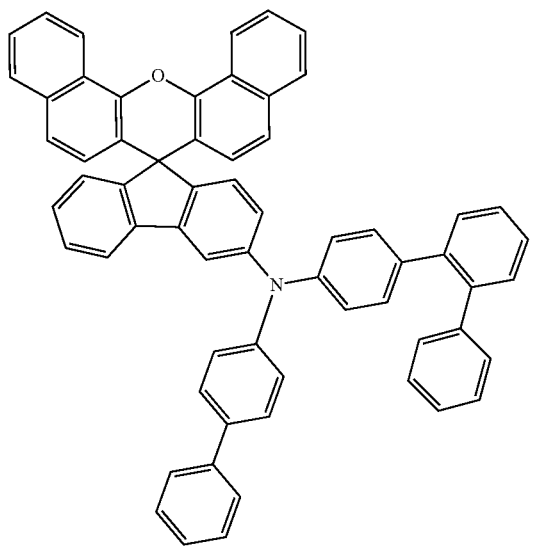
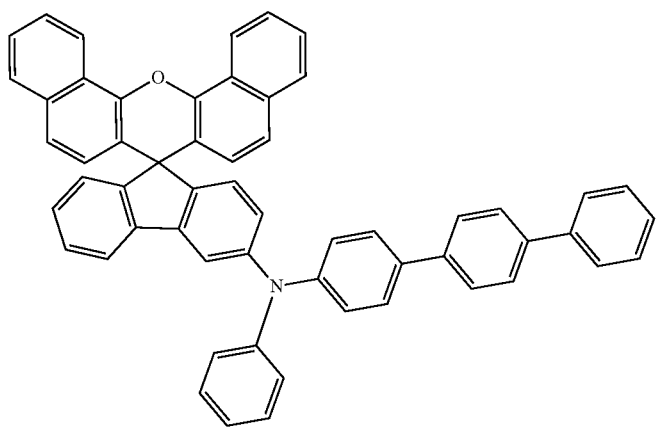
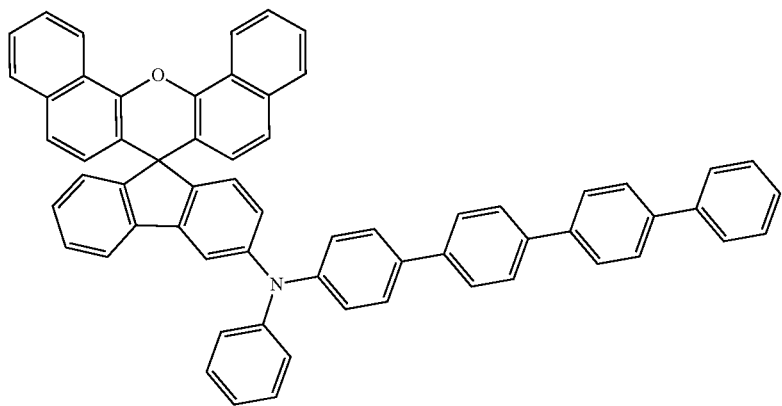

-continued
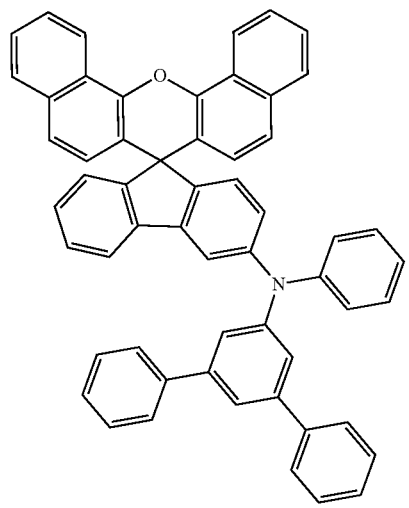
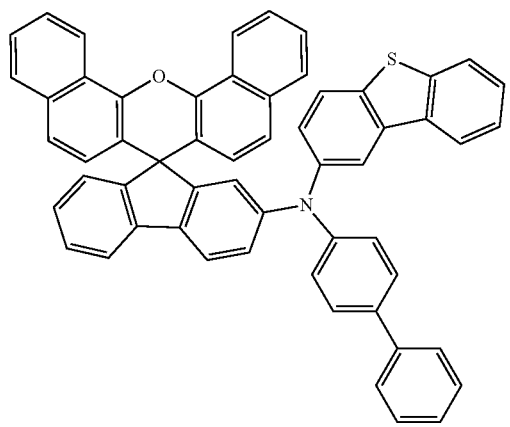
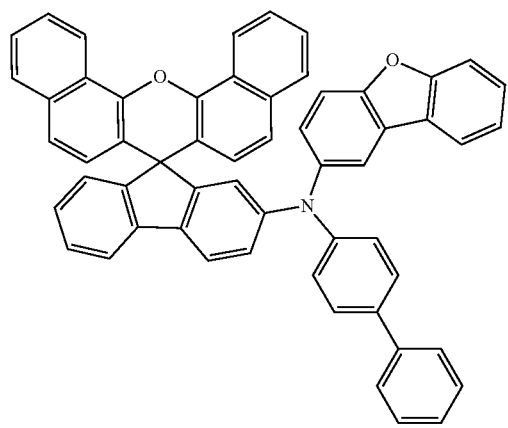
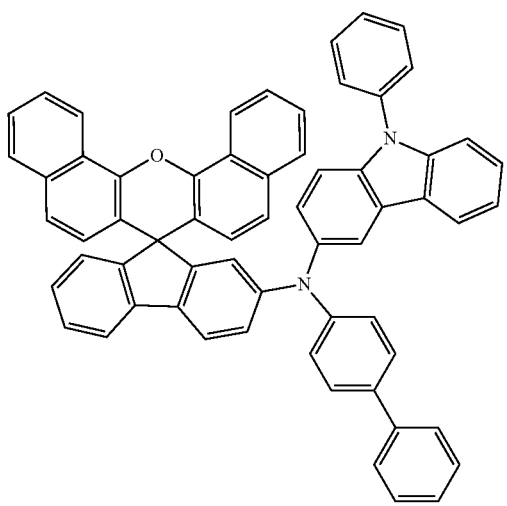
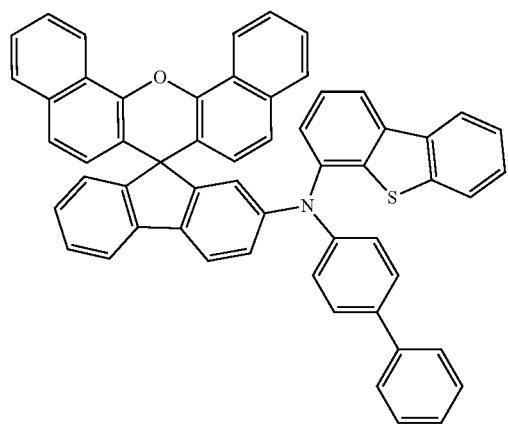
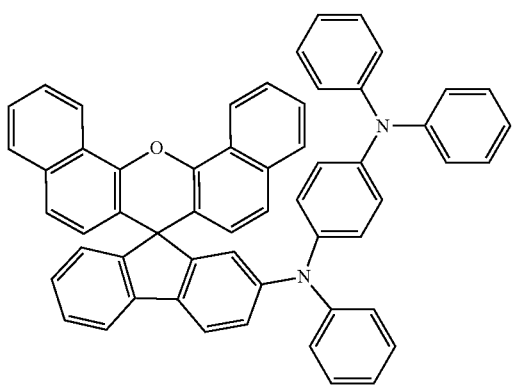

-continued
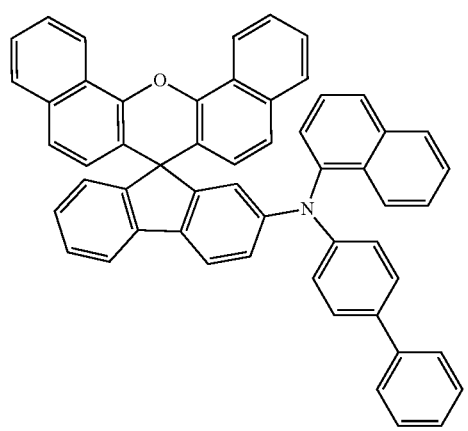
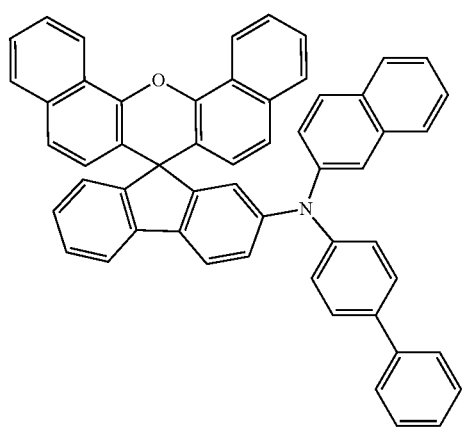
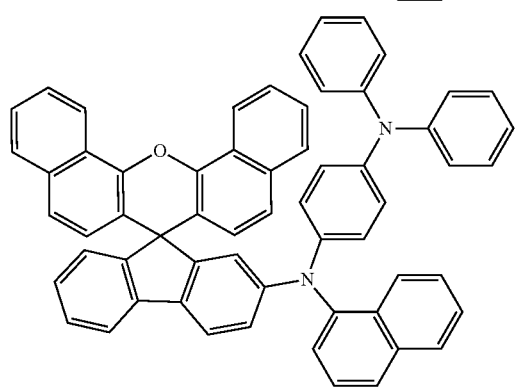
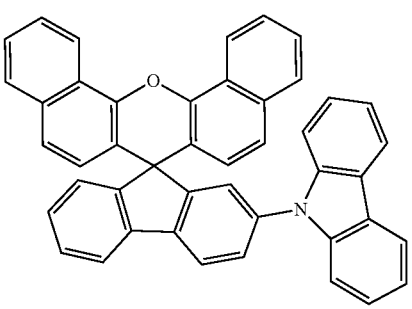
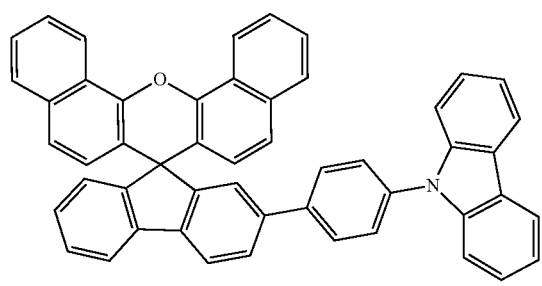
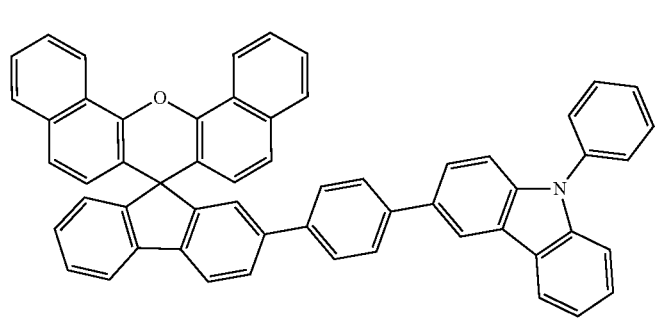
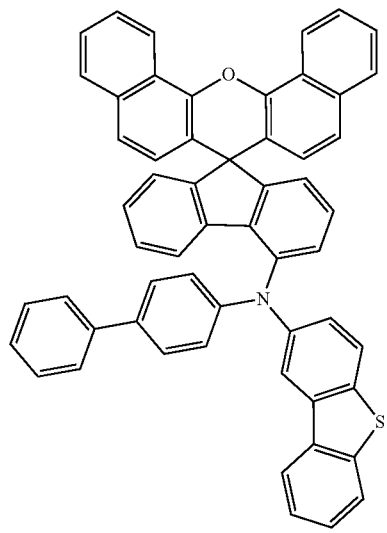

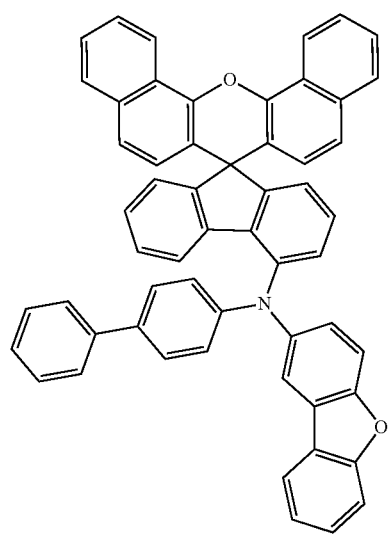
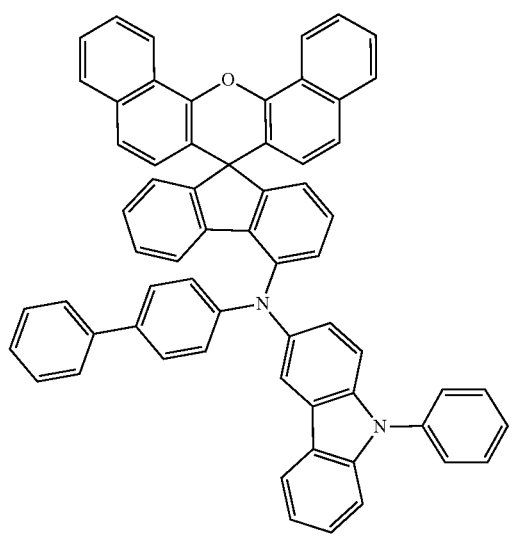
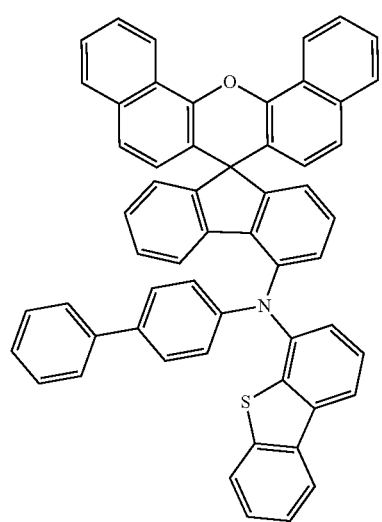
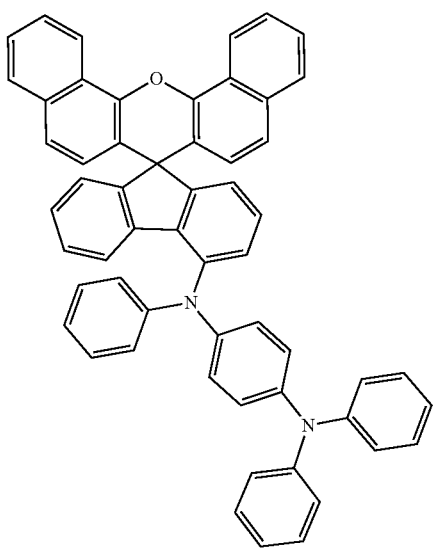
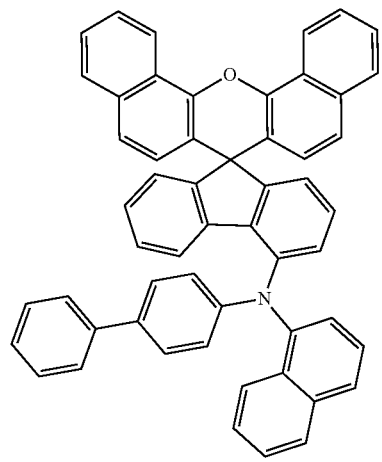
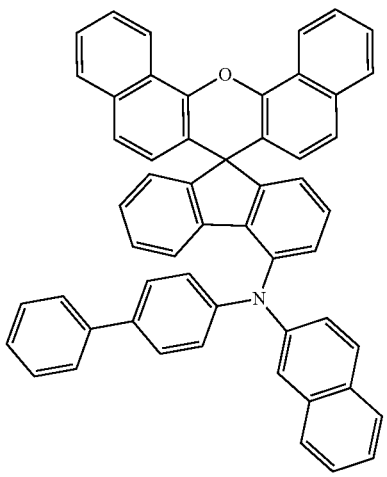

-continued
31
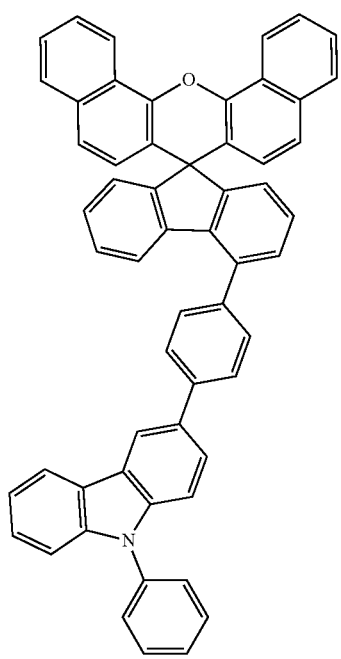
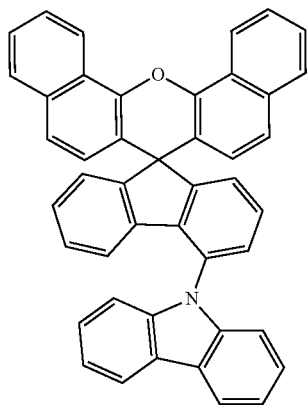
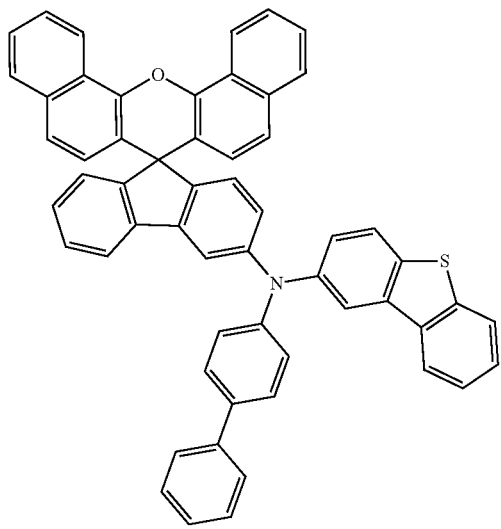
32
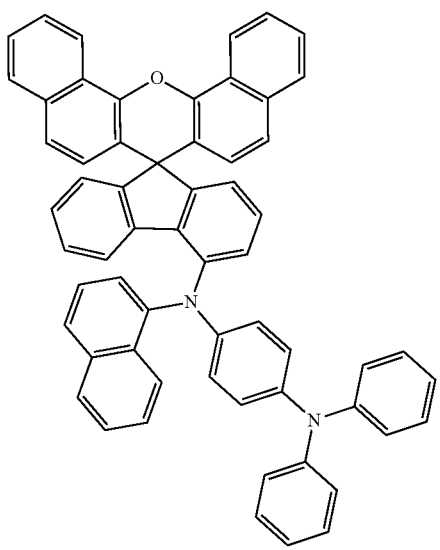
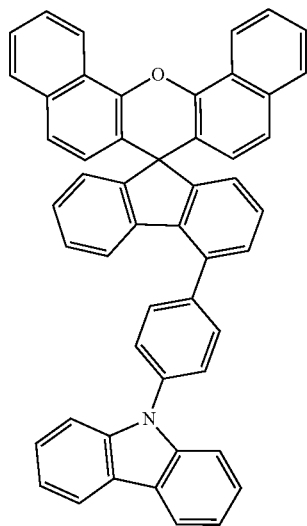
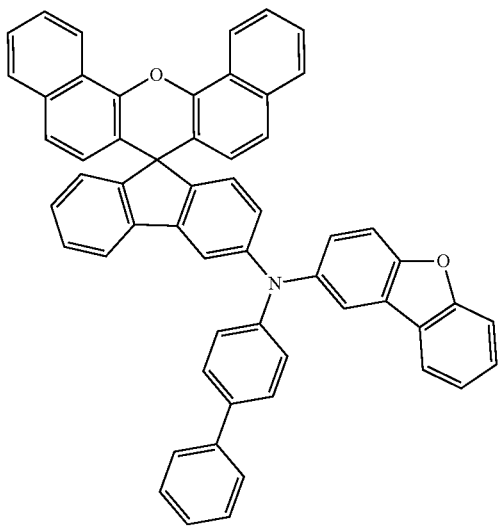

-continued
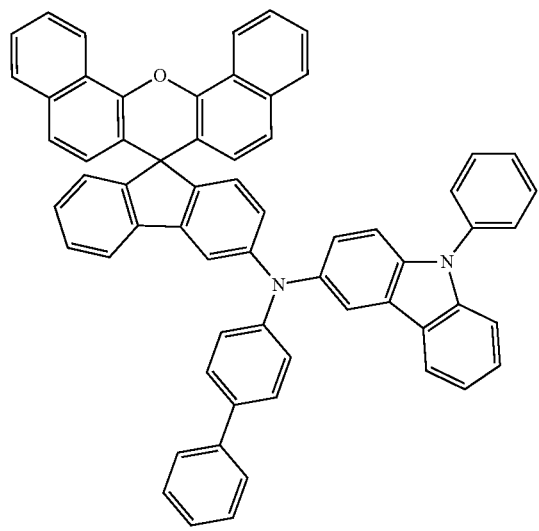
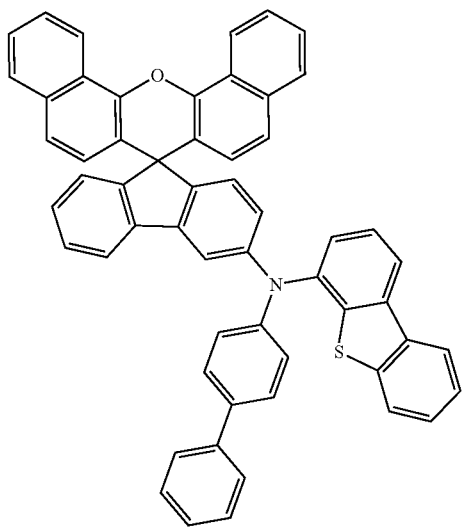
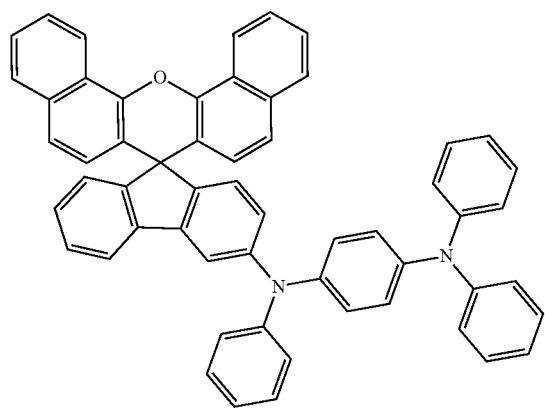
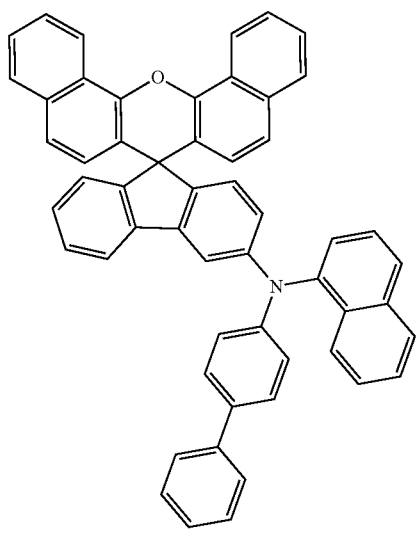
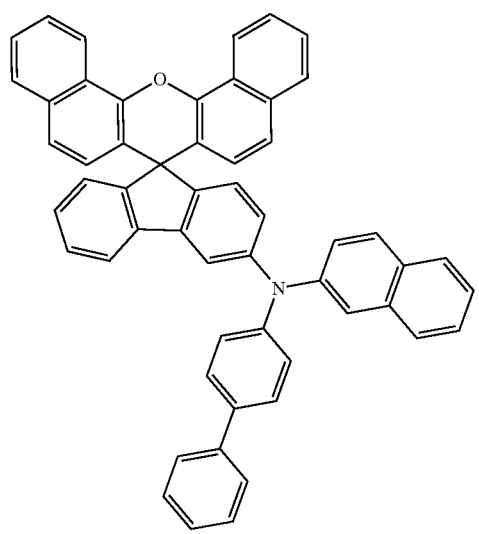
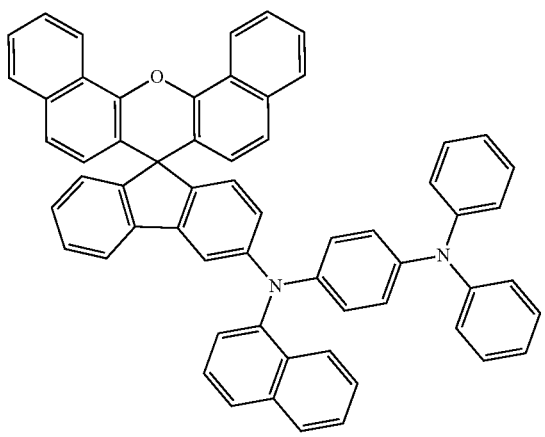

35
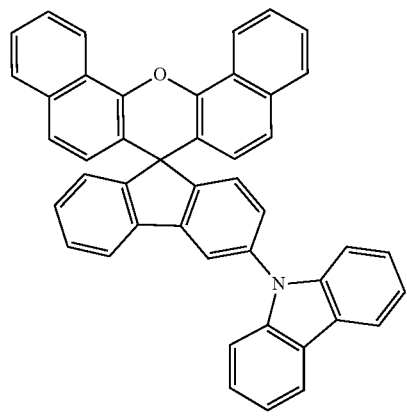
-continued
36
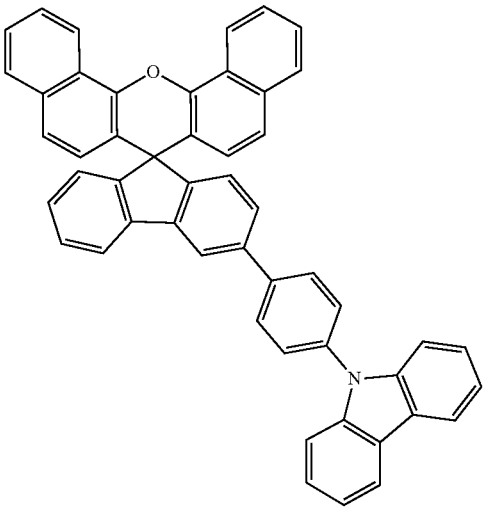
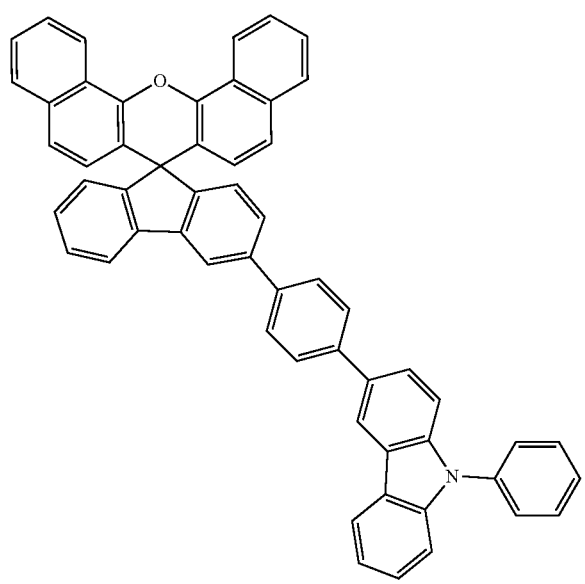
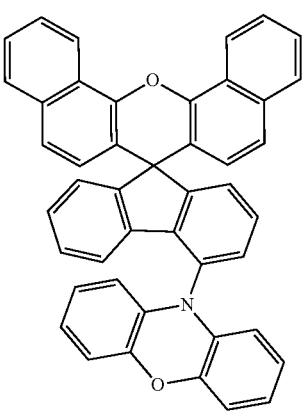
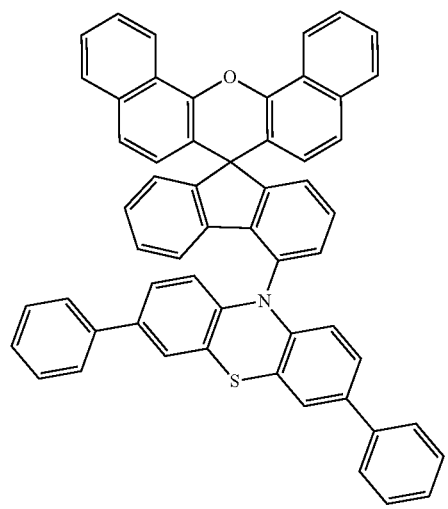

-continued
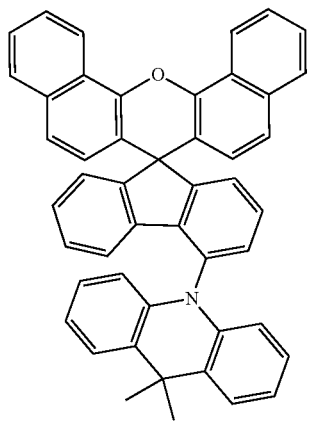
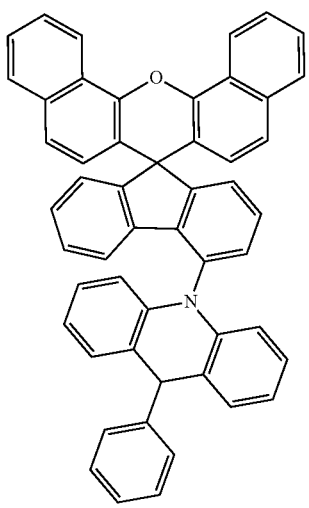
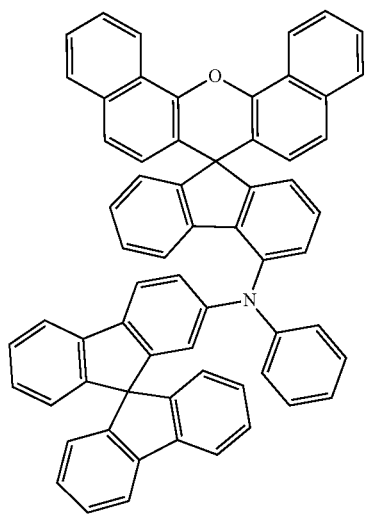
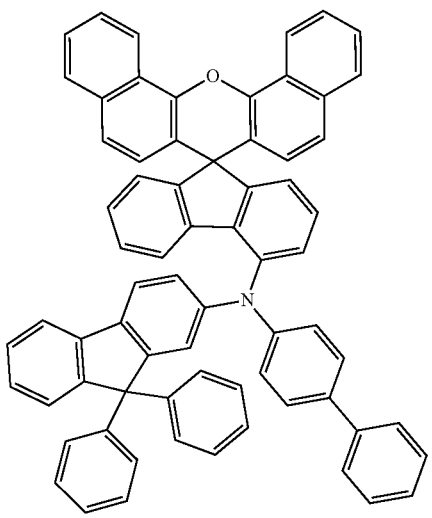
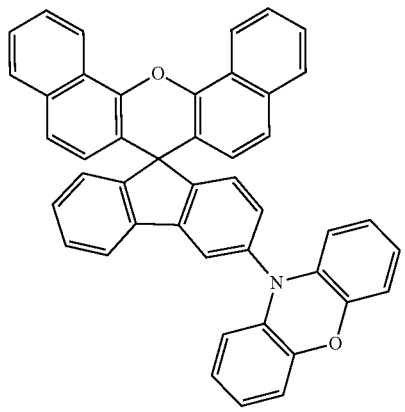
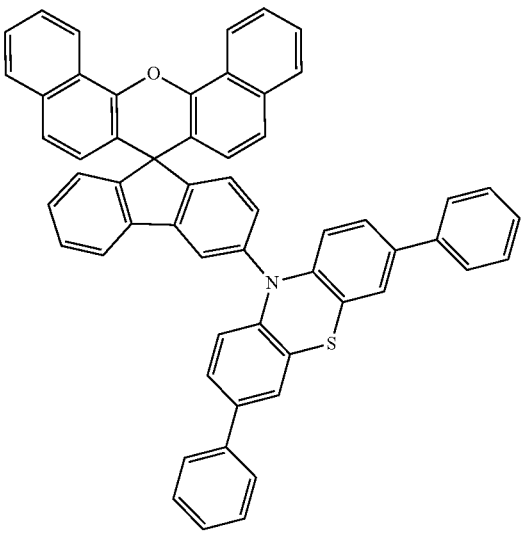

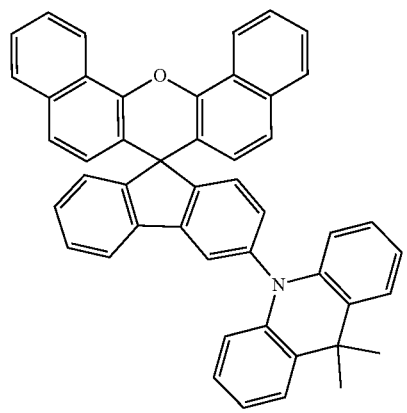
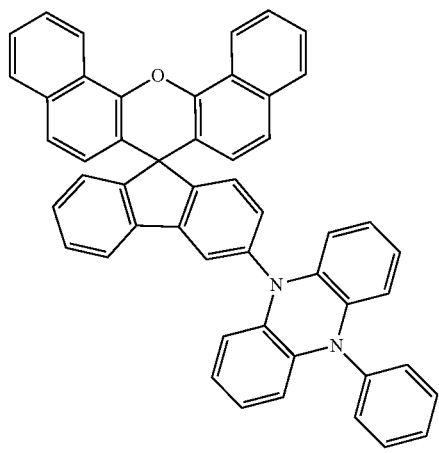
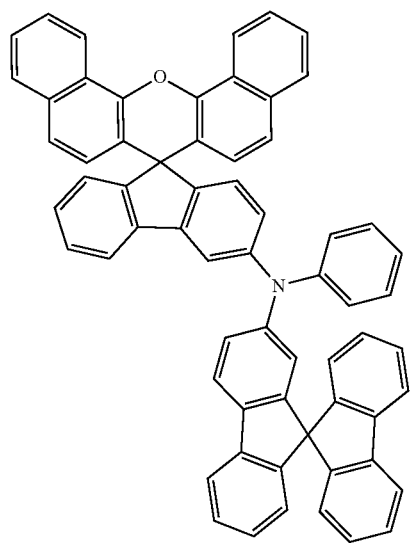
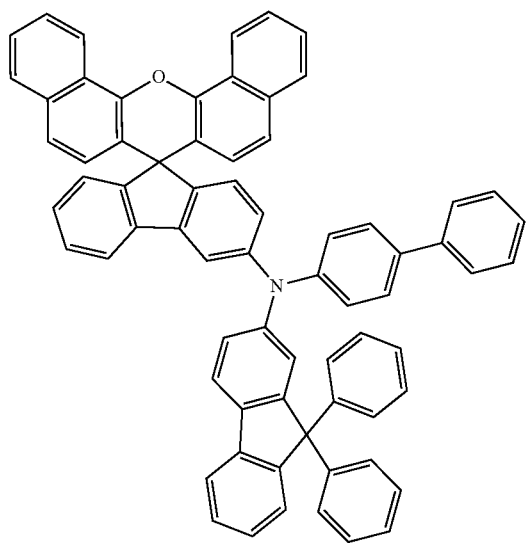
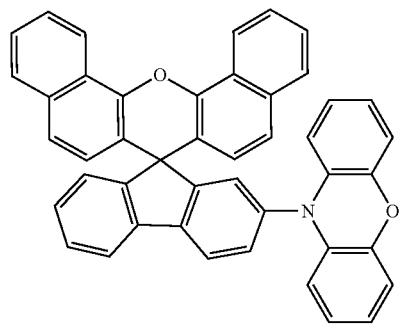
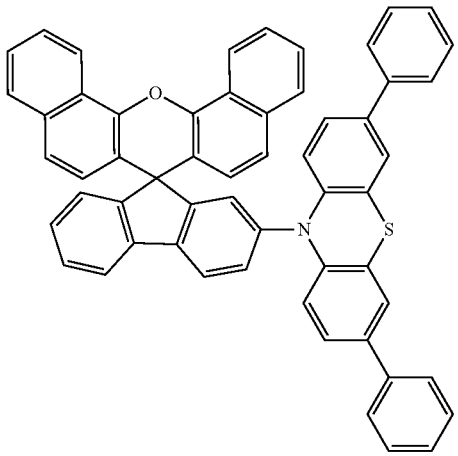

-continued
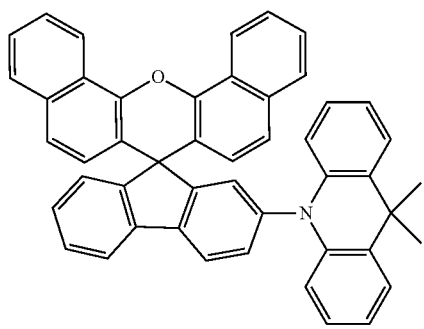
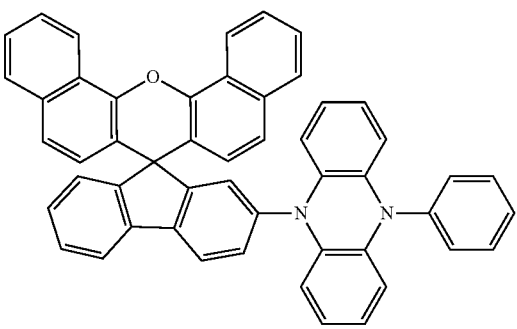
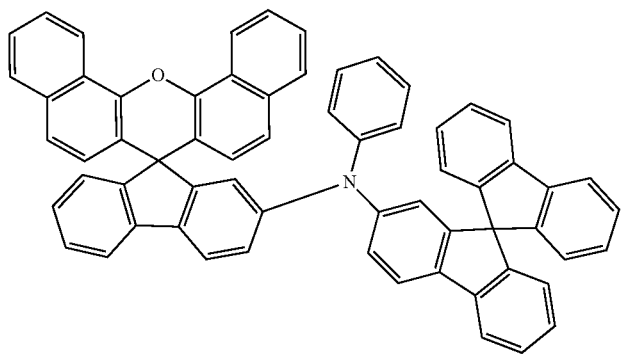
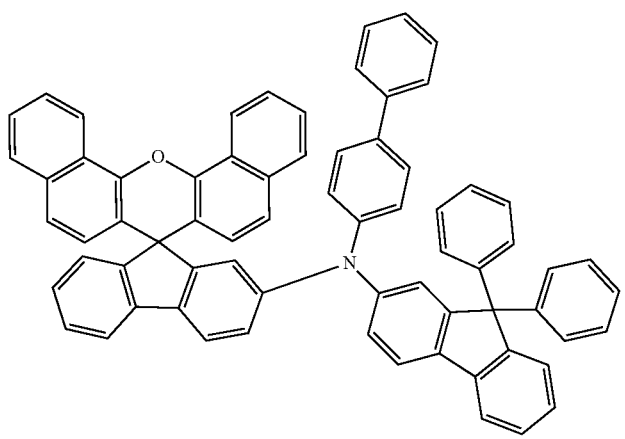
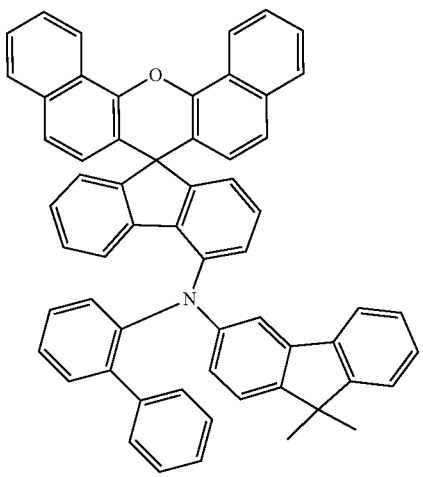
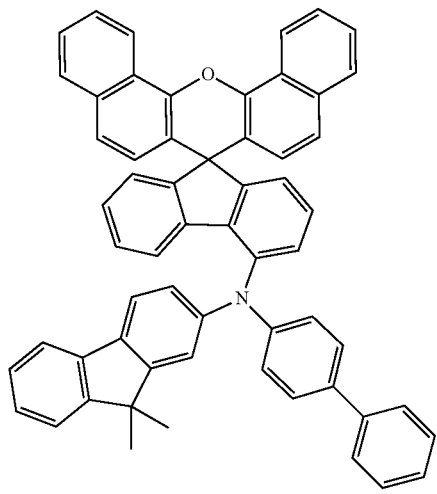
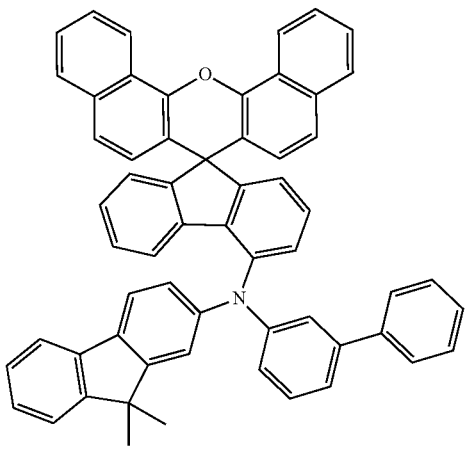

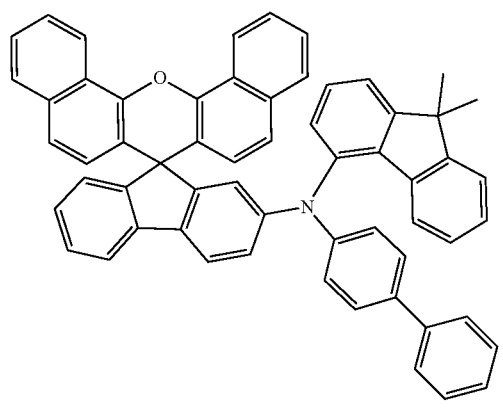
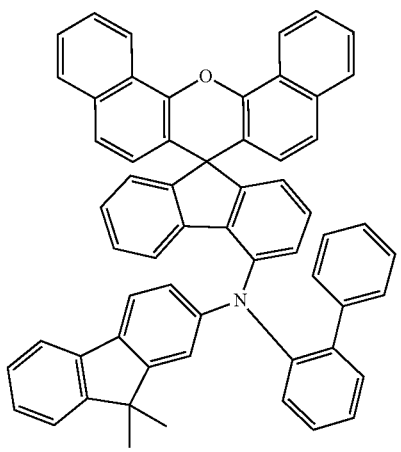
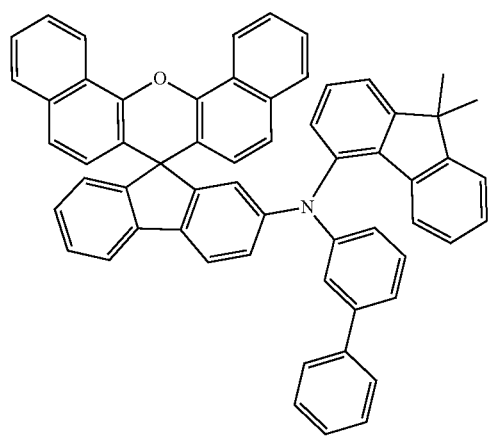
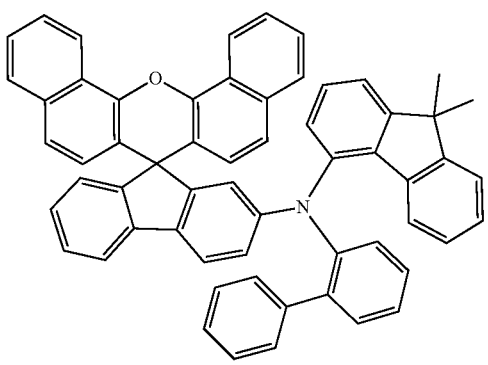
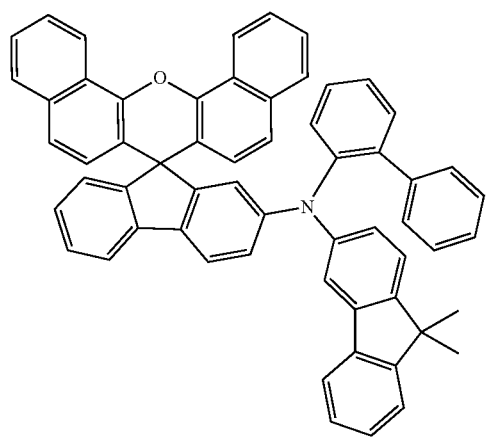
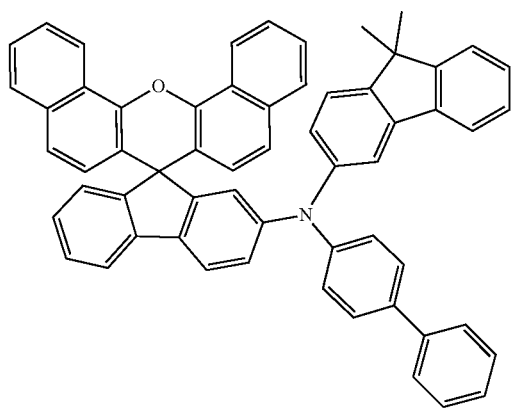

-continued
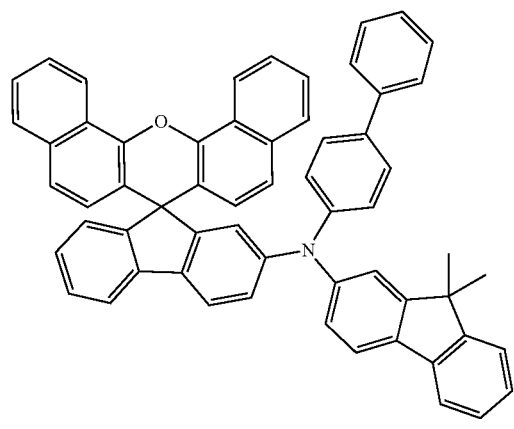
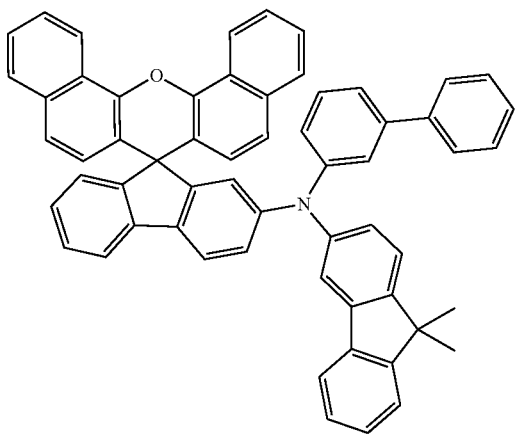
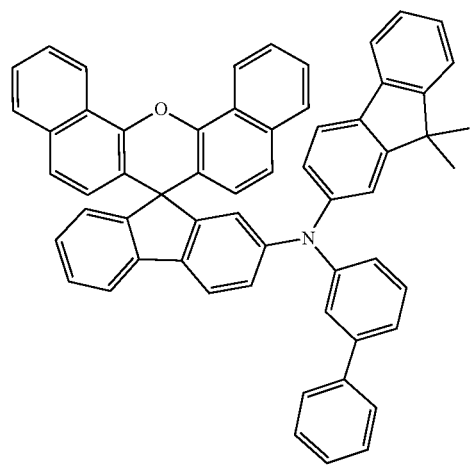
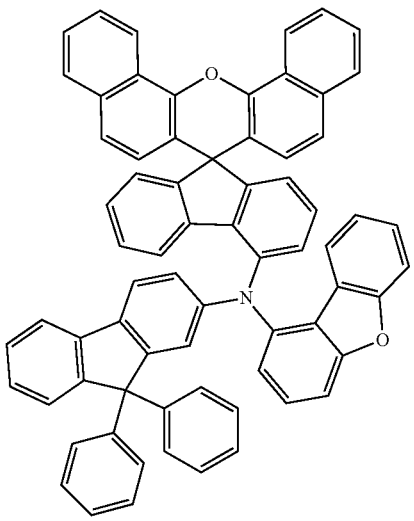
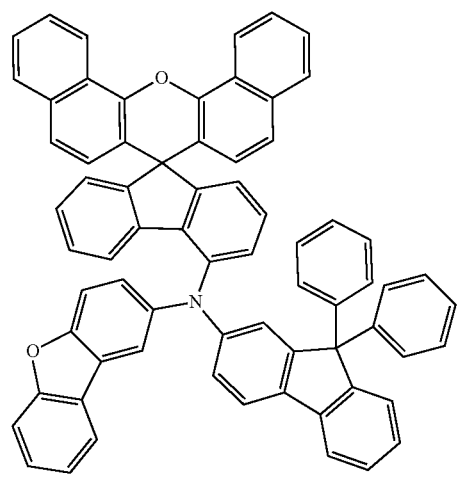
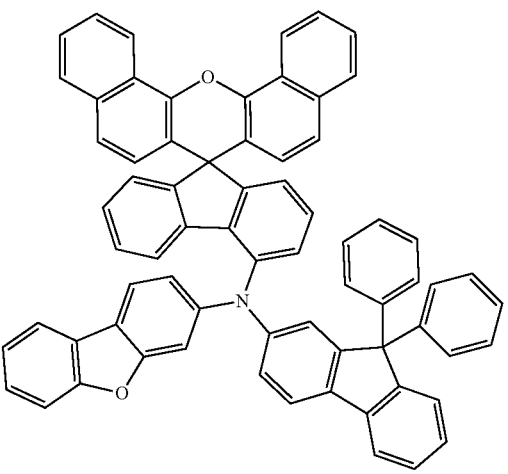

-continued
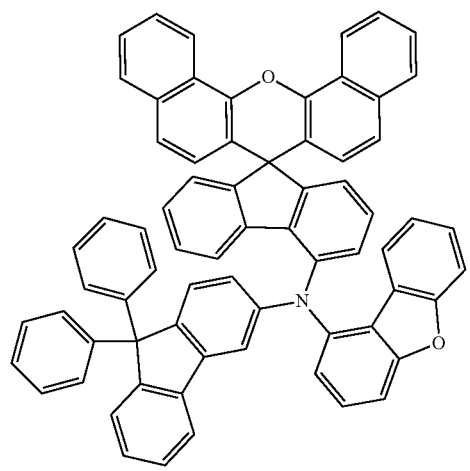
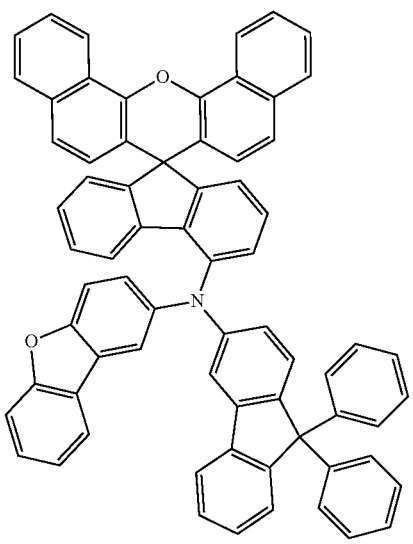
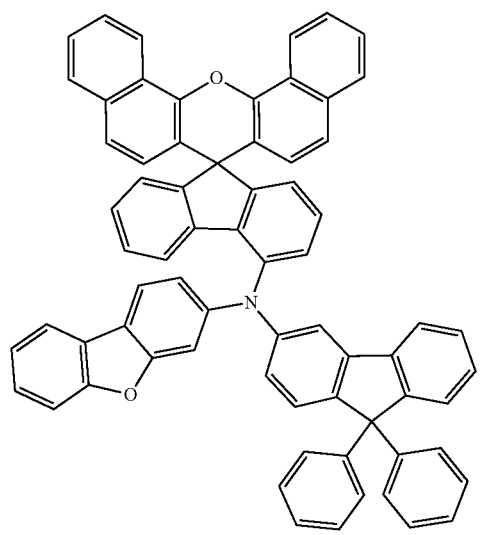
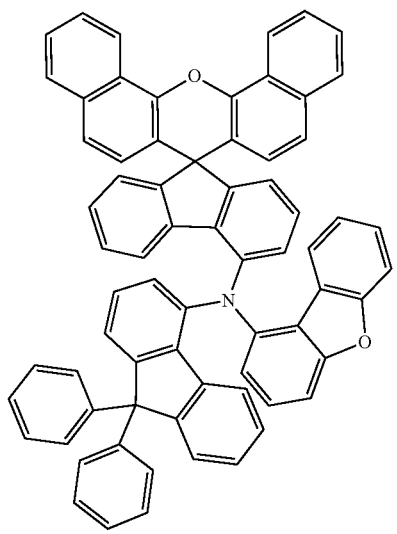
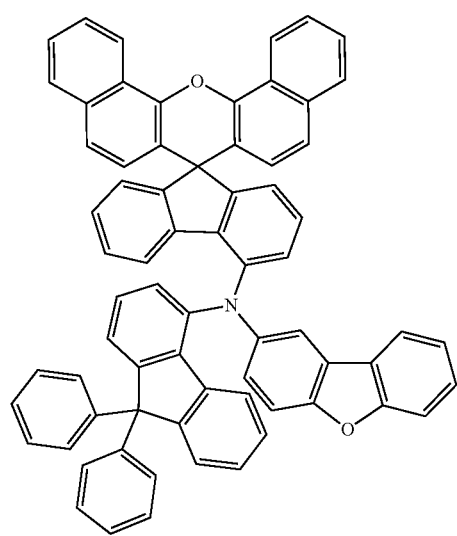
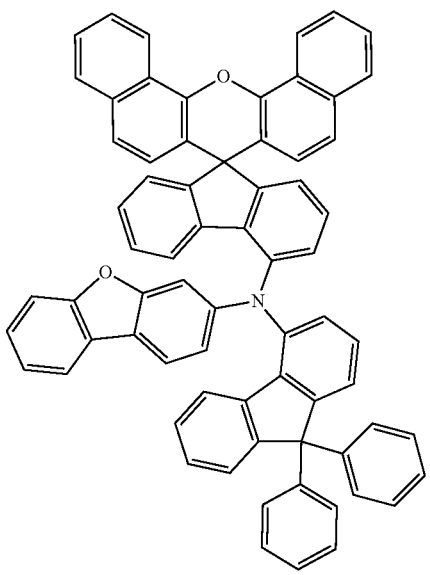

-continued
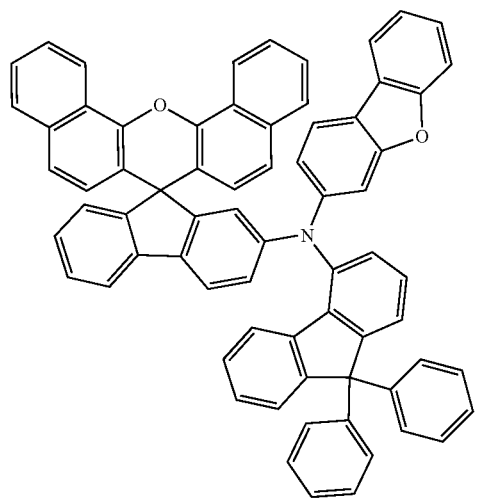
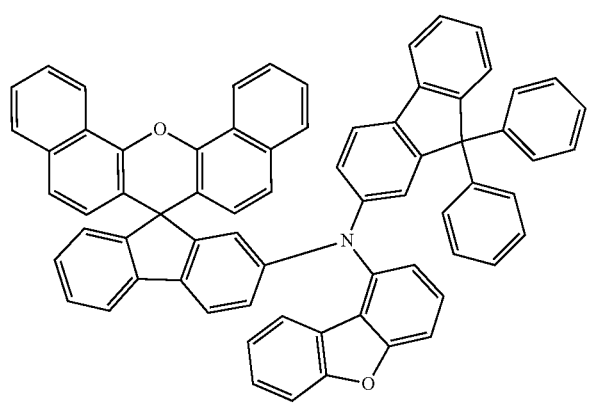
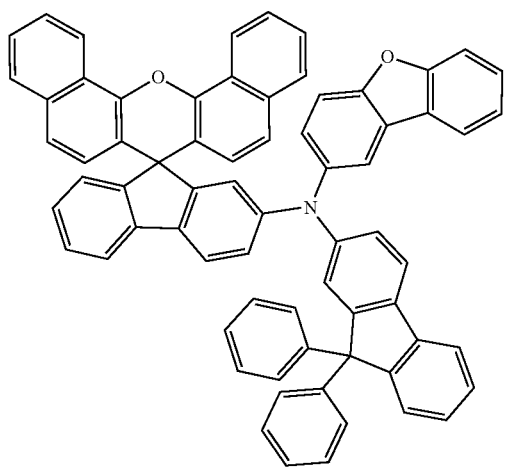
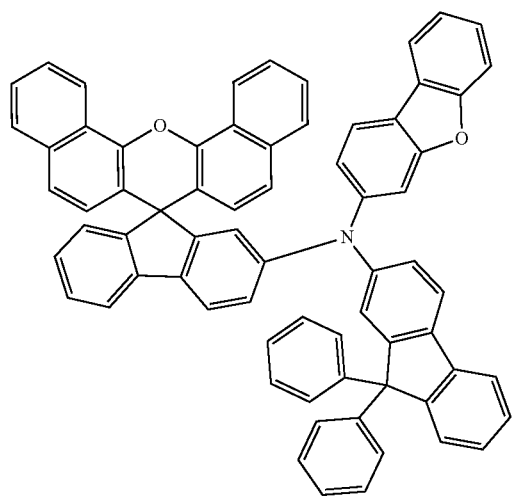
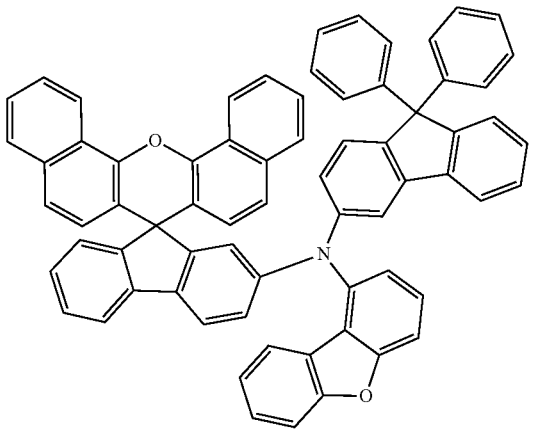

-continued
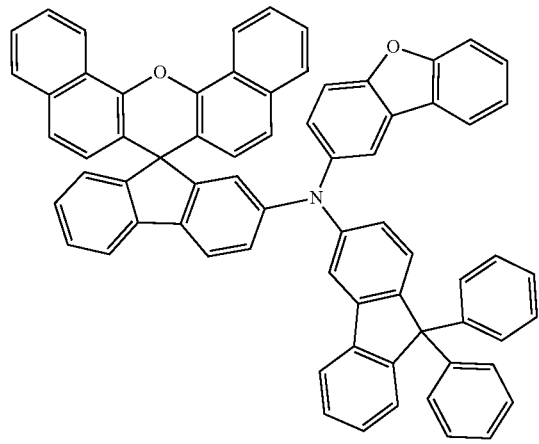
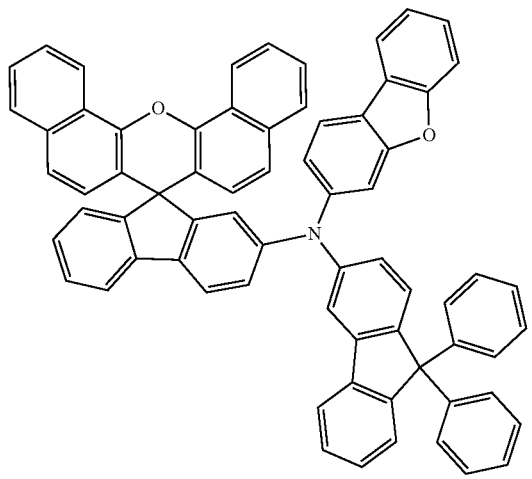
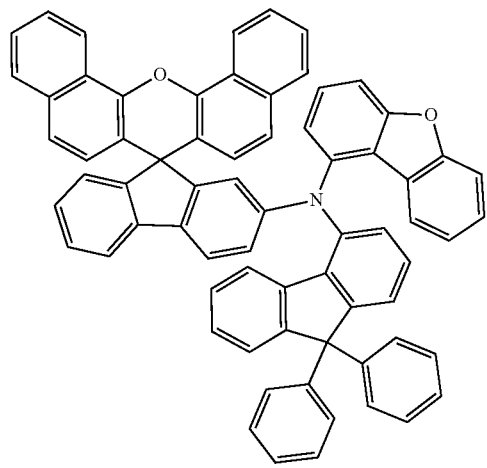
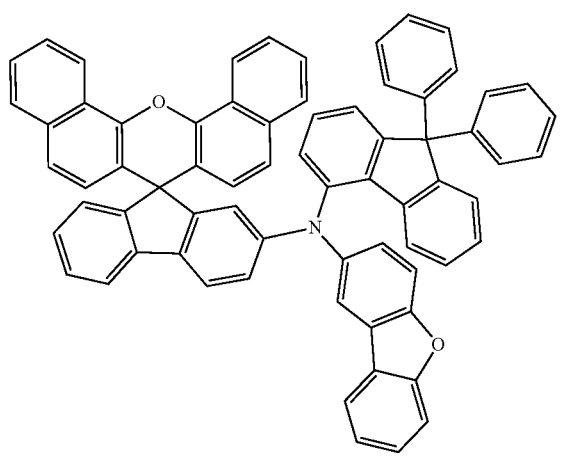
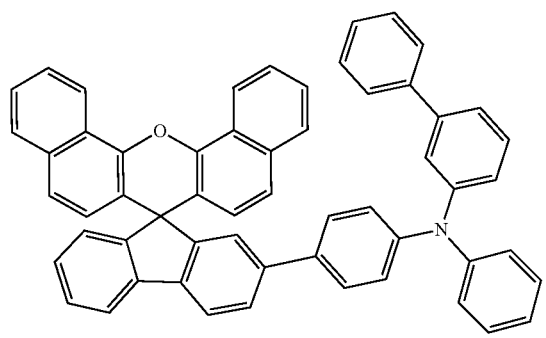
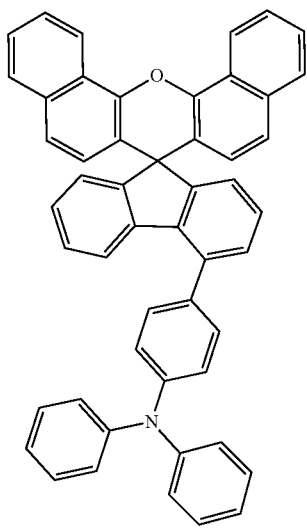

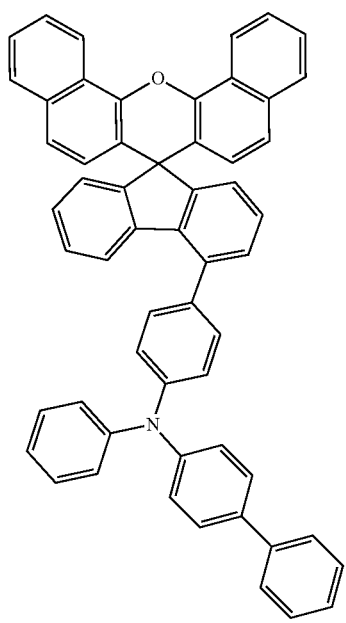
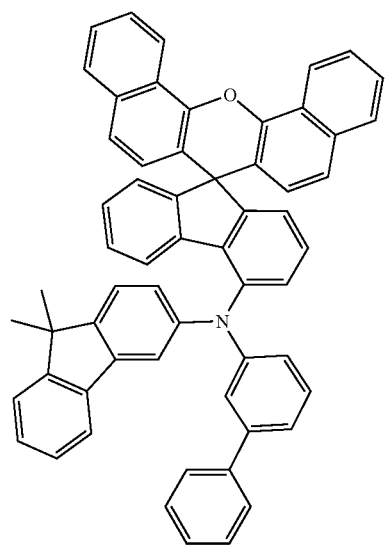
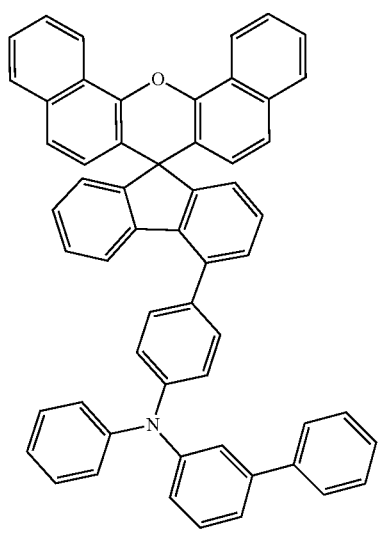
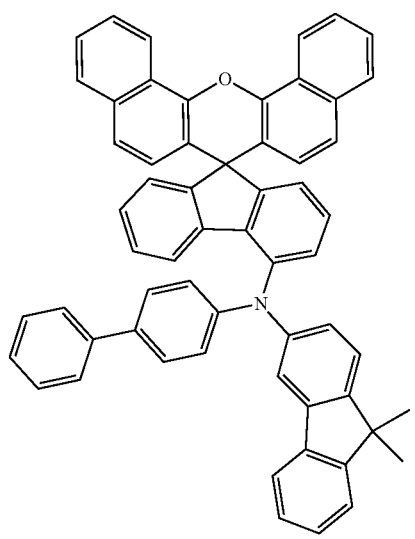
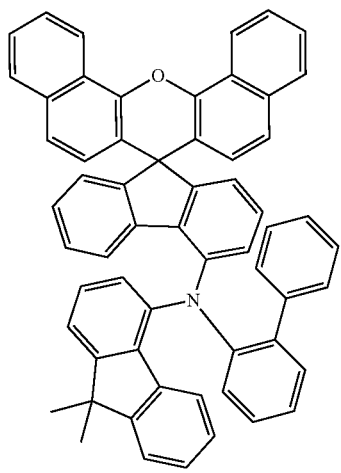
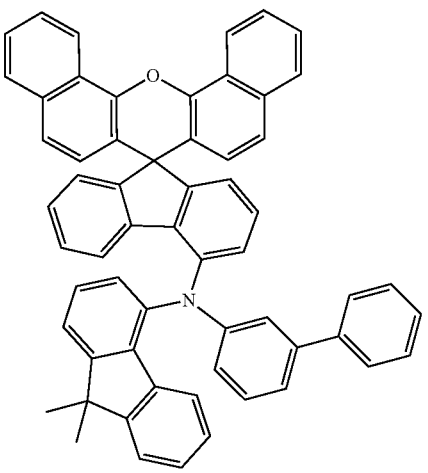

55
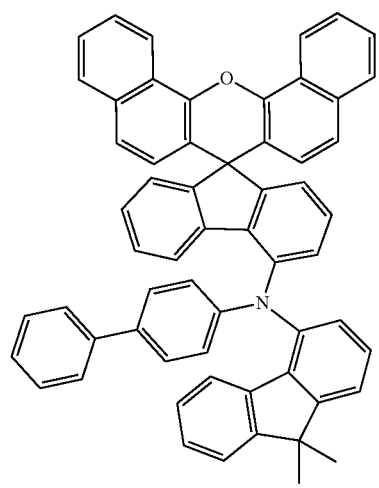
56
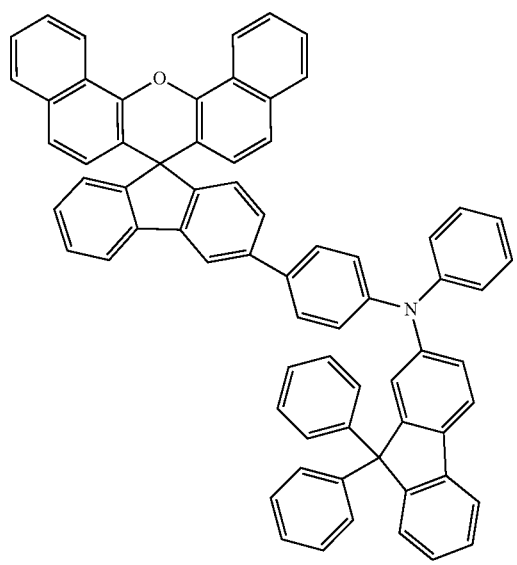
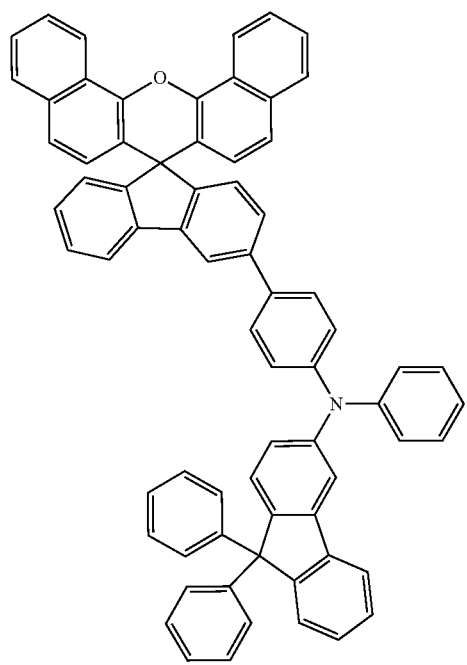
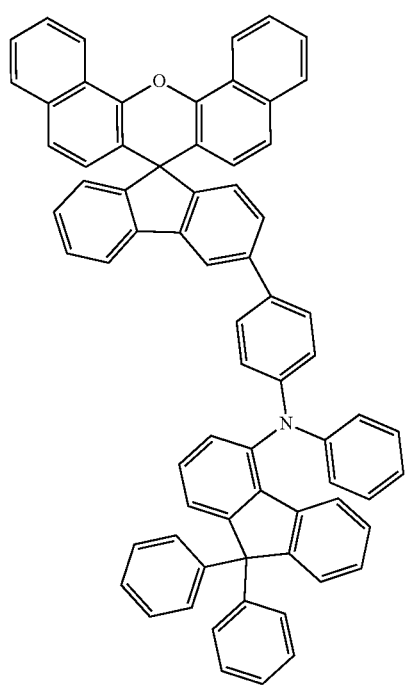

57
58
-continued
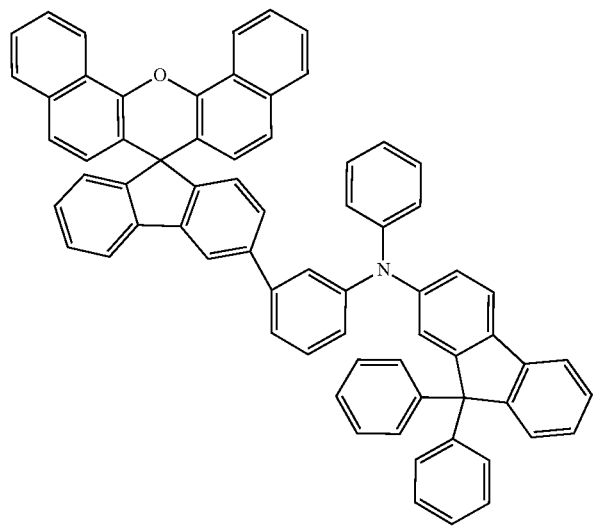
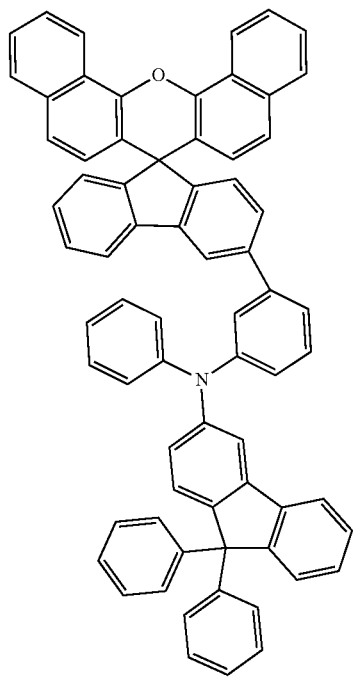
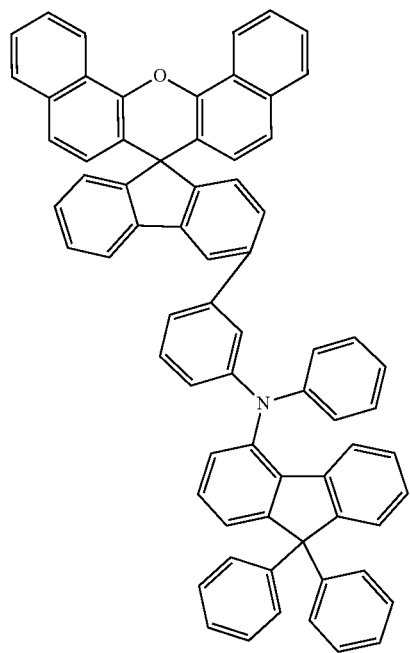
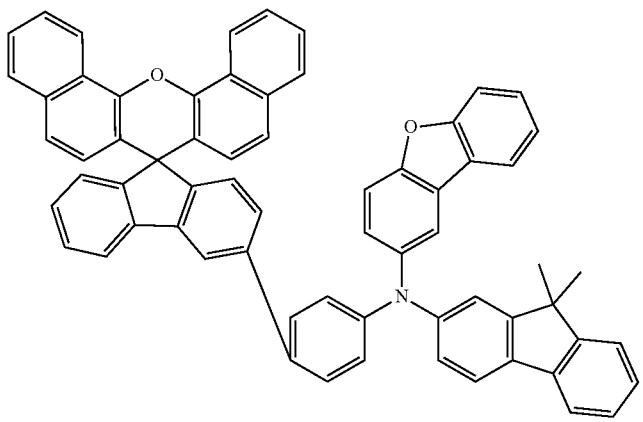

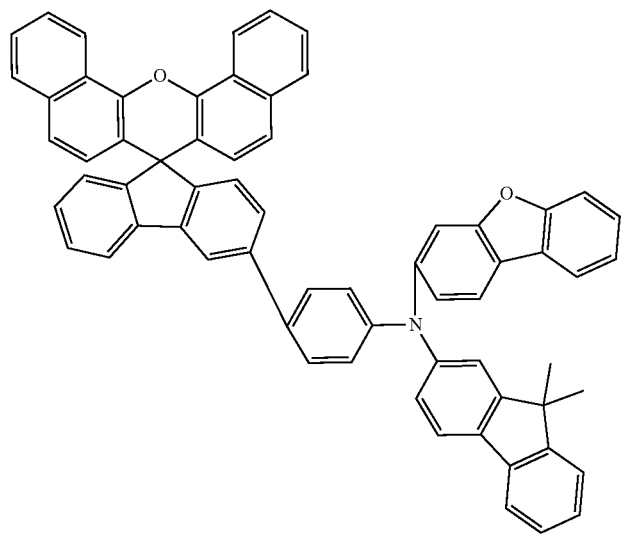
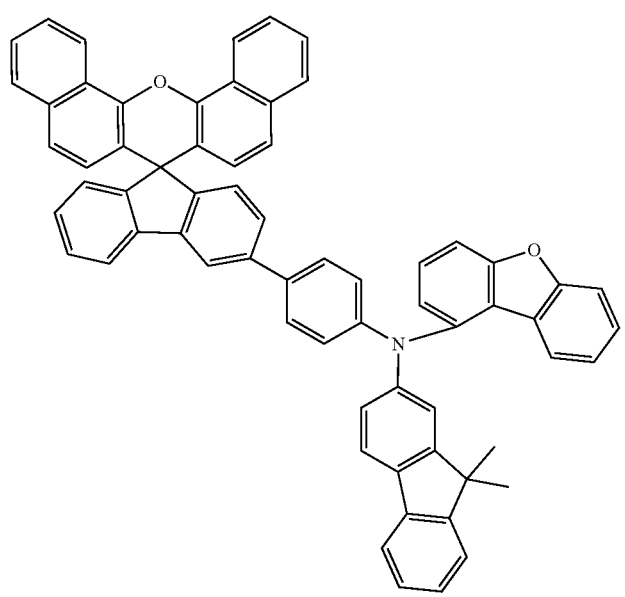

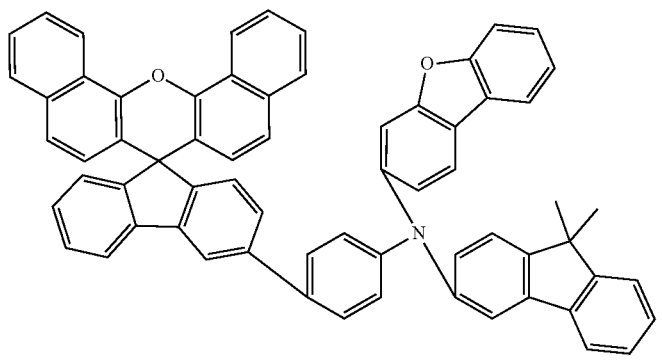
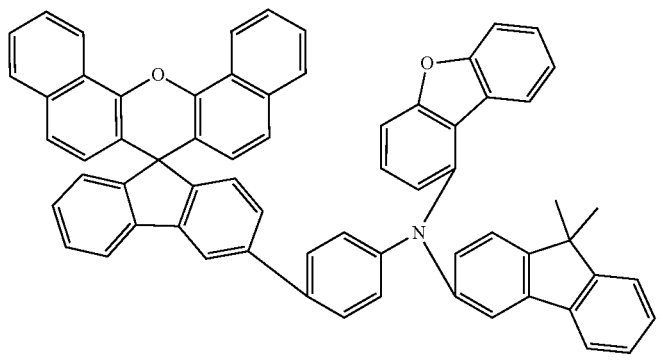
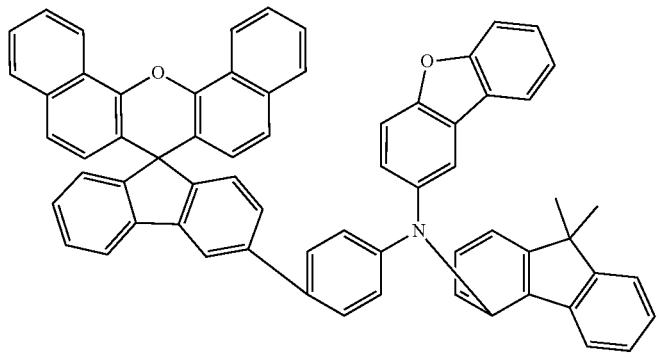
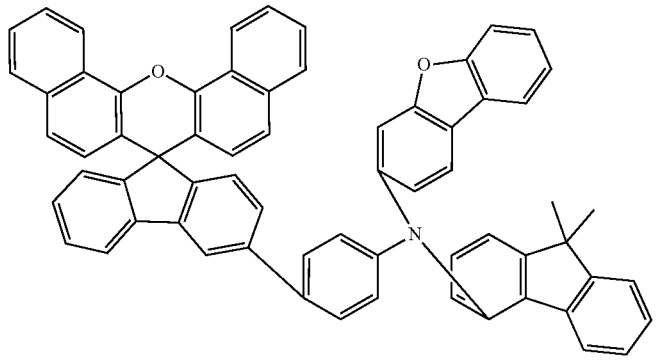

-continued
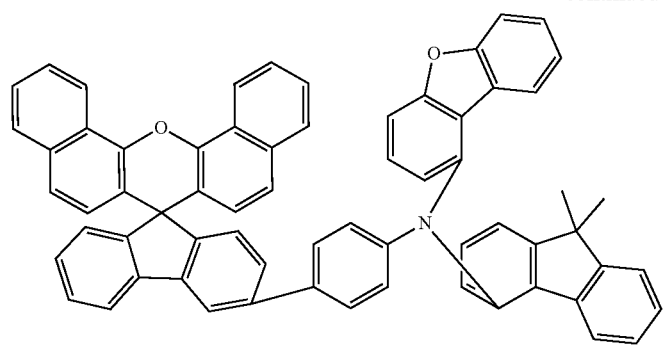
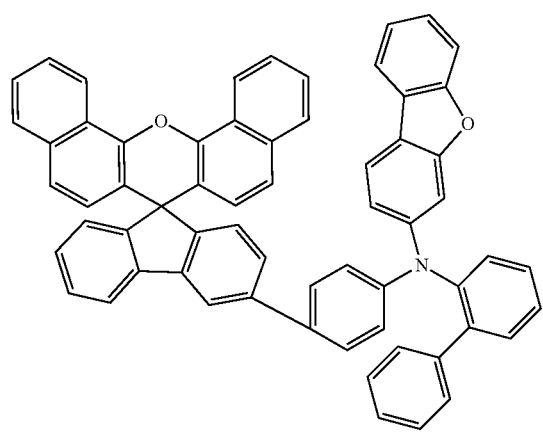
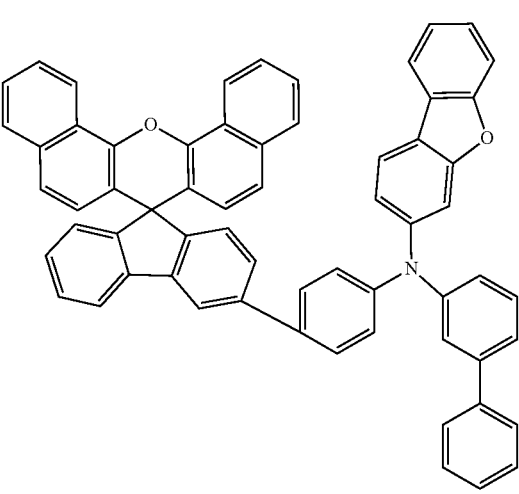
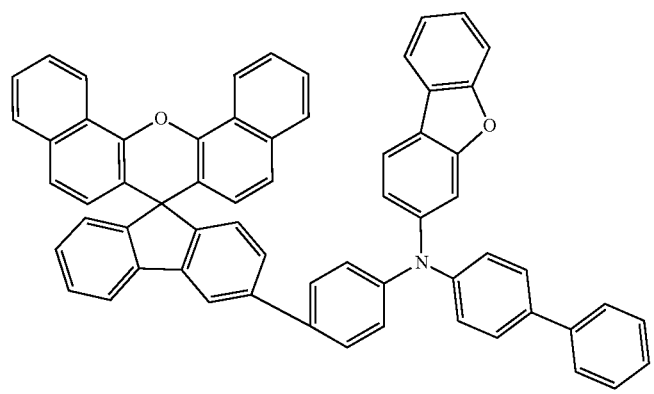

65
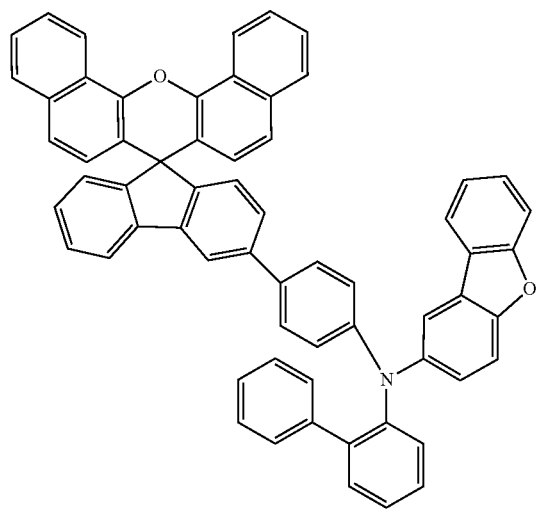
66
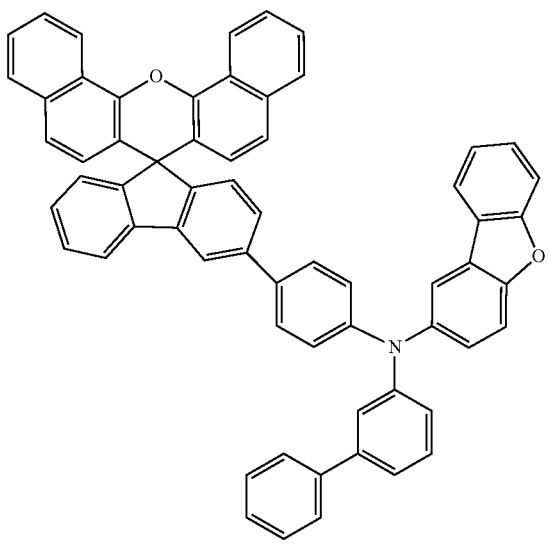
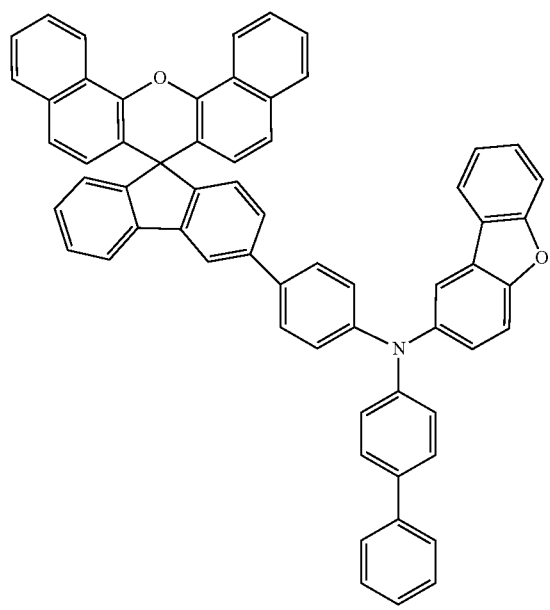
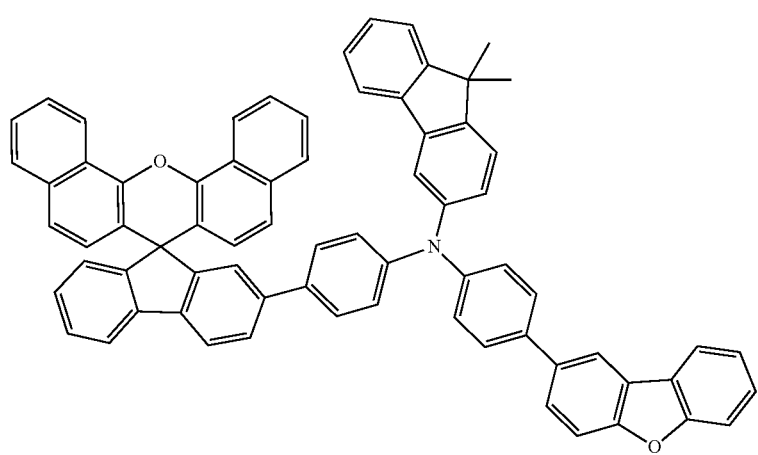

-continued
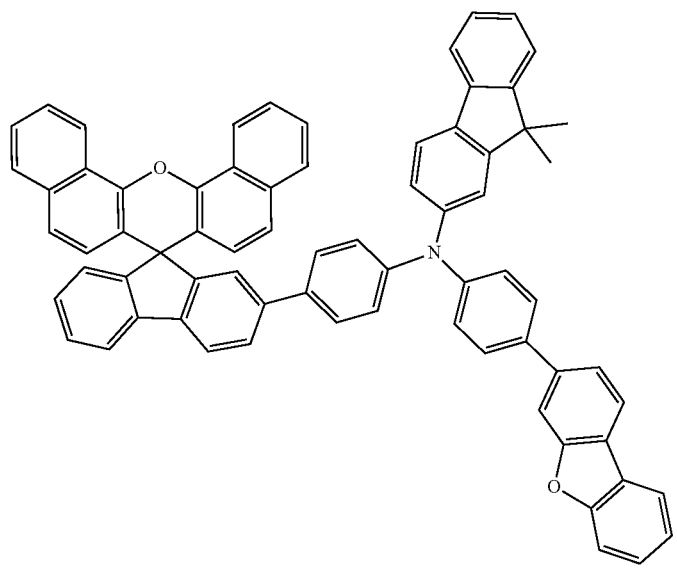
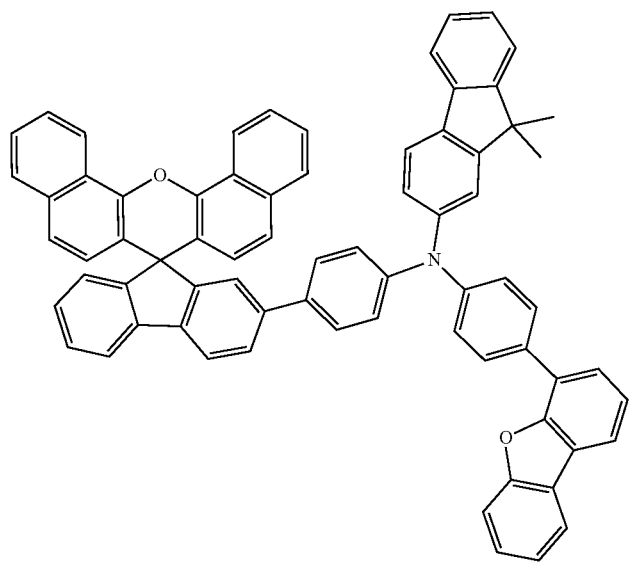
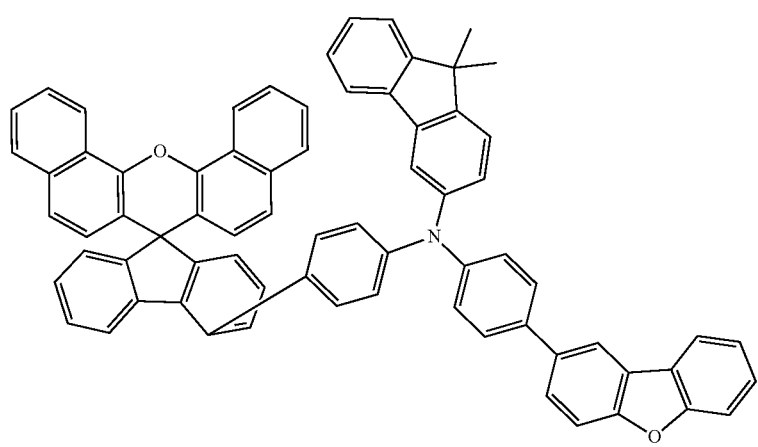

-continued
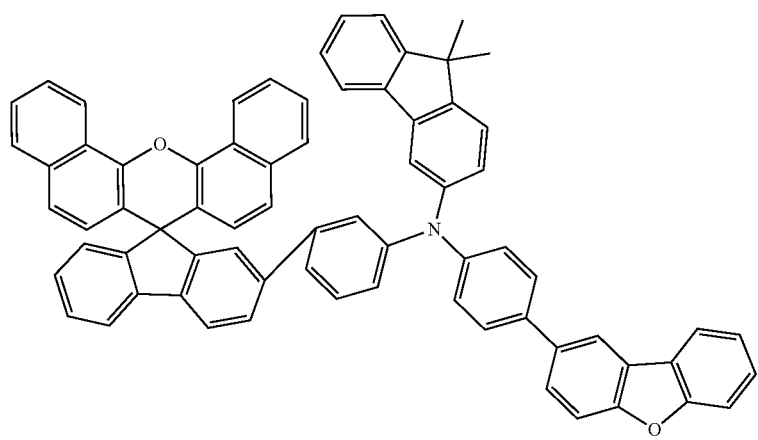
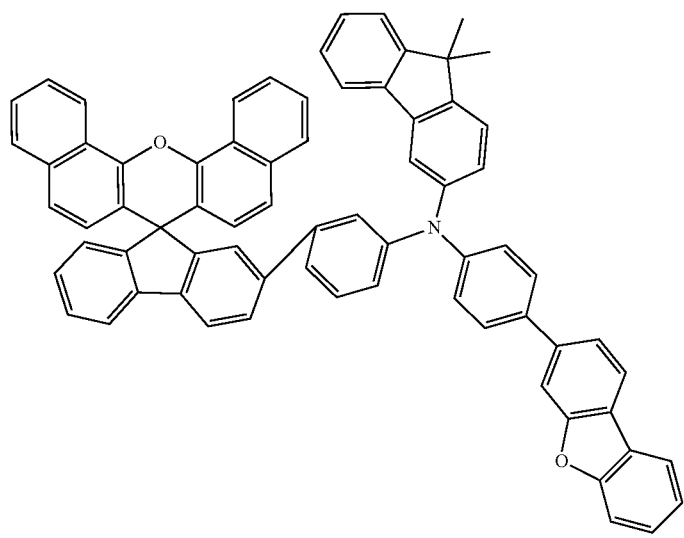
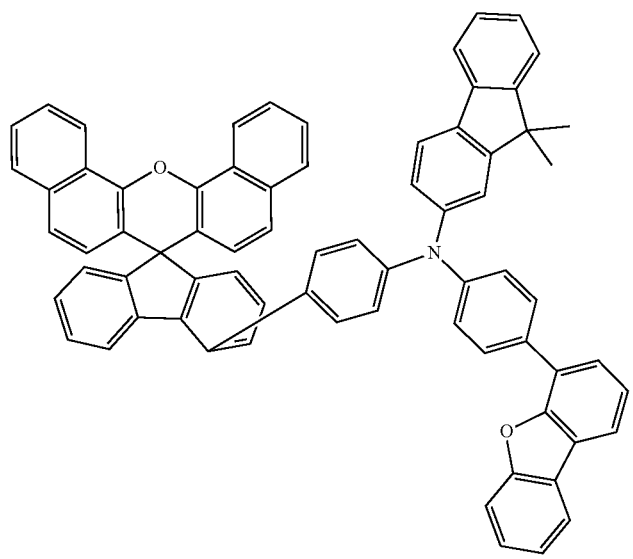

-continued
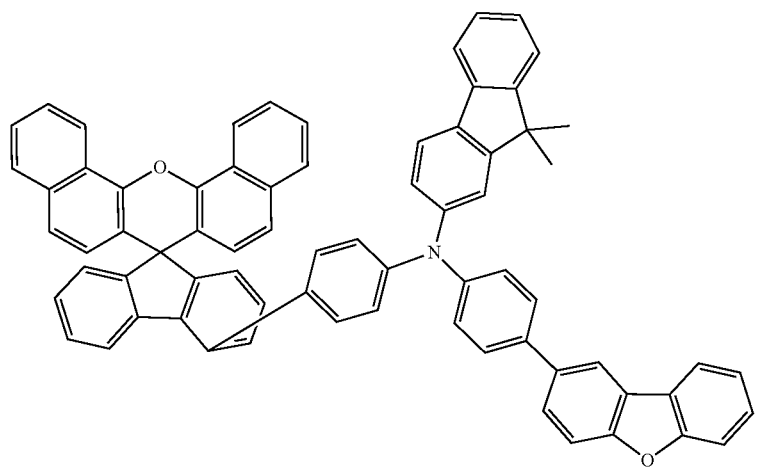
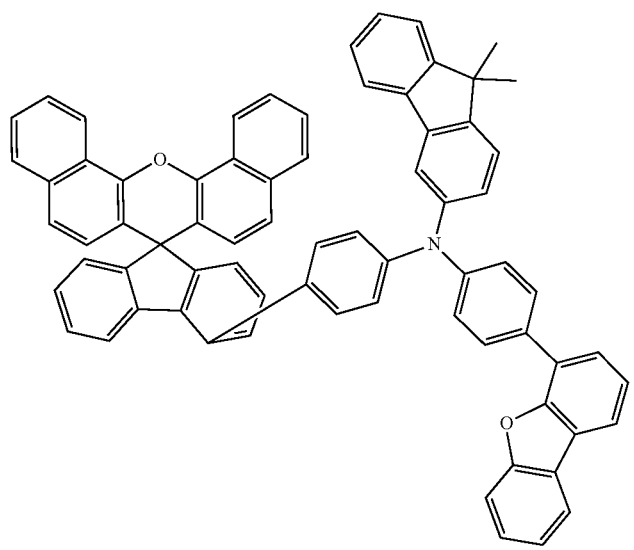
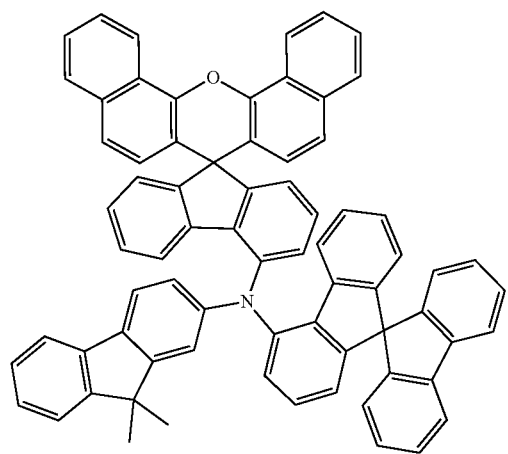
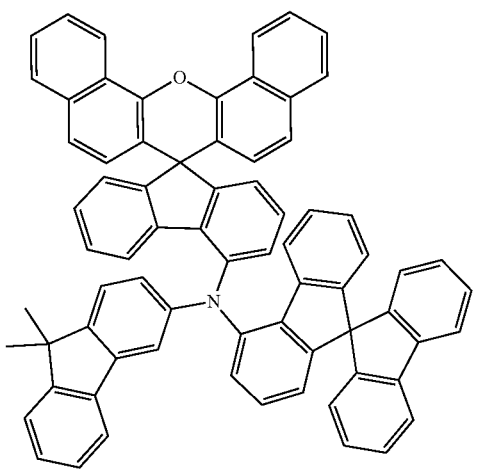

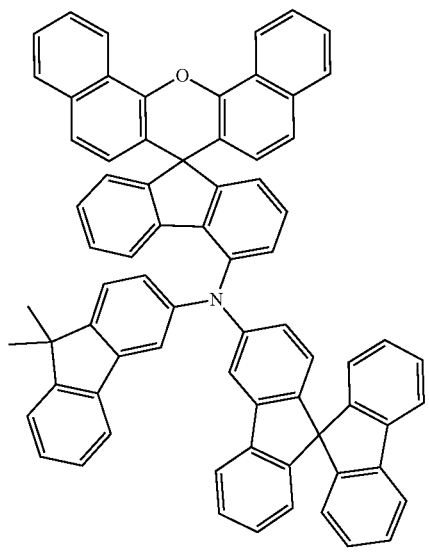
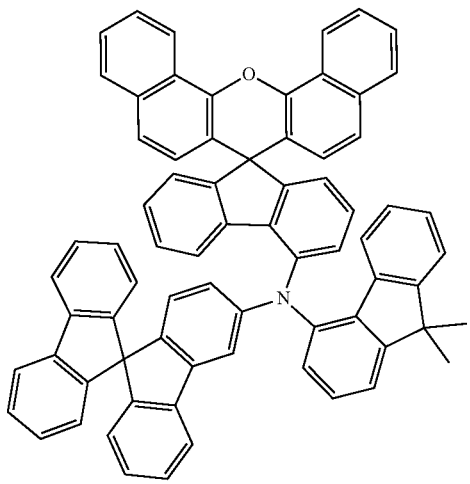
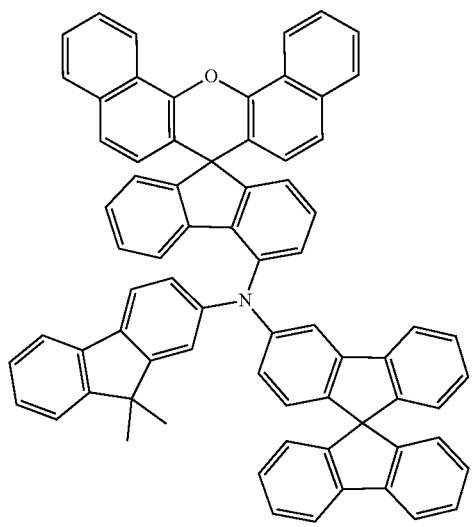
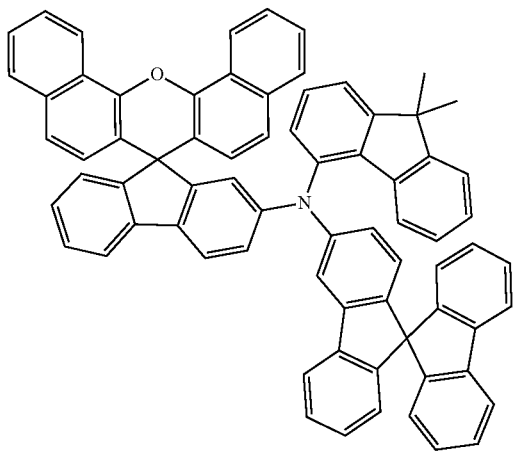
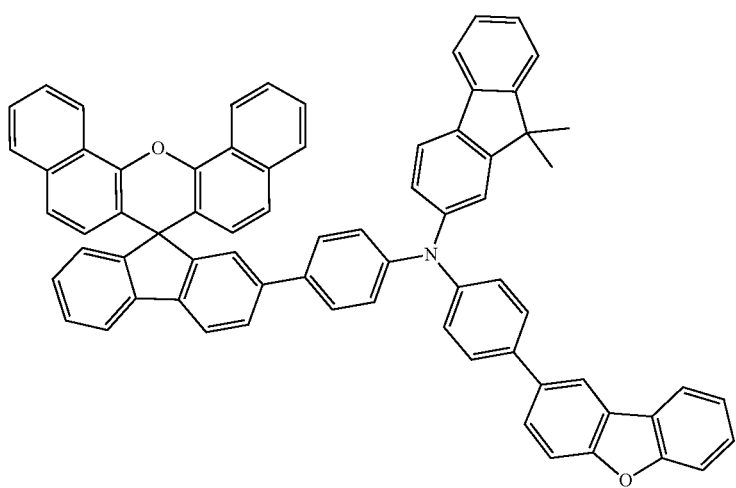

-continued
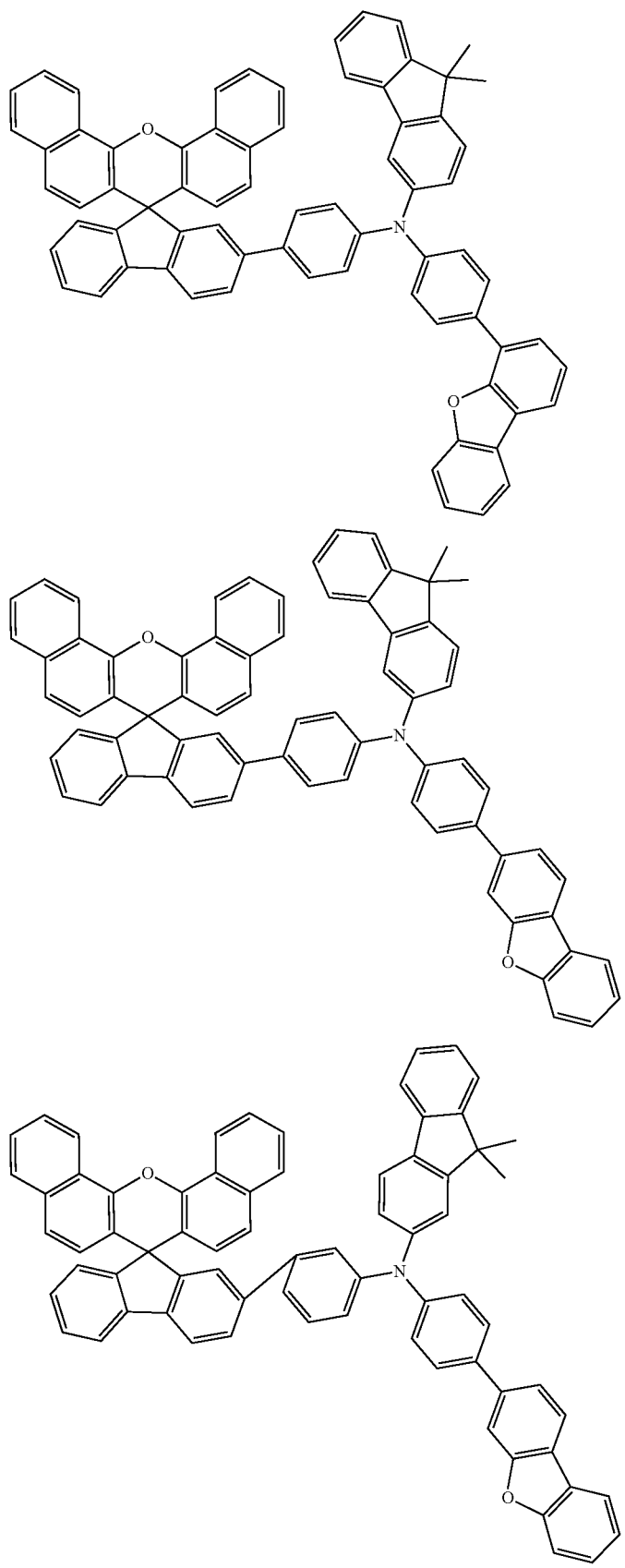

-continued
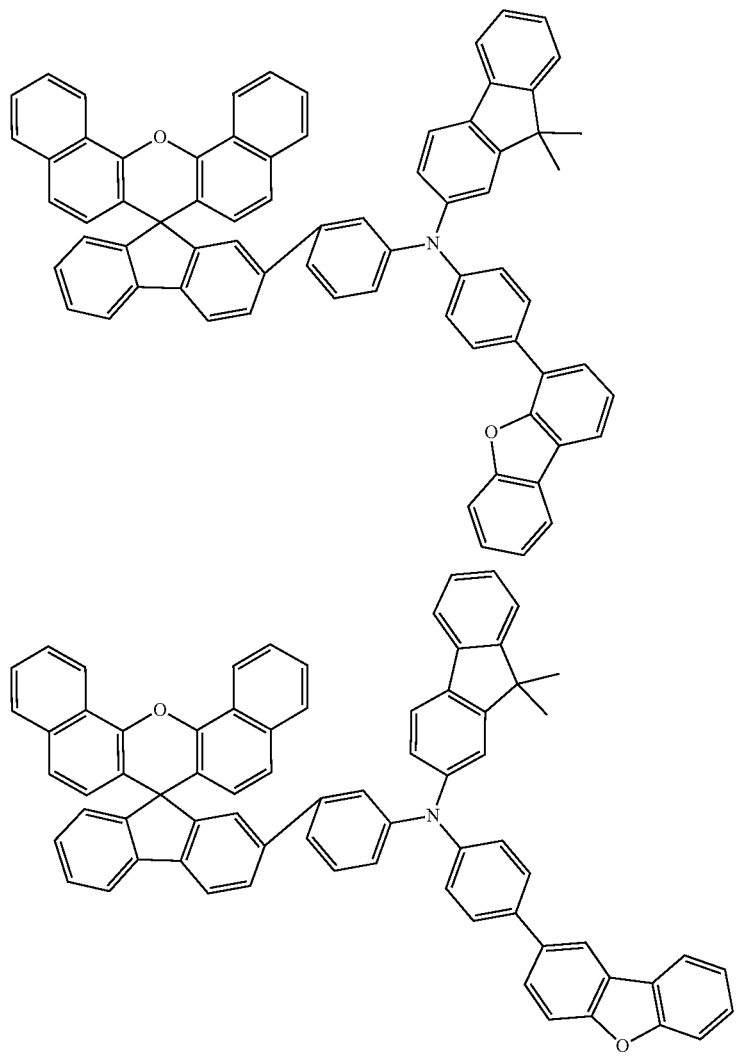
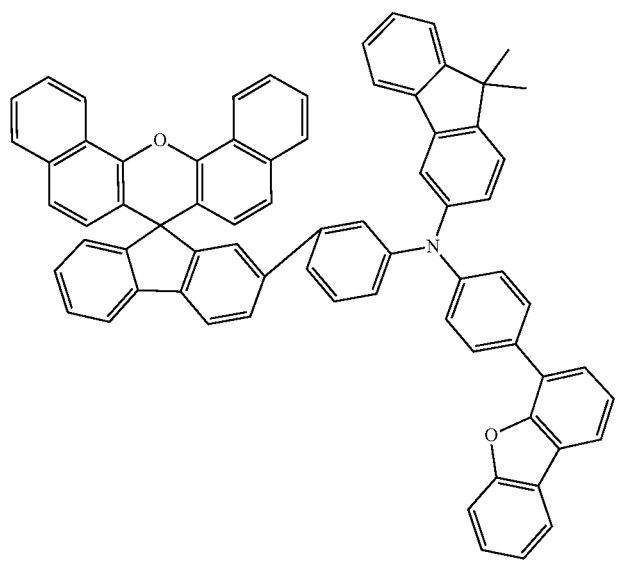

-continued
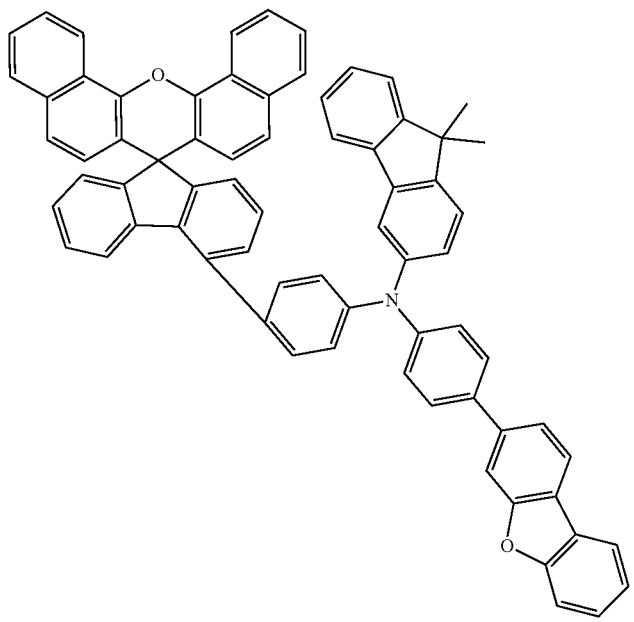
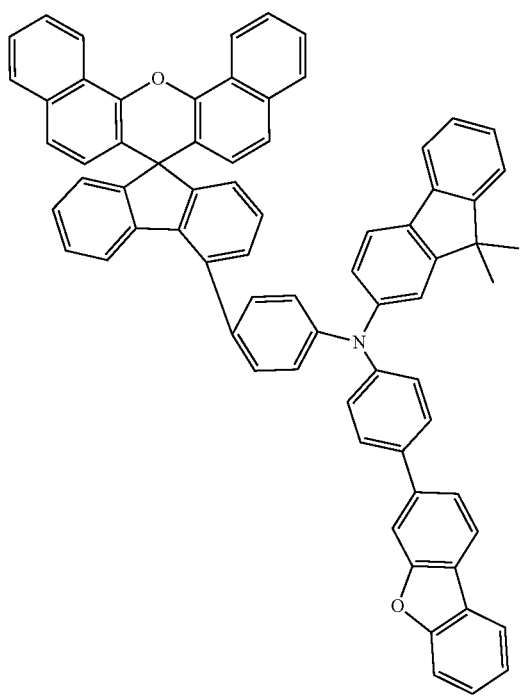
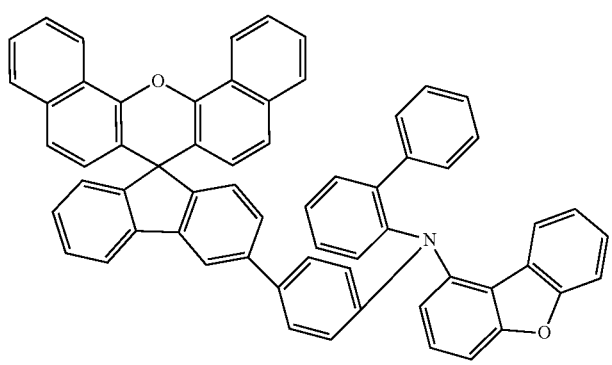

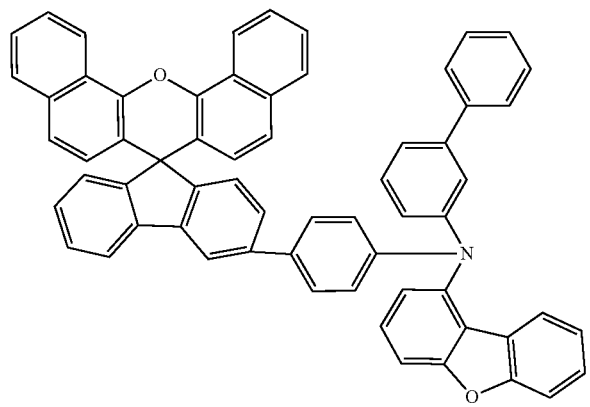
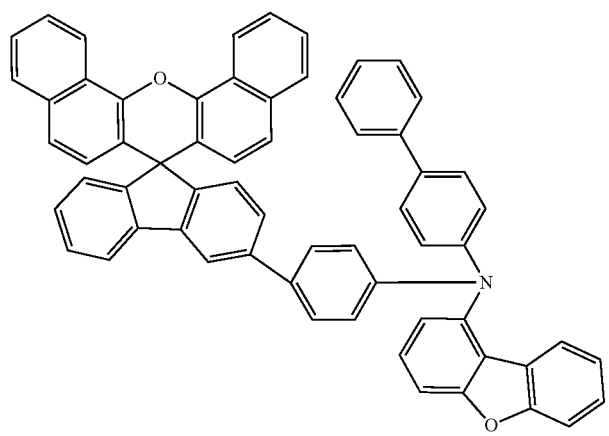
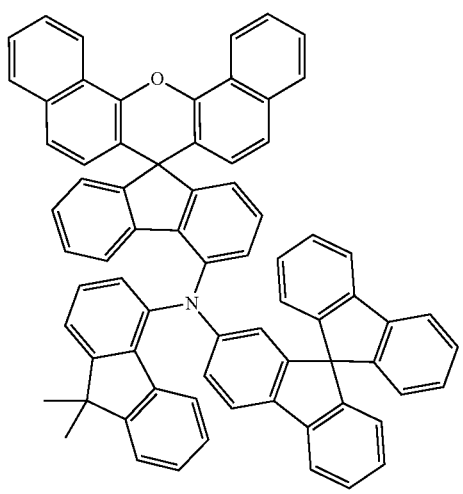
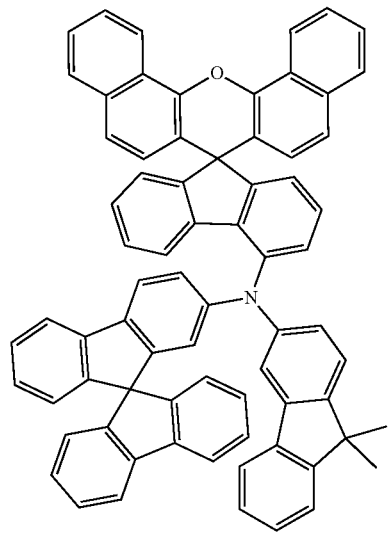
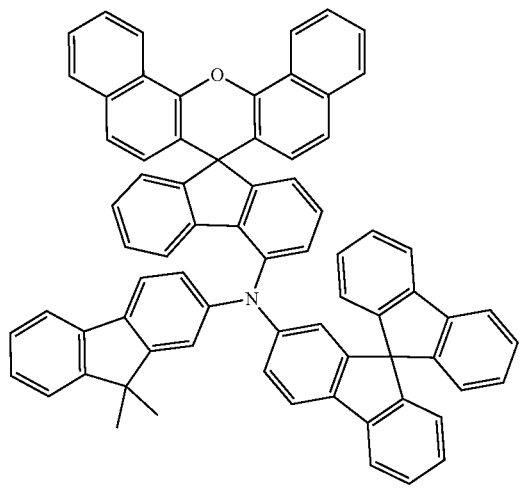

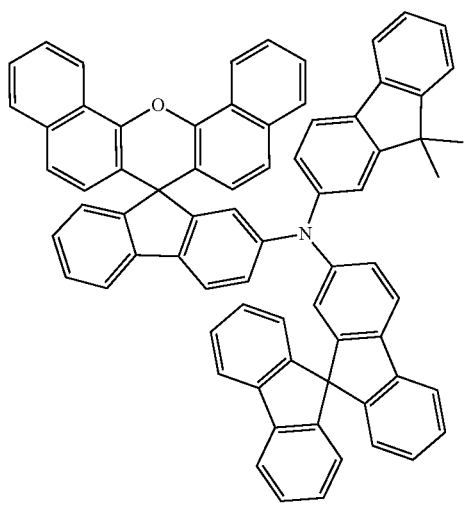
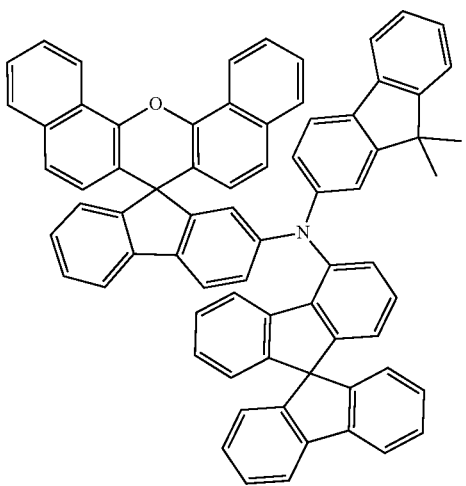
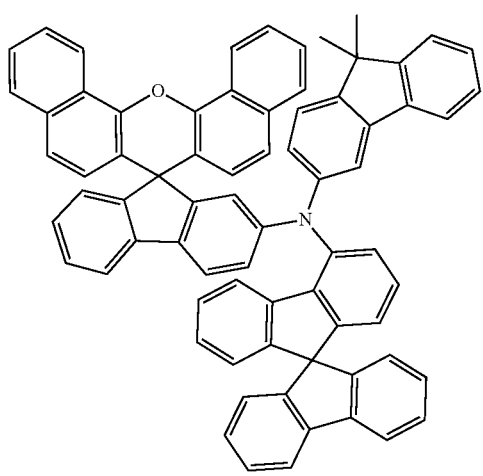
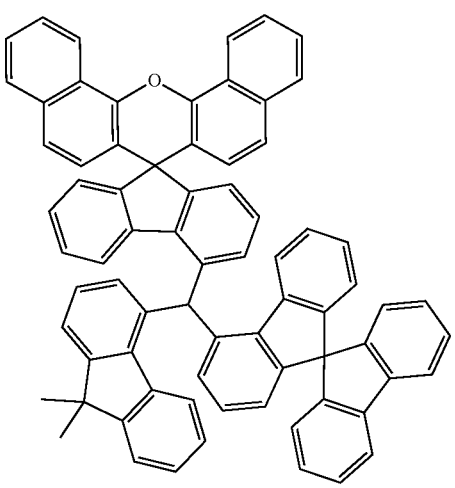
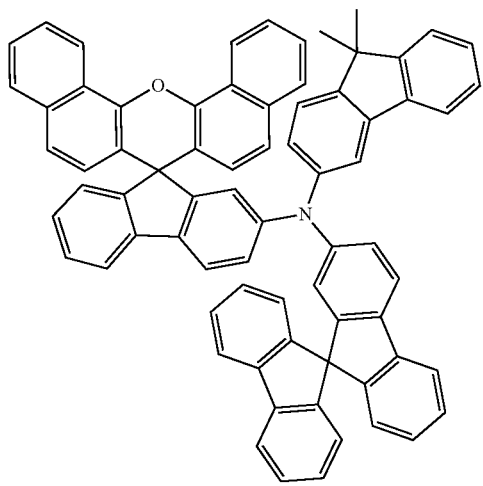
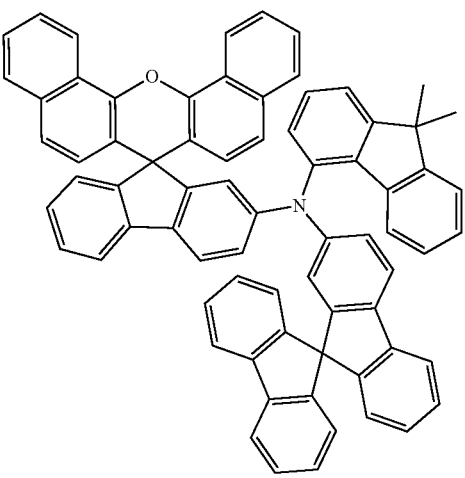

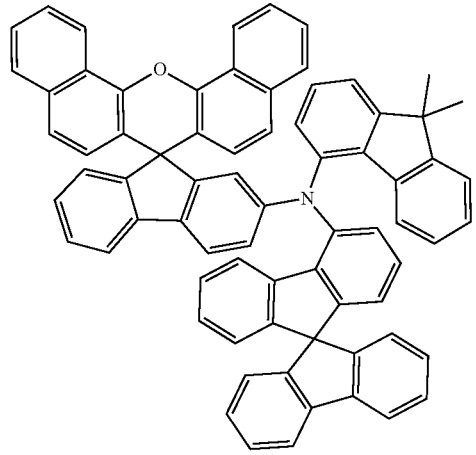
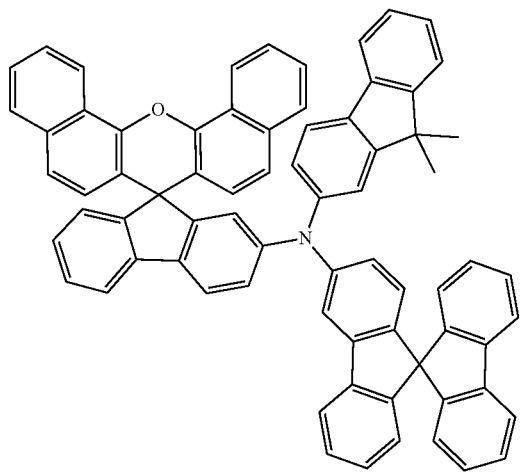
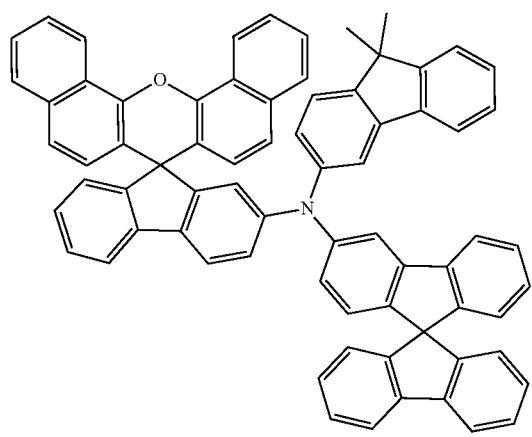
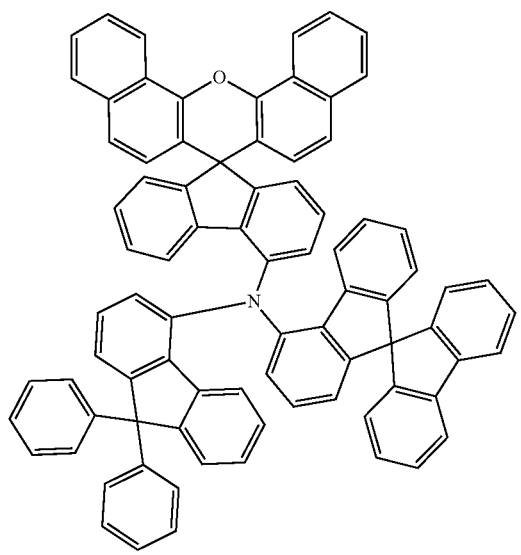
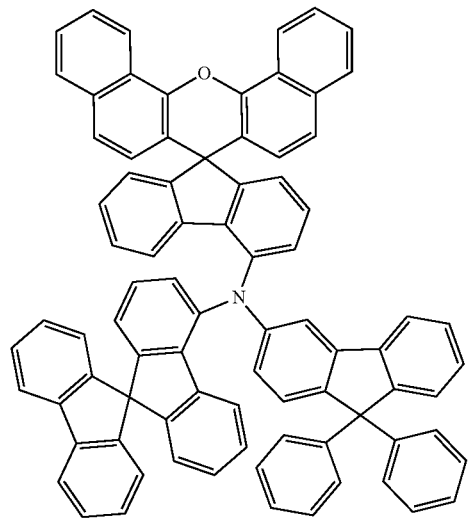
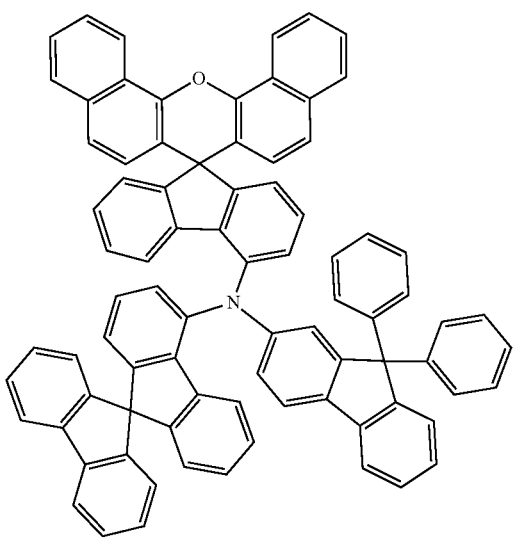

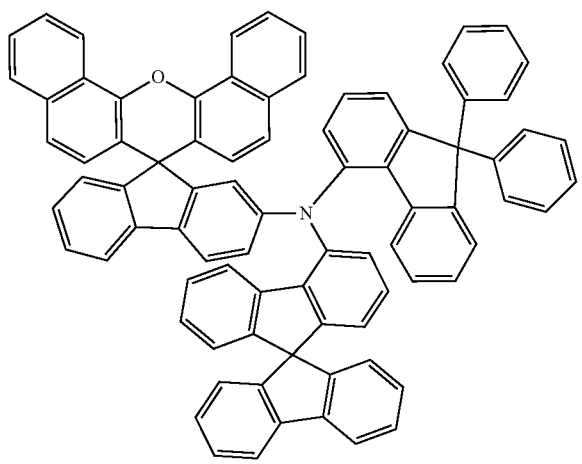
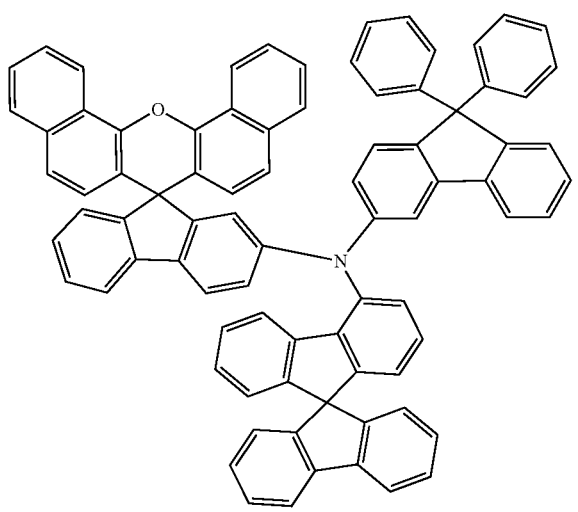
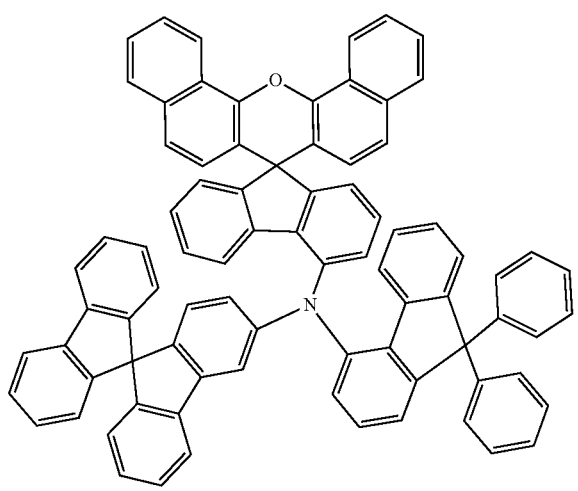
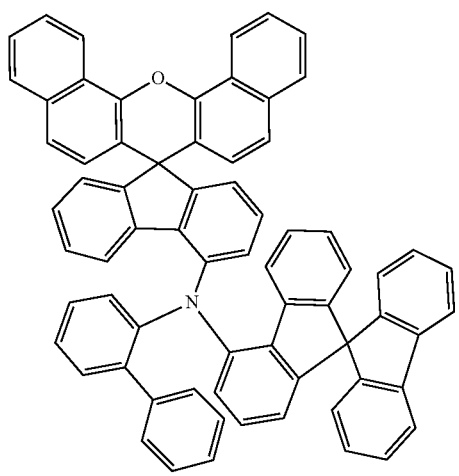
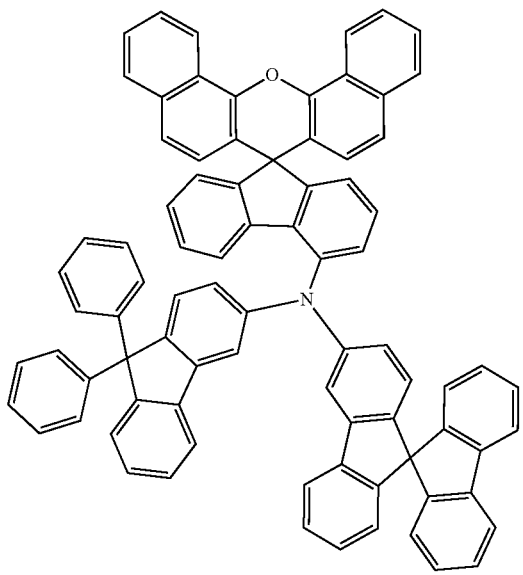

-continued
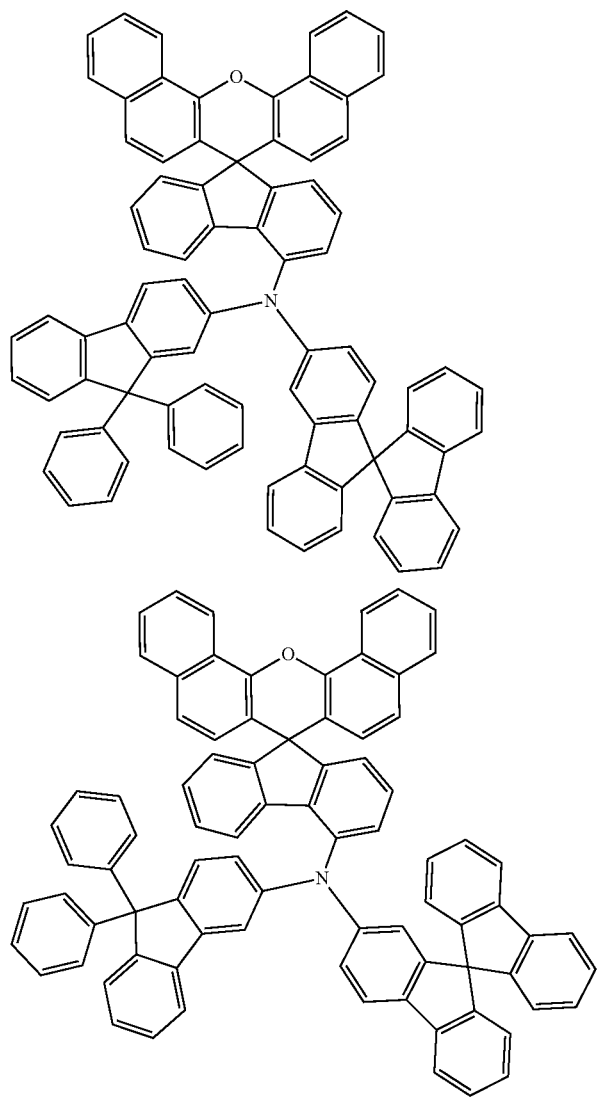
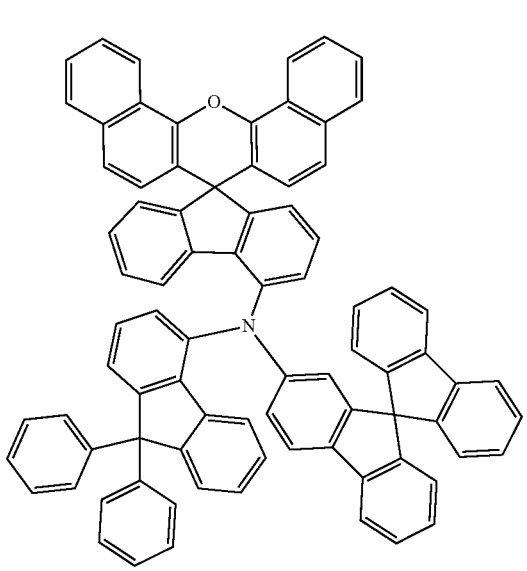
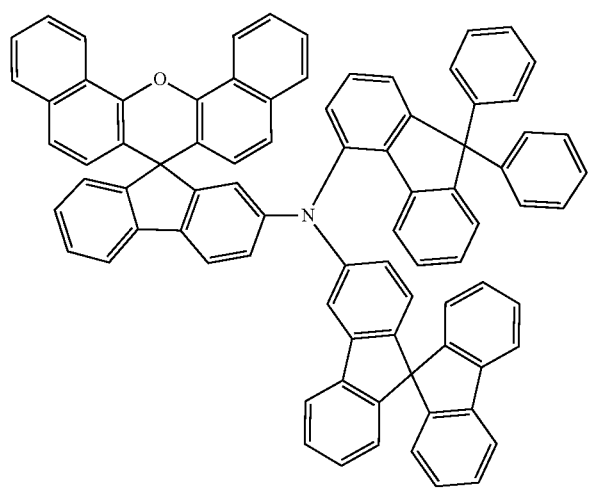

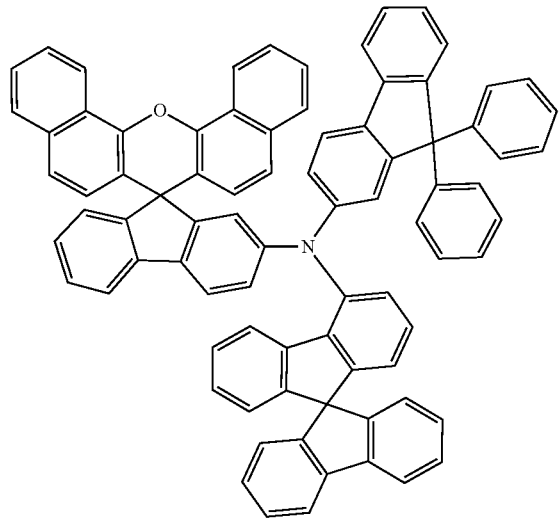
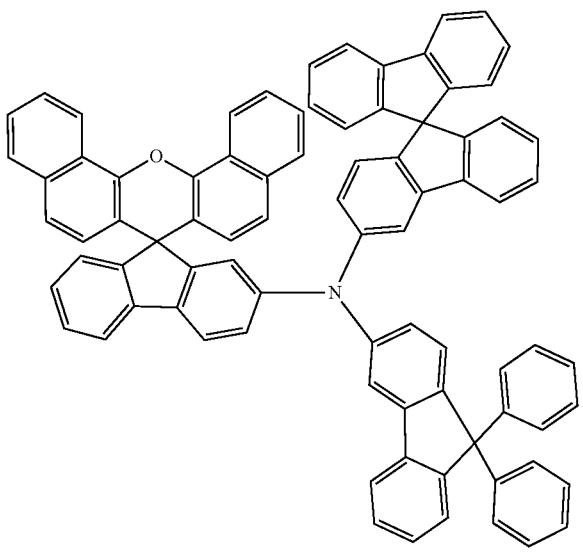
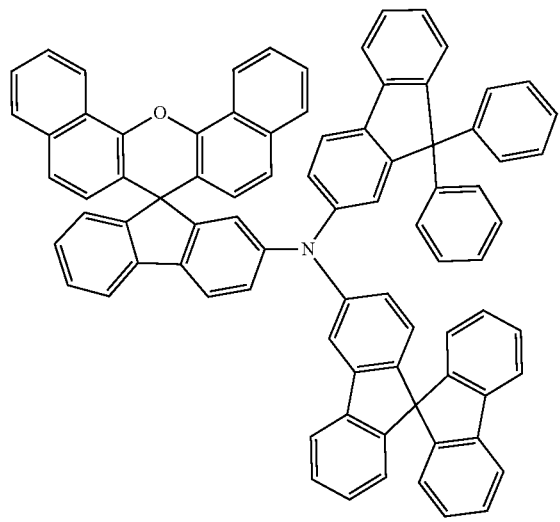
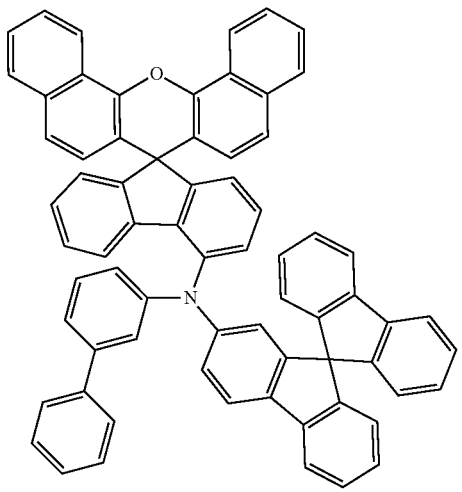
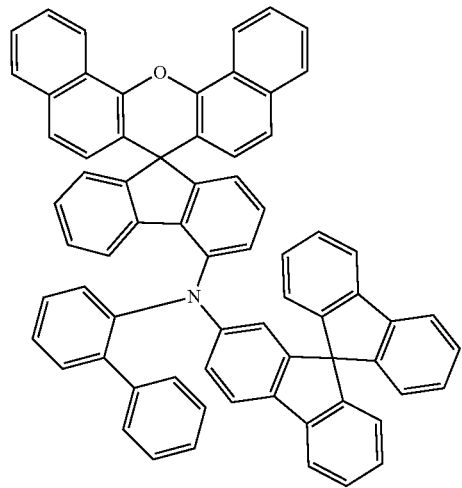
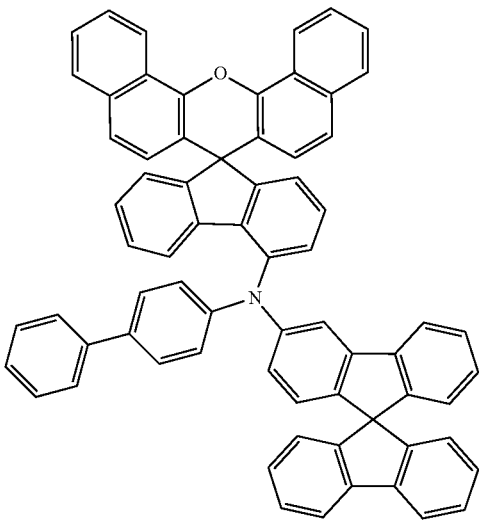

-continued
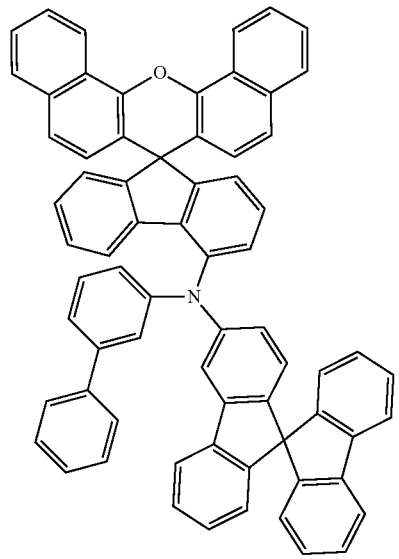
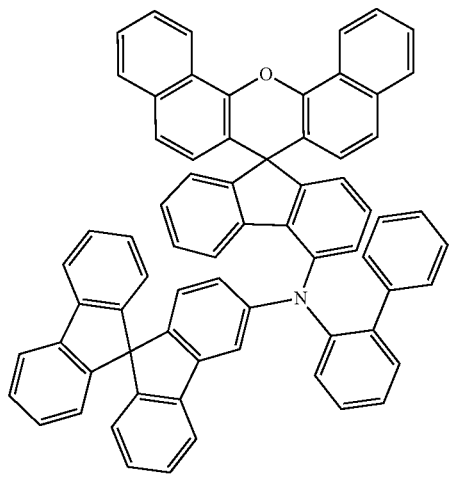
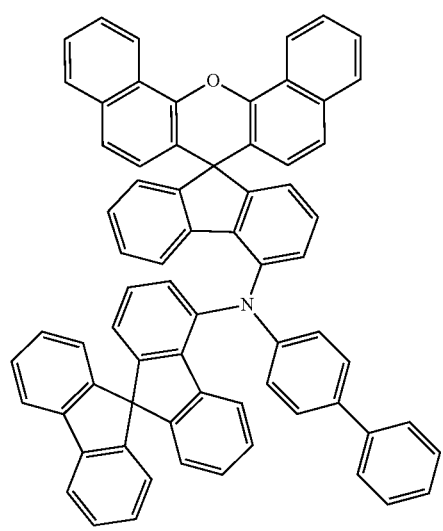
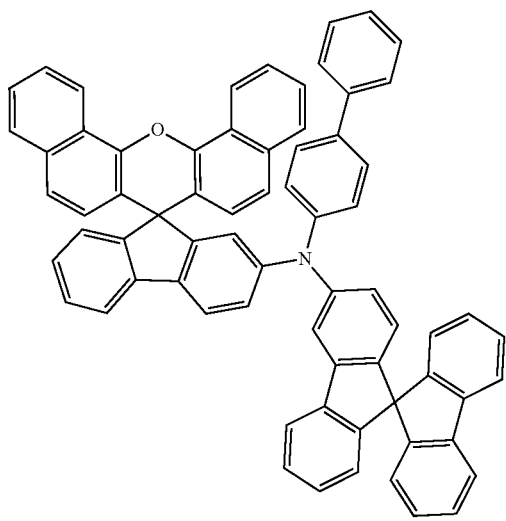
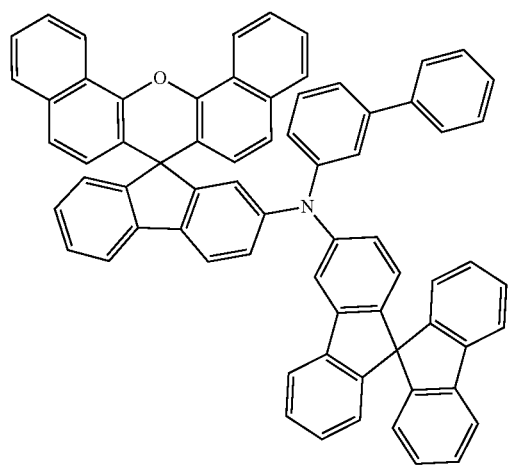
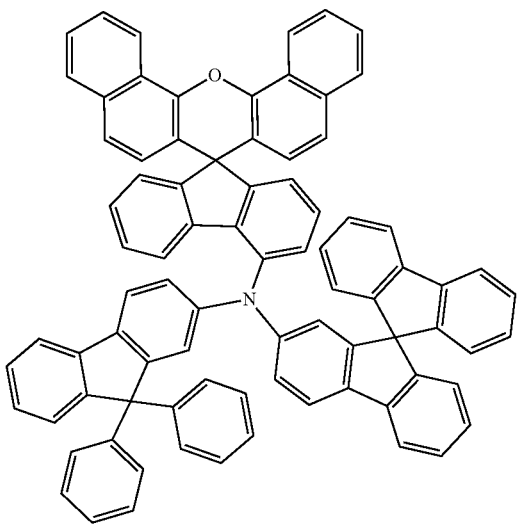

-continued
95
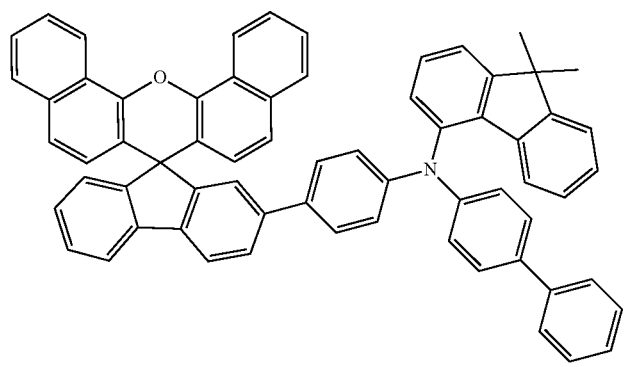
96
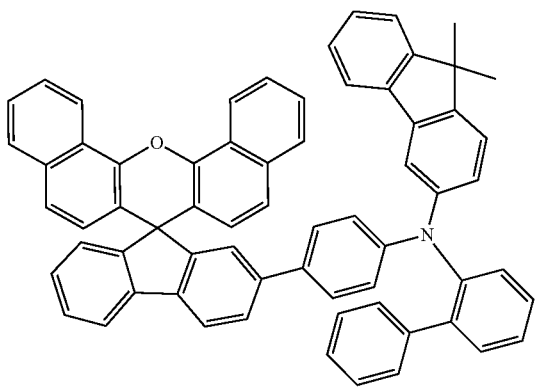
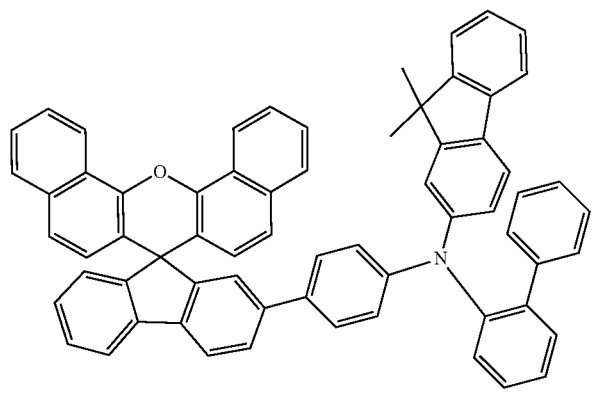
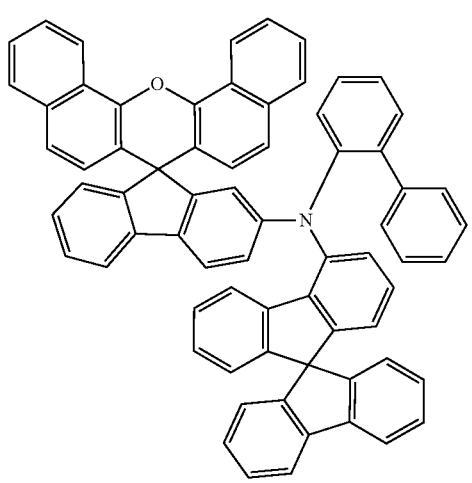
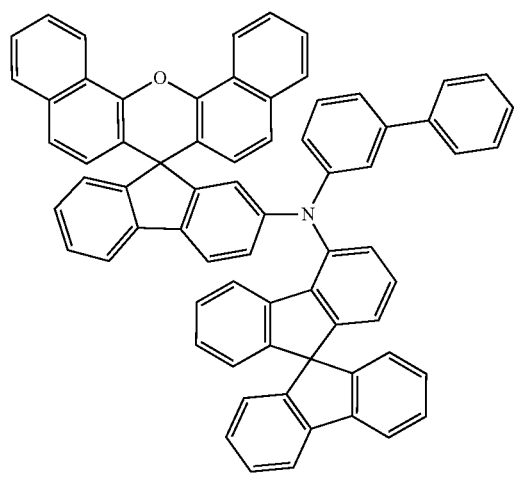
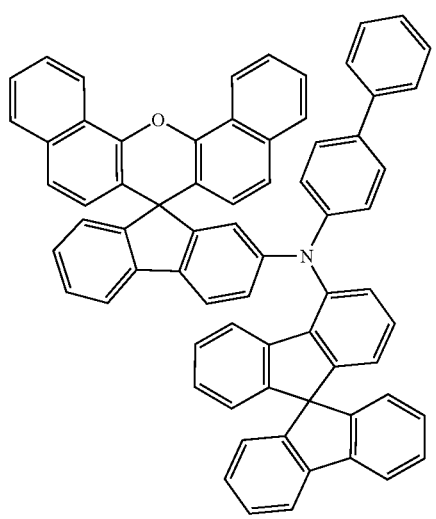

-continued
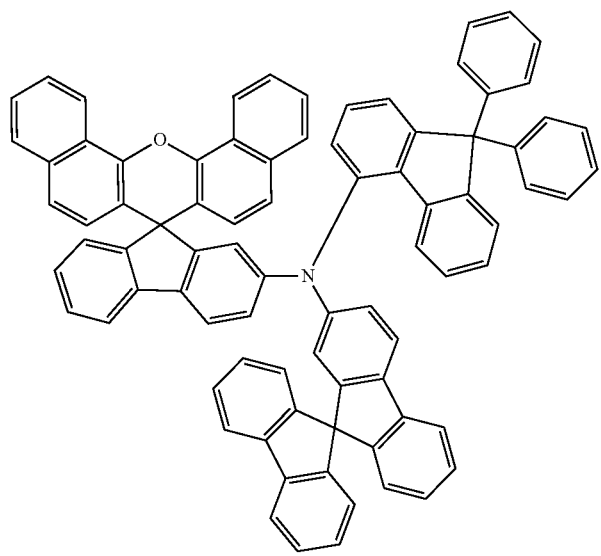
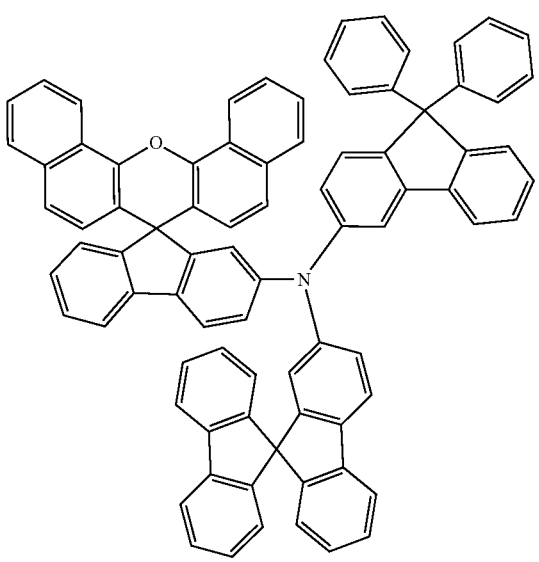
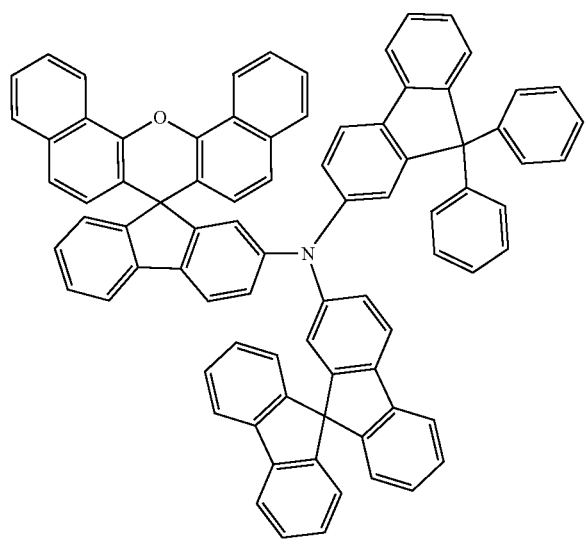
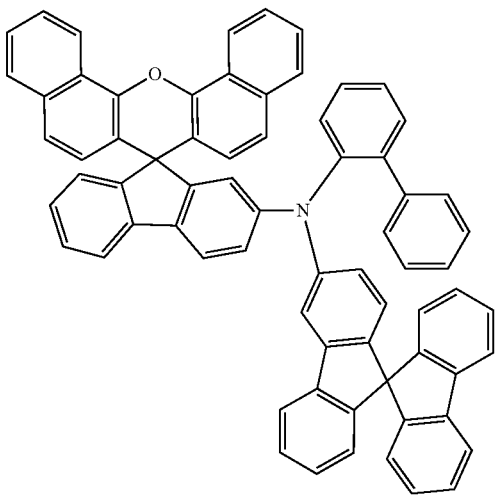
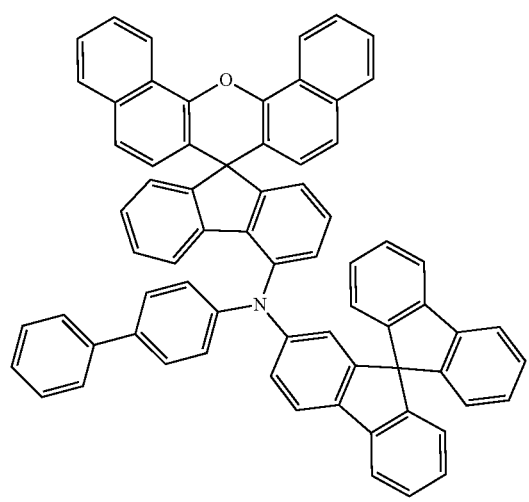
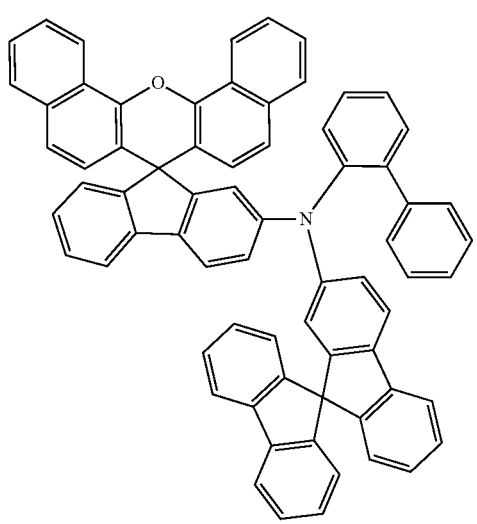

-continued
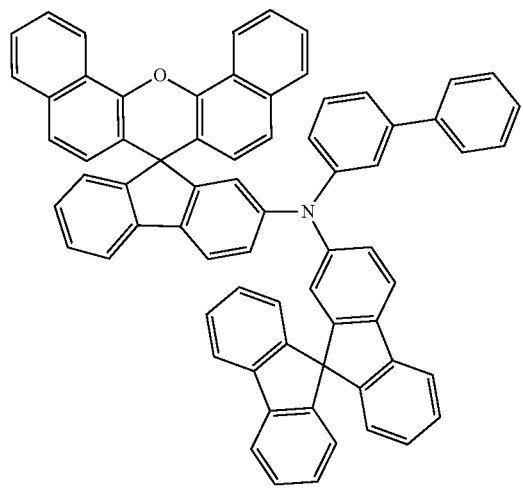
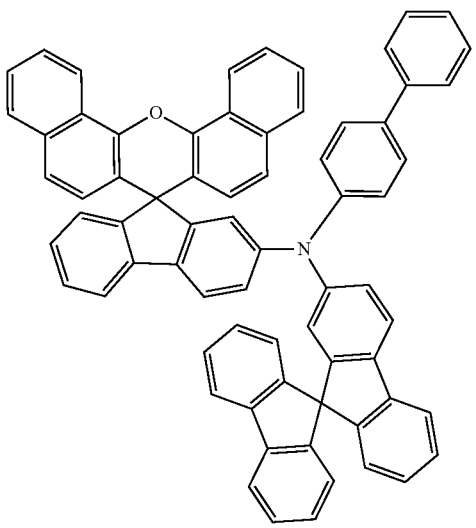
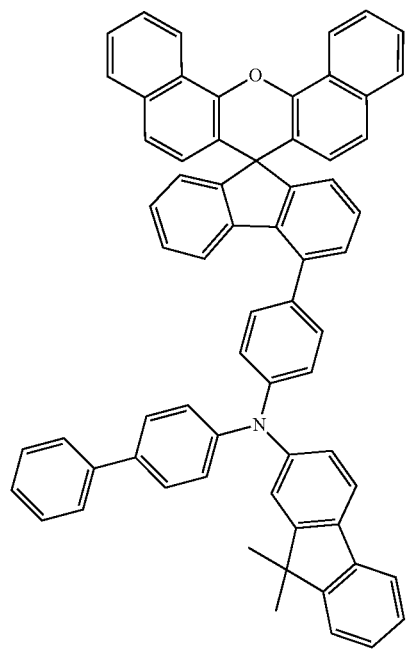
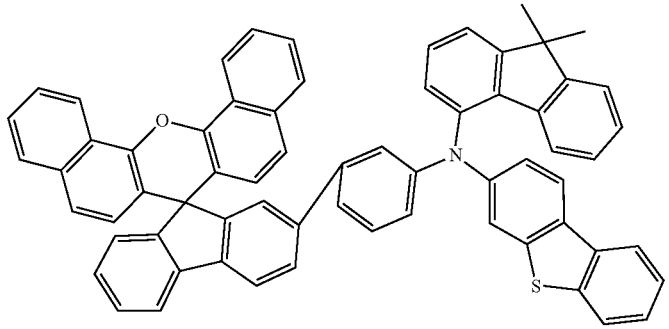
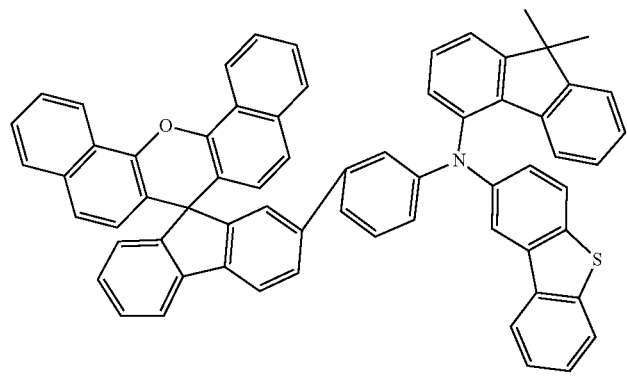

-continued
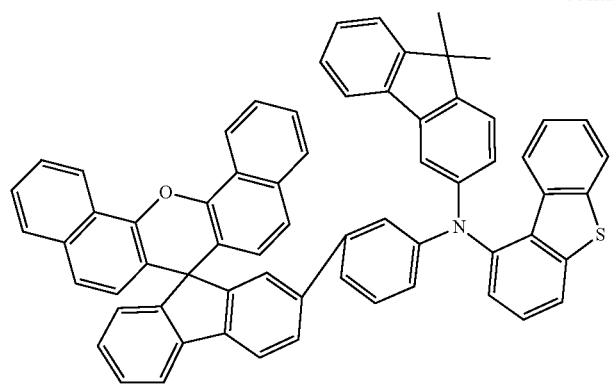
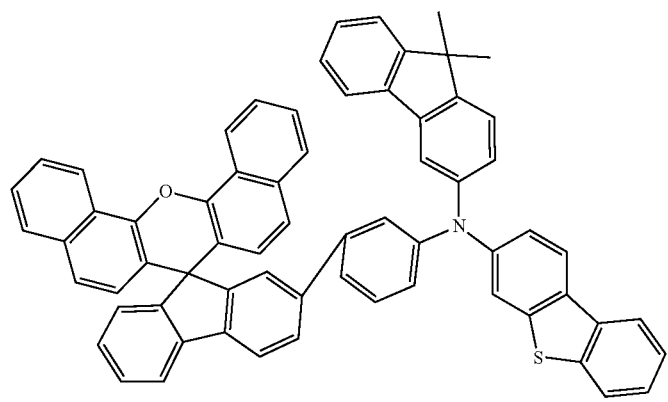
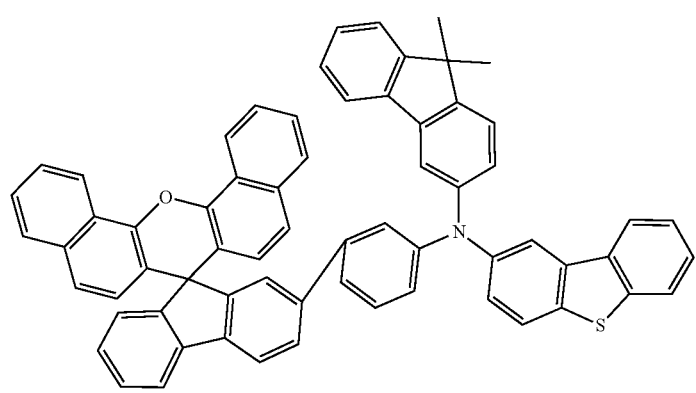
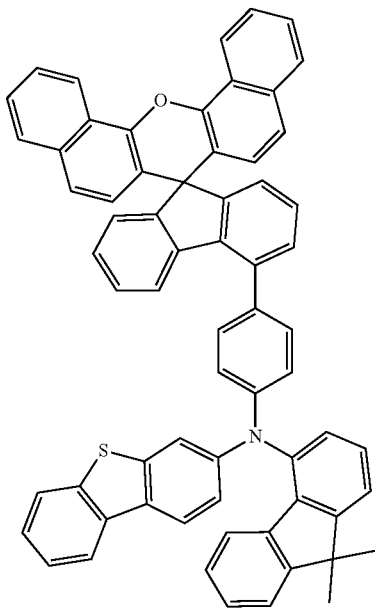

-continued
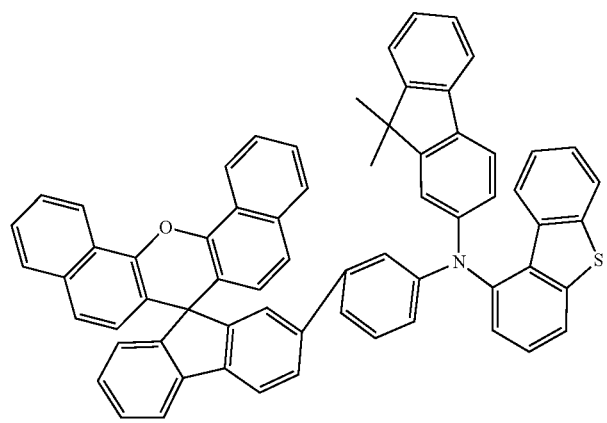
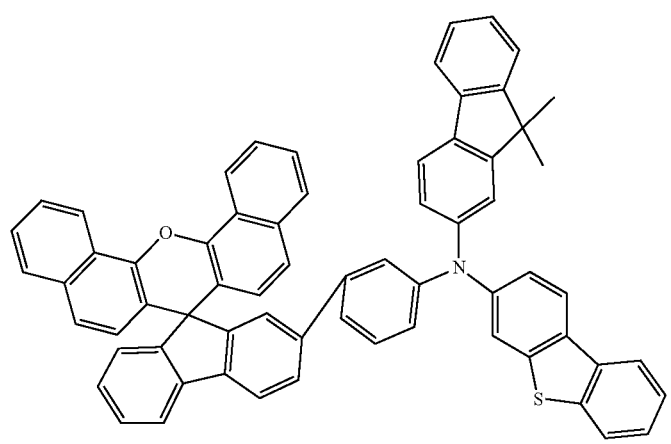
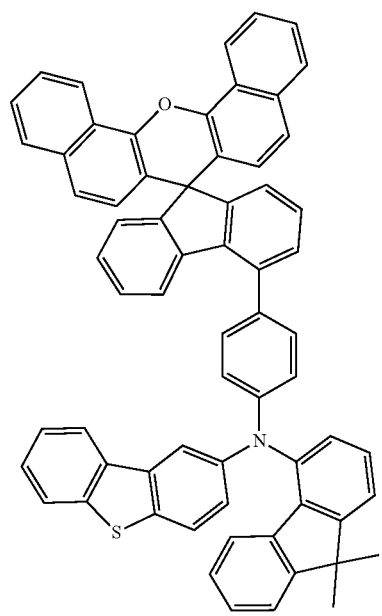
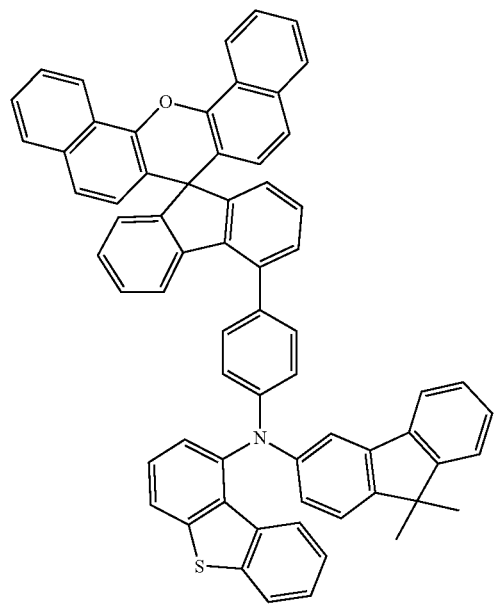
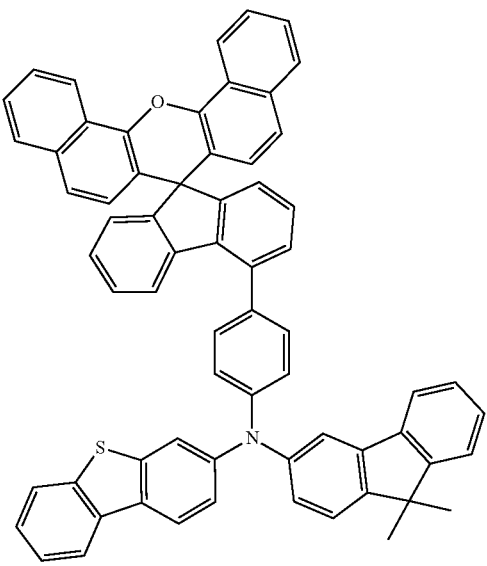

105
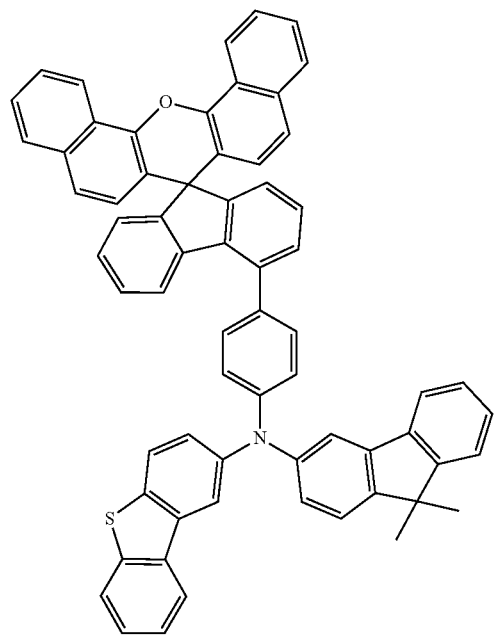
106
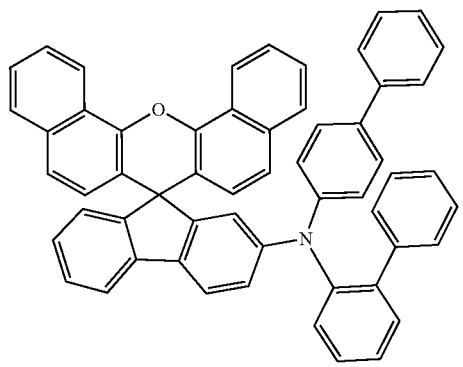
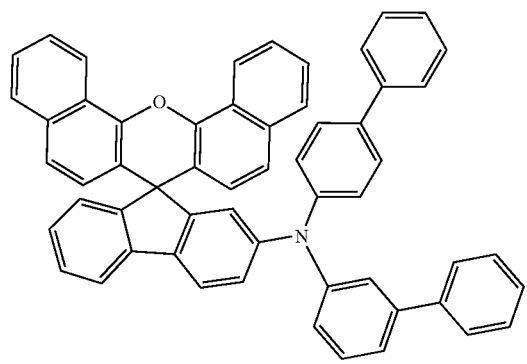
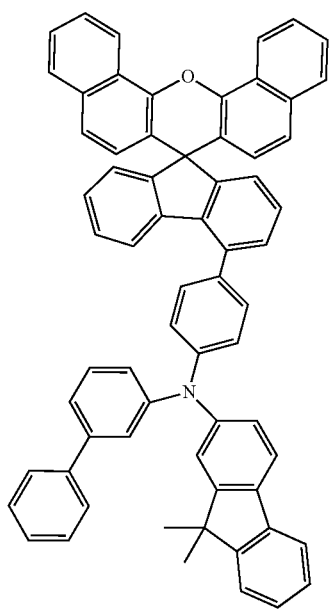

-continued
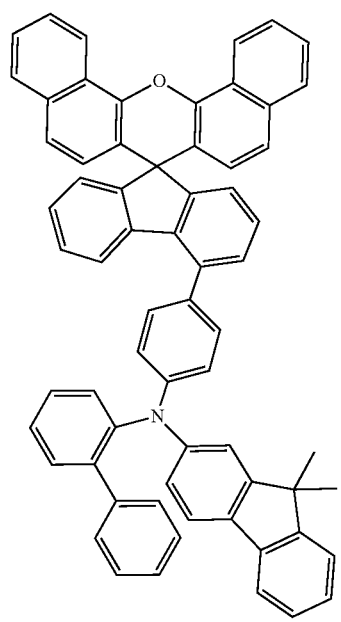
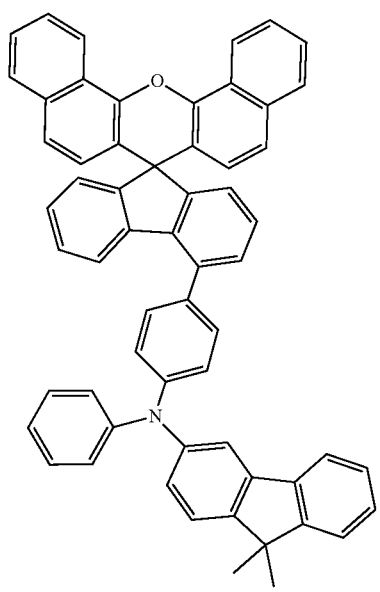
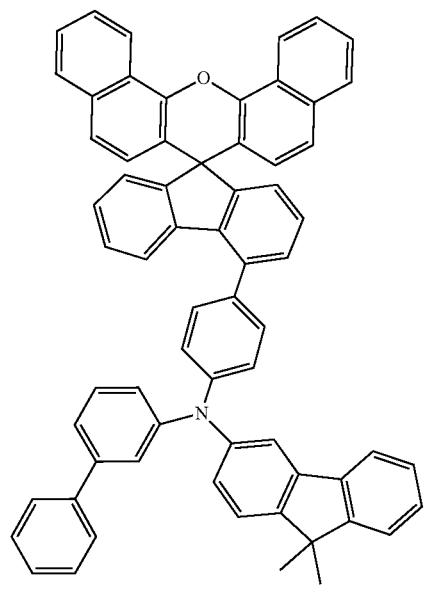
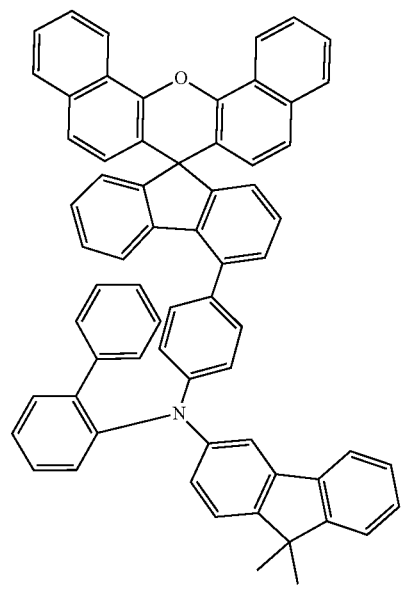

-continued
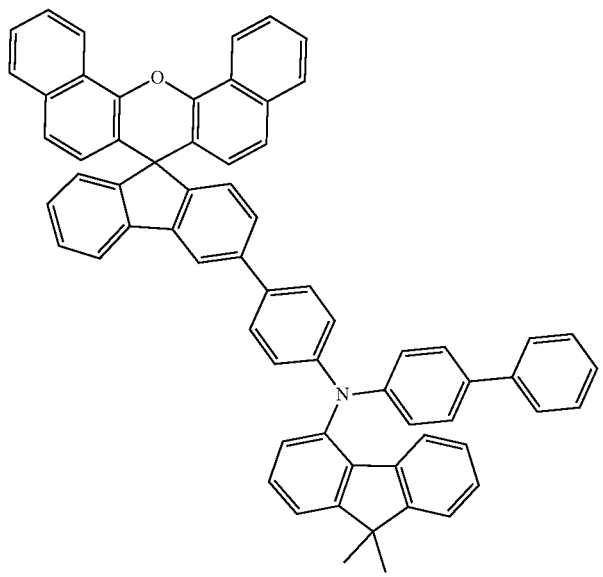
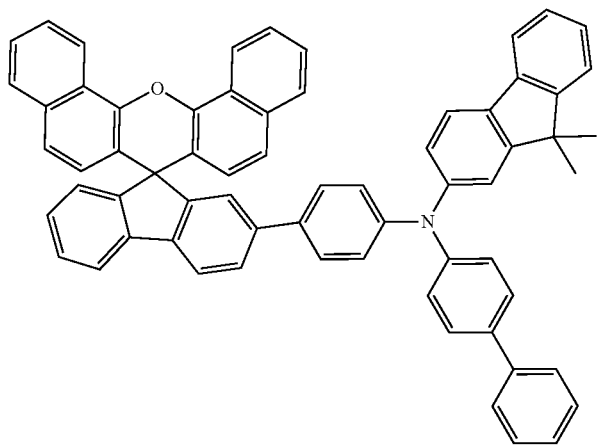
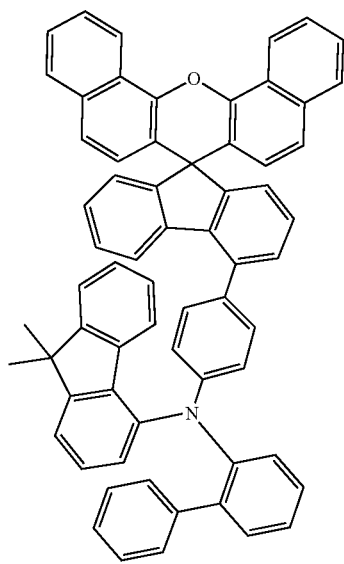
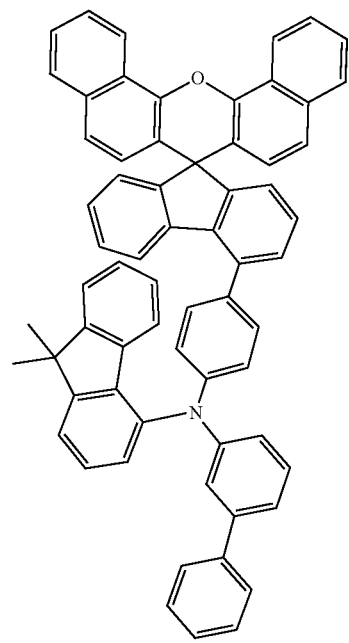

-continued
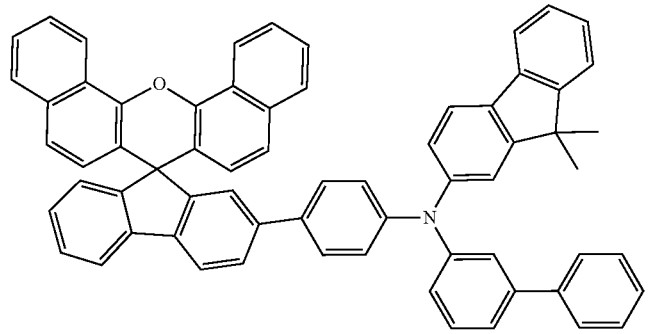
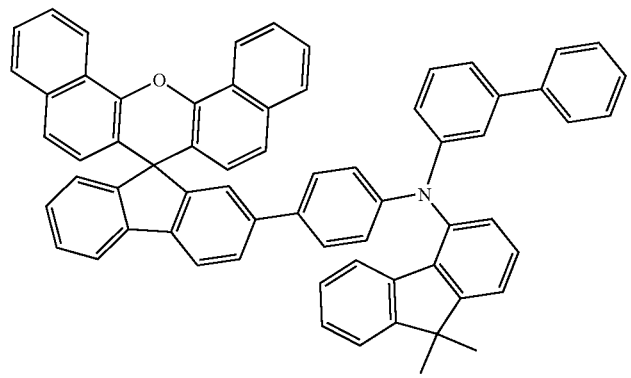
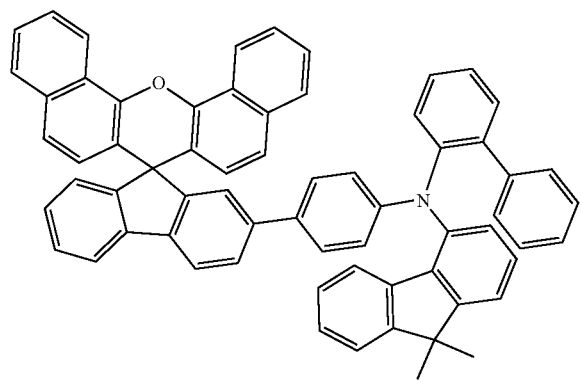
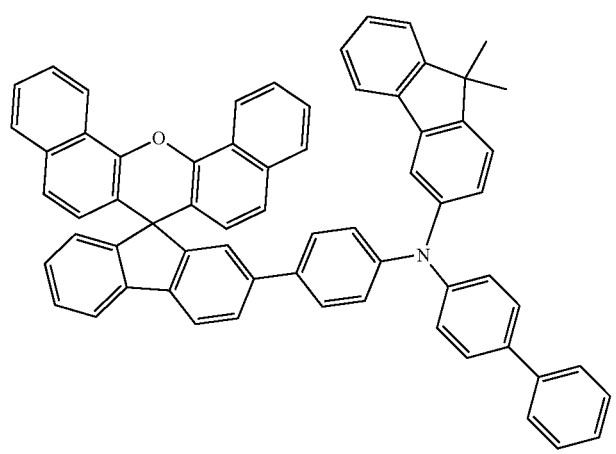

-continued
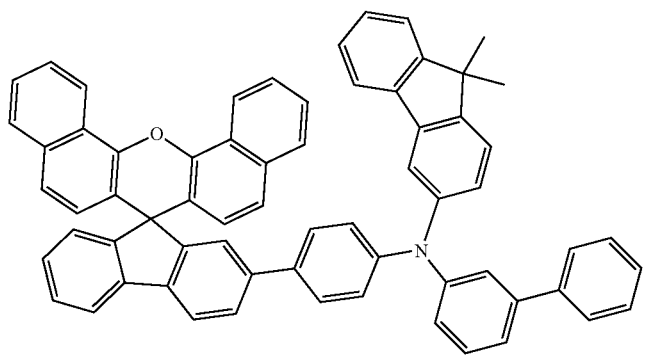
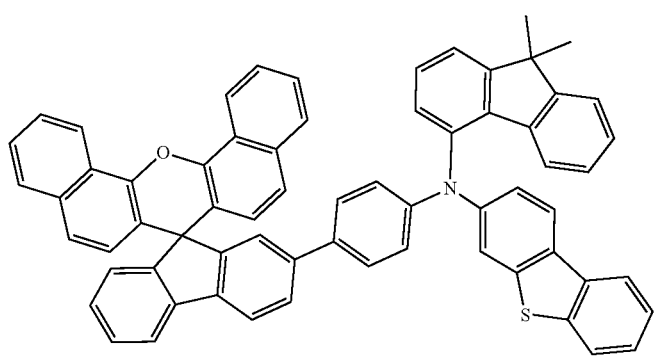
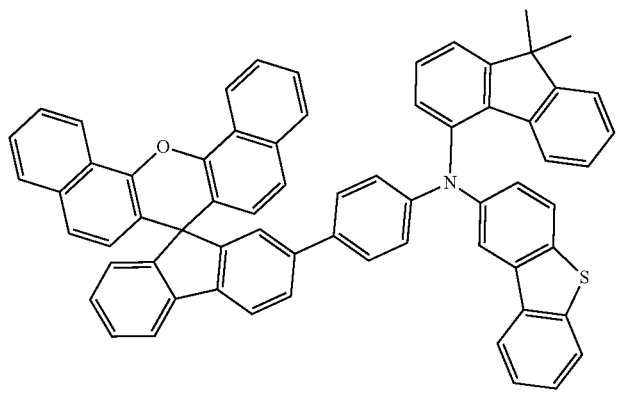
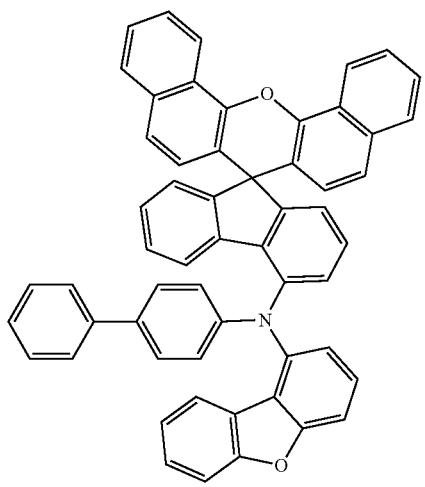
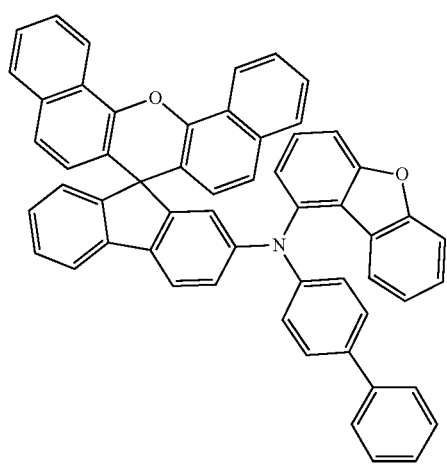
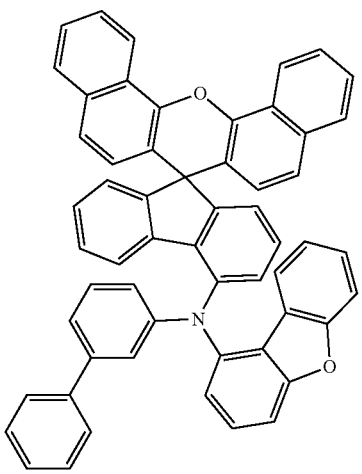

-continued
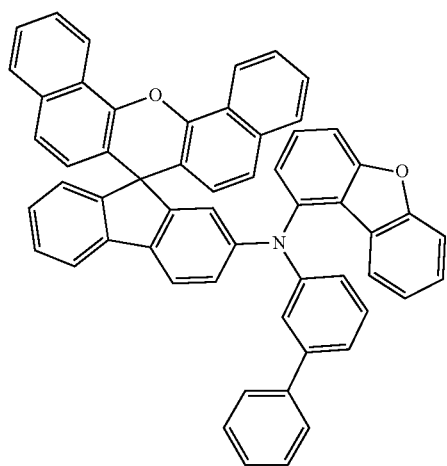
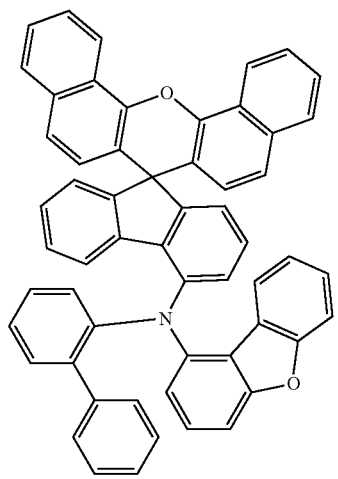
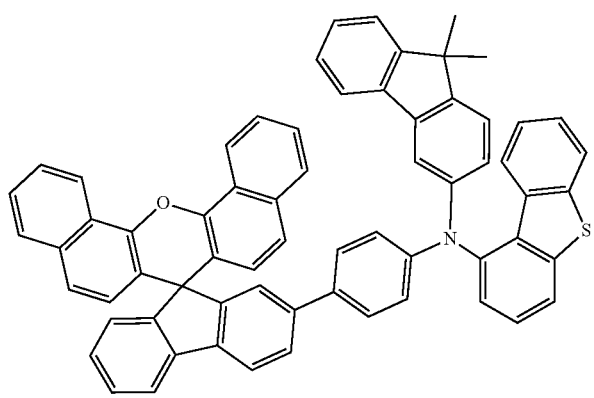
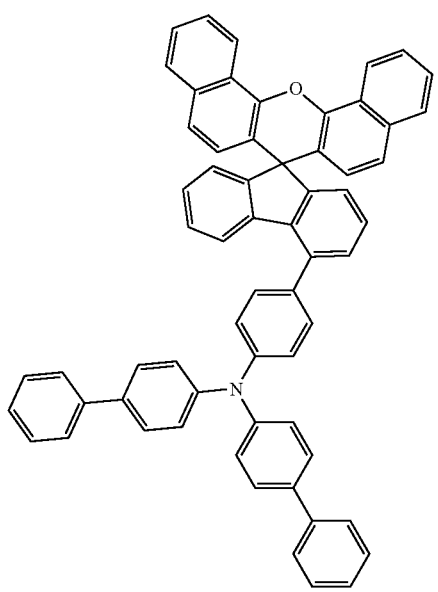
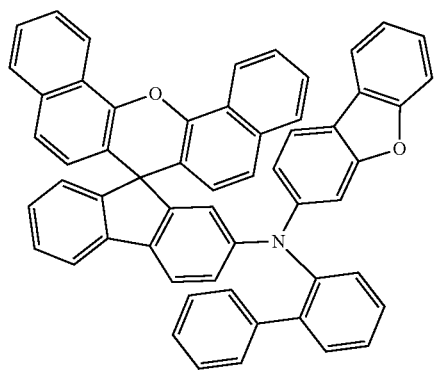
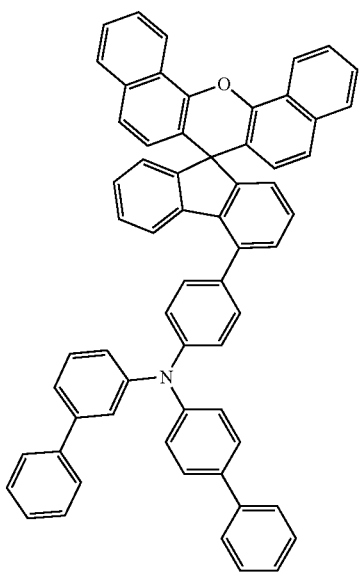

-continued
| 117 | 118 |
|---|---|
| 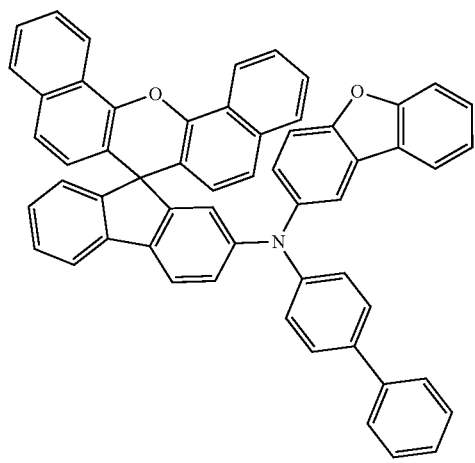 | 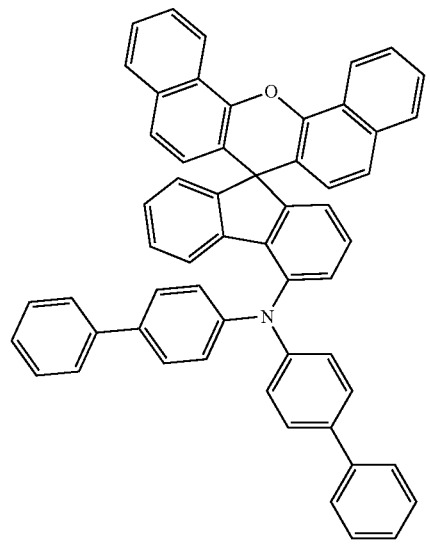 |
| 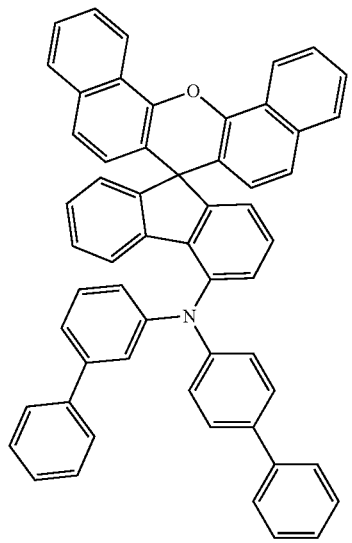 | 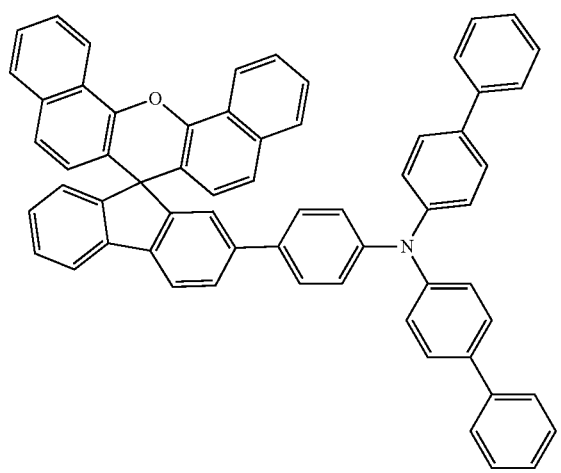 |
| 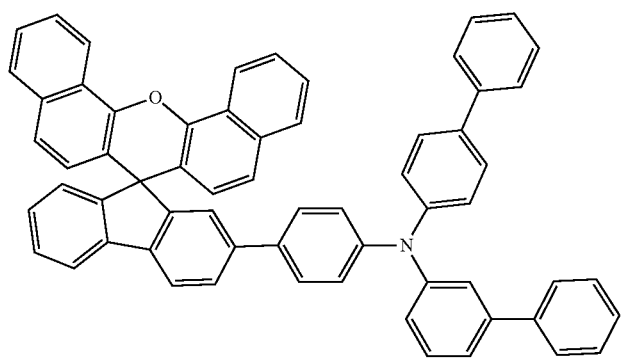 | 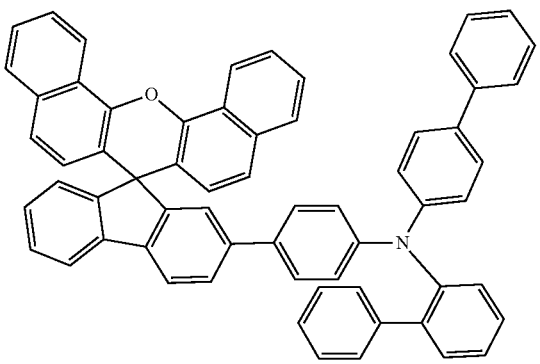 |

-continued
119
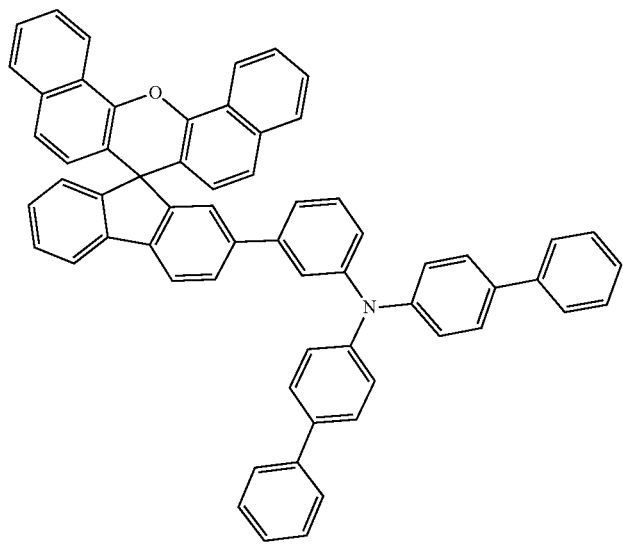
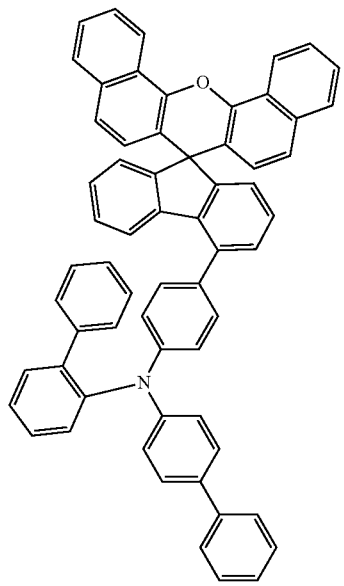
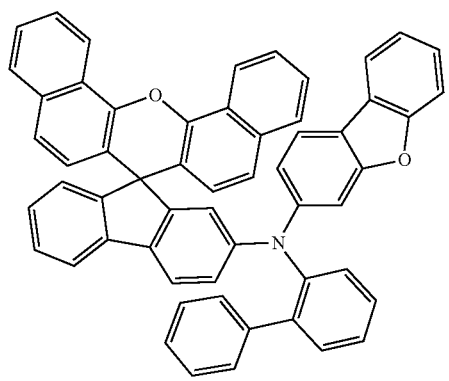
120
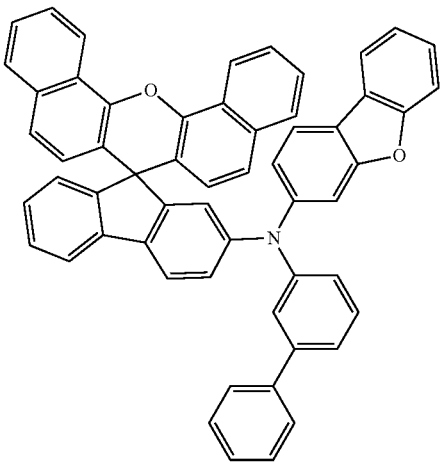
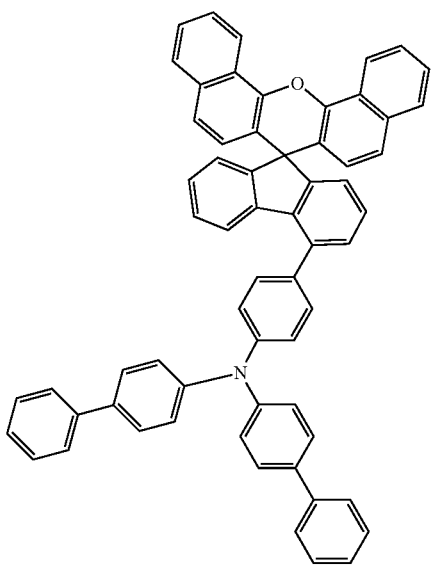
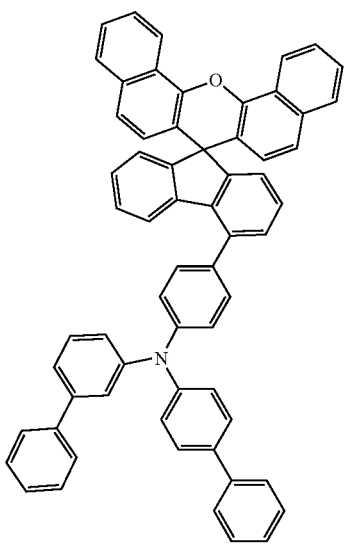

-continued
121
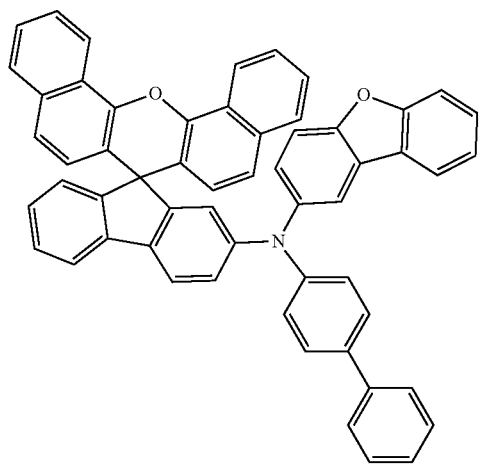
122
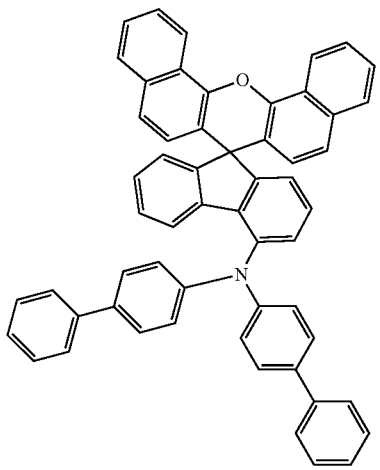
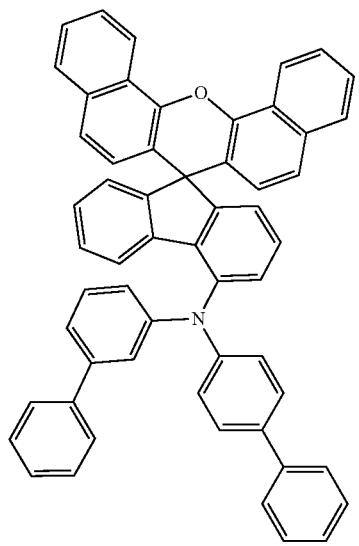
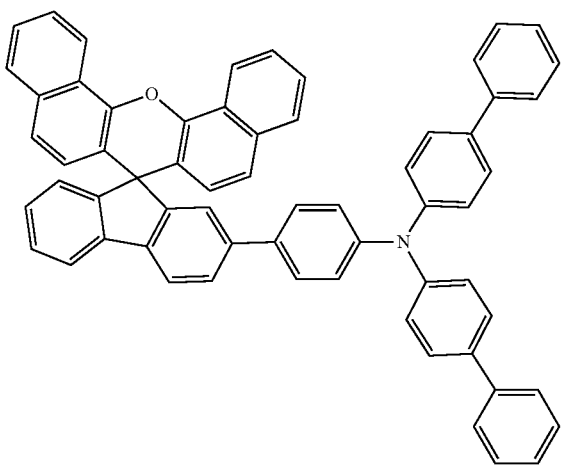
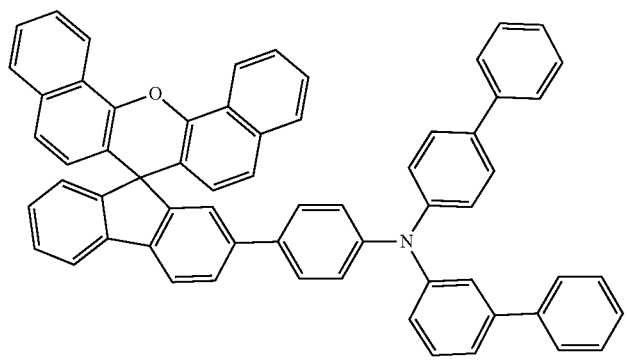

-continued
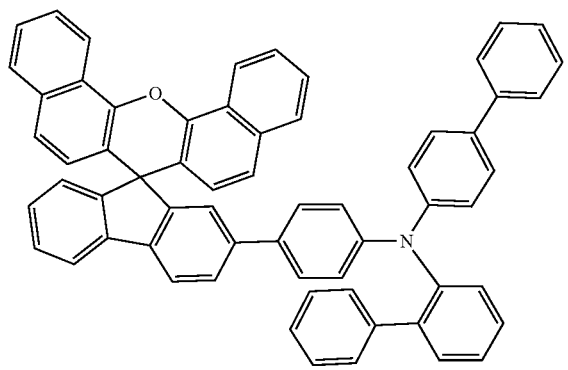
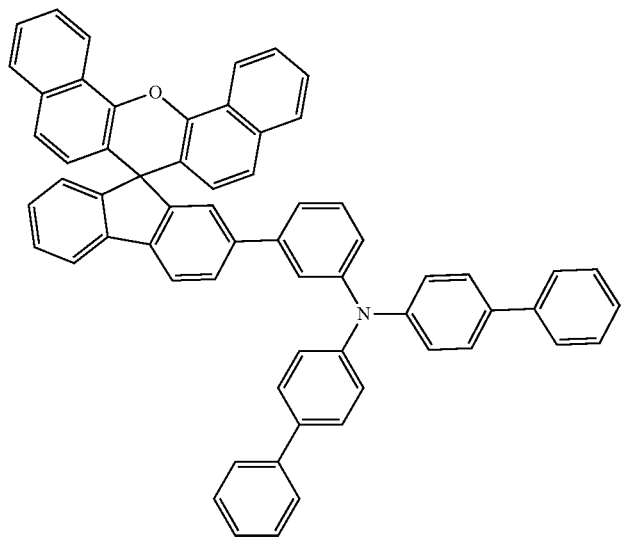
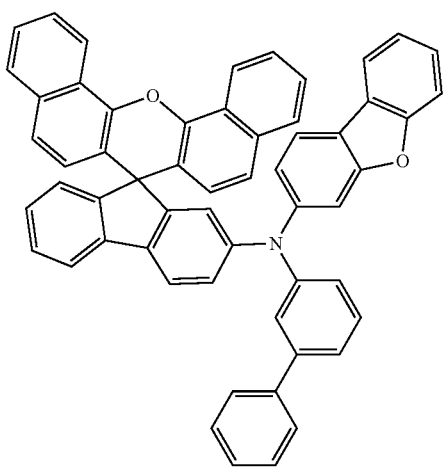
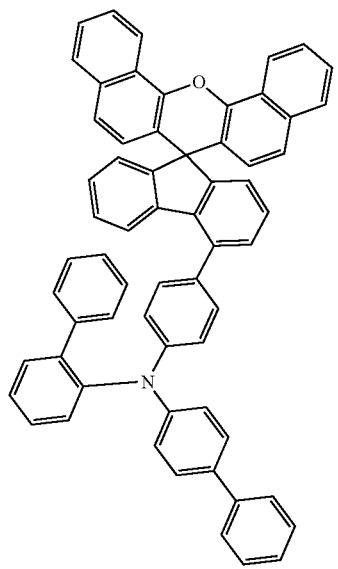
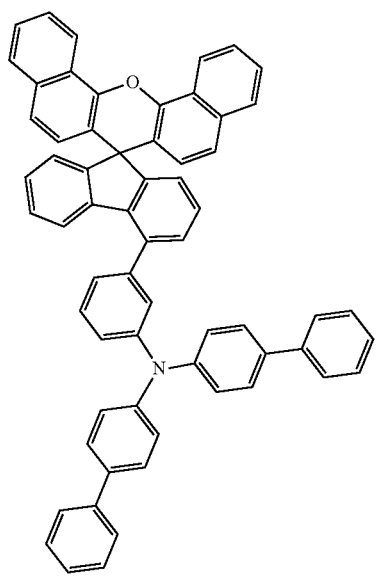

-continued
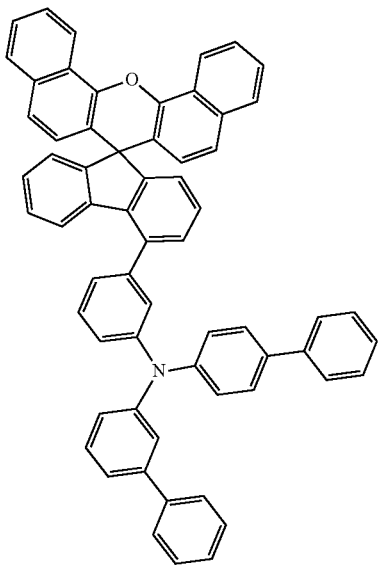
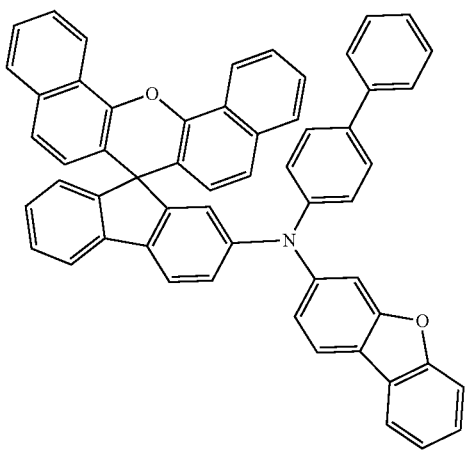
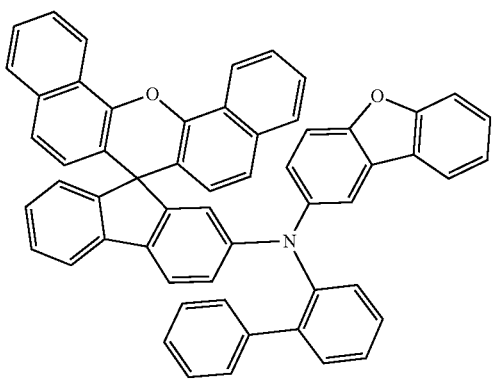
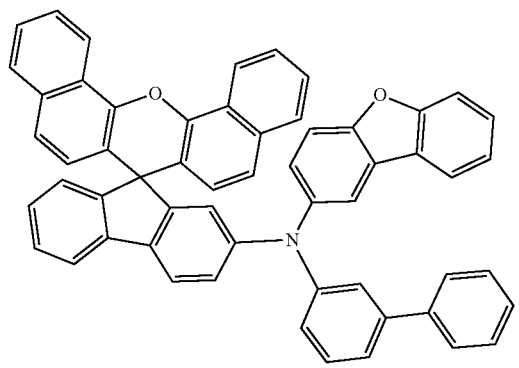
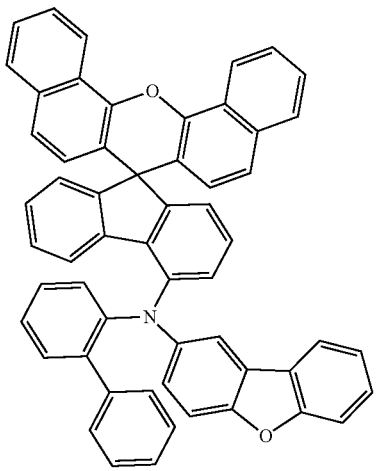
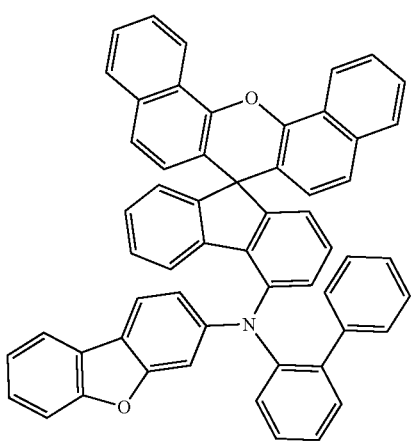

127
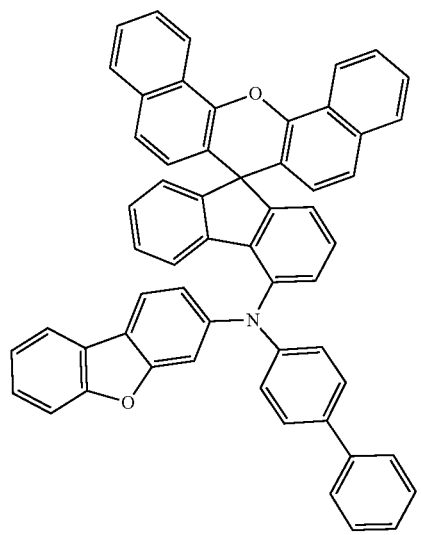
128
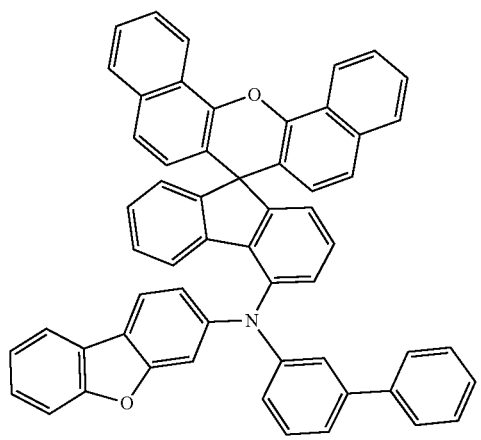
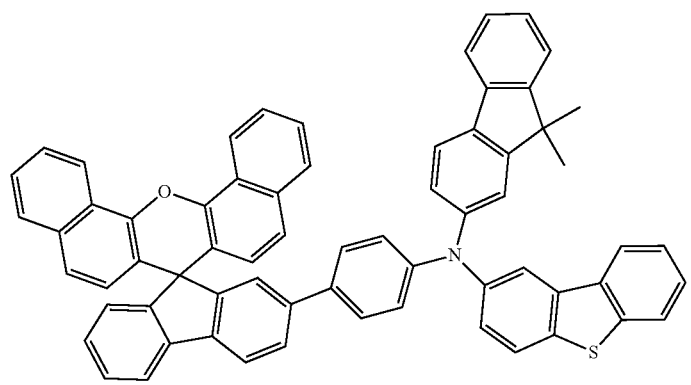
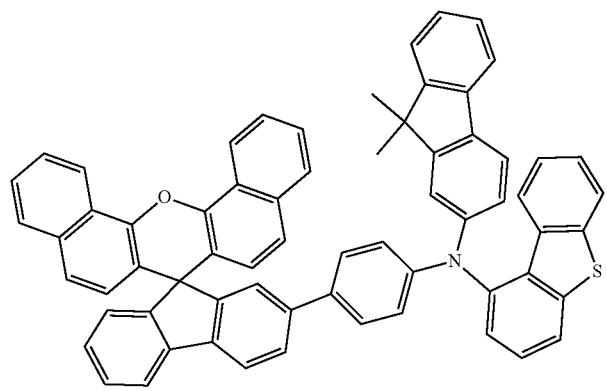

-continued
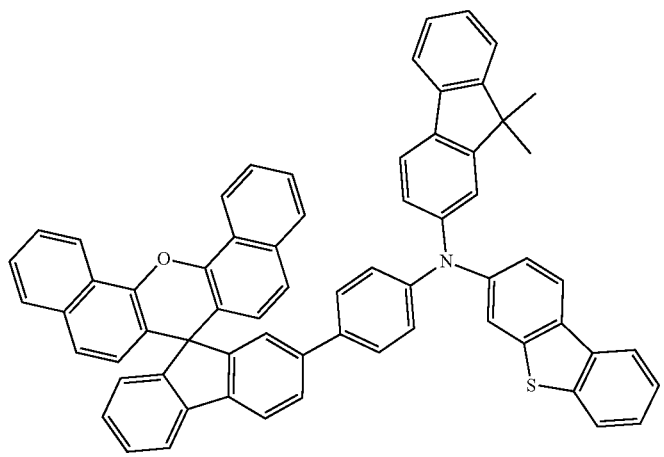
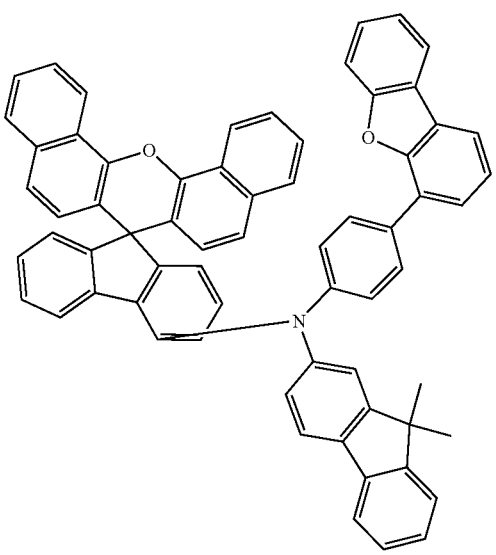
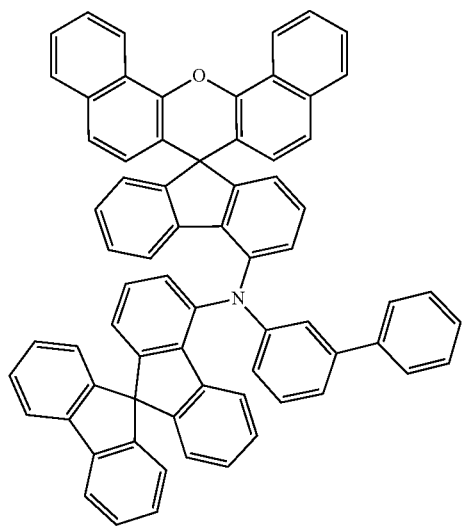
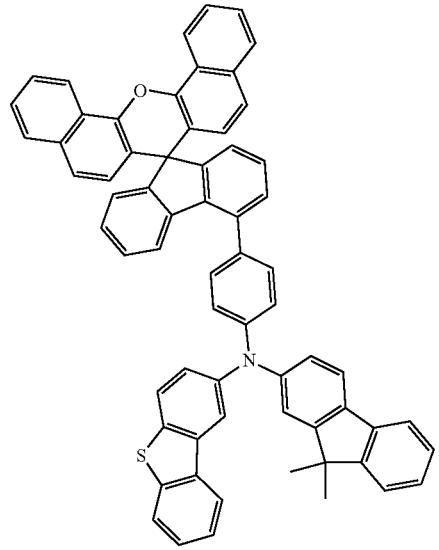
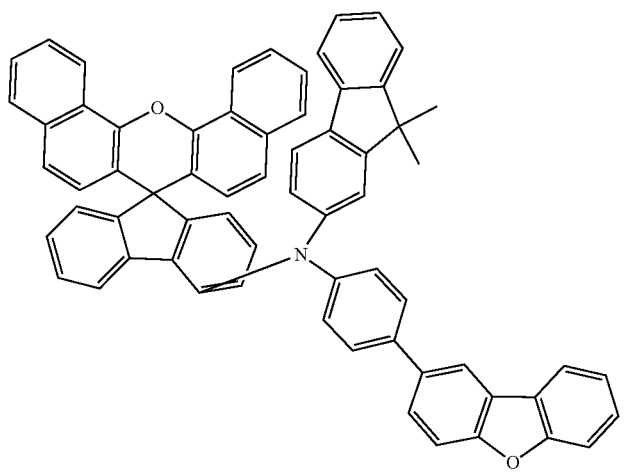

-continued
131
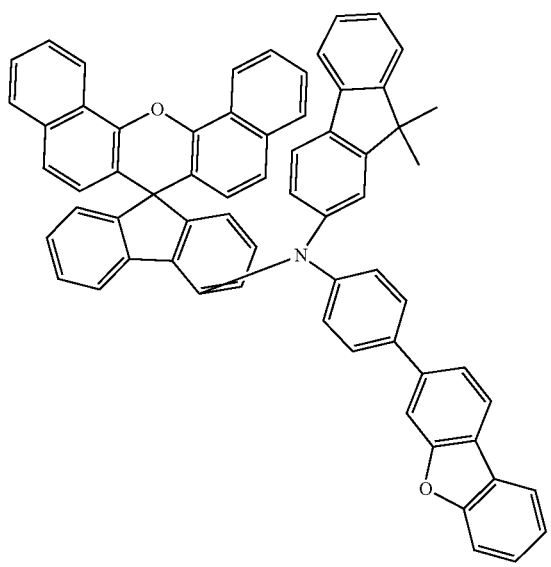
132
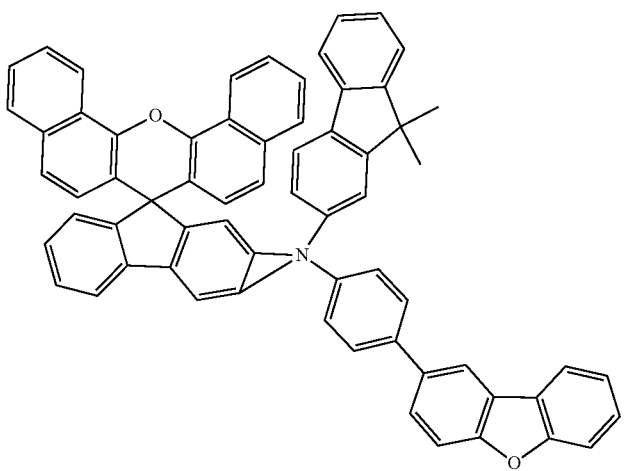
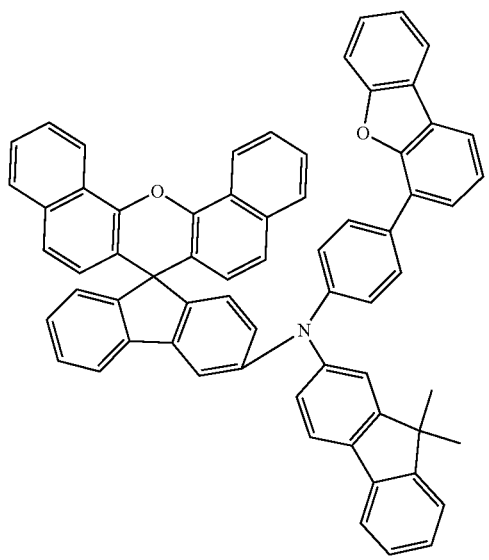
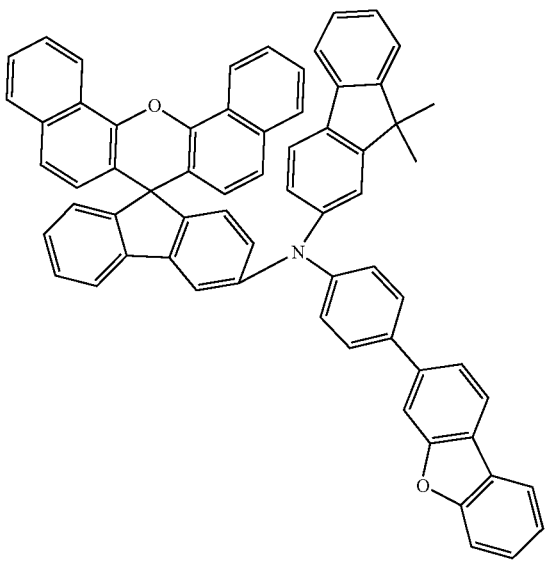
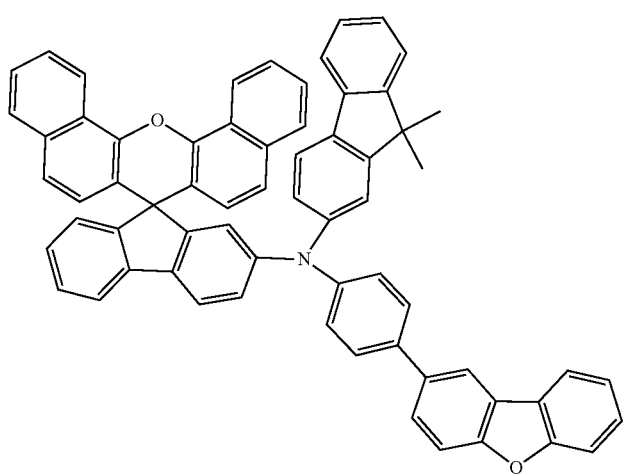

-continued
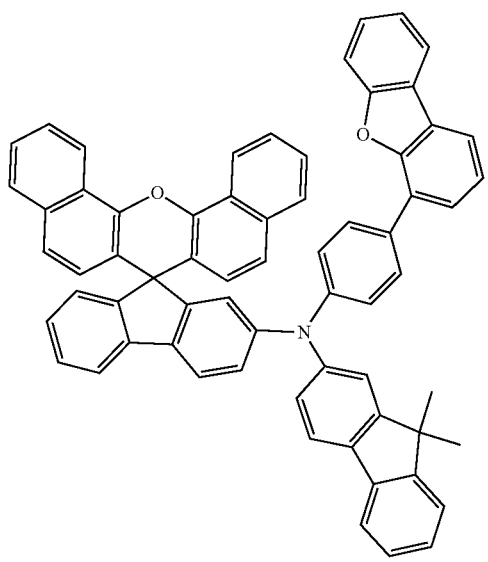
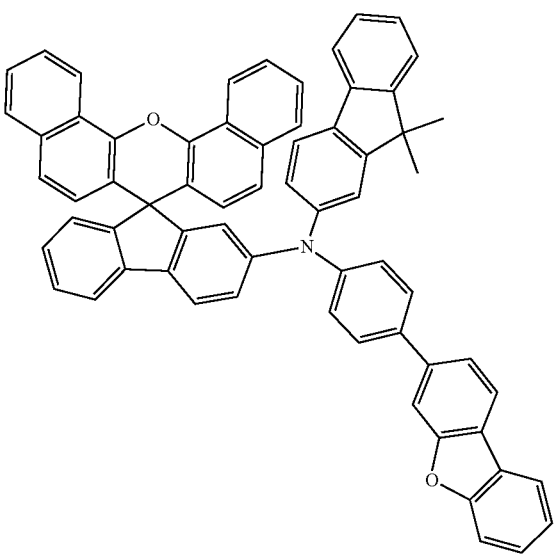
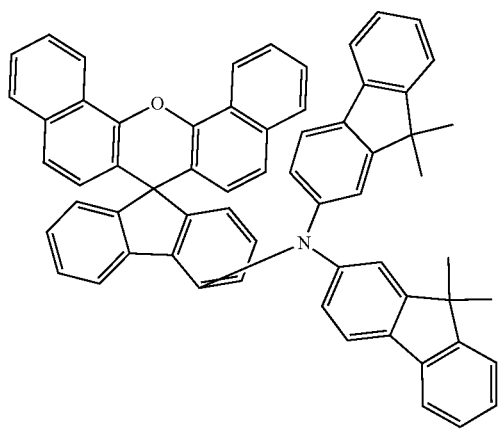
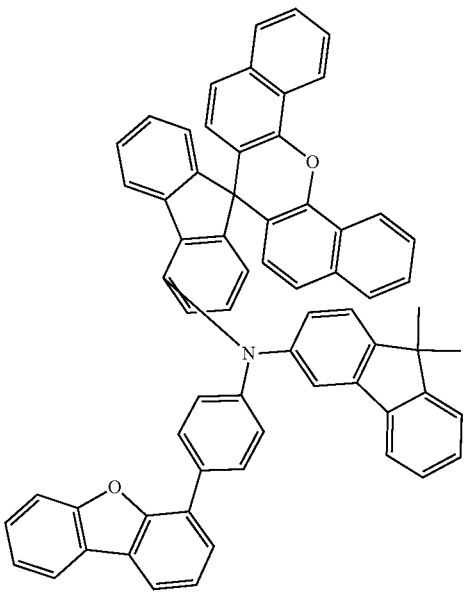
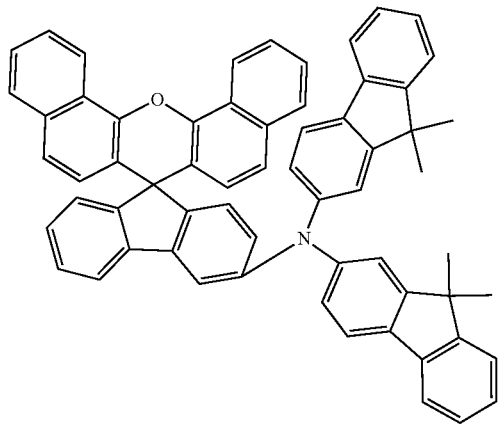
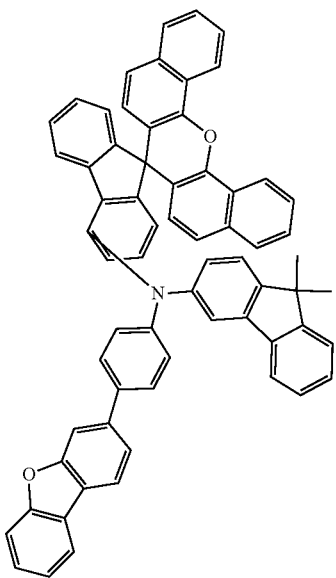

-continued
| 135 | 136 |
|---|---|
| 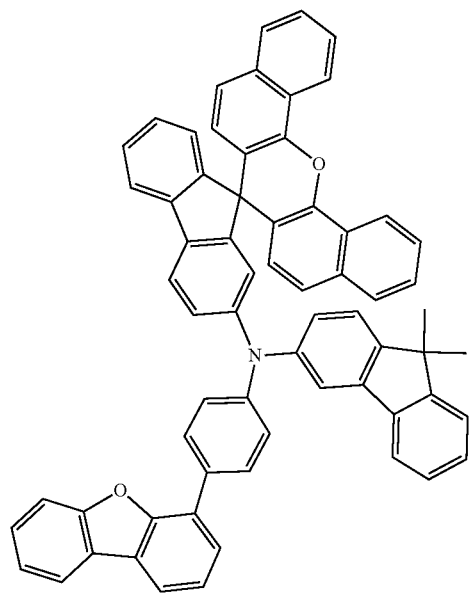 | 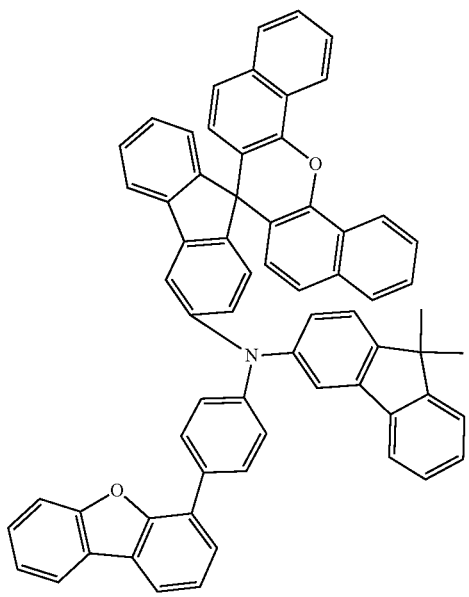 |
| 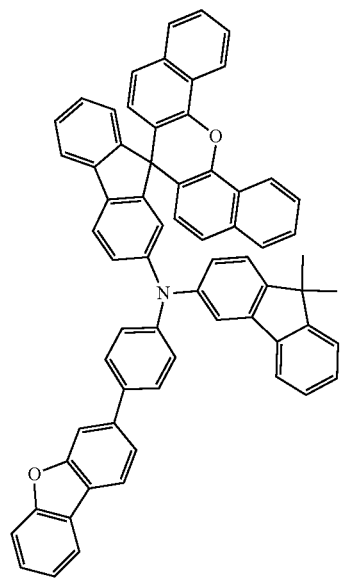 | 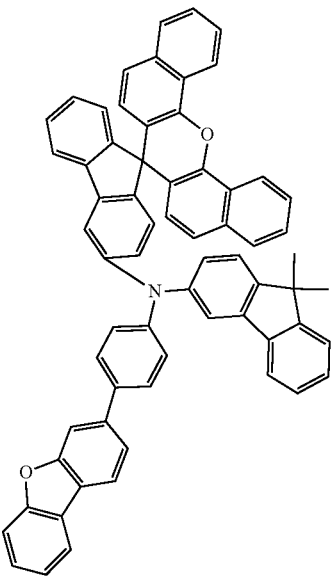 |

137
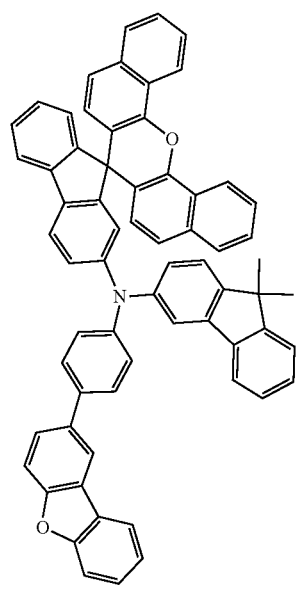
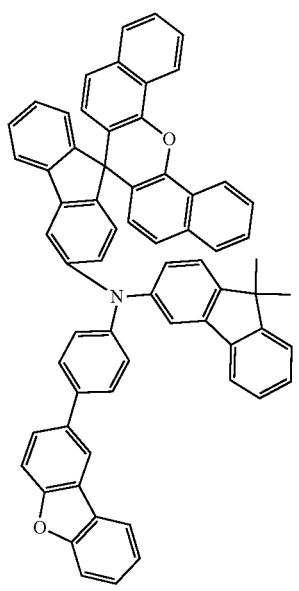
-continued
138
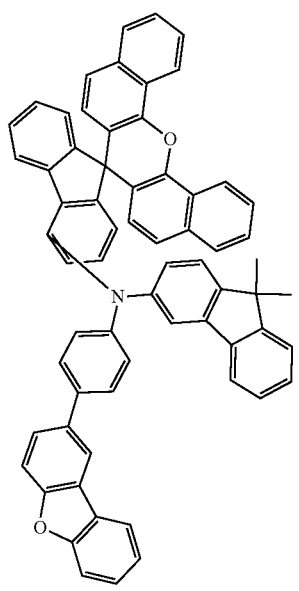
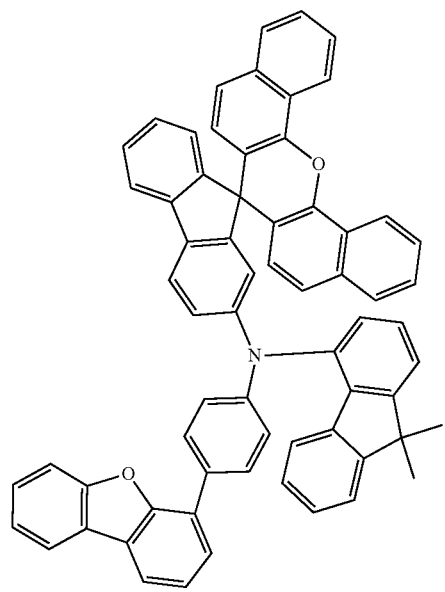
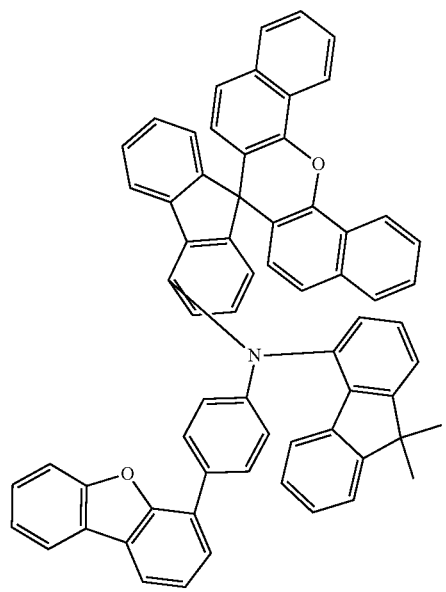

-continued
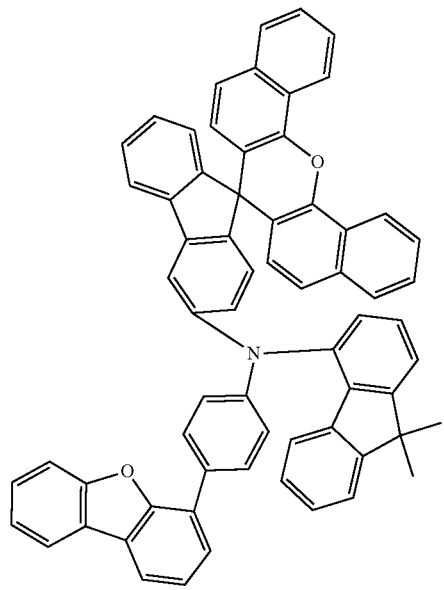
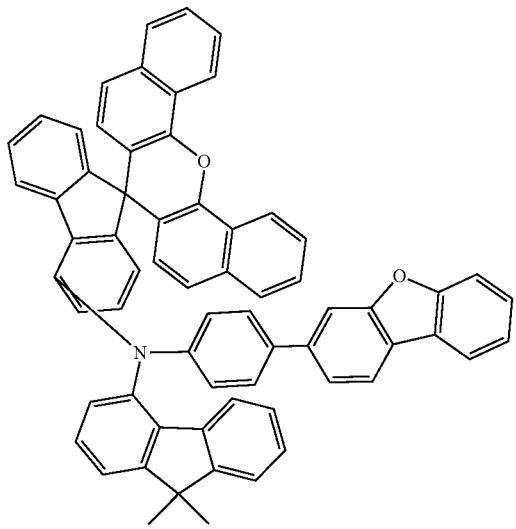
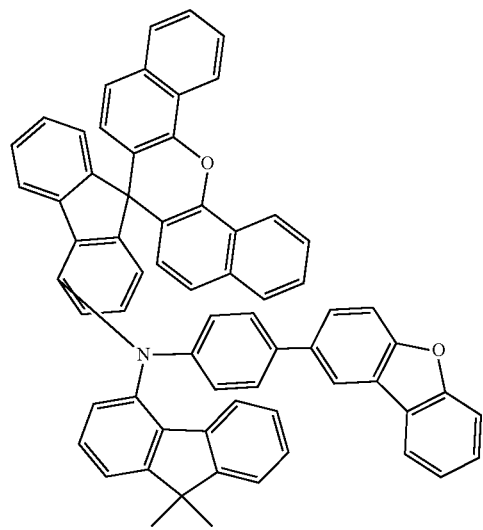
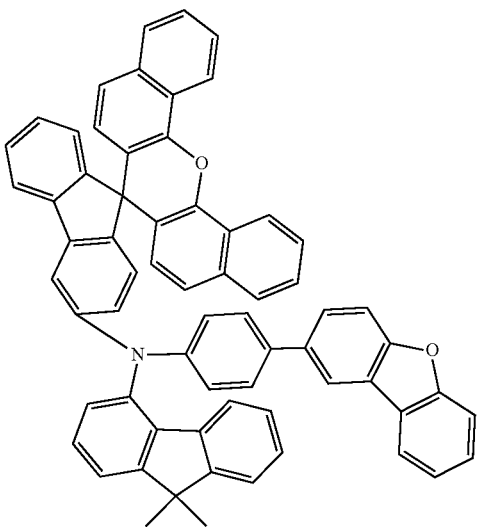
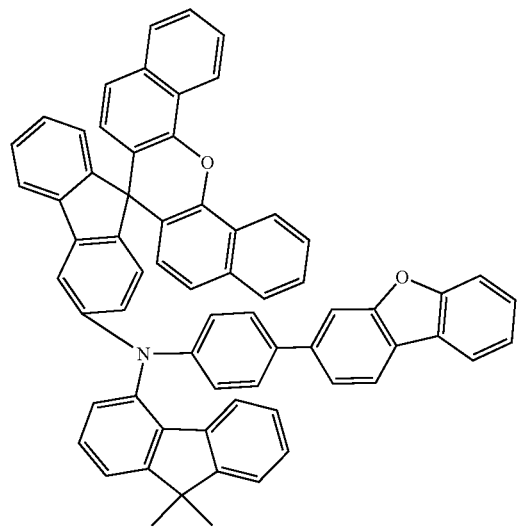
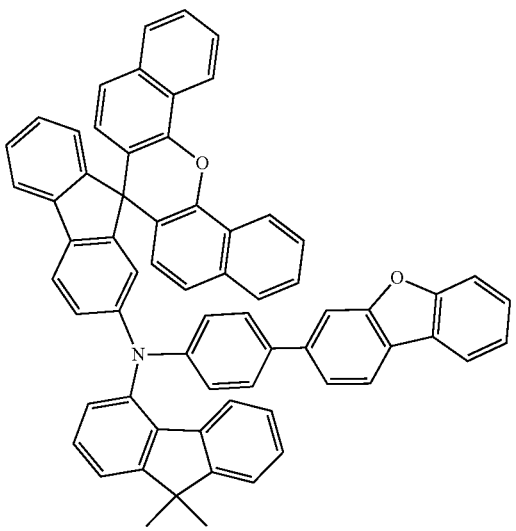

-continued
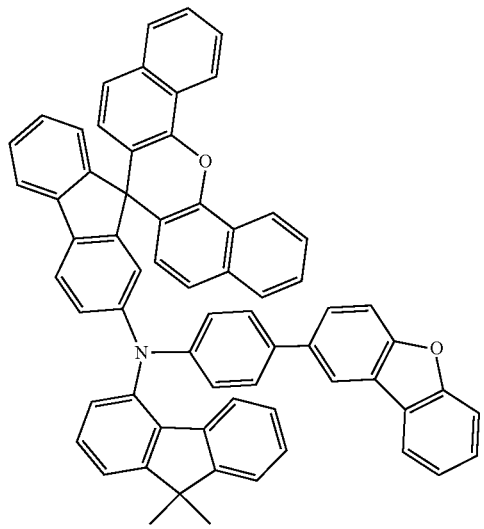
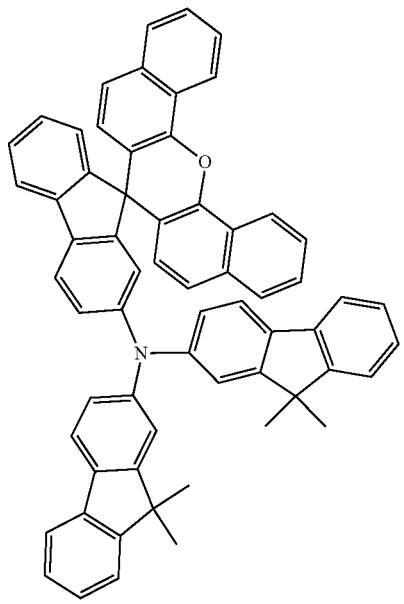
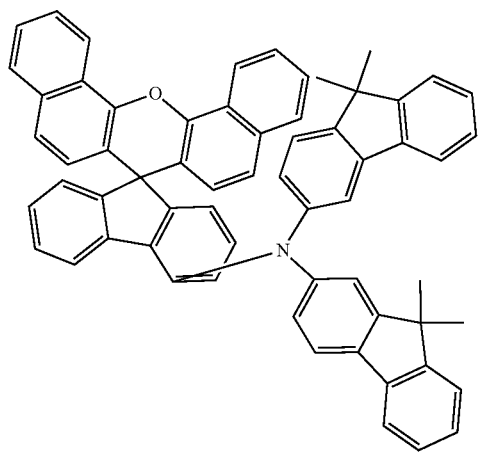
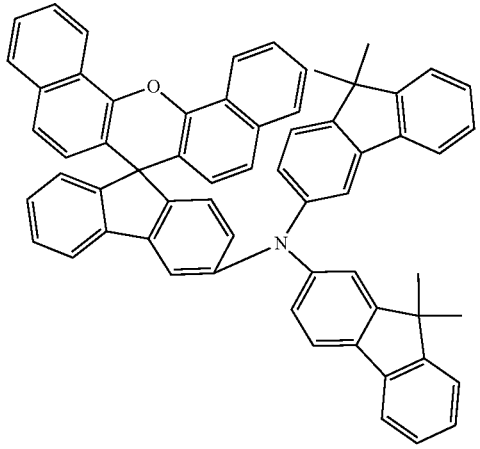
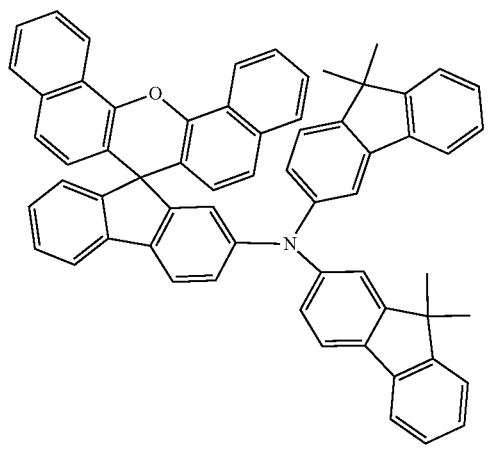
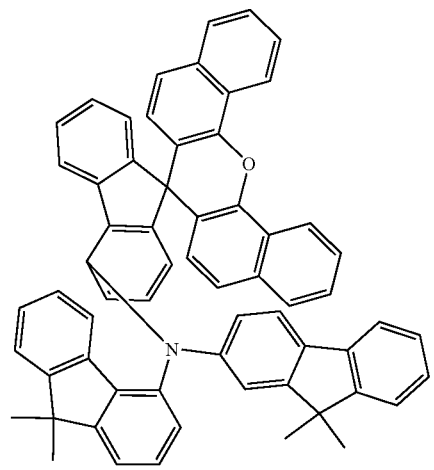

-continued
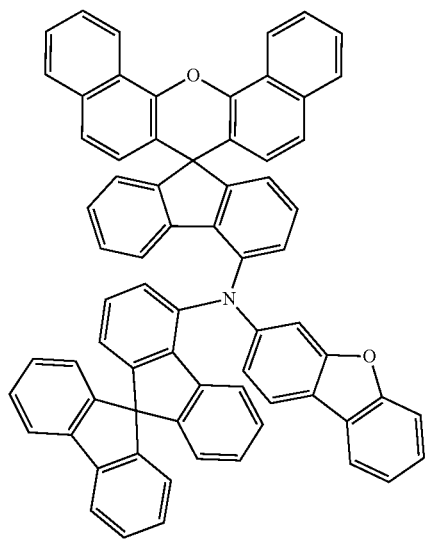
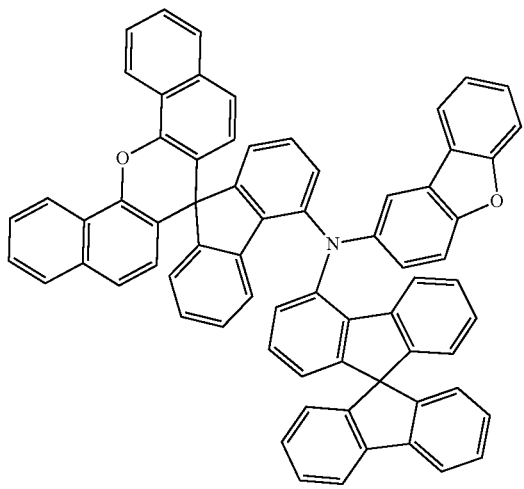
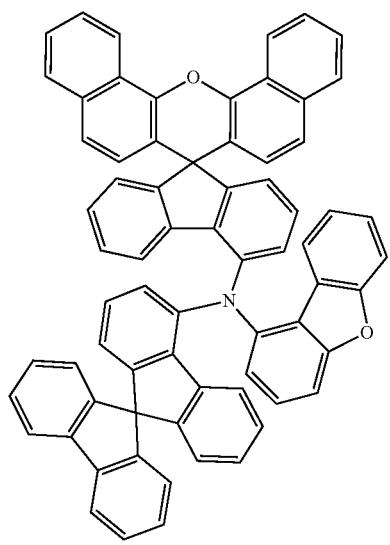
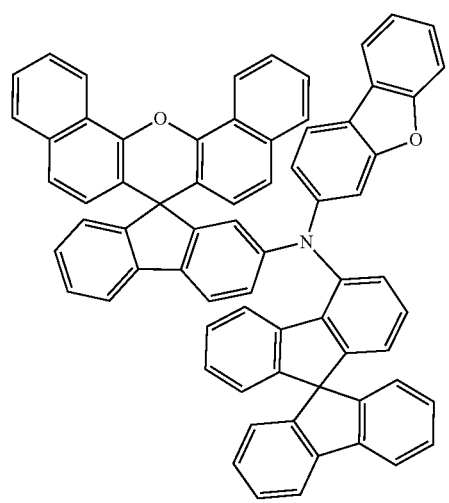
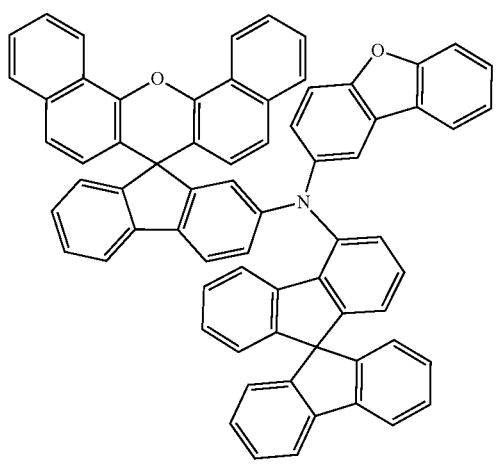
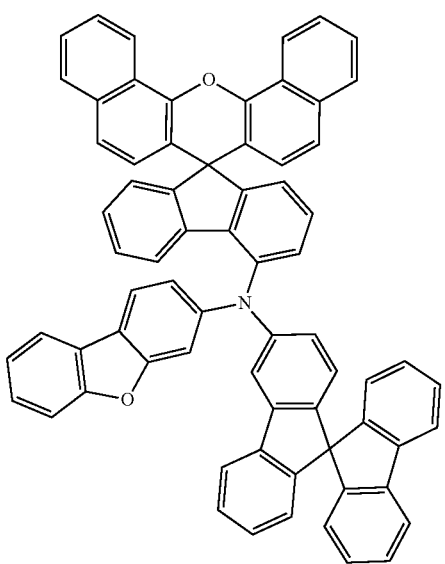

-continued
145
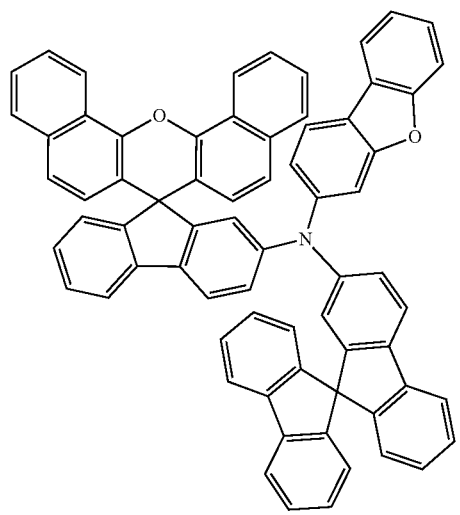
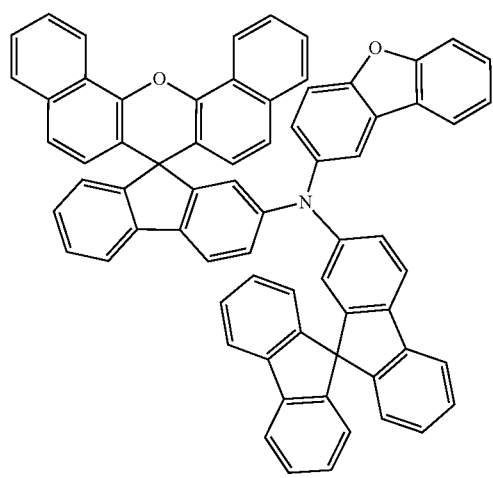
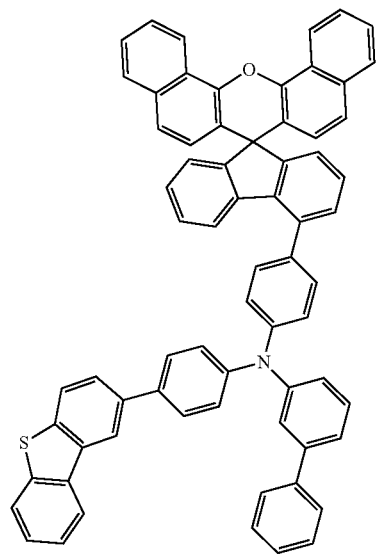
146
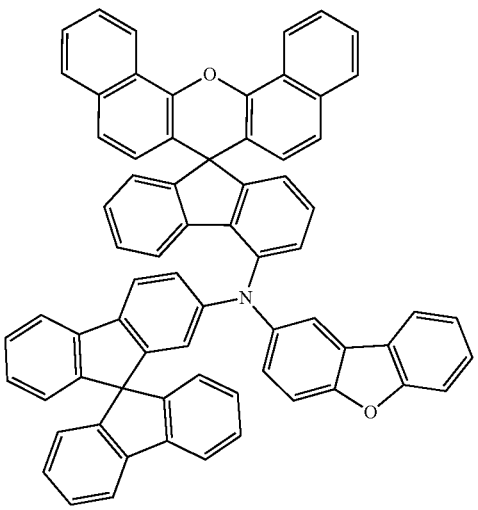
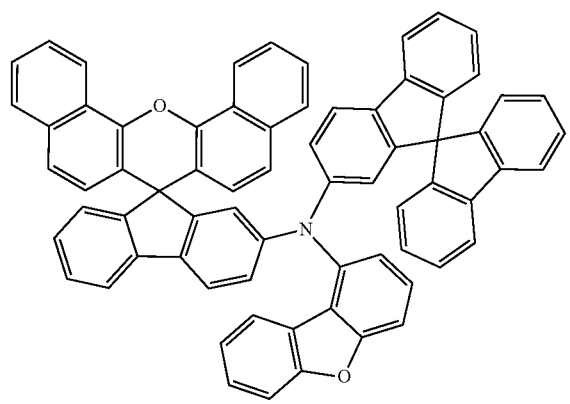
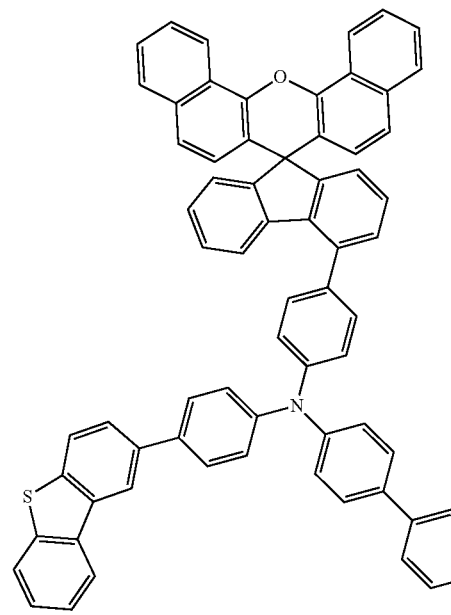

-continued
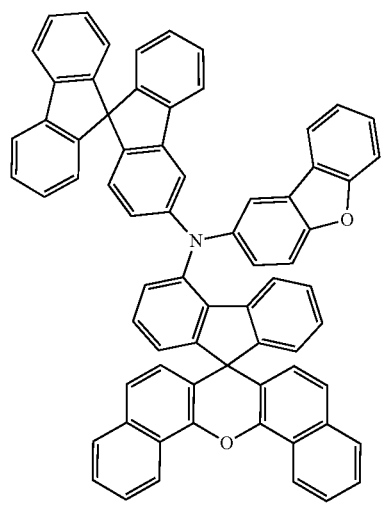
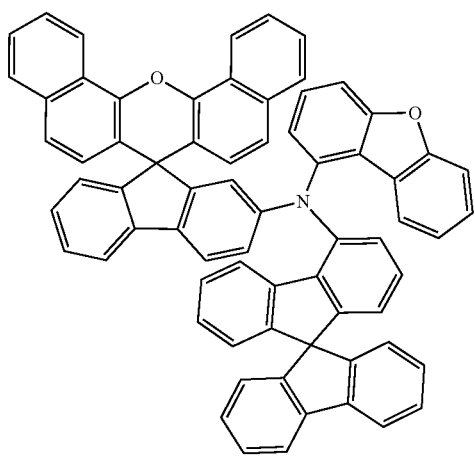
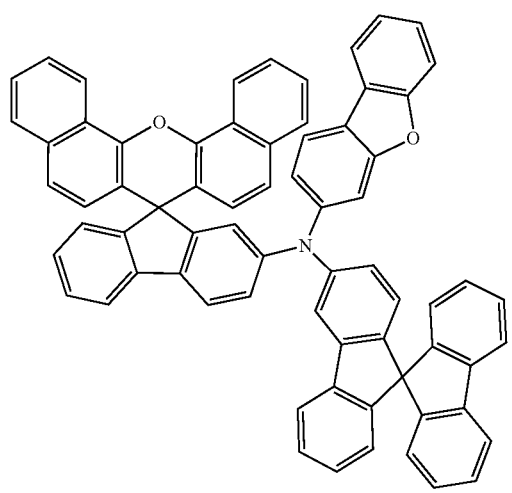
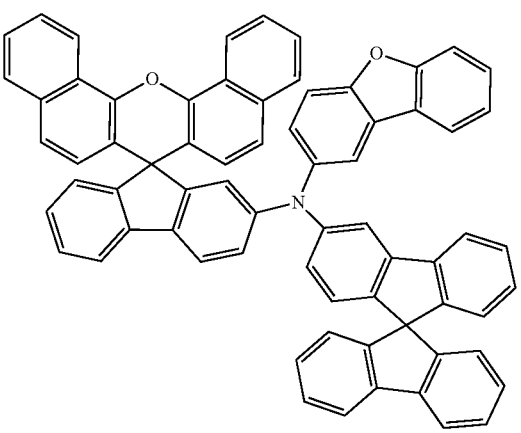
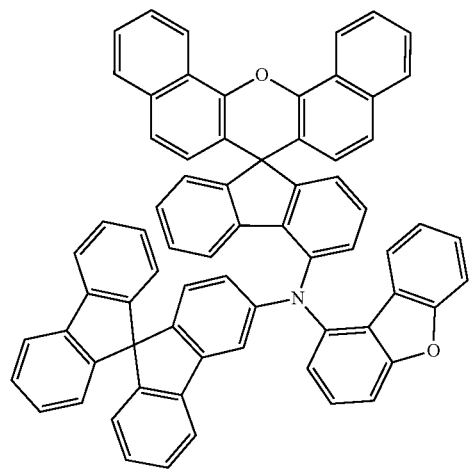
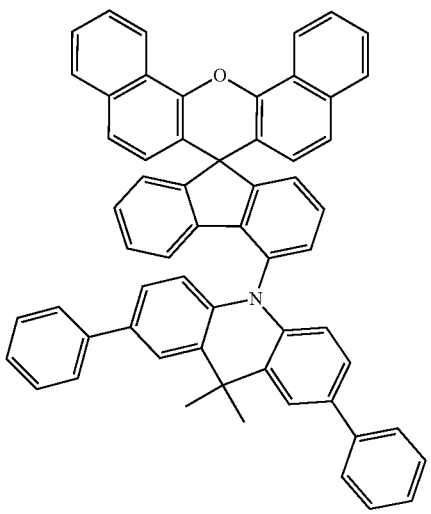

-continued
149
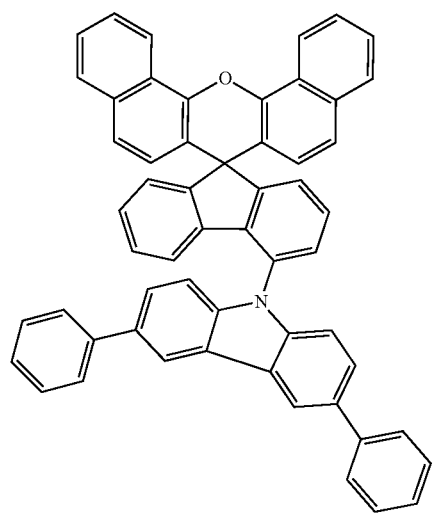
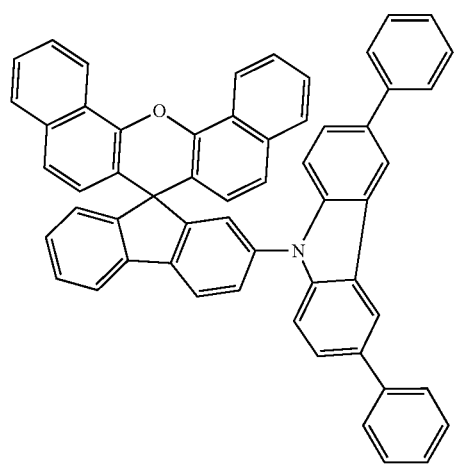
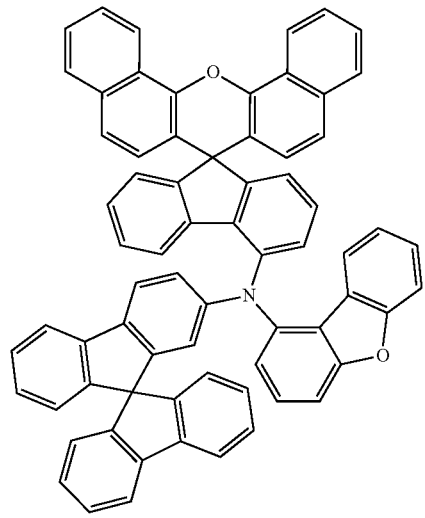
150
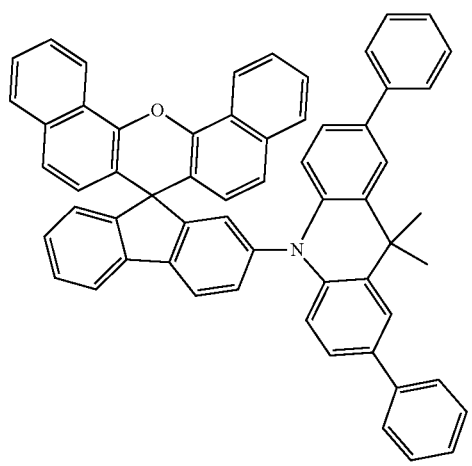
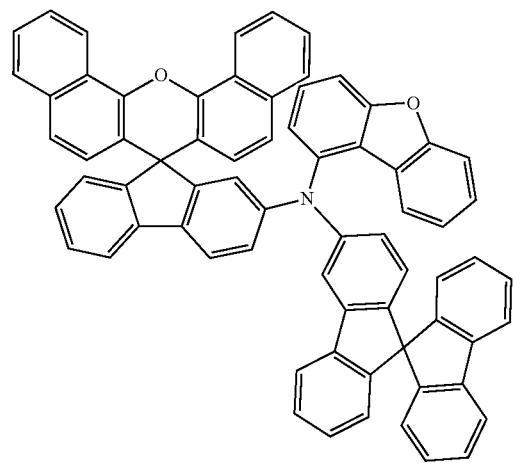
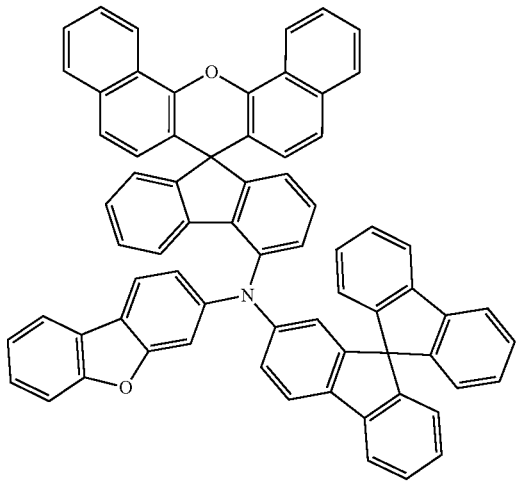

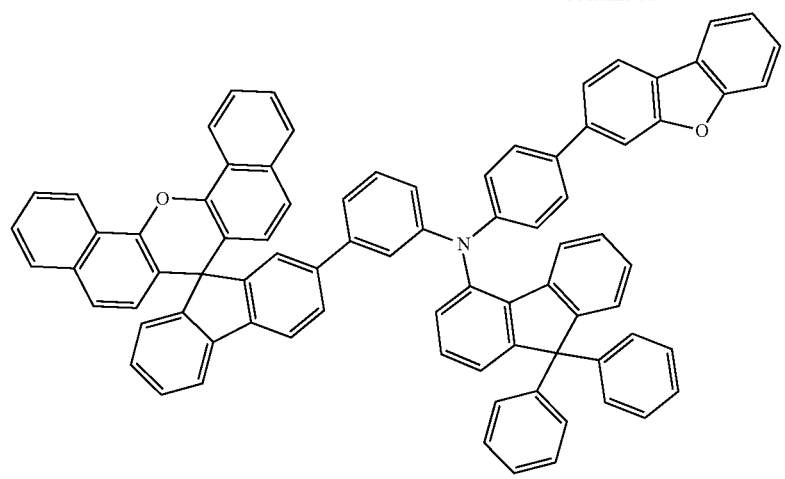
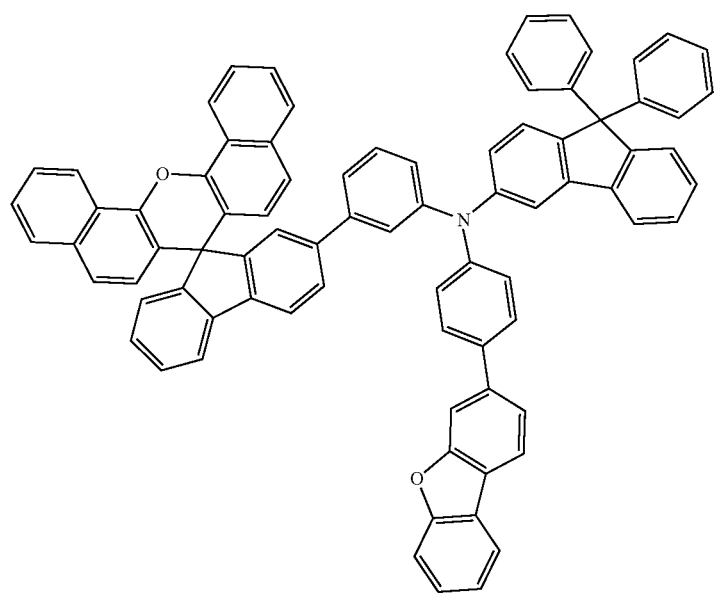
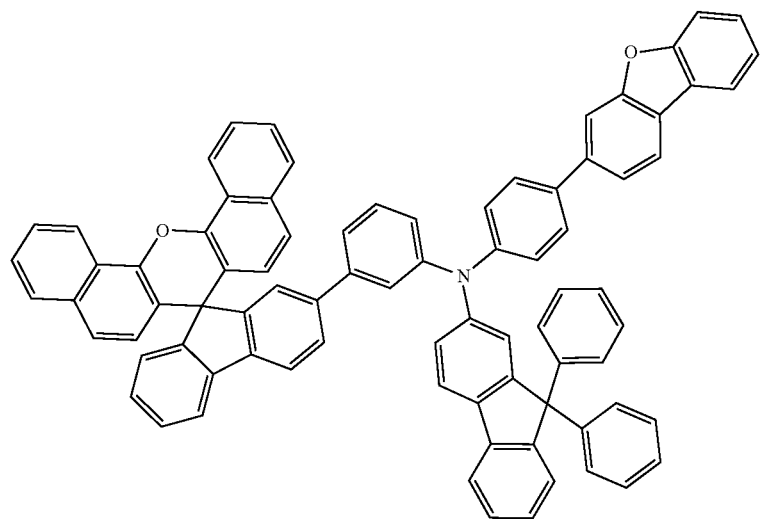

-continued
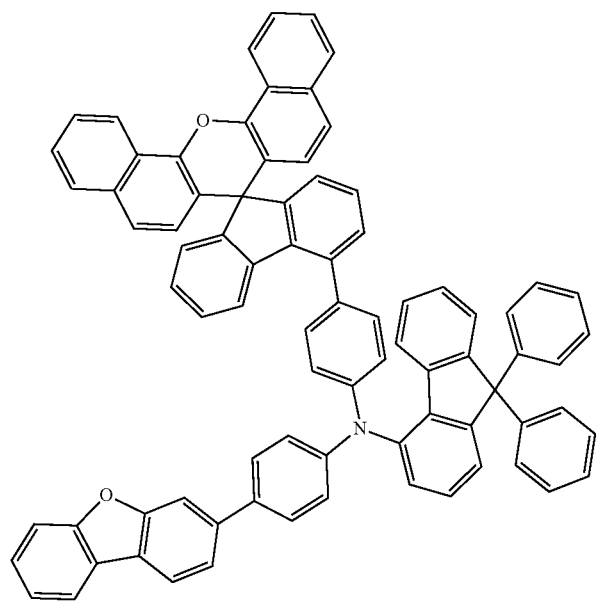
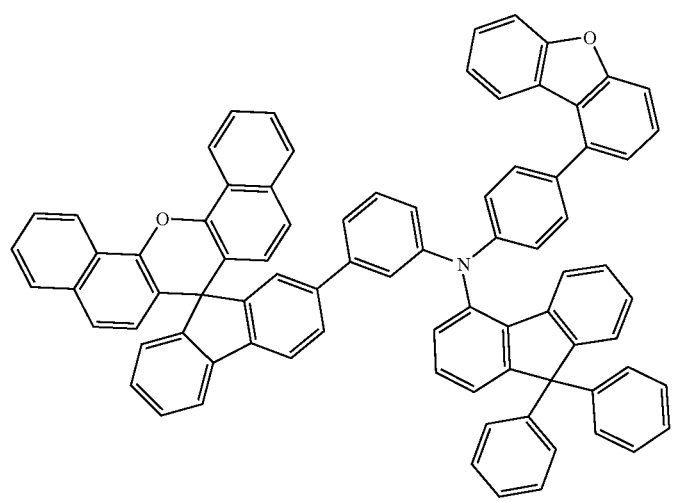
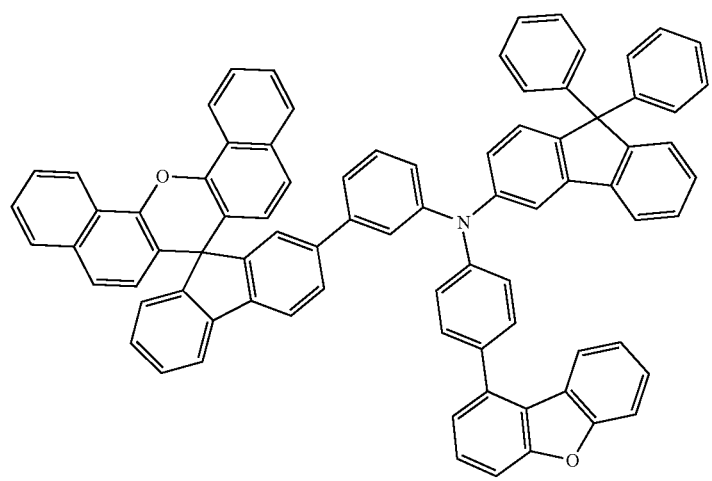

-continued
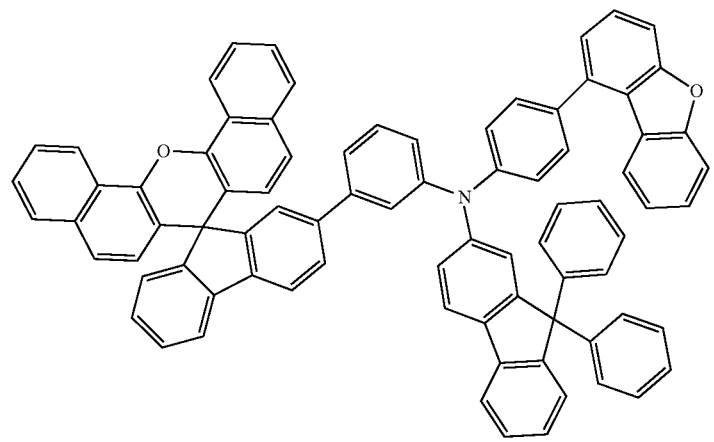
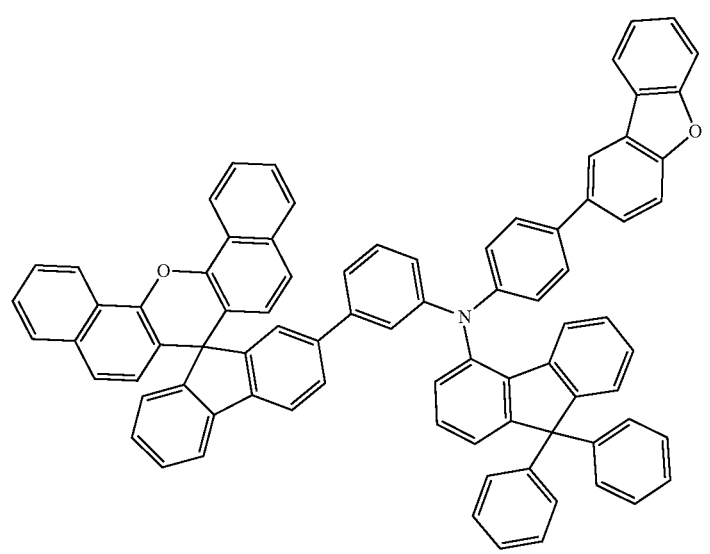
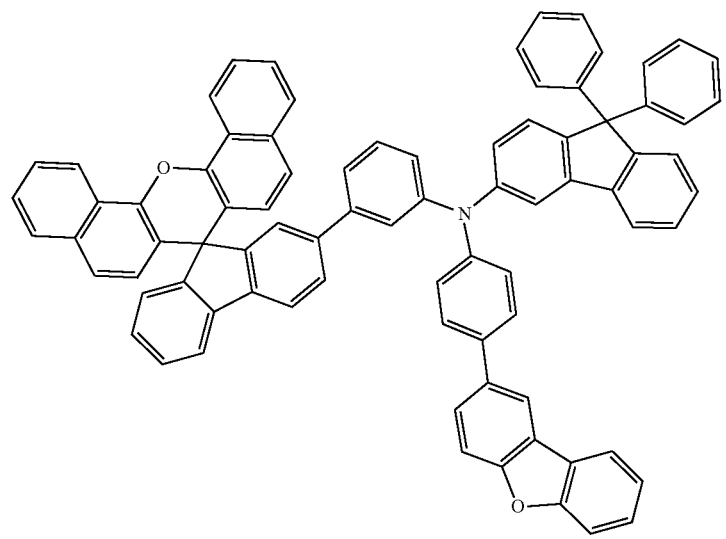

-continued
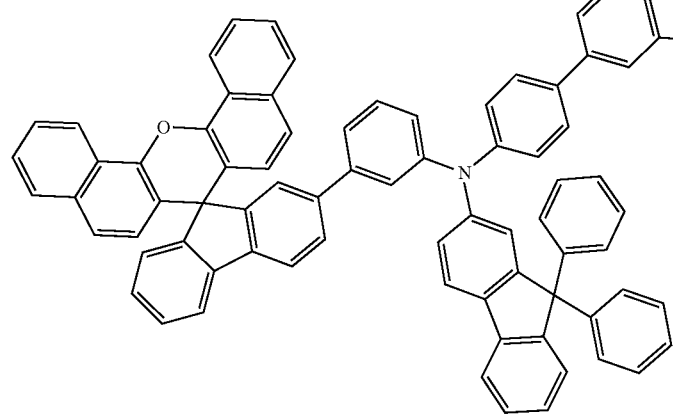
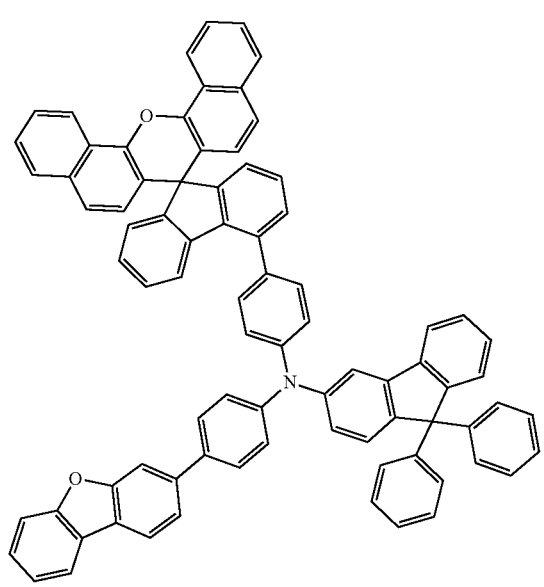
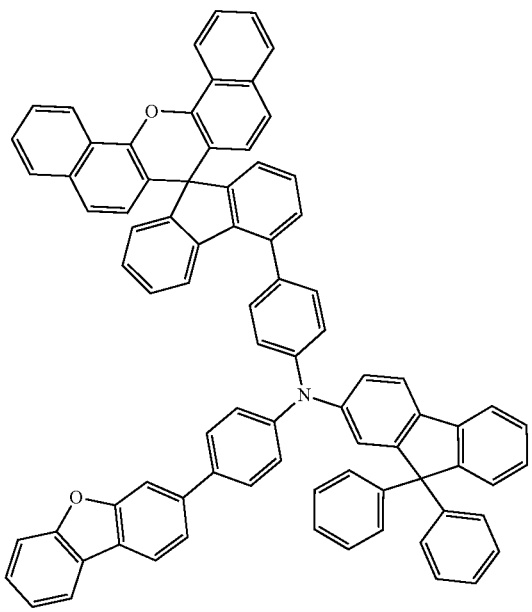
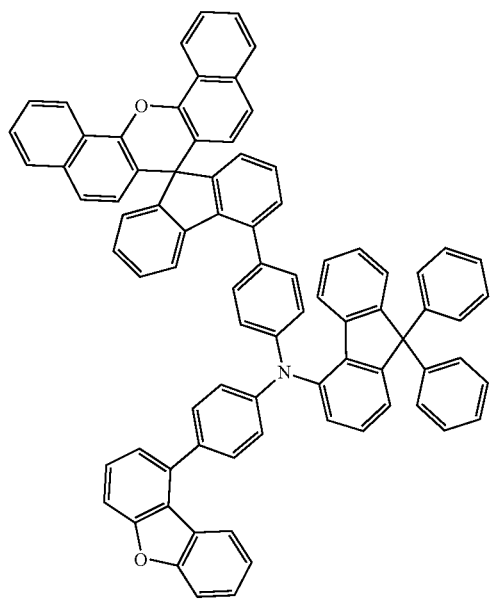
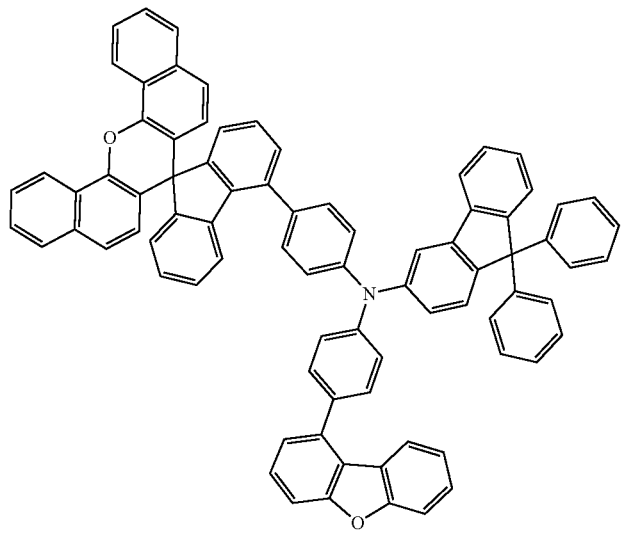

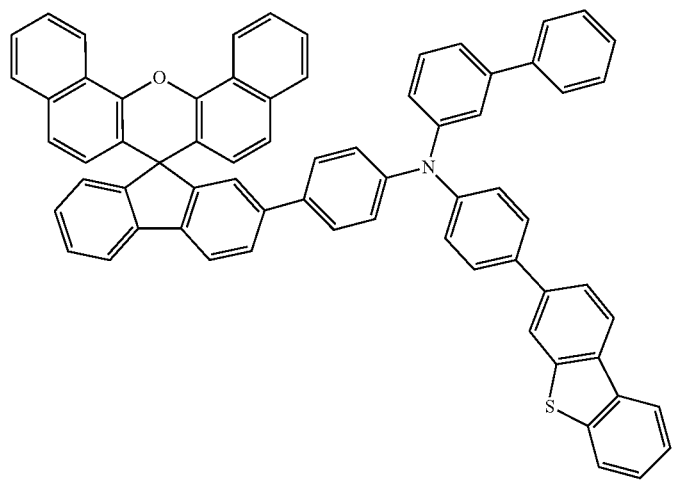
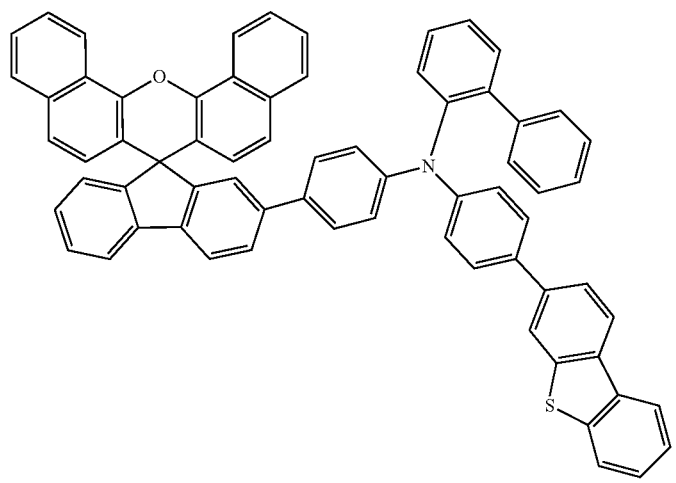
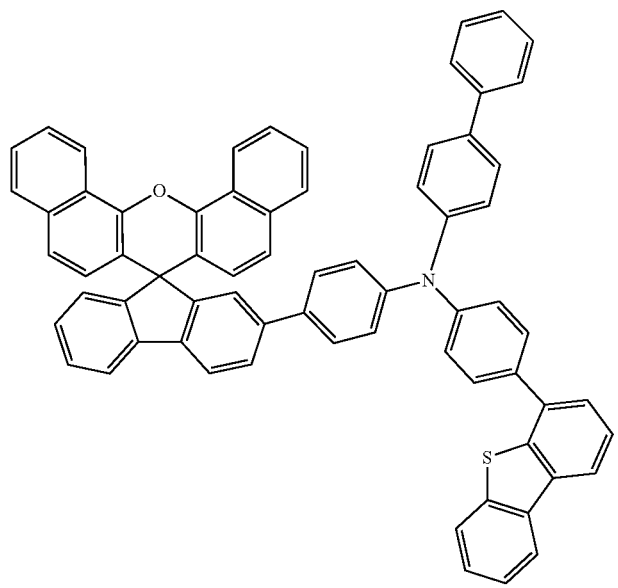

-continued
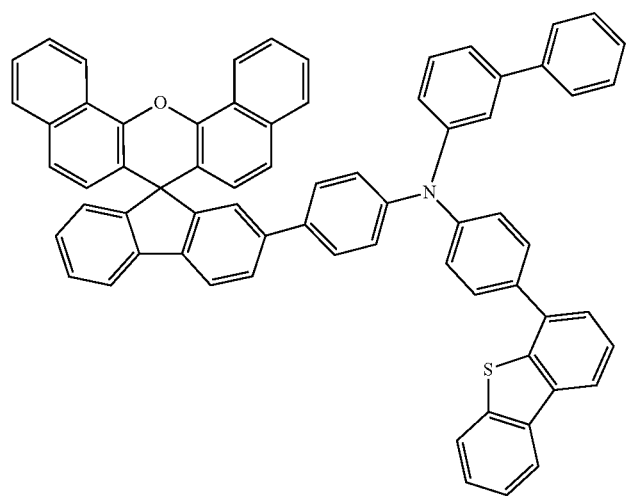
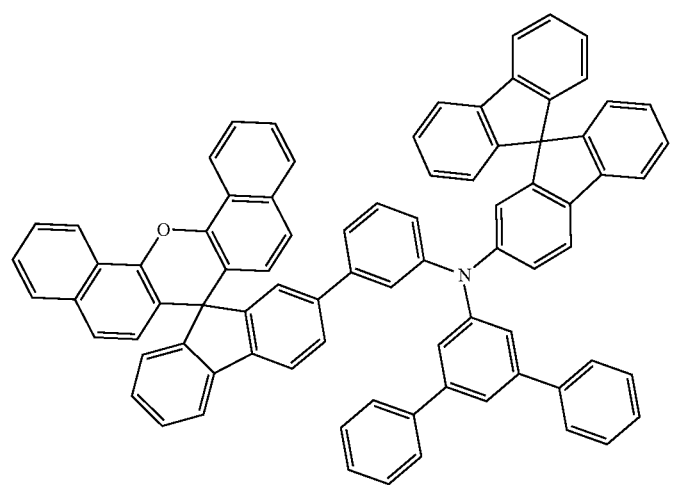
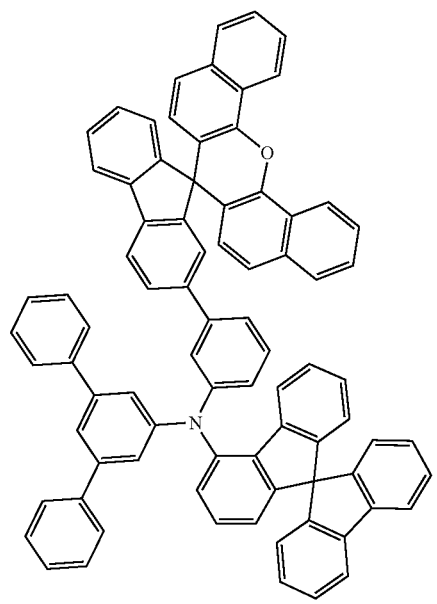
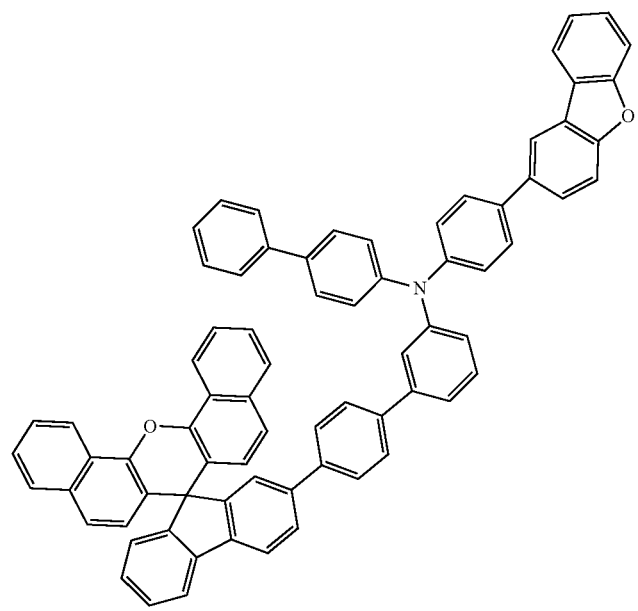

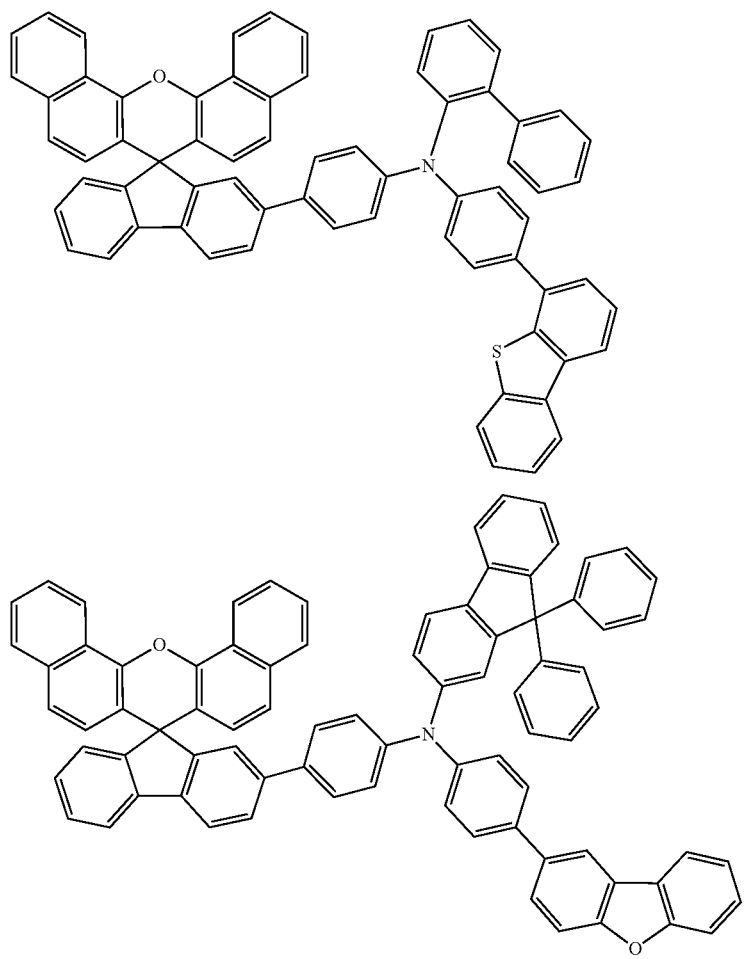
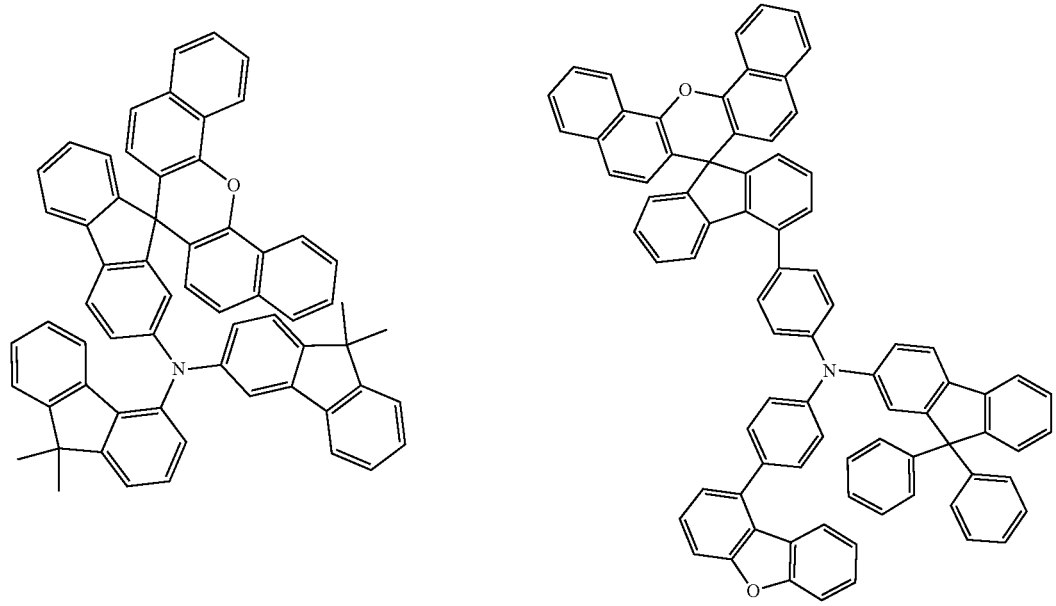

165
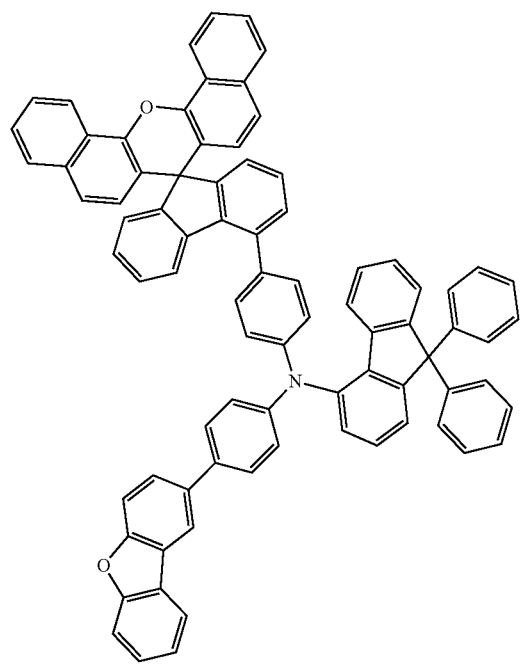
166
-continued
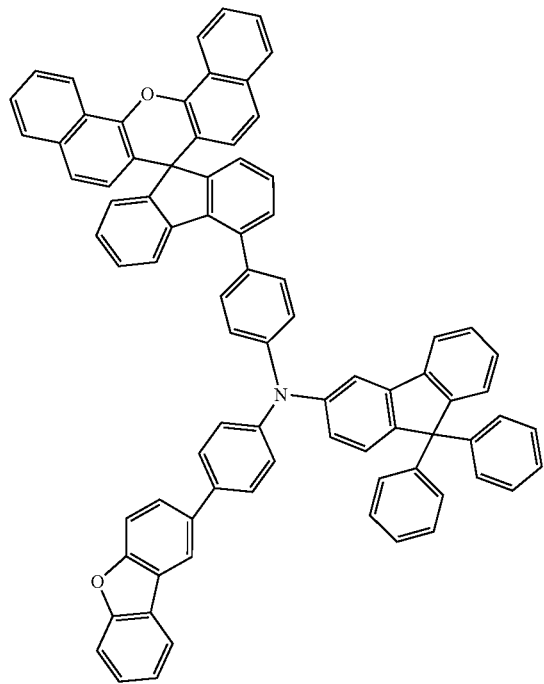
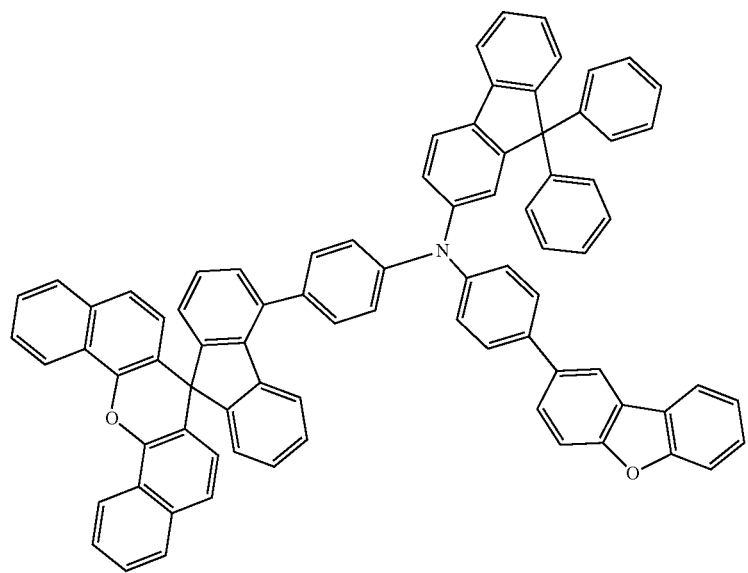

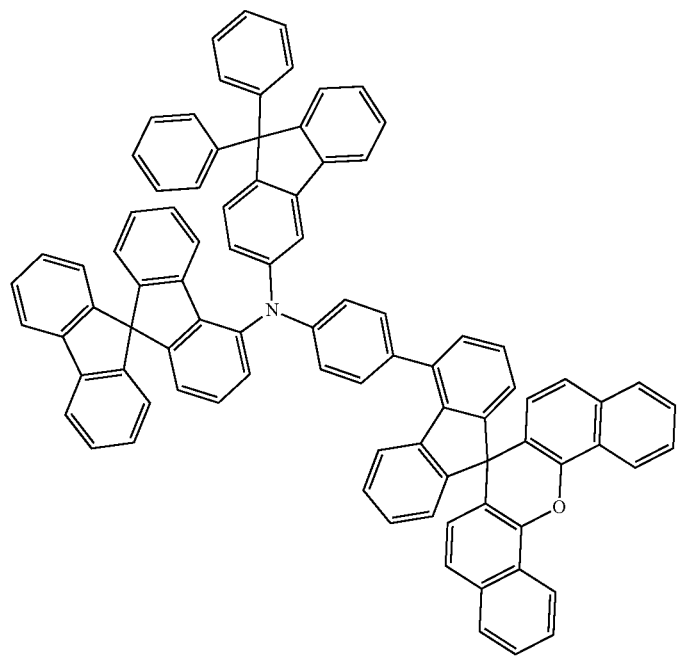
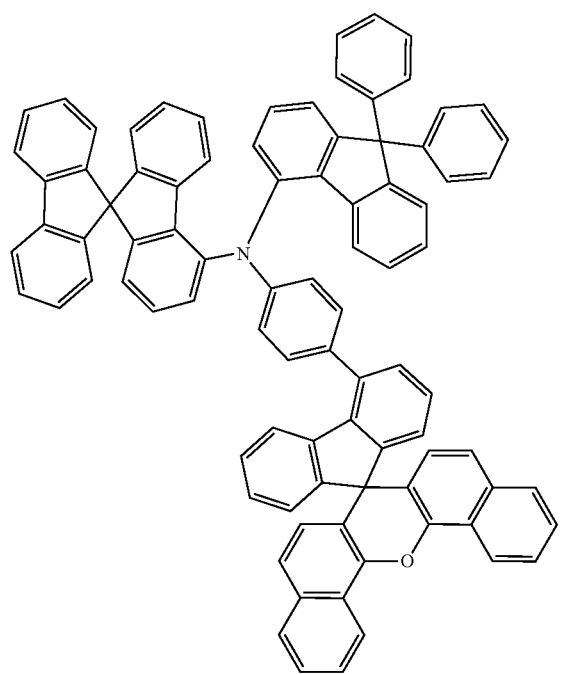
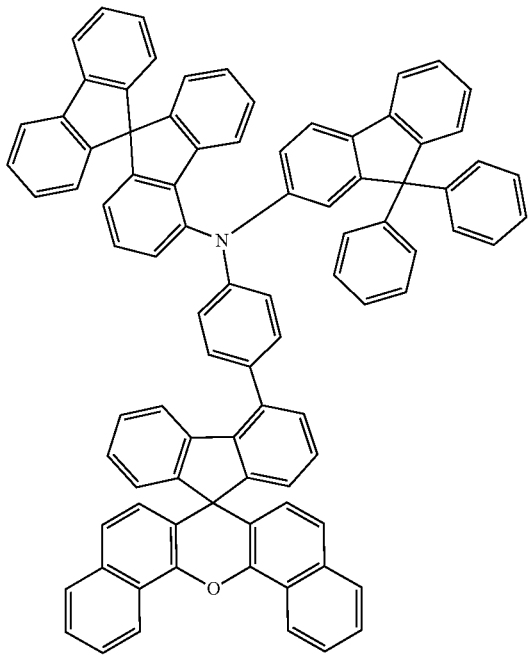

-continued
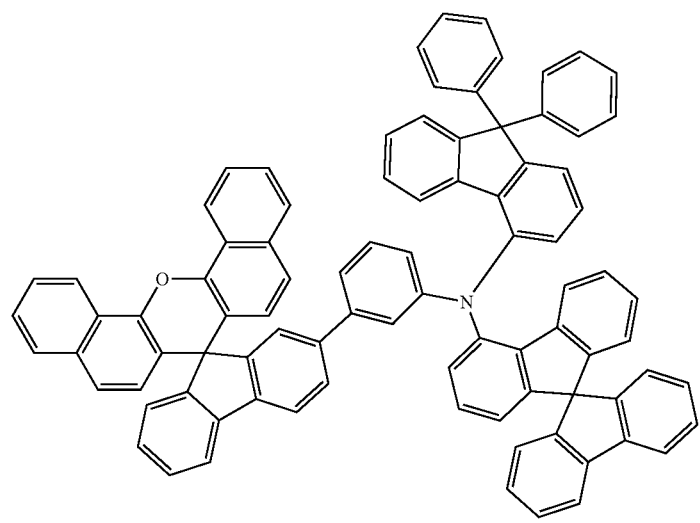
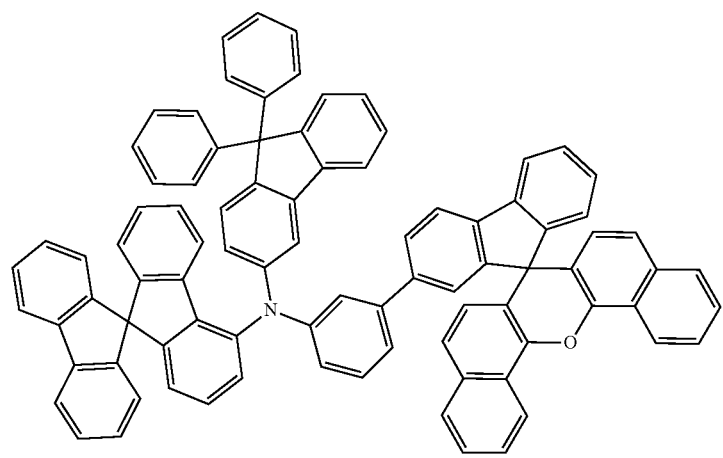
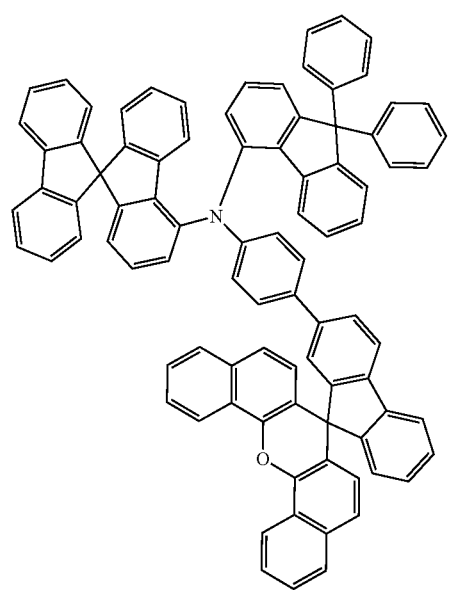
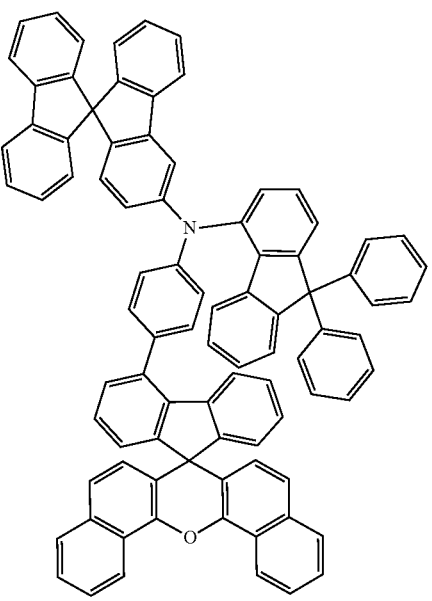

171 172
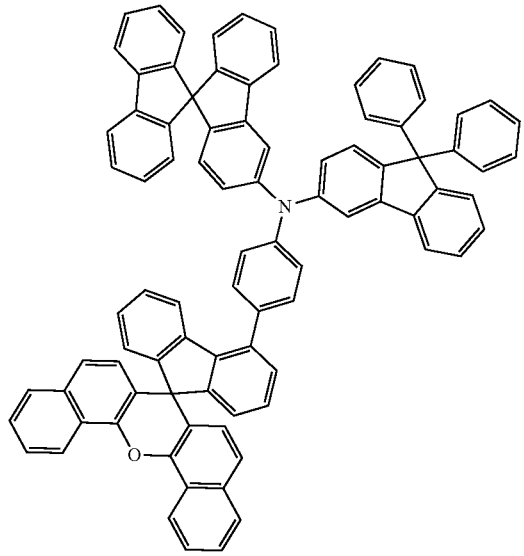
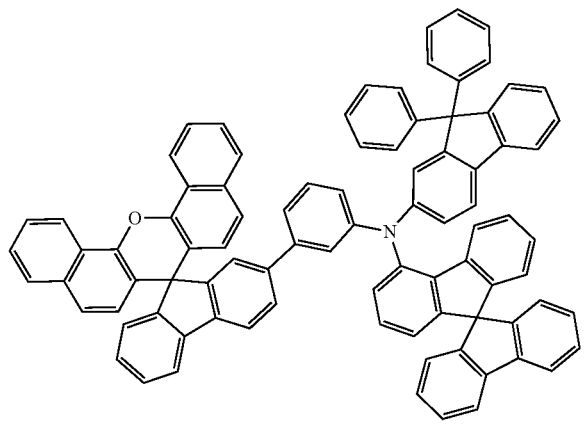
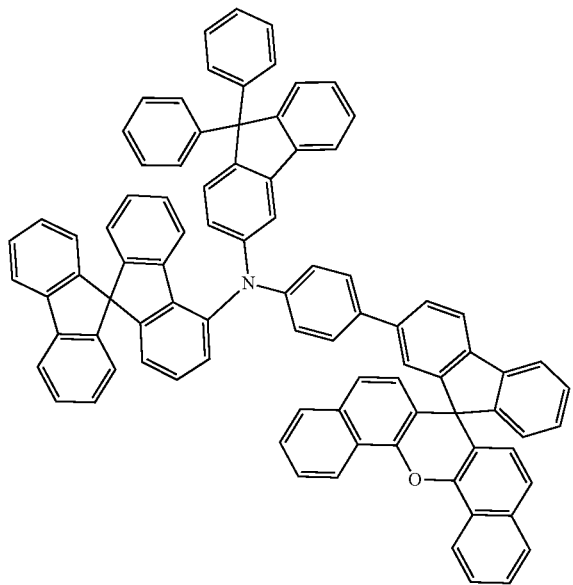
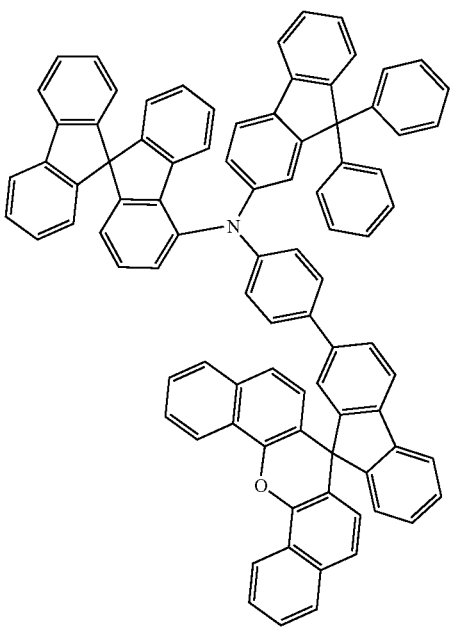

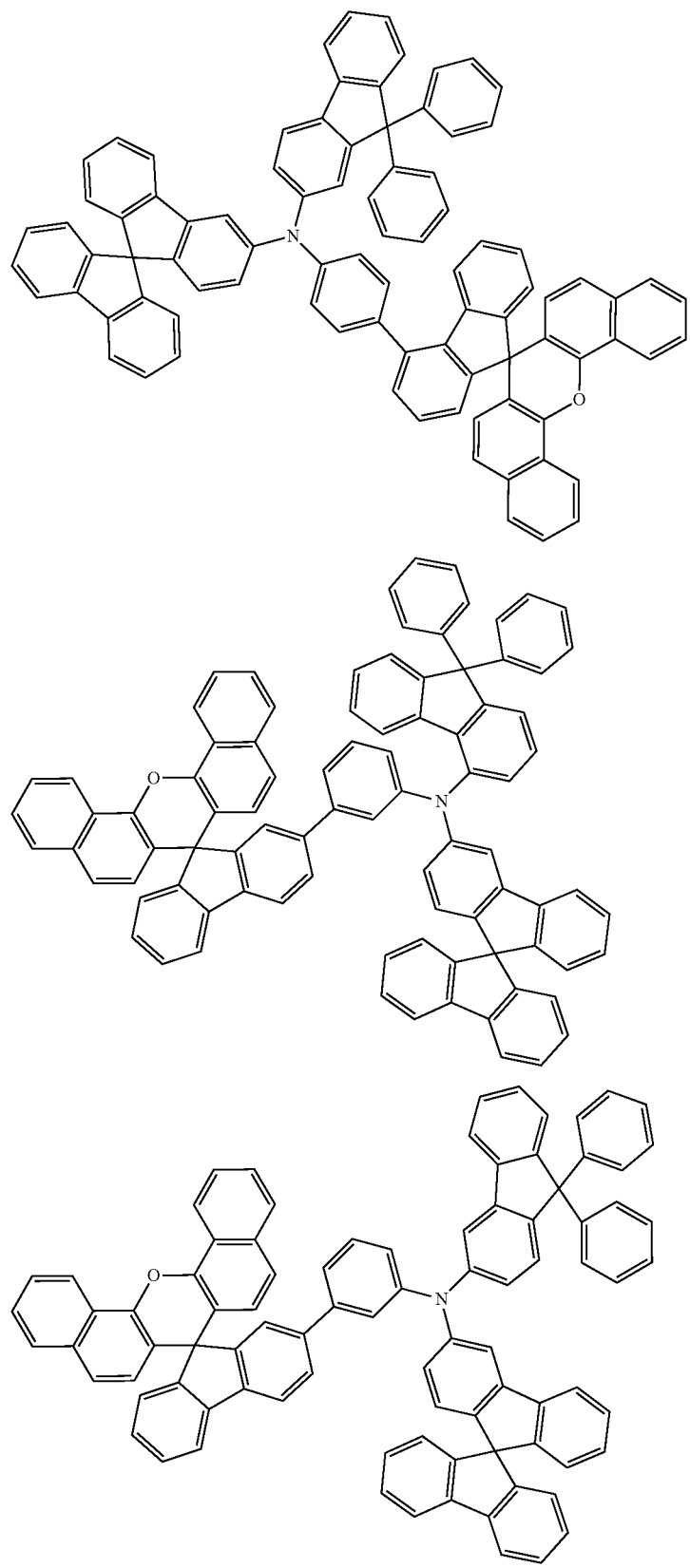

-continued
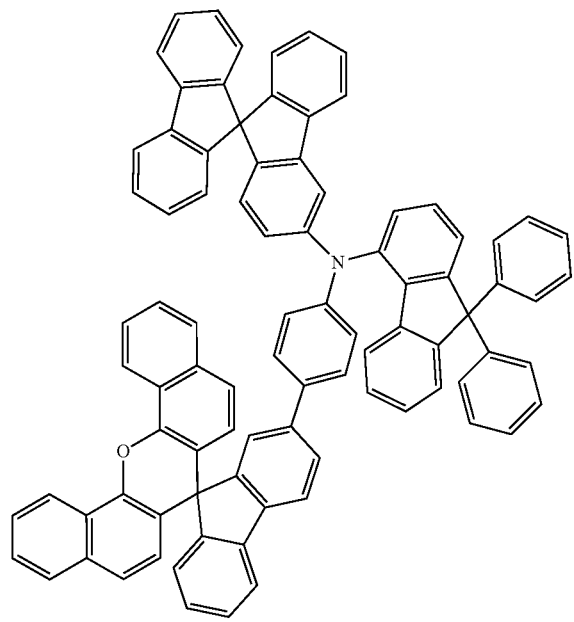
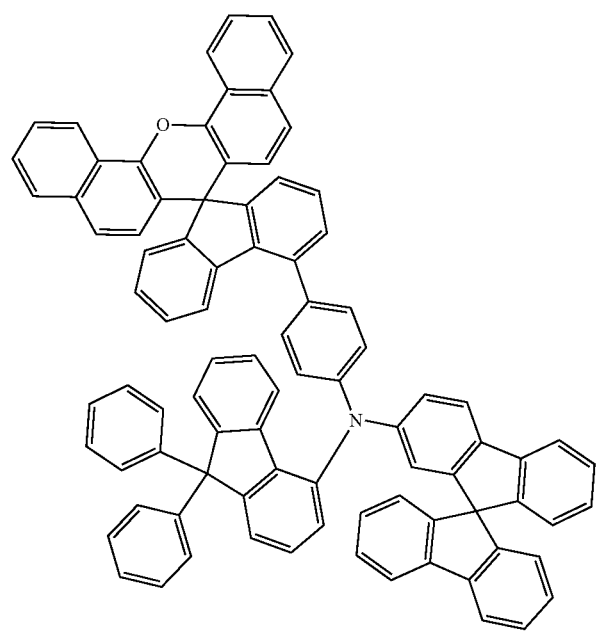

-continued
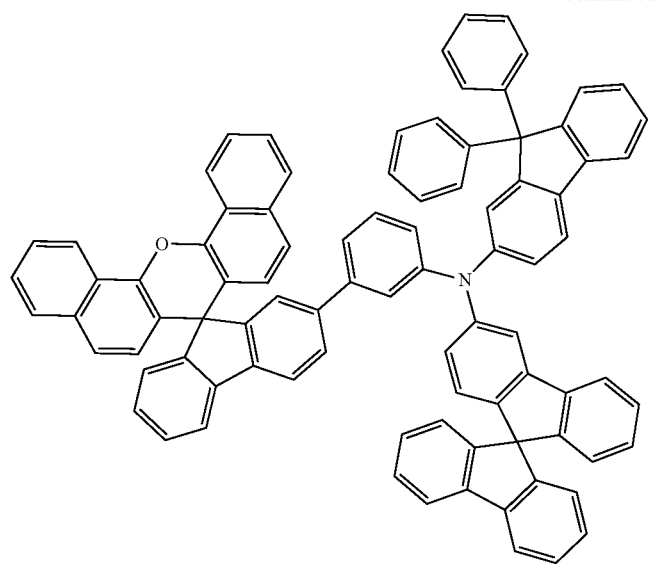
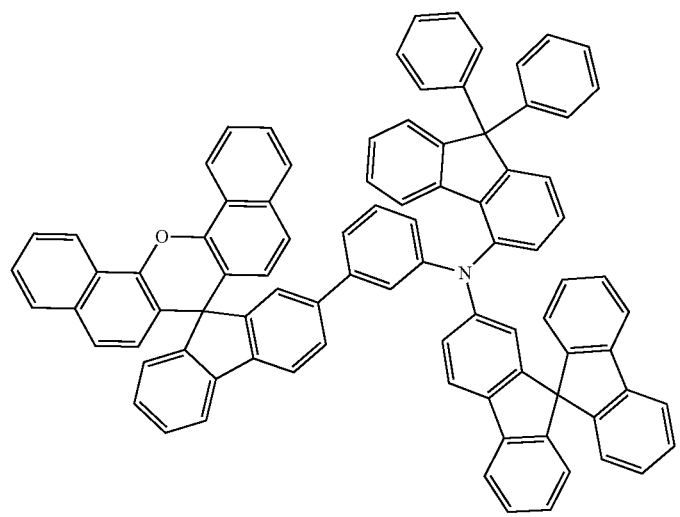
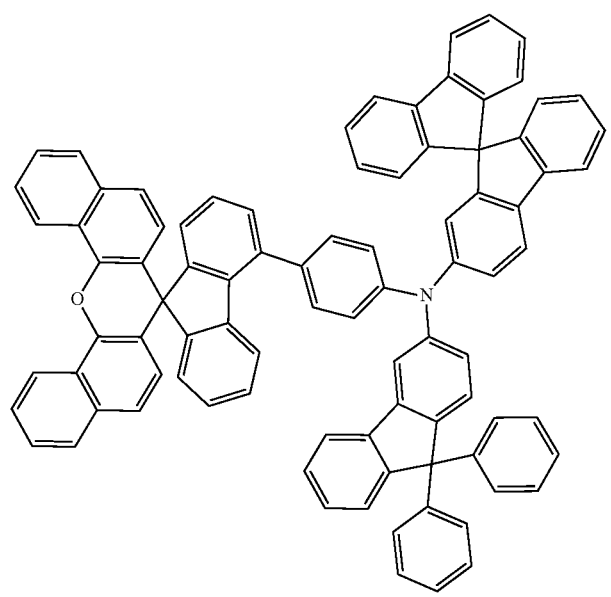

-continued
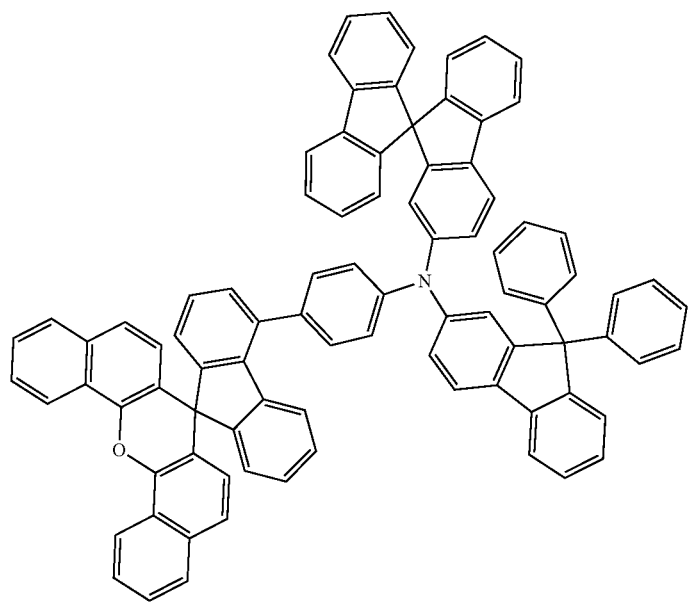
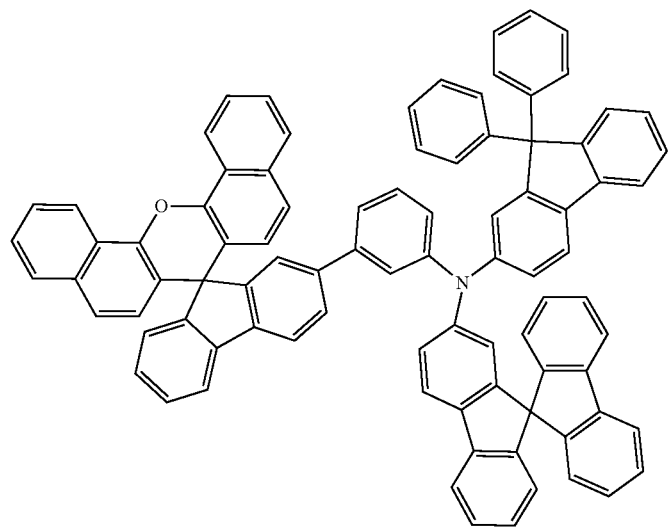
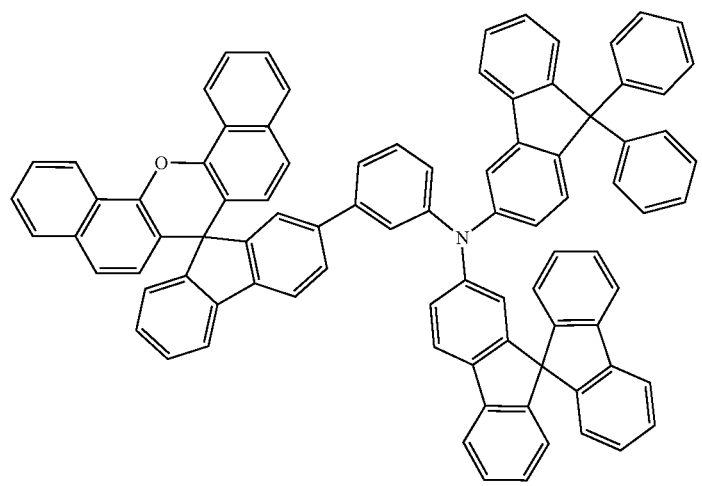

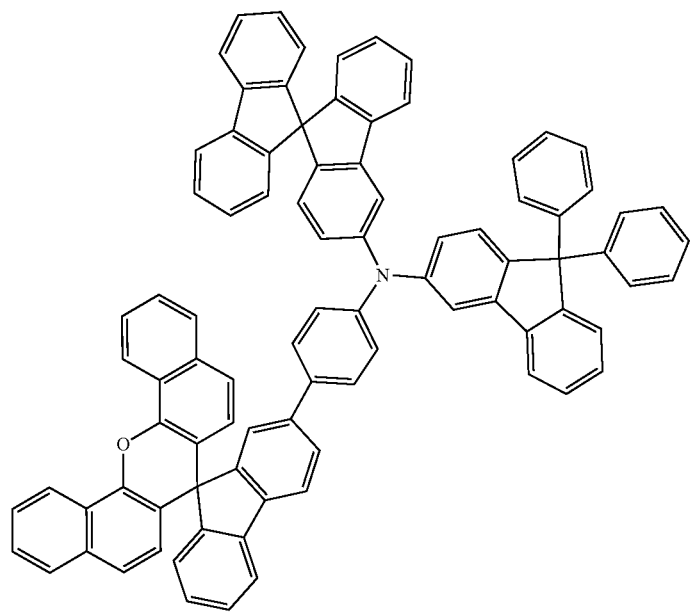
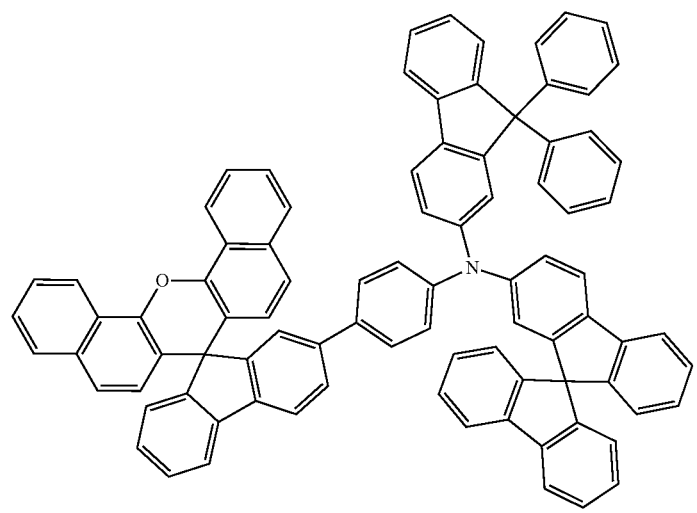

-continued
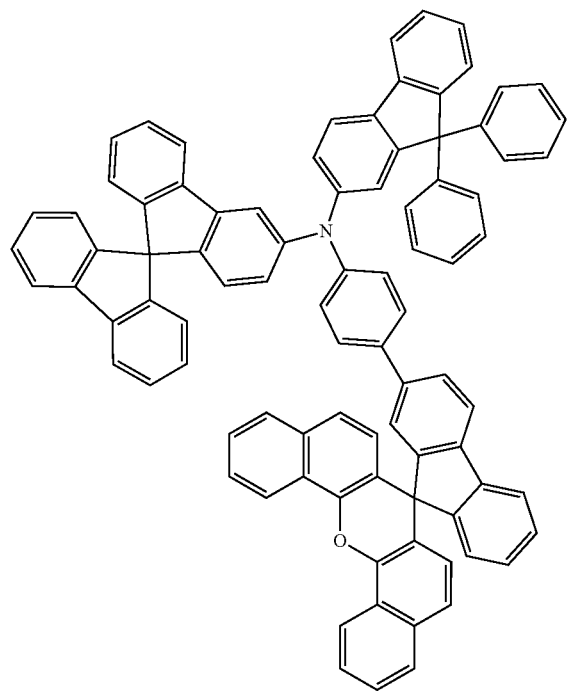
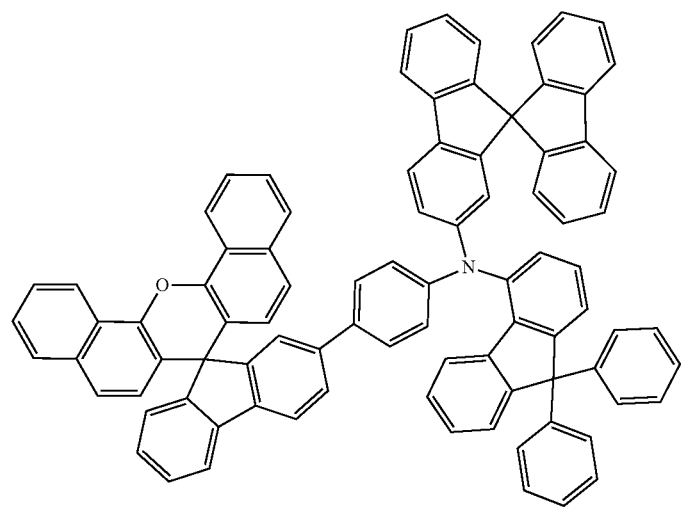

-continued
185
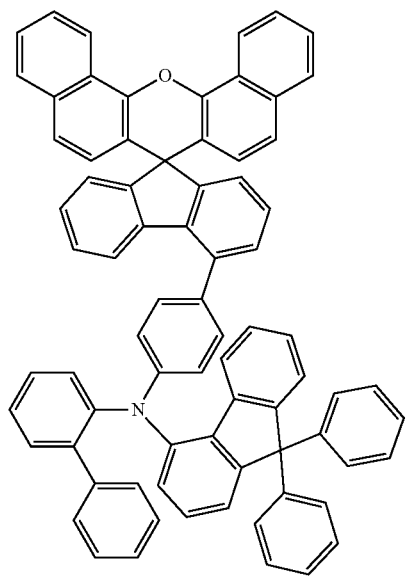
186
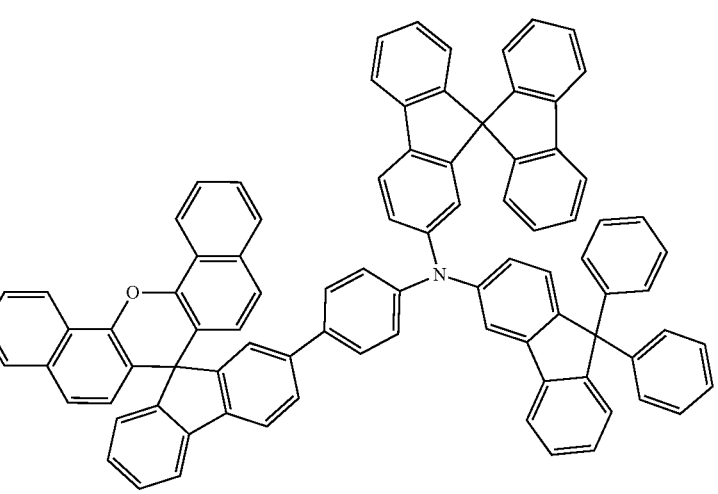
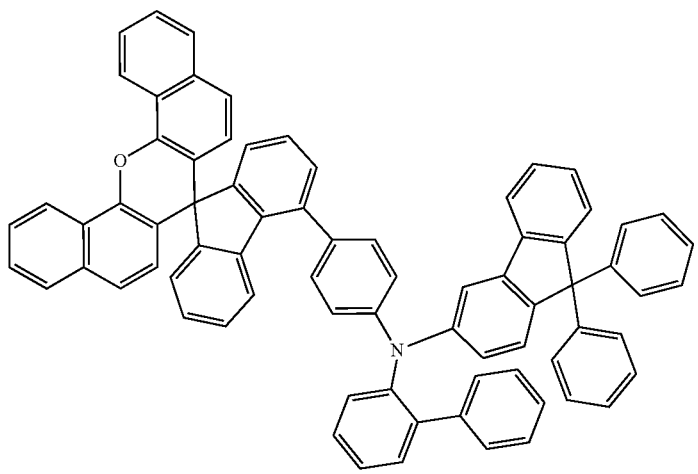
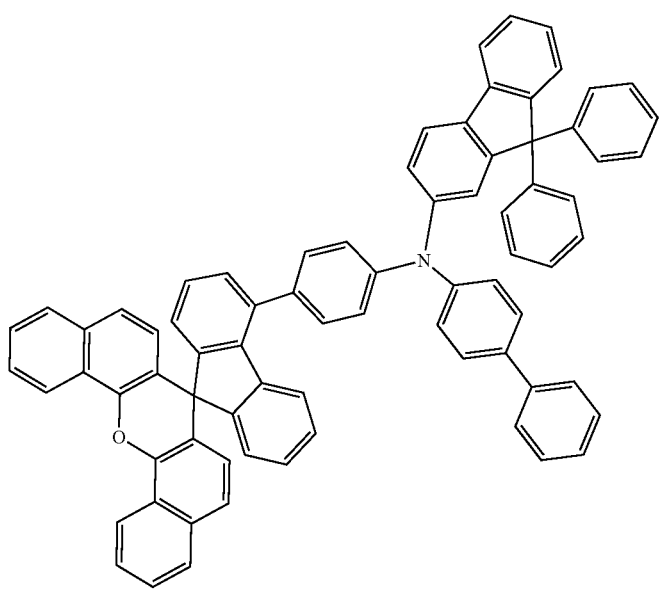

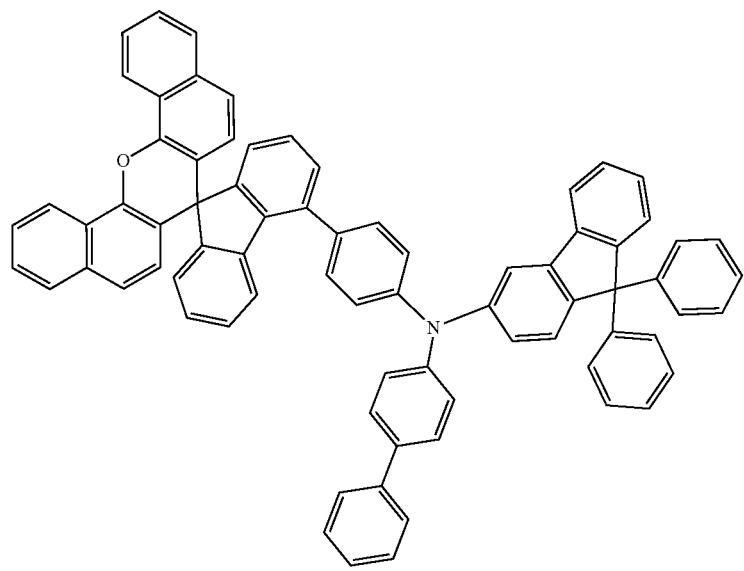
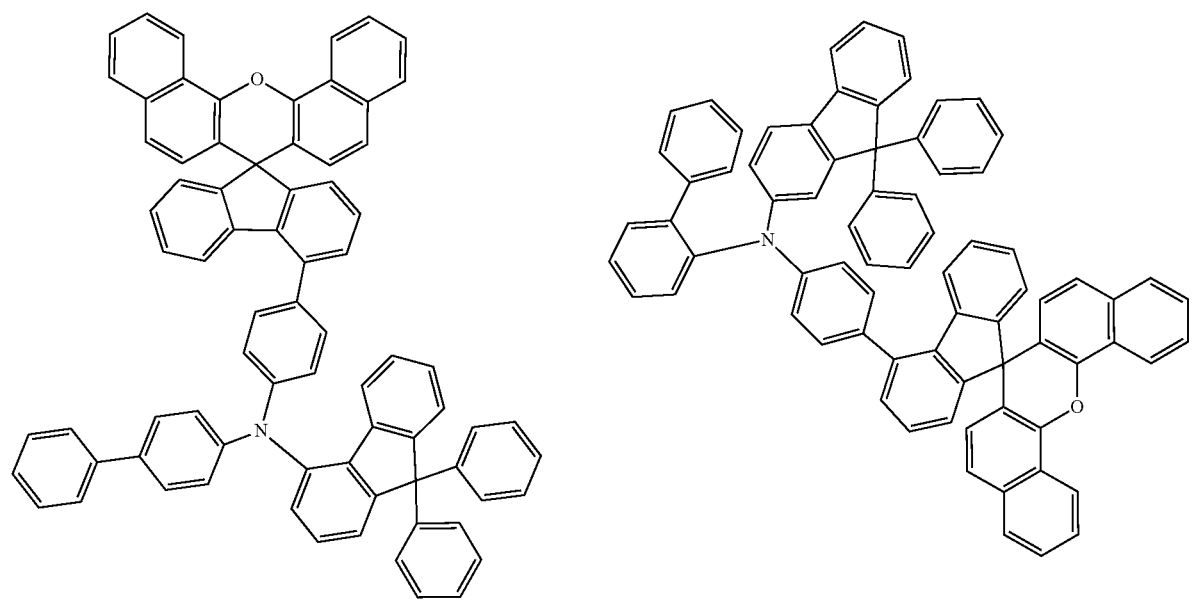

189
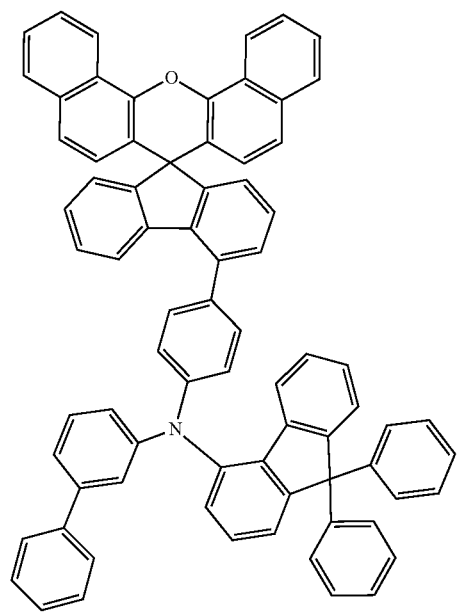
190
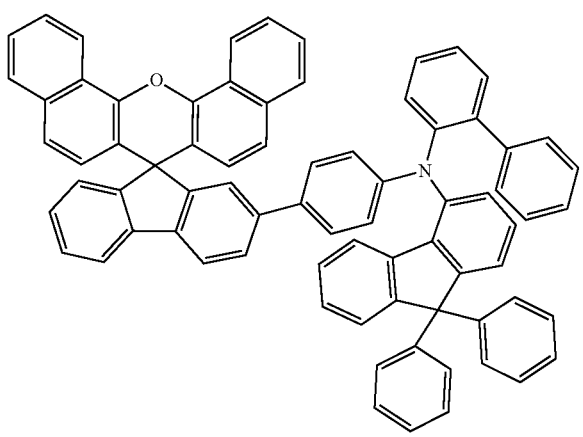
-continued
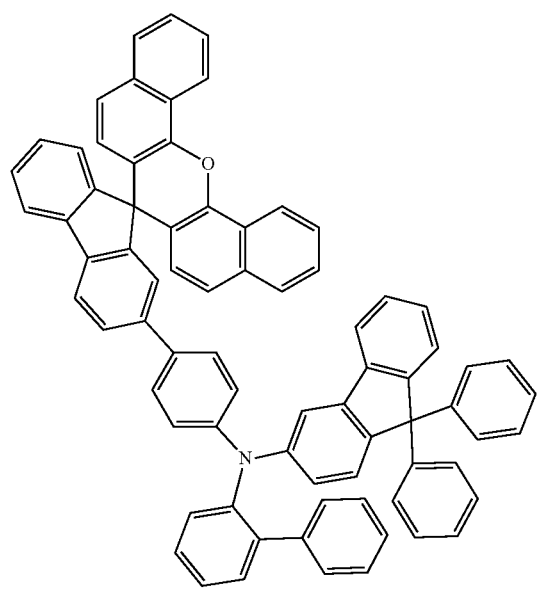
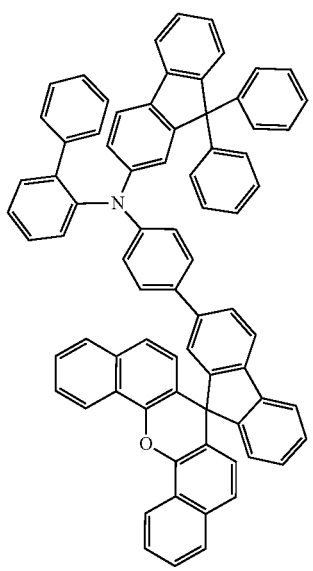

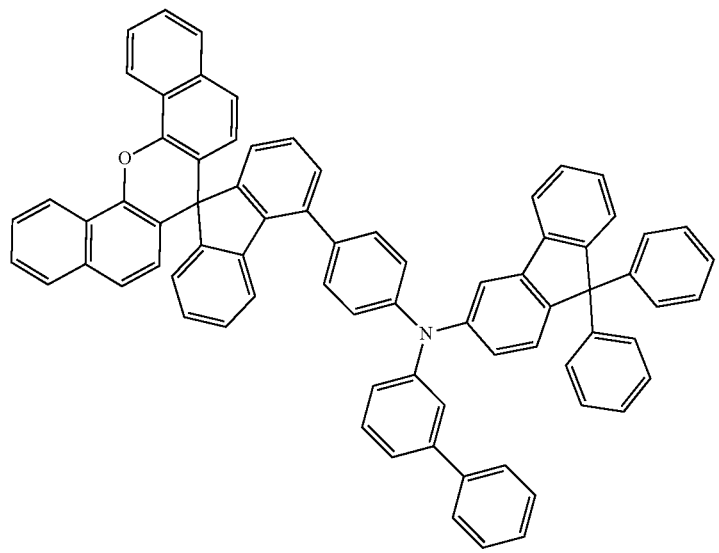
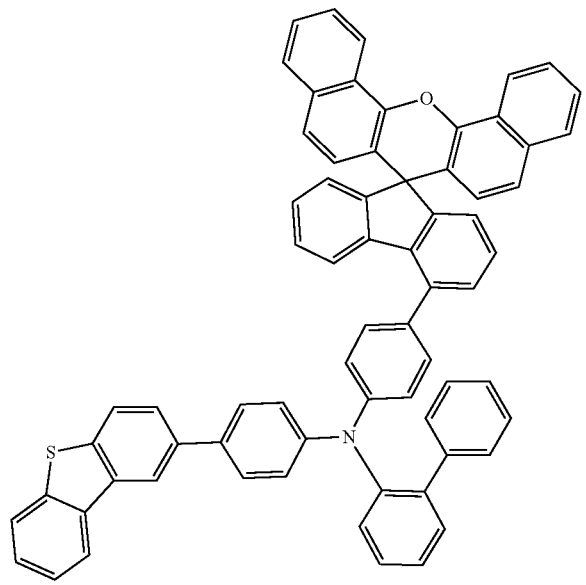
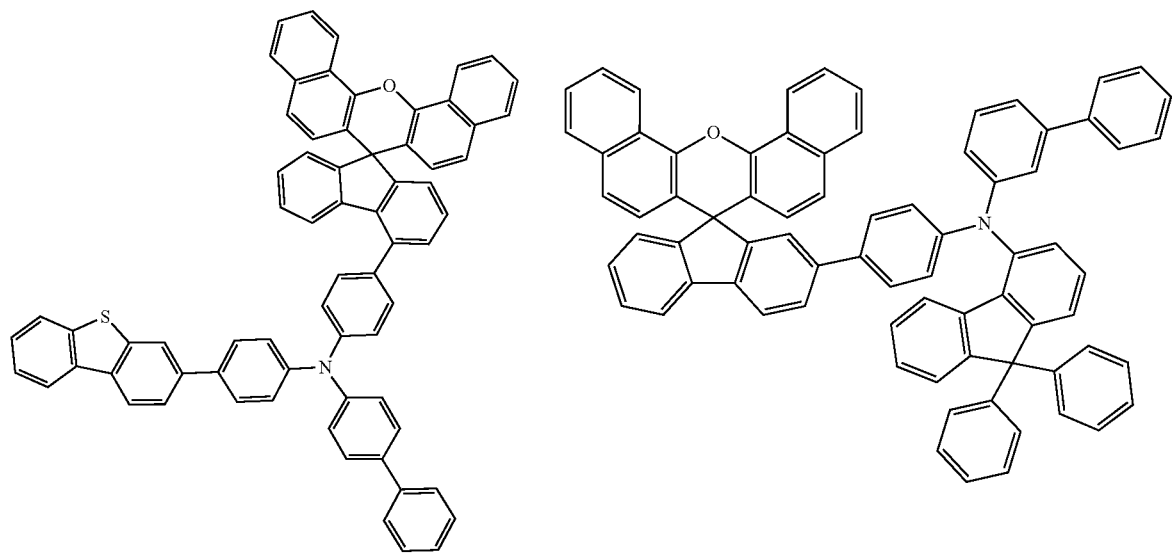

-continued
193
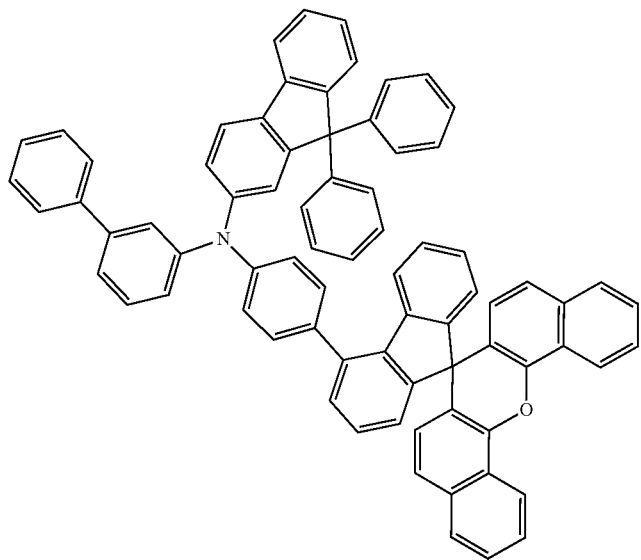
194
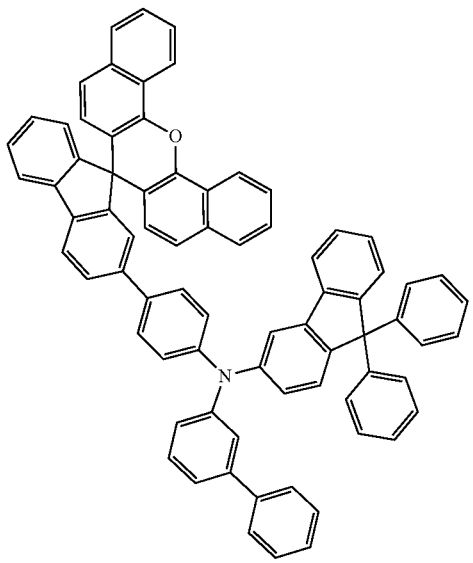
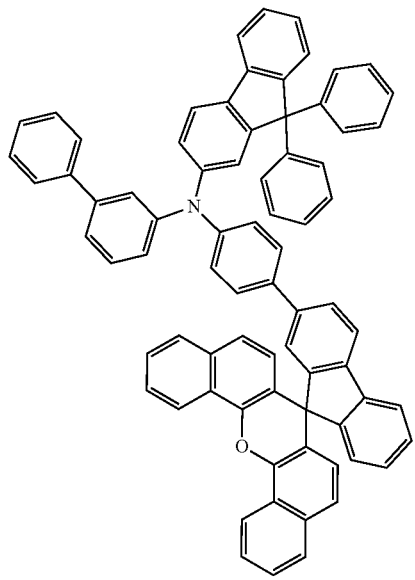
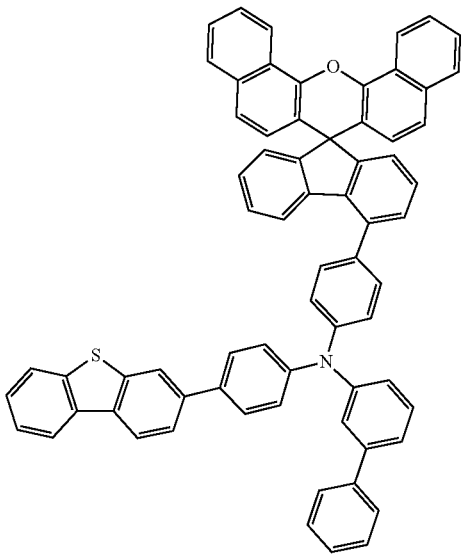
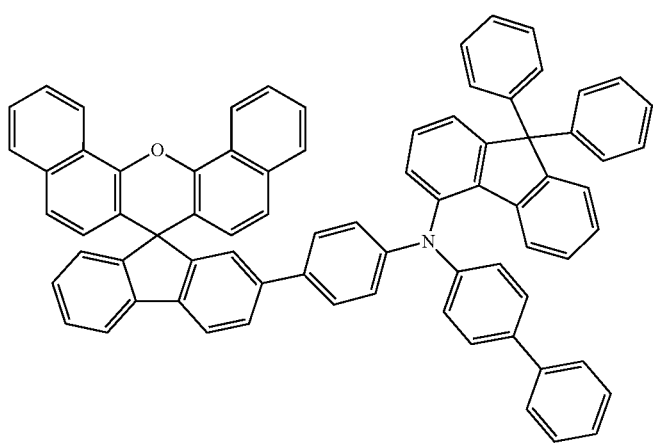
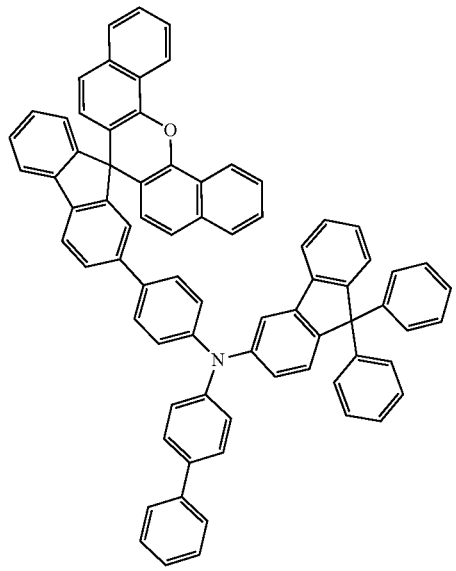

| 195 | 196 |
|---|---|
| 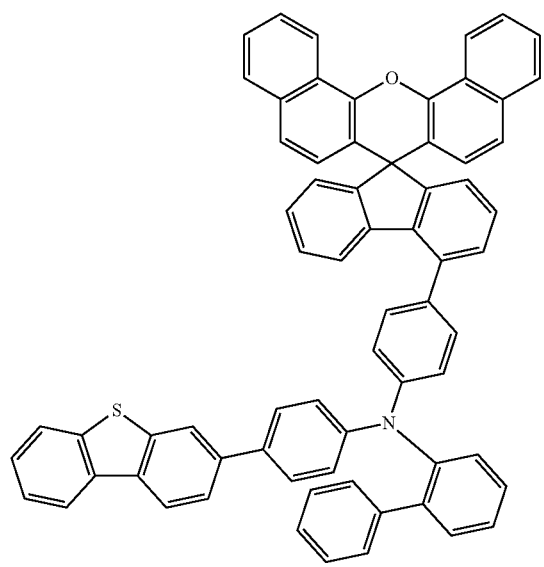 | 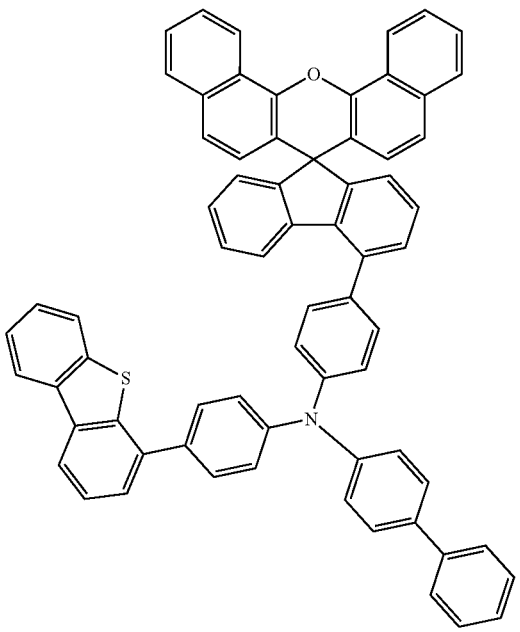 |
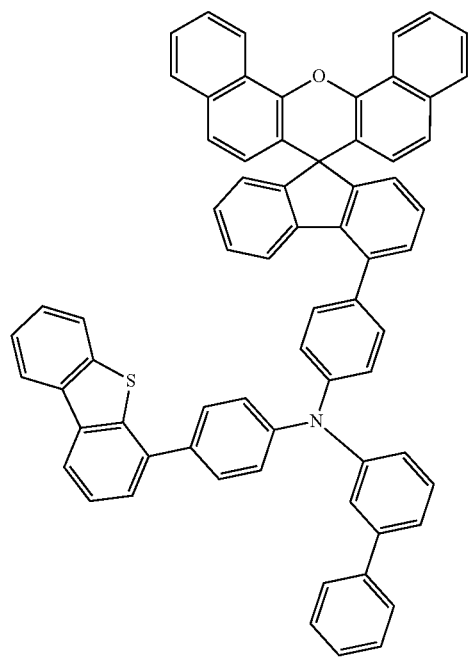

197
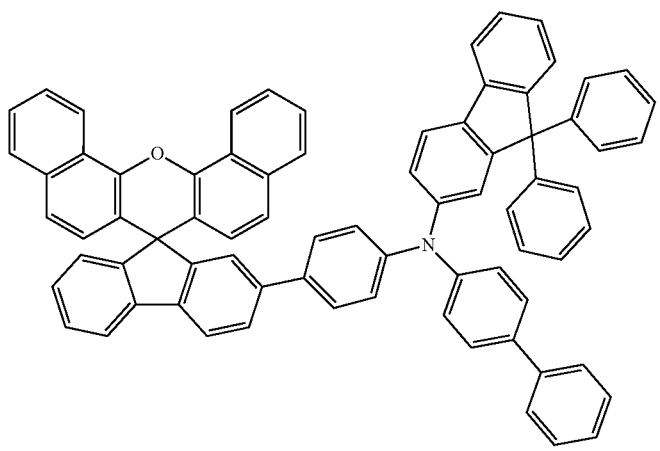
198
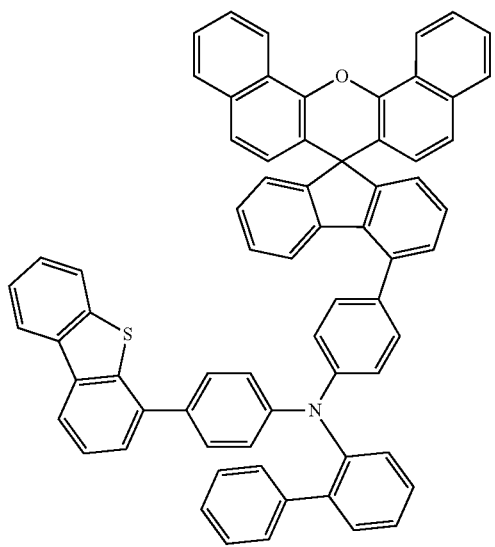
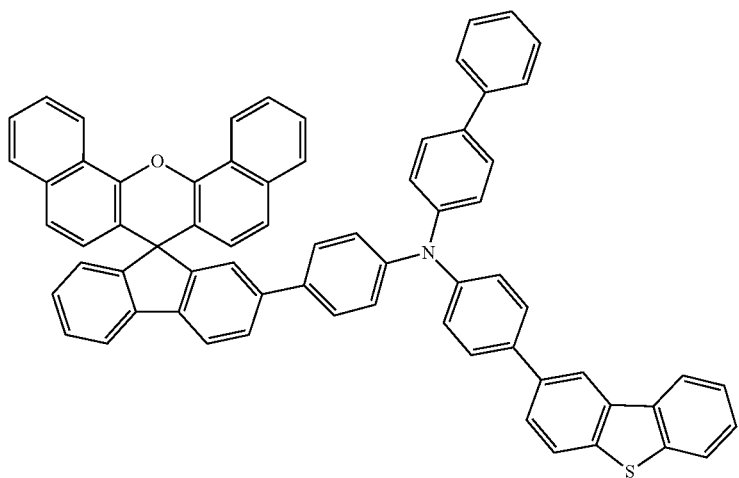
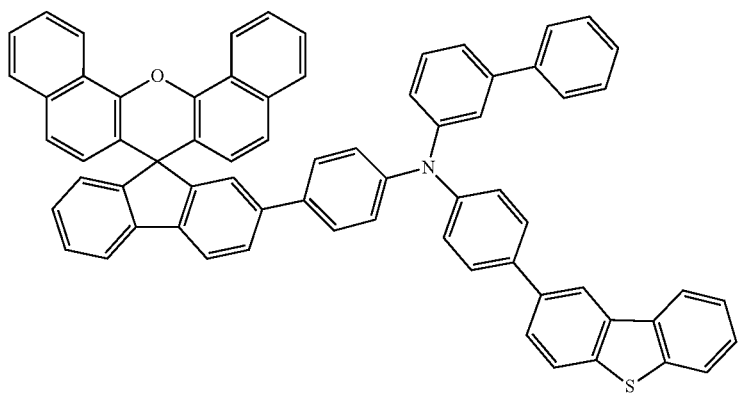

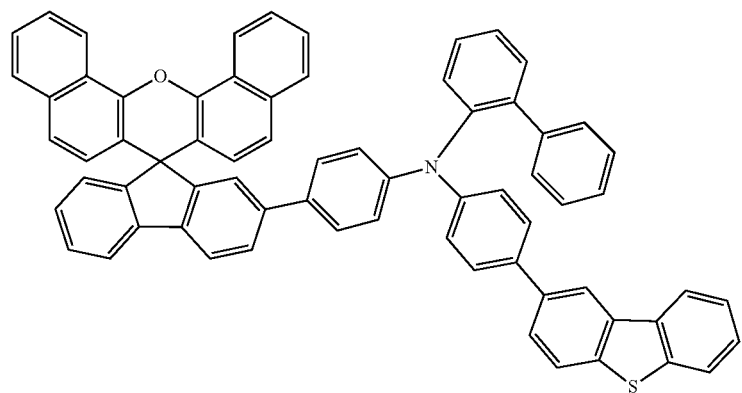
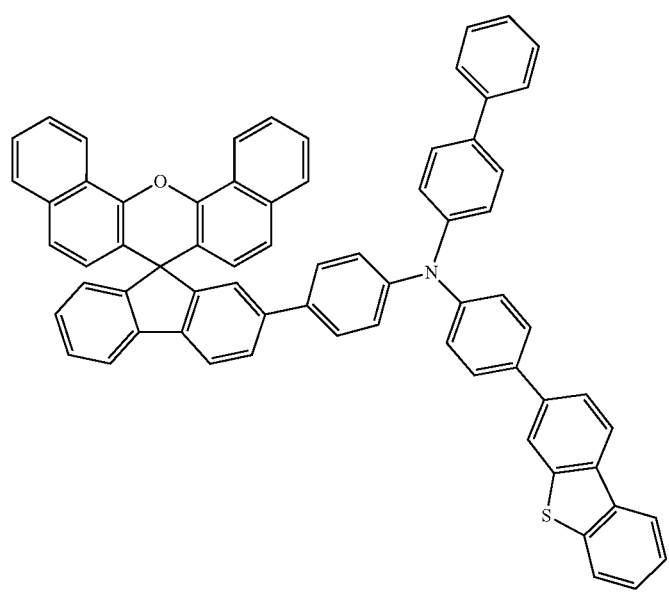
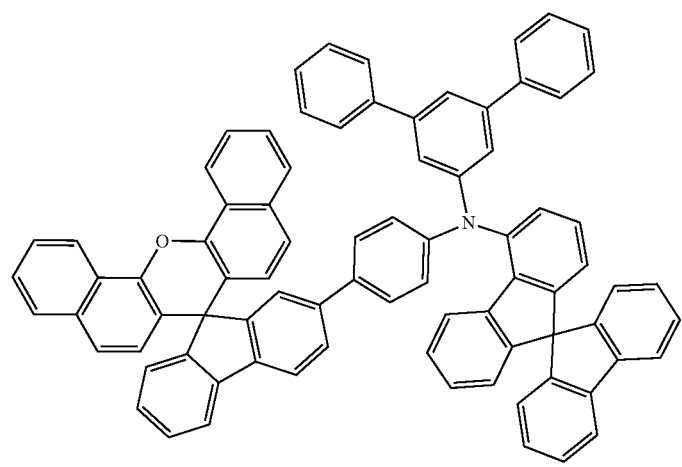

-continued
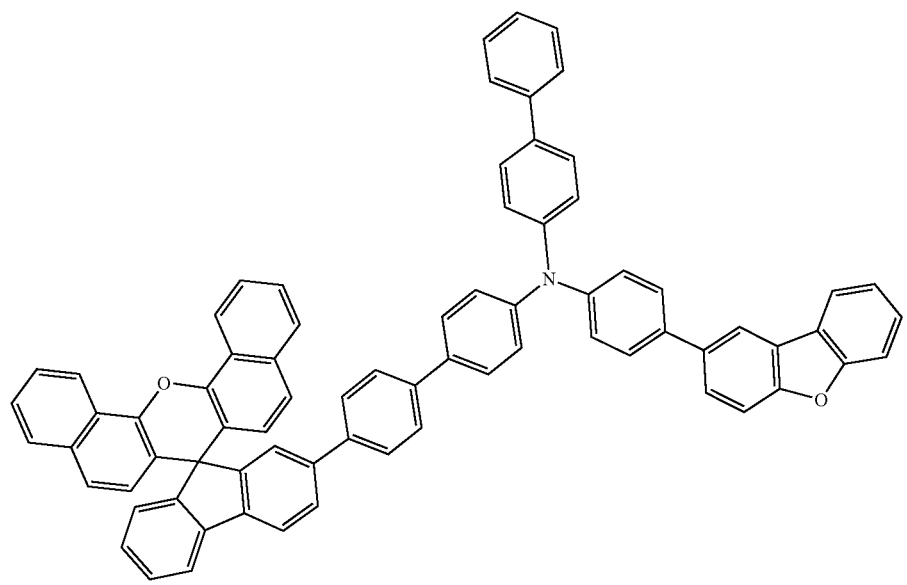
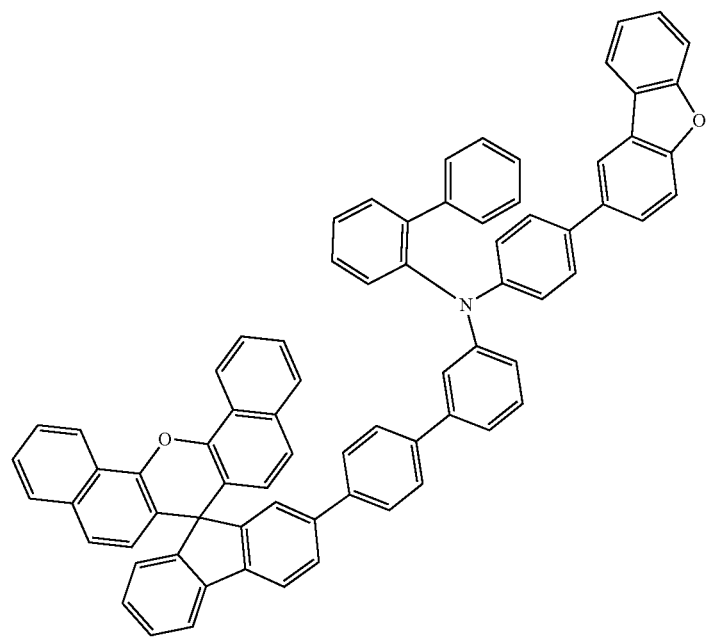

-continued
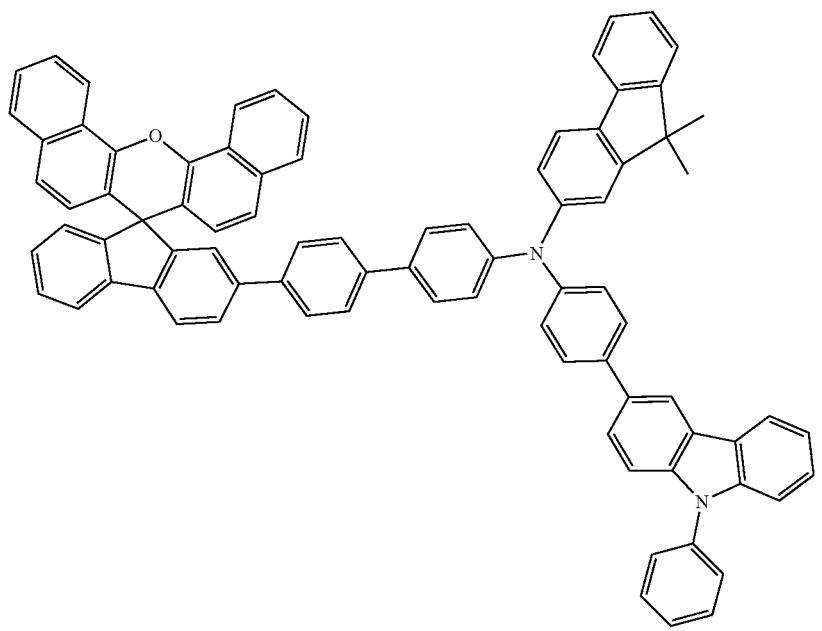
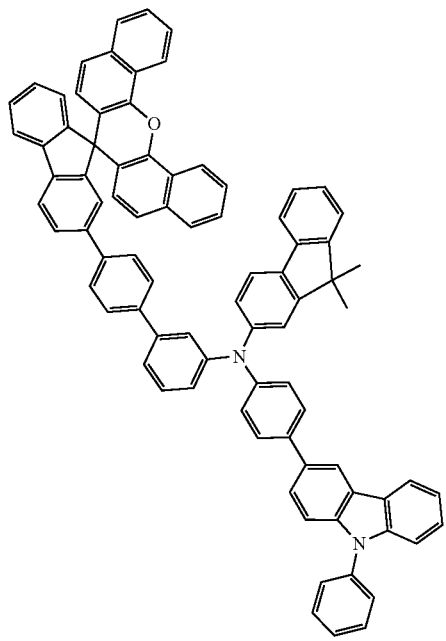
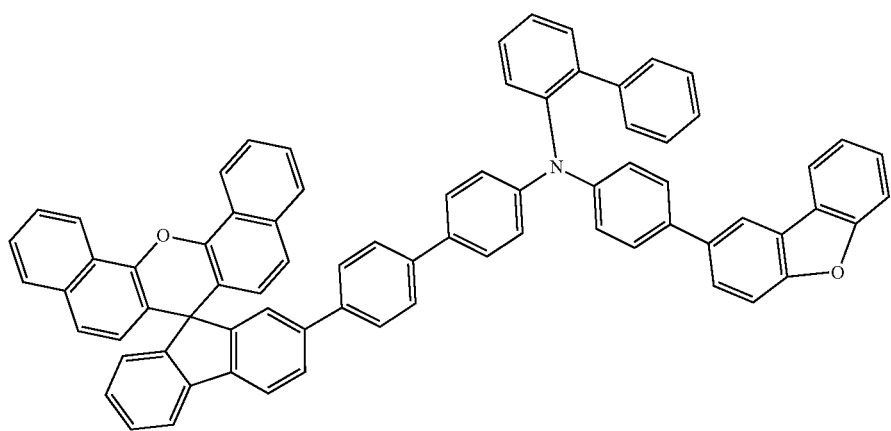

-continued
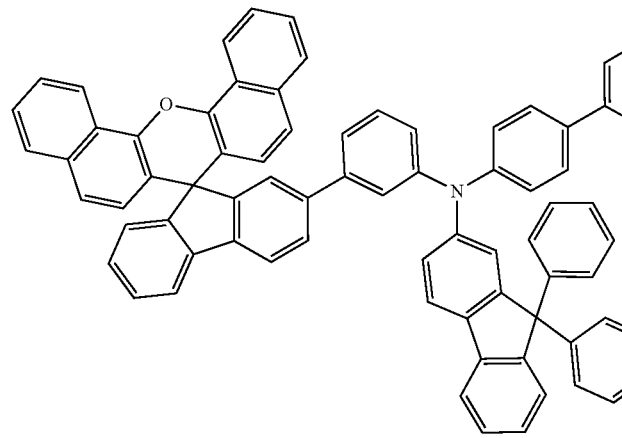
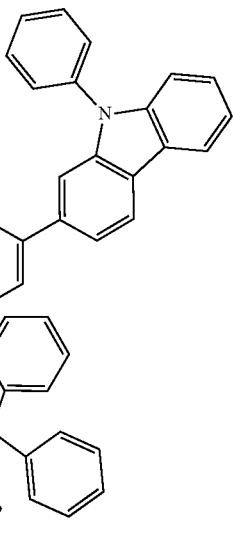
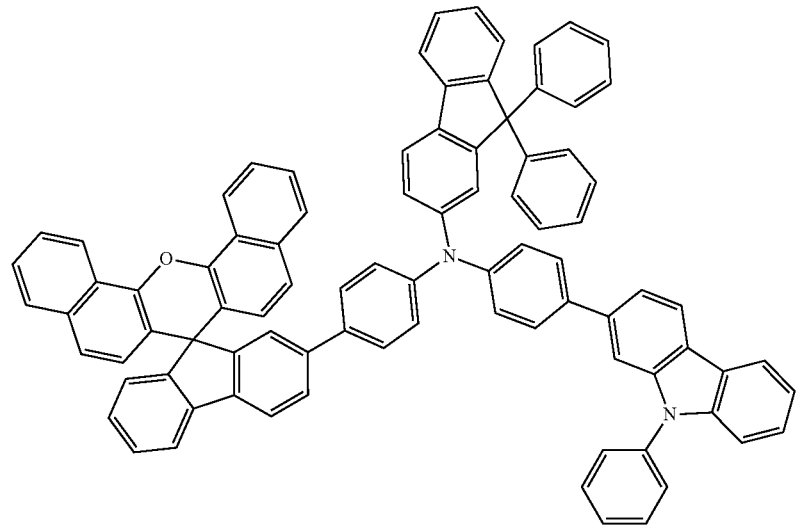
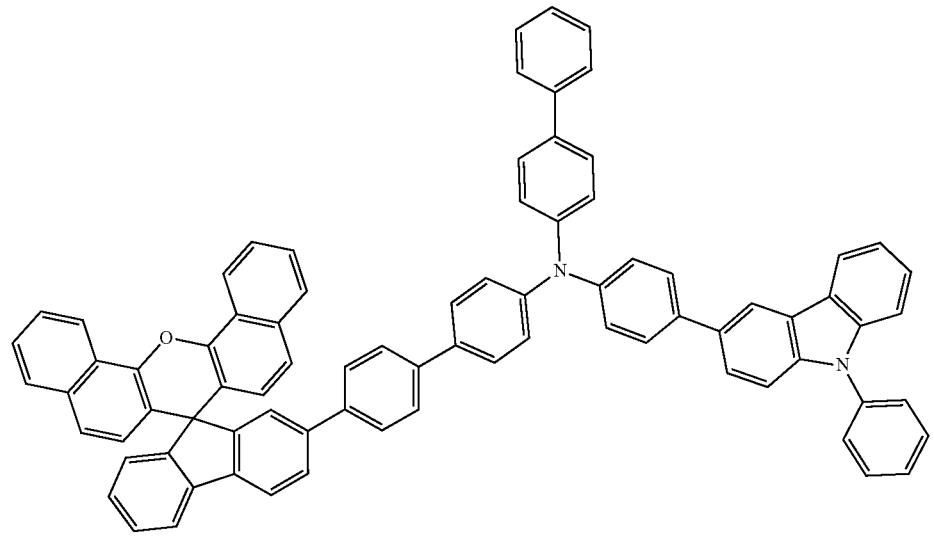

-continued
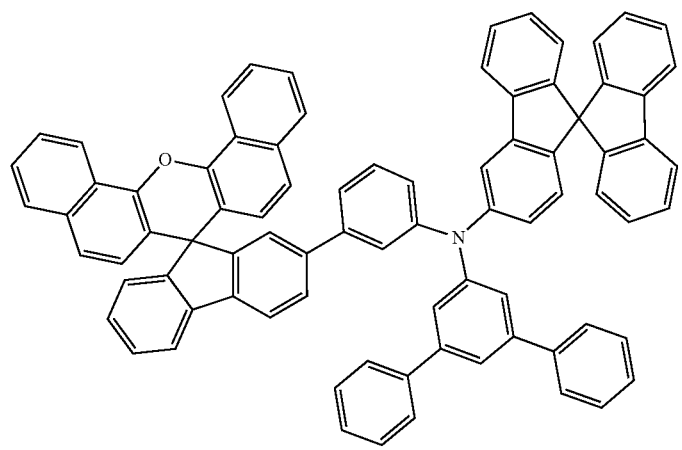
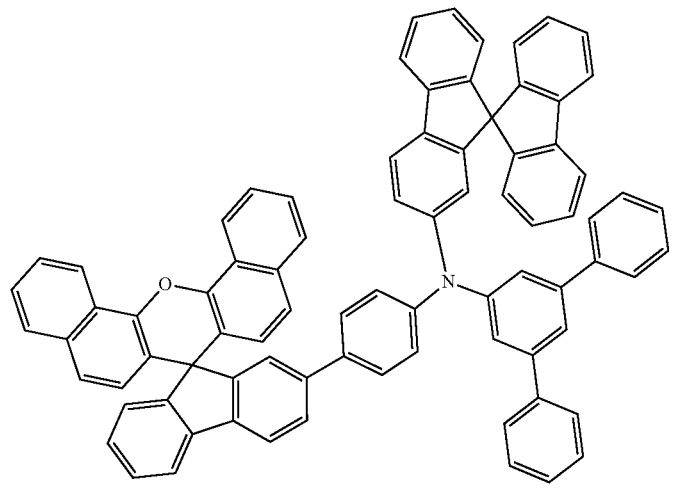
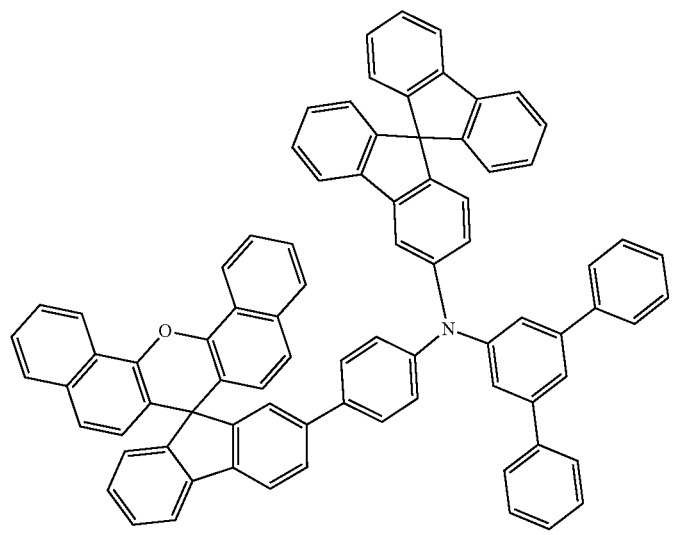

-continued
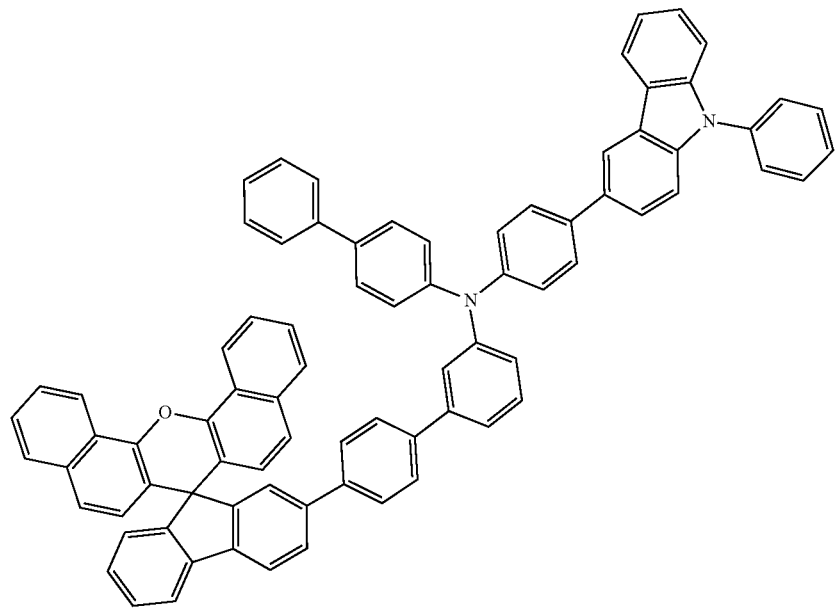
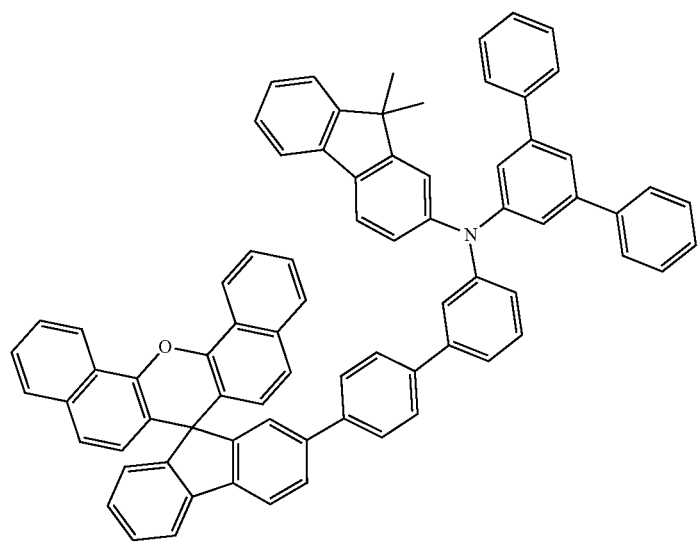
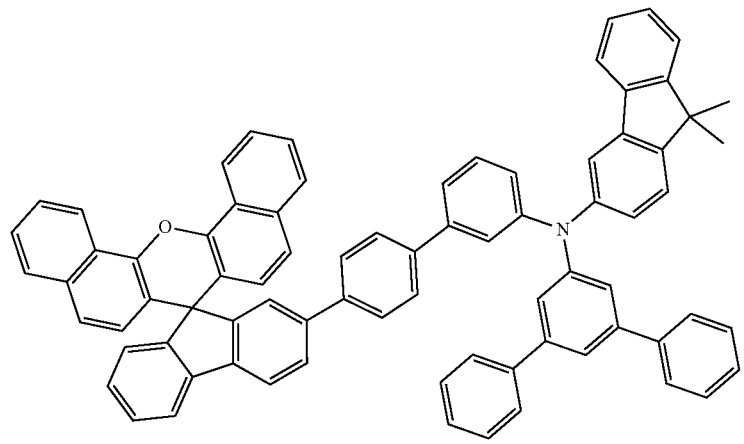

-continued
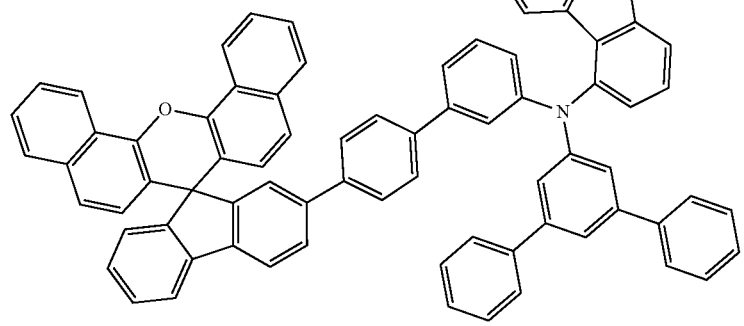
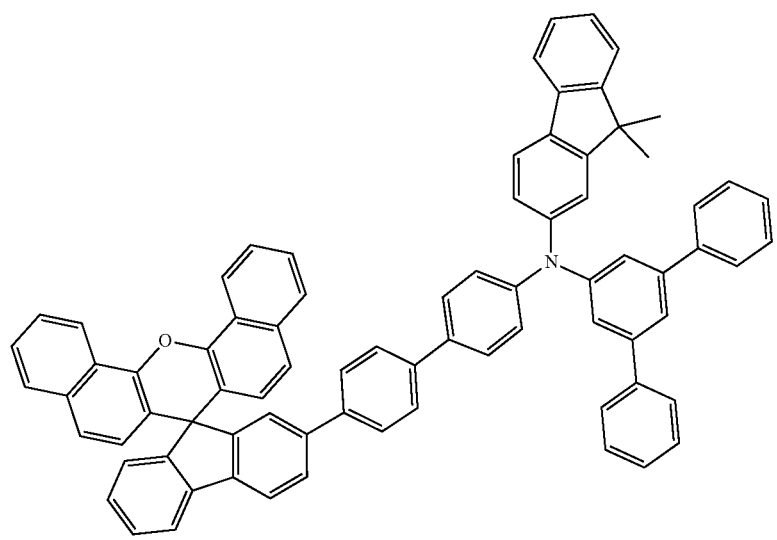
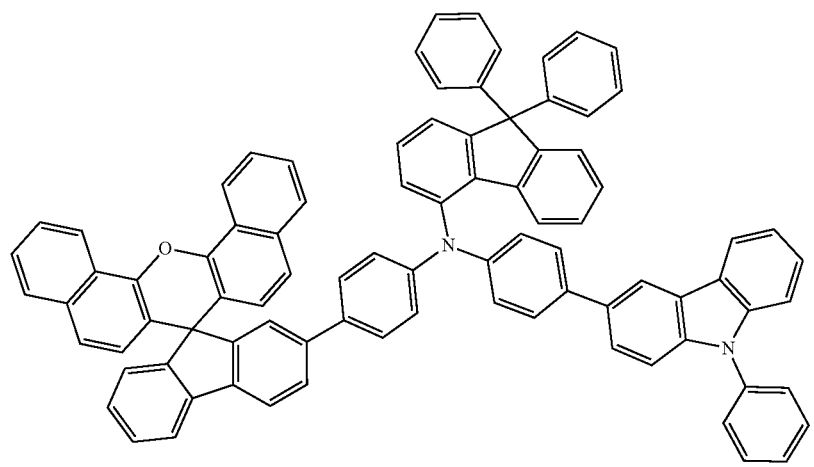

-continued
213
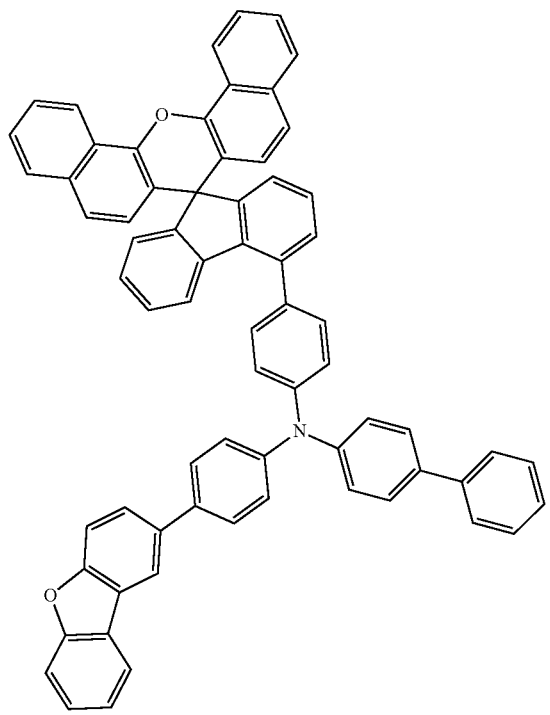
214
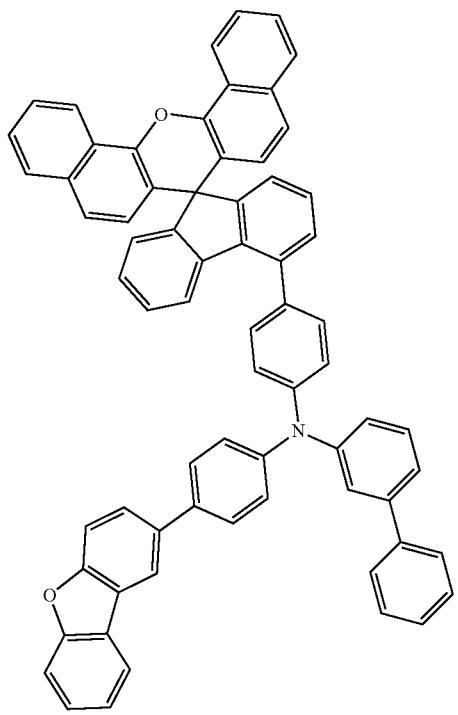
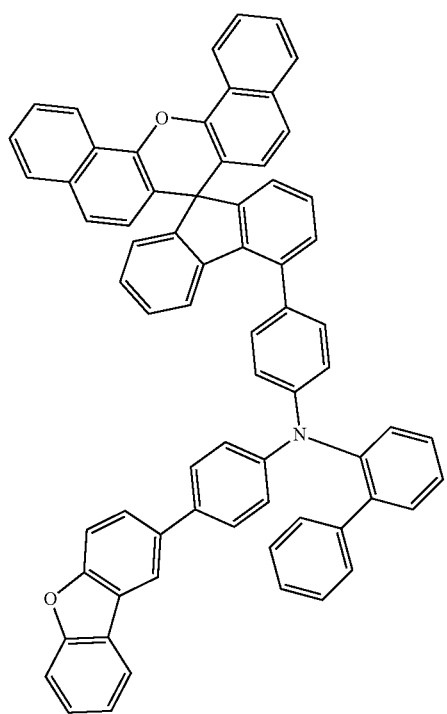

-continued
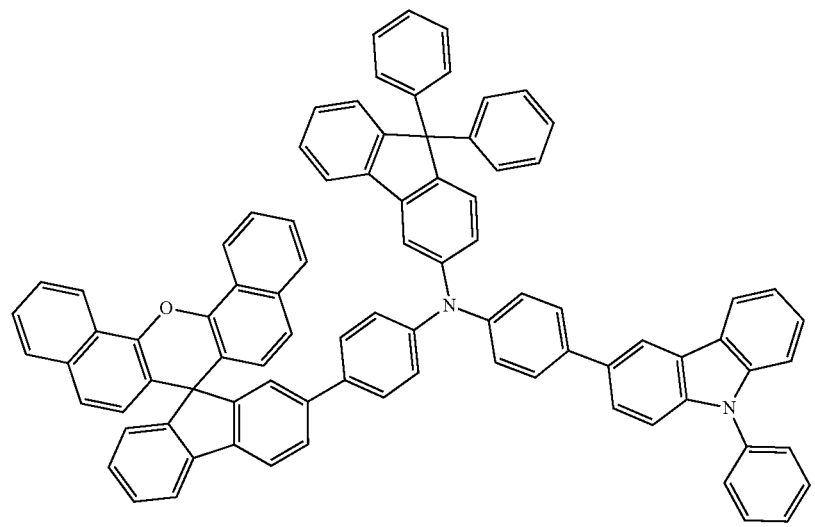
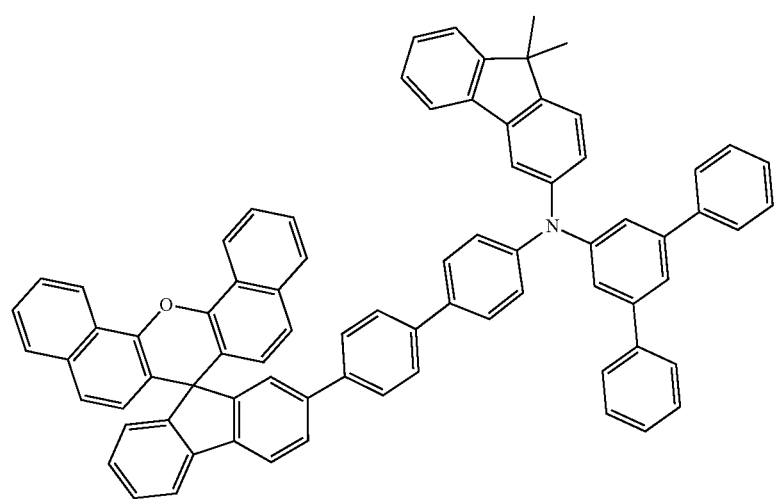
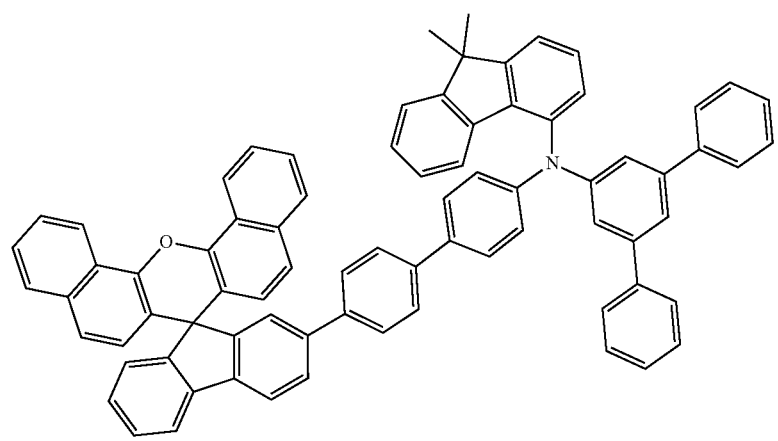

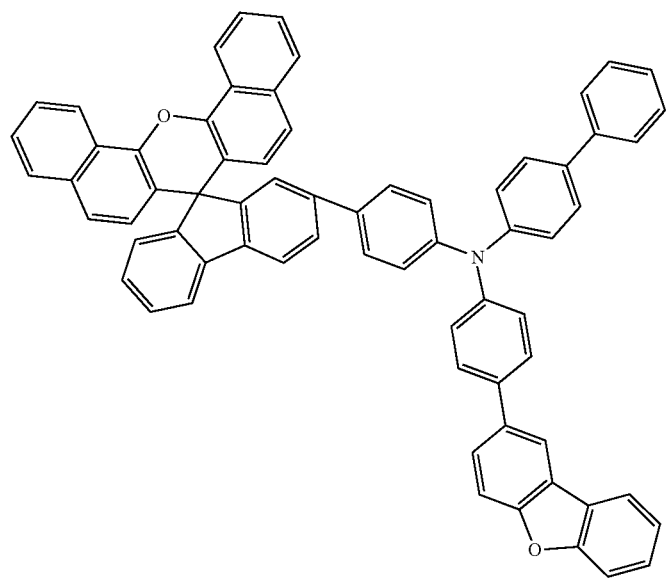
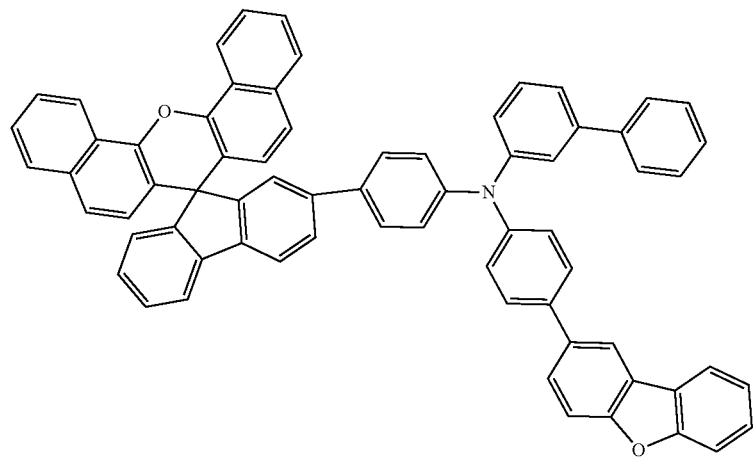
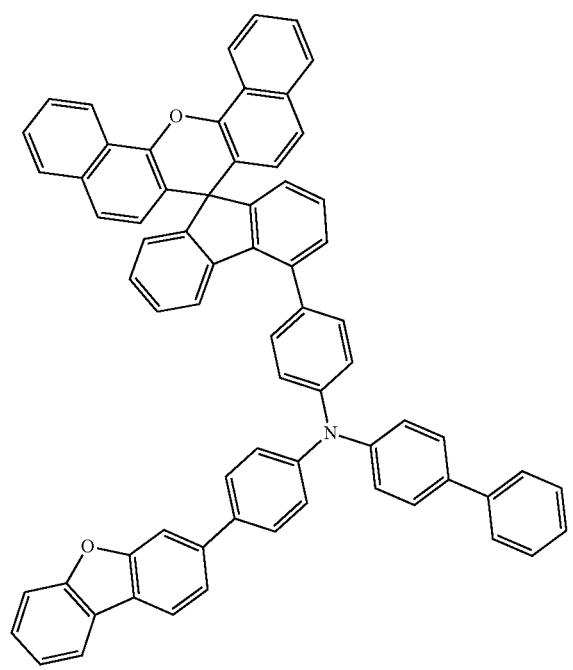

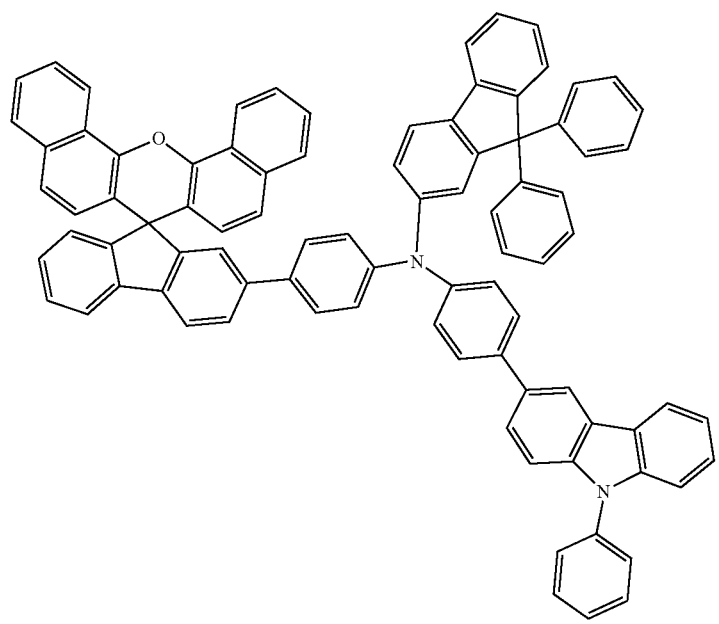
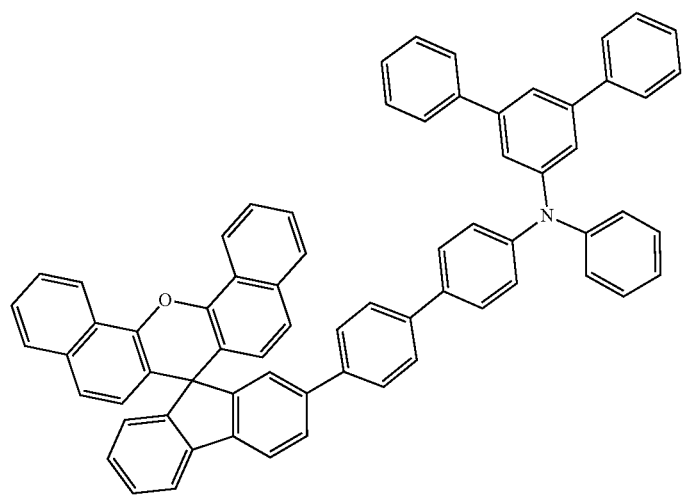
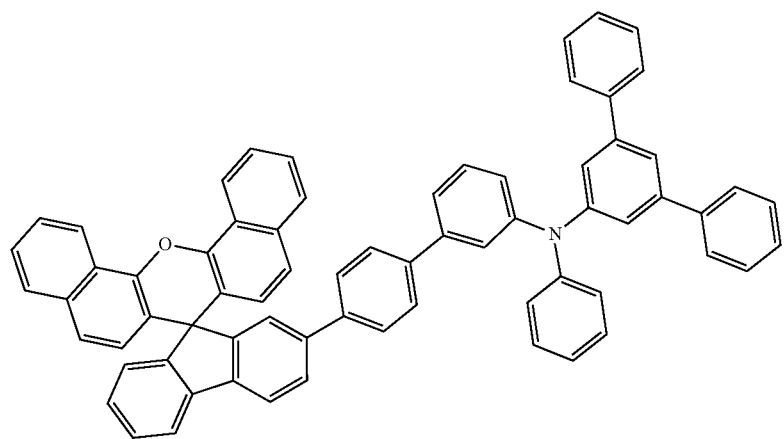

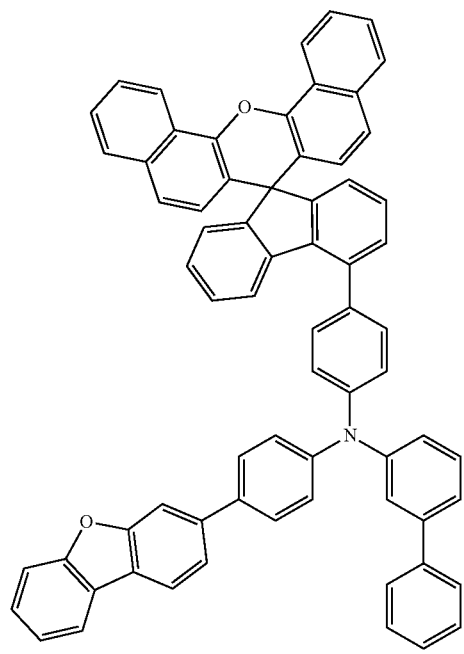
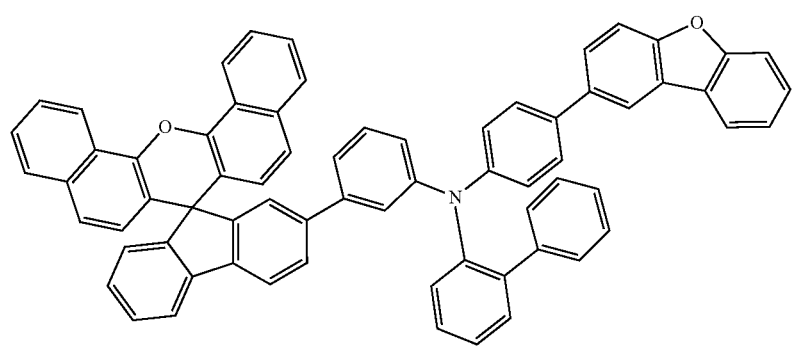
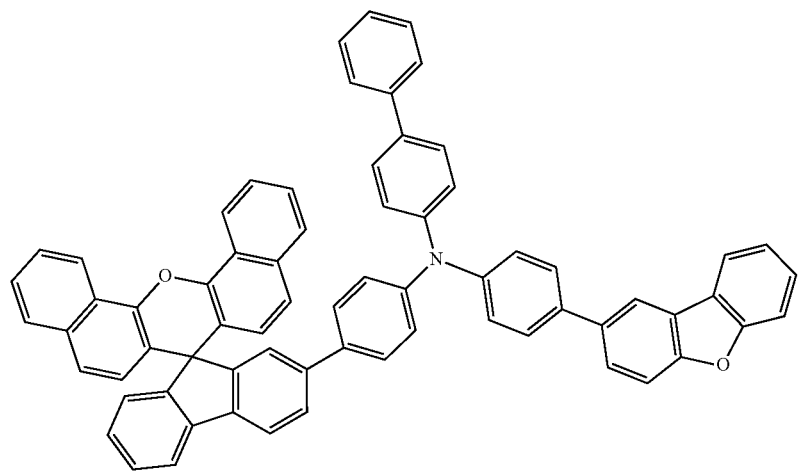

-continued
223
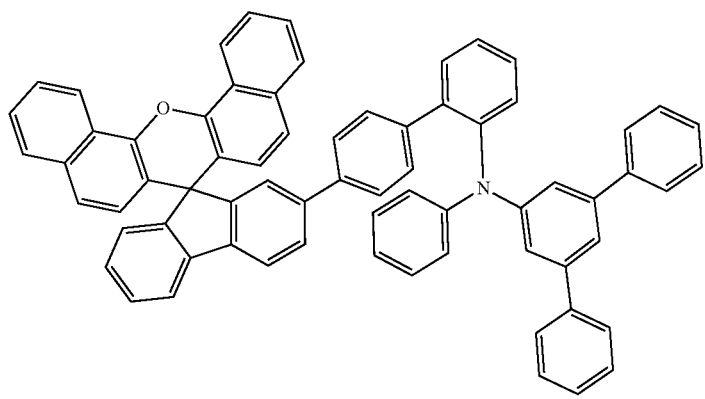
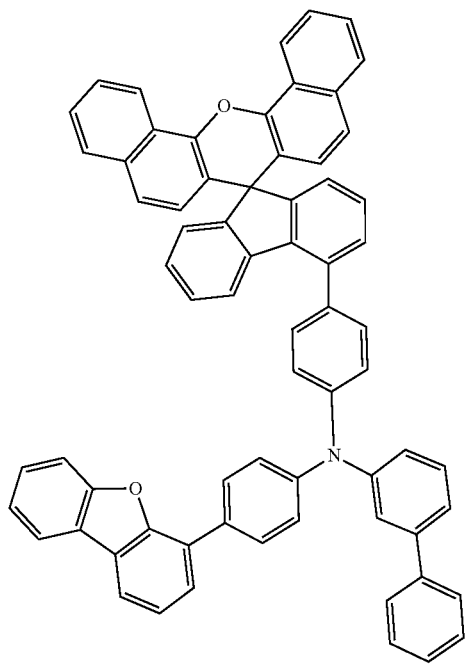
224
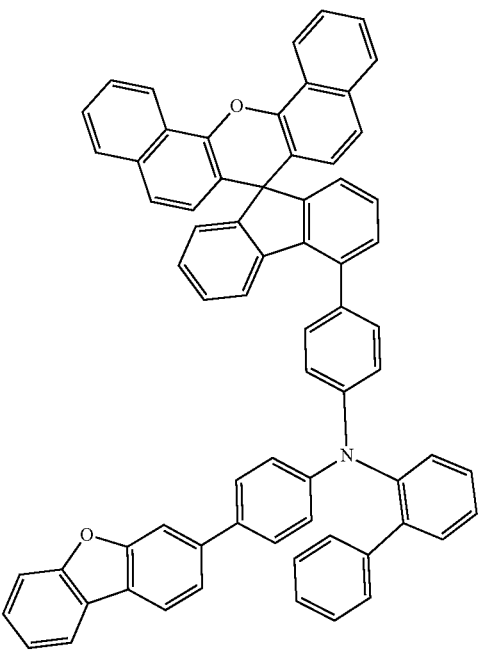
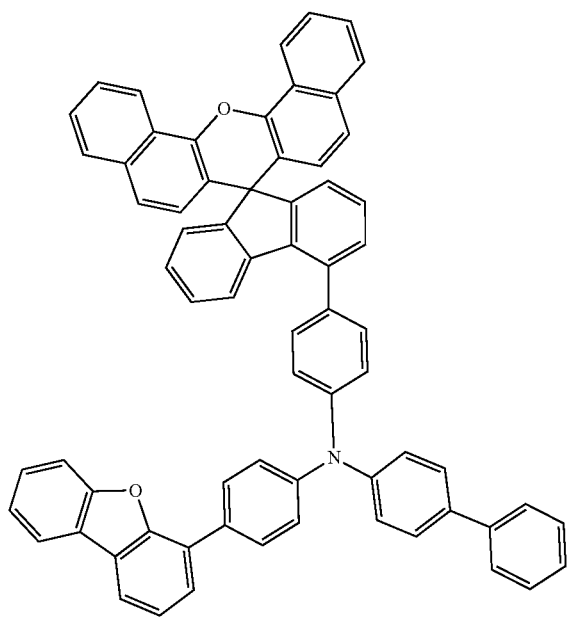

-continued
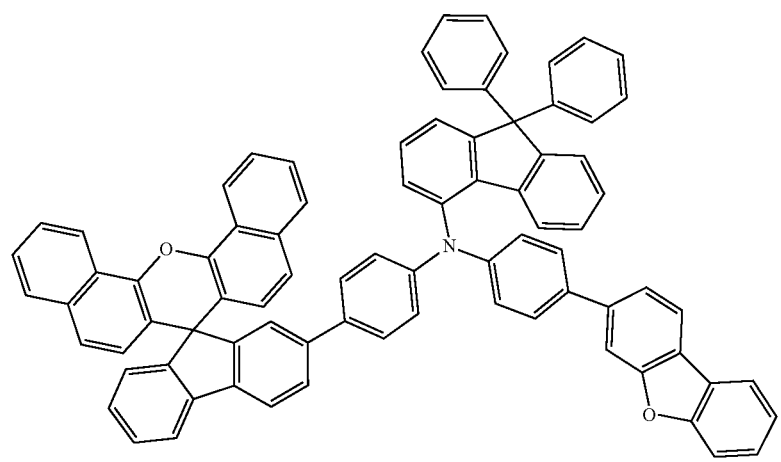
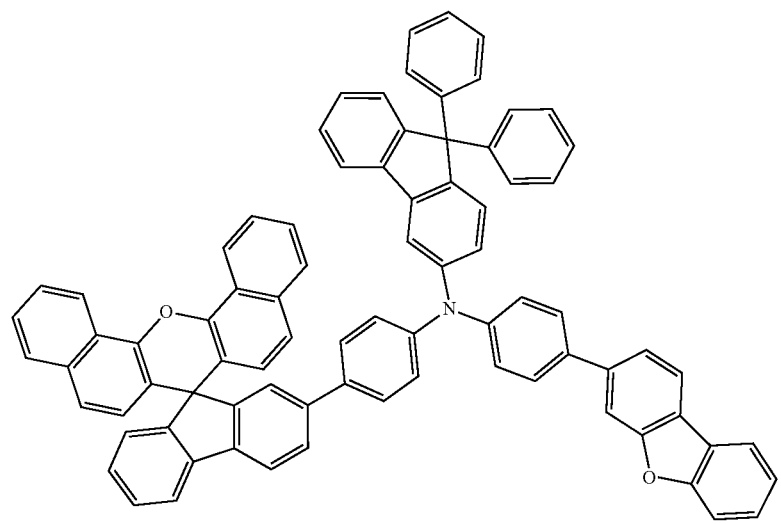
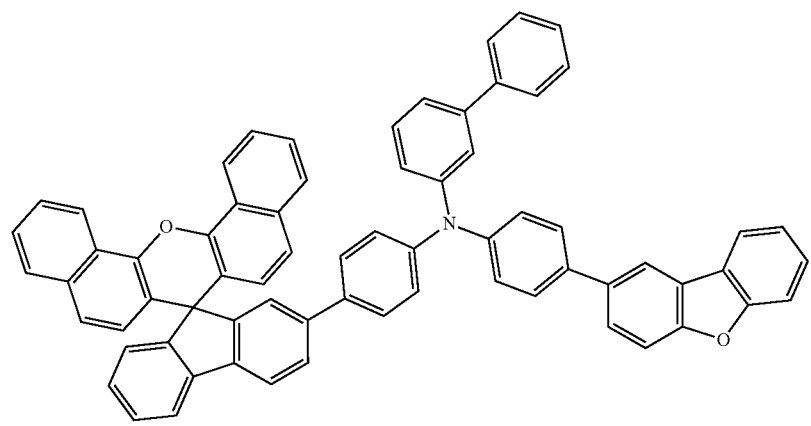

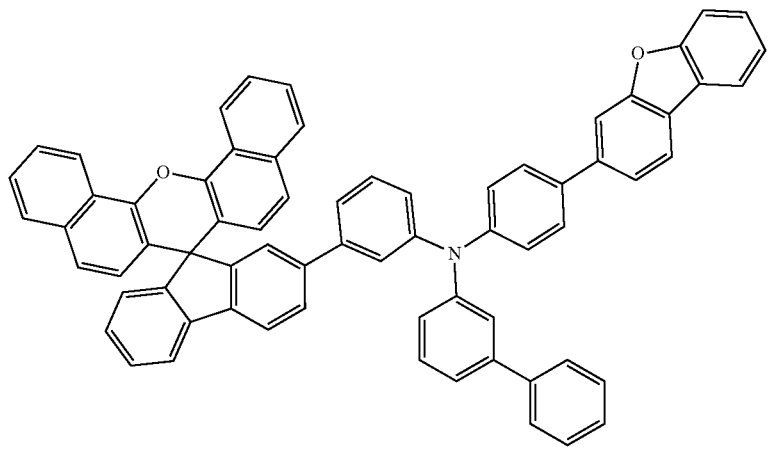
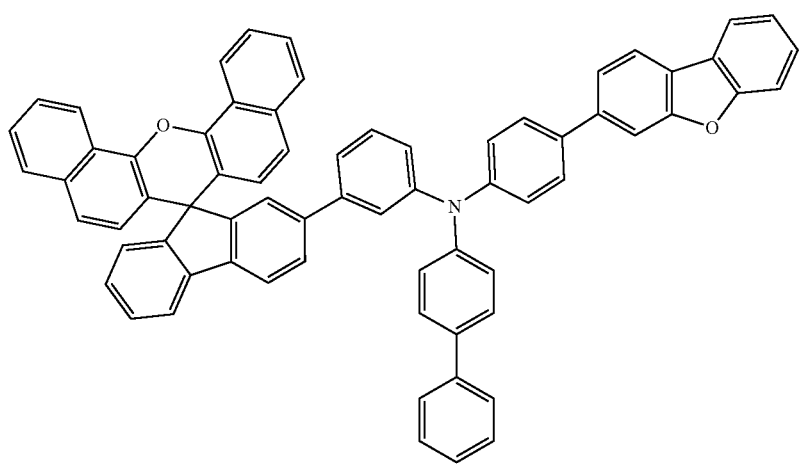
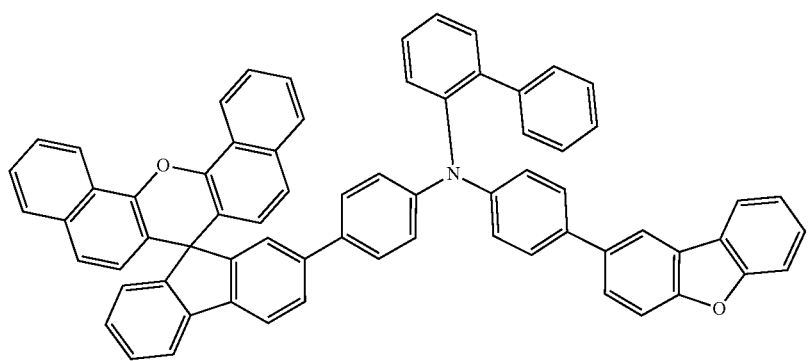

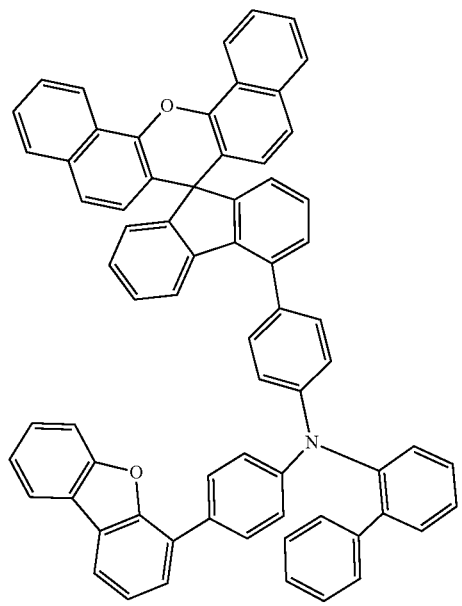
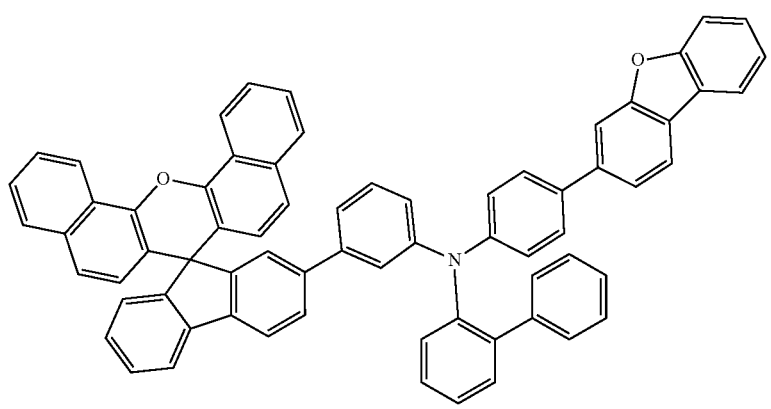
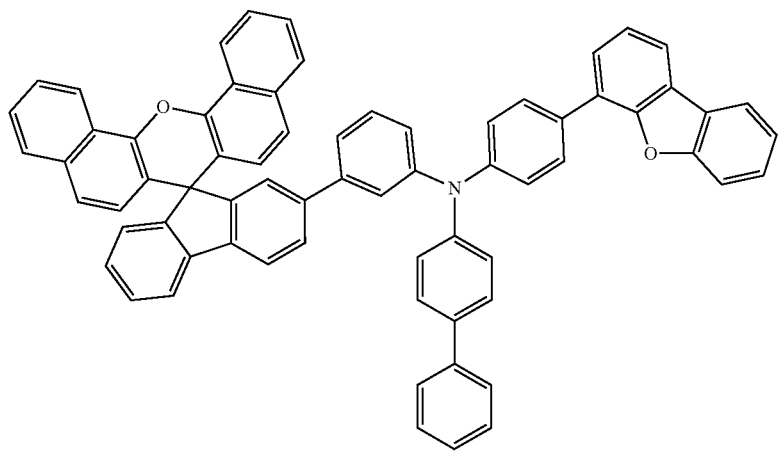

-continued
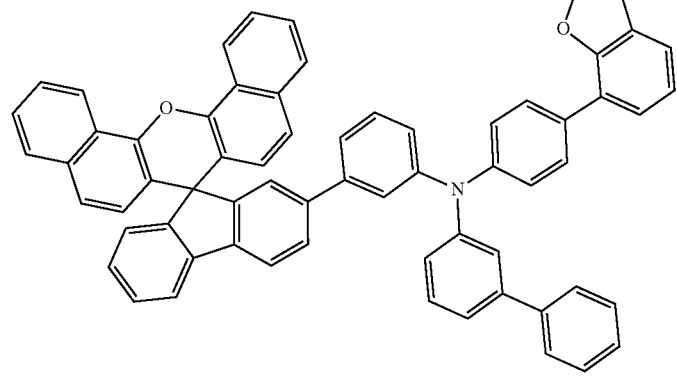
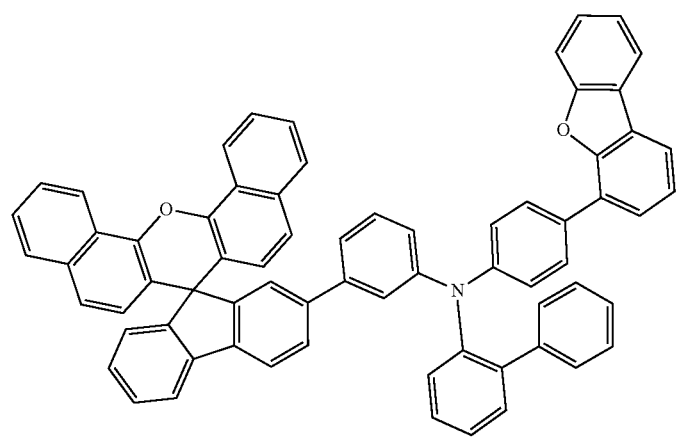
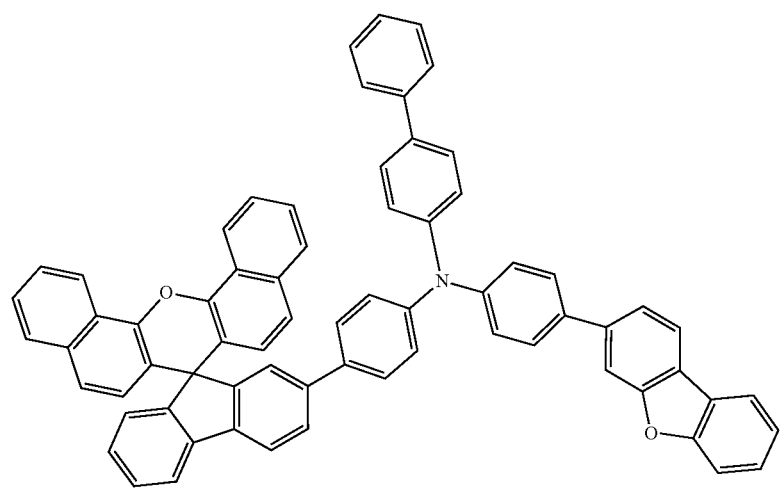

-continued
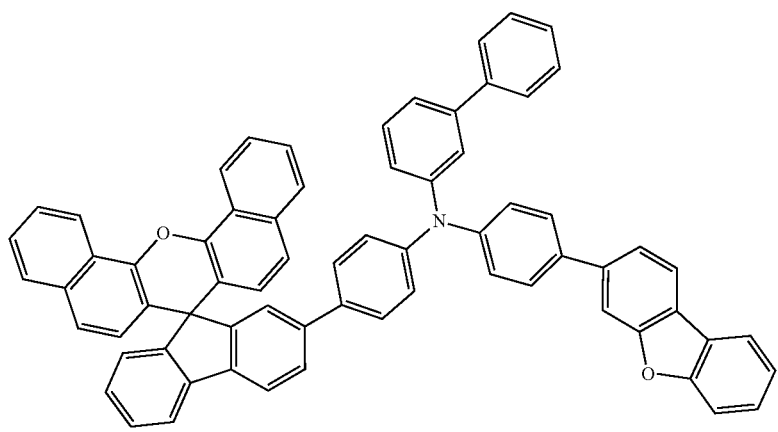
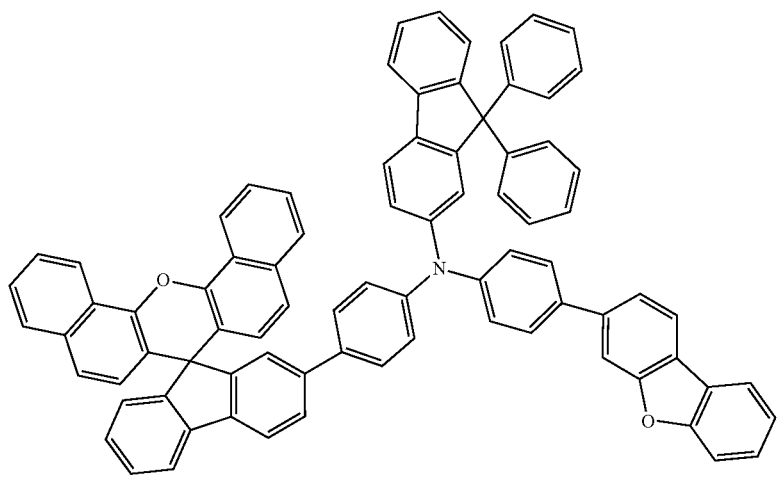
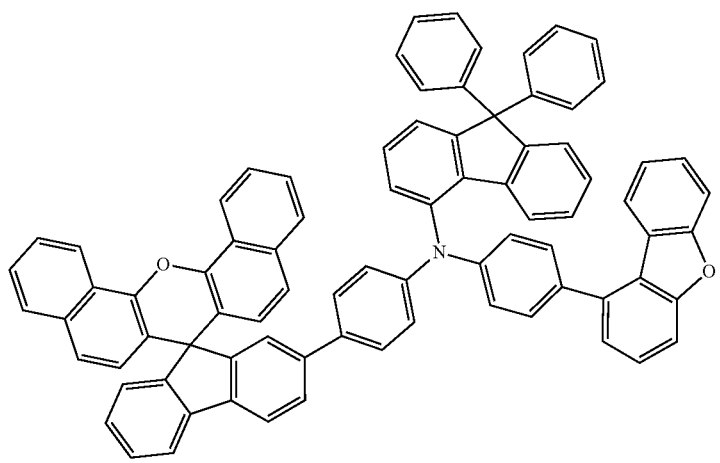

-continued
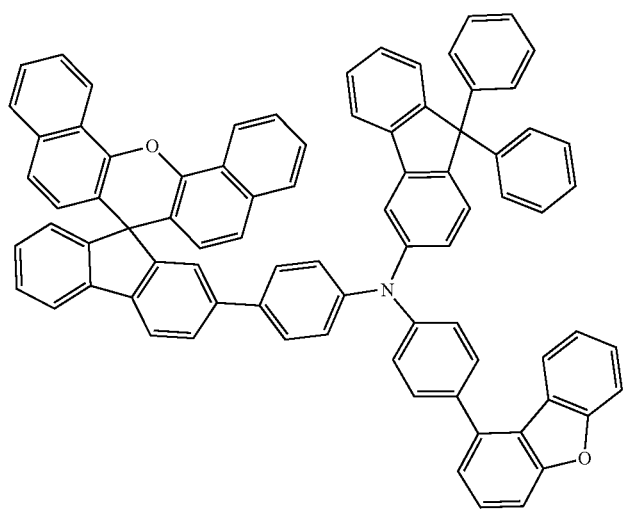
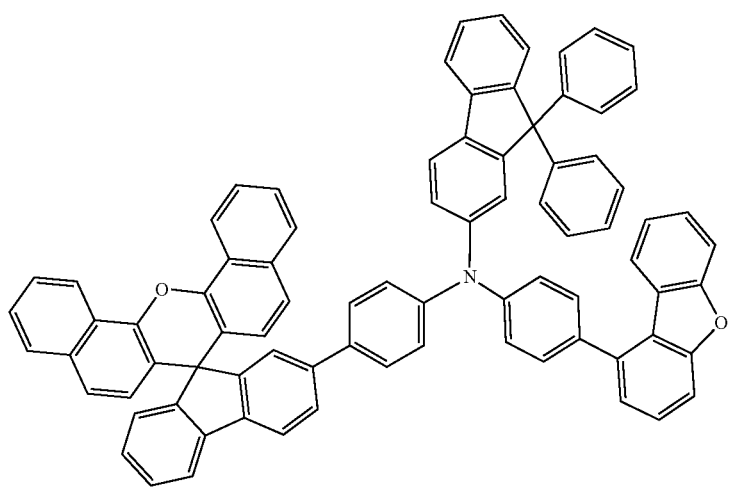
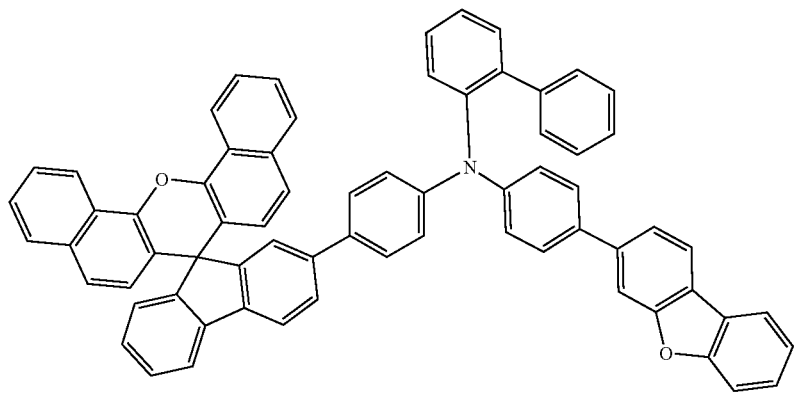

-continued
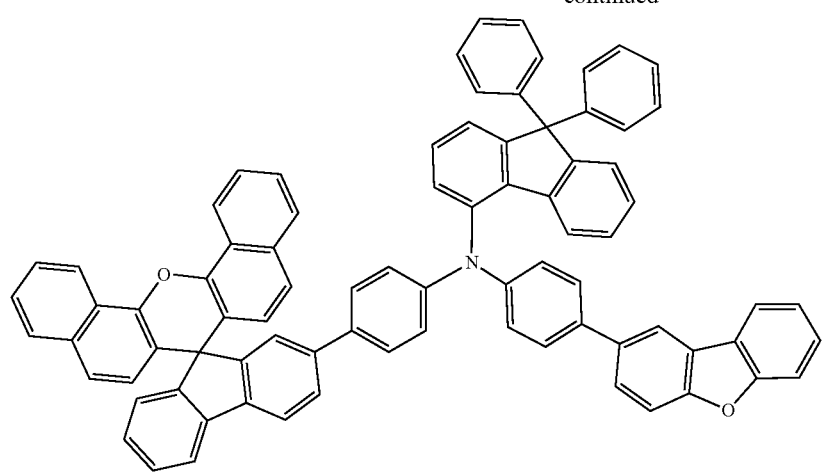
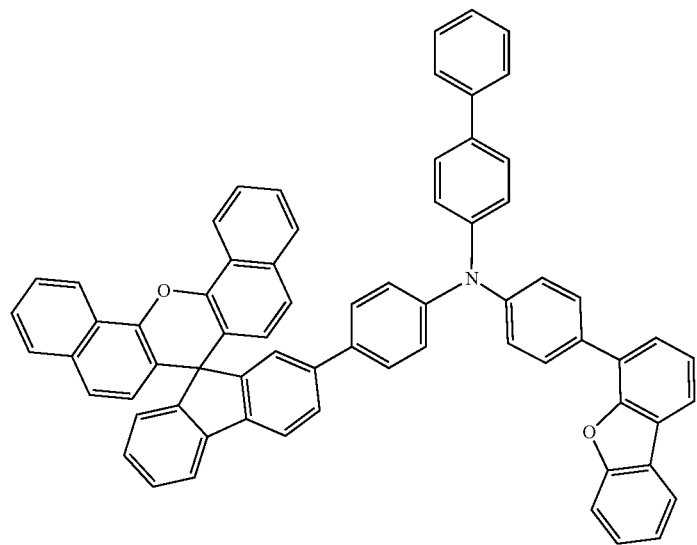
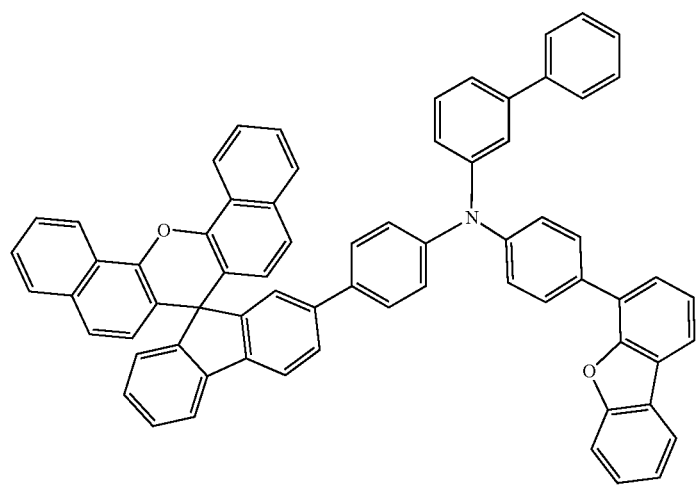

-continued
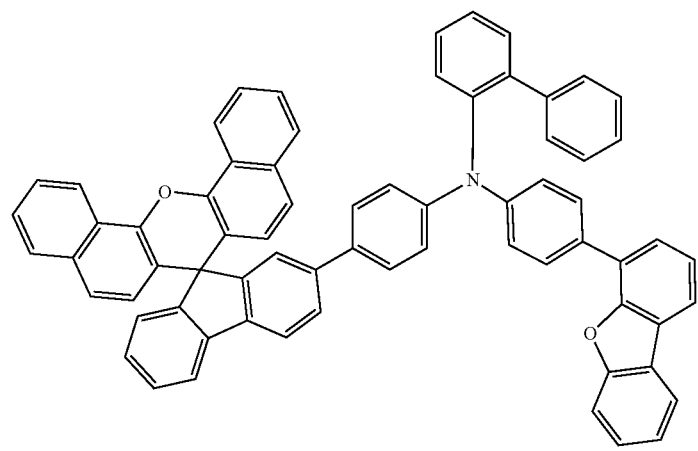
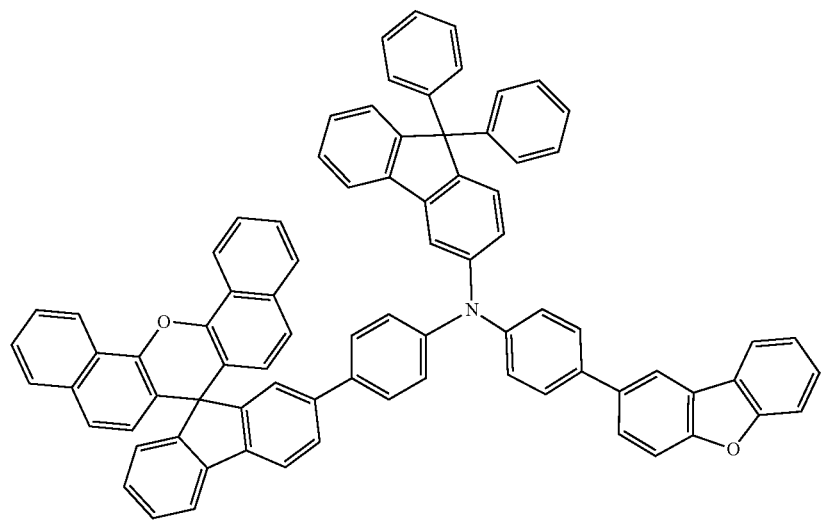
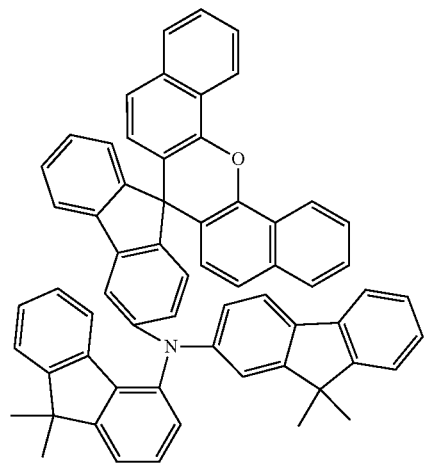
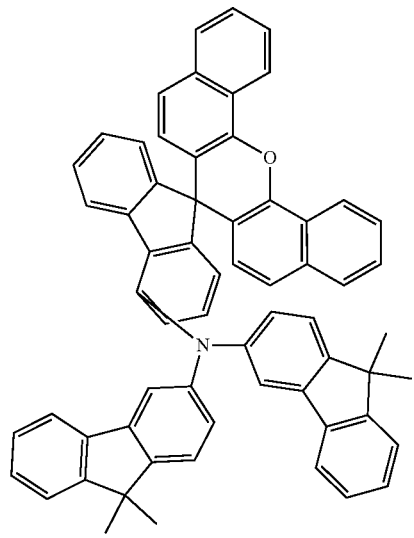

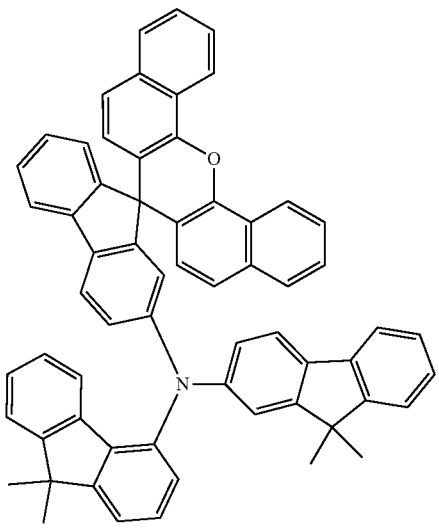
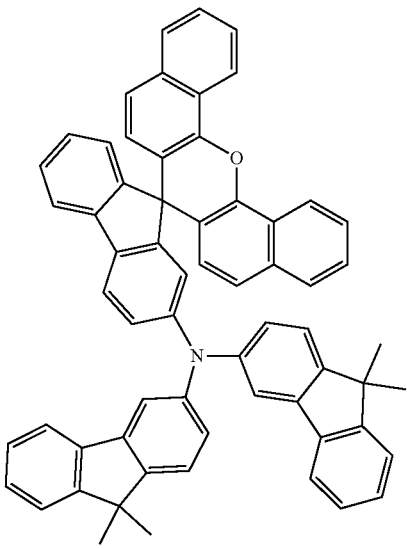
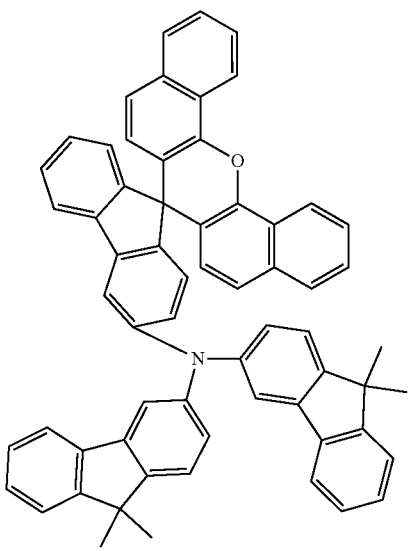
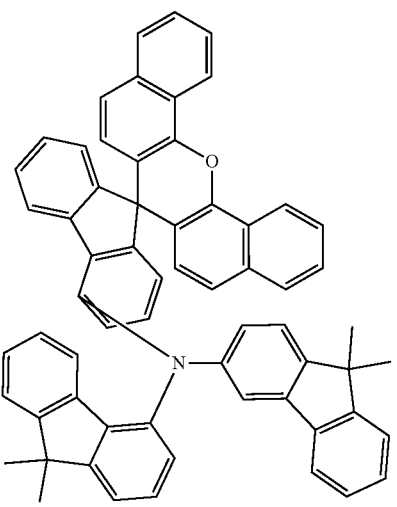
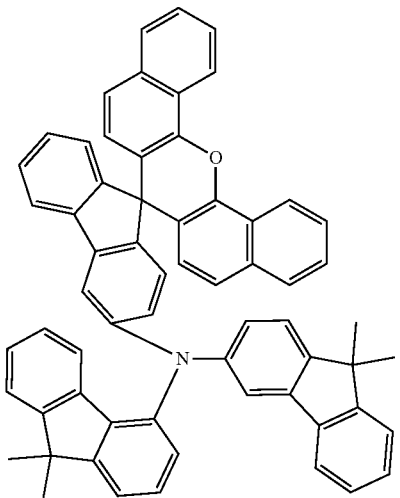

An exemplary embodiment of the present specification may provide an organic light emitting device including: a first electrode; a second electrode provided to face the first electrode; and one or more organic material layers provided between the first electrode and the second electrode, in which one or more layers of the organic material layers include the compound of Chemical Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole generation layer, a hole transport layer, a hole buffer layer, a light emitting layer, and the like as organic material layers. However, the structure of the organic light emitting device is not limited thereto, and may include a fewer number of organic layers.

According to an exemplary embodiment of the present specification, the organic material layer includes a hole generation layer, a hole transport layer, a hole buffer layer, or a layer which generates and transports holes simultaneously, and the hole generation layer, the hole transport layer, the hole buffer layer, or the layer which generates and transports holes simultaneously may include the compound of Chemical Formula 1.

According to another exemplary embodiment, the organic material layer may include a light emitting layer, and the light emitting layer may include the compound of Chemical Formula 1.

According to another exemplary embodiment, the organic light emitting device may be an organic light emitting device having a structure (normal type) in which a positive electrode, one or more organic material layers, and a negative electrode are sequentially stacked on a substrate.

According to still another exemplary embodiment, the organic light emitting device may be an organic light emitting device having a reverse-direction structure (inverted type) in which a negative electrode, one or more organic material layers, and a positive electrode are sequentially stacked on a substrate.

The organic light emitting device of the present specification may have stacked structures as described below, but is not limited thereto.

(1) First electrode/Hole transport layer/Light emitting layer/Second electrode (2) First electrode/Hole injection layer/Hole transport layer/Light emitting layer/Second electrode (3) First electrode/Hole injection layer/Hole buffer layer/Hole transport layer/Light emitting layer/Second electrode (4) First electrode/Hole transport layer/Light emitting layer/Electron transport layer/Second electrode (5) First electrode/Hole transport layer/Light emitting layer/Electron transport layer/Electron injection layer/Second electrode (6) First electrode/Hole injection layer/Hole transport layer/Light emitting layer/Electron transport layer/Second electrode (7) First electrode/Hole injection layer/Hole transport layer/Light emitting layer/Electron transport layer/Electron injection layer/Second electrode (8) First electrode/Hole injection layer/Hole buffer layer/Hole transport layer/Light emitting layer/Electron transport layer/Second electrode (9) First electrode/Hole injection layer/Hole buffer layer/Hole transport layer/Light emitting layer/Electron transport layer/Electron injection layer/Second electrode

(10) First electrode/Hole transport layer/Electron blocking layer/Light emitting layer/Electron transport layer/Second electrode

(11) First electrode/Hole transport layer/Electron blocking layer/Light emitting layer/Electron transport layer/Electron injection layer/Second electrode

(12) First electrode/Hole injection layer/Hole transport layer/Electron blocking layer/Light emitting layer/Electron transport layer/Second electrode

(13) First electrode/Hole injection layer/Hole transport layer/Electron blocking layer/Light emitting layer/Electron transport layer/Electron injection layer/Second electrode

(14) First electrode/Hole transport layer/Light emitting layer/Hole blocking layer/Electron transport layer/Second electrode

(15) First electrode/Hole transport layer/Light emitting layer/Hole blocking layer/Electron transport layer/Electron injection layer/Second electrode

(16) First electrode/Hole injection layer/Hole transport layer/Light emitting layer/Hole blocking layer/Electron transport layer/Second electrode

(17) First electrode/Hole injection layer/Hole transport layer/Light emitting layer/Hole blocking layer/Electron transport layer/Electron injection layer/Second electrode A first electrode is an electrode which injects holes, and a material for the first electrode may be usually a material having a large work so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as $ZnO:Al$ or $SnO_2:Sb$; an electrically conductive polymer, such as poly(3-methylthiophene), poly[3,4-(ethylene-1,2-dioxy)thiophene] (PEDOT), polypyrrole, and polyaniline, and the like, but are not limited thereto.

A hole injection layer may serve to smoothly inject holes into a light emitting layer from the first electrode. The hole injection layer may include the compound of Chemical Formula 1. In this case, the hole injection layer may also be composed of only the compound of Chemical Formula 1, but the compound of Chemical Formula 1 may be present in a mixed or doped state in other materials for the hole injection layer known in the art. The compound of Chemical Formula 1 may also account for 100% of the hole injection layer, but may also be doped in an amount of 0.1 to 50 wt %. The compound of Chemical Formula 1 is a derivative having an indenofluorene structure and has excellent electron accepting ability, and thus may improve the power consumption and lower the driving voltage. The hole injection layer may have a thickness of 1 to 150 nm. Here, when the hole injection layer has a thickness of 1 nm or more, there is an advantage in that it is possible to prevent hole injection characteristics from deteriorating, and when the hole injection layer has a thickness of 150 nm or less, there is an advantage in that the thickness of the hole injection layer is so thick that it is possible to prevent the driving voltage from being increased in order to improve the movement of holes. As the other materials for the hole injection layer, a hole injection material known in the art may be used. For example, as the material for the hole injection layer, it is possible to use any one or more selected from the group consisting of copper phthalocyanine (CuPc), poly(3,4)-ethylenedioxythiophene (PEDOT), polyaniline (PANT), and N,N-dinaphthyl-N,N'-diphenyl benzidine (NPD), but the material is not limited thereto.

A hole transport layer may serve to smoothly transport holes. The hole transport layer may include the compound of Chemical Formula 1. In this case, the hole transport layer may also be composed of only the compound of Chemical Formula 1, but the compound of Chemical Formula 1 may be present in a mixed or doped state in other materials for the hole transport layer known in the art. The compound of Chemical Formula 1 may also account for 100% of the hole transport layer, but may also be doped in an amount of 0.1 to 50 wt %. As the other materials for the hole transport layer, a hole transport material known in the art may be used. For example, the hole transport layer may be composed of one or more selected from the group consisting of N,N-dinaphthyl-N,N'-diphenylbenzidine (NPD), N,N'-bis-(3-methylphenyl)-N,N'-bis-(phenyl)-benzidine (TPD), s-TAD, and 4,4',4"-tris(N-3-methylphenyl-N-phenyl-amino)-triphenylamine (MTDATA), but the material is not limited thereto. Examples of a material for the hole transport layer include a triazole derivative, an oxadiazole derivative, an imidazole derivative, a polyarylalkane derivative, a pyrazoline derivative and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, a polysilane-based copolymer, an aniline-based copolymer, an electrically conductive high-molecular oligomer (particularly, a thiophene oligomer), and the like.

A hole buffer layer may be additionally provided between a hole injection layer and a hole transport layer. The hole buffer layer may include the compound of Chemical Formula 1, and may include other hole injection or transport materials known in the art. Even when the hole buffer layer includes the compound of Chemical Formula 1, the hole buffer layer may also be composed of only the compound of Chemical Formula 1, but may be formed in a state where another host material is mixed or doped with the compound of Chemical Formula 1.

An electron blocking layer may be provided between a hole transport layer and a light emitting layer, and the compound of Chemical Formula 1 or a material known in the art may be used.

The light emitting layer may emit red, green, and/or blue light, and may be composed of a phosphorescent material or a fluorescent material. As the material for the light emitting layer, those publicly known in the art may be used. As a light emitting host material, carbazole biphenyl (CBP) or 1,3-bis (carbazol-9-yl) (mCP) may be used, but the material is not limited thereto.

When the light emitting layer emits red light, it is possible to use, as a light emitting dopant, a phosphorescent material such as bis(1-phenylisoquinoline)acetylacetonate iridium (PIQIr(acac)), bis(1-phenylquinoline)acetylacetonate iridium (PQIr(acac)), tris(1-phenylquinoline)iridium (PQIr), or octaethylporphyrin platinum (PtOEP), or a fluorescent material such as tris(8-hydroxyquinolino)aluminum ($Alq_3$), but the light emitting dopant is not limited thereto. When the light emitting layer emits green light, it is possible to use, as a light emitting dopant, a phosphorescent material such as fac tris(2-phenylpyridine)iridium ($Ir(ppy)_3$), or a fluorescent material such as tris(8-hydroxyquinolino)aluminum ($Alq_3$), but the light emitting dopant is not limited thereto. When the light emitting layer emits blue light, it is possible to use, as a light emitting dopant, a phosphorescent material such as $(4,6-F_2ppy)_2Irpic$, or a fluorescent material such as spiro-DPVBi, spiro-6P, distyrylbenzene (DSB), distyrylarylene (DSA), a PFO-based polymer or a PPV-based polymer, but the light emitting dopant is not limited thereto.

A hole blocking layer may be provided between an electron transport layer and a light emitting layer, and materials known in the art may be used.

An electron transport layer may serve to smoothly transport electrons. A material known in the art, such as tris(8-hydroxyquinolino)aluminum ($Alq_3$), PBD, TAZ, spiro-PBD, BAlq, and SAlq may be used. The electron transport layer may have a thickness of 1 to 50 nm. Here, when the electron transport layer has a thickness of 1 nm or more, there is an advantage in that it is possible to prevent electron transport characteristics from deteriorating, and when the electron transport layer has a thickness of 50 nm or less, there is an advantage in that the thickness of the electron transport layer is so thick that it is possible to prevent the driving voltage from being increased in order to improve the movement of electrons.

The electron injection layer may serve to smoothly inject electrons. The electron injection layer may be composed of an organic material known in the art, such as tris(8-hydroxyquinolino)aluminum ($Alq_3$), PBD, TAZ, spiro-PBD, BAlq, or SAlq, or a complex or a metal compound. As the metal compound, a metal halide may be used, and for example, LiQ, LiF, NaF, KF, RbF, CsF, FrF, $BeF_2$, $MgF_2$, $CaF_2$, $SrF_2$, $BaF_2$ and $RaF_2$, and the like may be used. The electron injection layer may have a thickness of 1 to 50 nm. Here, when the electron injection layer has a thickness of 1 nm or more, there is an advantage in that it is possible to prevent electron injection characteristics from deteriorating, and when the electron injection layer has a thickness of 50 nm or less, there is an advantage in that the thickness of the electron injection layer is so thick that it is possible to prevent the driving voltage from being increased in order to improve the movement of electrons.

The second electrode is an electron injection electrode, and may be usually a material having a small work function so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The organic light emitting device of the present specification may be manufactured by the materials and methods known in the art, except that one or more layers of the organic material layers include the compound of the present specification, that is, the compound of Chemical Formula 1.

When the organic light emitting device includes a plurality of organic material layers, the organic material layers may be formed of the same material or different materials.

The organic light emitting device of the present specification may be manufactured by the materials and methods known in the art, except that one or more layers of the organic material layers include the compound of Chemical Formula 1, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

According to an exemplary embodiment of the present specification, the first electrode may be a positive electrode, and the second electrode may be a negative electrode.

According to another exemplary embodiment, the first electrode may be a negative electrode, and the second electrode may be a positive electrode.

The hole injection material is a layer which injects holes from an electrode, and is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes transported from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport material is a material which receives electrons from an electron injection layer and transports the electrons to a light emitting layer, and an electron transport material is suitably a material which may inject electrons well from a negative electrode and may transfer the electrons to a light emitting layer, and has large mobility for the electrons. Specific examples thereof include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The organic light emitting device according to the present specification may be a top emission type, a bottom emission type, or a dual emission type according to the material to be used.

Hereinafter, exemplary embodiments described in the present specification will be exemplified through Examples. However, the following Examples are provided only to exemplify the present invention, but are not intended to limit the scope of the present invention.

Preparation Example 1 (Synthesis of Compounds 1 to 3)

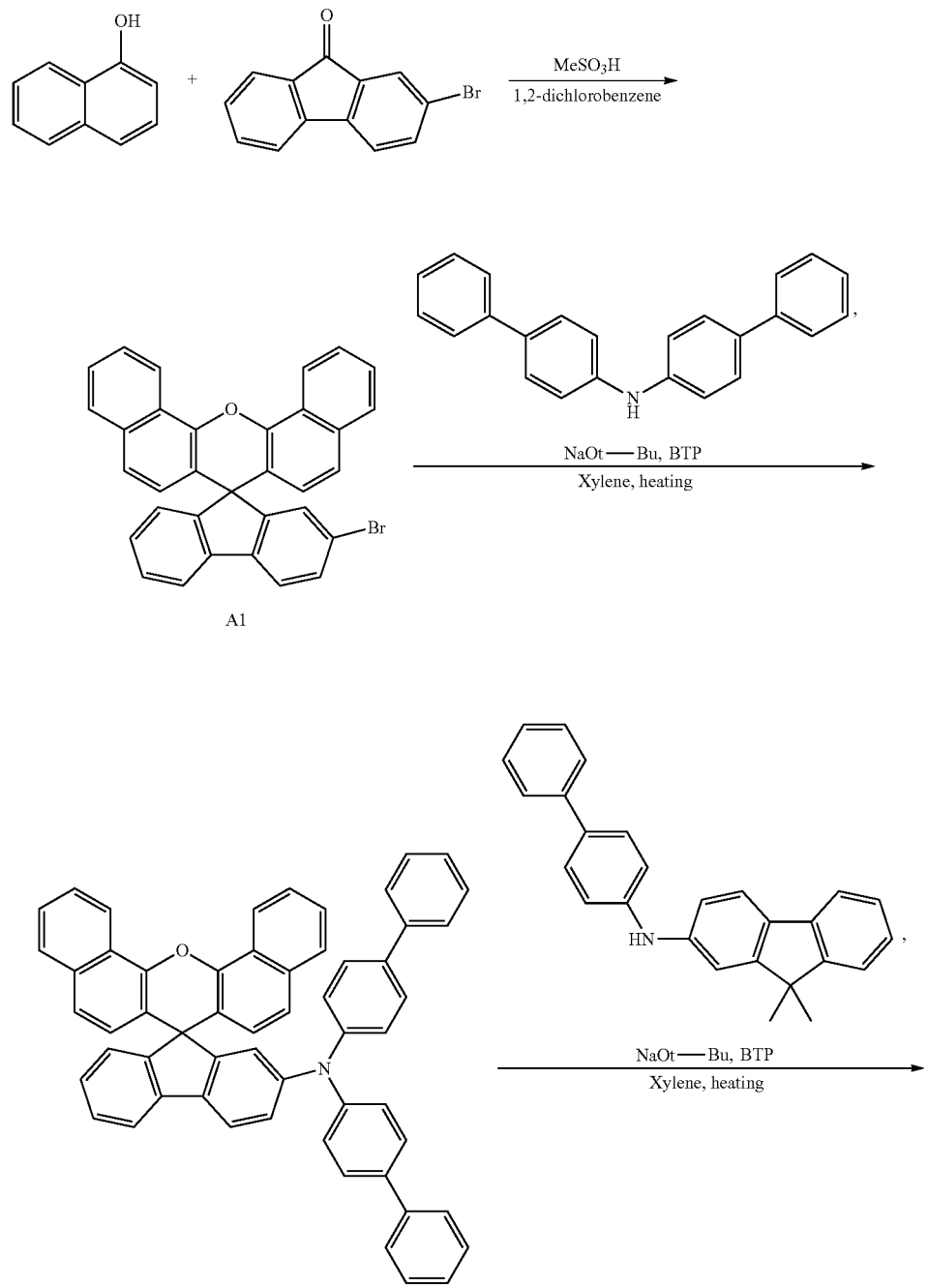

-continued

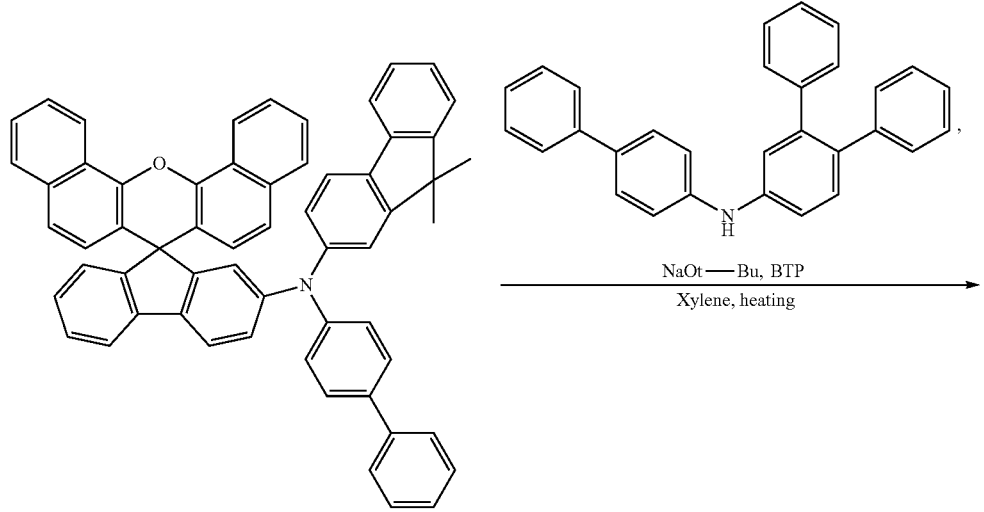

2

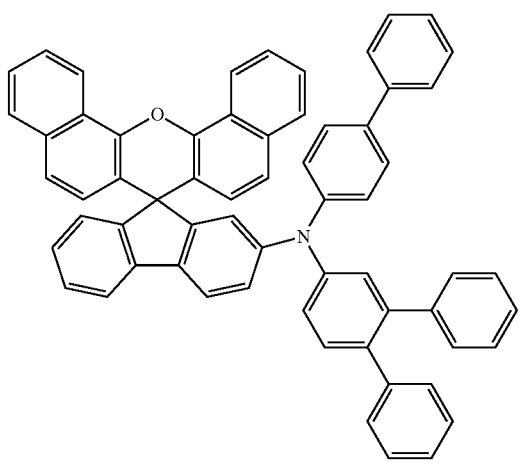

3

Synthesis of A1

1-naphthol (22.26 g, 154.4 mmol) and 2-bromofluorene (20 g, 77.2 mmol) were added to 1,2-dichlorobenzene (300 ml), and then methanesulfonic acid (10 ml) was added thereto, and the resulting mixture was heated and stirred at 160° C. for 24 hours. The temperature was lowered to normal temperature, the reaction was terminated, and then the resulting product was extracted with chloroform and water, and then recrystallized with tetrahydrofuran and ethyl acetate to prepare Compound A1 (31.6 g, yield 80%).
MS[M+H]$^+$=512.42

Preparation Example 1-1 (Synthesis of Compound 1)

A1 (10 g, 19.55 mmol), di([1,1'-biphenyl]-4-yl)amine (6.47 g, 20.14 mmol), and sodium-t-butoxide (2.6 g, 27.4 mmol) were put into toluene, and the resulting mixture was heated and stirred and then refluxed, and [bis(tri-t-butyl-phosphine)]palladium (200 mg, 2 mmol %) was put thereinto. The temperature was lowered to normal temperature, the reaction was terminated, and then the resulting product was recrystallized by using chloroform and ethyl acetate to prepare Compound 1.
MS[M+H]$^+$=752.94

Preparation Example 1-2 (Synthesis of Compound 2)

Compound 2 was prepared by performing the synthesis in the same manner as in the synthesis of Compound 1, except that N-([1,1'-diphenyl]-4-yl)-9,9-dimethyl-9H-fluoren-2-amine was used instead of di([1,1'-biphenyl]-4-yl)amine.
MS[M+H]$^+$=793.00

Preparation Example 1-3 (Synthesis of Compound 3)

Compound 3 was prepared by performing the synthesis in the same manner as in the synthesis of Compound 1, except that N-([1,1'-diphenyl]-4-yl)-[1,1':2',1''-terphenyl]-4-amine was used instead of di([1,1'-biphenyl]-4-yl)amine.
MS[M+H]$^+$=824.03

Preparation Example 2 (Synthesis of Compounds 4 and 5)
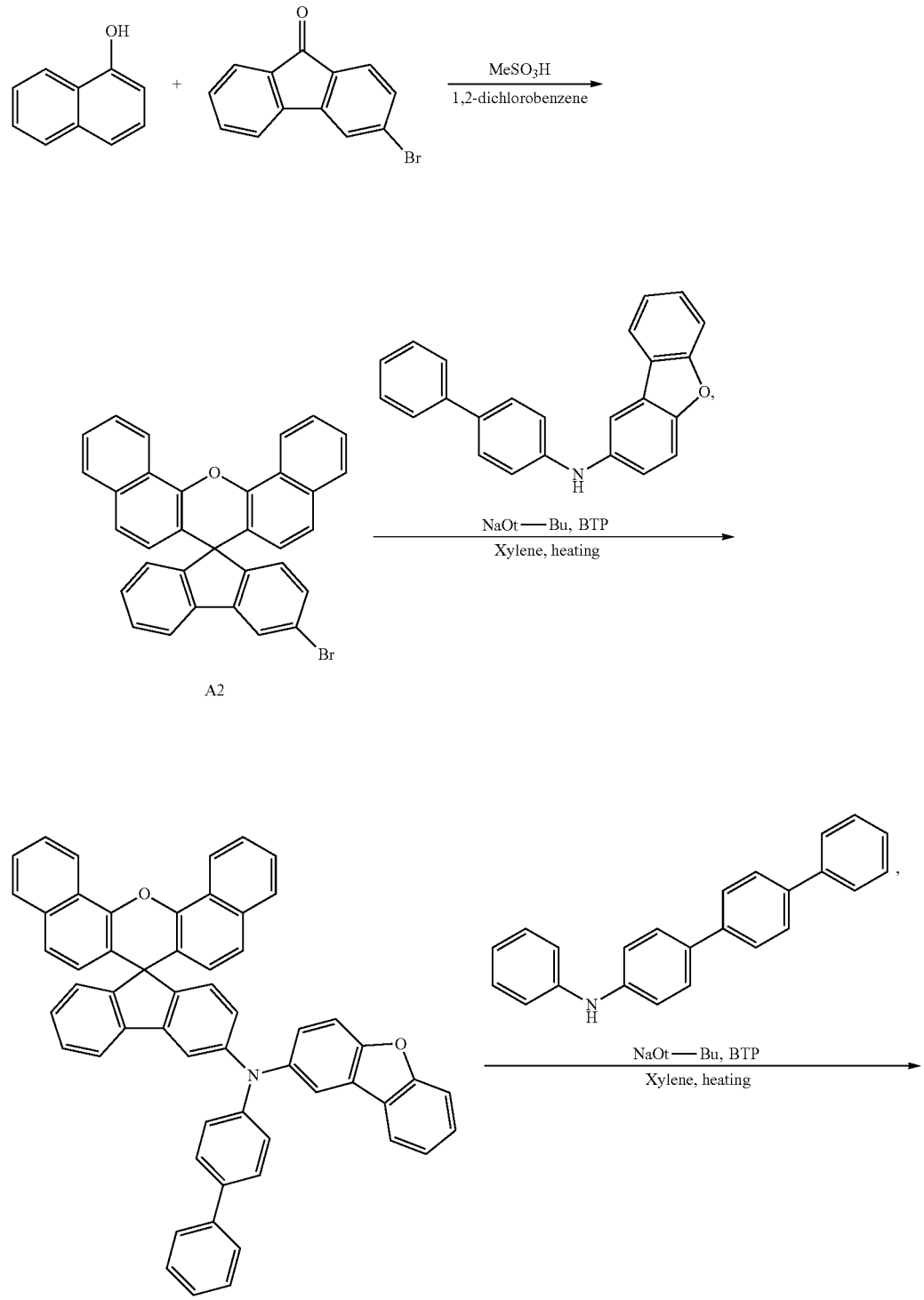

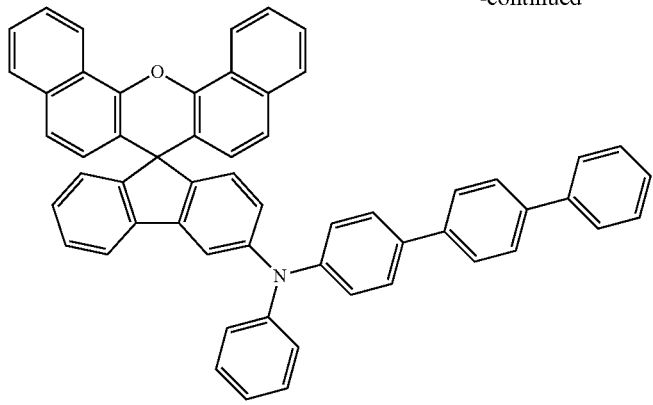

5

Synthesis of A2

Compound A2 was prepared by performing the synthesis in the same manner as in the synthesis of A1, except that 3-bromofluorene was used instead of the compound 2-bromofluorene.

MS[M+H]$^+$=512.42

Preparation Example 2-1 (Synthesis of Compound 4)

A2 (10 g, 19.55 mmol), N-([1,1'-diphenyl]-4-yl)dibenzo[b,d]furan-2-amine (6.75 g, 20.14 mmol), and sodium-t-butoxide (2.6 g, 27.4 mmol) were put into toluene, and the resulting mixture was heated and stirred and then refluxed, and [bis(tri-t-butylphosphine)]palladium (200 mg, 2 mmol %) was put thereinto. The temperature was lowered to normal temperature, the reaction was terminated, and then the resulting product was recrystallized by using chloroform and ethyl acetate to prepare Compound 4.

MS[M+H]$^+$=766.91

Preparation Example 2-2 (Synthesis of Compound 5)

Compound 5 was prepared by performing the synthesis in the same manner as in the synthesis of Compound 4, except that N-phenyl-[1,1,4',1''-terphenyl]-4-amine was used instead of N-([1,1'-diphenyl]-4-yl)dibenzo[b,d]furan-2-amine.

MS[M+H]$^+$=752.93

Preparation Example 3 (Synthesis of Compounds 6 to 8)

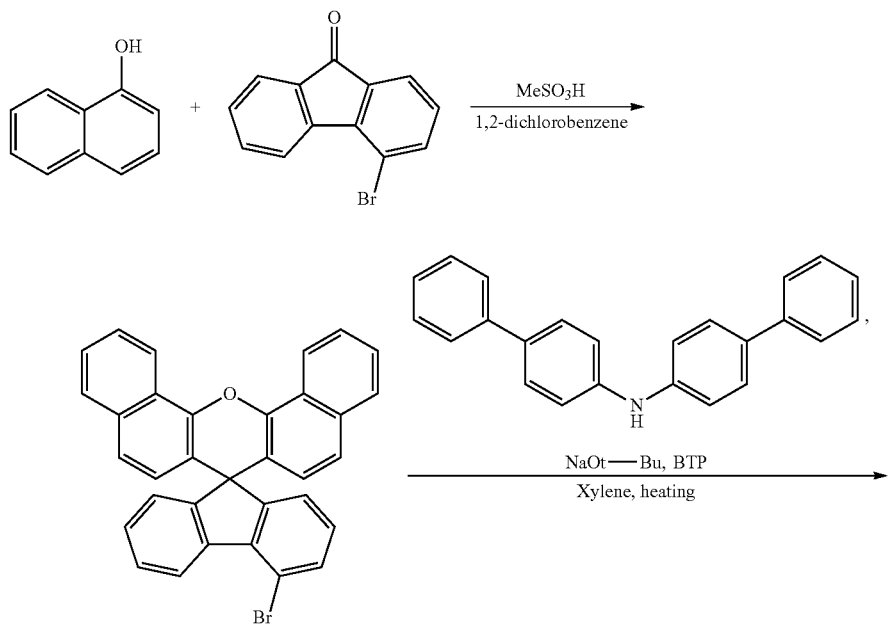

-continued
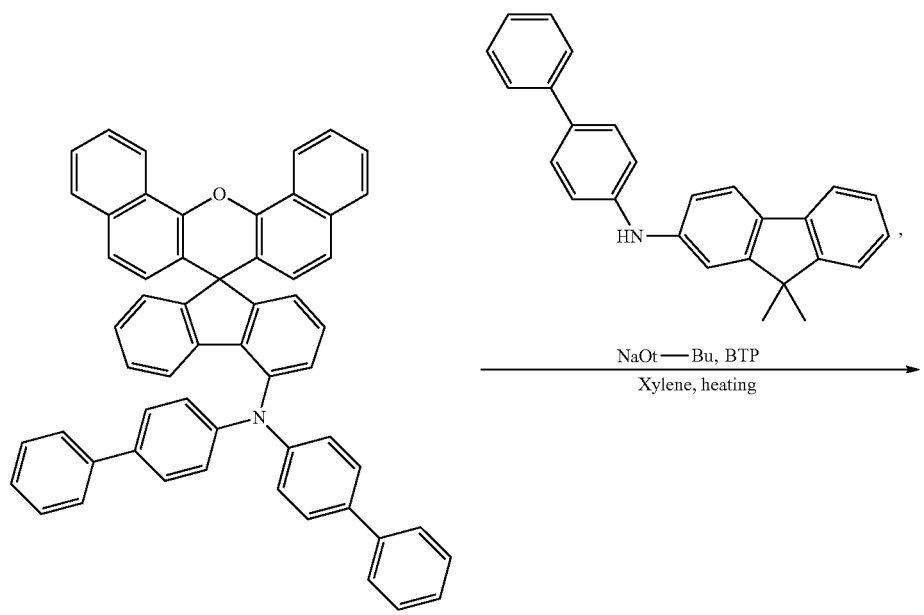
6
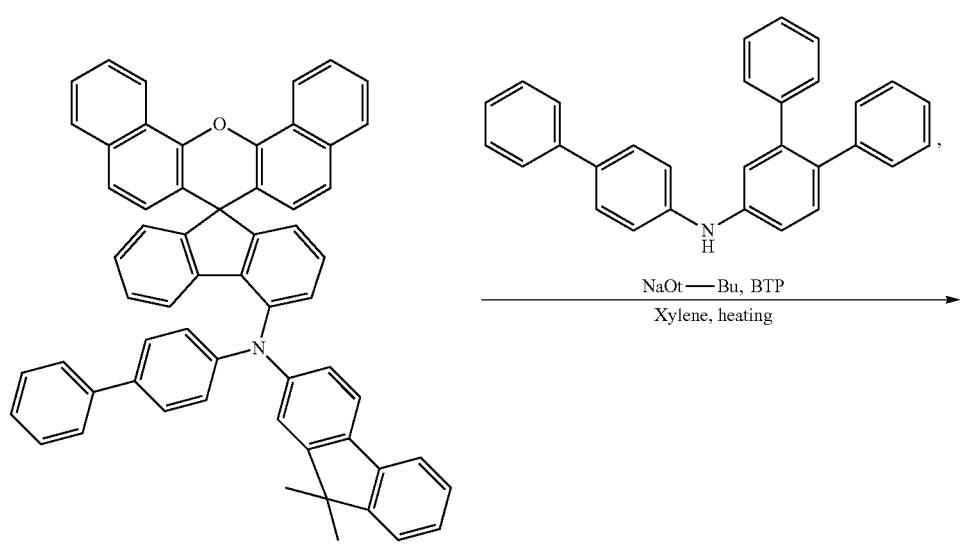
7

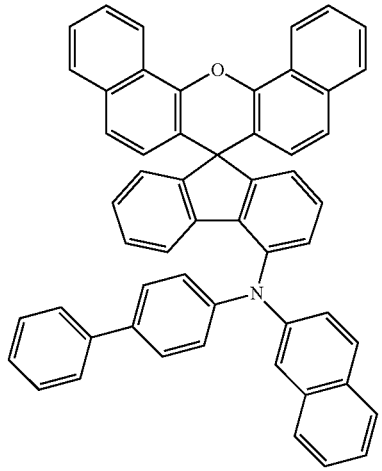

8

Synthesis of A3

Compound A3 was prepared by performing the synthesis in the same manner as in the synthesis of A1, except that 4-bromofluorene was used instead of the compound 2-bromofluorene.

MS[M+H]$^+$=512.42

Preparation Example 3-1 (Synthesis of Compound 6)

A3 (10 g, 19.55 mmol), di([1,1'-biphenyl]-4-yl)amine (6.47 g, 20.14 mmol), and sodium-t-butoxide (2.6 g, 27.4 mmol) were put into toluene, and the resulting mixture was heated and stirred and then refluxed, and [bis(tri-t-butylphosphine)]palladium (200 mg, 2 mmol %) was put thereinto. The temperature was lowered to normal temperature, the reaction was terminated, and then the resulting product was recrystallized by using chloroform and ethyl acetate to prepare Compound 6.

MS[M+H]$^+$=752.94

Preparation Example 3-2 (Synthesis of Compound 7)

Compound 7 was prepared by performing the synthesis in the same manner as in the synthesis of Compound 5, except that N-([1,1'-diphenyl]-4-yl)-9,9-dimethyl-9H-fluoren-2-amine was used instead of di([1,1'-biphenyl]-4-yl)amine.

MS[M+H]$^+$=793.00

Preparation Example 3-3 (Synthesis of Compound 8)

Compound 8 was prepared by performing the synthesis in the same manner as in the synthesis of Compound 5, except that N-([1,1'-diphenyl]-4-yl)naphthalen-2-amine was used instead of di([1,1'-biphenyl]-4-yl)amine.

MS[M+H]$^+$=726.89

Example 1

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene was thermally vacuum deposited to have a thickness of 500 Å on a transparent ITO electrode thus prepared, thereby forming a hole injection layer. Compound 1 (300 Å) synthesized in Preparation Example 1-1, which is a material for transporting holes, was vacuum deposited thereon, and then HT2 was sequentially vacuum deposited to have a film thickness of 100 Å on the hole transport layer, thereby forming a hole adjusting layer. As a compound light emitting layer, a compound of host H1 and dopant D1 (25:1) was vacuum deposited to have a thickness of 300 Å. And then, the E1 compound (300 Å) was thermally vacuum deposited as an electron injection and transport layer. A negative electrode was formed by sequentially depositing lithium fluoride (LiF) and aluminum to have a thickness of 12 Å and 2,000 Å, respectively, on the electron injection and transport layer, thereby manufacturing an organic light emitting device.

In the aforementioned procedure, the deposition rates of the organic material, lithium fluoride, and aluminum were maintained at 1 Å/sec, 0.2 Å/sec, and 3 to 7 Å/sec, respectively.

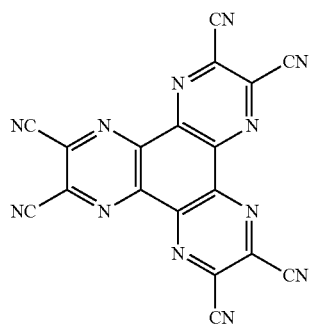

[Hexanitrile hexaazatriphenylene]

[HT1]

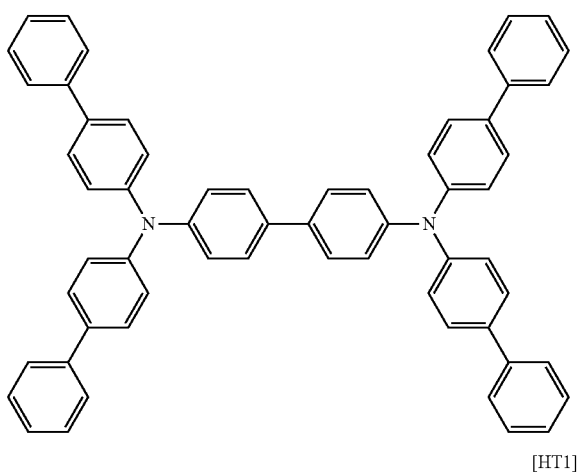

[E1]

[D1]

Example 2

An experiment was performed in the same manner as in Example 1, except that as the hole transport layer, Compound 2 was used instead of Compound 1.

Example 3

An experiment was performed in the same manner as in Example 1, except that as the hole transport layer, Compound 3 was used instead of Compound 1.

Example 4

An experiment was performed in the same manner as in Example 1, except that as the hole transport layer, Compound 4 was used instead of Compound 1.

Example 5

An experiment was performed in the same manner as in Example 1, except that as the hole transport layer, Compound 5 was used instead of Compound 1.

Comparative Example 1

An experiment was performed in the same manner as in Example 1, except that as the hole transport layer, HT1 was used instead of Compound 1.

The results in which organic light emitting devices manufactured by using each compound as a hole transport layer material as in Examples 1 to 5 and Comparative Example 1 were experimented are shown in Table 1.

TABLE 1

| Experimental Example 50 mA/cm² | HTL material | Voltage (V) | Current efficiency (cd/A) |
|---|---|---|---|
| Comparative Example 1 | HT1 | 4.11 | 5.32 |
| Example 1 | Compound 1 | 3.70 | 5.80 |
| Example 2 | Compound 2 | 3.46 | 5.75 |
| Example 3 | Compound 3 | 3.59 | 5.62 |
| Example 4 | Compound 4 | 3.66 | 5.91 |
| Example 5 | Compound 5 | 3.52 | 5.99 |

As in Table 1, it can be seen that the compounds used in Examples 1 to 5 were used as a hole transport layer in the organic light emitting devices, and exhibited lower voltage and higher efficiency characteristics than Comparative Example 1, which is a benzidine-type material.

Example 6

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene was thermally vacuum deposited to have a thickness of 500 Å on a transparent ITO electrode thus prepared, thereby forming a hole injection layer. HT1 (300 Å) synthesized in Preparation Example 2-1, which is a material for transporting holes, was vacuum deposited thereon, and then Compound 6 was sequentially vacuum deposited to have a film thickness of 100 Å on the hole transport layer, thereby forming a hole adjusting layer. As a compound light emitting layer, a compound of host H1 and dopant D1 (25:1) was vacuum deposited to have a thickness of 300 Å. And then, the E1 compound (300 Å) was thermally vacuum deposited as an electron injection and transport layer. A negative electrode was formed by sequentially depositing lithium fluoride (LiF) and aluminum to have a thickness of 12 Å and 2,000 Å, respectively, on the electron injection and transport layer, thereby manufacturing an organic light emitting device.

In the aforementioned procedure, the deposition rates of the organic material, lithium fluoride, and aluminum were maintained at 1 Å/sec, 0.2 Å/sec, and 3 to 7 Å/sec, respectively.

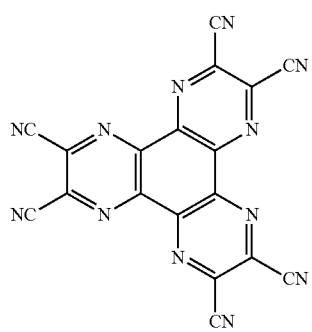

[Hexanitrile hexaazatriphenylene]

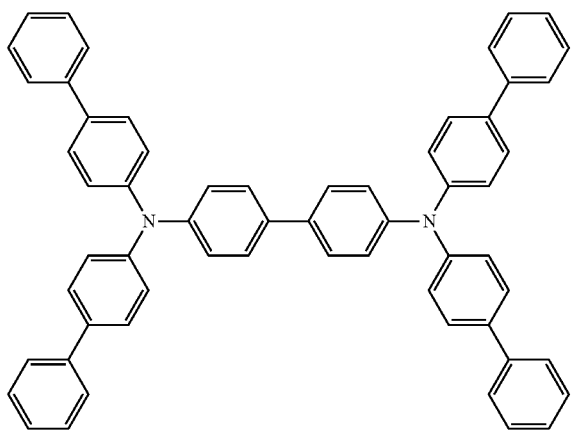

[HT1]

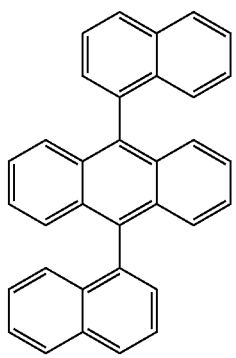

[H1]

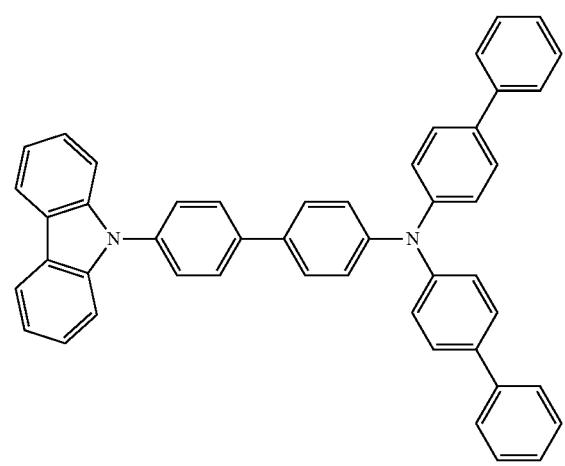

[HT2]

-continued

[E1]

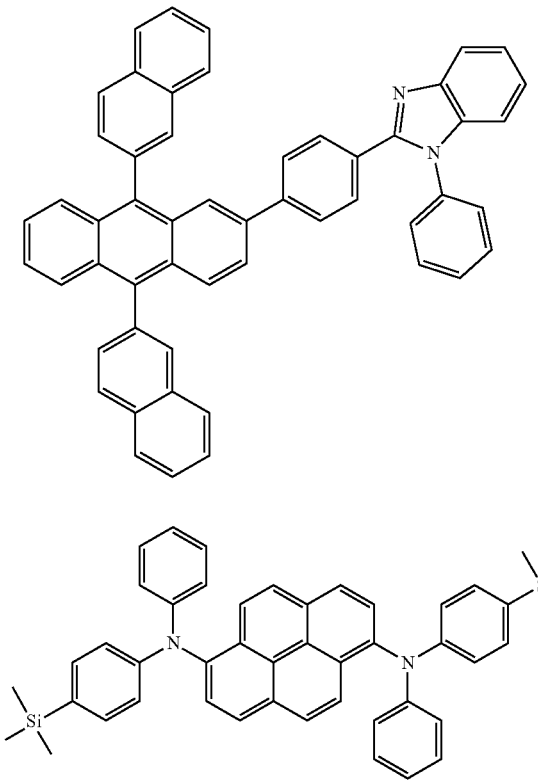

[D1]

Example 7

An experiment was performed in the same manner as in Example 6, except that as the hole adjusting layer, Compound 7 was used instead of Compound 6.

Example 8

An experiment was performed in the same manner as in Example 6, except that as the hole adjusting layer, Compound 8 was used instead of Compound 6.

Comparative Example 2

An experiment was performed in the same manner as in Example 6, except that as the hole adjusting layer, [HT2] was used instead of Compound 6.

TABLE 2

| Experimental Example 50 mA/cm² | HTL material | Voltage (V) | Current efficiency (cd/A) |
|---|---|---|---|
| Comparative Example 2 | HT2 | 4.02 | 5.11 |
| Example 6 | Compound 6 | 3.73 | 5.80 |
| Example 7 | Compound 7 | 3.56 | 5.76 |
| Example 8 | Compound 8 | 3.51 | 5.63 |

As in Table 2, it can be seen that the compounds used in Examples 6 to 8 were used as a hole adjusting layer in the organic light emitting devices, and exhibited lower voltage and higher efficiency characteristics than Comparative Example 2.

The compound derivative of the chemical formula according to the present invention may serve to transport and adjust holes in an organic electronic device including an organic light emitting device, and the device according to the present invention exhibits excellent characteristics in terms of efficiency, driving voltage, and stability.

The invention claimed is:
1. A compound represented by the following Chemical Formula 1:

[Chemical Formula 1]

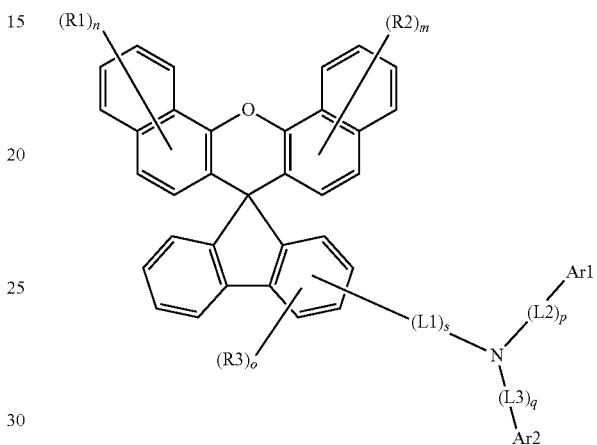

R1 to R3 are each independently any one selected from a group consisting of hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted aralkylamine group; a substituted or unsubstituted arylamine group; a substituted or unsubstituted arylphosphine group; a substituted or unsubstituted phosphine oxide group; a substituted or unsubstituted aryl group; and a substituted or unsubstituted heterocyclic group, L1 to L3 are any one selected from the group consisting of a direct bond; a substituted or unsubstituted alkylene group; a substituted or unsubstituted cycloalkylene group; a substituted or unsubstituted alkenylene group; a substituted or unsubstituted aralkylene group; a substituted or unsubstituted aralkenylene group; a substituted or unsubstituted alkylarylene group; a substituted or unsubstituted divalent amine group; a substituted or unsubstituted divalent aralkylamine group; a substituted or unsubstituted divalent arylamine group; a substituted or unsubstituted arylene group; and a substituted or unsubstituted heterocyclic group, Ar1 and Ar2 are each independently any one selected from a group consisting of hydrogen;

deuterium; a halogen group; a nitrile group; a nitro group; a substituted or unsubstituted amine group; a substituted or unsubstituted alkyl group; a substituted or unsubstituted alkoxy group; a substituted or unsubstituted aryl group; a substituted or unsubstituted fluorene group; and a substituted or unsubstituted heterocyclic group, L1 to L3, Ar1, and Ar2 optionally combine with an adjacent group to form a substituted or unsubstituted ring, n and m are each an integer of 0 to 6, o+s is an integer of 1 to 4, and s, p, and q are an integer of 1 to 4.

2. The compound of claim 1, wherein L1 to L3 are any one of the following chemical formulae:

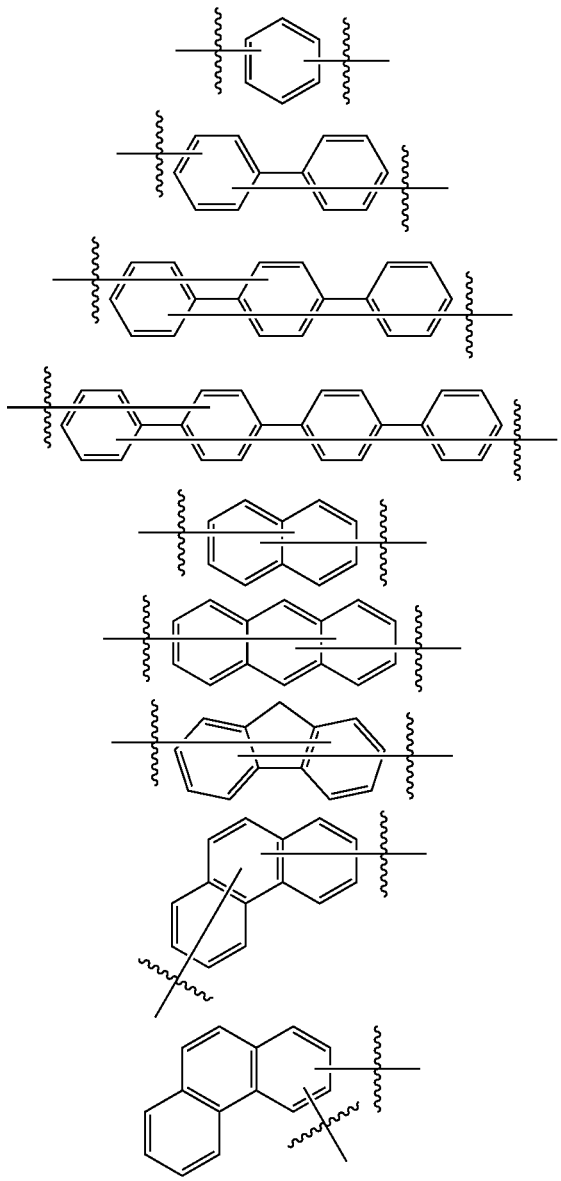

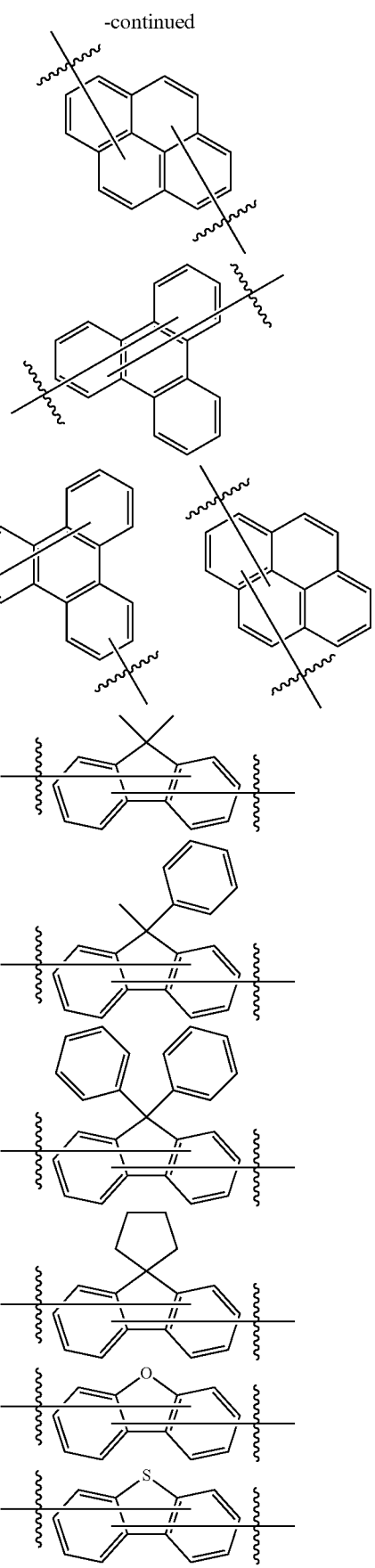

-continued

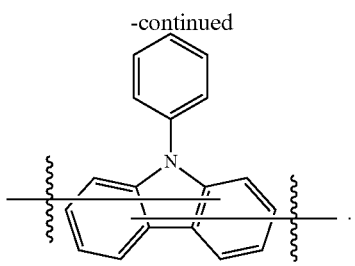

3. The compound of claim 1, wherein Ar1 and Ar2 are each independently any one selected from a group consisting of a substituted or unsubstituted aryl group; a substituted or unsubstituted fluorene group; and a substituted or unsubstituted heterocyclic group.

4. The compound of claim 1, wherein the substituted or unsubstituted ring formed by combining Ar1 and Ar2 with each other is any one of the following chemical formulae:

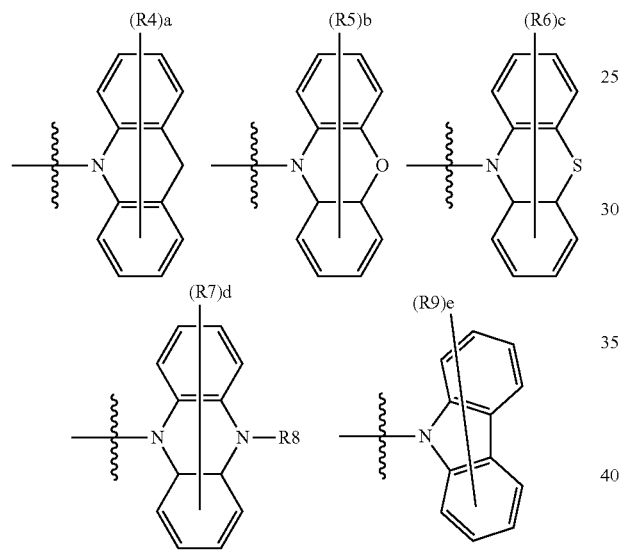

R4 to R9 are each independently selected from a group consisting of a substituted or unsubstituted alkyl group; a substituted or unsubstituted aryl group; a substituted or unsubstituted fluorene group; and a substituted or unsubstituted heterocyclic group,
a is an integer of 1 to 10, and
b to e are each an integer of 1 to 8.

5. The compound of claim 1, wherein the substituted or unsubstituted ring formed by combining L1 to L3 and Ar1 or Ar2 with each other is any one of the following chemical formulae:

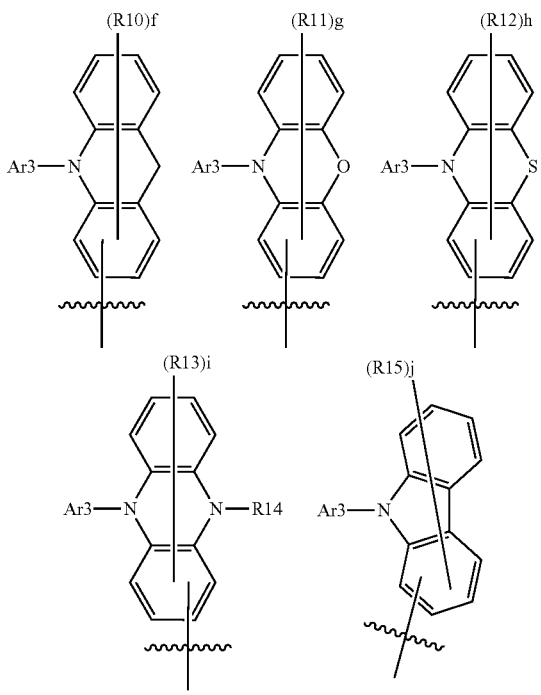

R10 to R15 are each independently selected from a group consisting of a substituted or unsubstituted alkyl group; a substituted or unsubstituted aryl group; a substituted or unsubstituted fluorene group; and a substituted or unsubstituted heterocyclic group,
Ar3 is Ar1 or Ar2,
f is an integer of 1 to 9, and
g to j are each an integer of 1 to 7.

6. The compound of claim 1, wherein the compound is any one of the following chemical formulae:

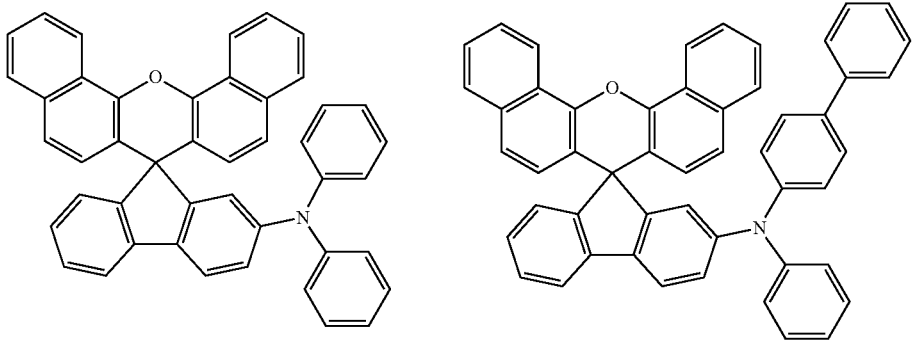

-continued
| 271 | 272 |
|---|---|
| 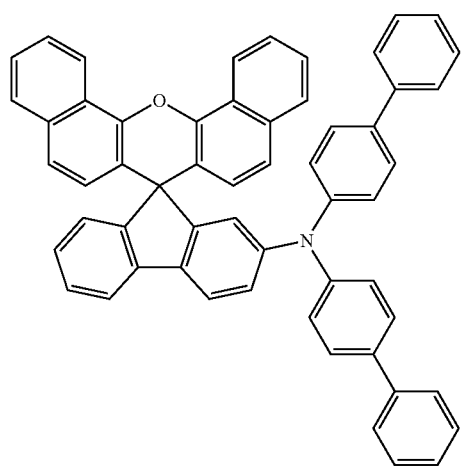 | 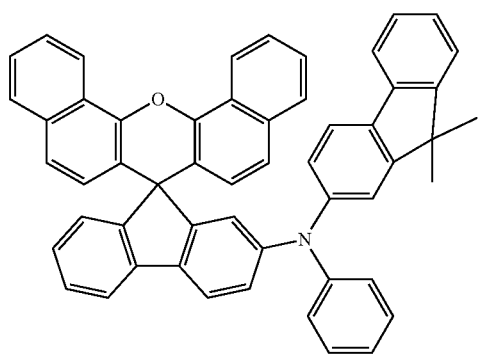 |
| 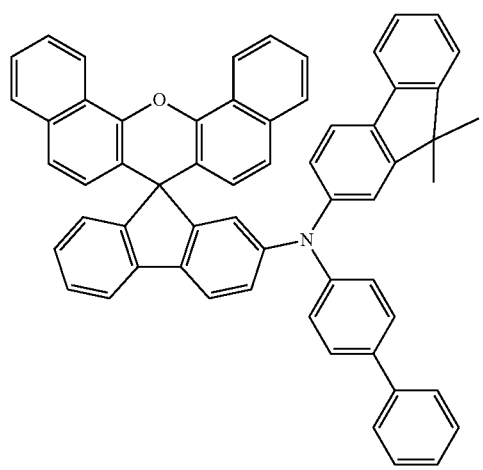 | 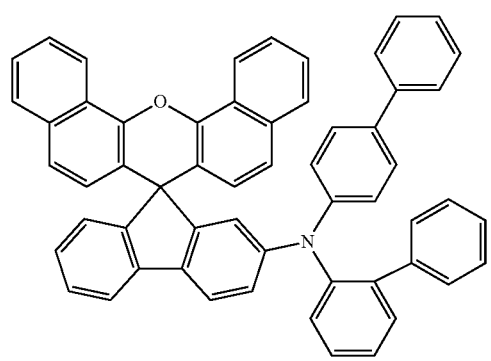 |
| 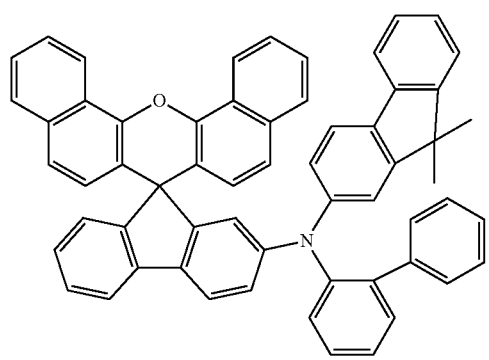 | 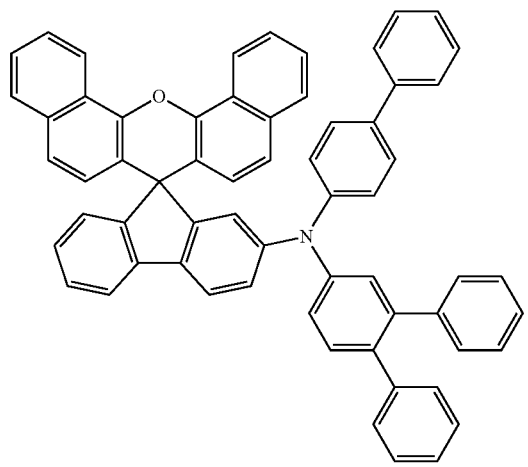 |

273 274
-continued
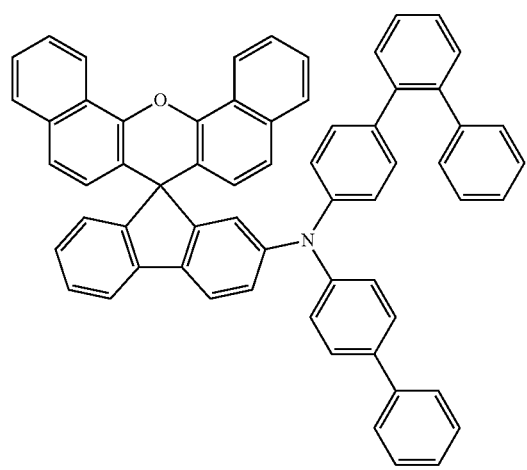
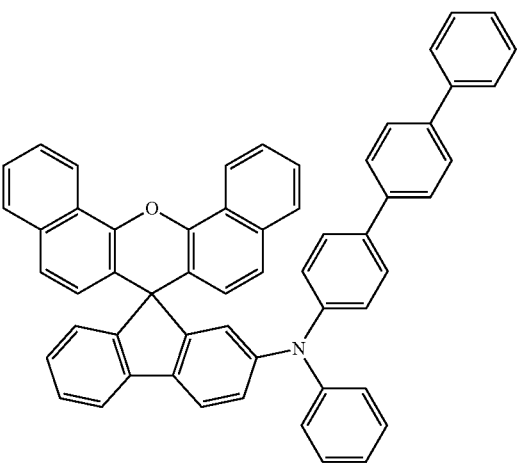
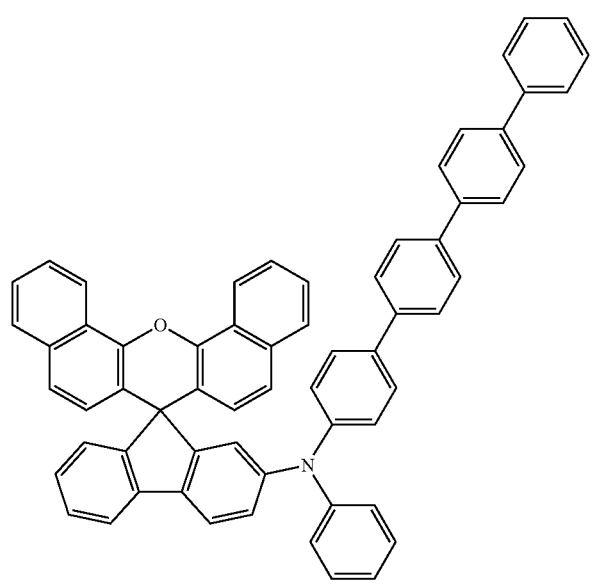
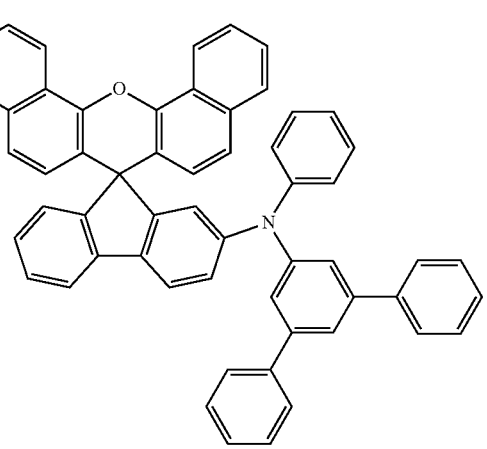
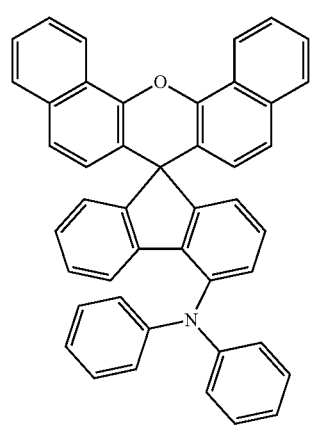
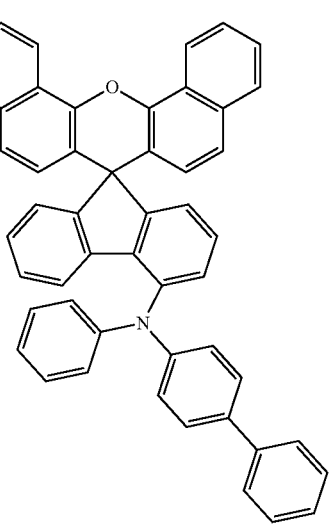
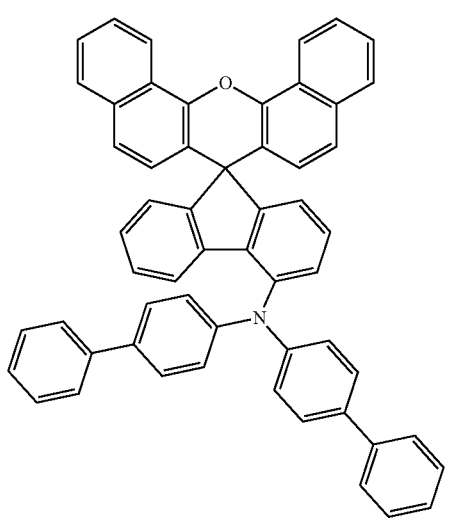

-continued
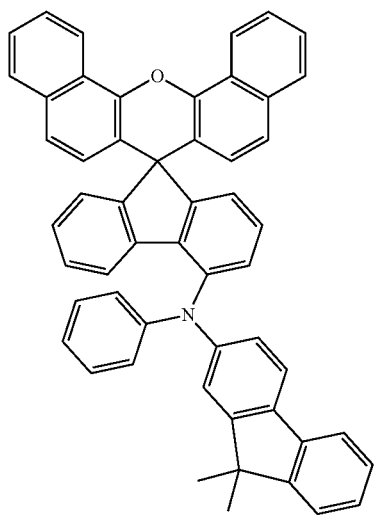
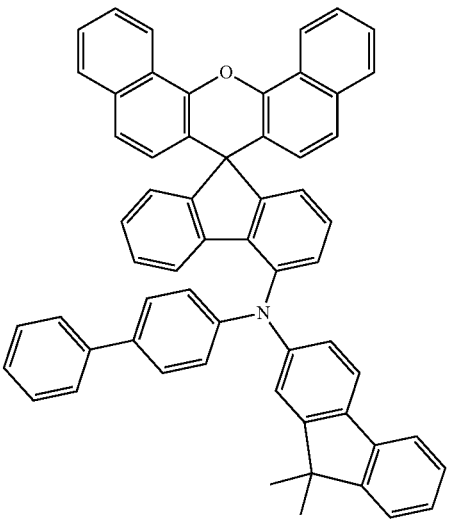
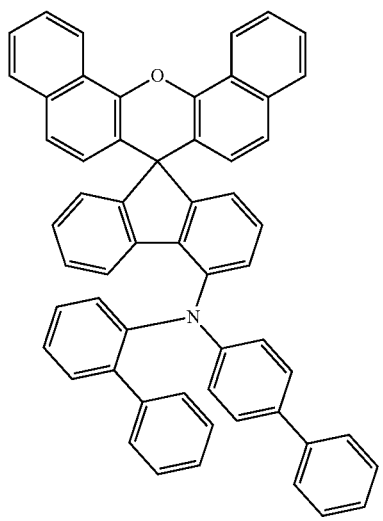
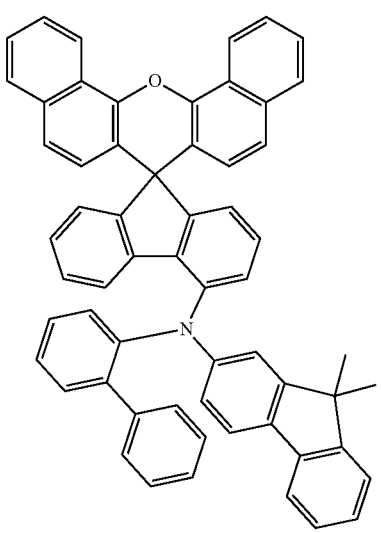
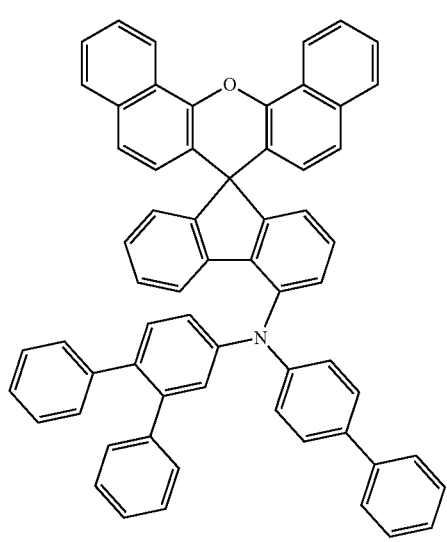
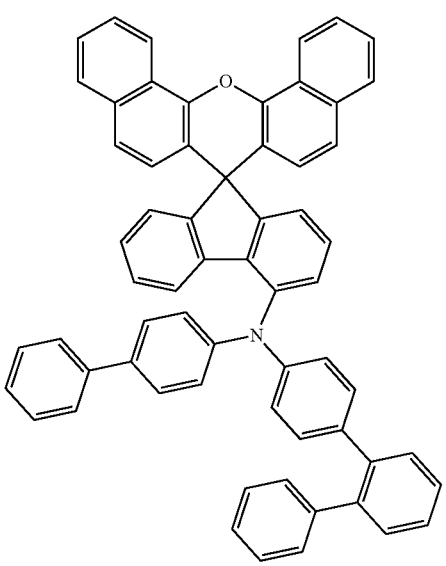

-continued
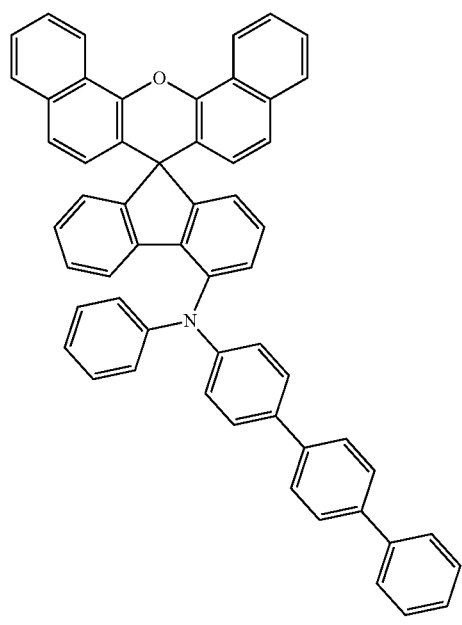
277
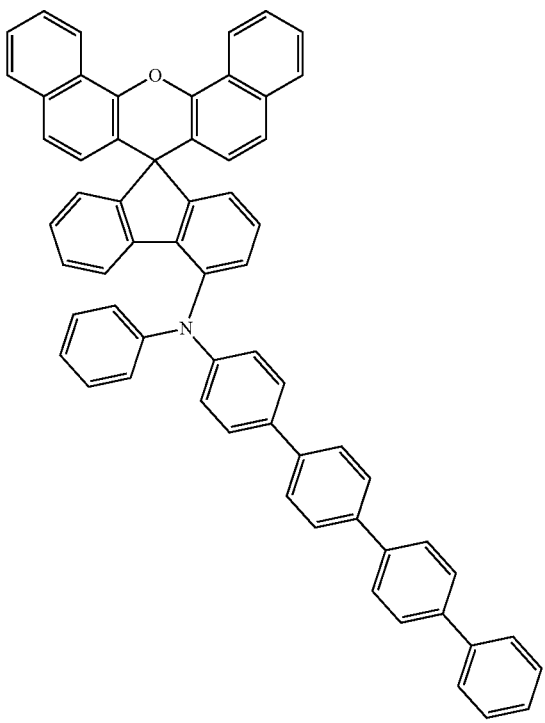
278
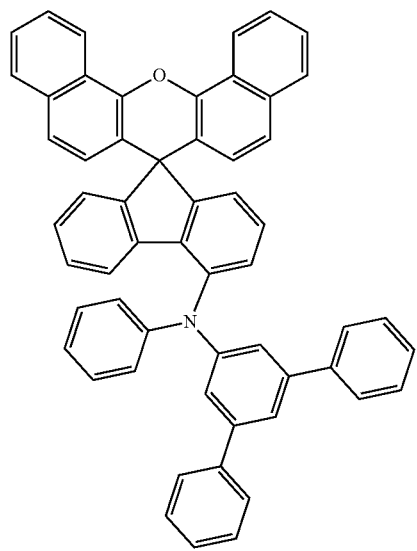
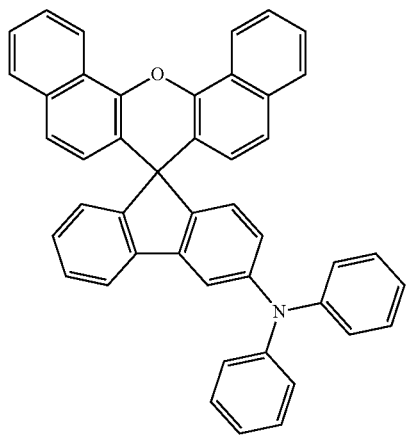

279
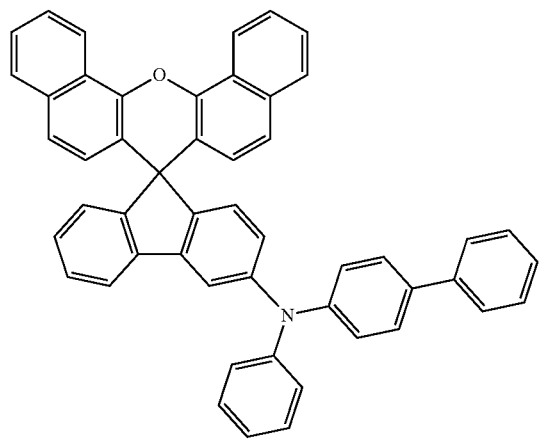
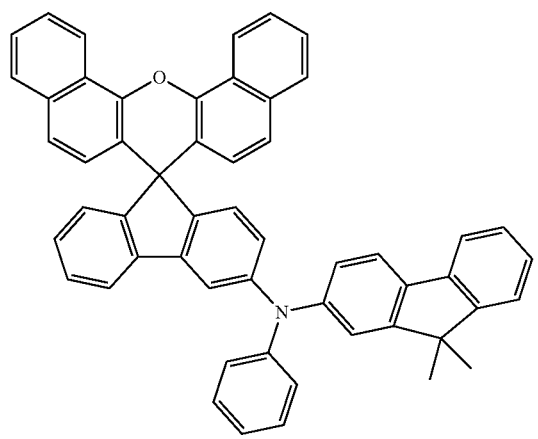
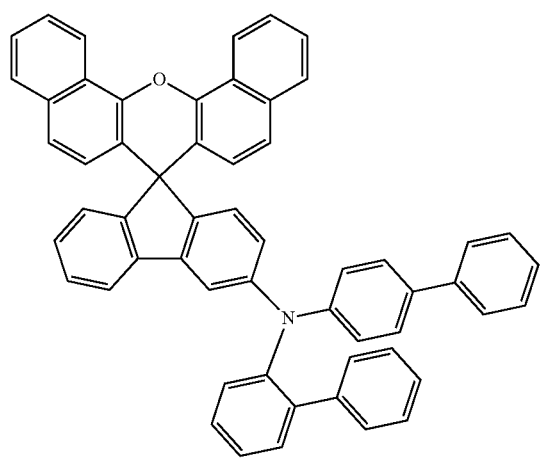
280
-continued
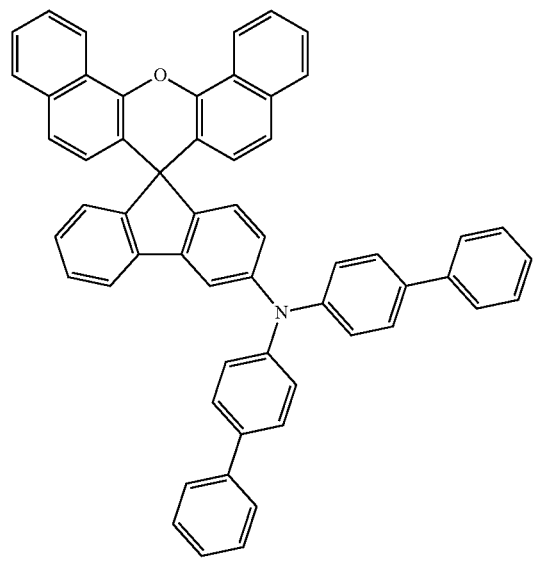
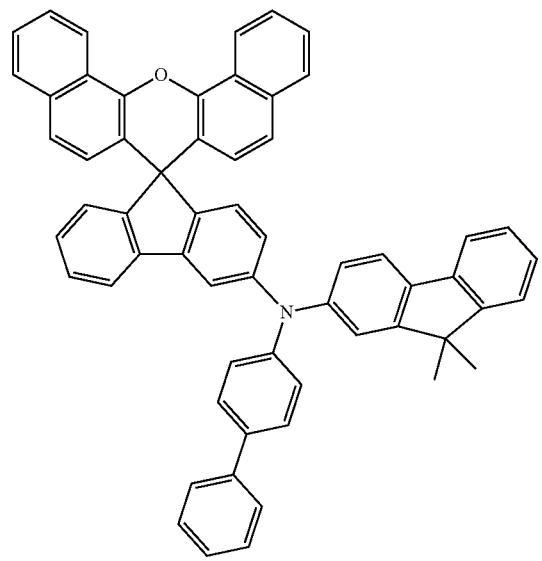
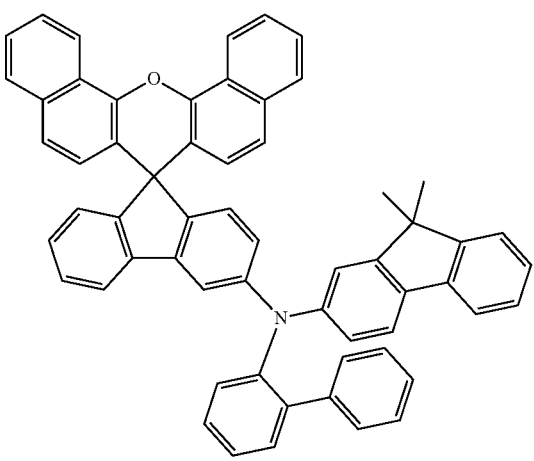

281
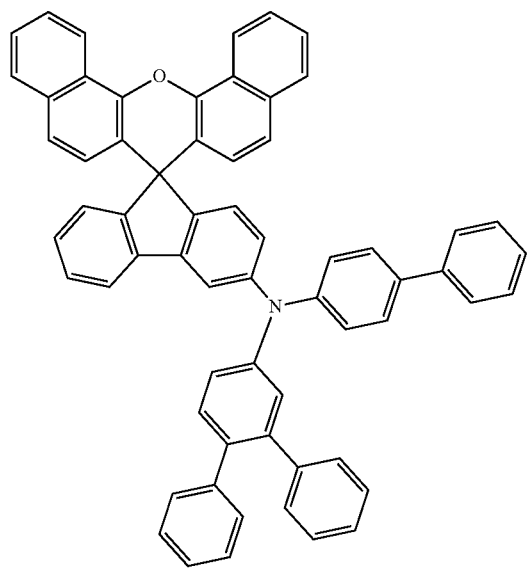
-continued
282
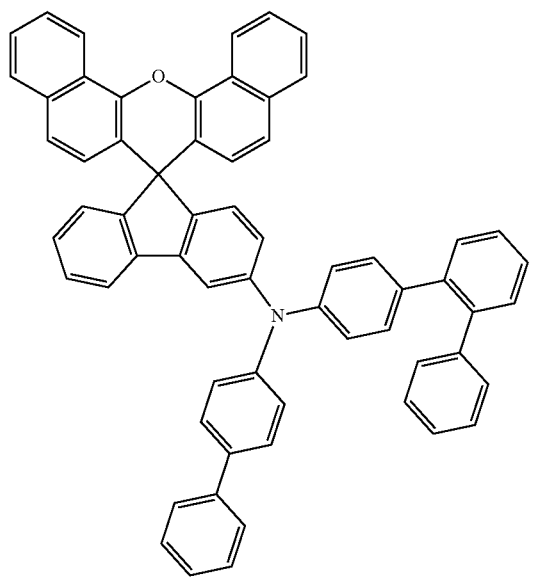
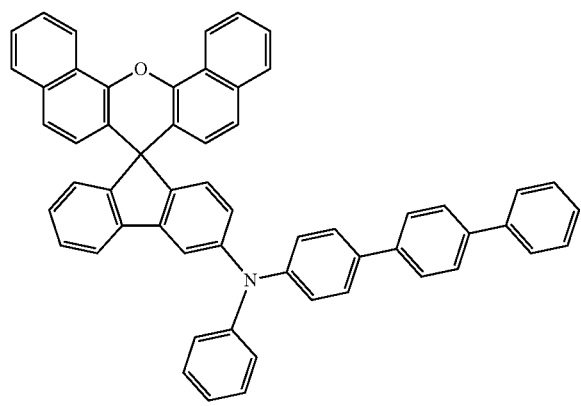
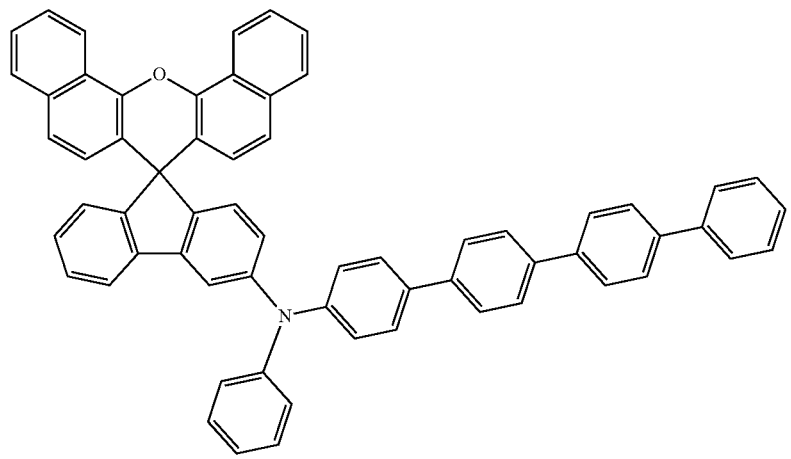

283 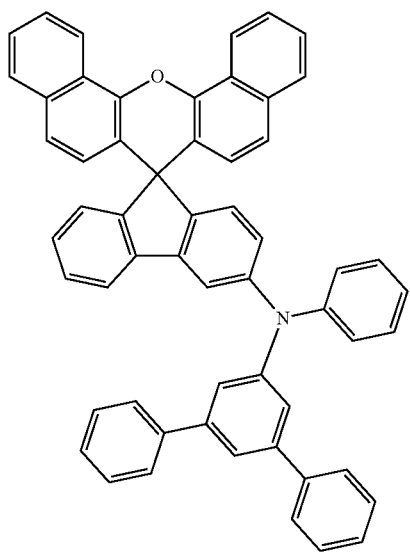
284 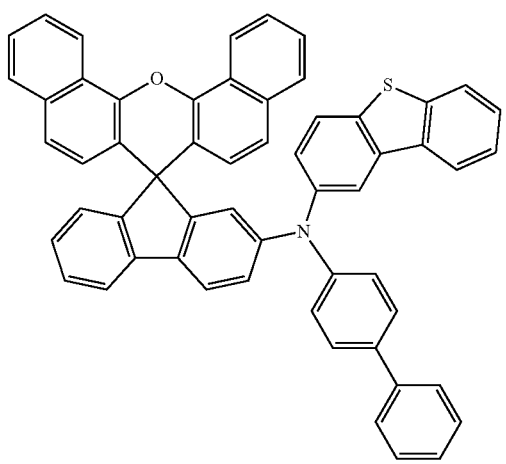
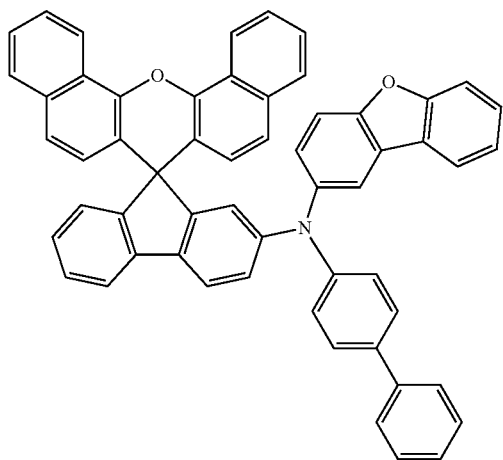
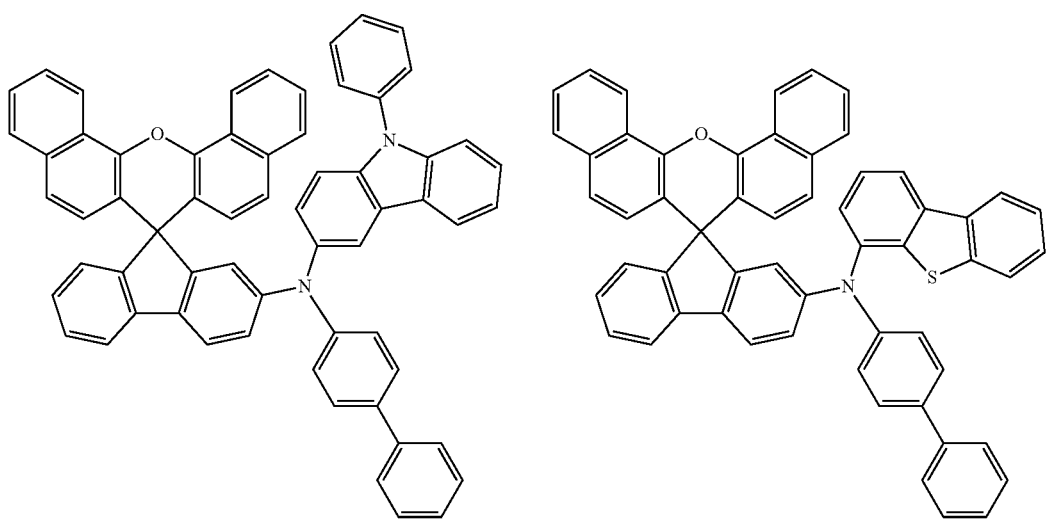

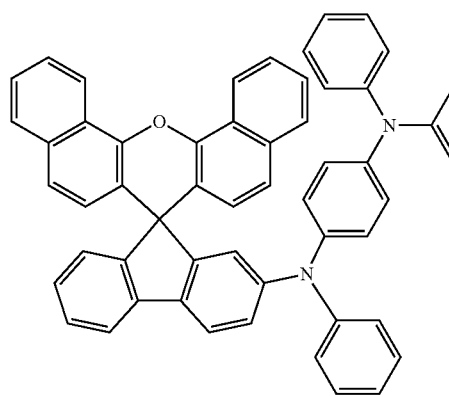
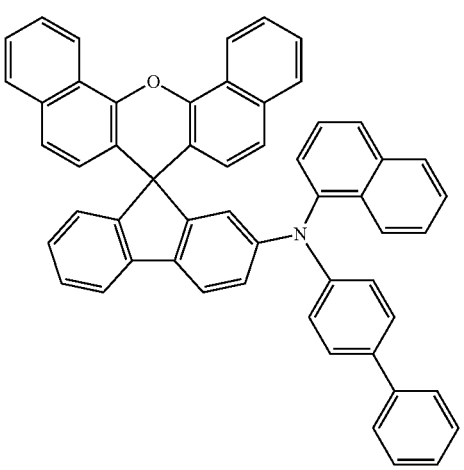
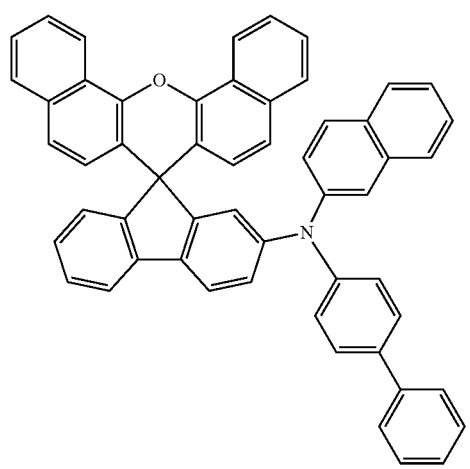
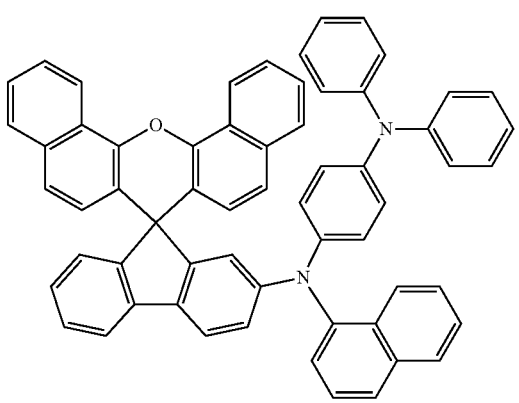
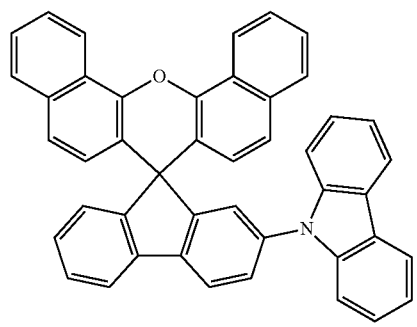
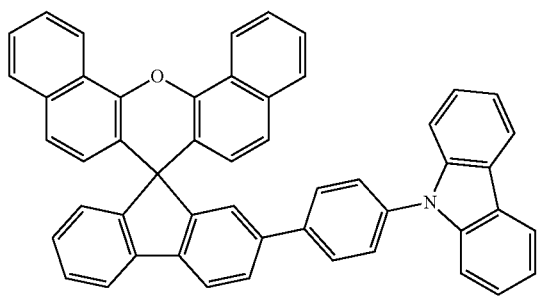

-continued
287
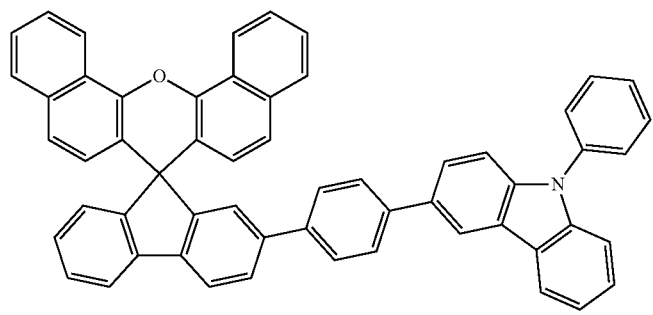
288
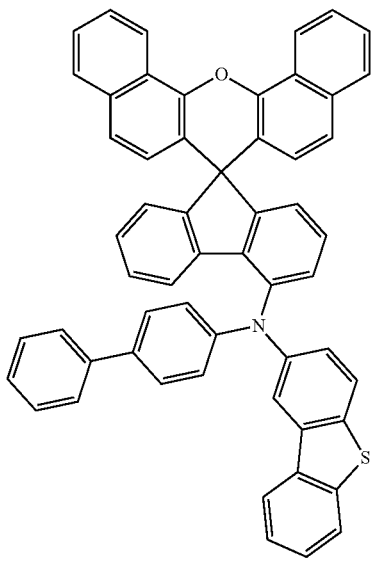
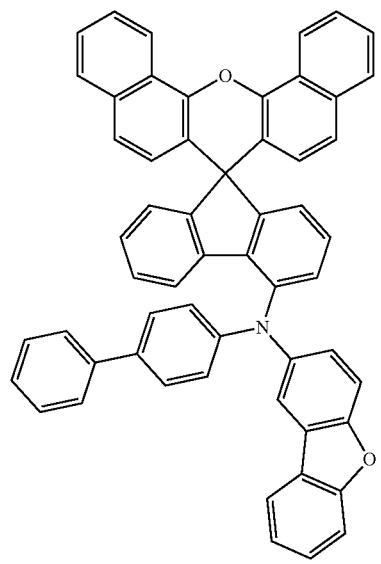
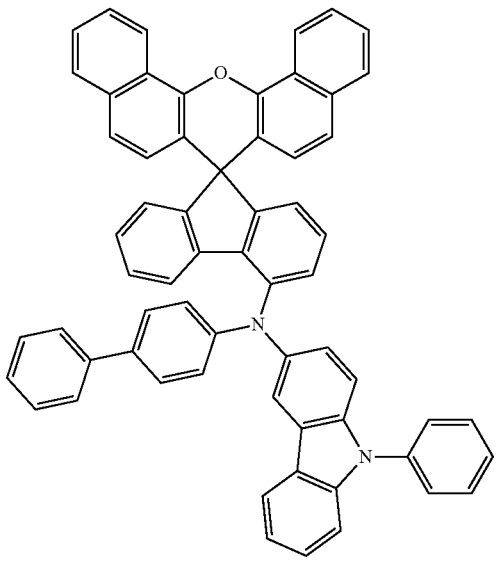
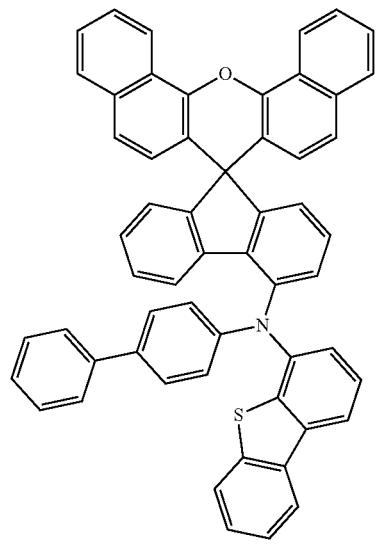
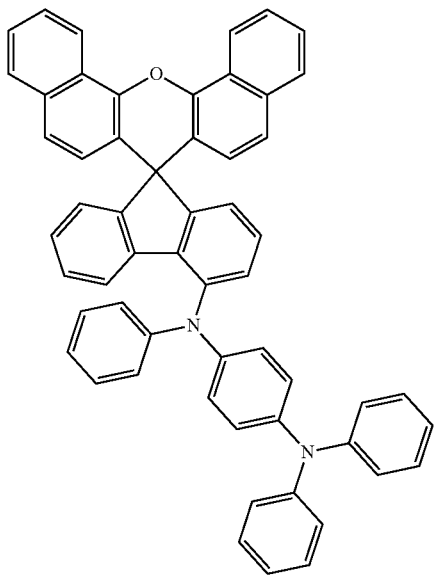

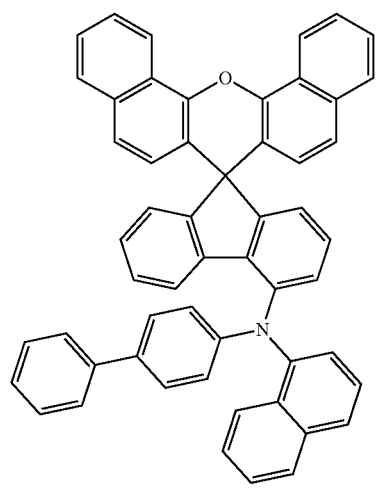
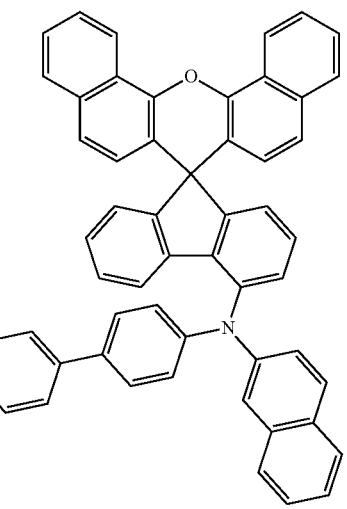
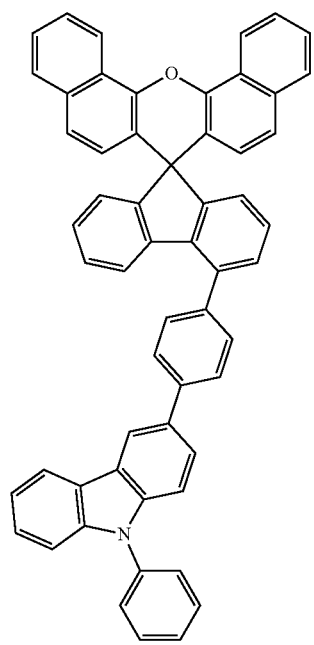
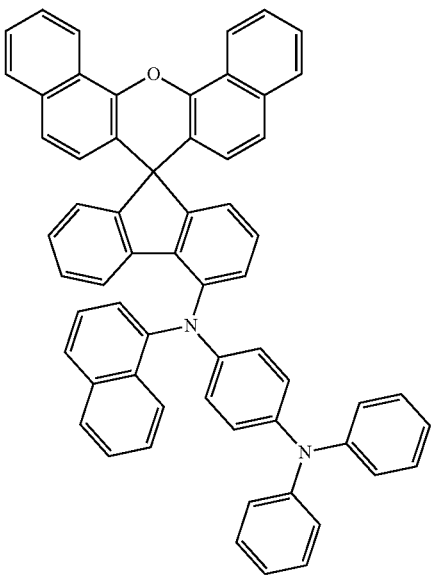
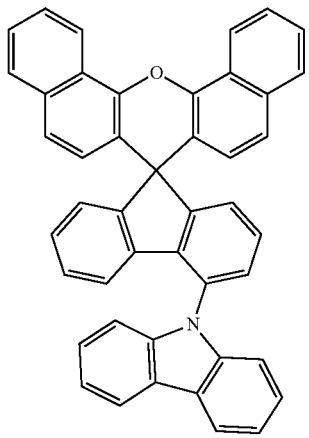
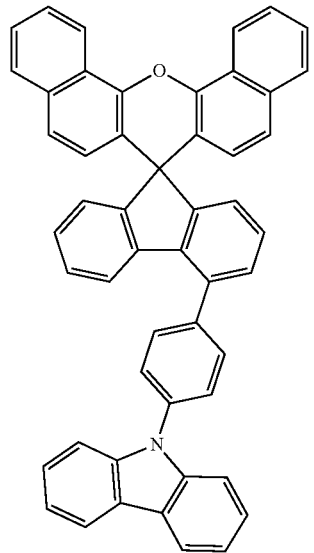
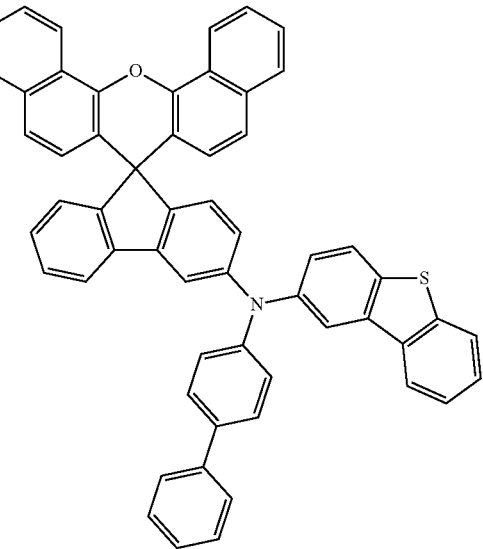

291
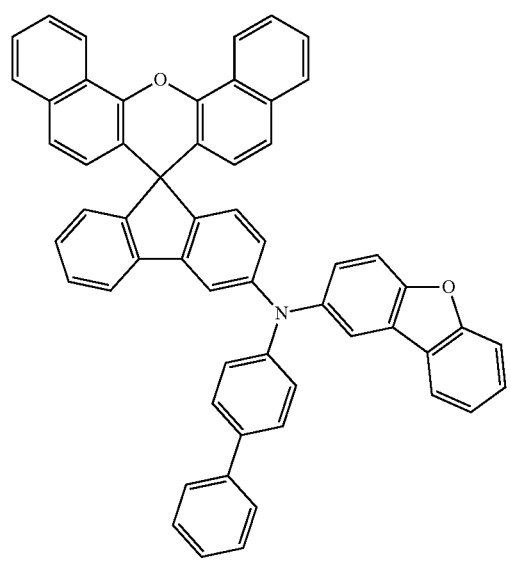
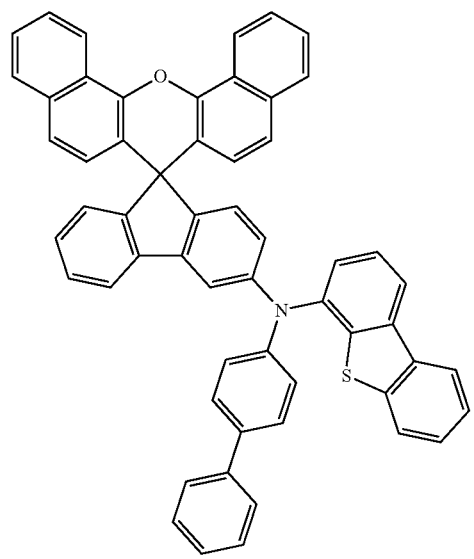
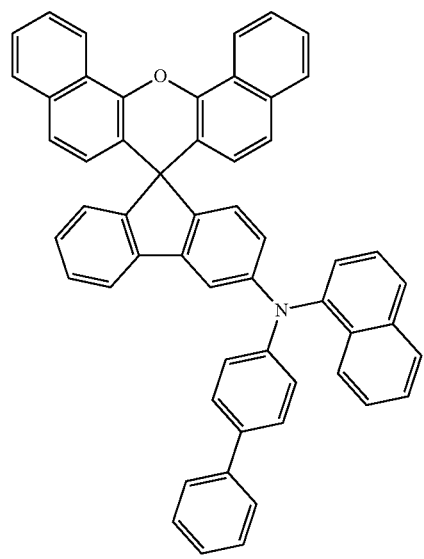
292
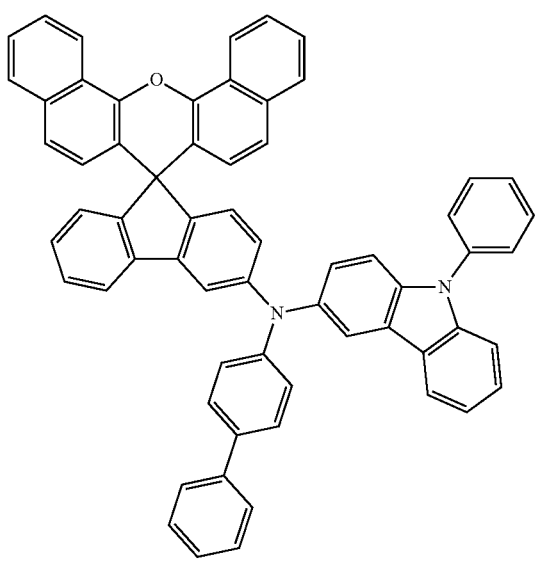
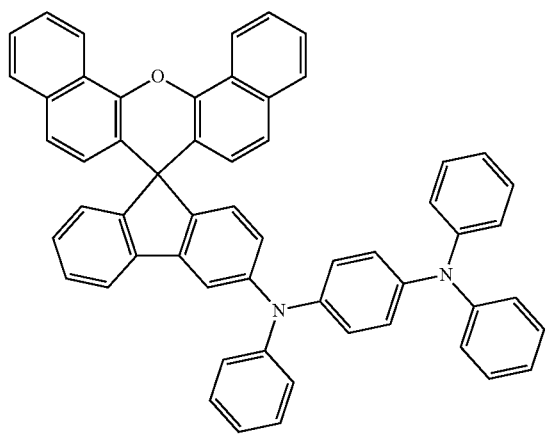
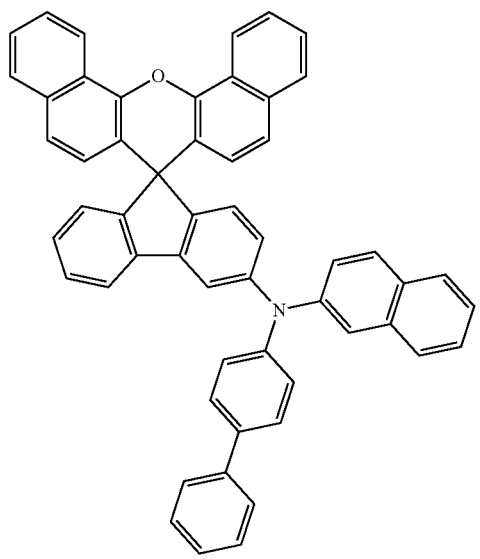

-continued
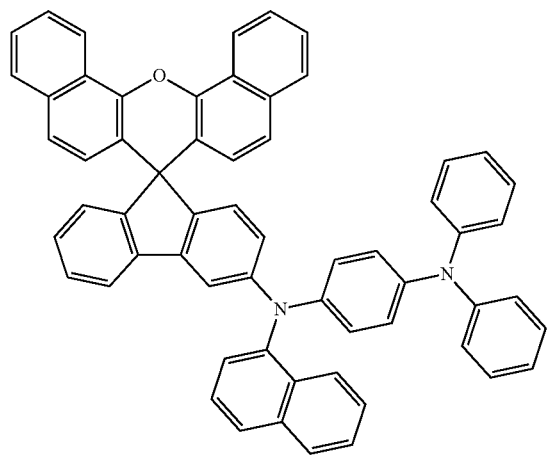
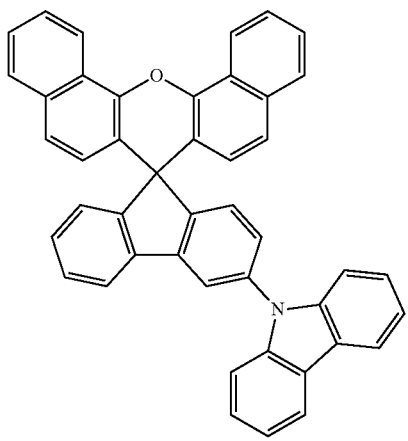
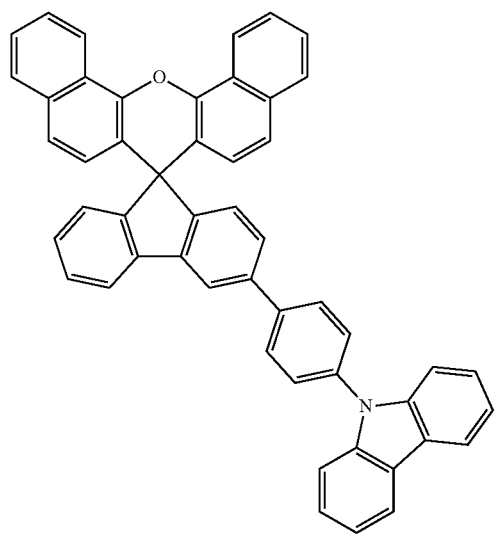
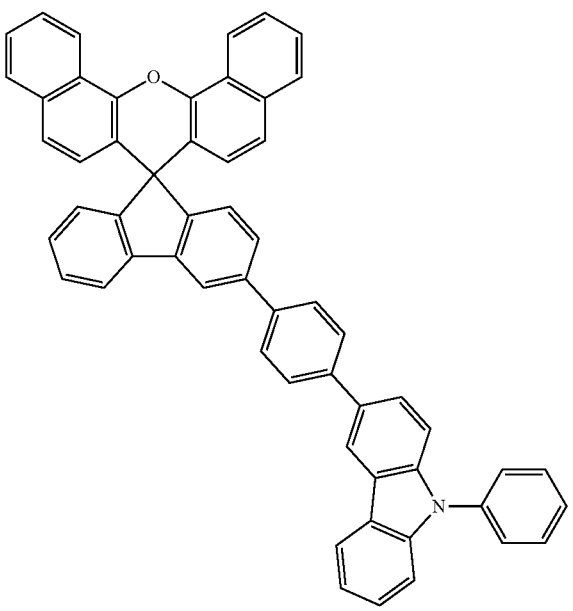
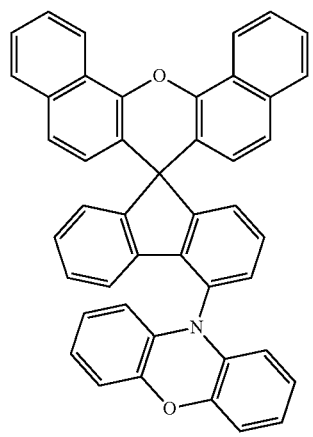
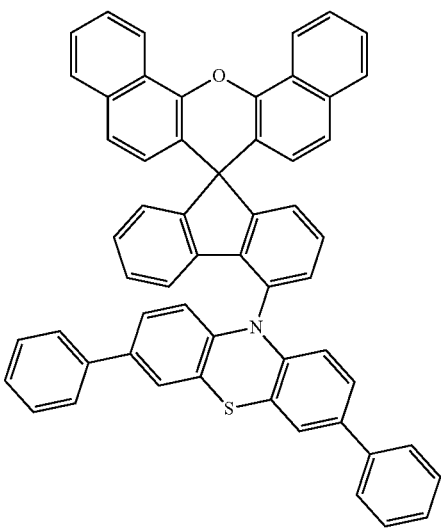

295
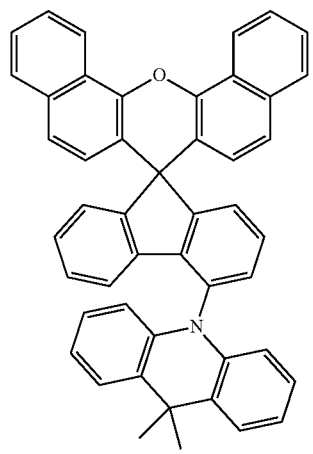
-continued
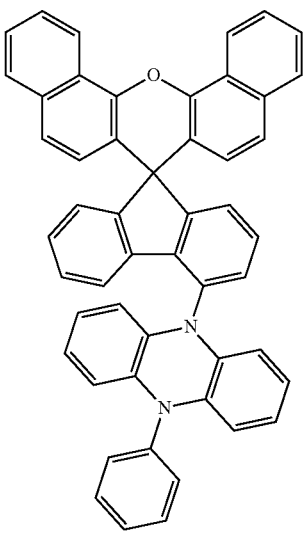
296
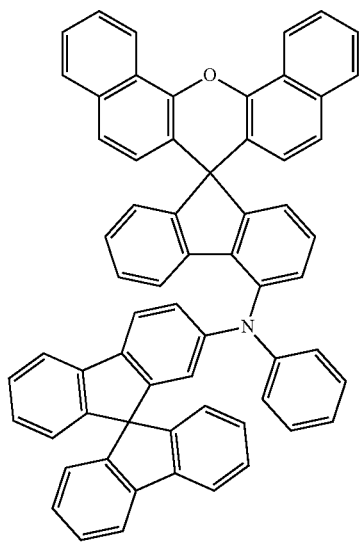
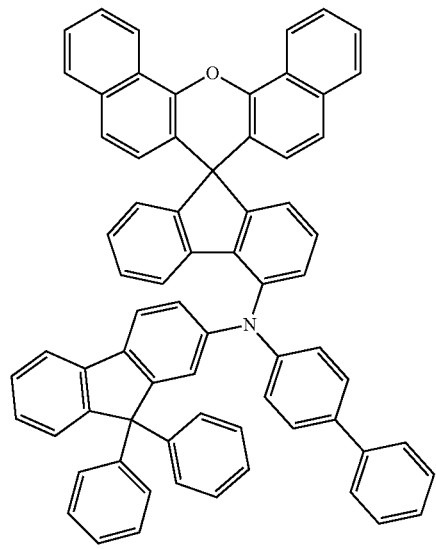
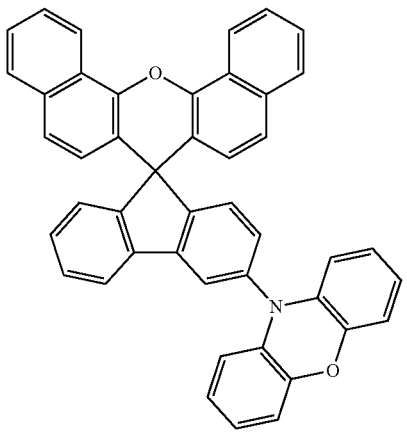
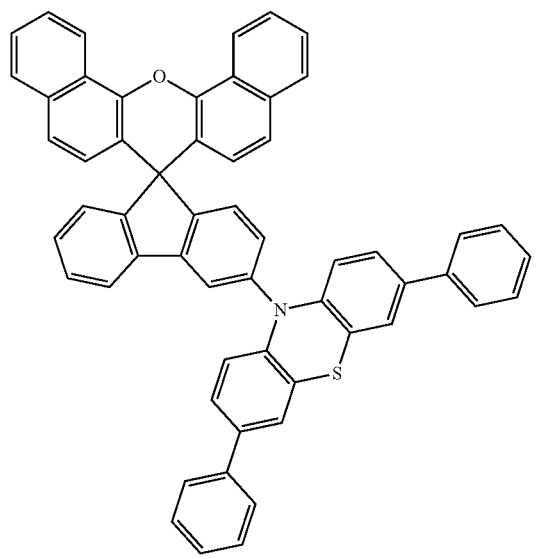
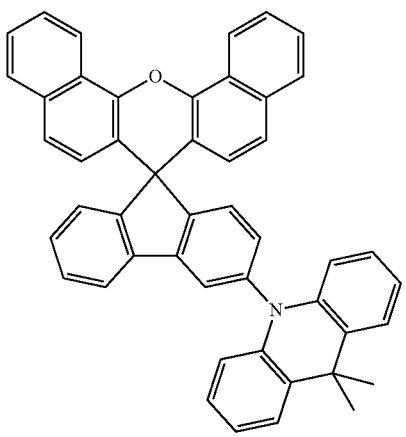

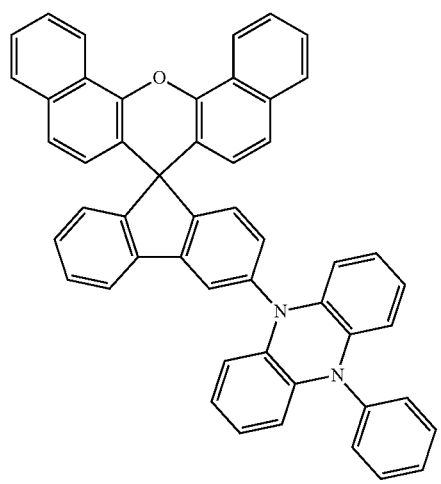
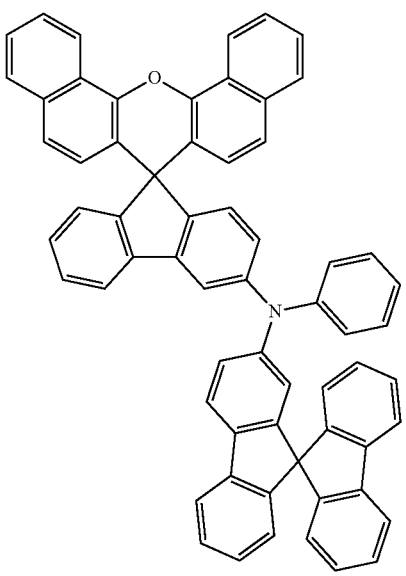
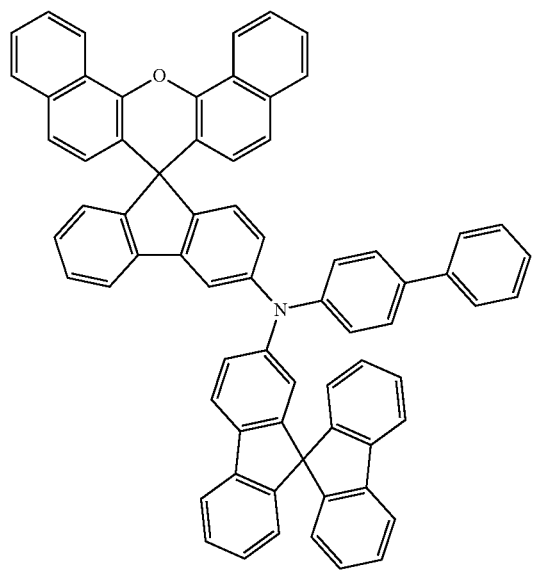
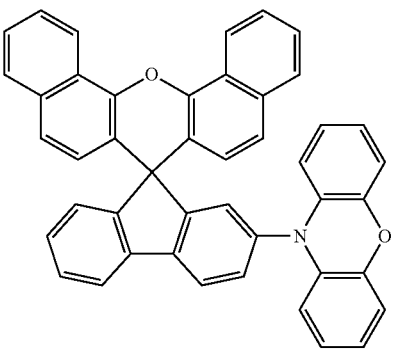
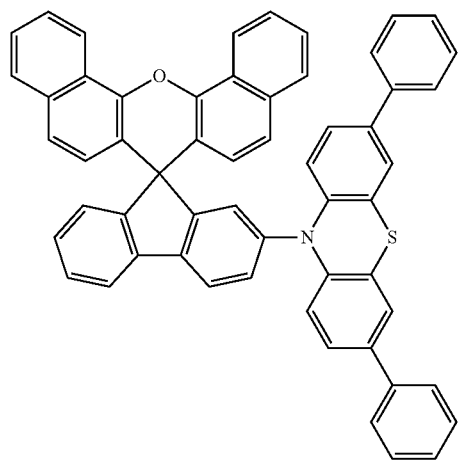
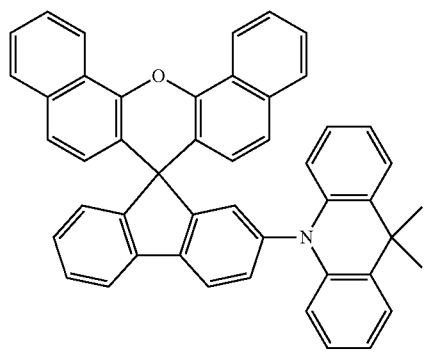

299
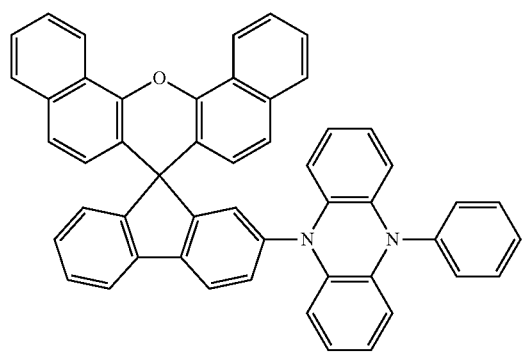
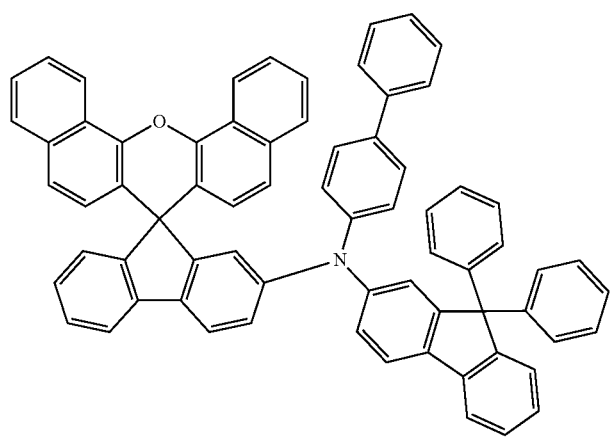
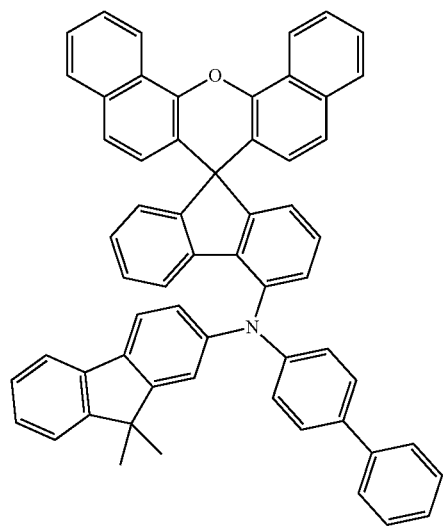
-continued
300
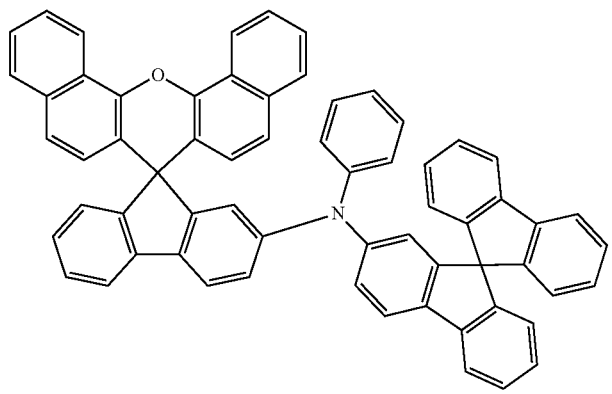
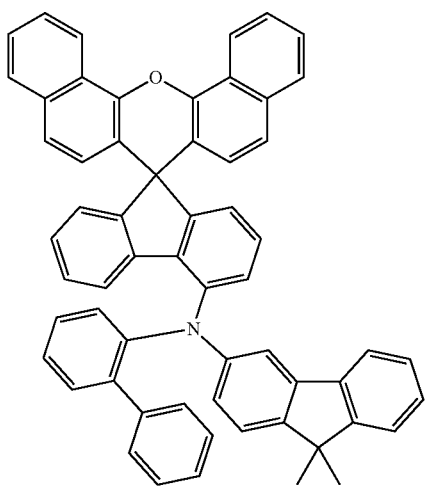
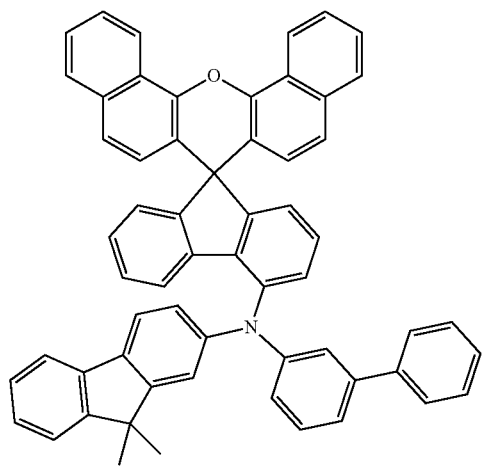

301
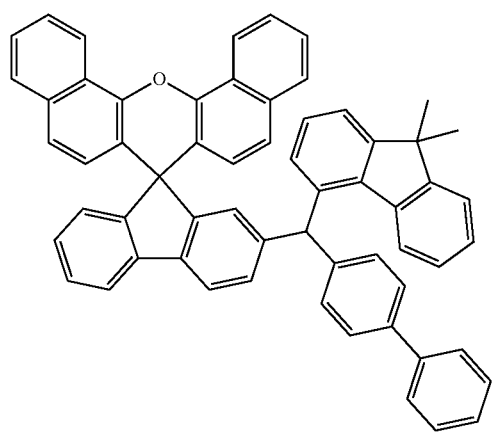
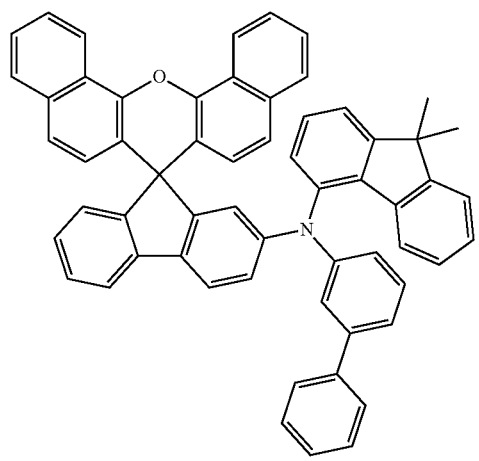
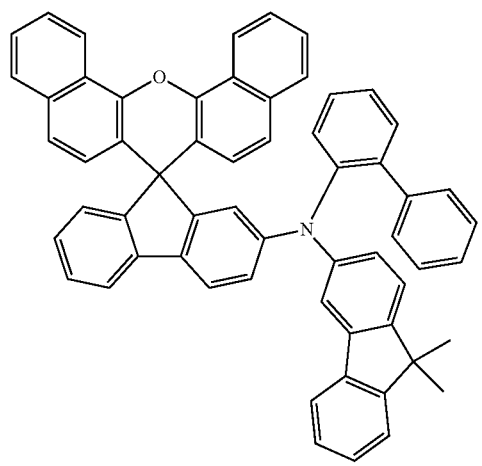
-continued
302
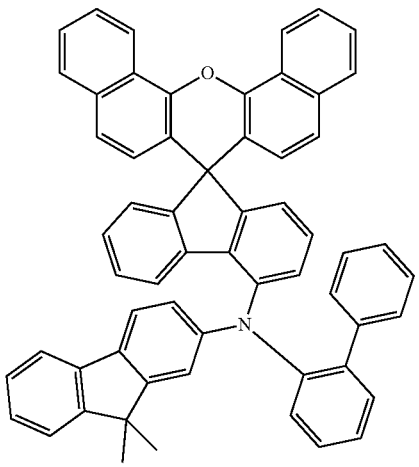
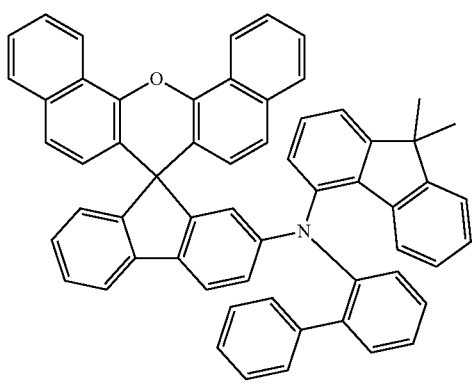
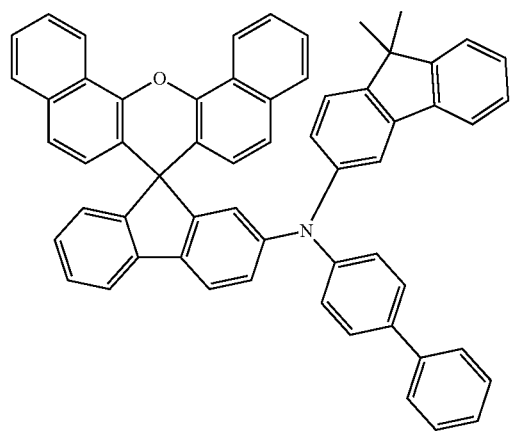

303
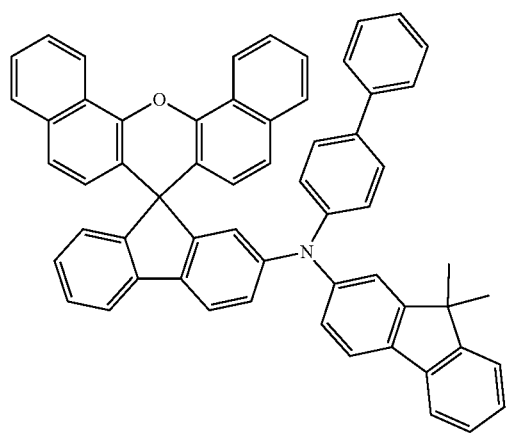
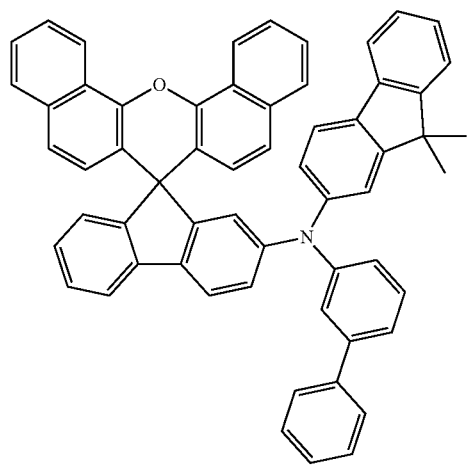
304
-continued
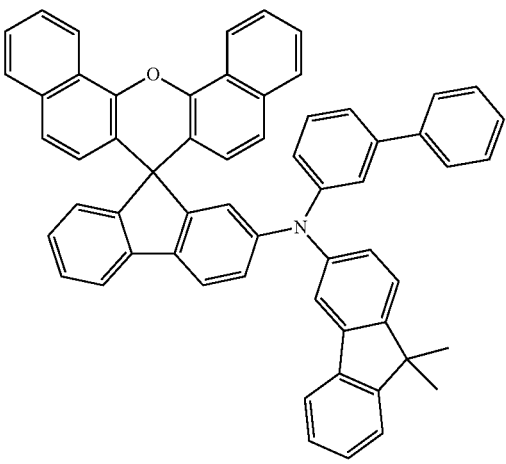
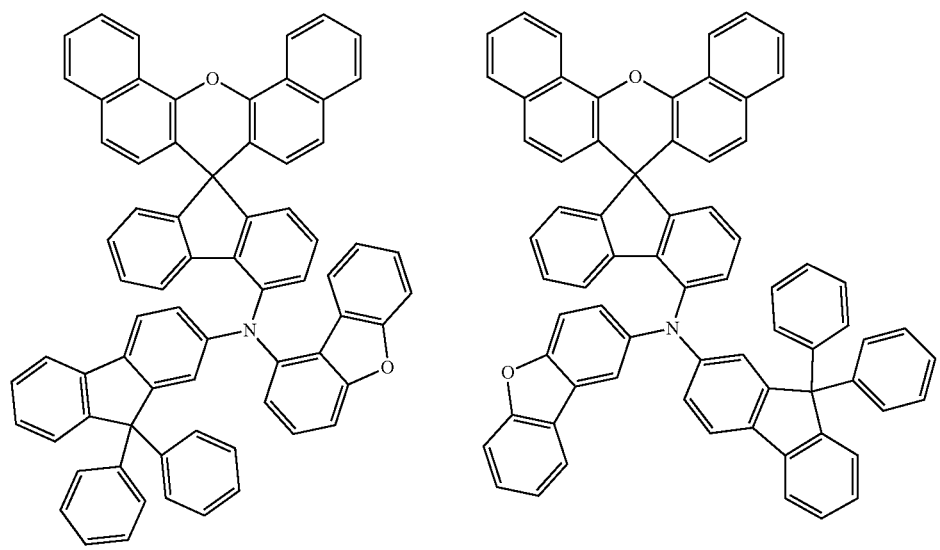

305
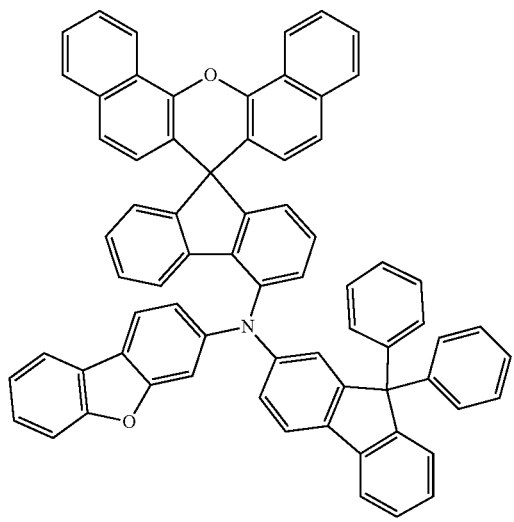
306
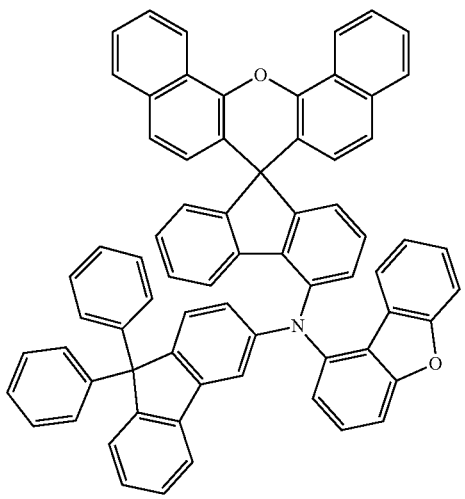
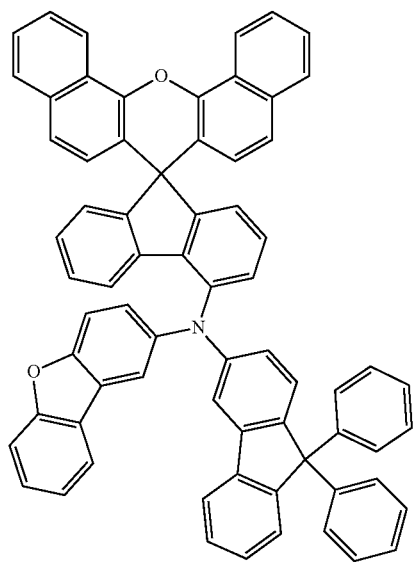
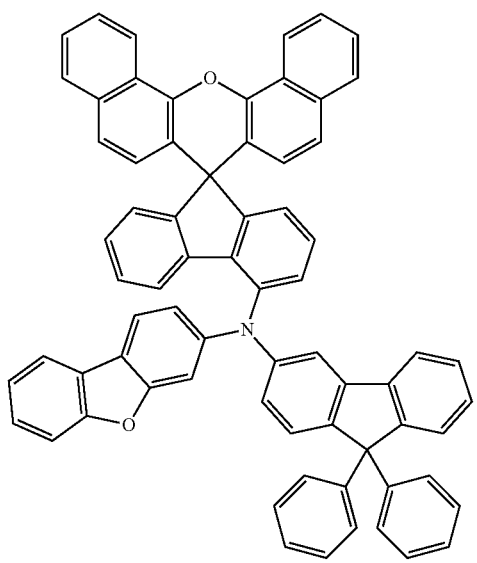
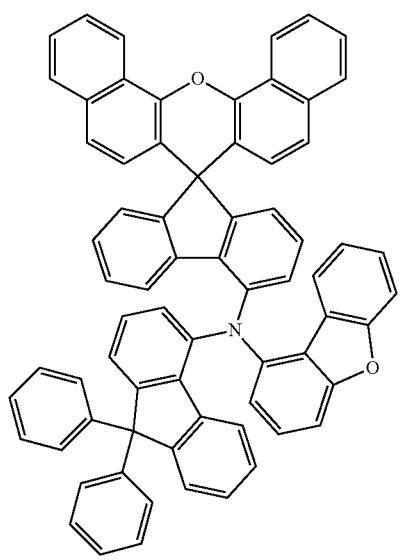
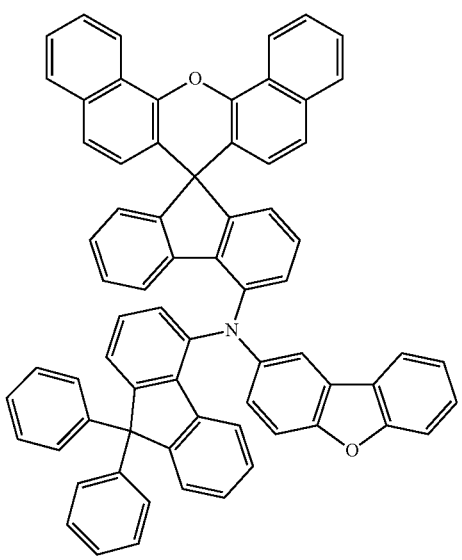

-continued
307
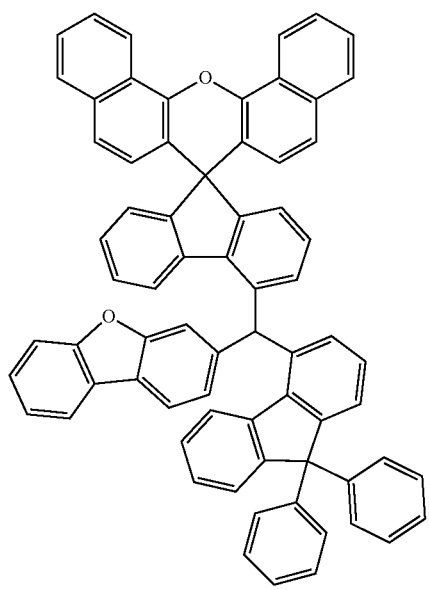
308
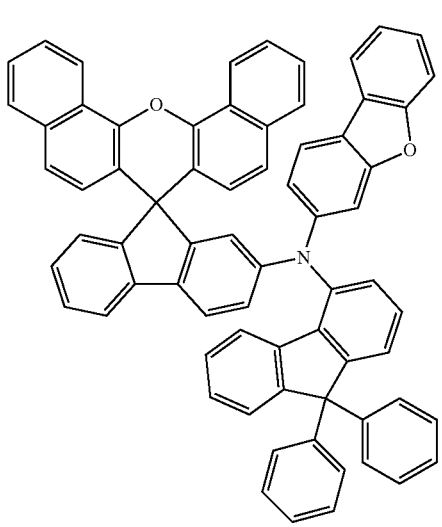
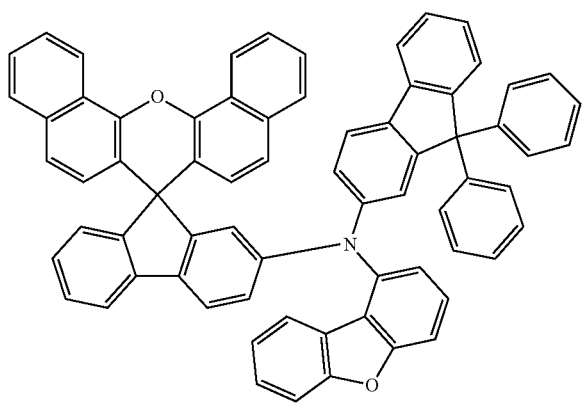
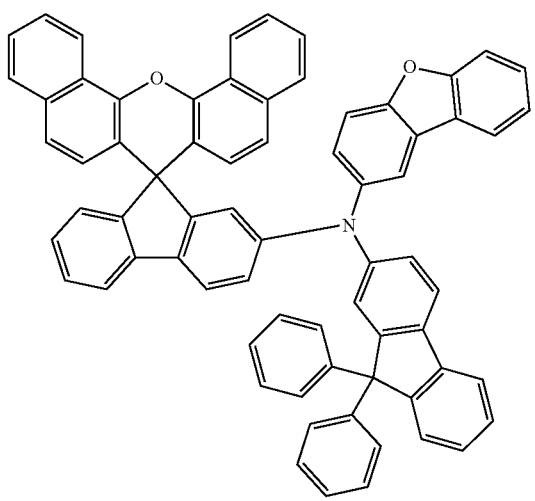
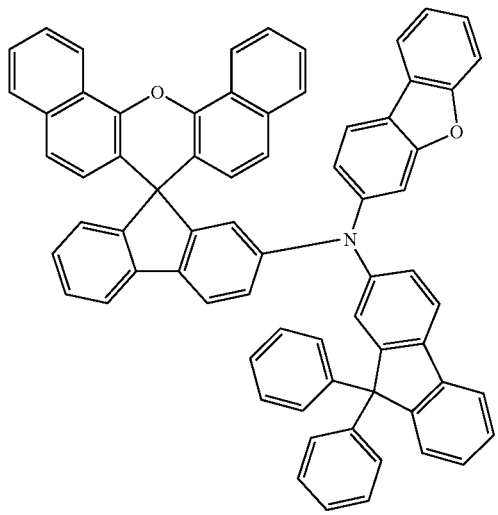
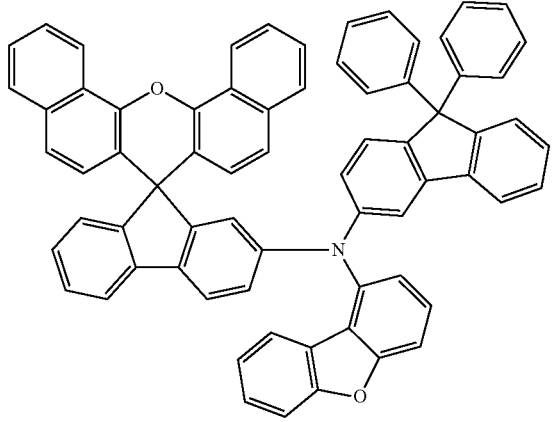

309
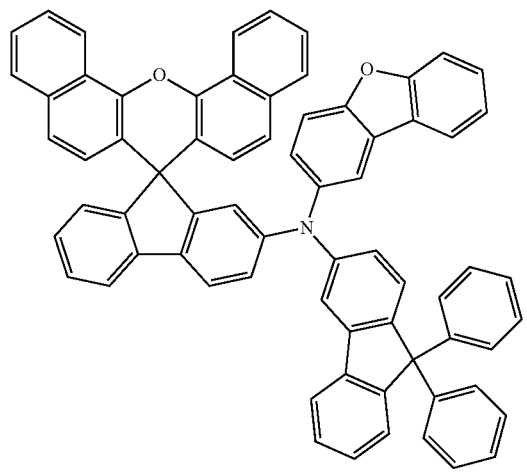
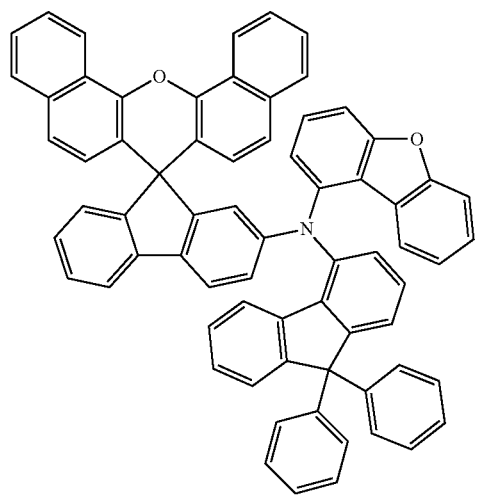
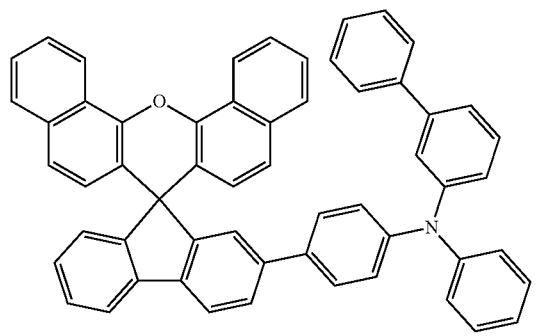
310
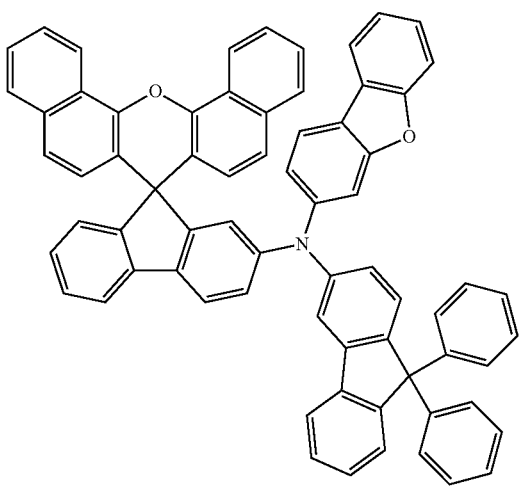
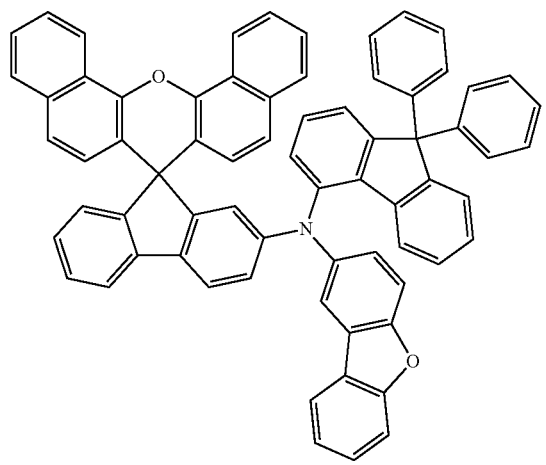
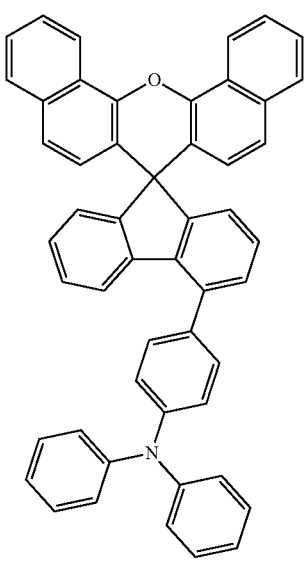

311 312
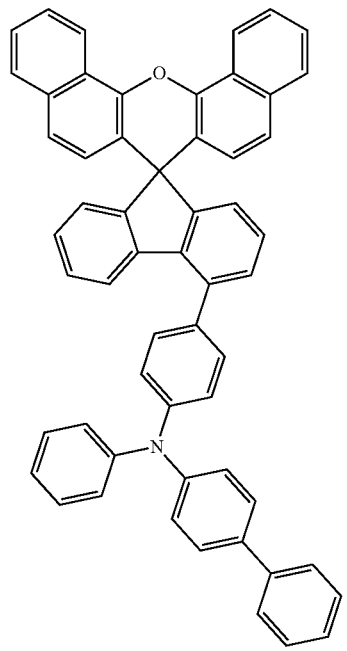 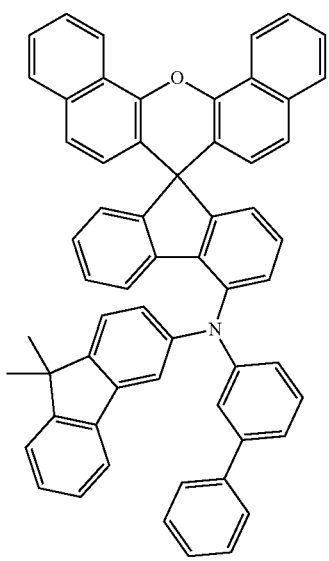 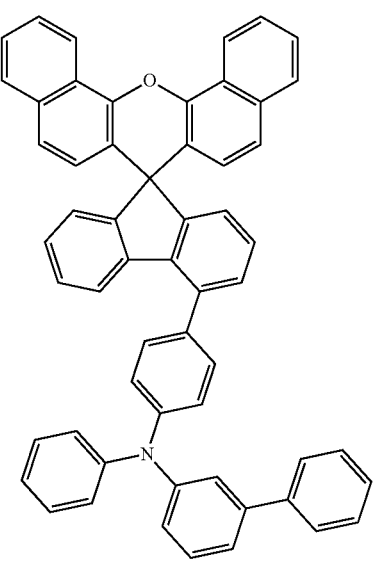
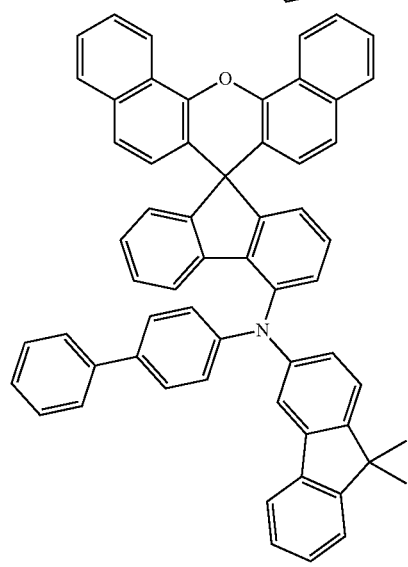 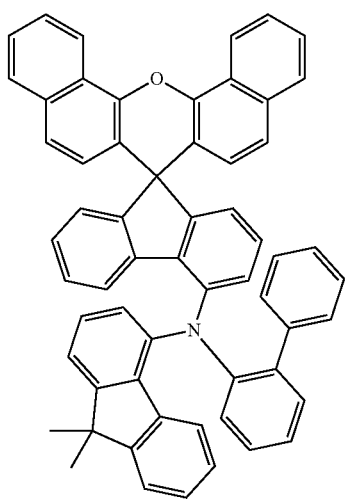
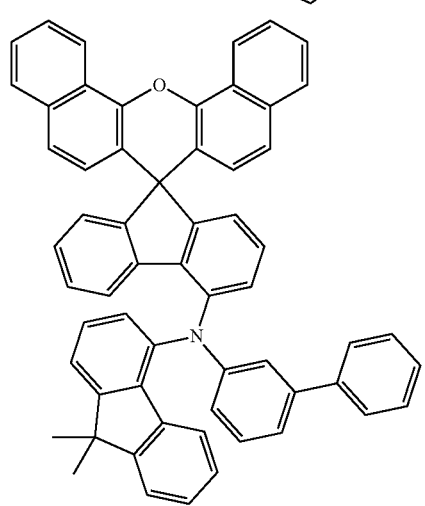 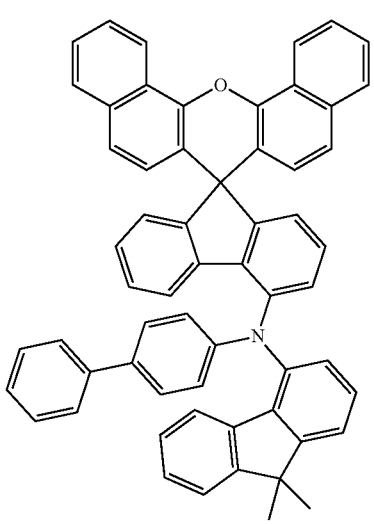

313
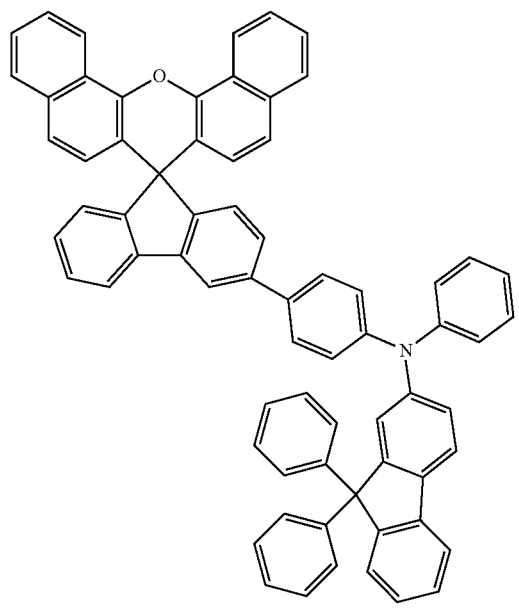
314
-continued
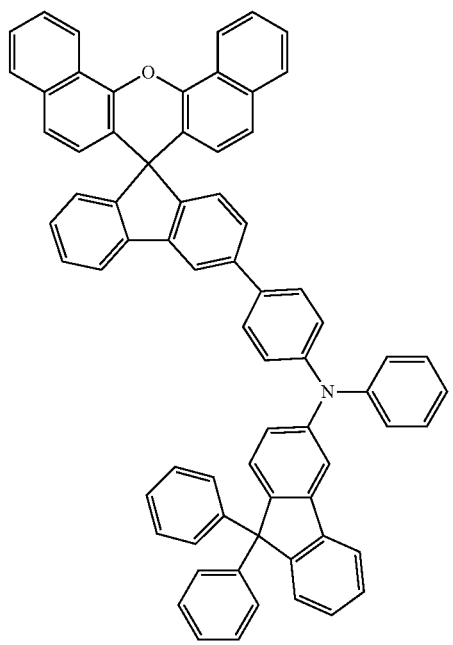
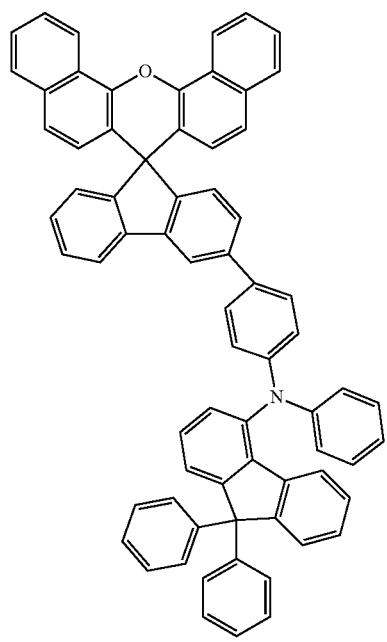
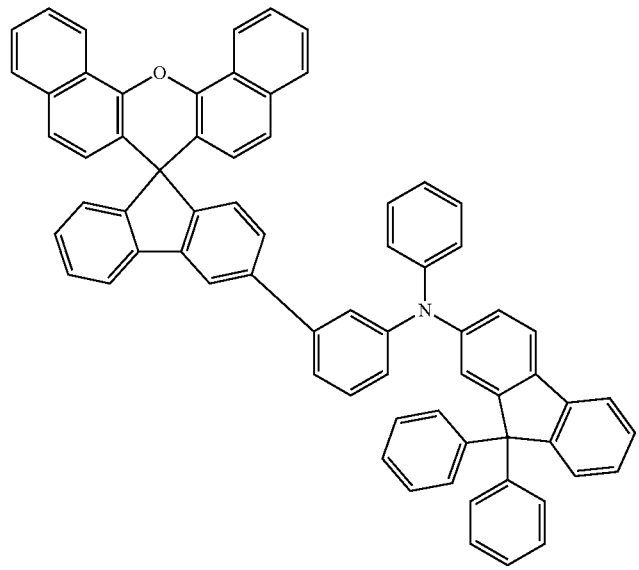

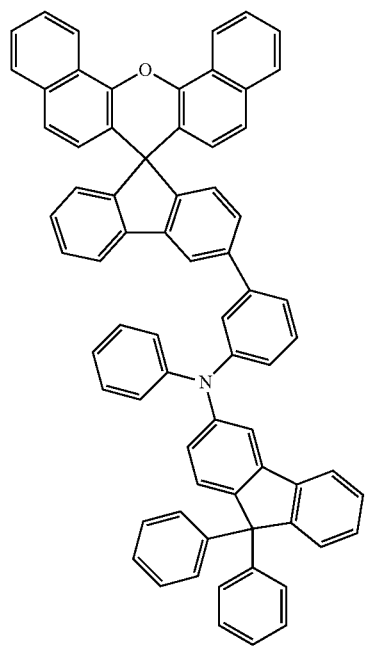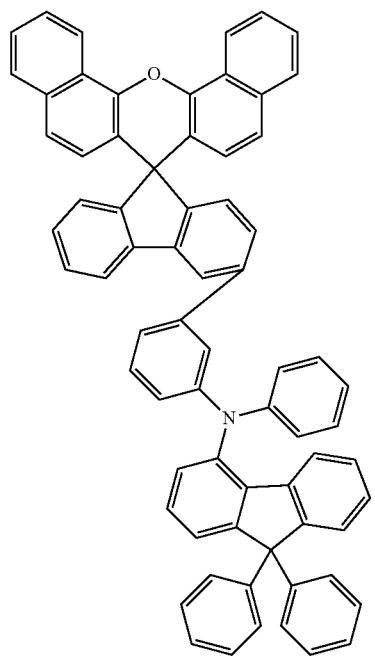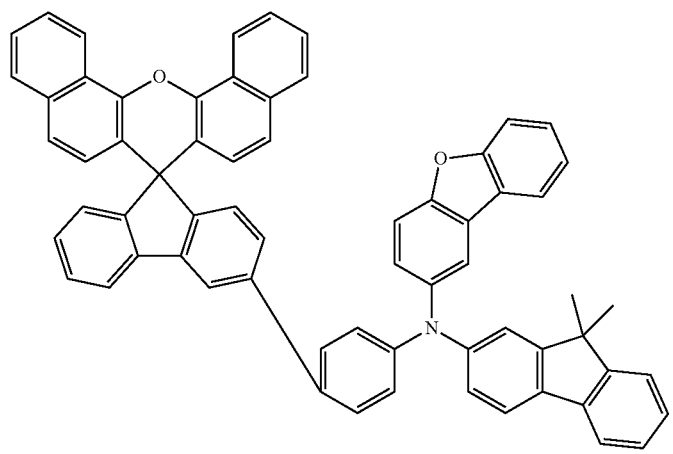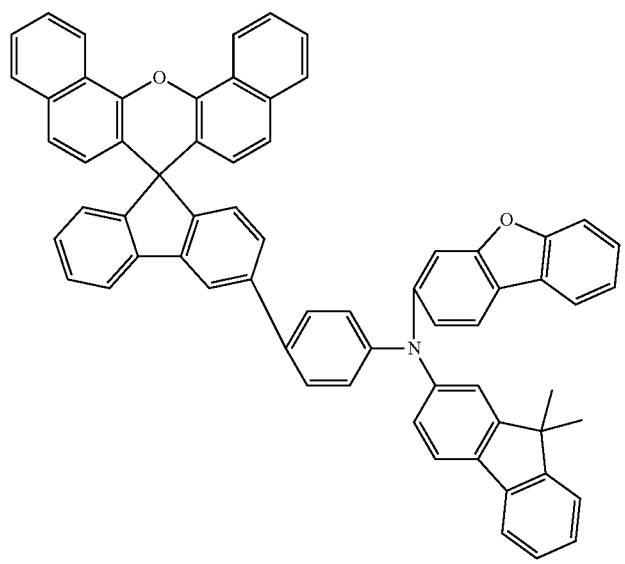

-continued
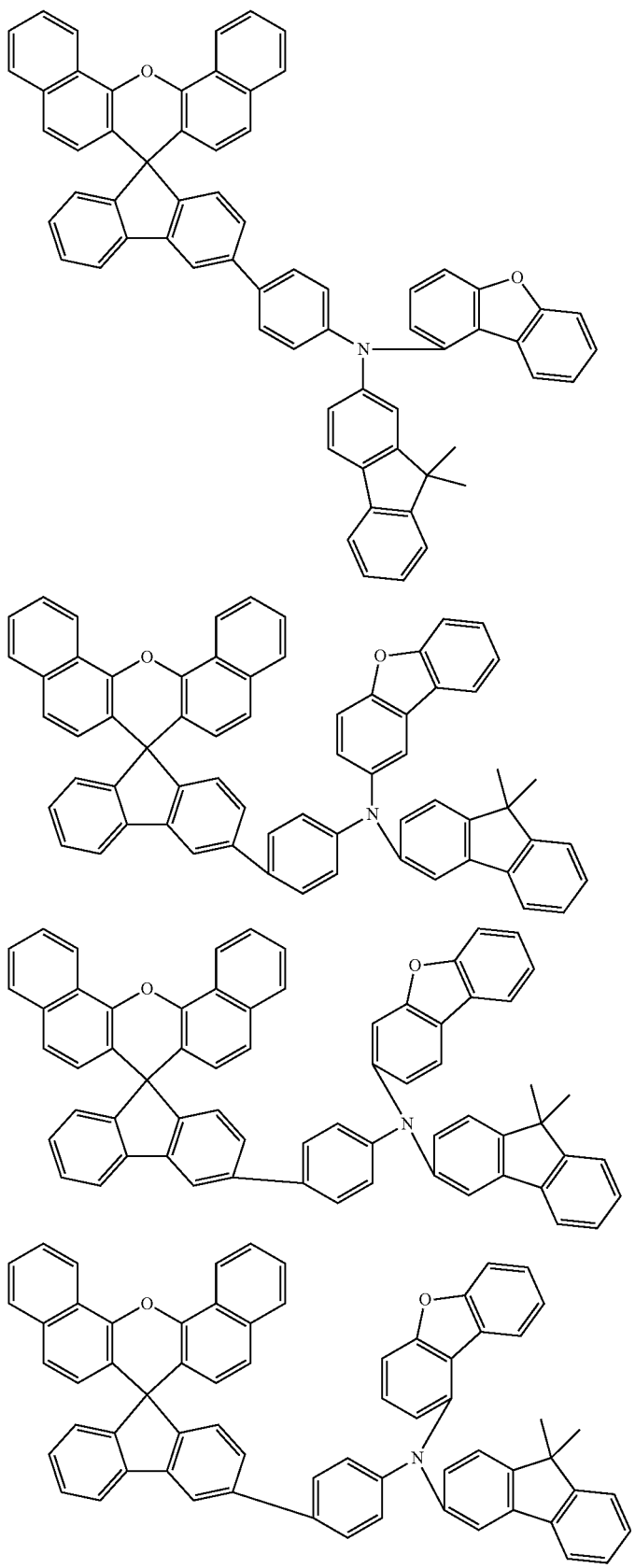

-continued
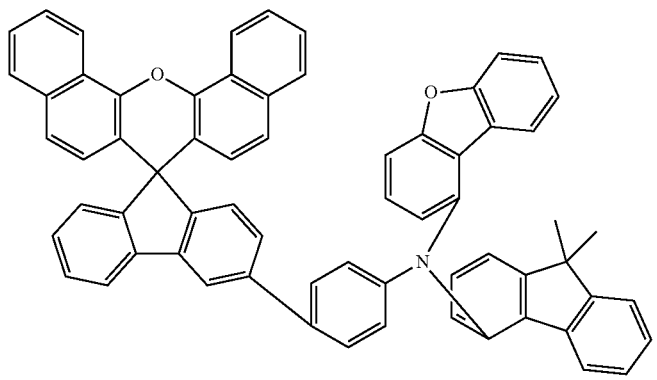
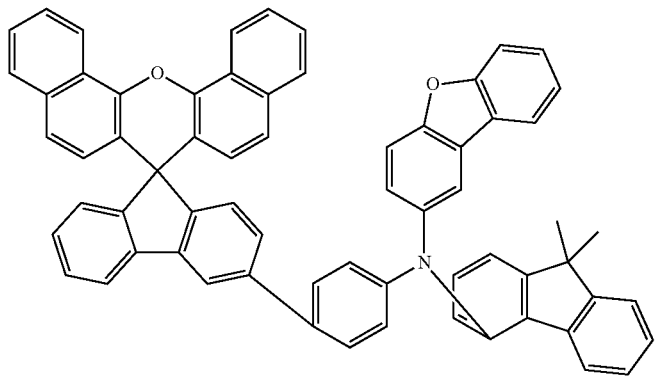
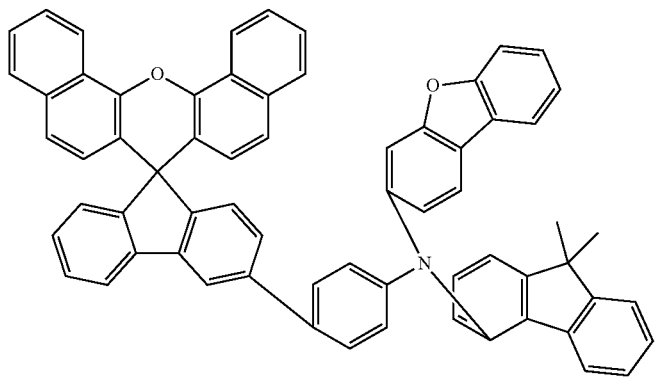
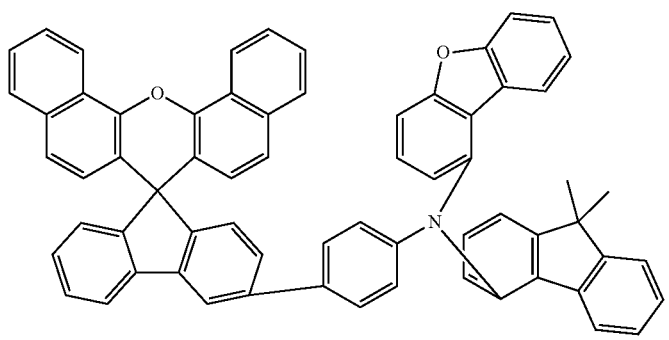

-continued
| 321 | 322 |
|---|---|
| 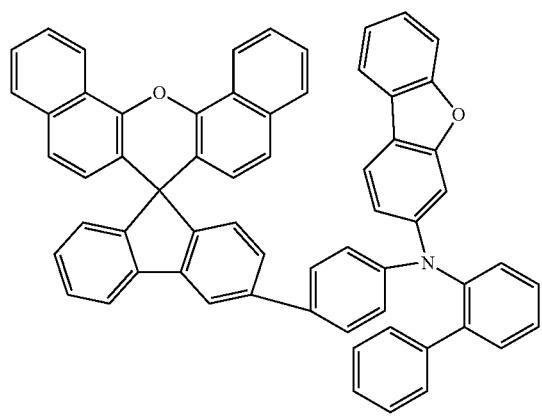 | 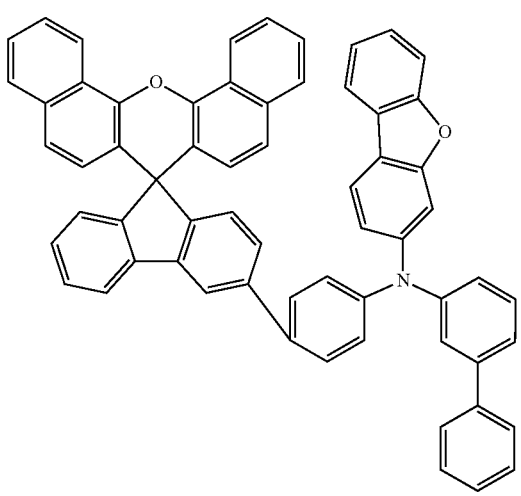 |
| 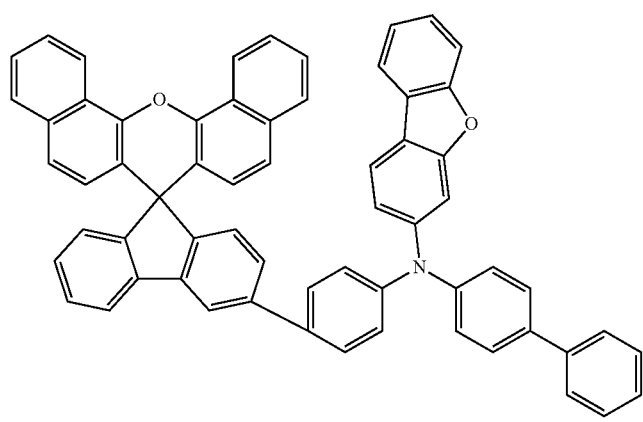 | |
| 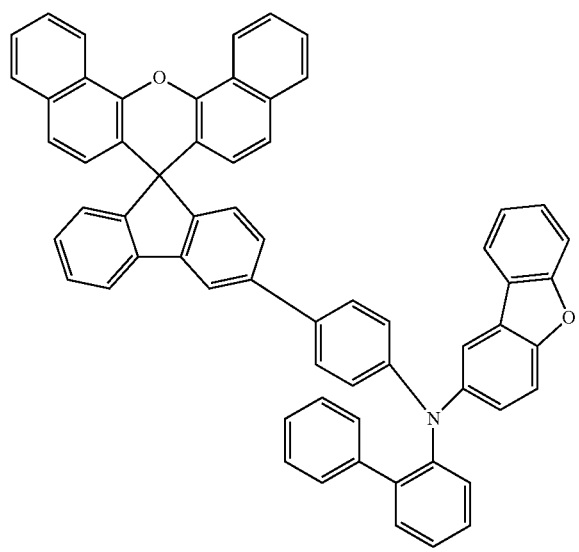 | 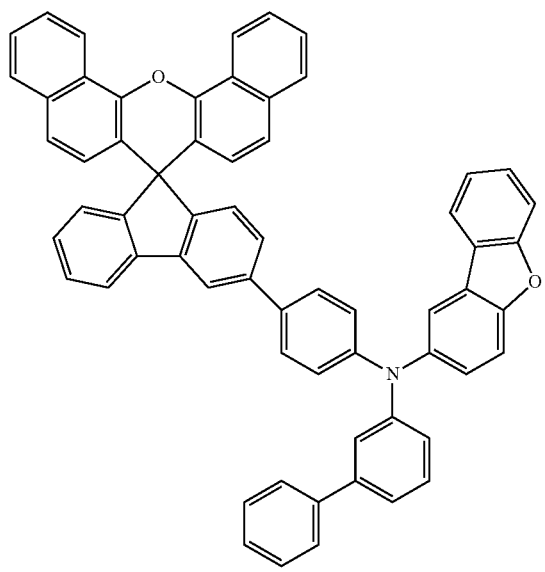 |

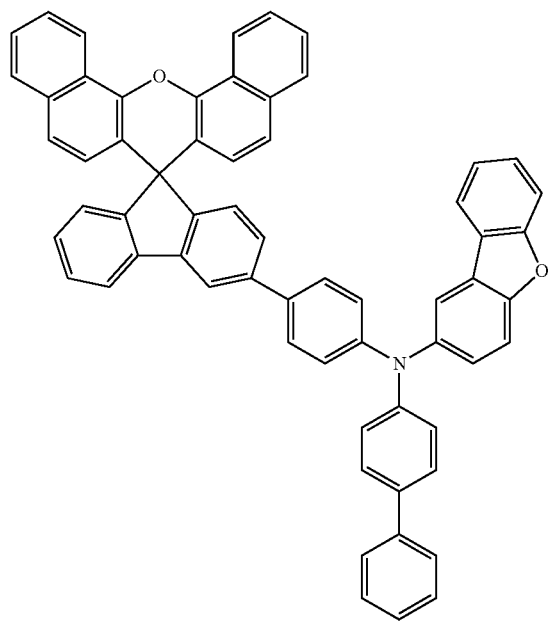
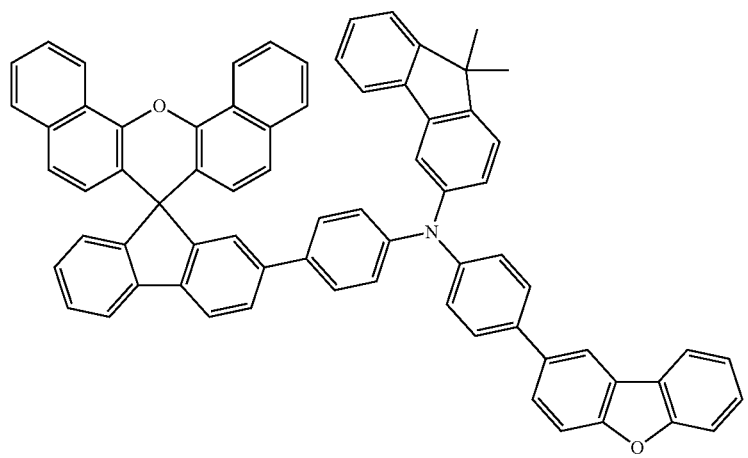
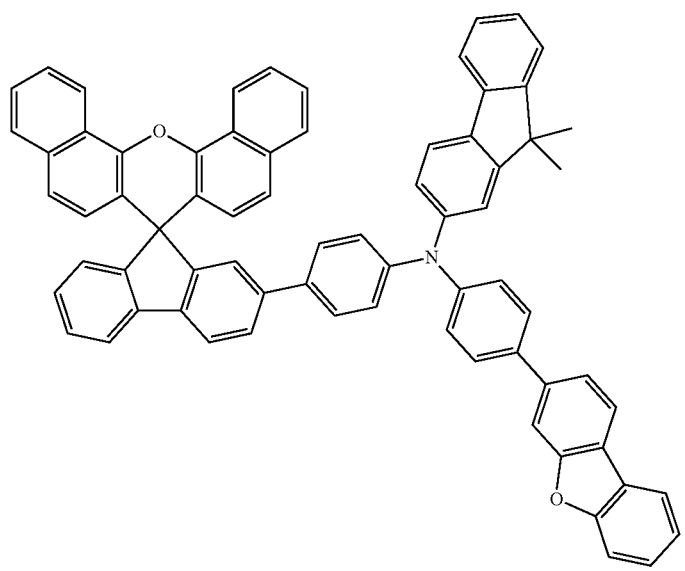

-continued
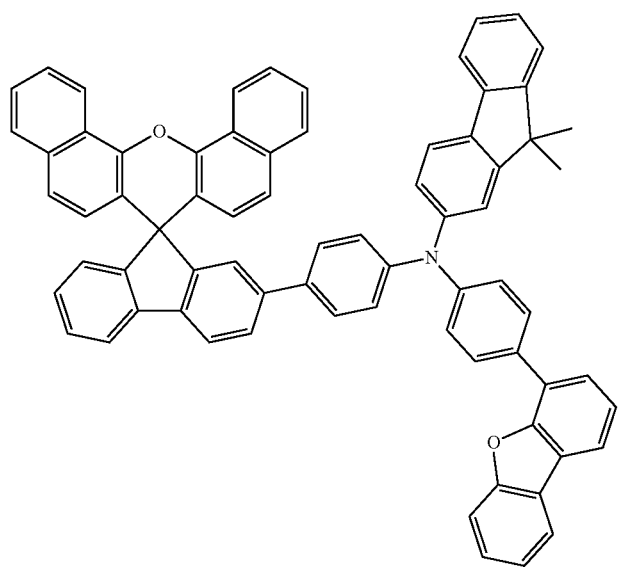
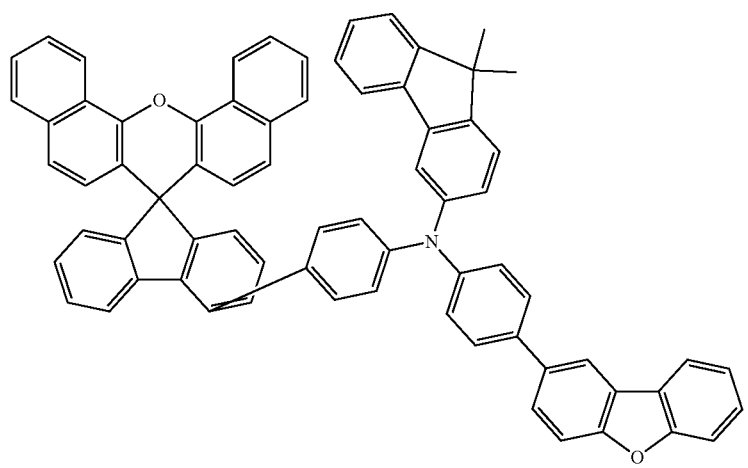
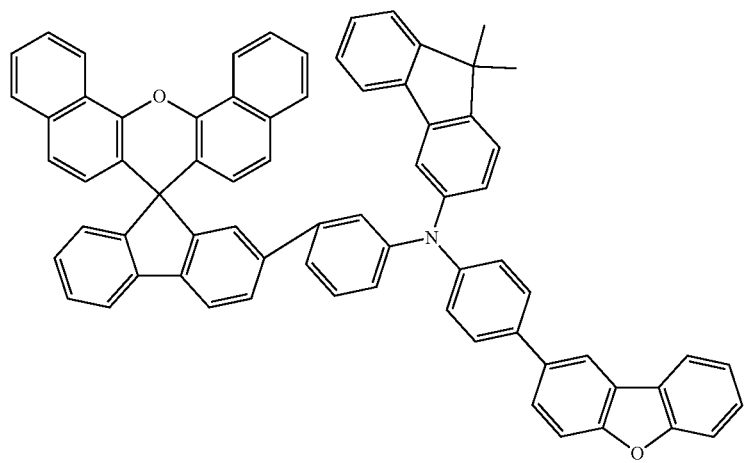

-continued
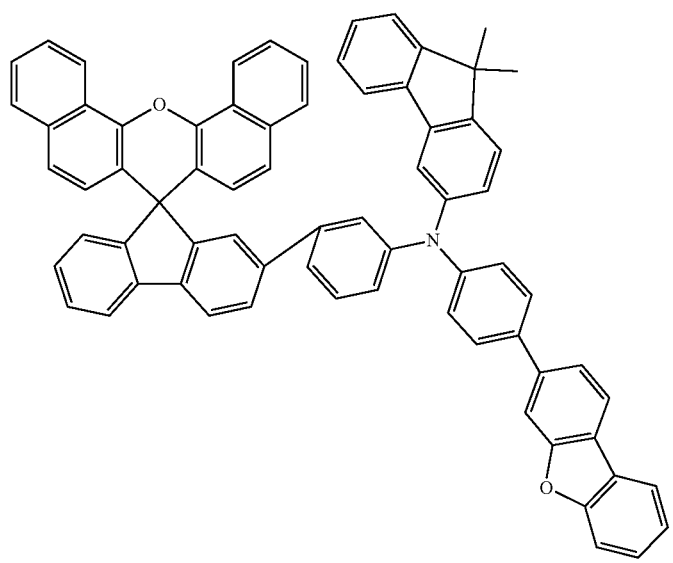
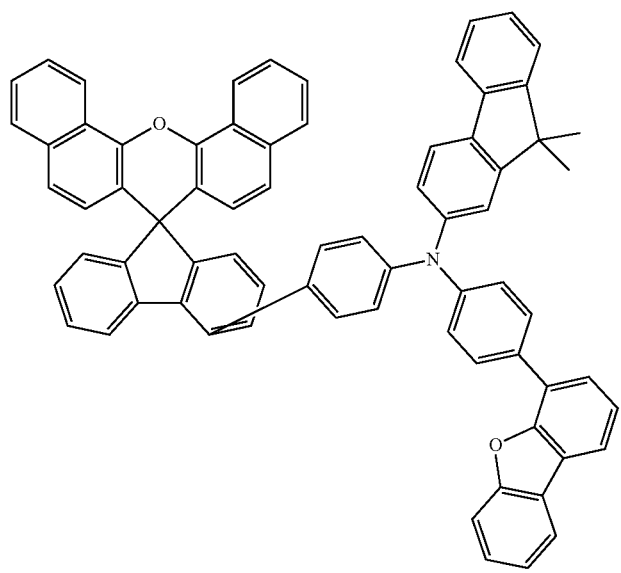
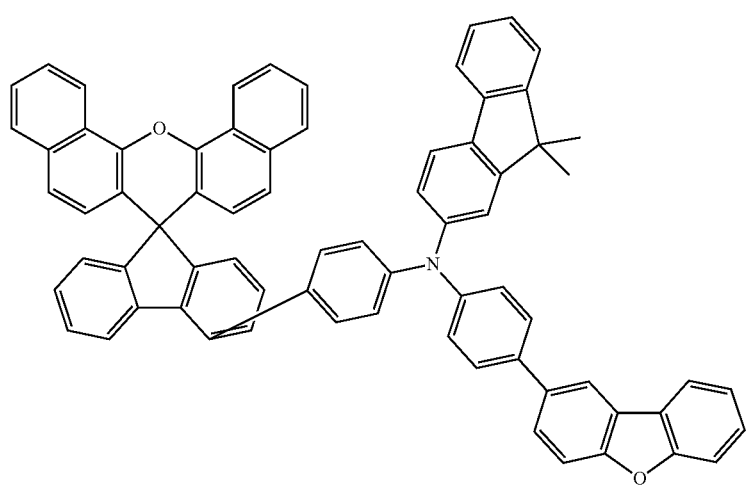

-continued
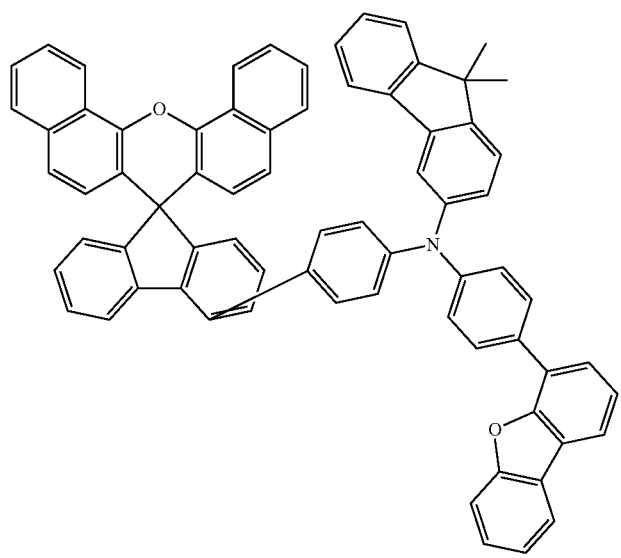
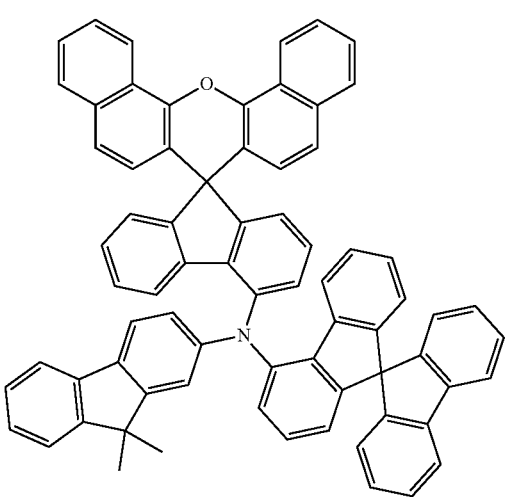
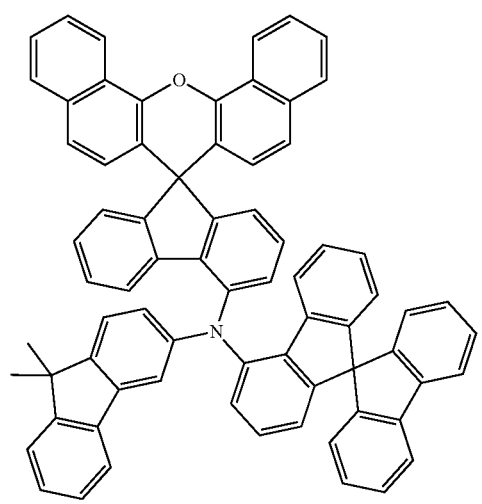
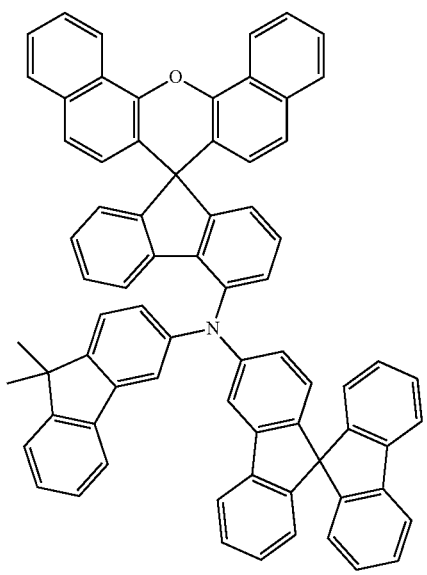
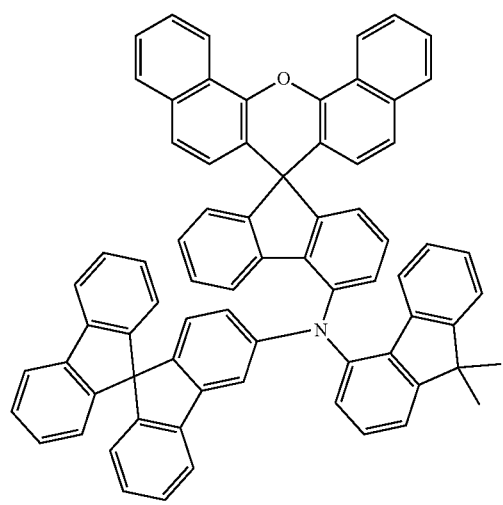
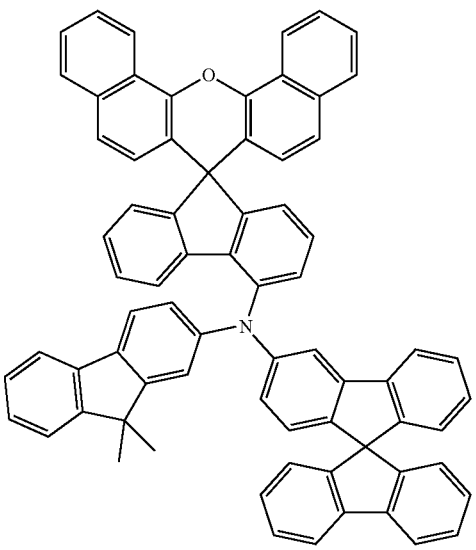

-continued
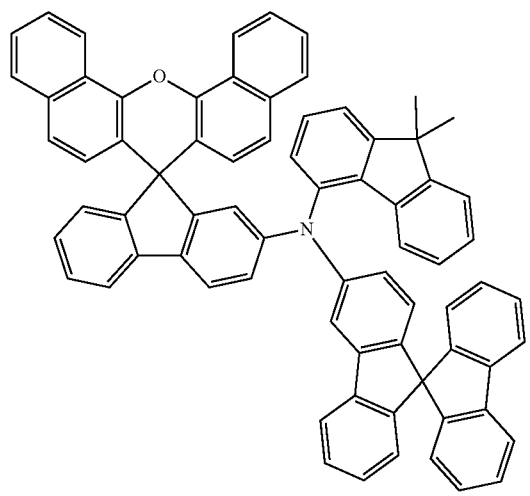
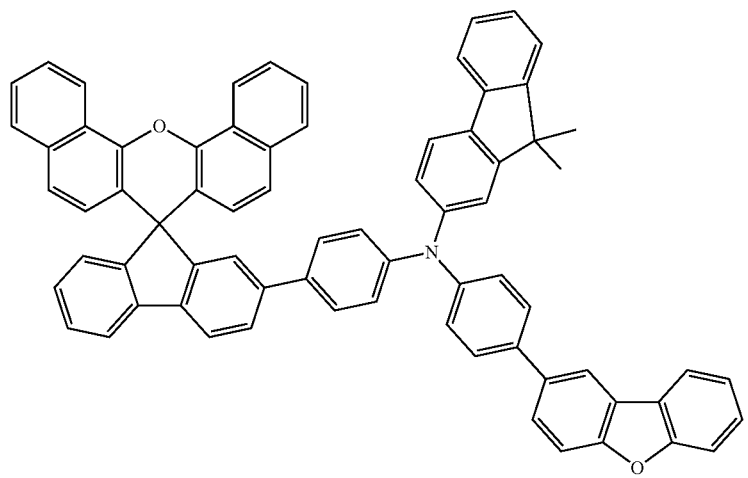
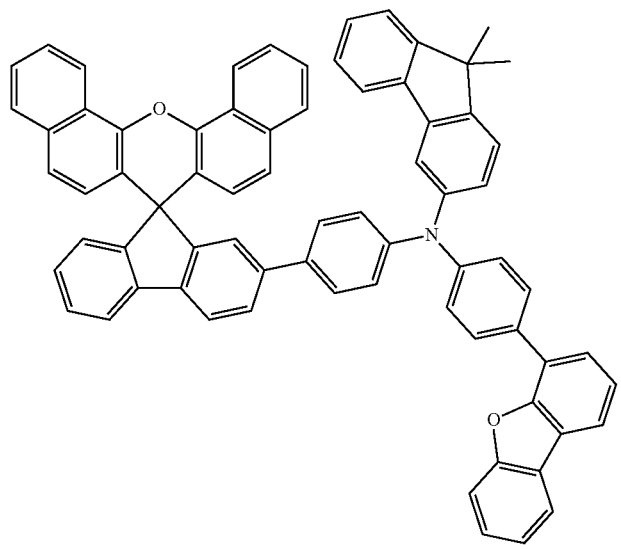

-continued
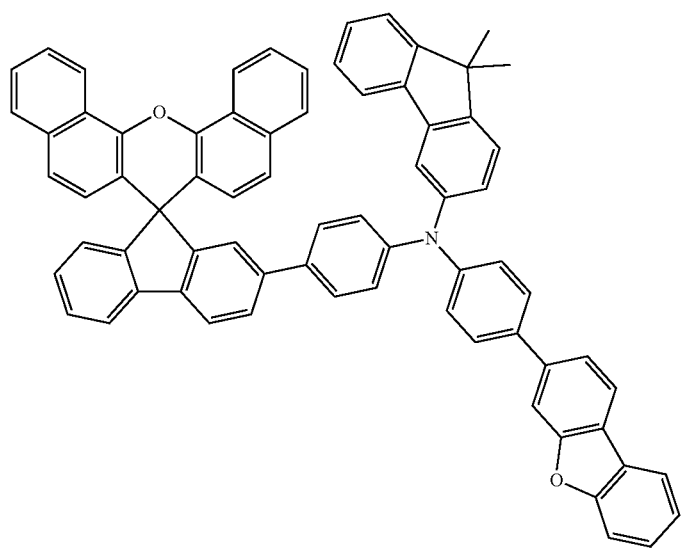

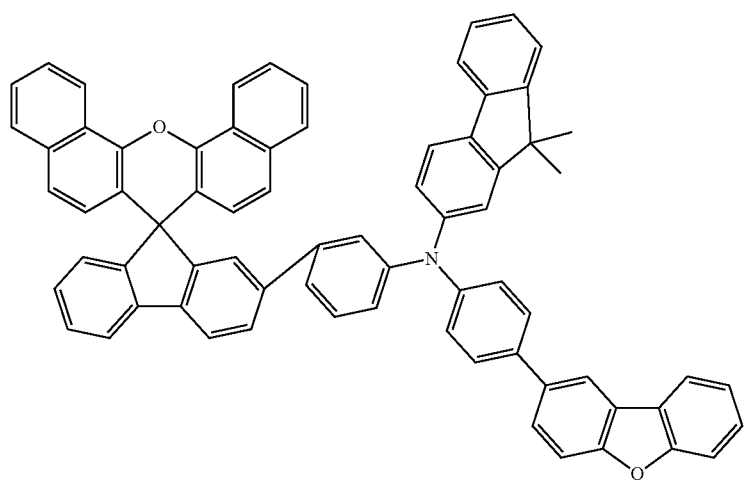
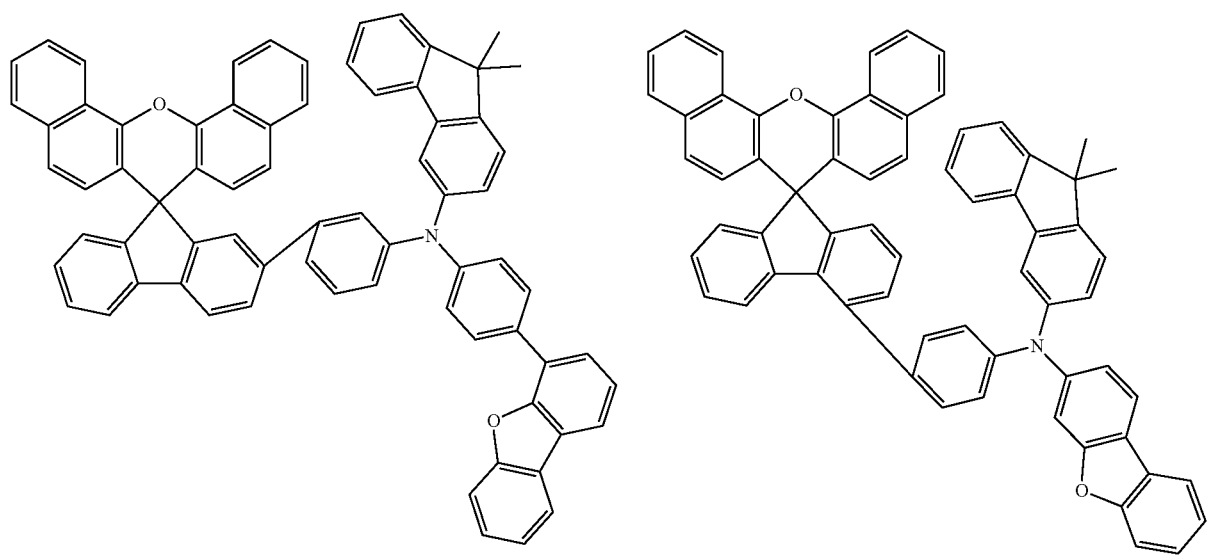
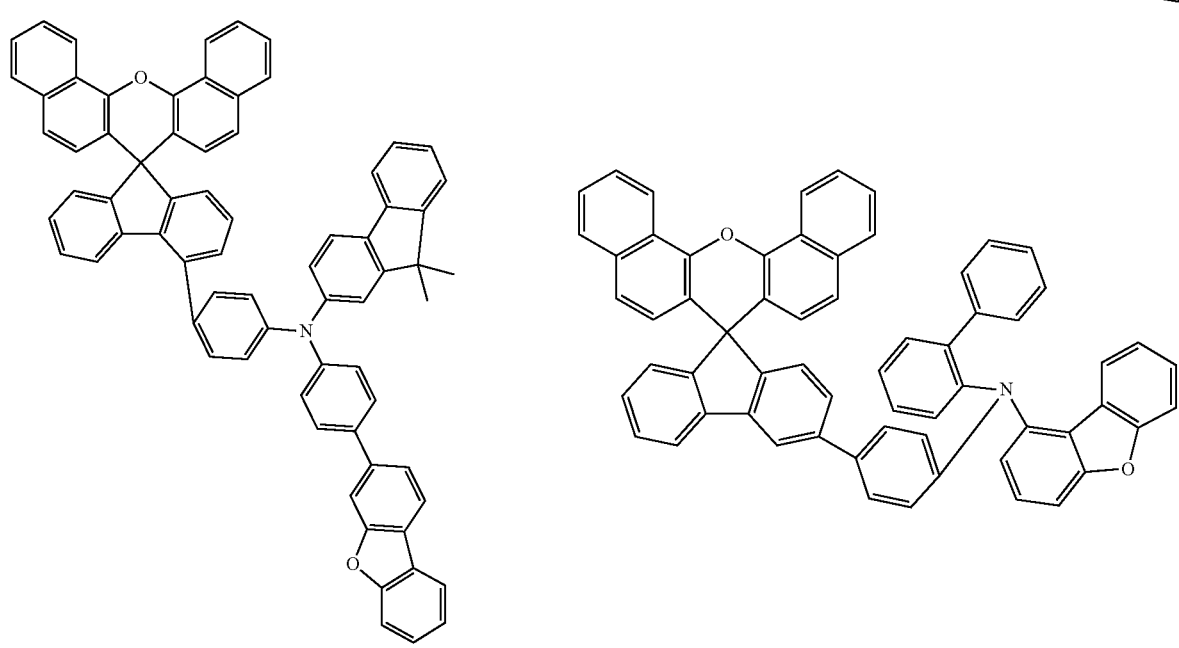

-continued
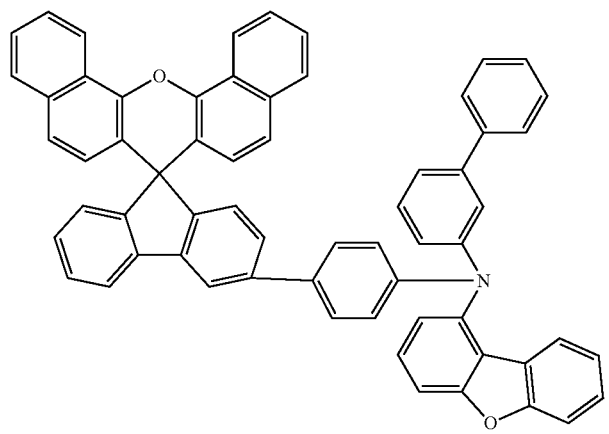
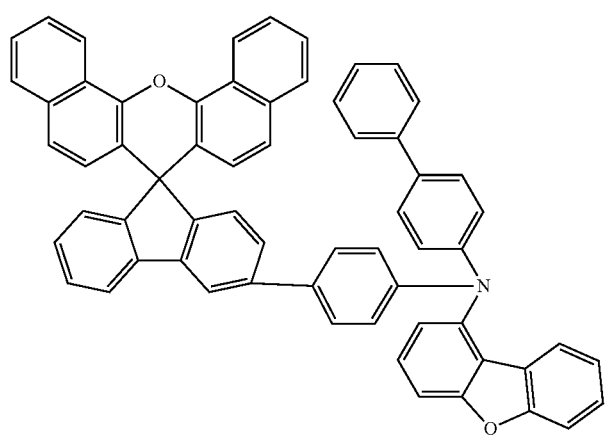
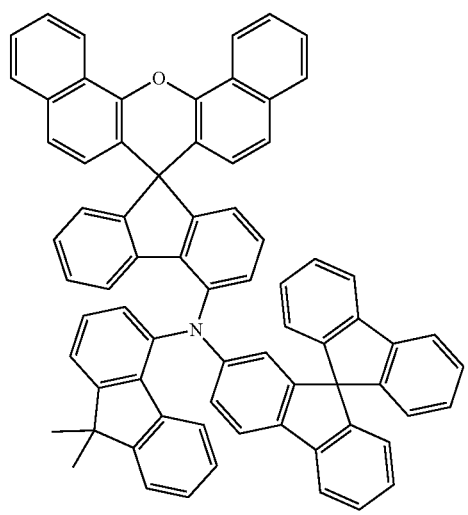
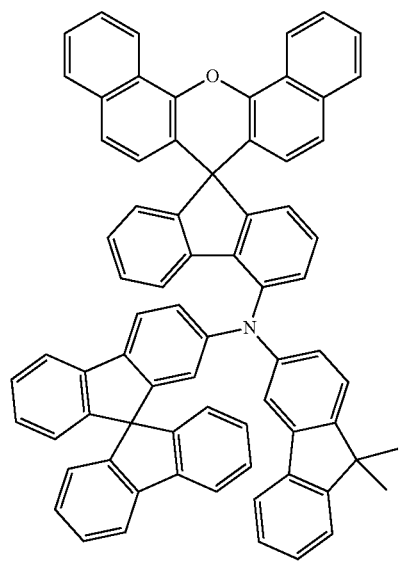
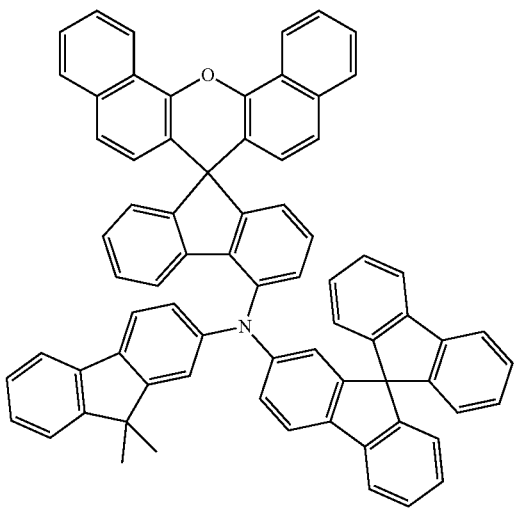

339
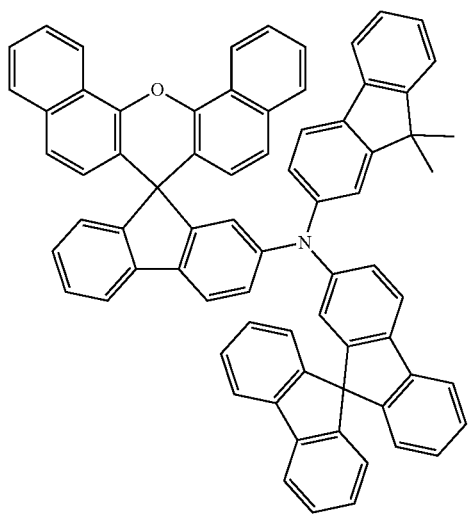
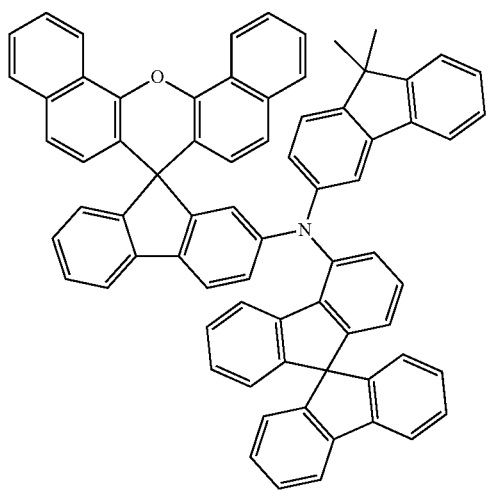
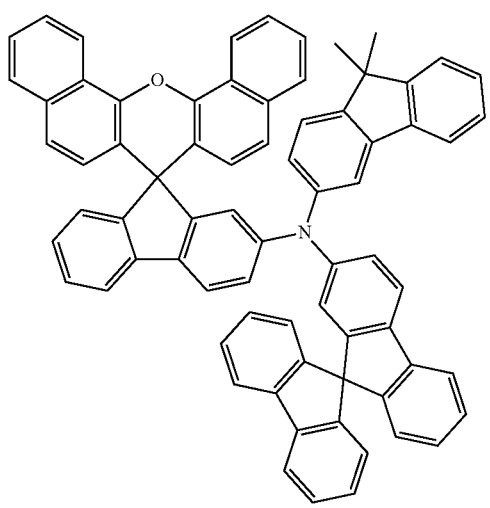
-continued
340
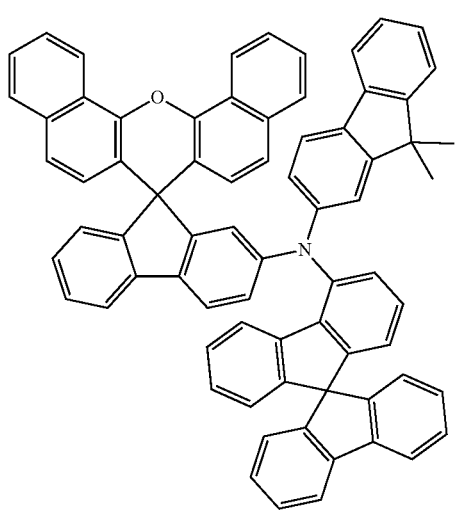
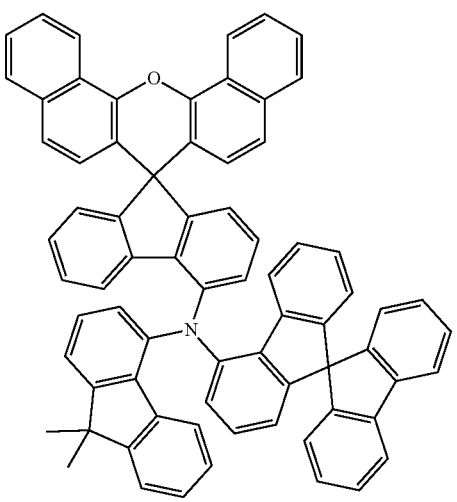
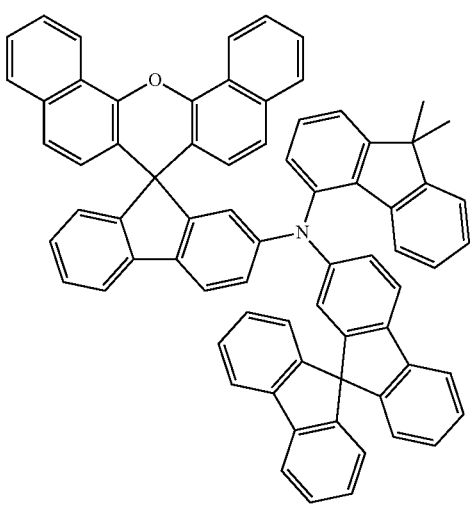

341
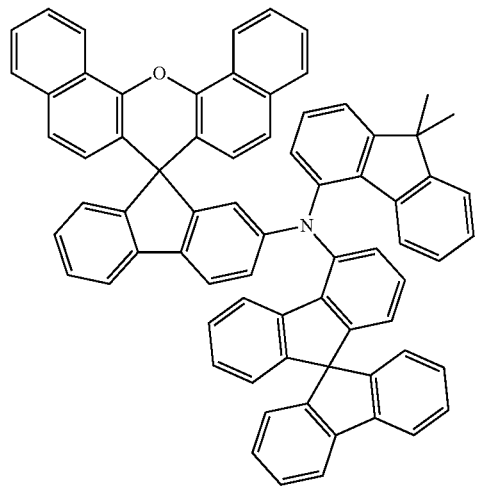
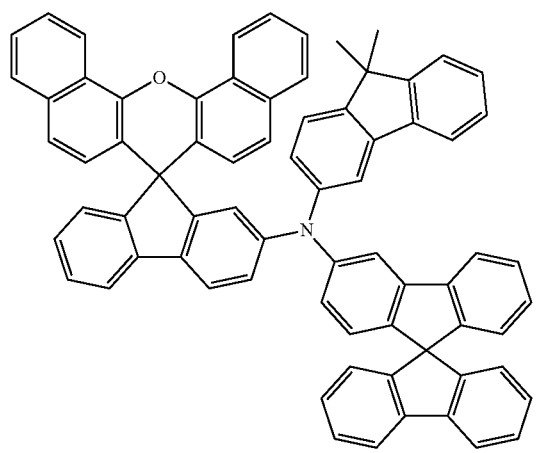
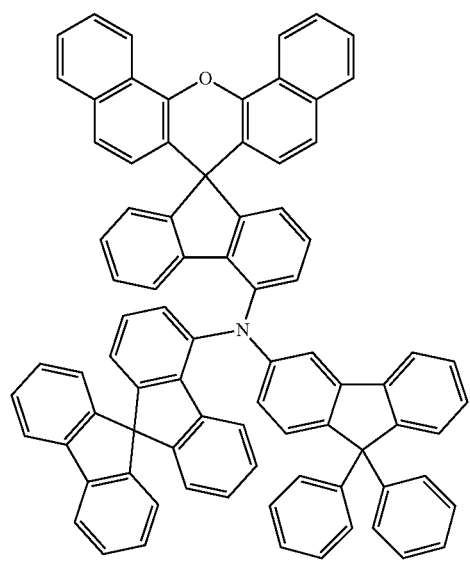
-continued
342
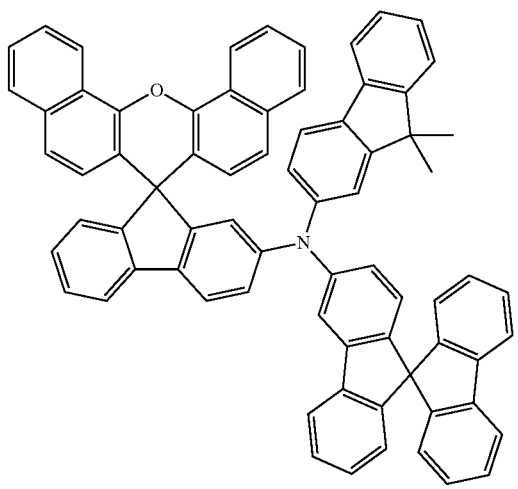
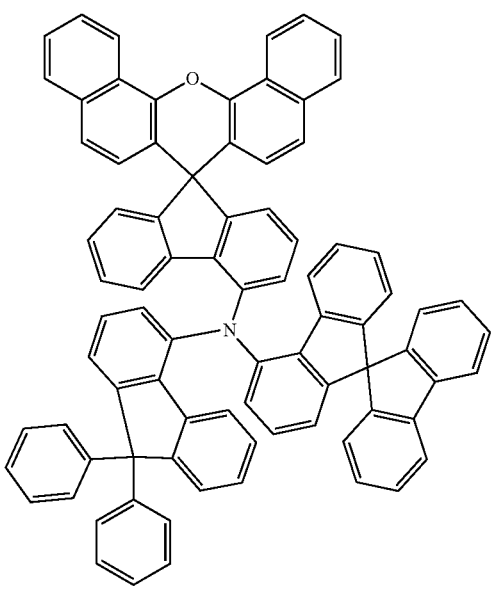
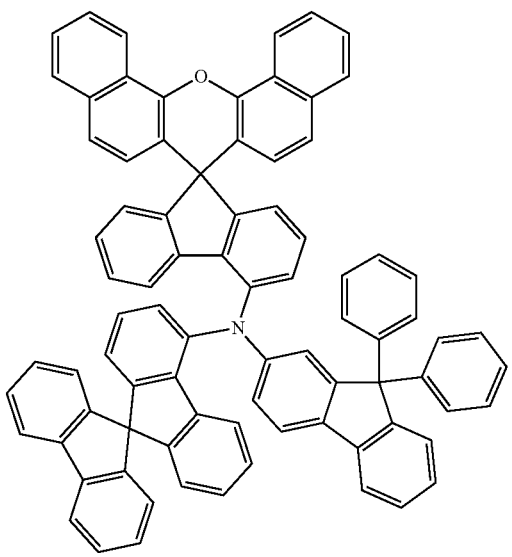

-continued
343
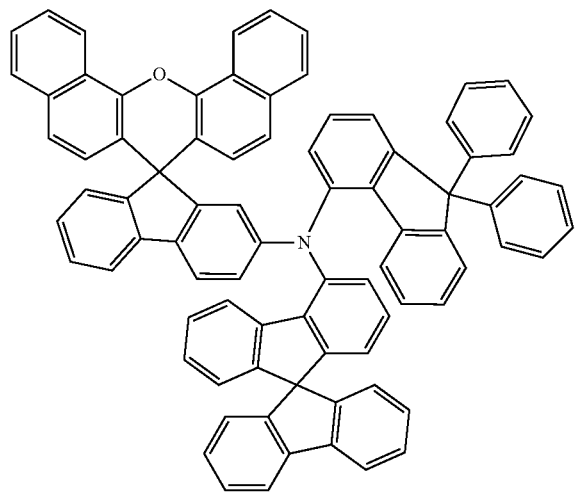
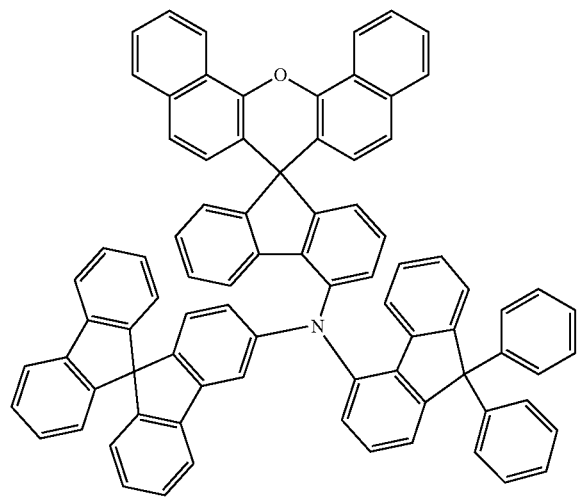
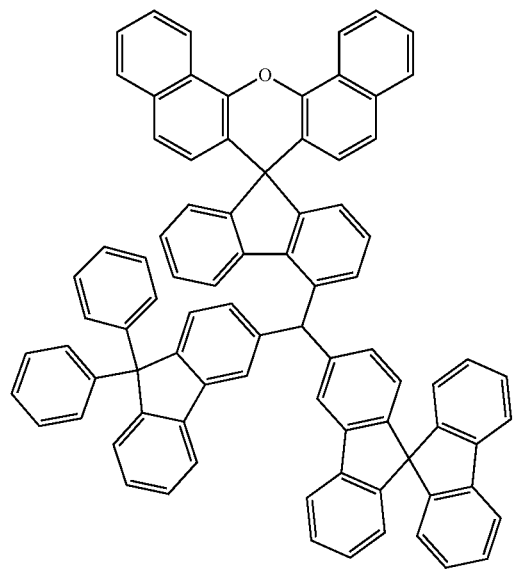
344
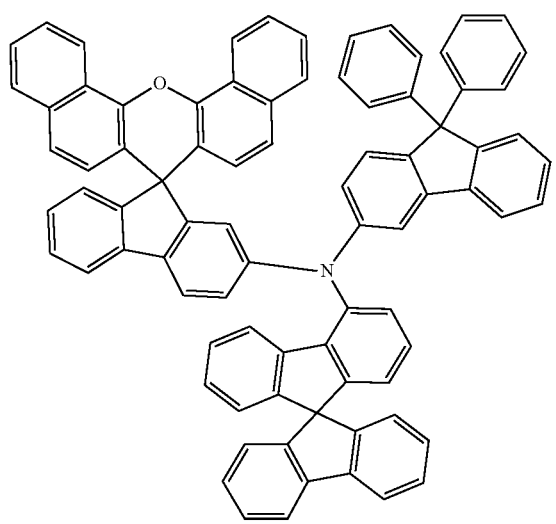
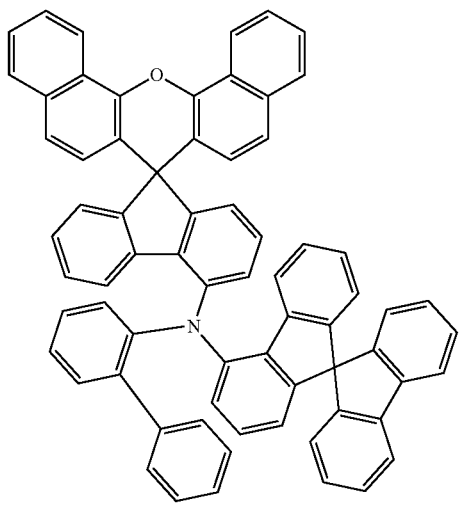
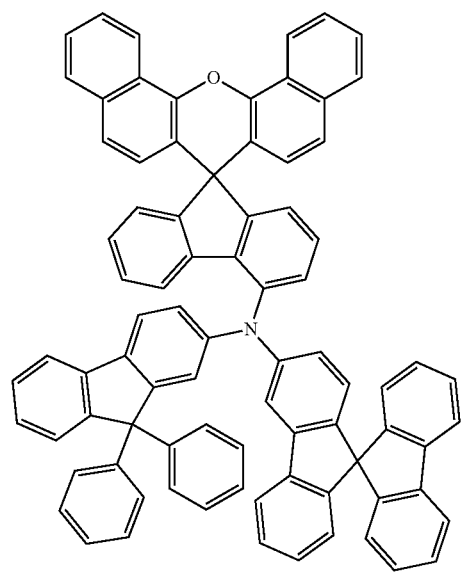

345 346
-continued
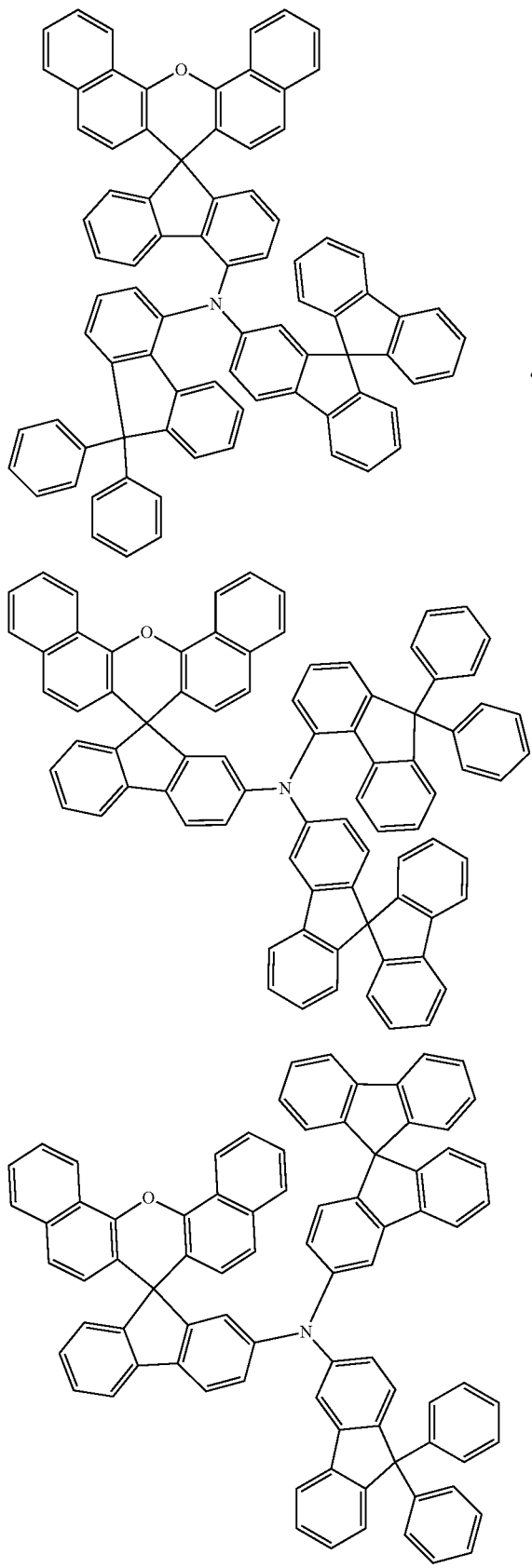
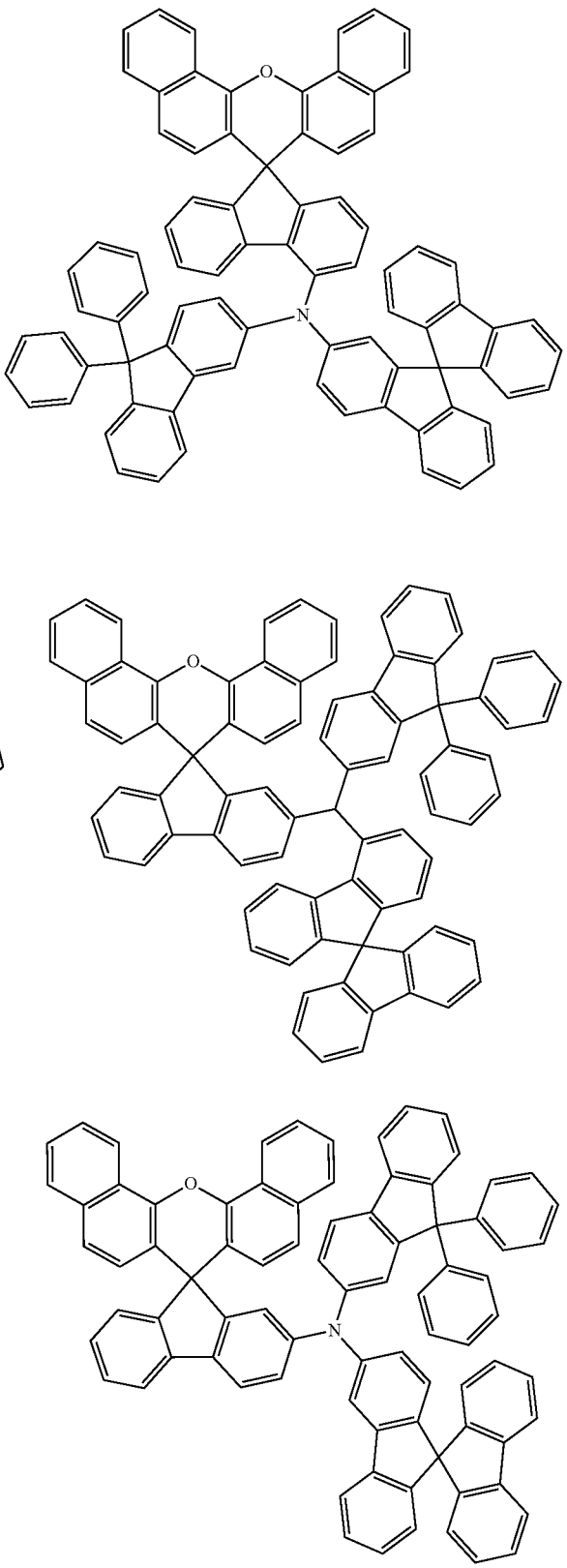

-continued
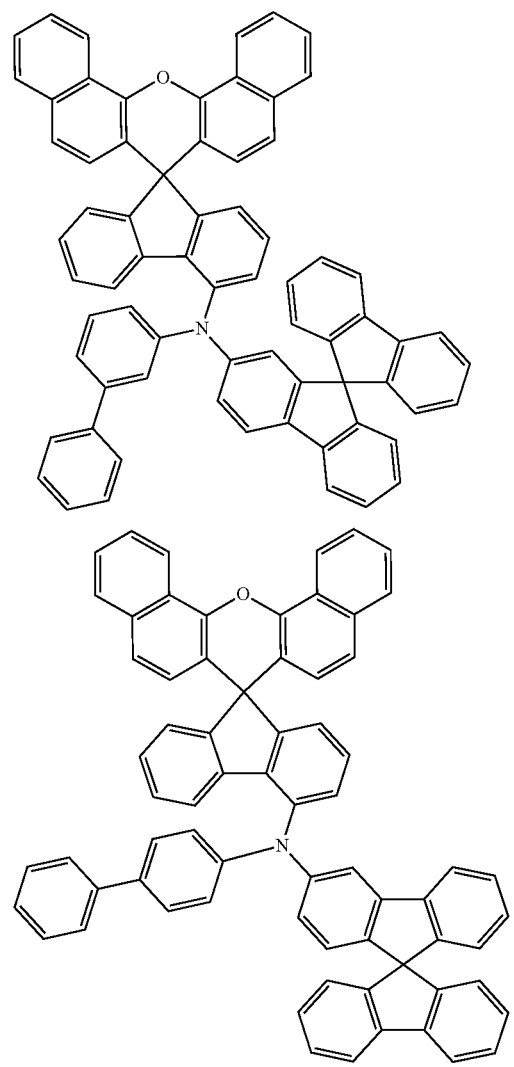
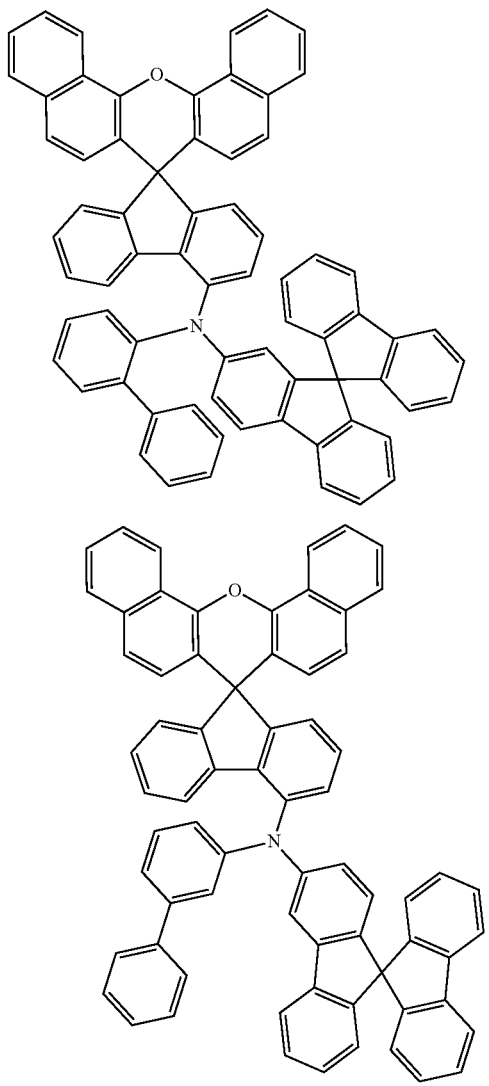
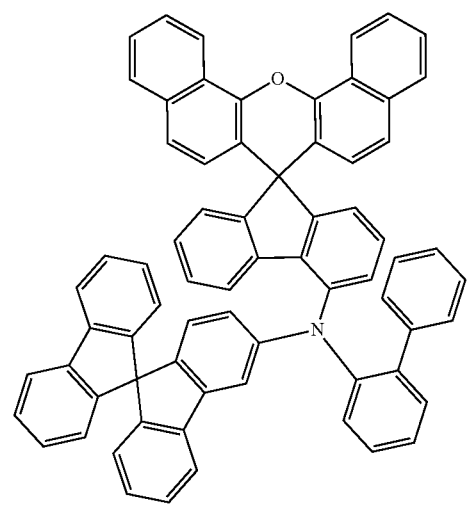
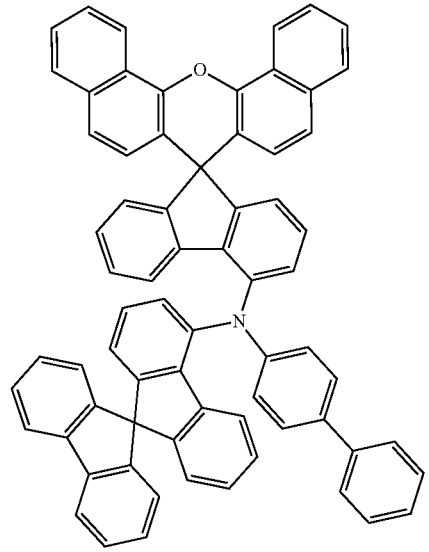

349
350
-continued
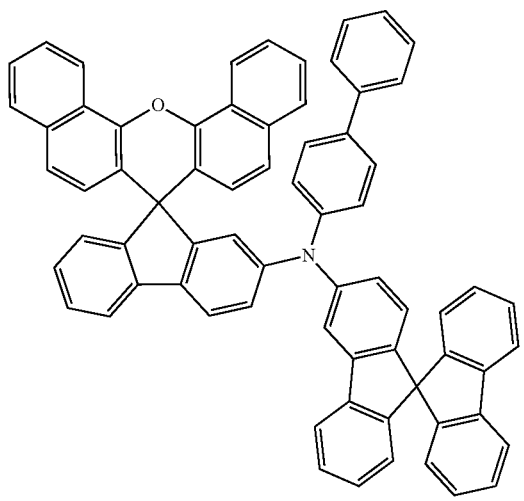
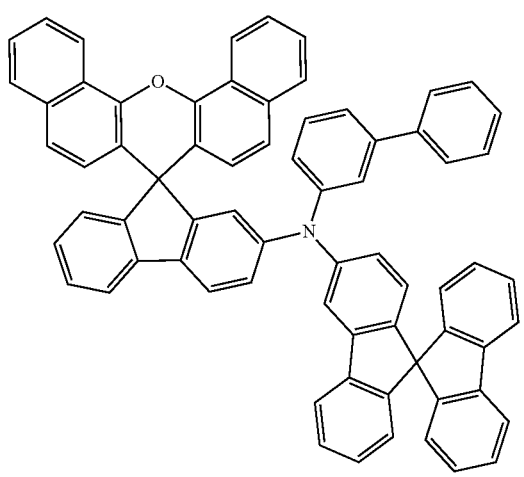
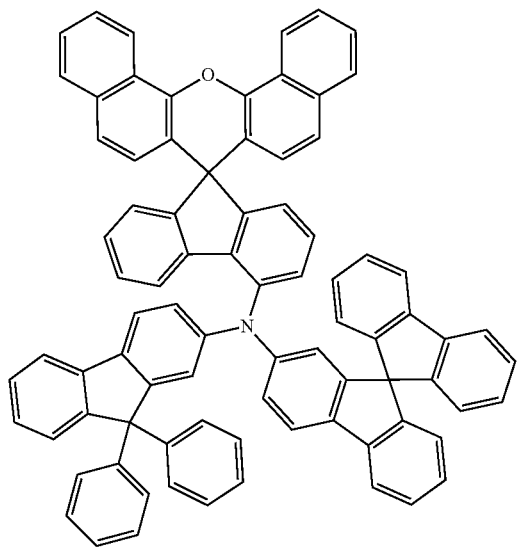
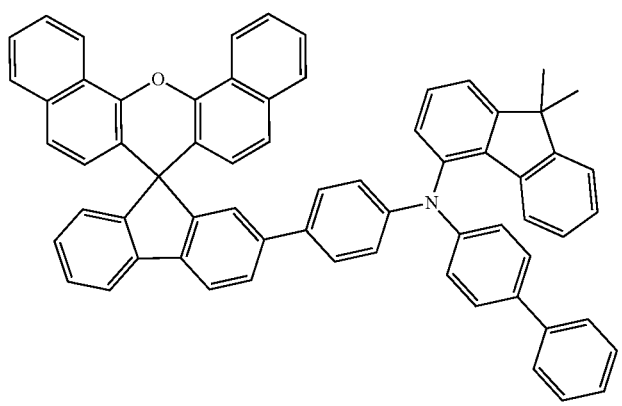
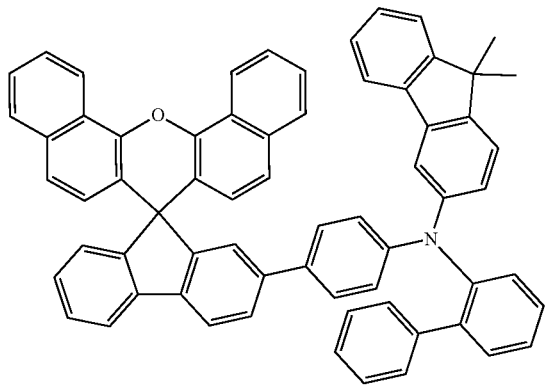
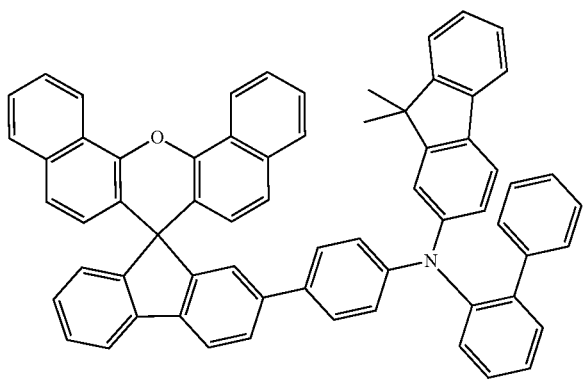

-continued
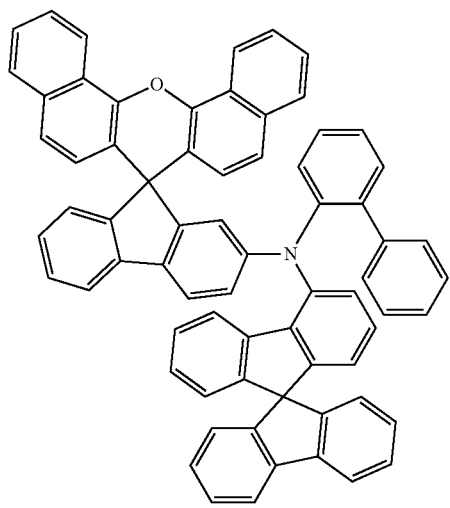
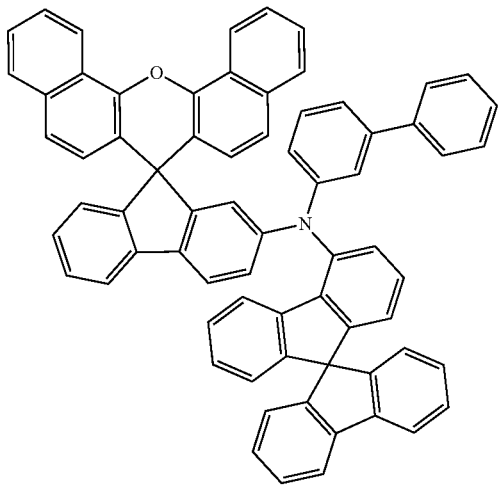
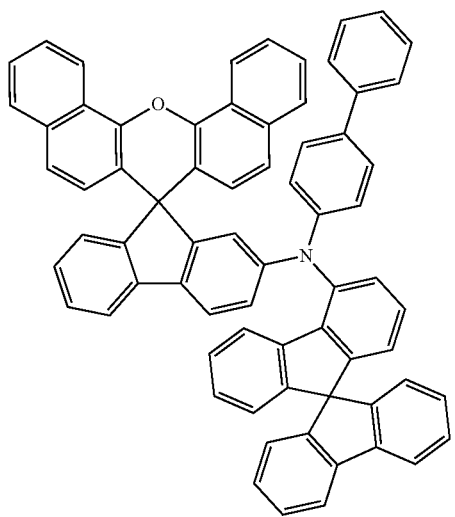
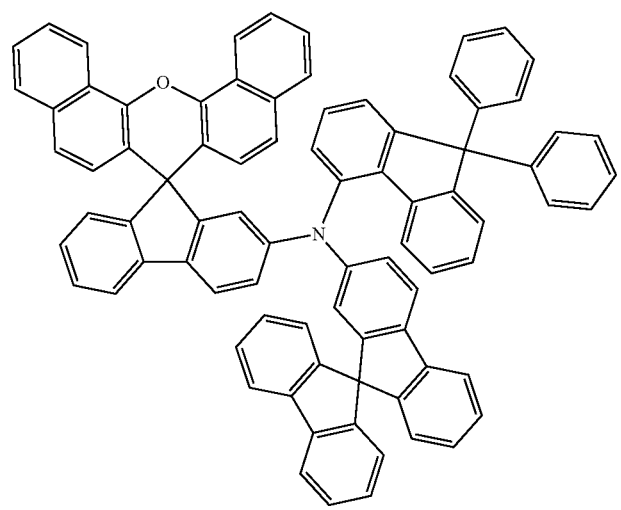
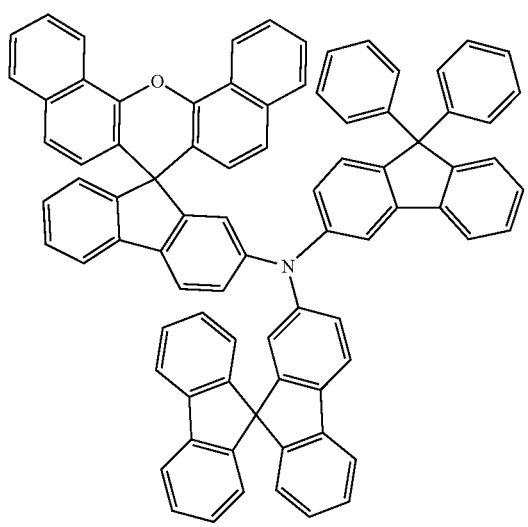
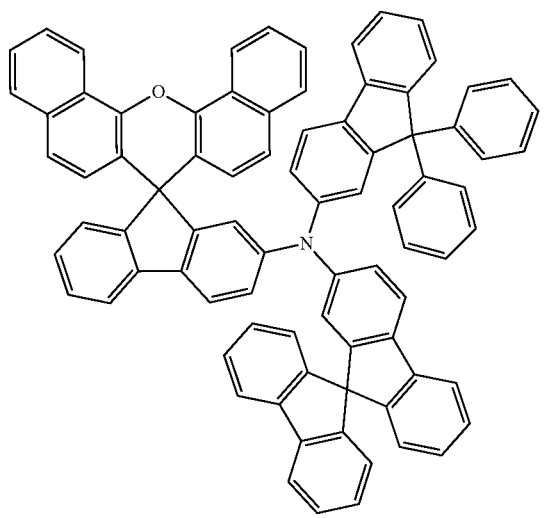

-continued
353
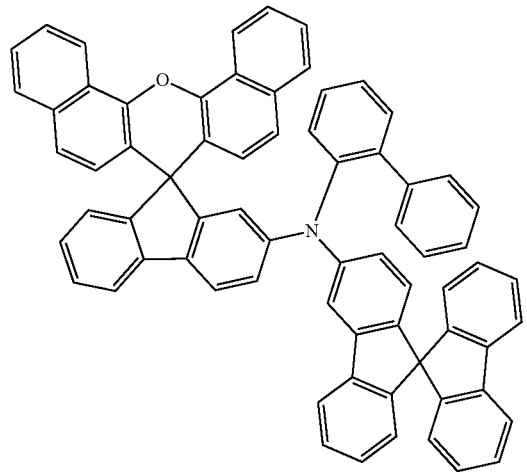
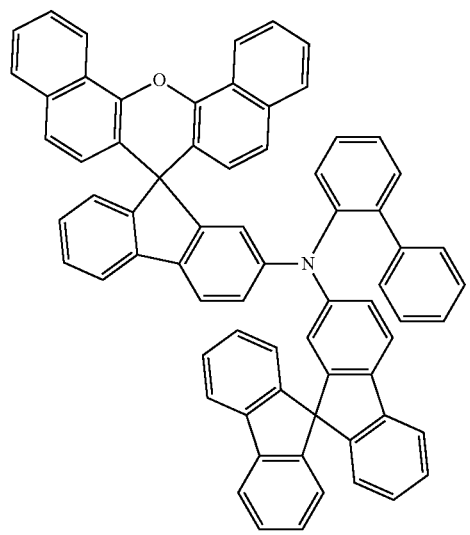
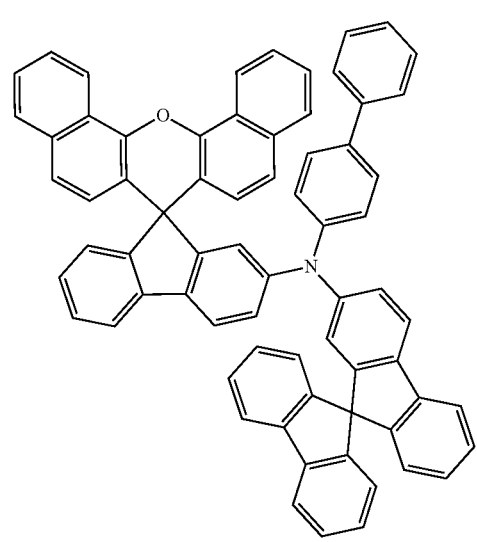
354
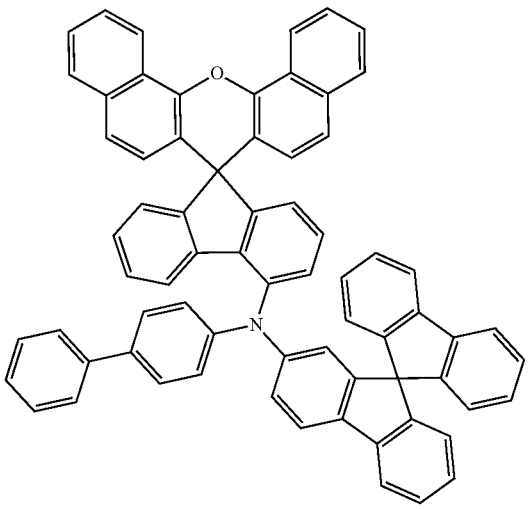
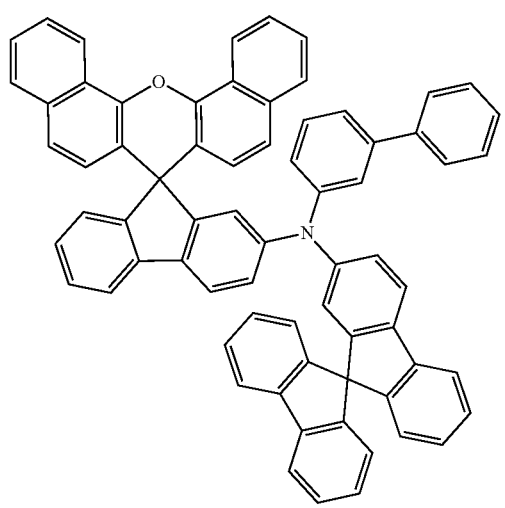
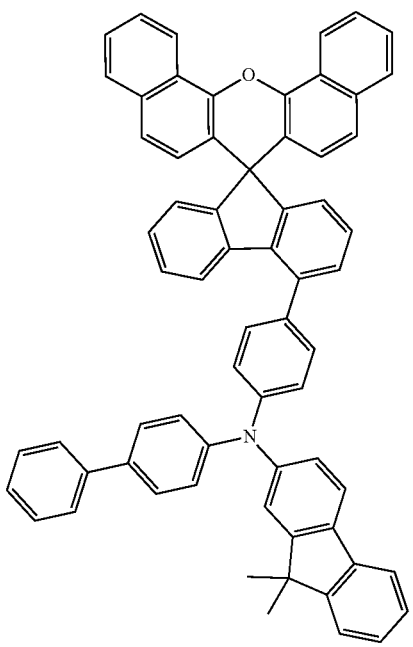

-continued
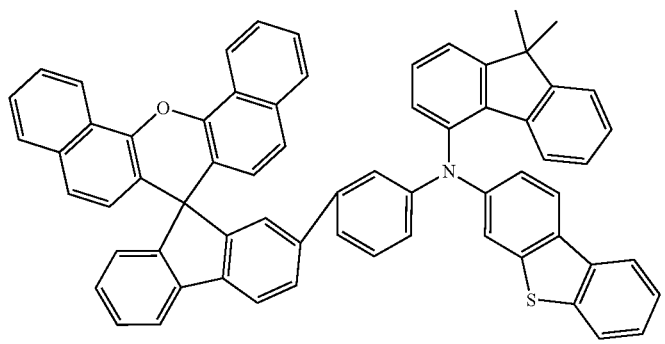
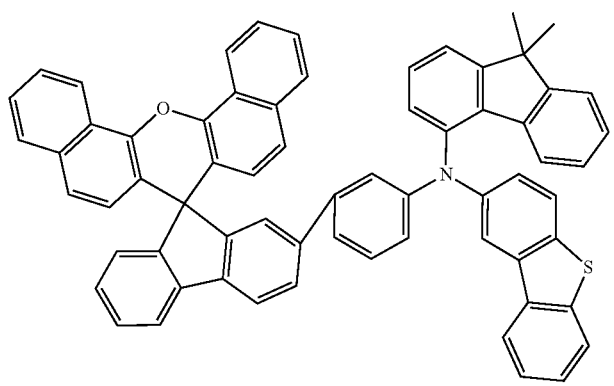
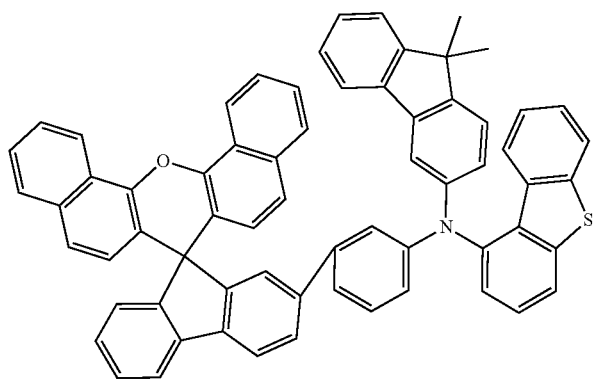
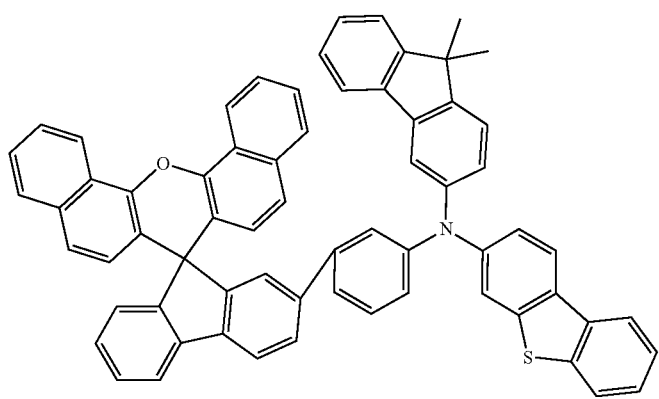

-continued
357
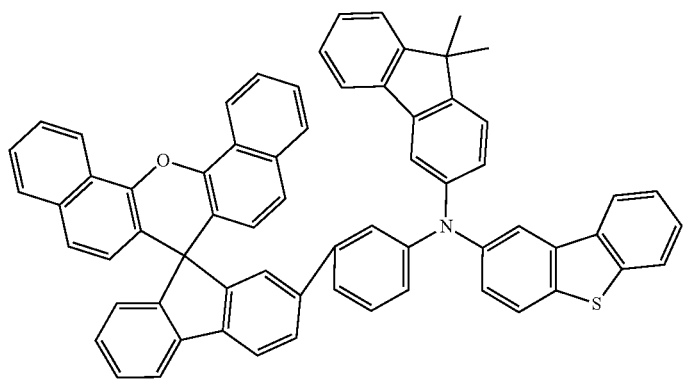
358
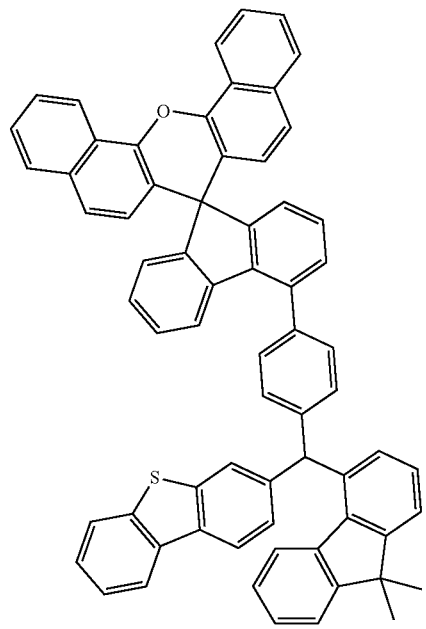
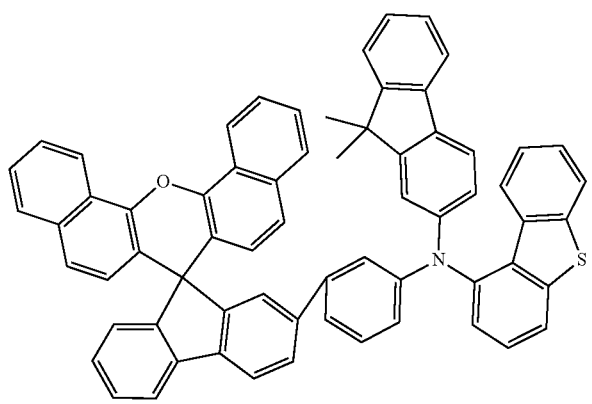
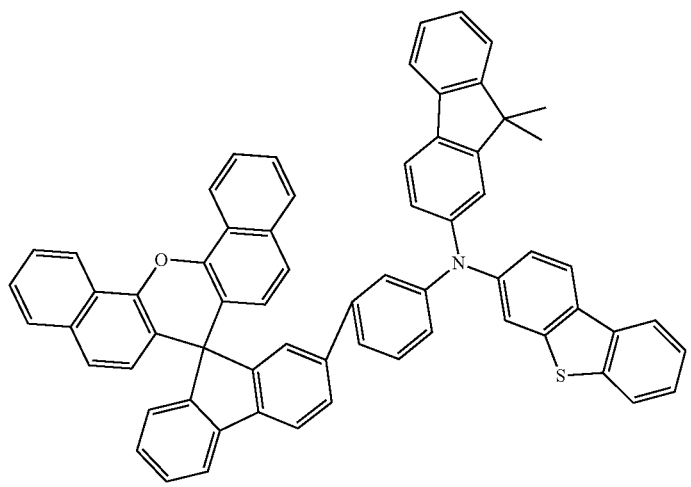
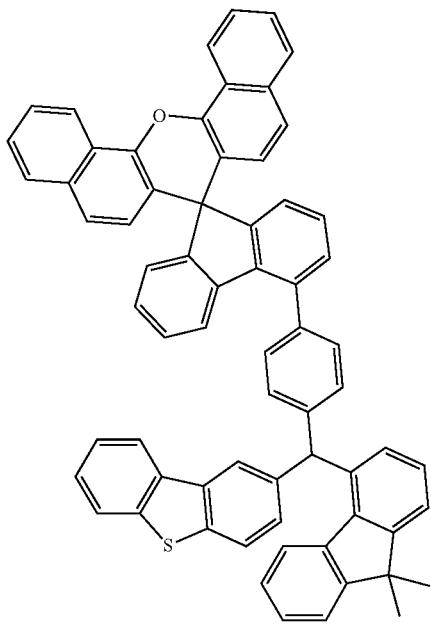

-continued
| 359 | 360 |
|---|---|
| 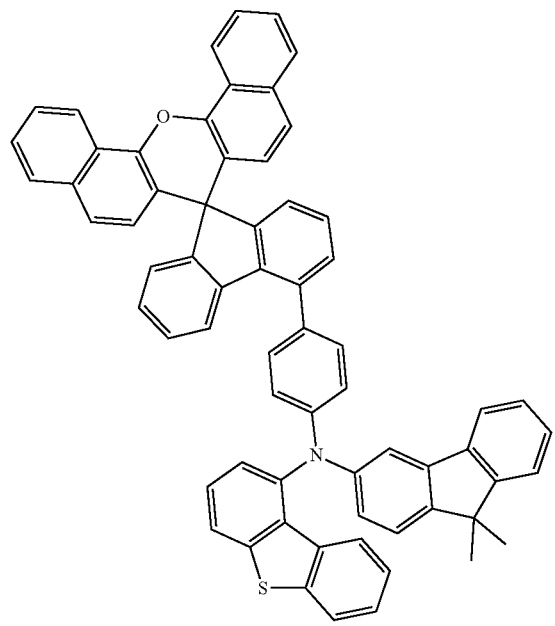 | 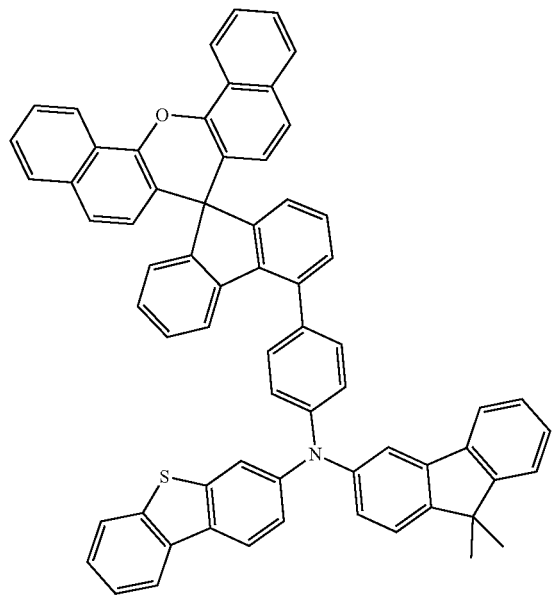 |
| 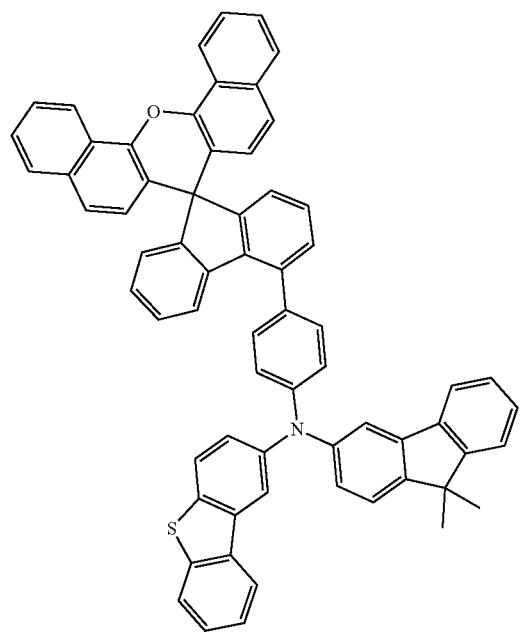 | 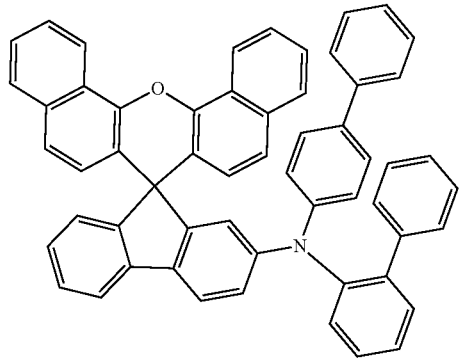 |

361
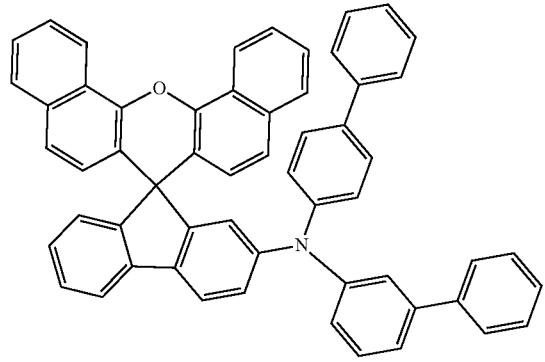
362
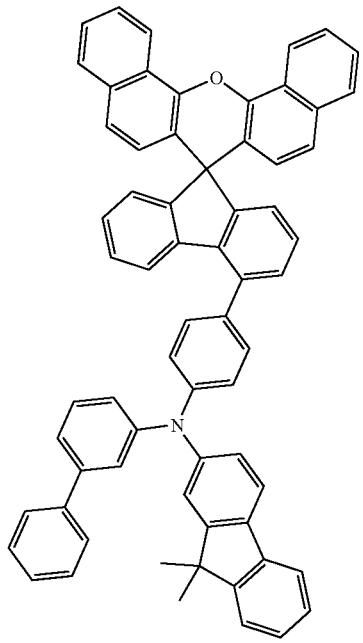
-continued
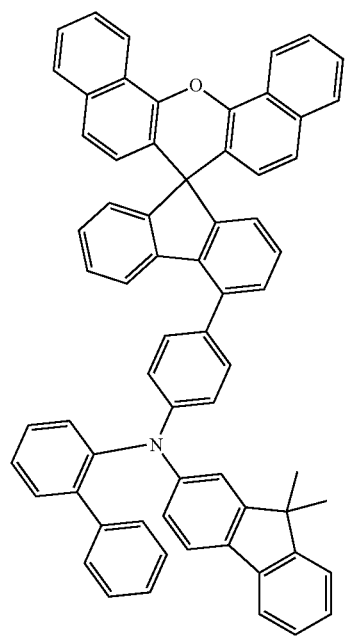
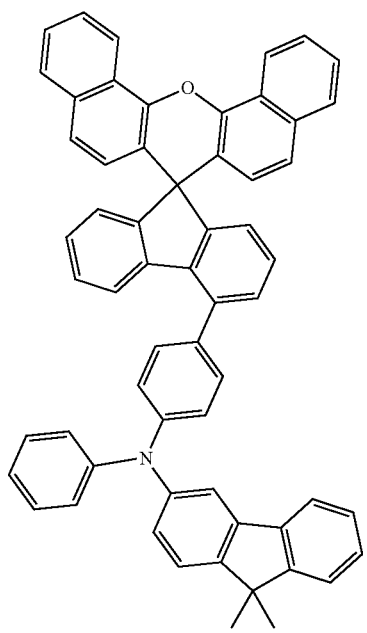

363
364
-continued
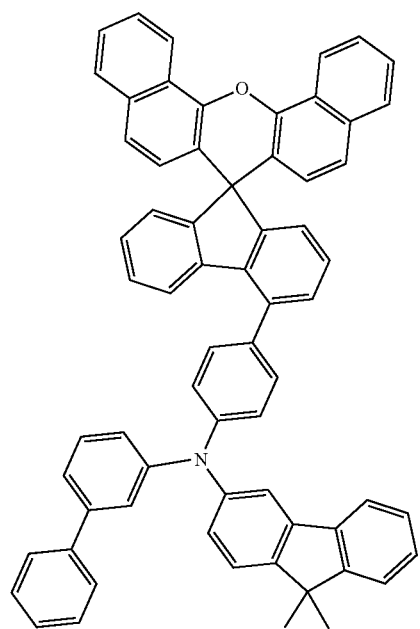
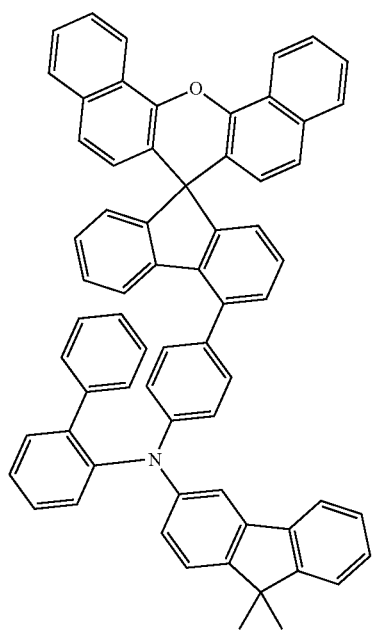
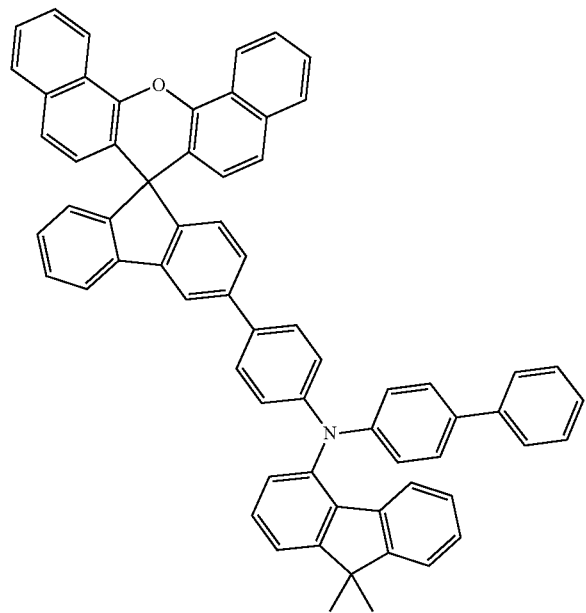
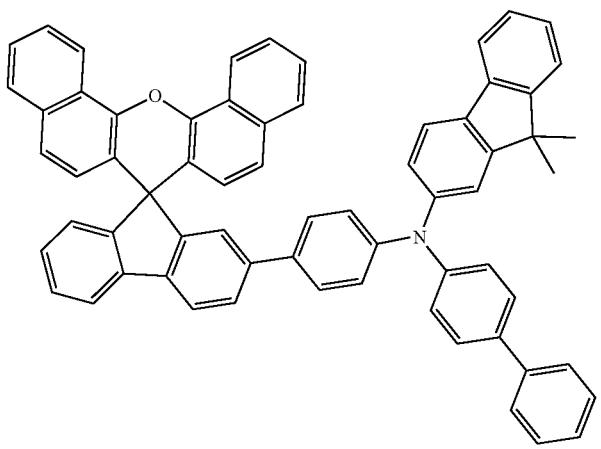

-continued
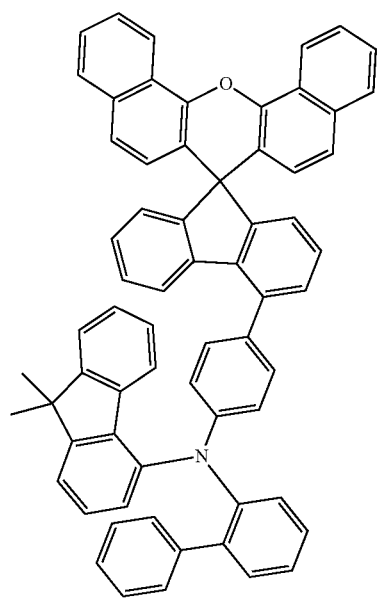
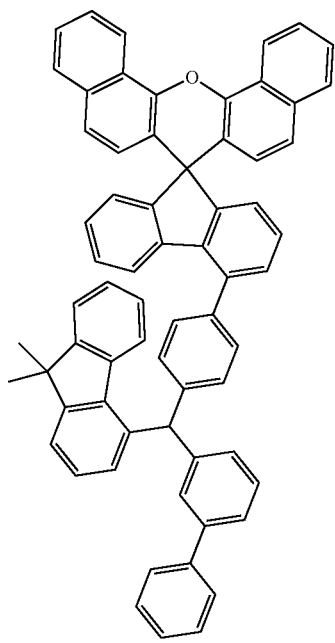
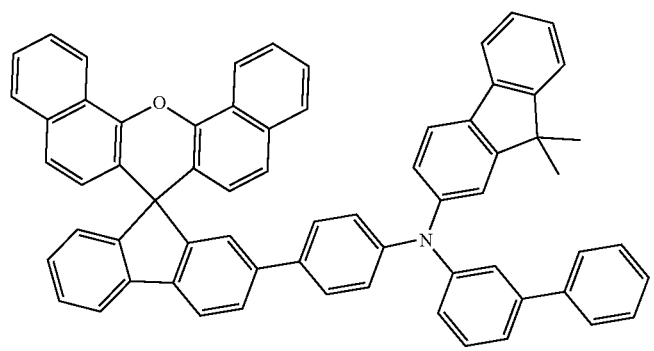
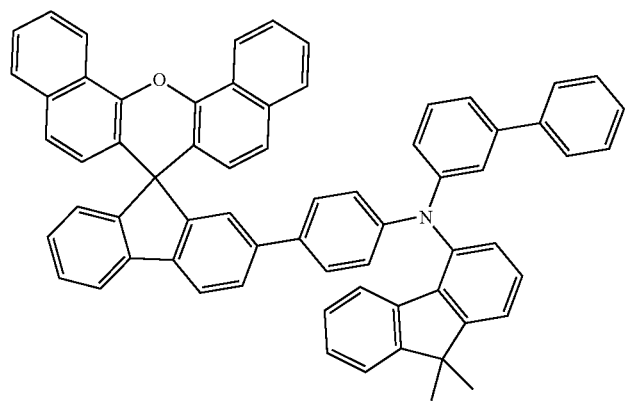

-continued
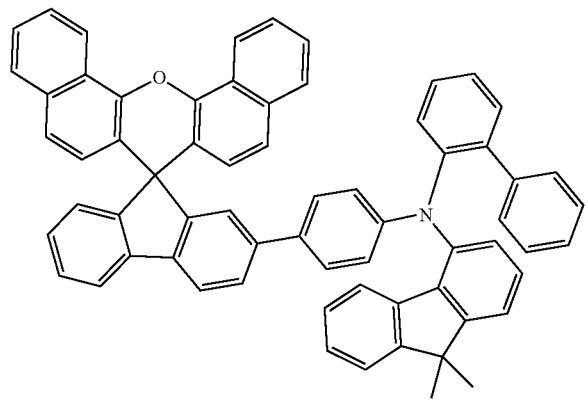
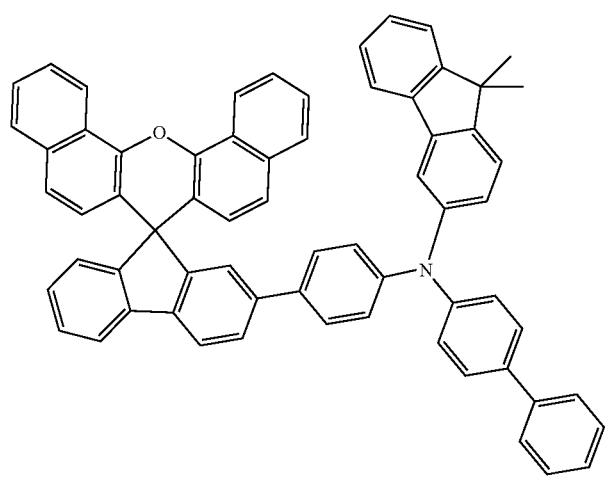
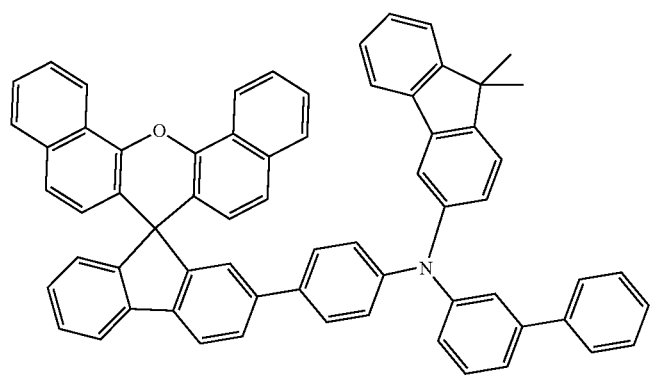
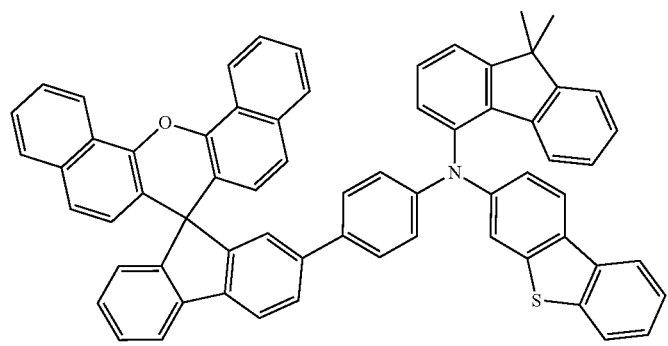

-continued
| 369 | 370 |
|---|---|
| 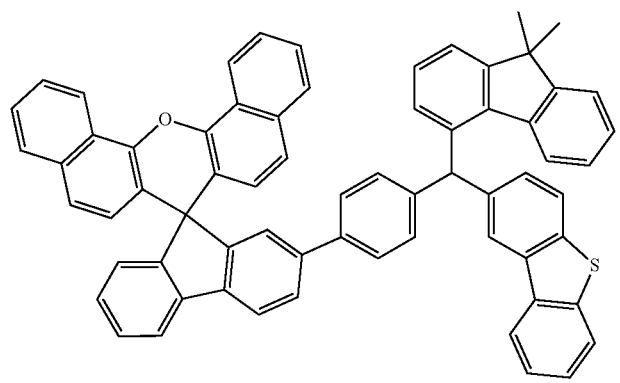 | 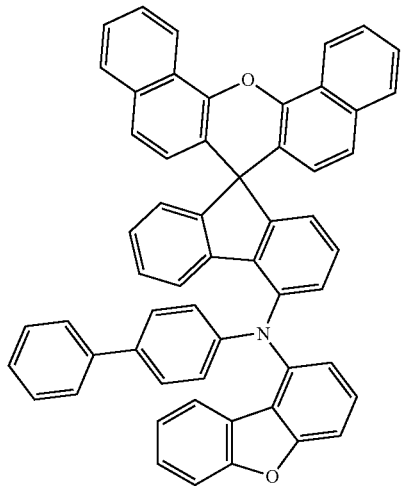 |
| 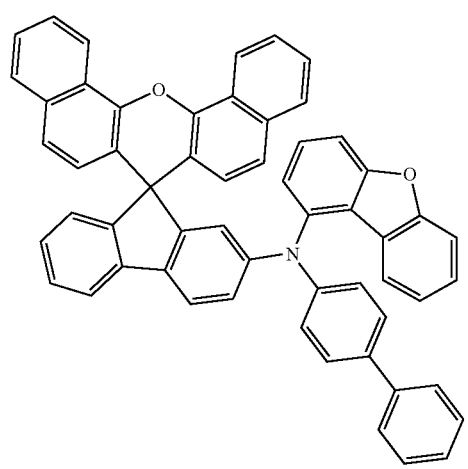 | 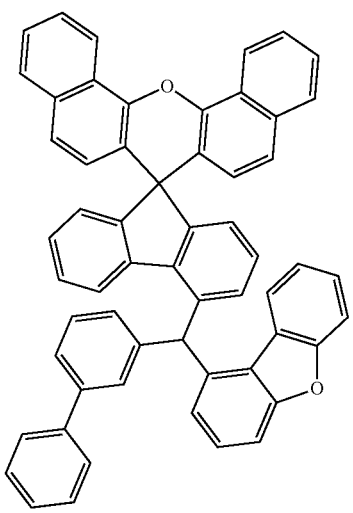 |
| 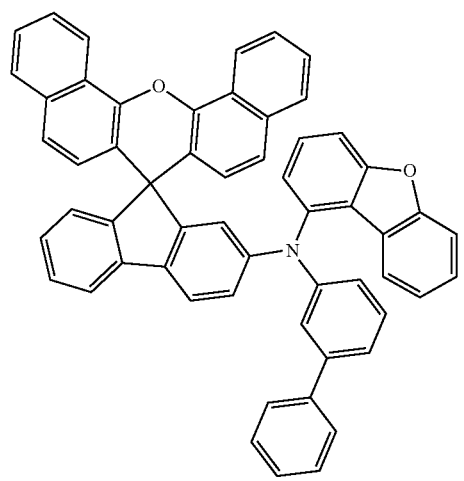 | 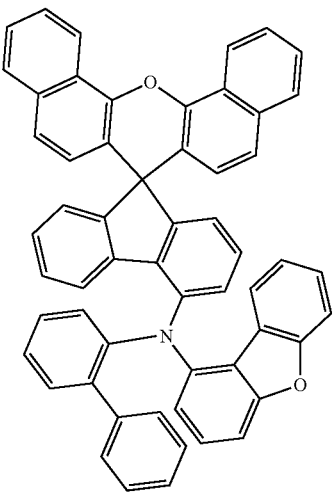 |

371 372
-continued
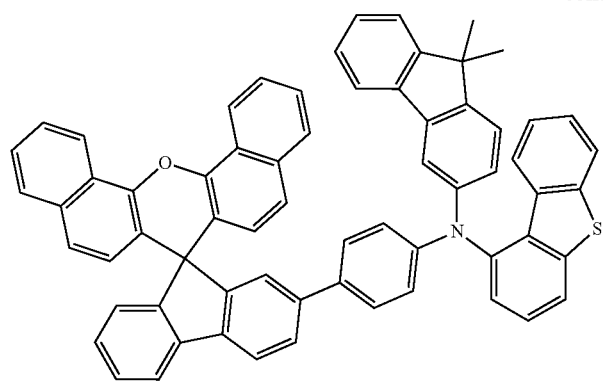
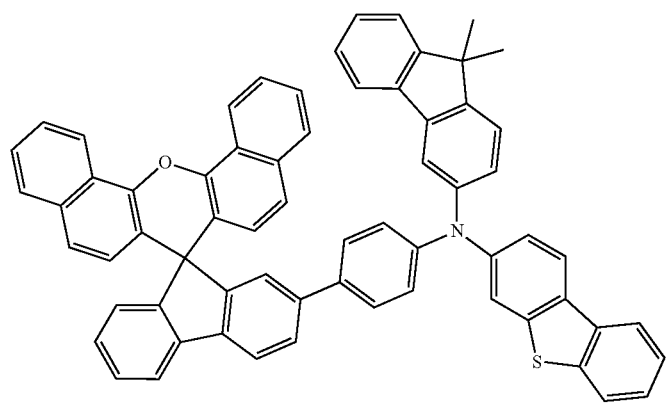
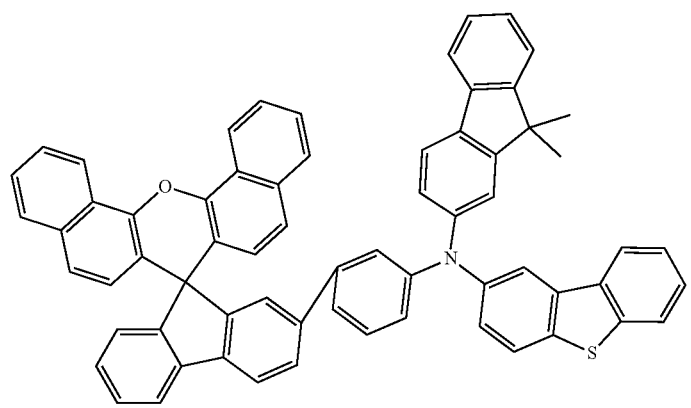
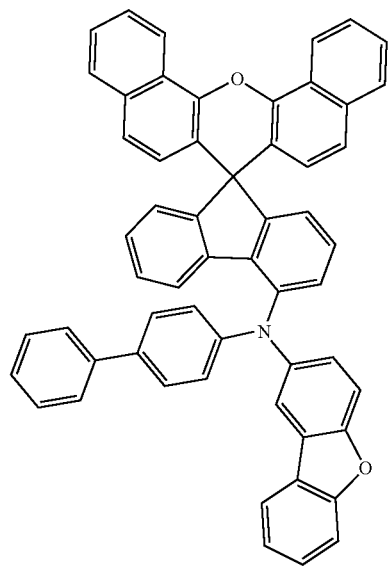

373
374
-continued
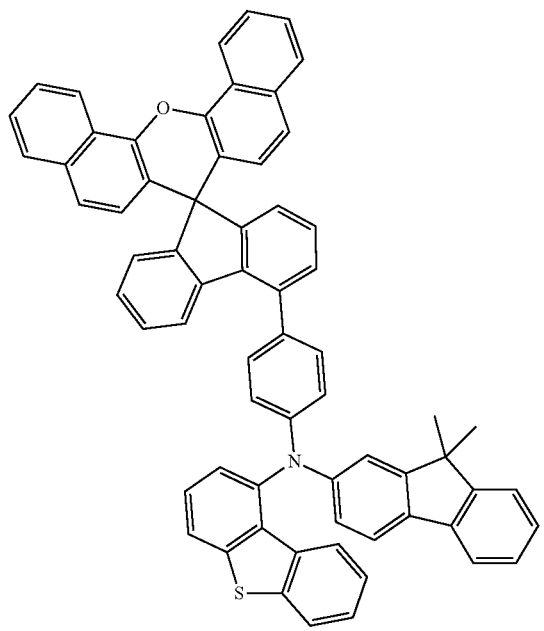
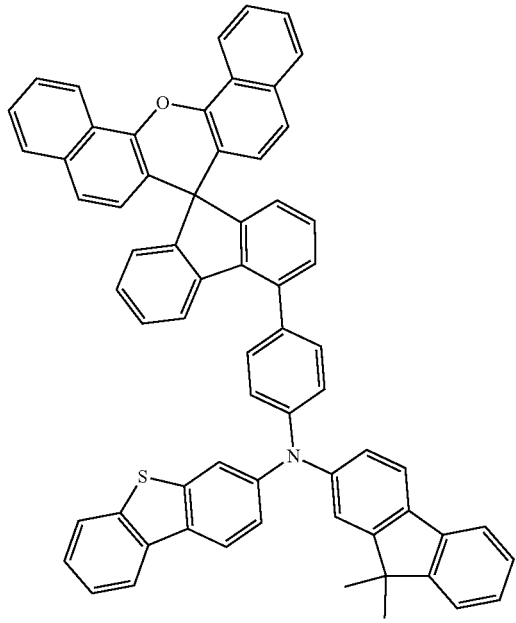
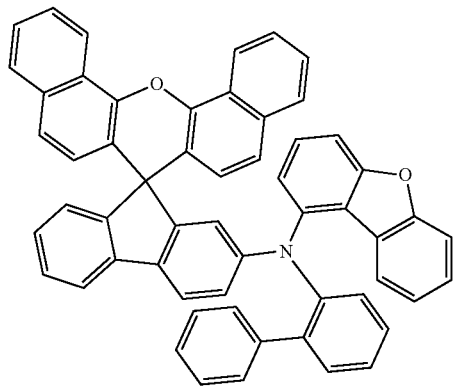
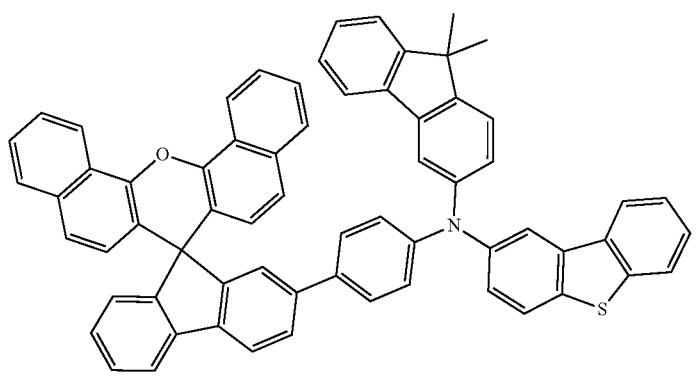
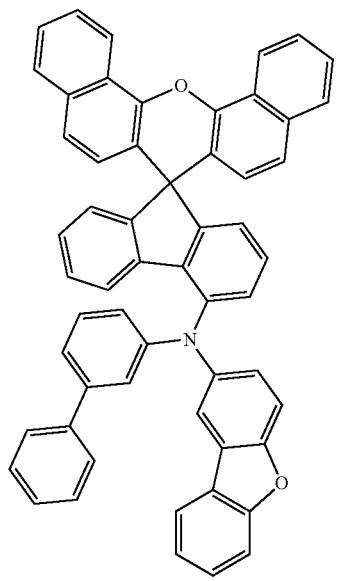
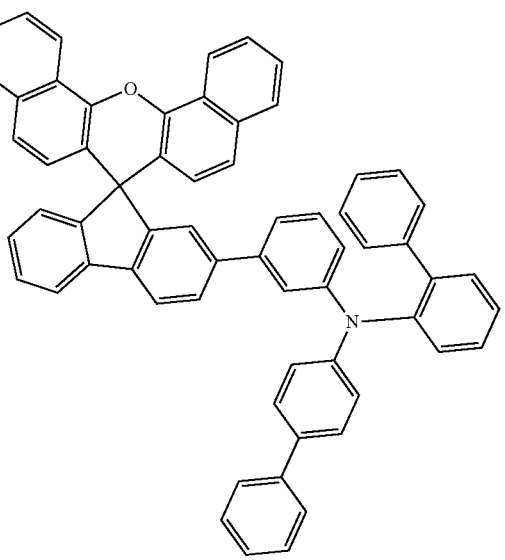

-continued
375
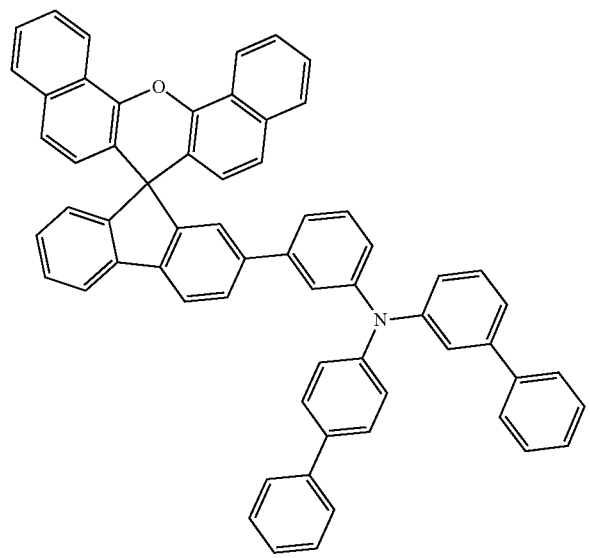
376
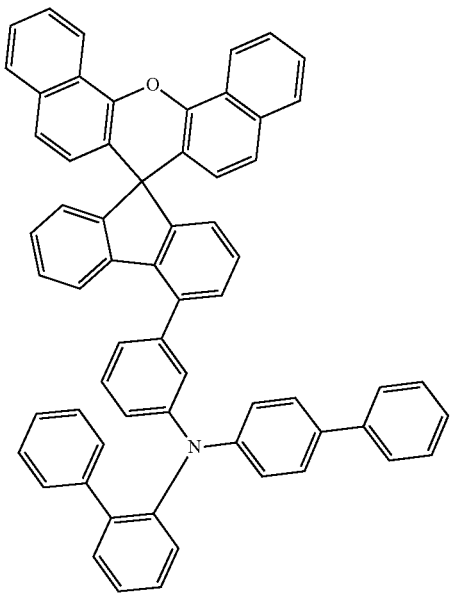
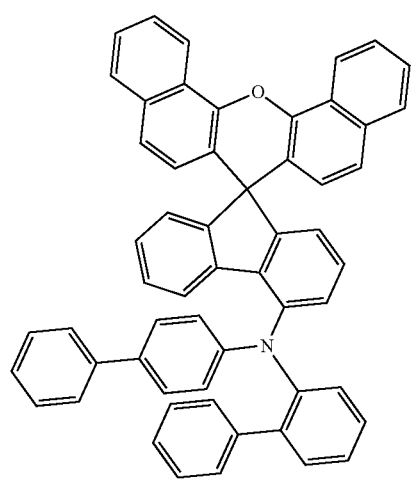
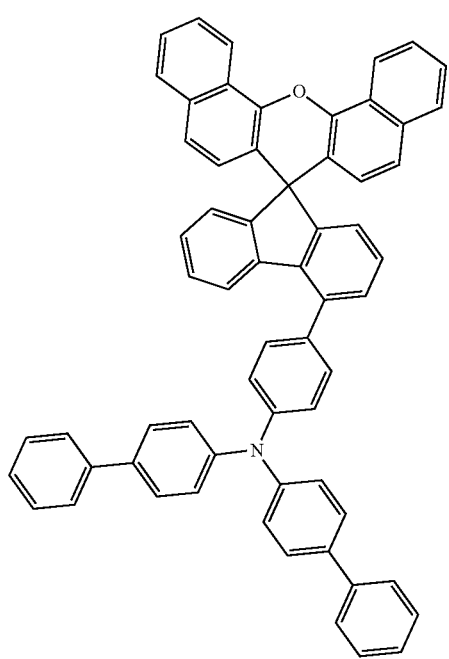

377
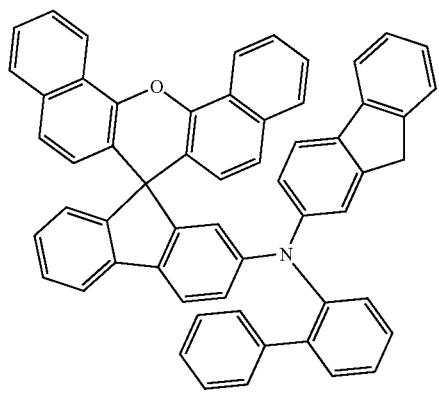
-continued
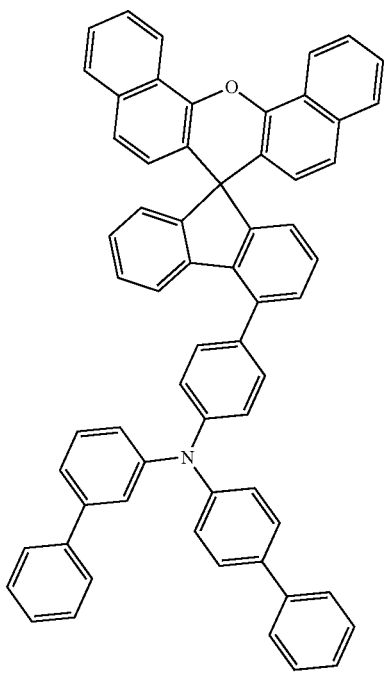
378
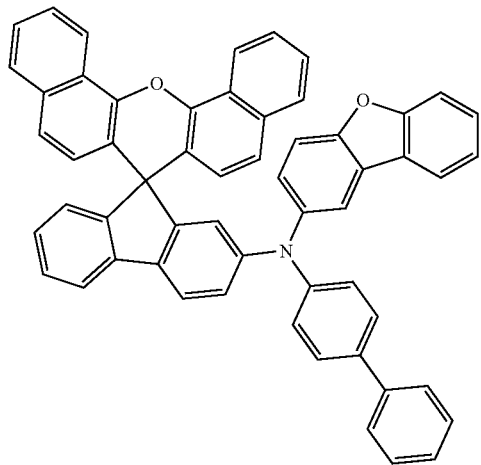
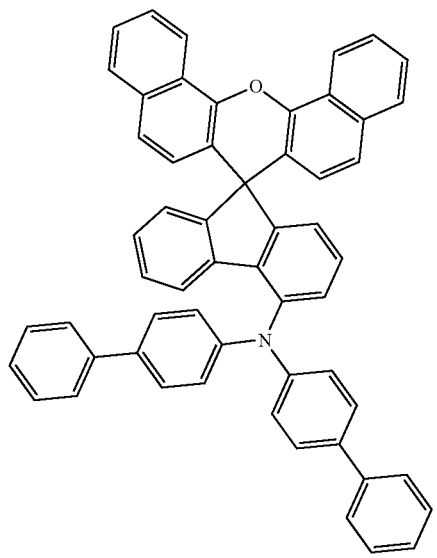

379
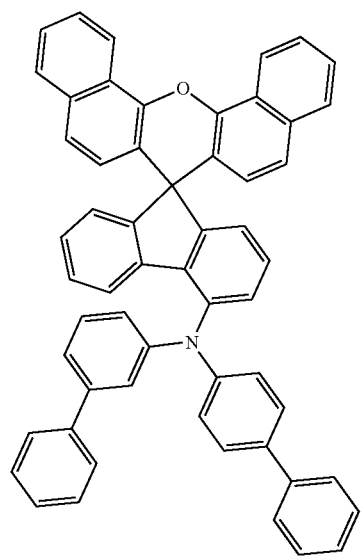
380
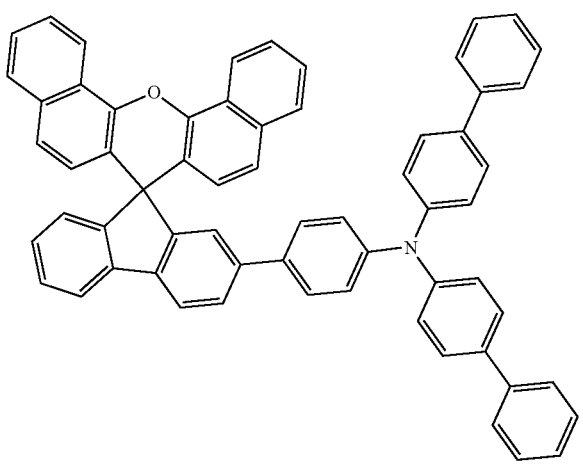
-continued
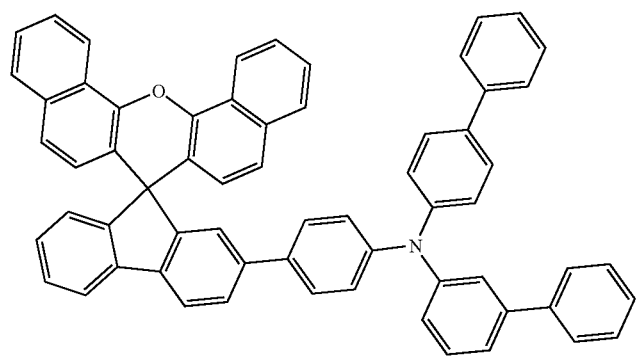
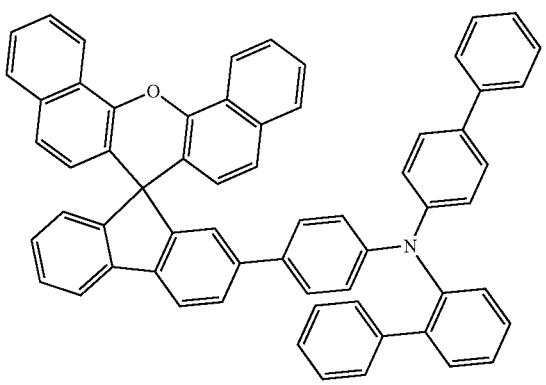
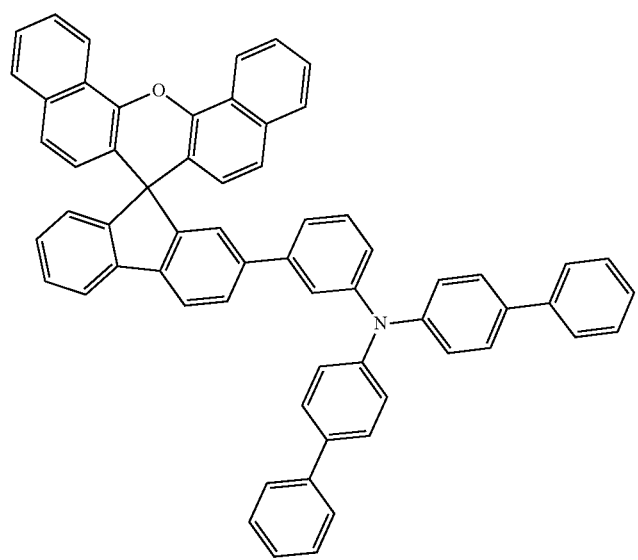
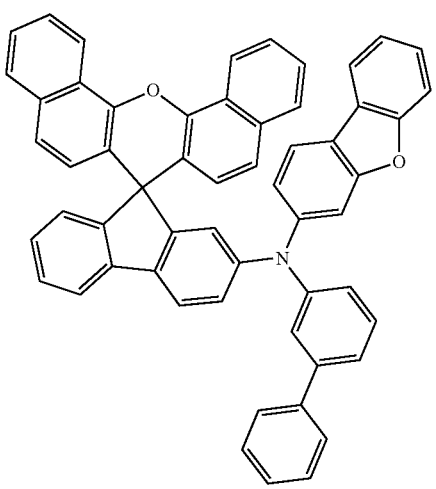

381
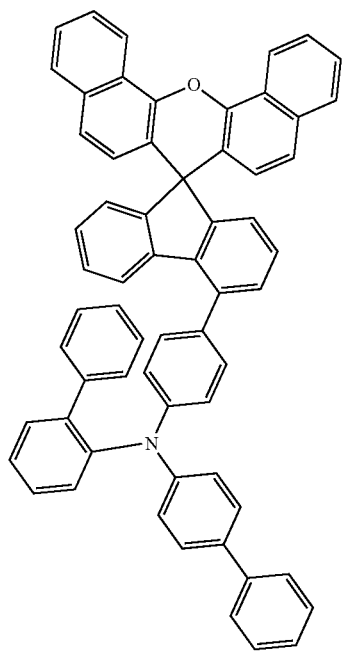
382
-continued
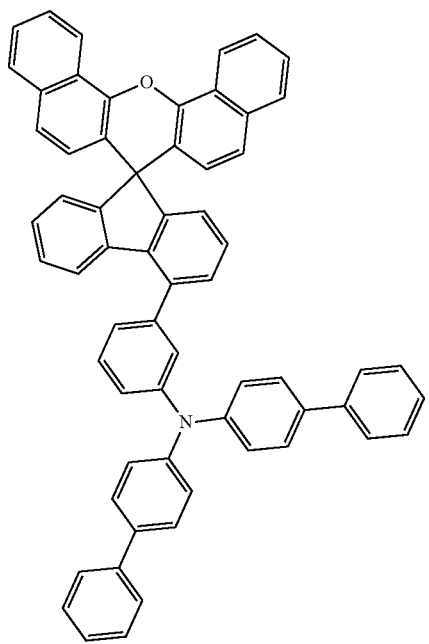
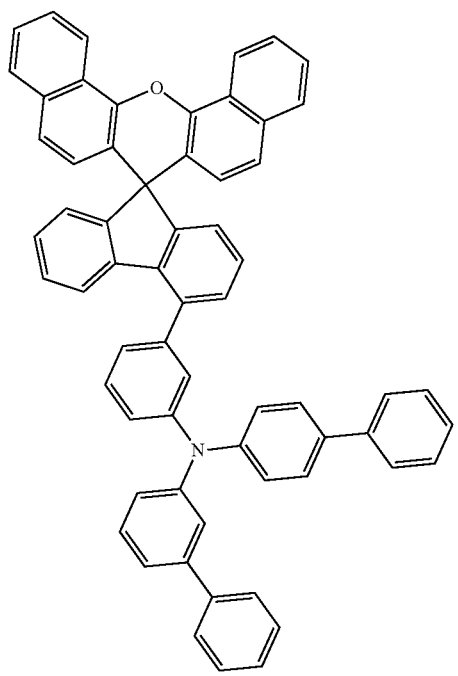
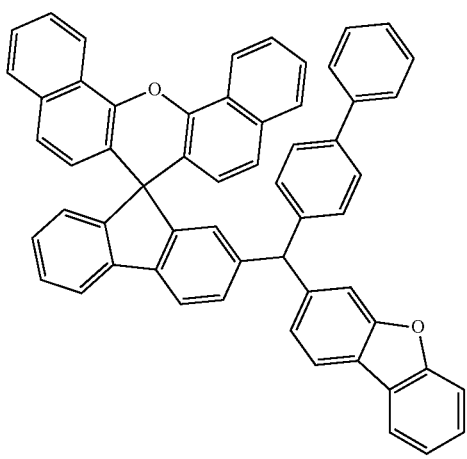
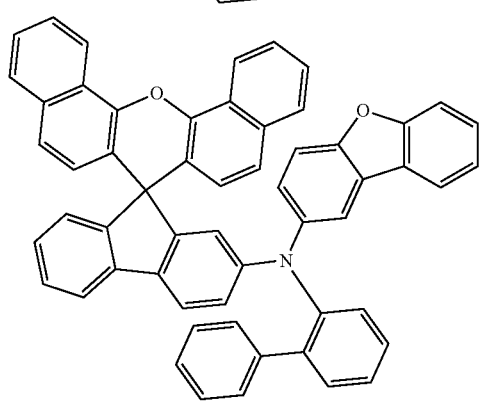
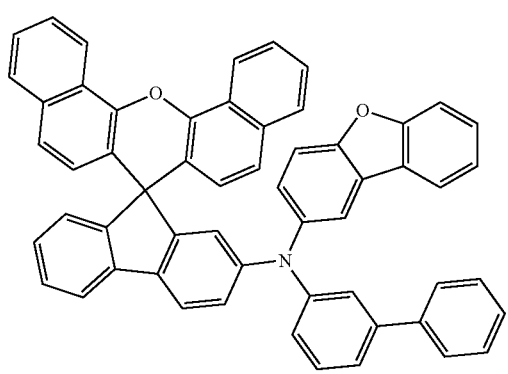

383
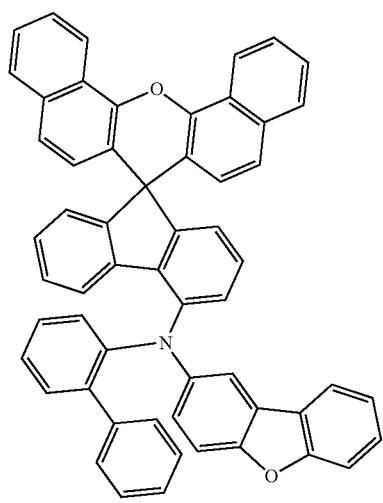
384
-continued
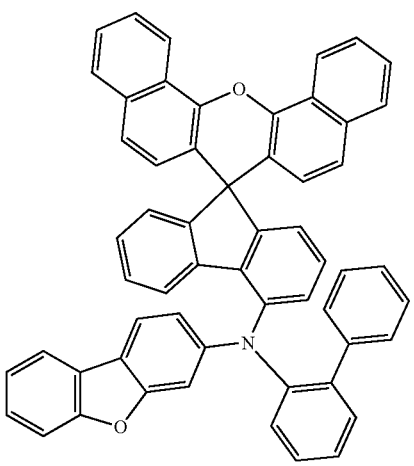
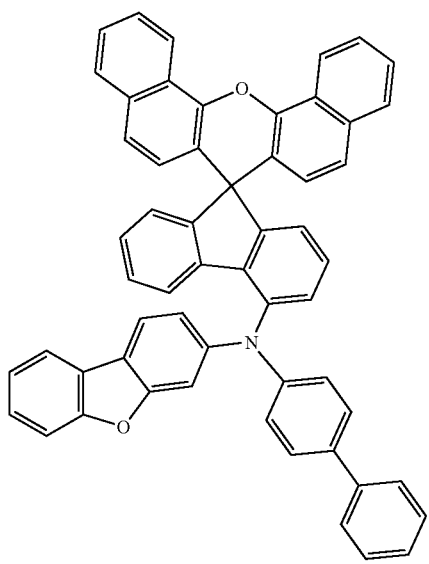
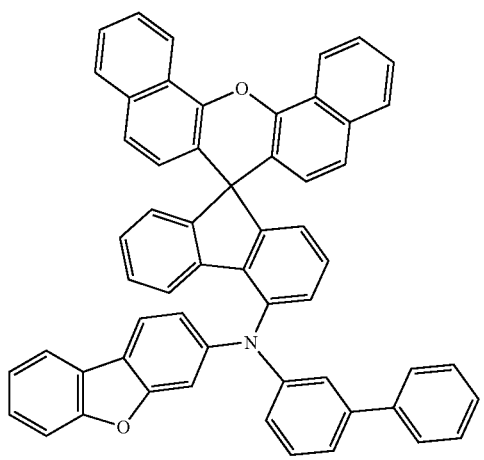
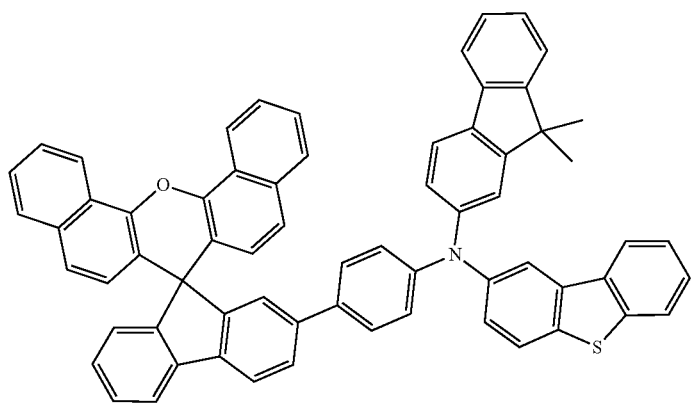

-continued
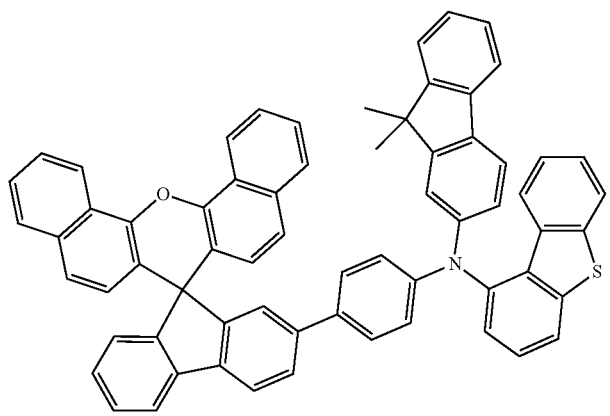
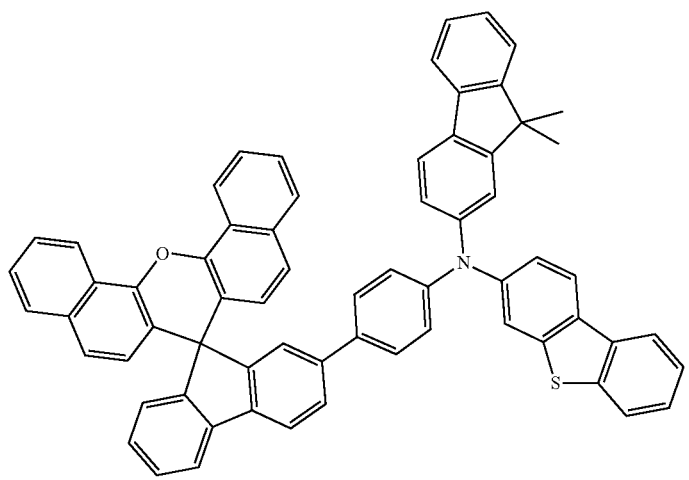
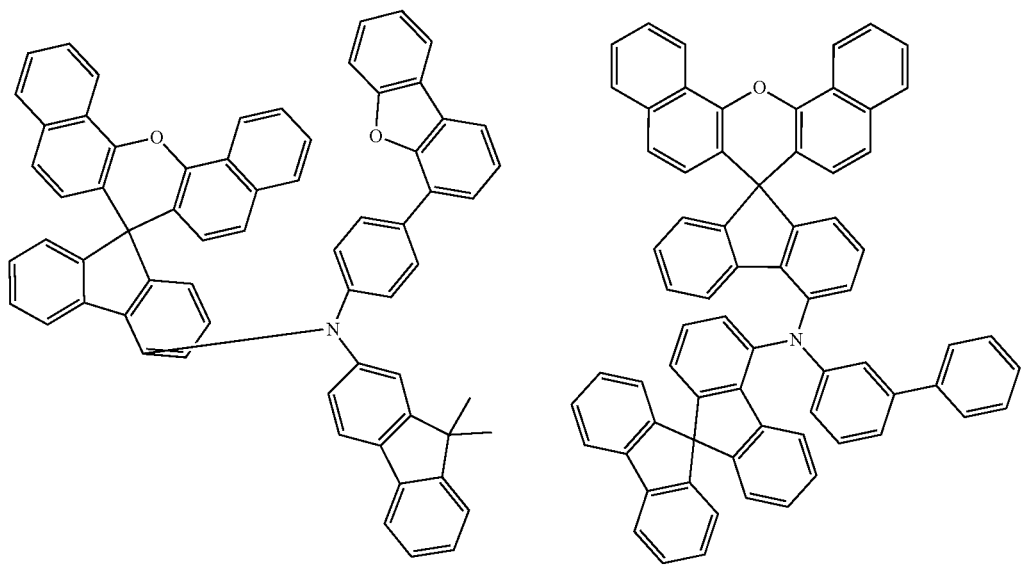

387
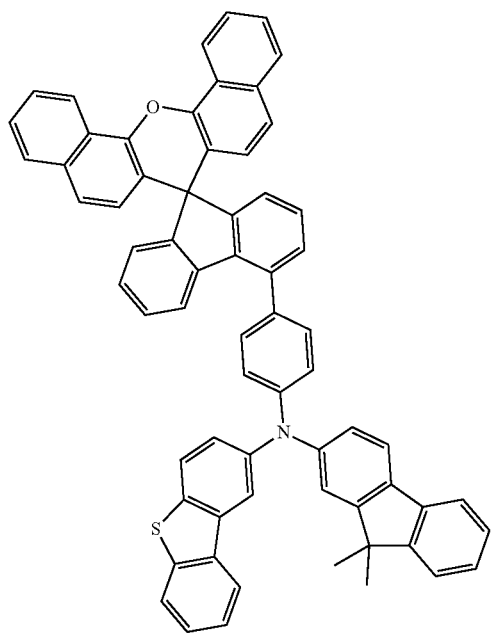
388
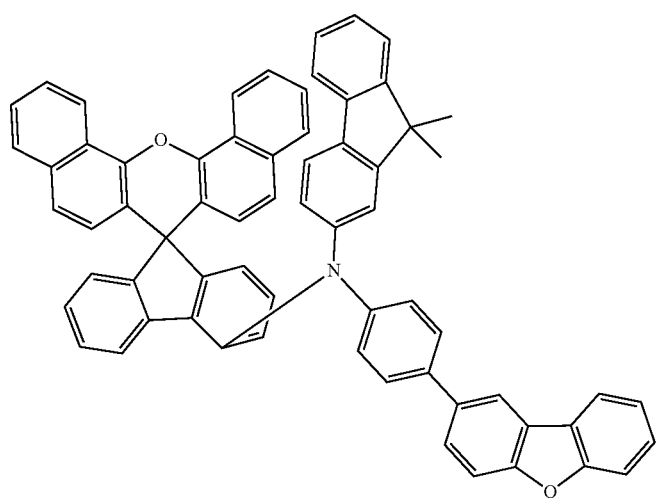
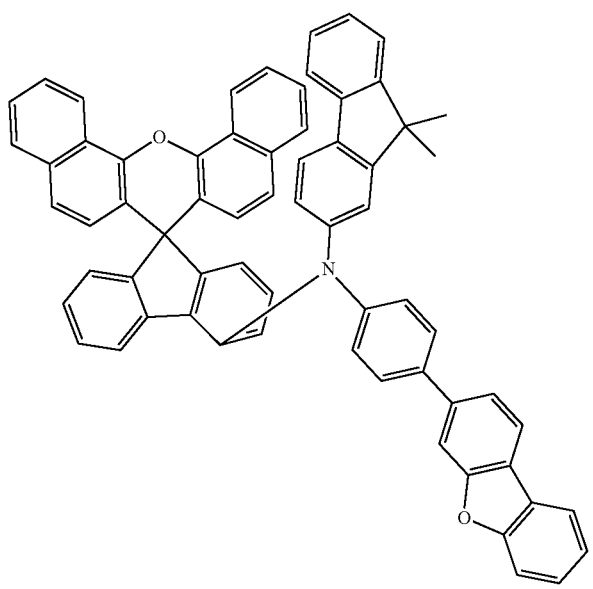
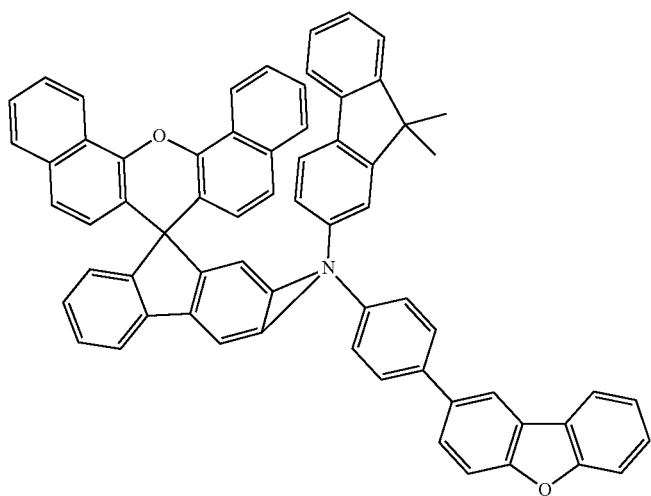

389
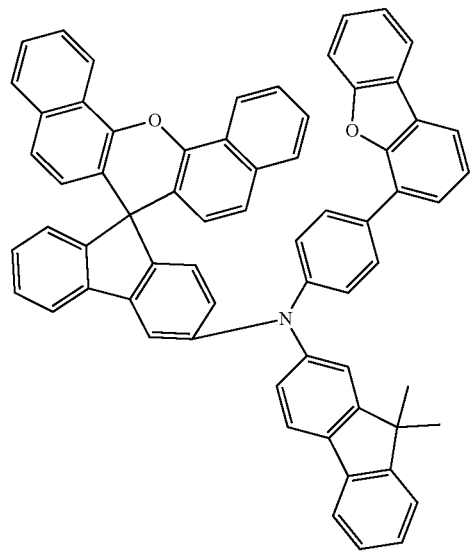
390
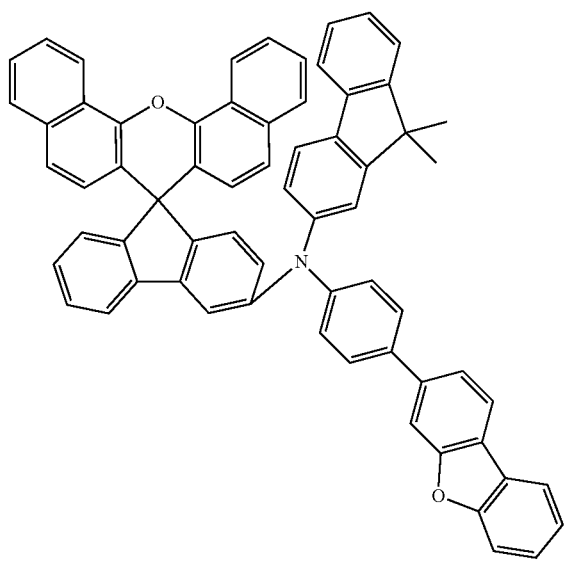
-continued
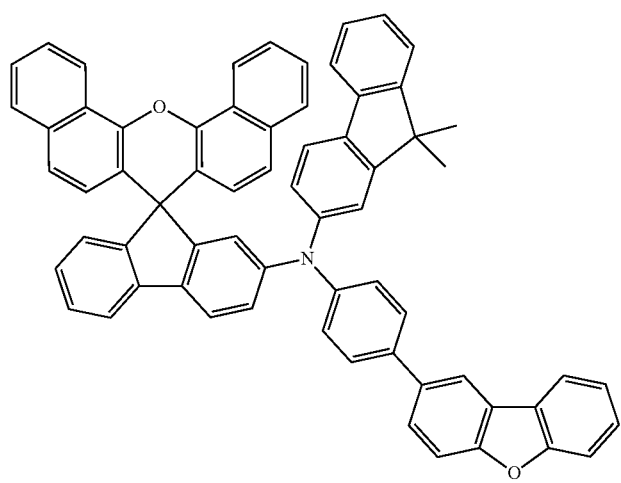
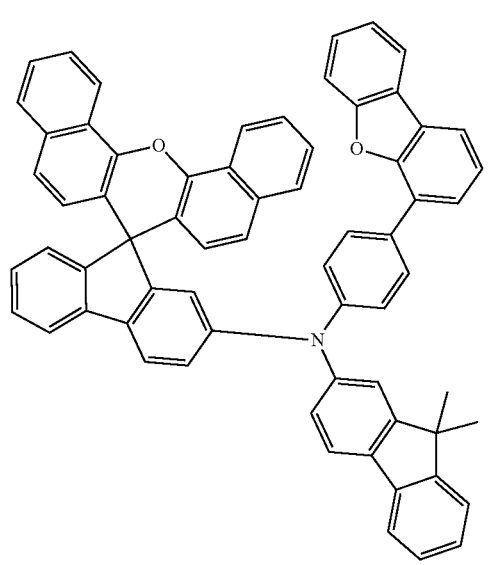

391 392
-continued
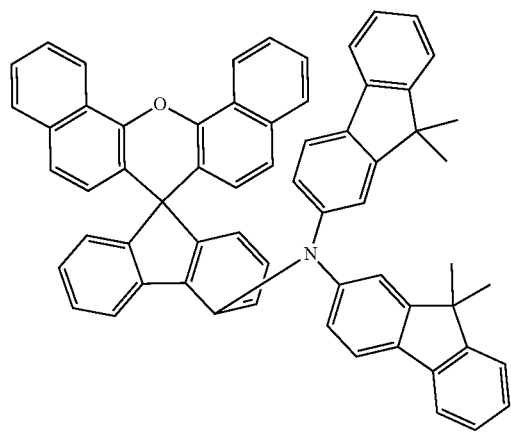
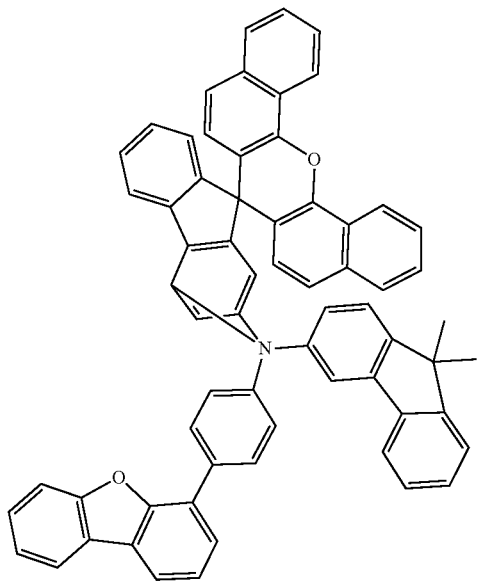
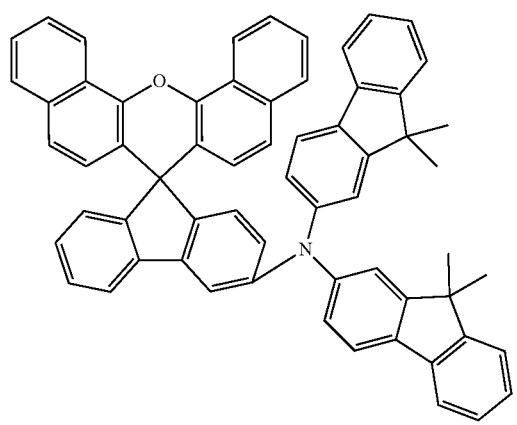
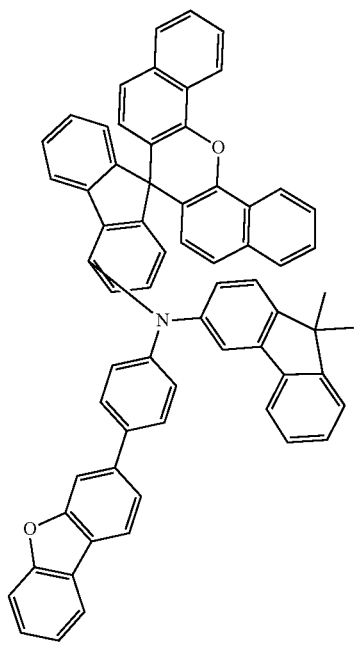

393
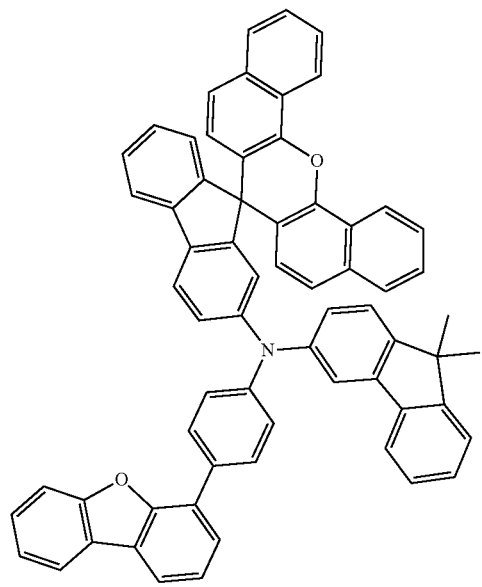
394
-continued
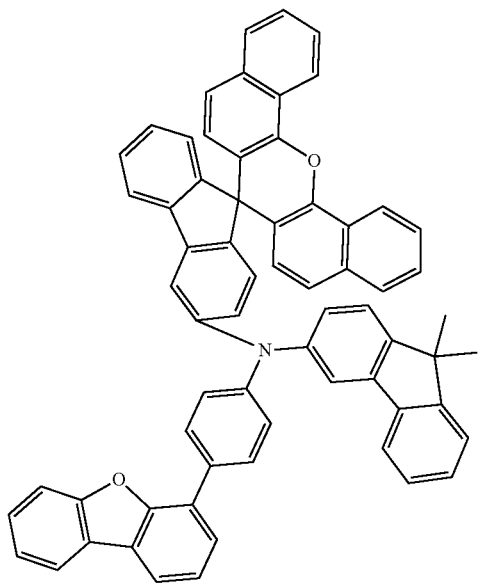
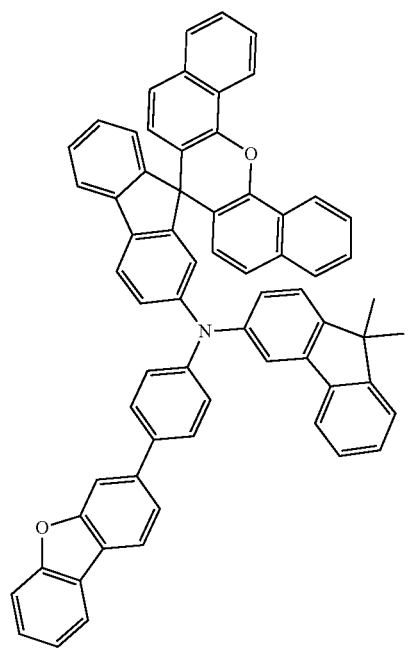
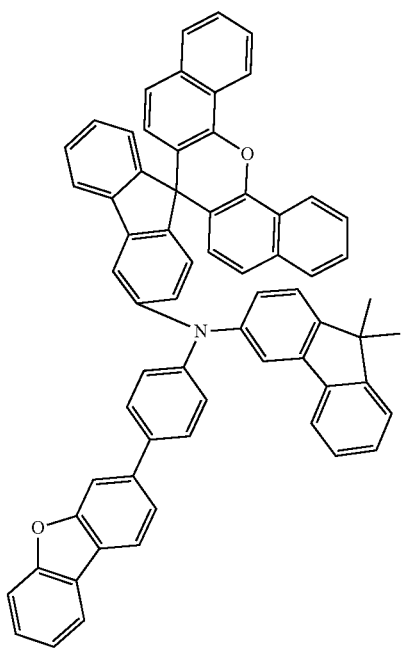

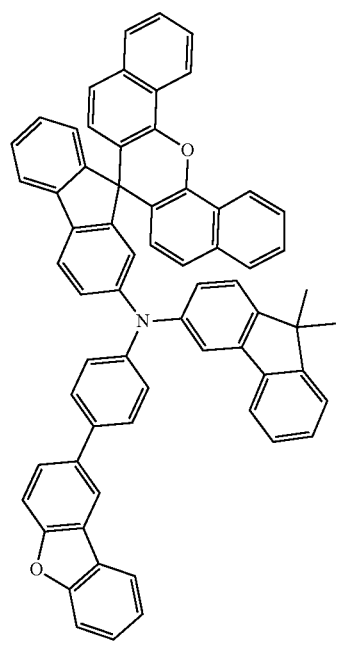
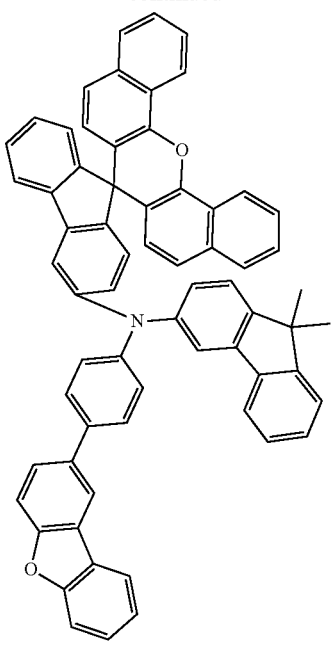
-continued
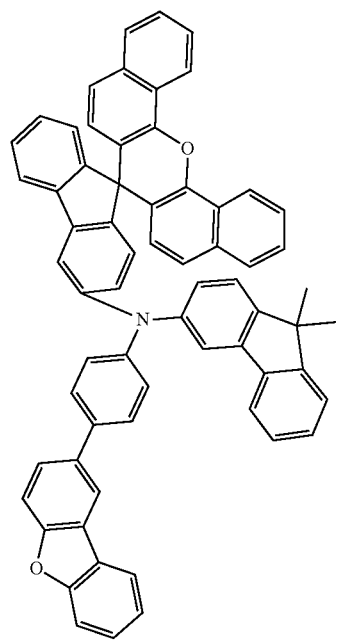
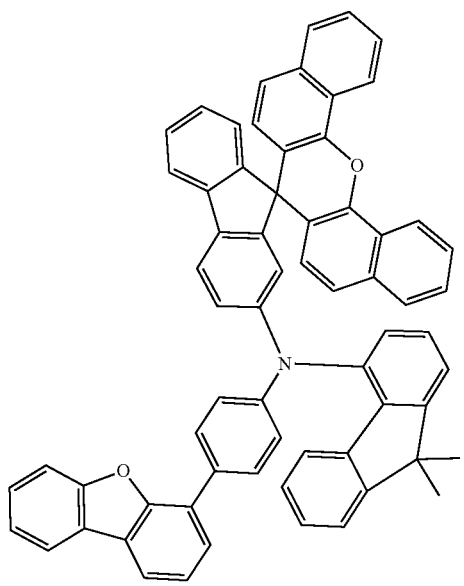

397 398
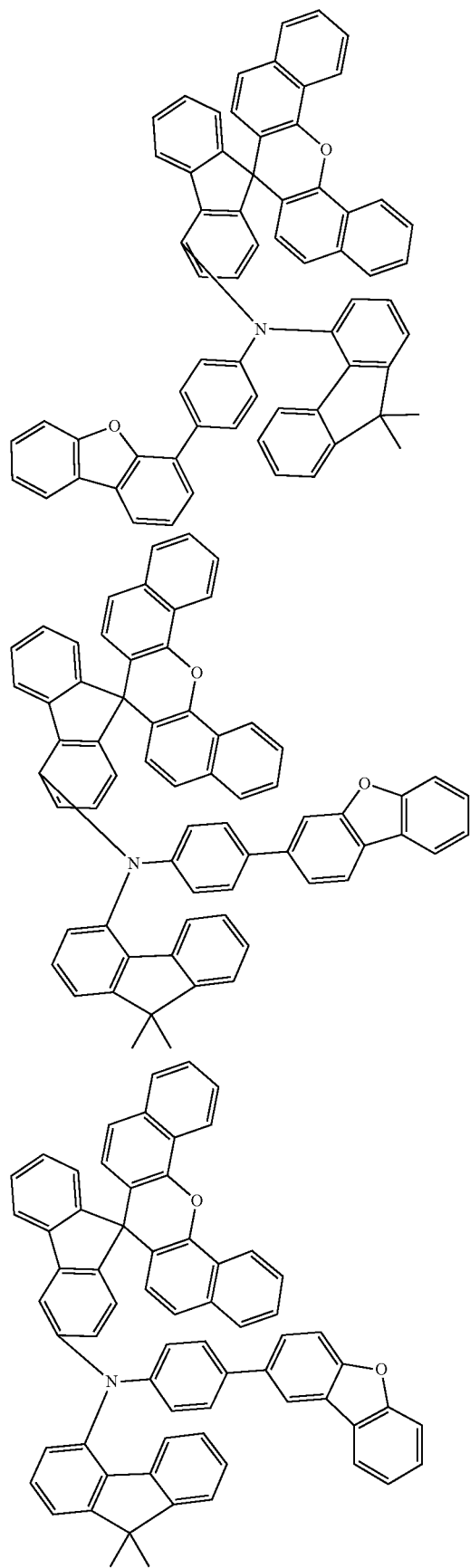
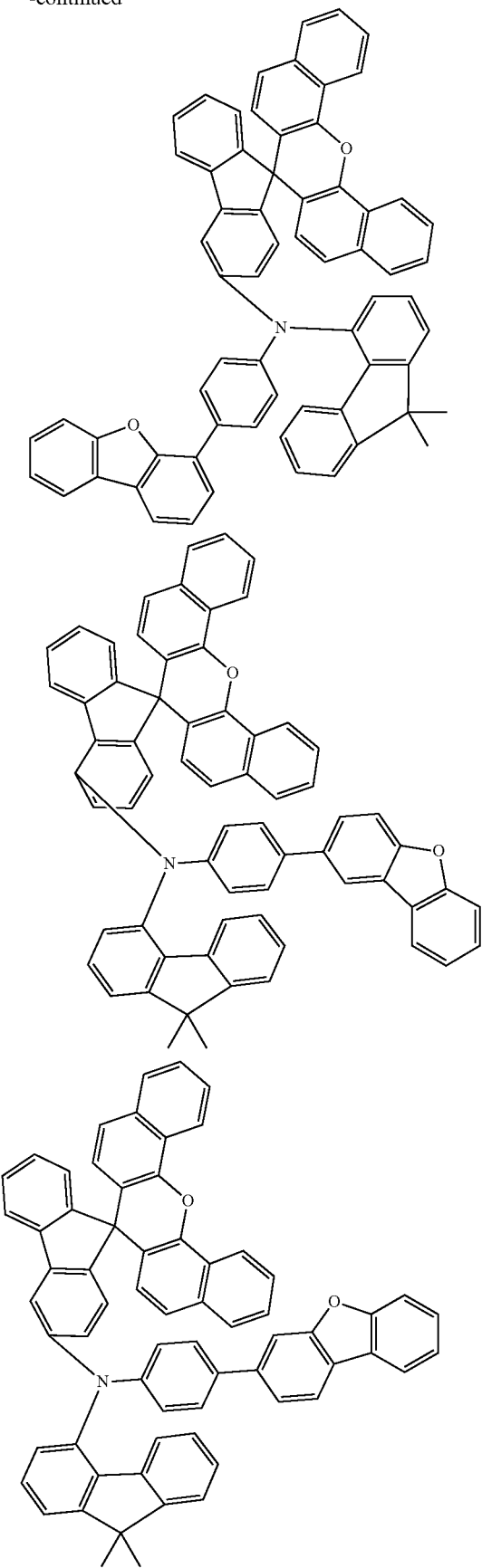
-continued

399
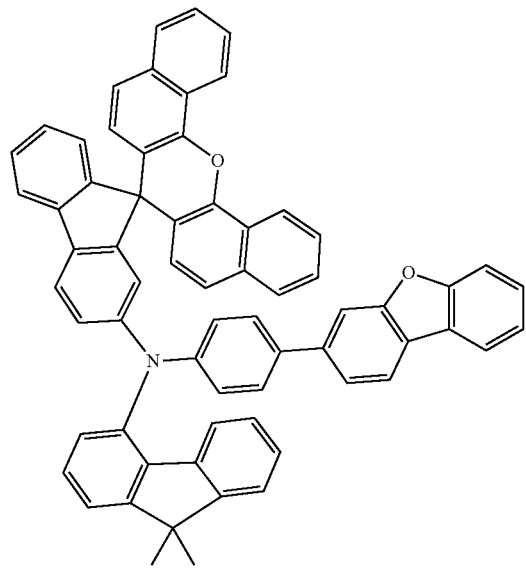
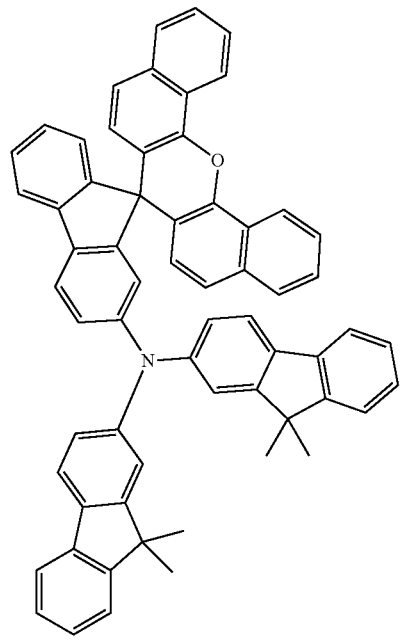
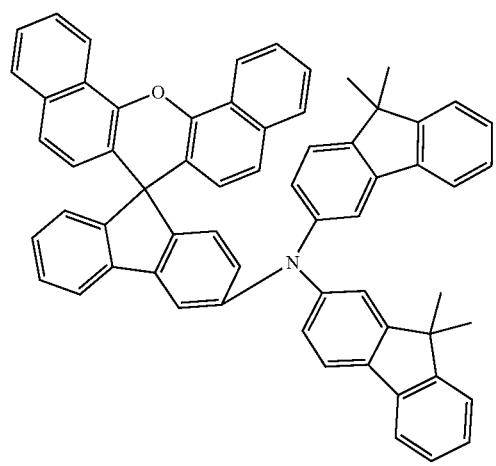
400
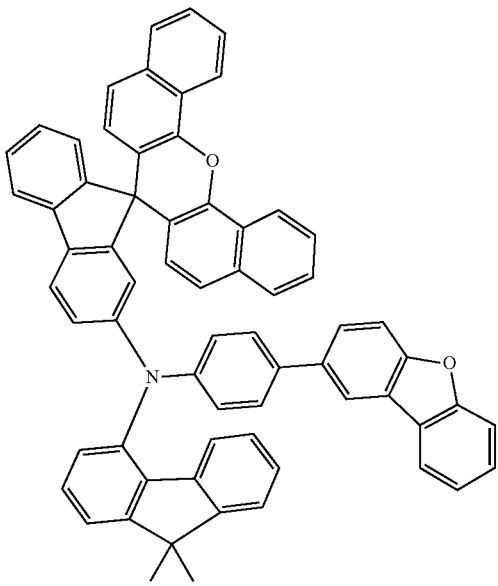
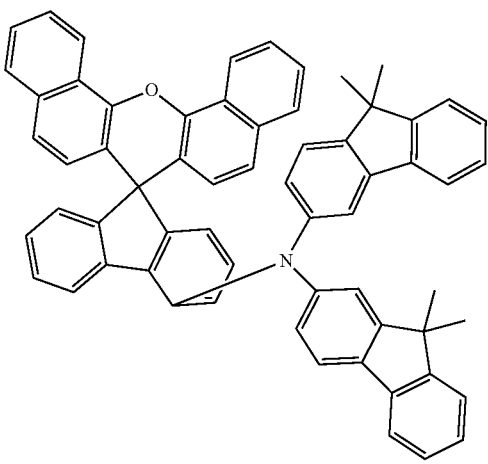
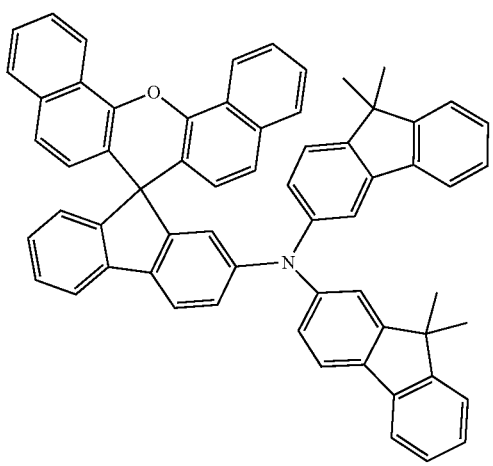

401
402
-continued
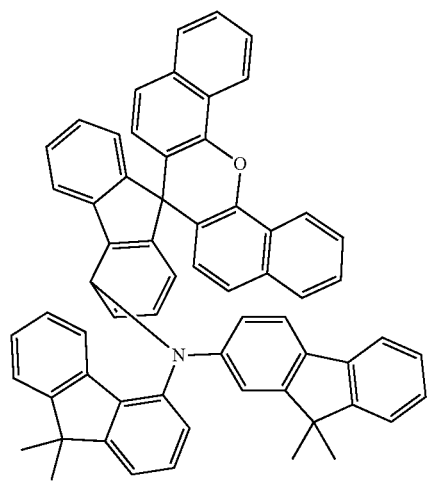
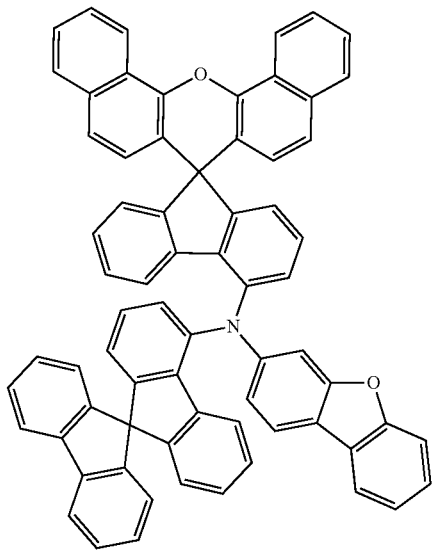
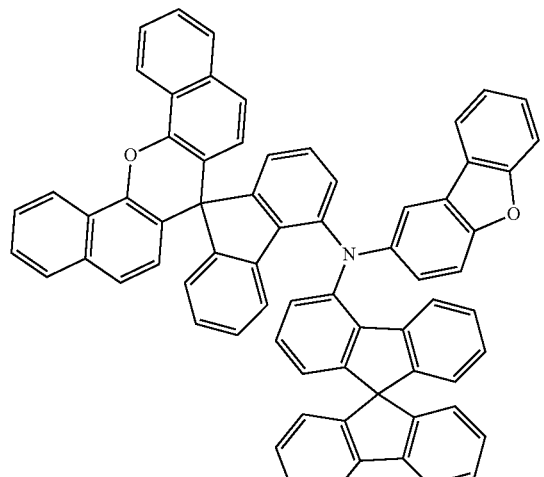
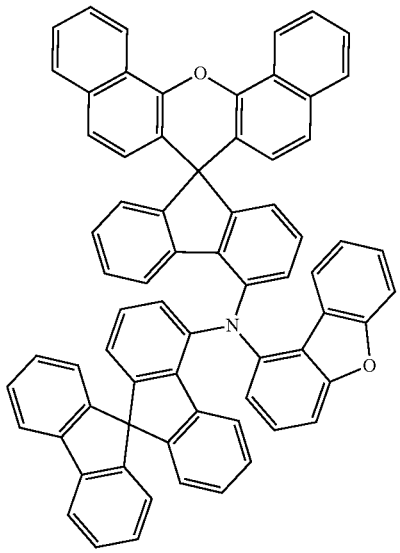
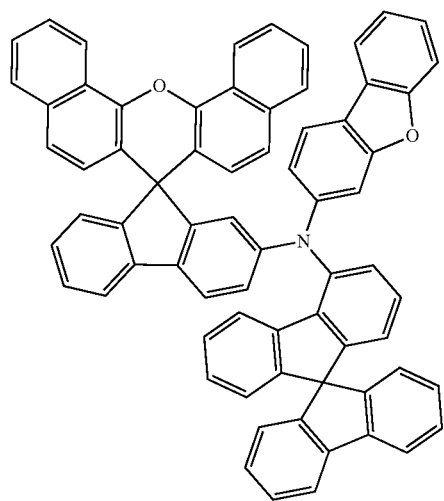
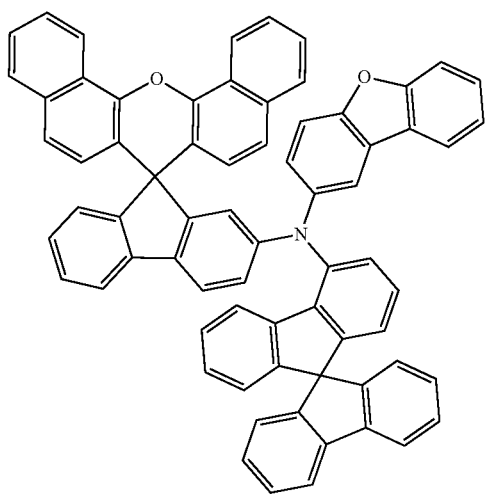

403
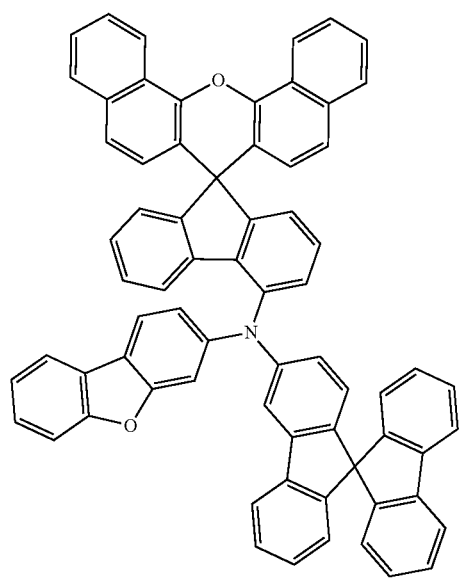
404
-continued
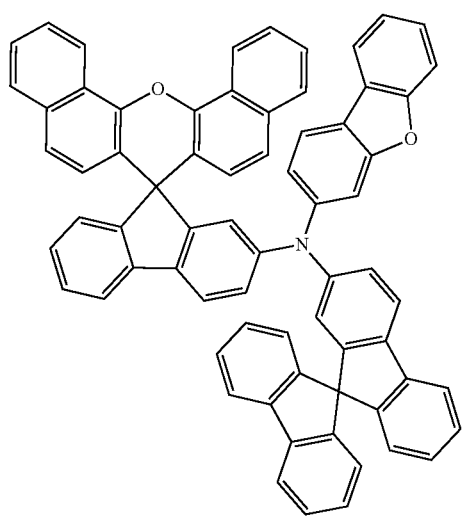
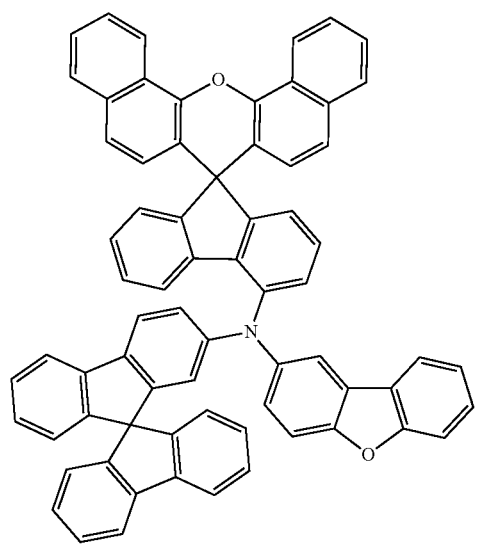
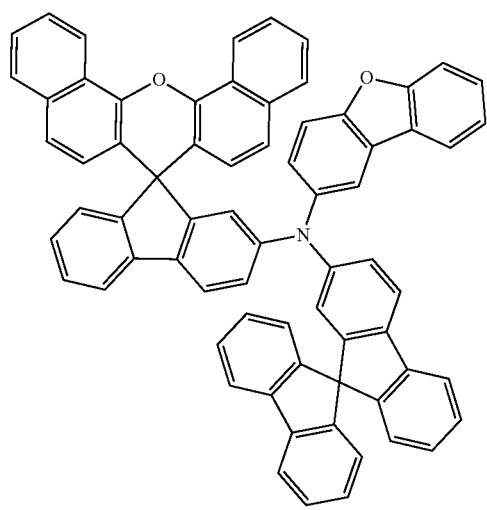

405
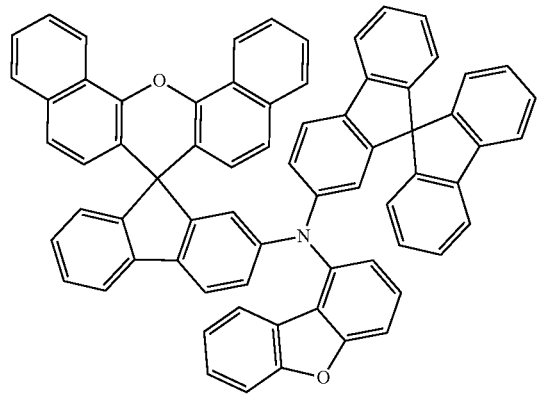
406
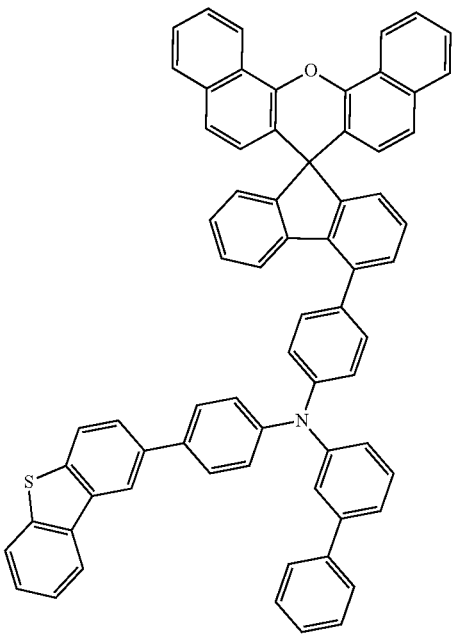
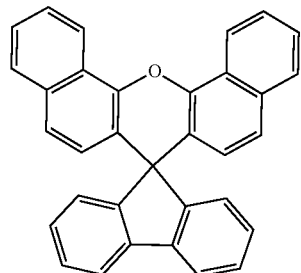
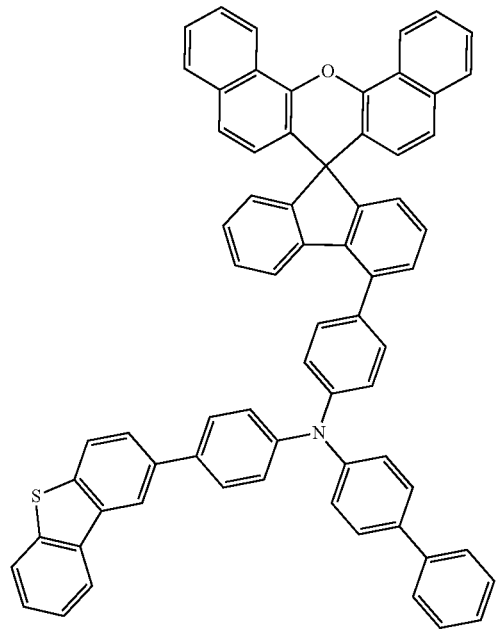
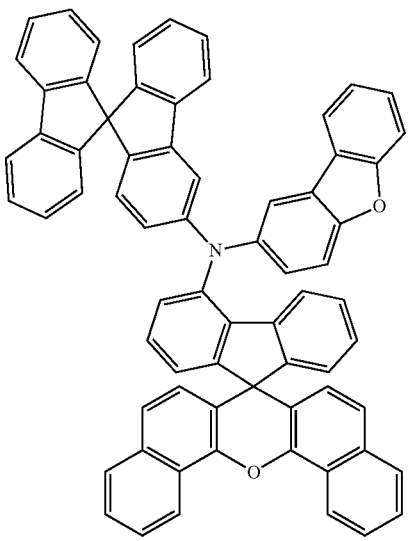

407
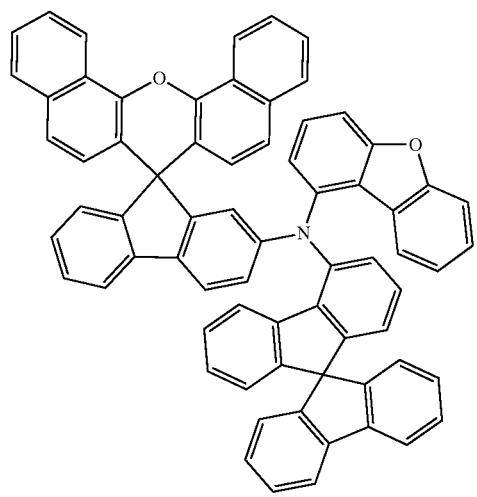
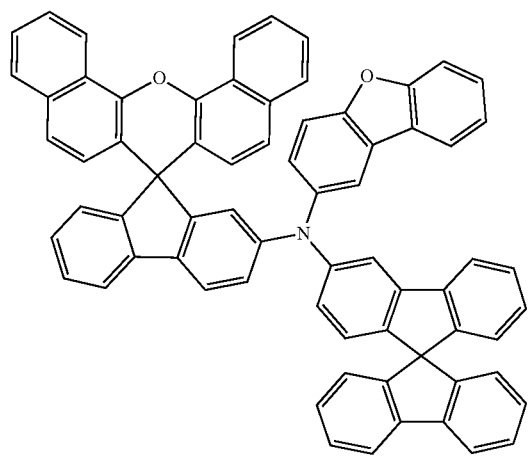
408
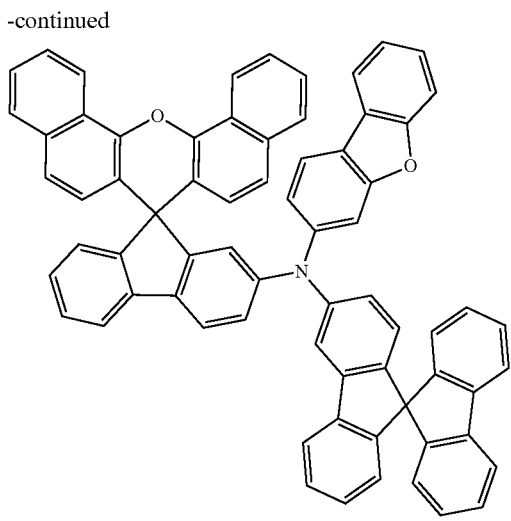
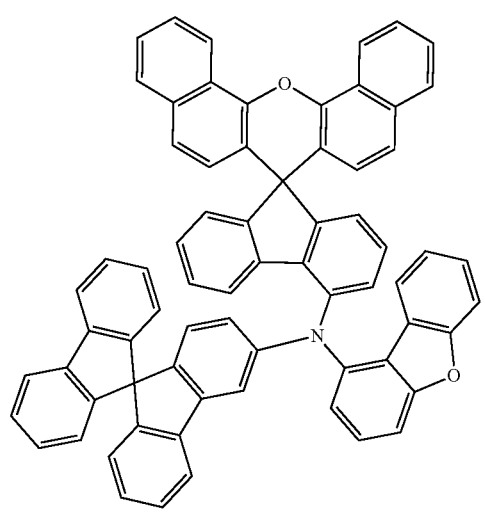
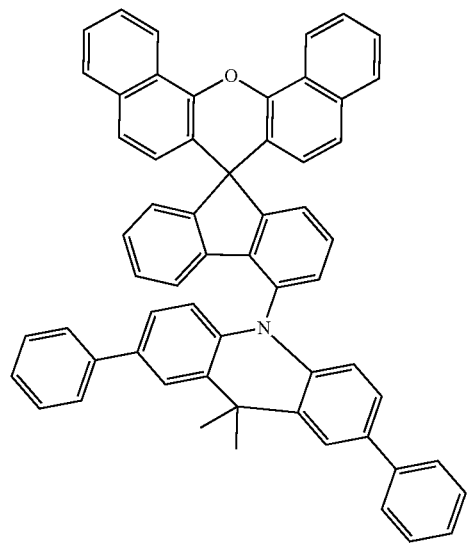
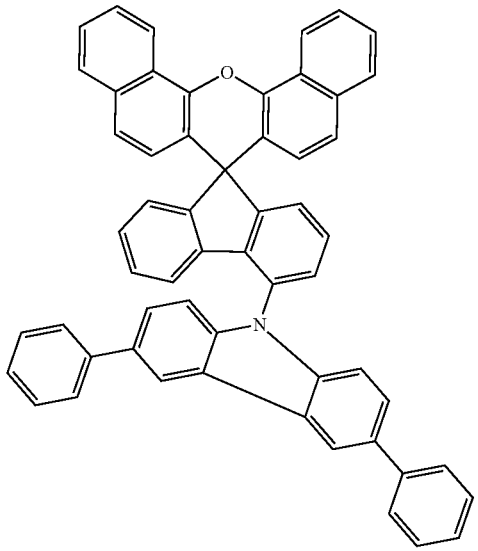

409
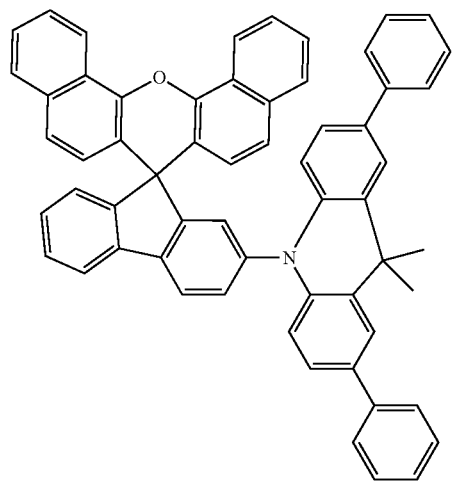
410
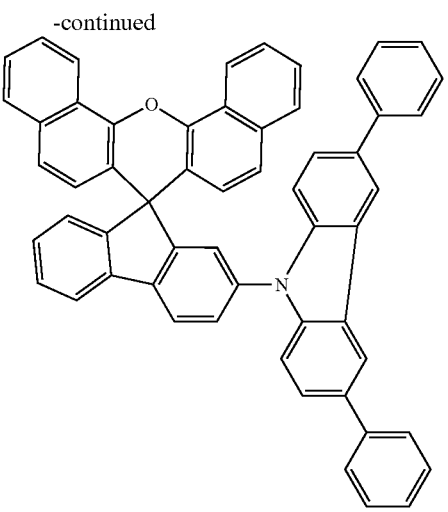
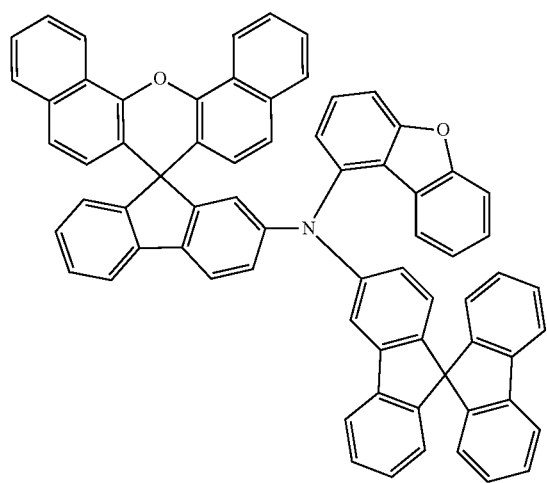
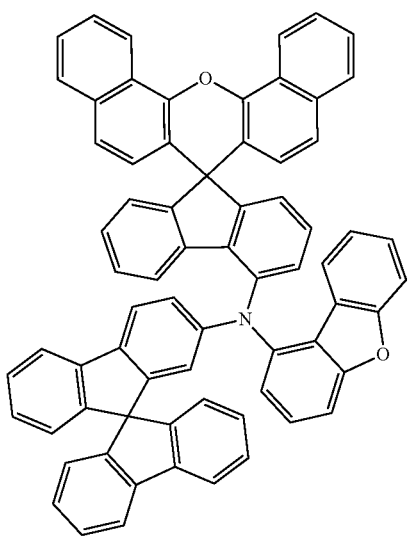
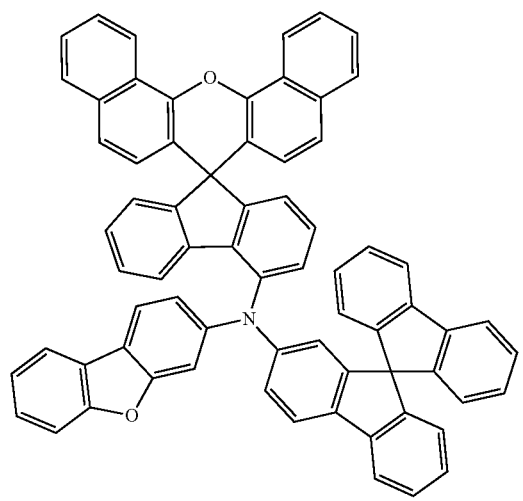

-continued
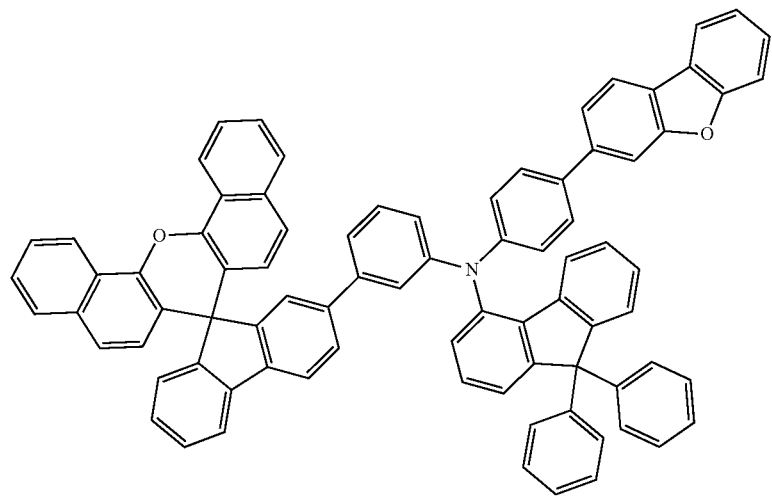
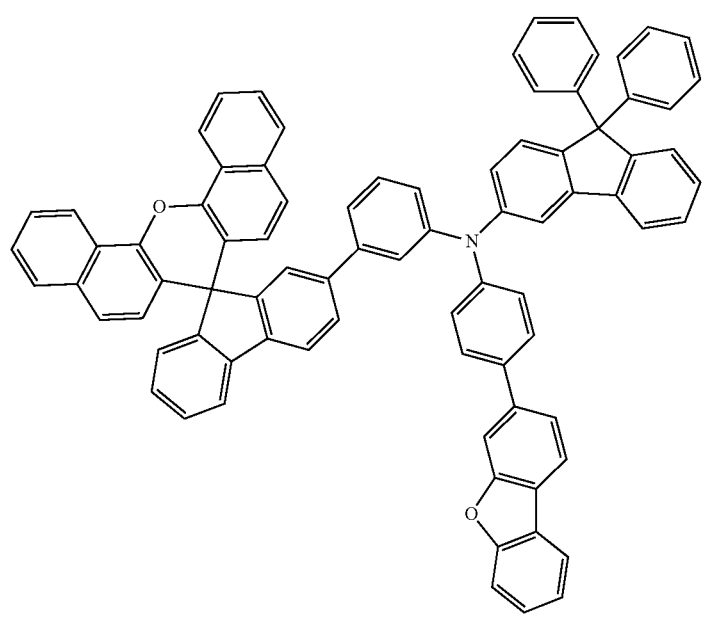
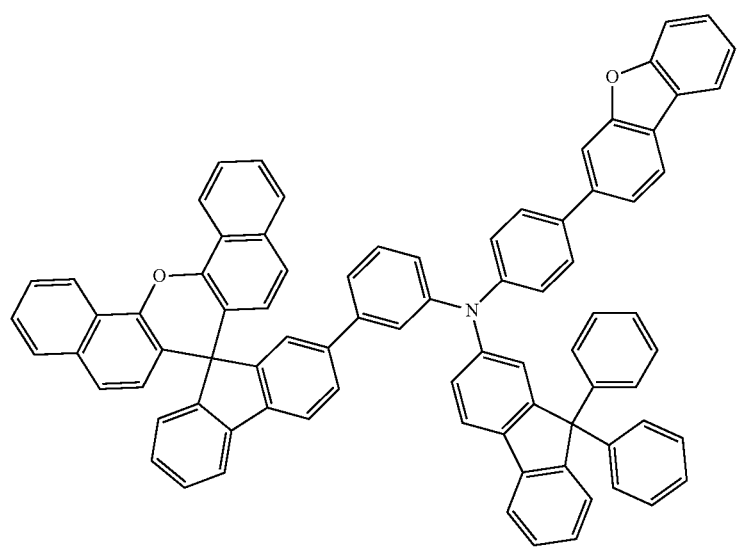

-continued
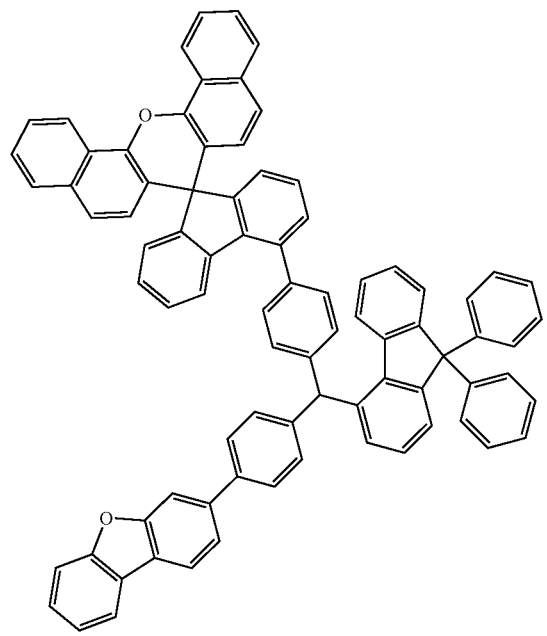
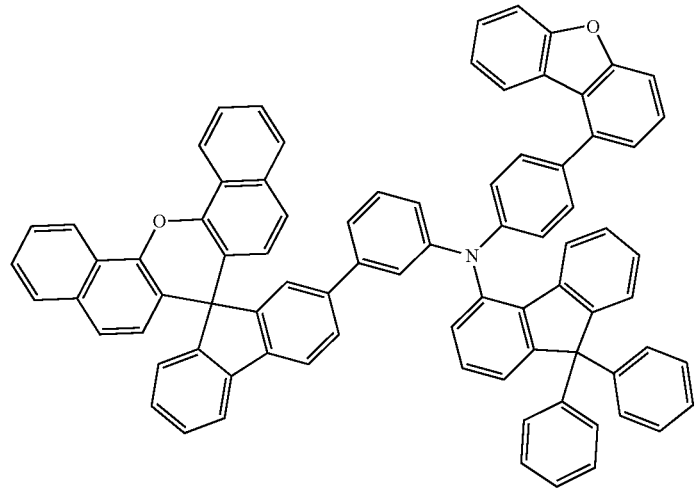
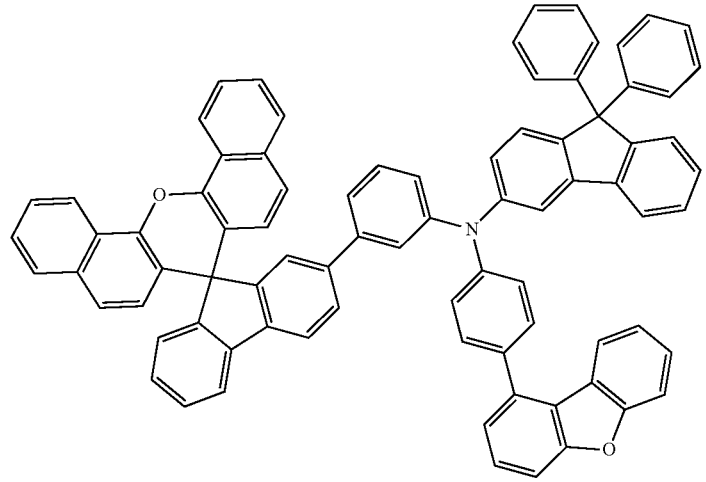

-continued
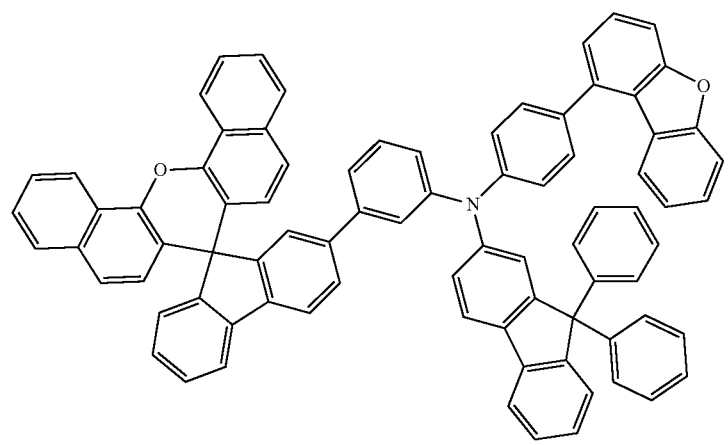
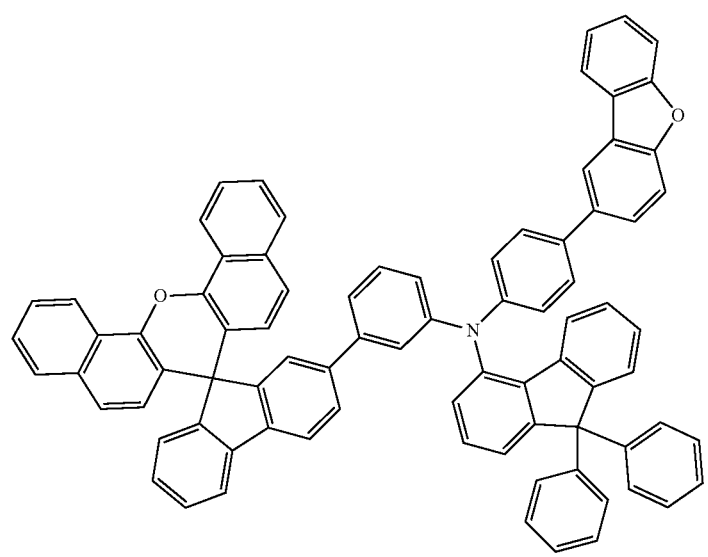
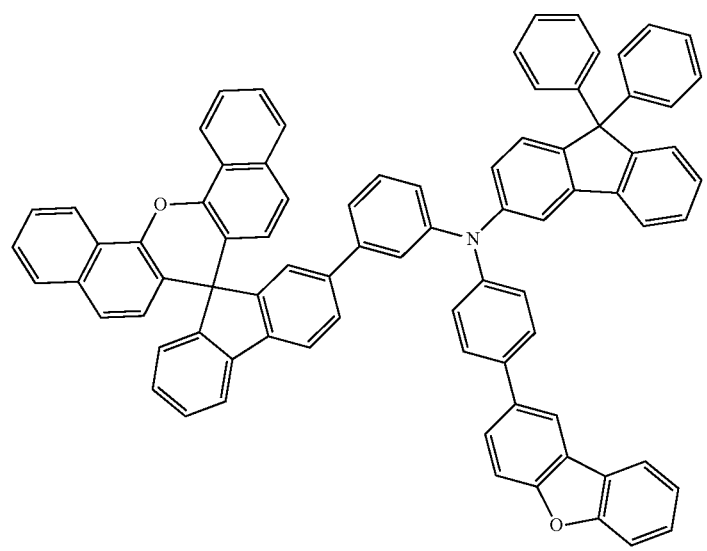

417
-continued
418
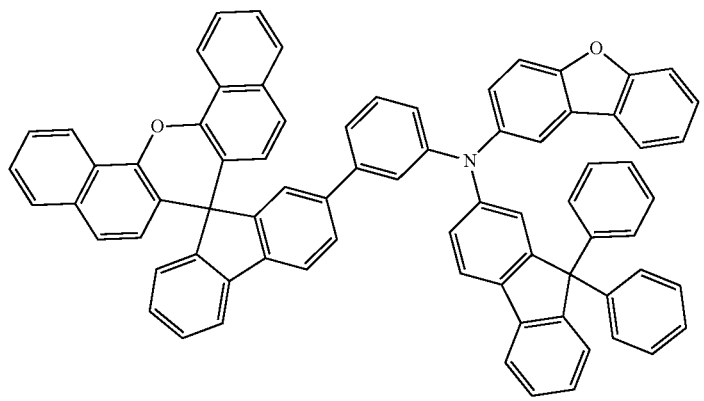
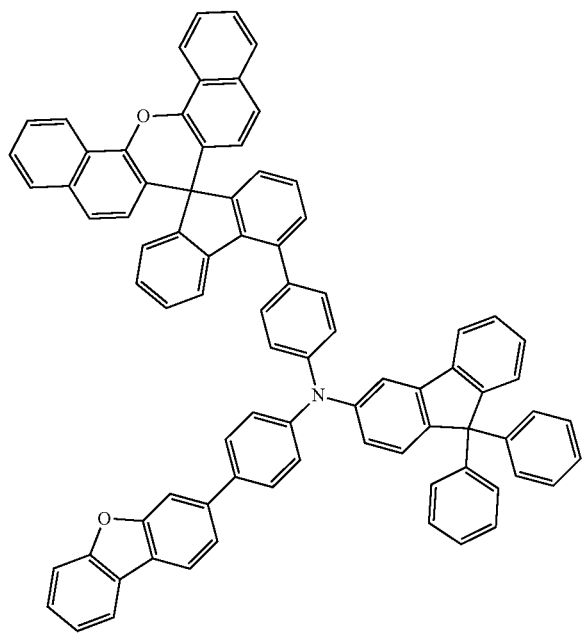
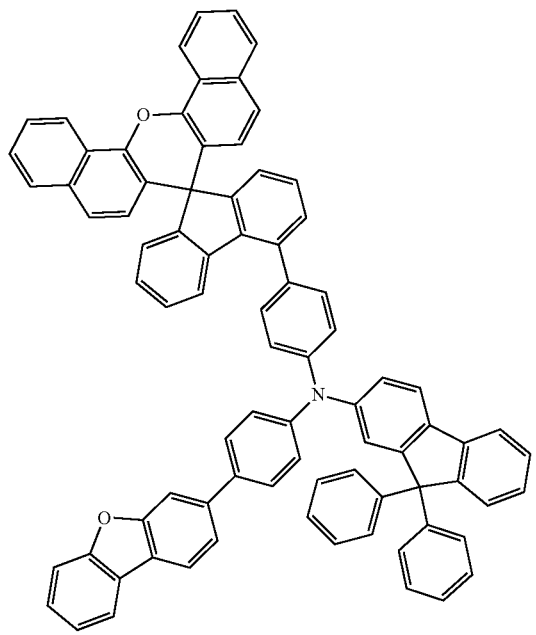
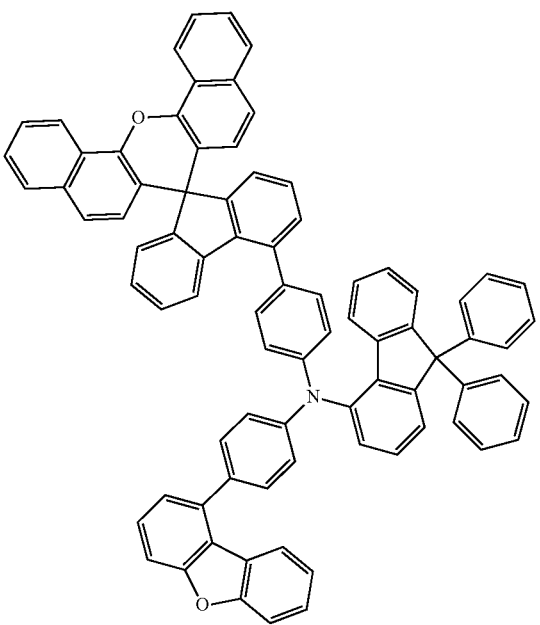

-continued
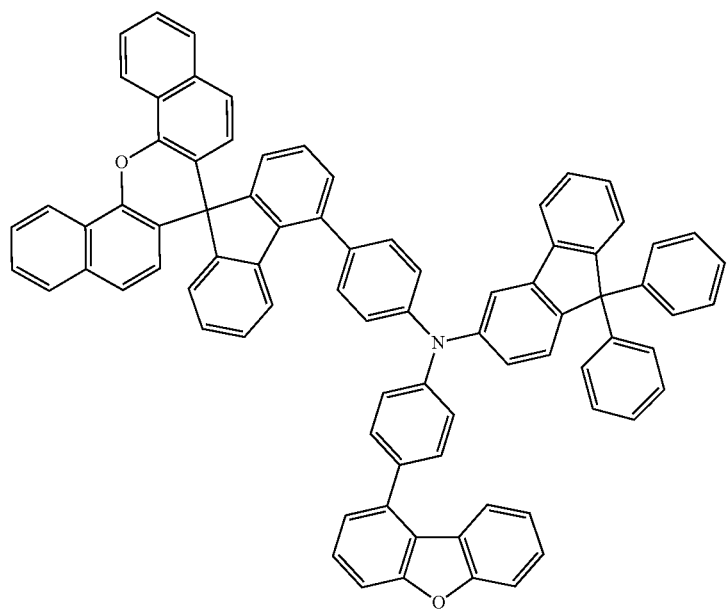
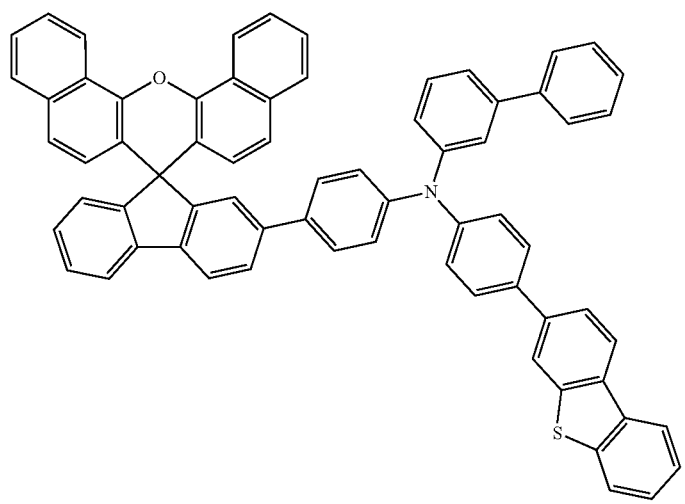
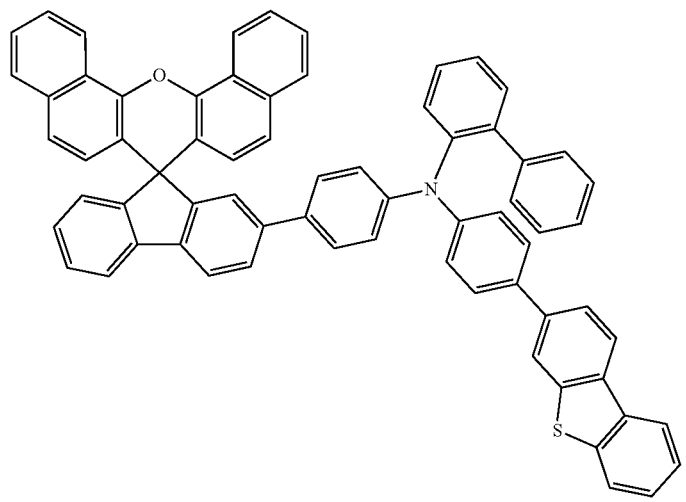

-continued
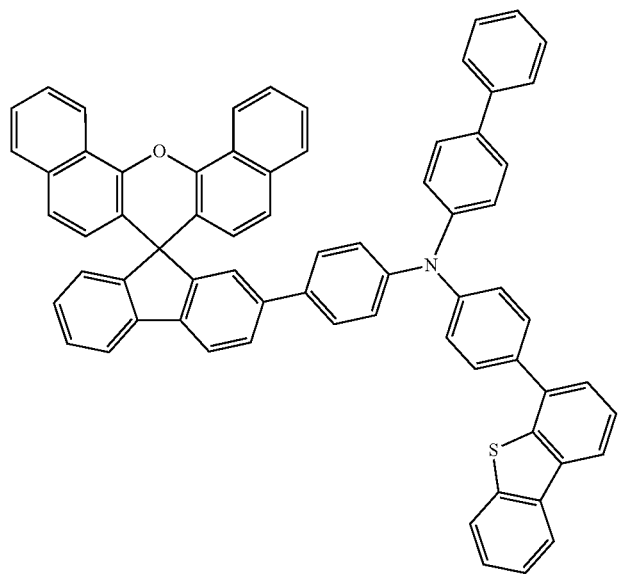
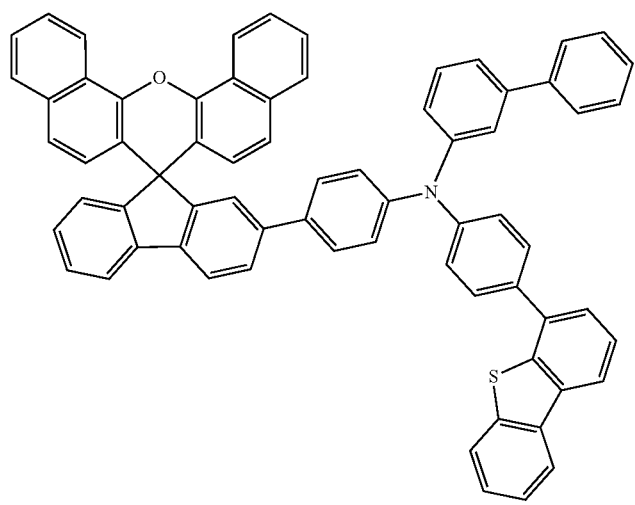
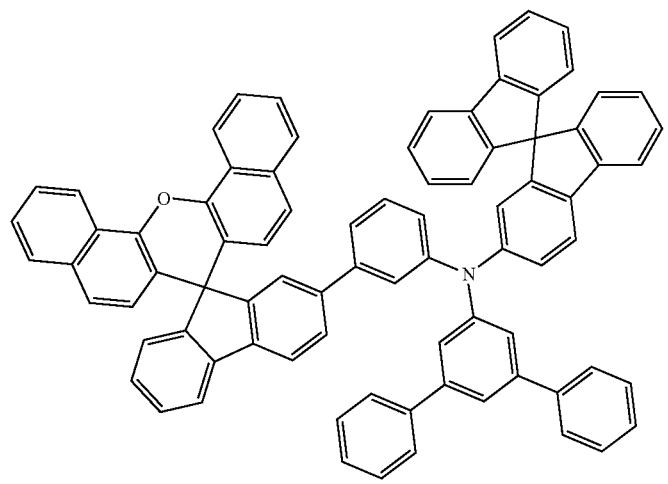

423
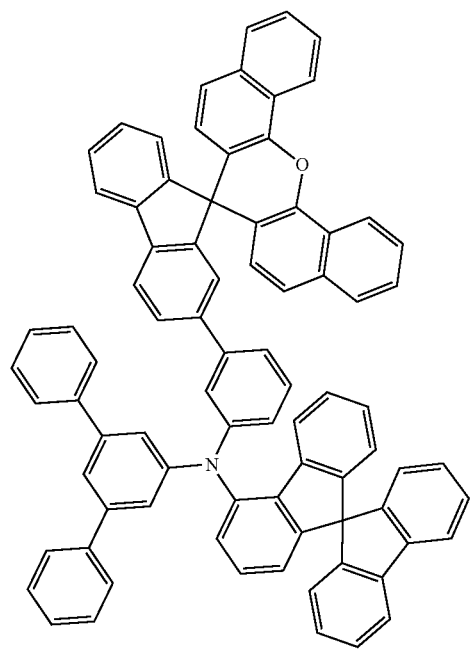
424
-continued
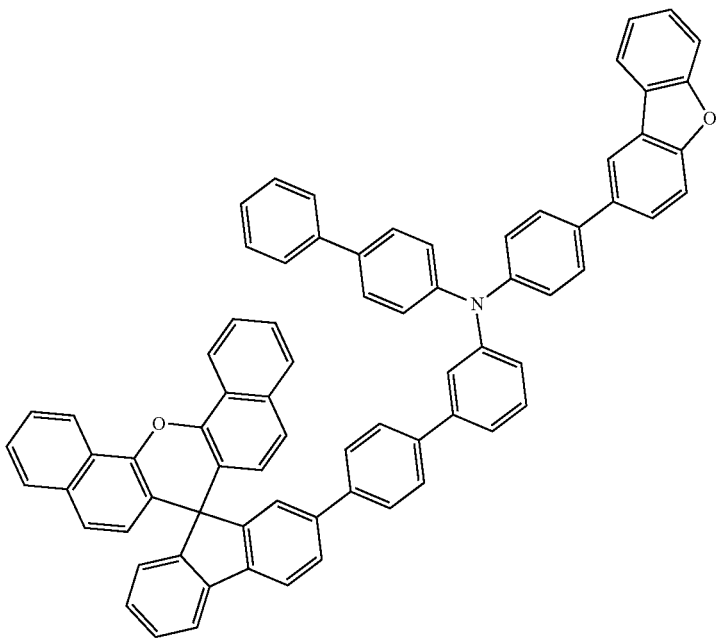
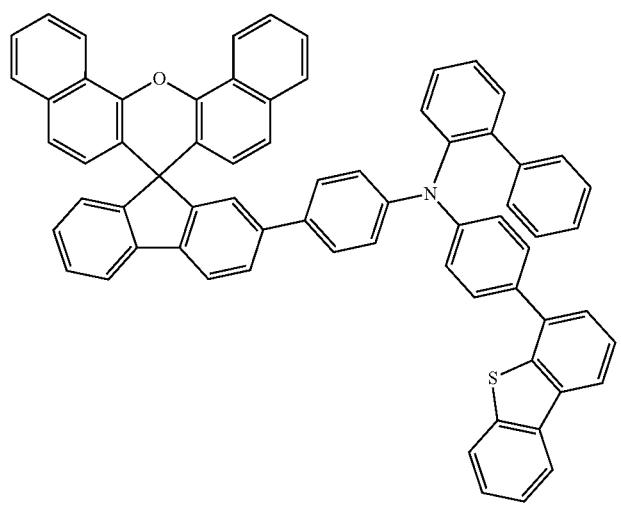
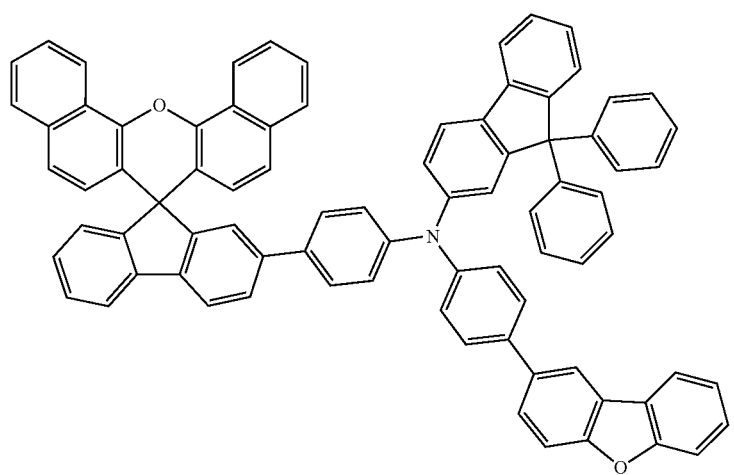

-continued
425
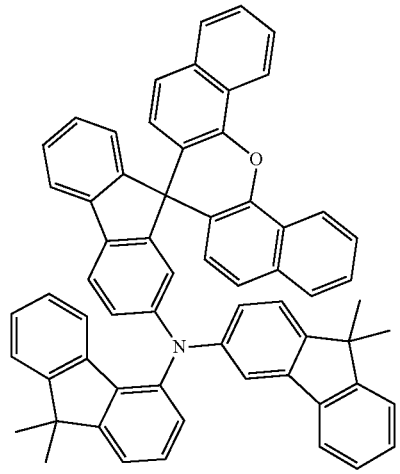
426
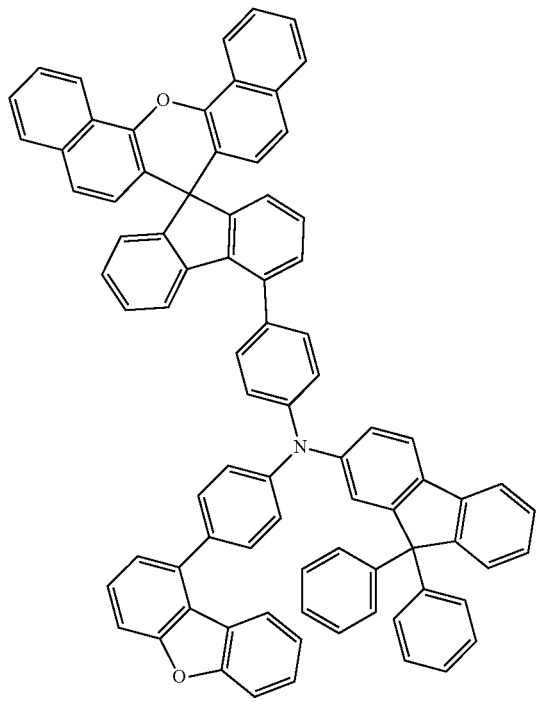
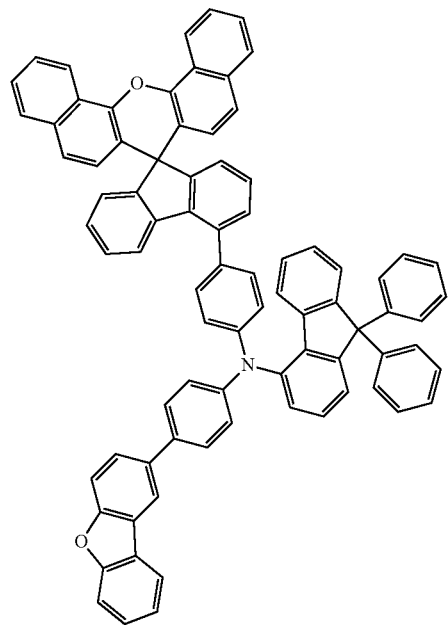
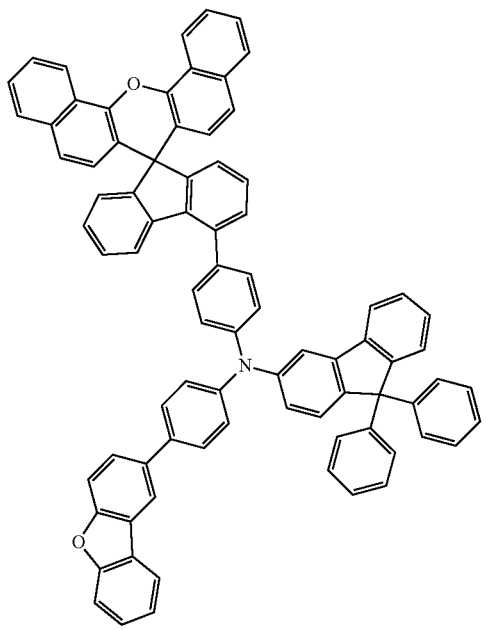

-continued
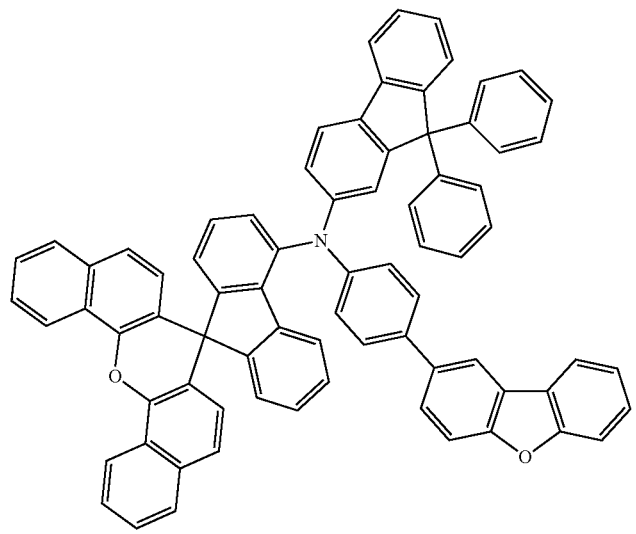
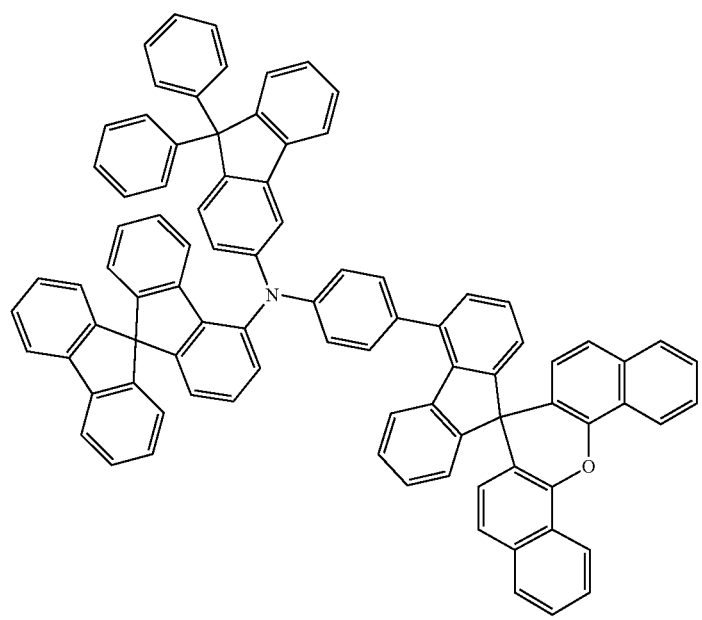

429
430
-continued
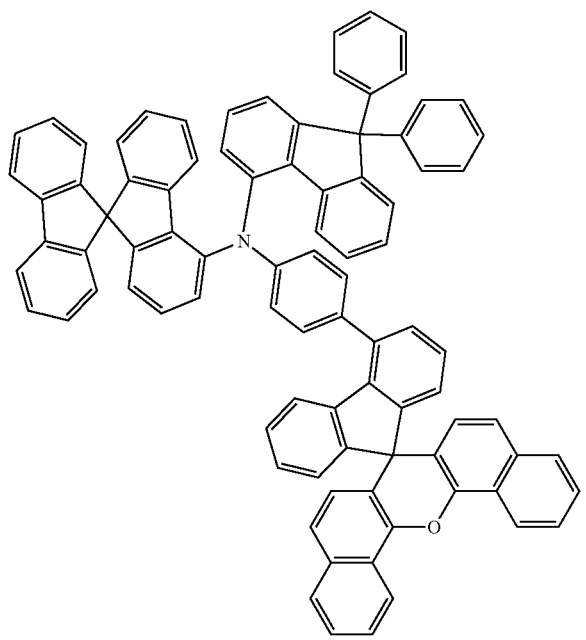
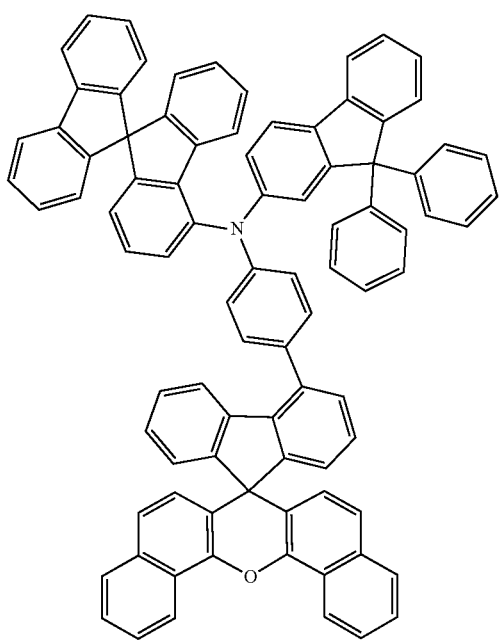
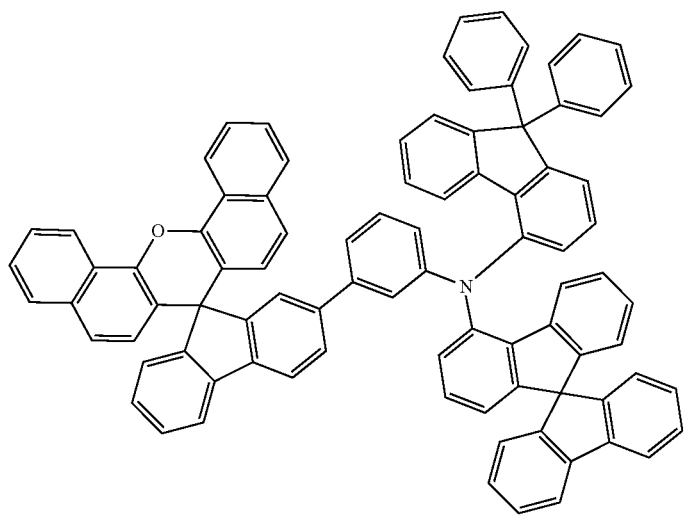
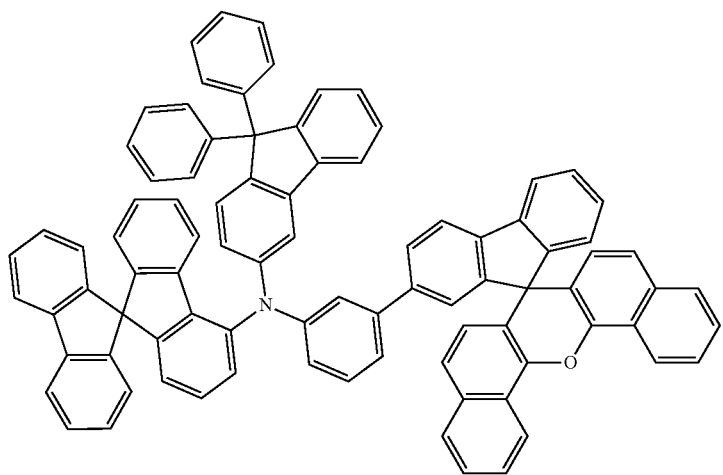

-continued
431 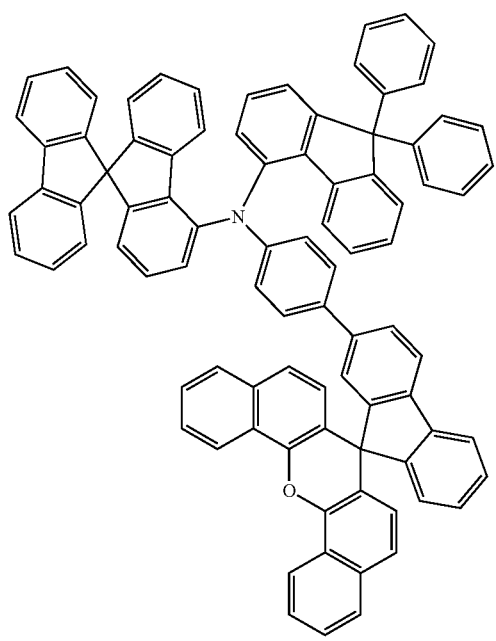 432 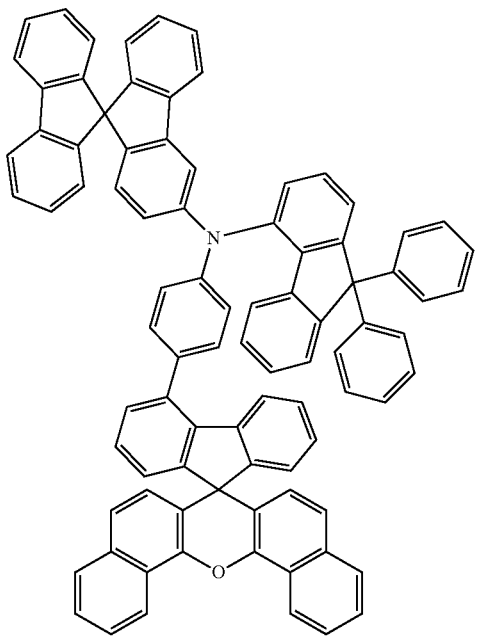
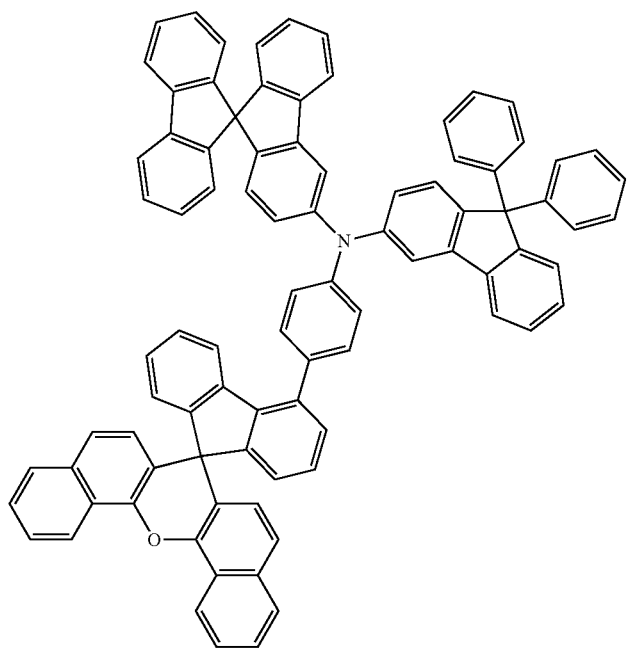

-continued
433
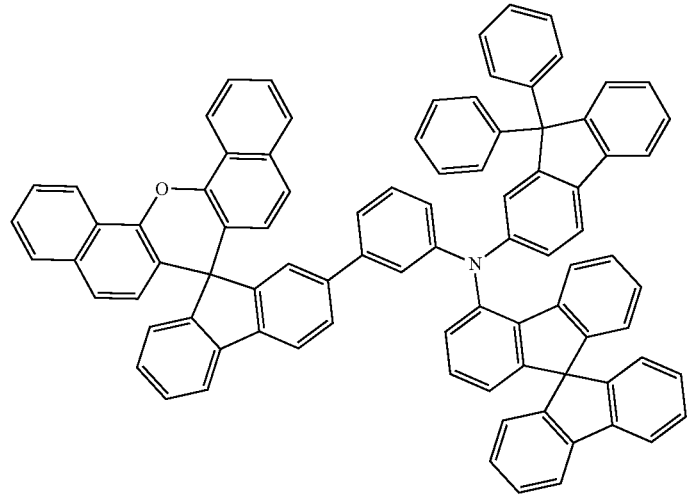
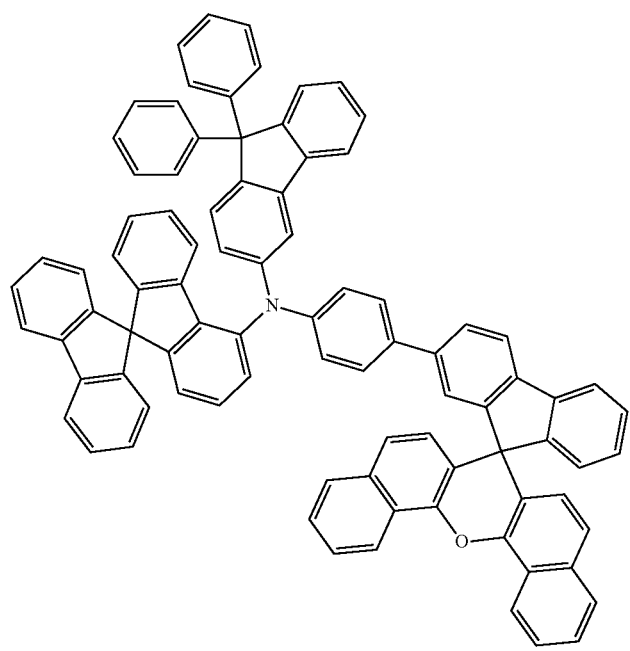
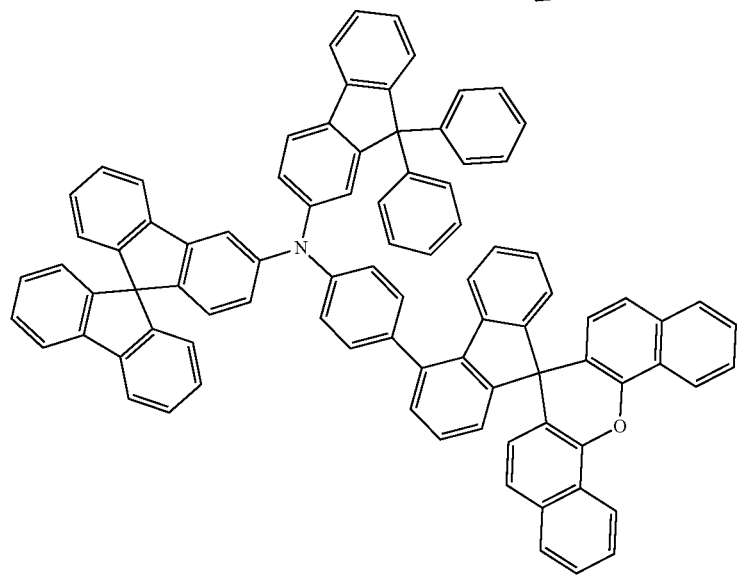
434
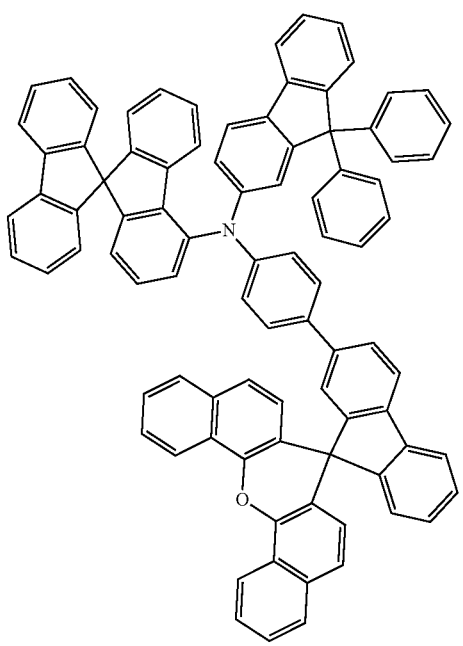

-continued
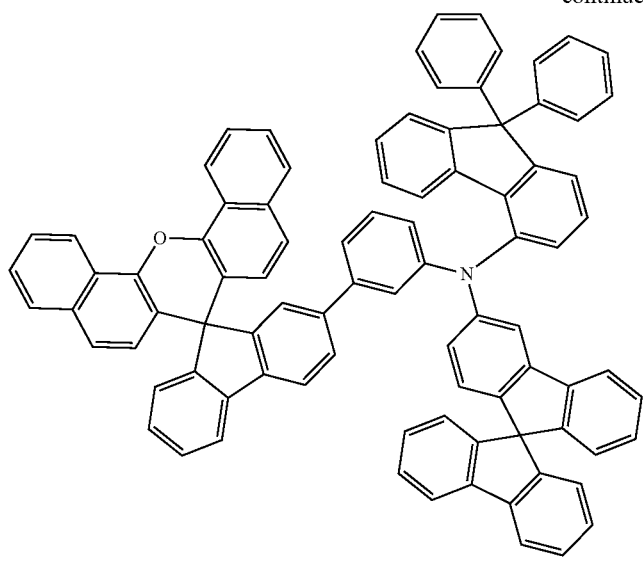
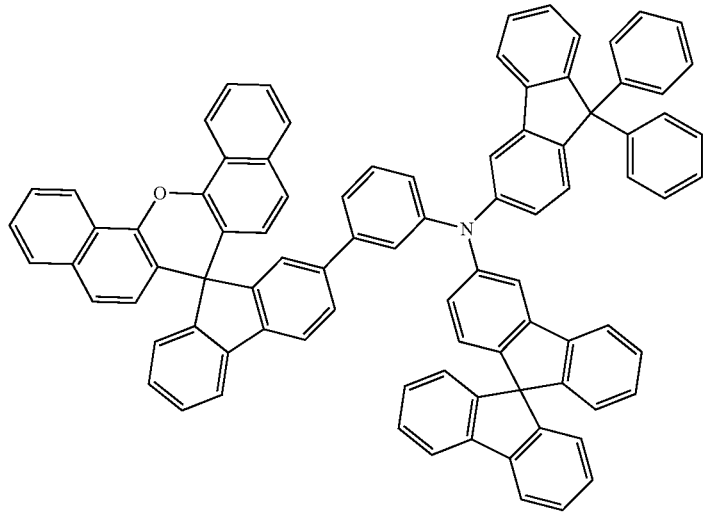
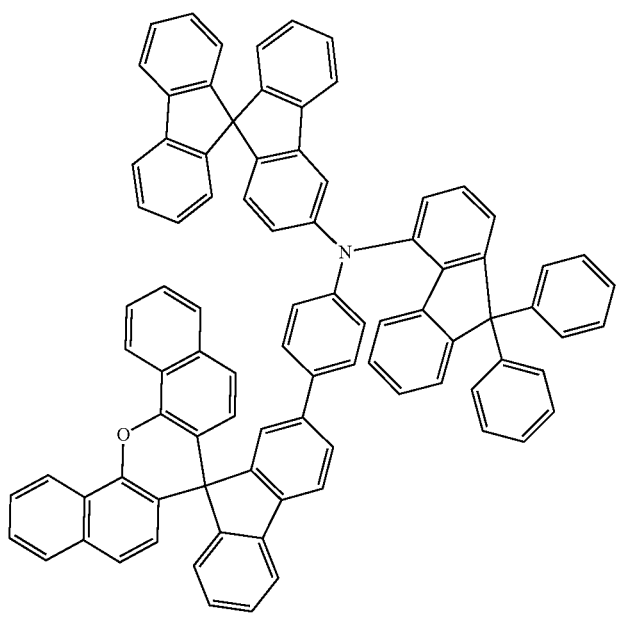
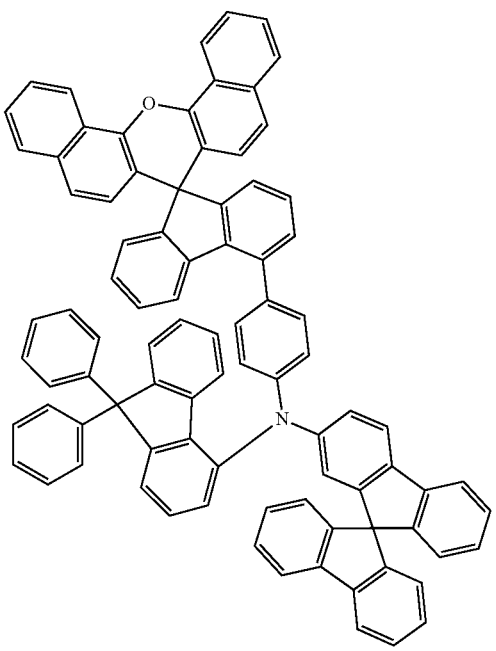

-continued
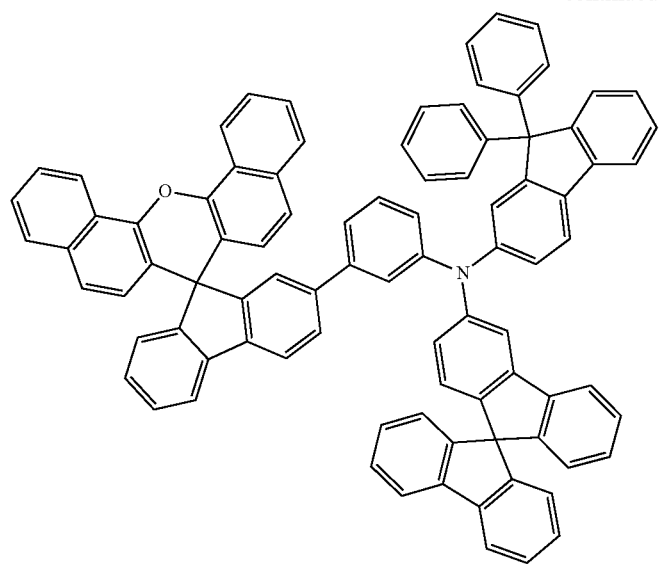
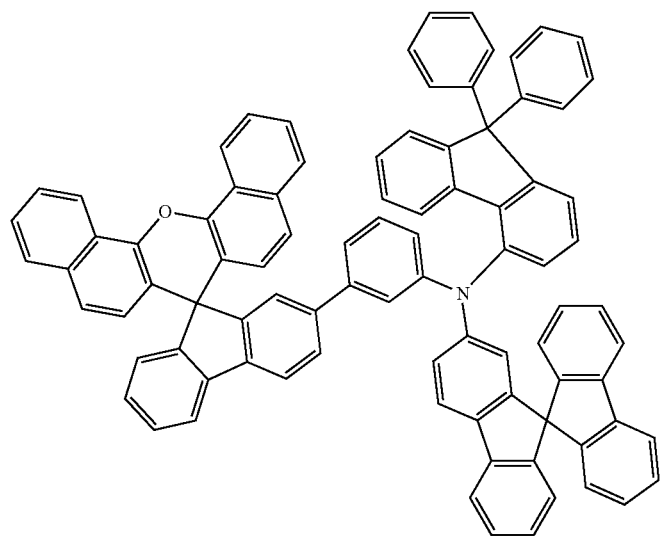
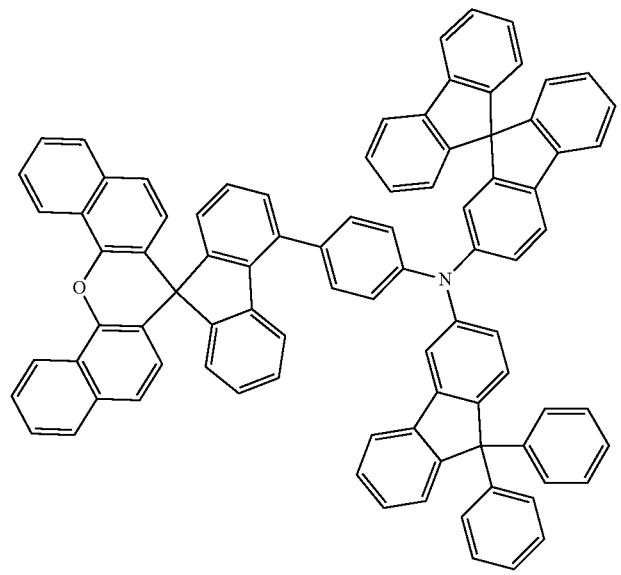

-continued
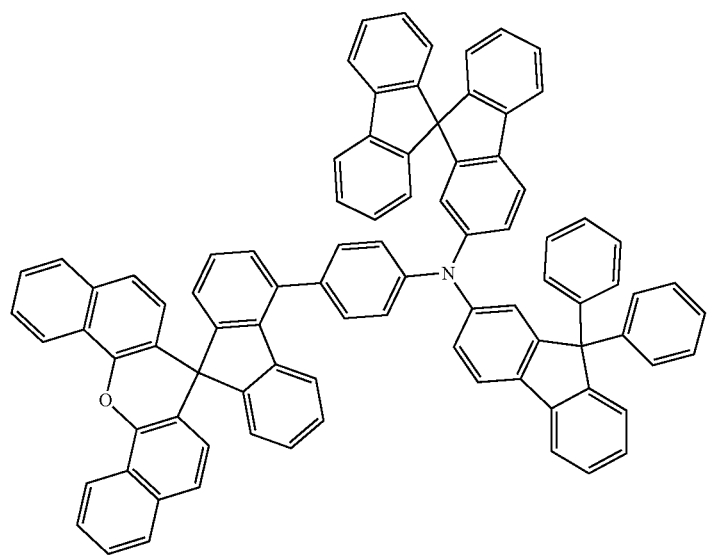
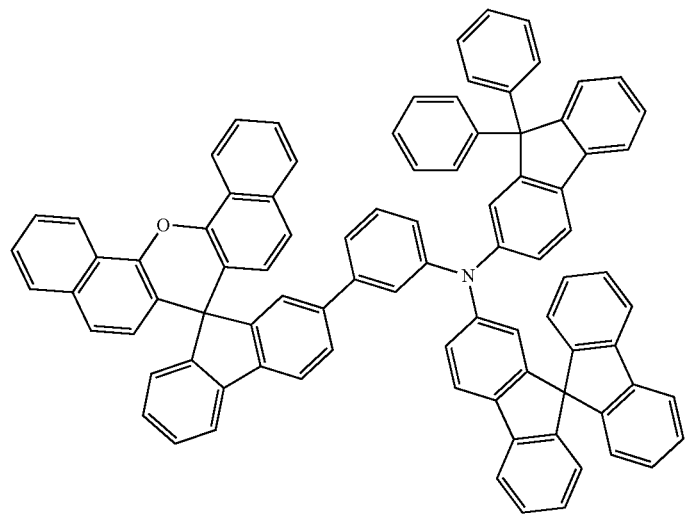
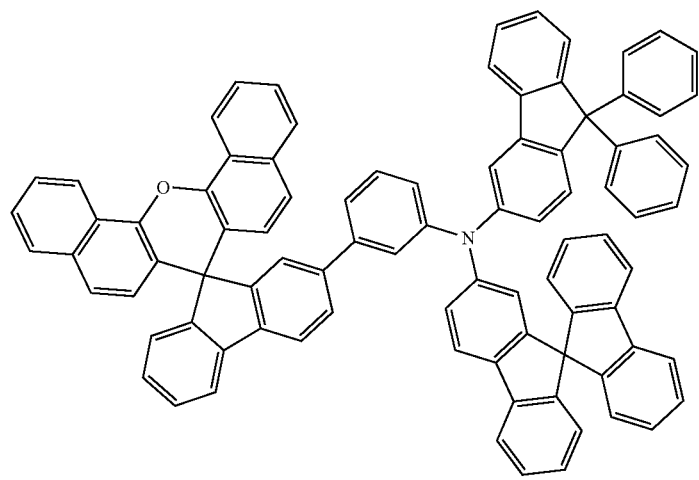

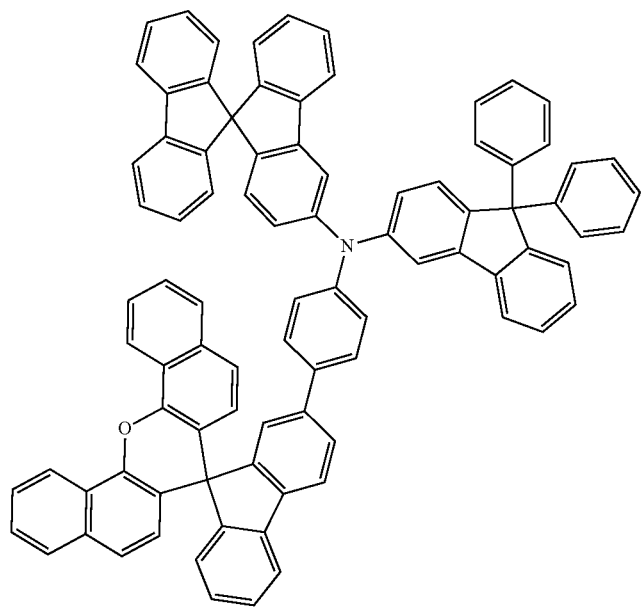
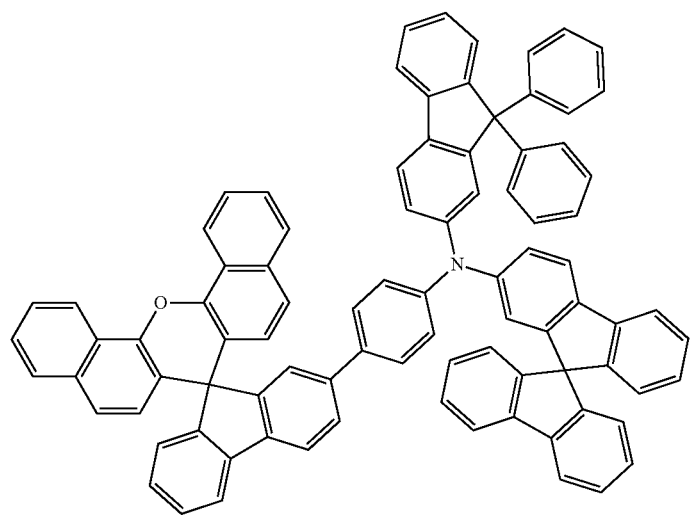

443
-continued
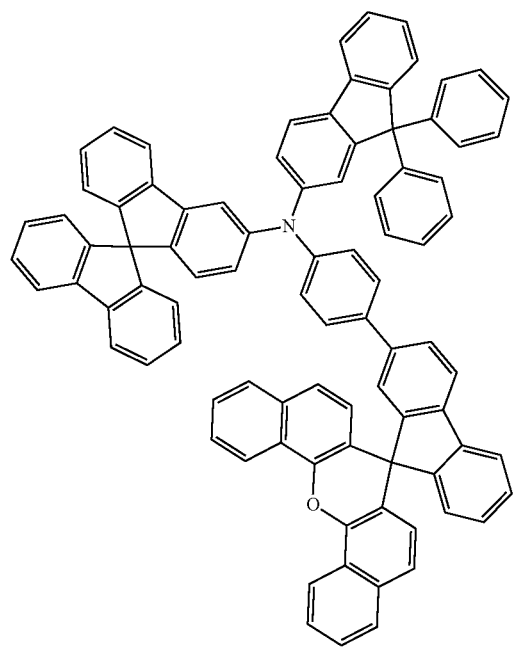
444
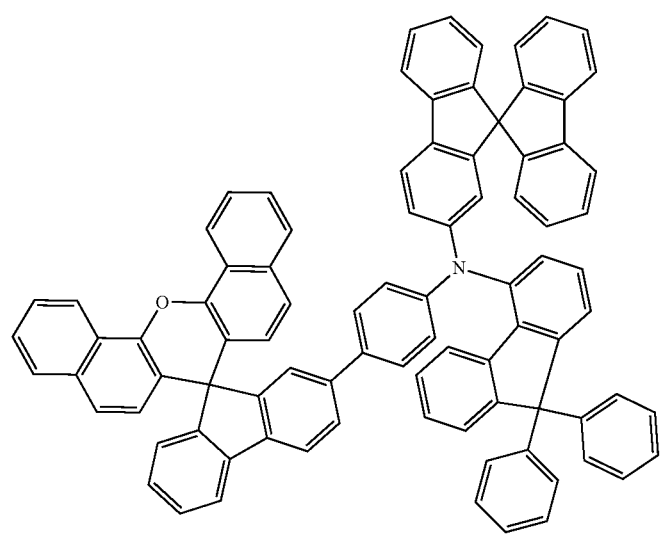
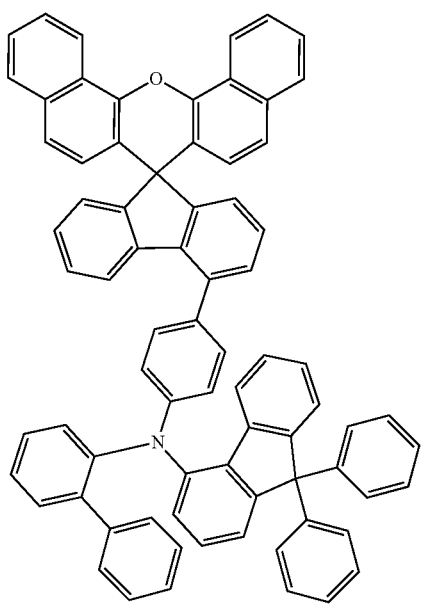

-continued
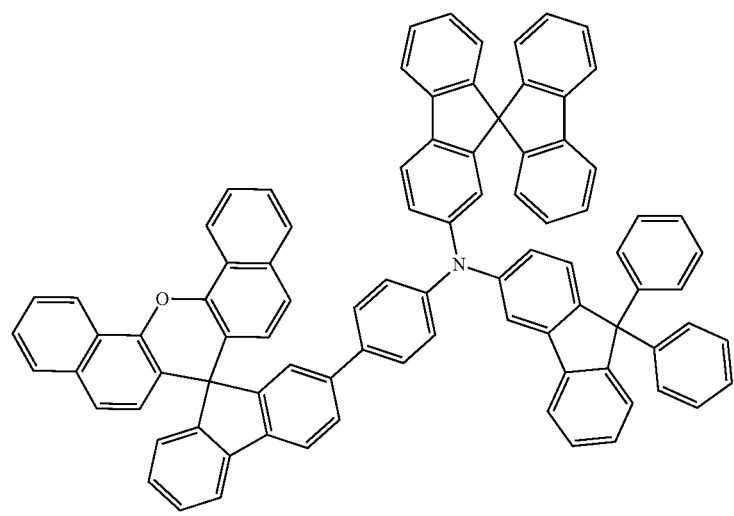
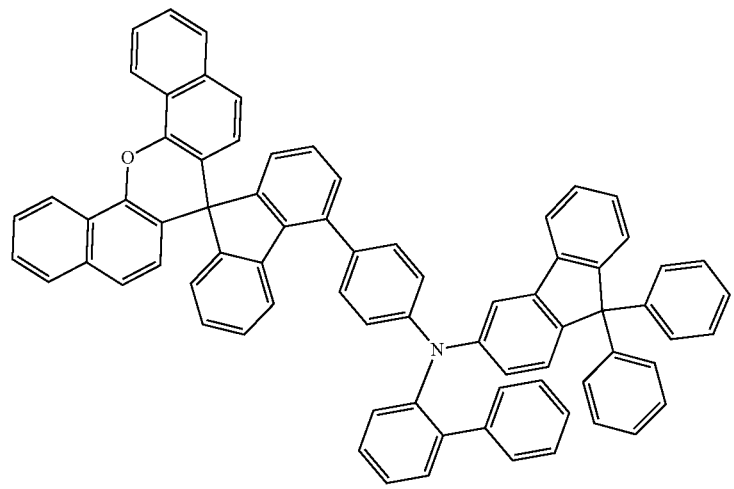
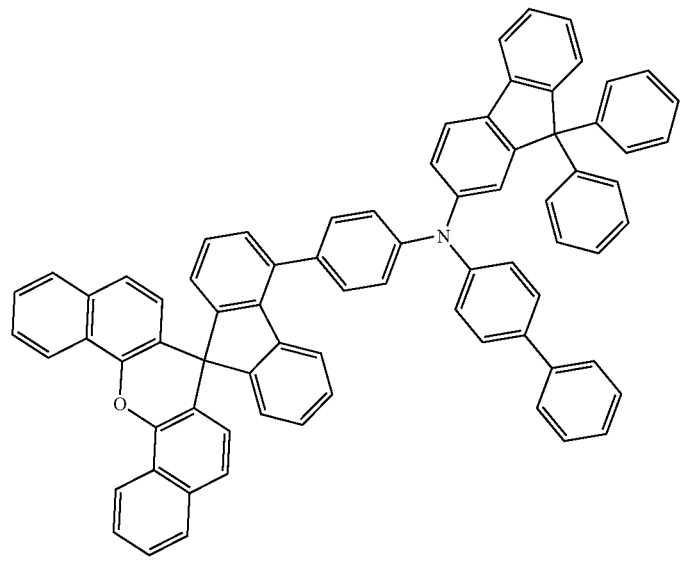

-continued
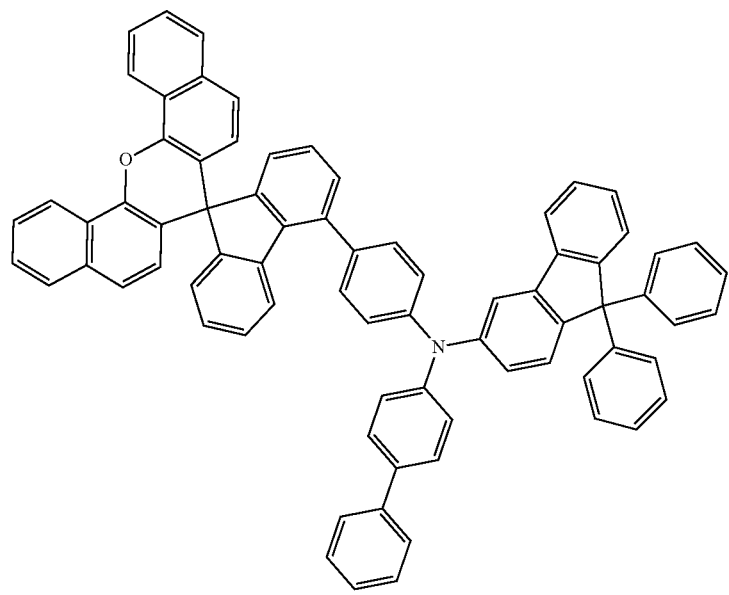
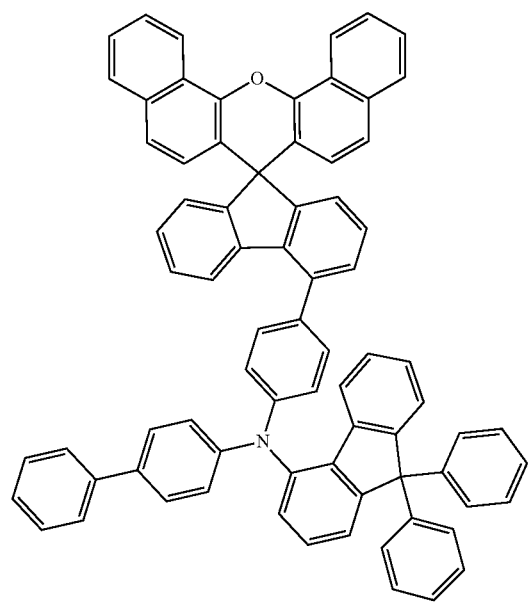
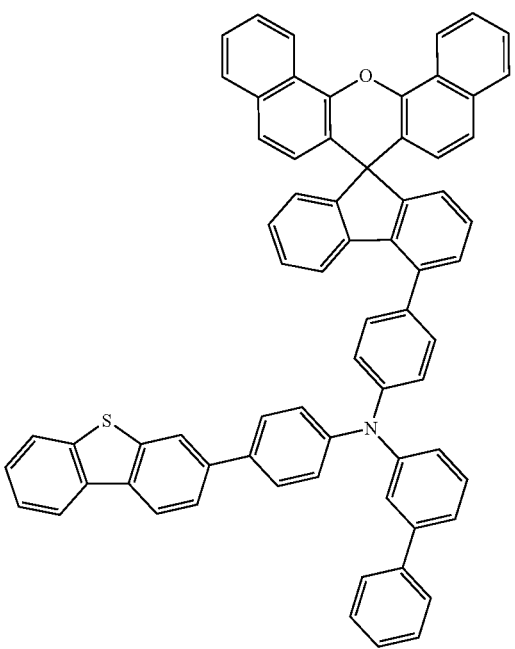
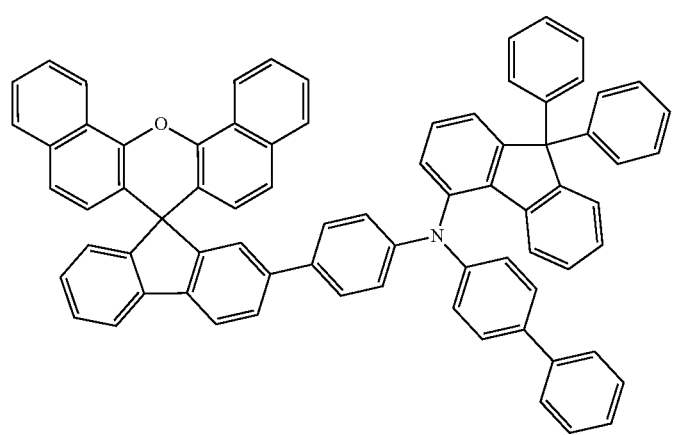

-continued
| 449 | 450 |
|---|---|
| 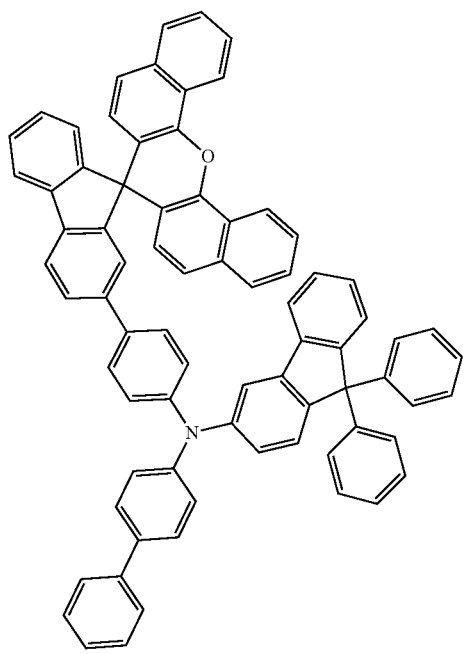 | 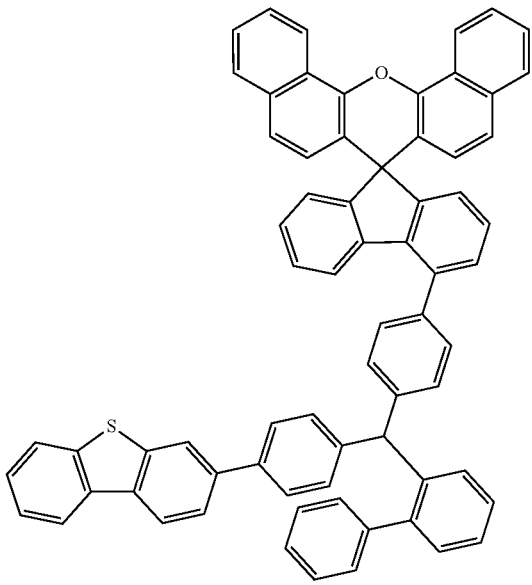 |
| 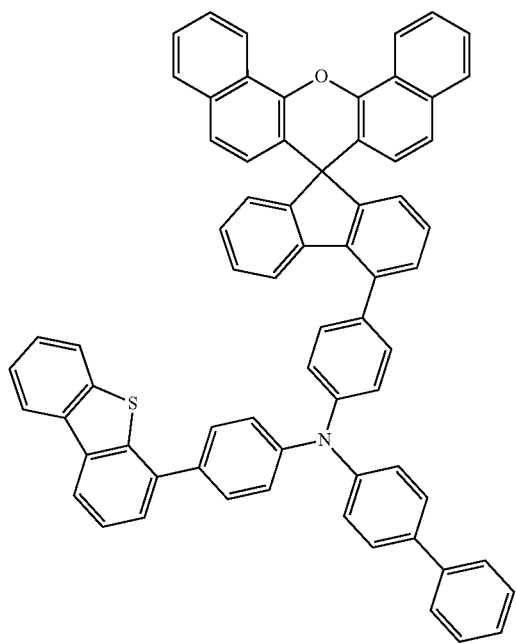 | 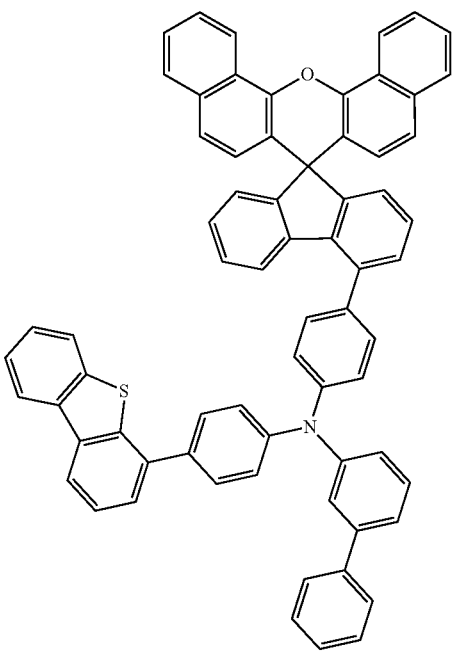 |

-continued
451
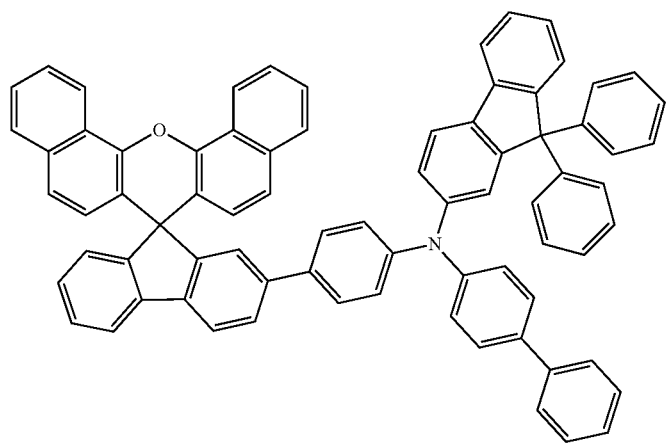
452
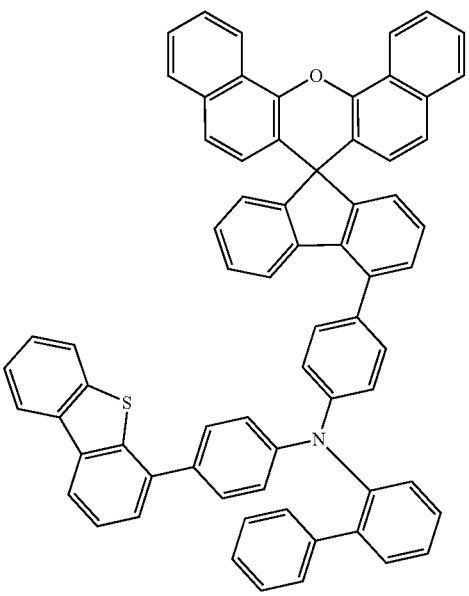
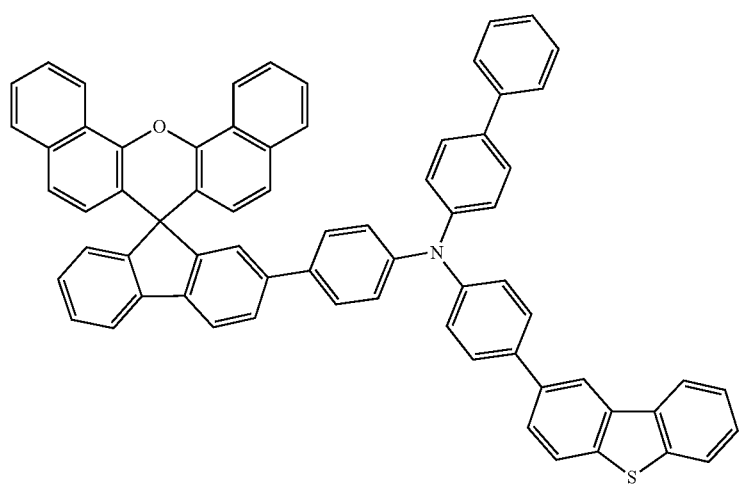
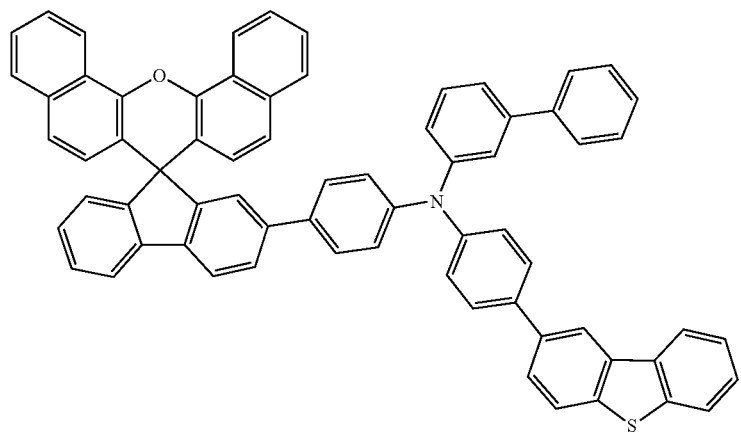

-continued
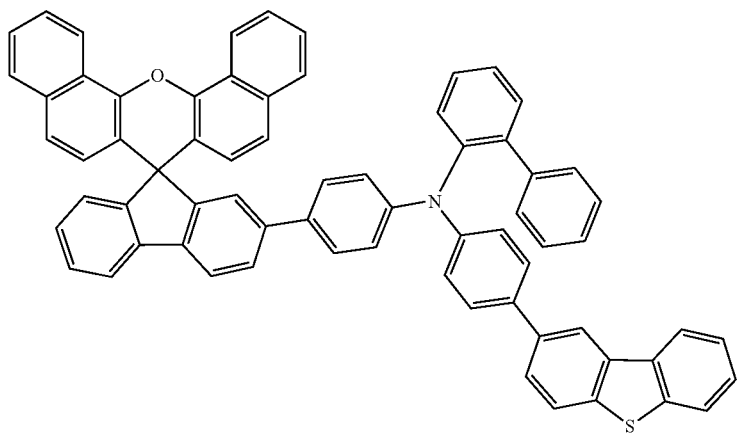
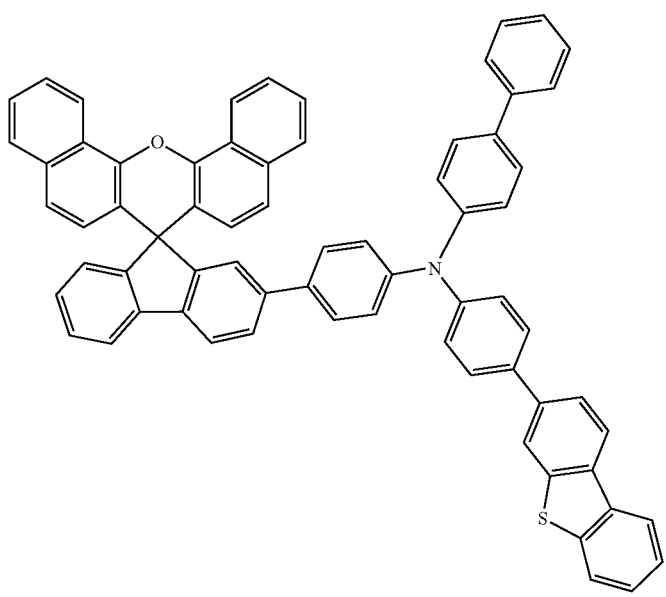
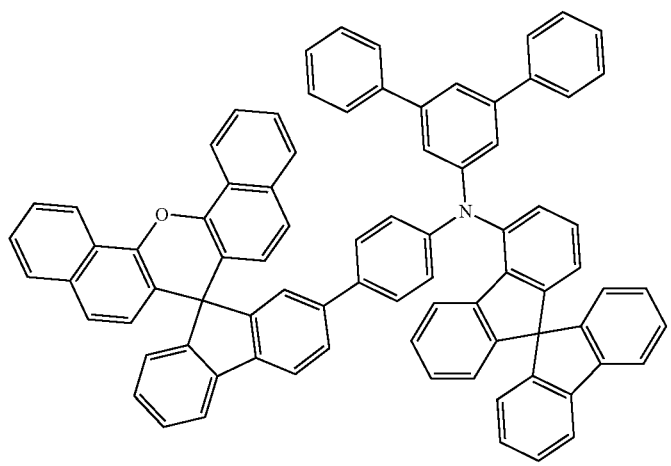

-continued
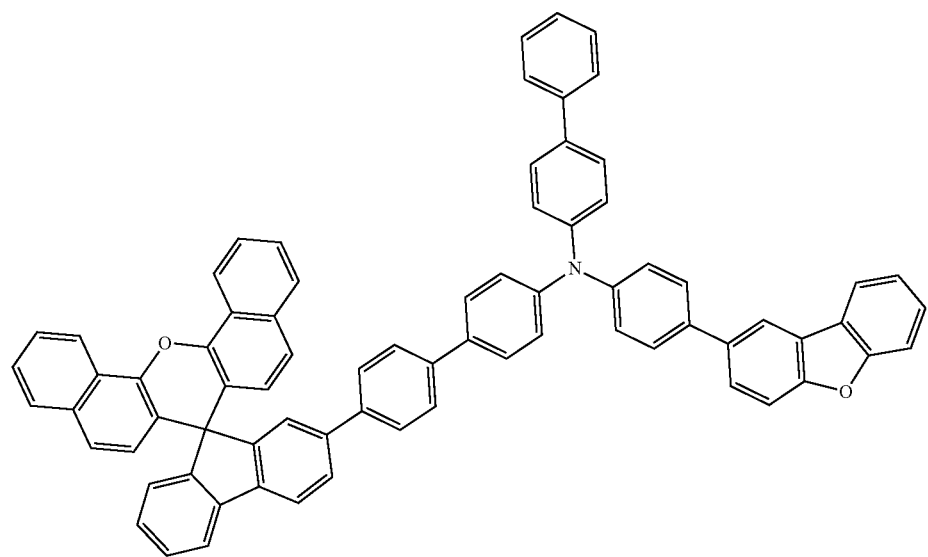
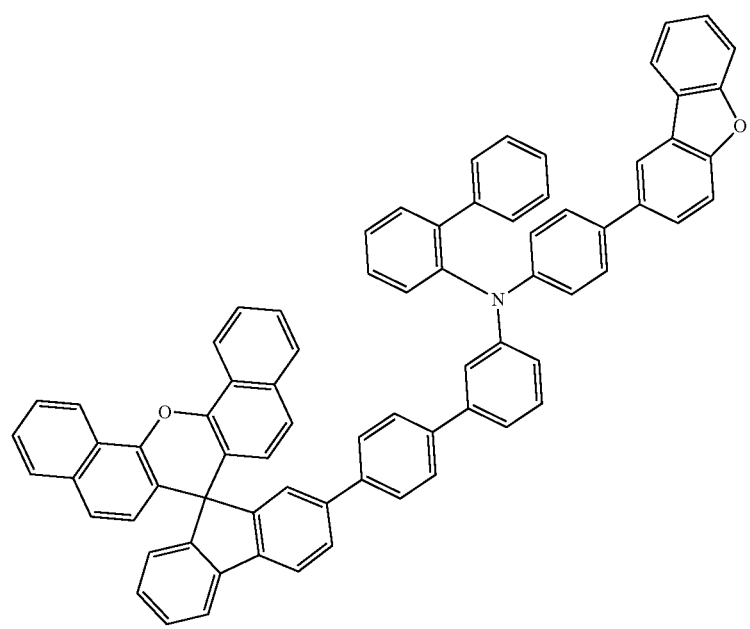

-continued
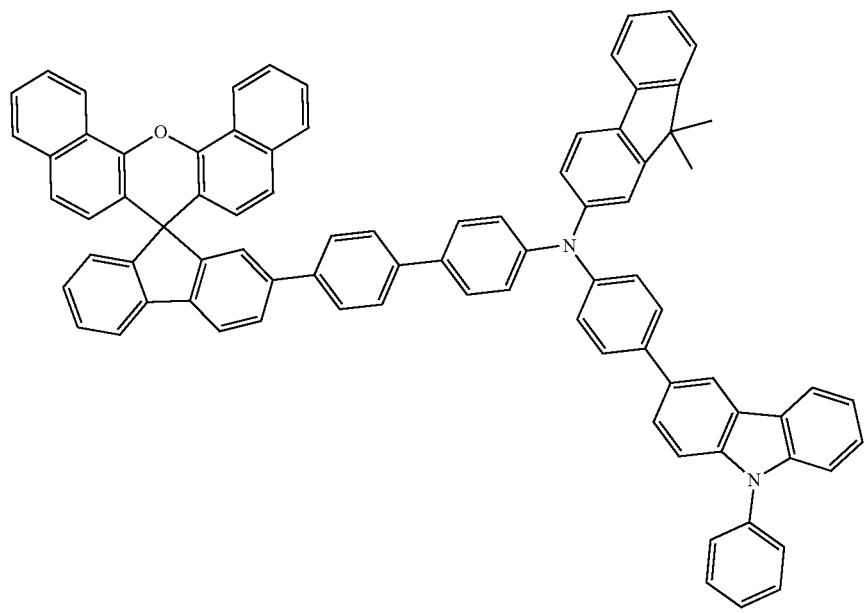
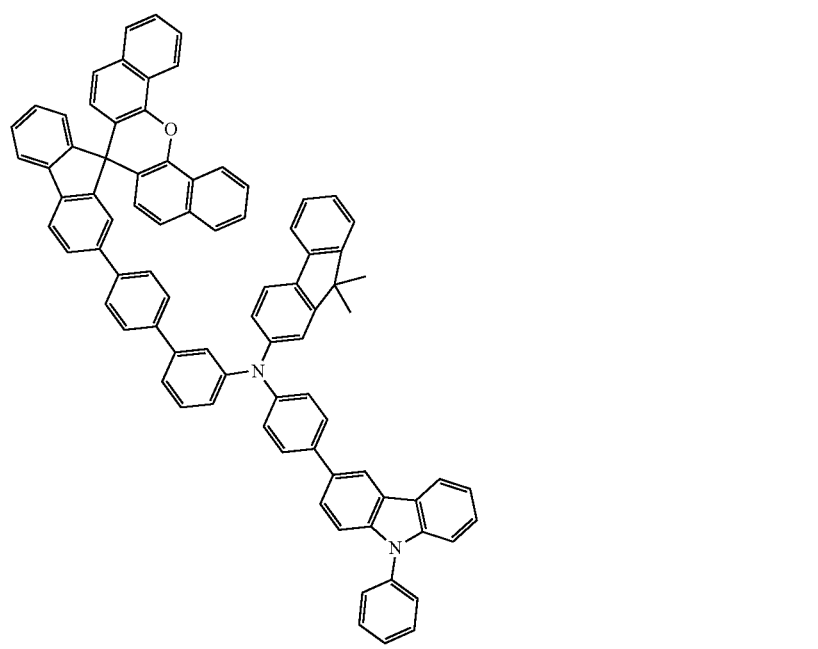
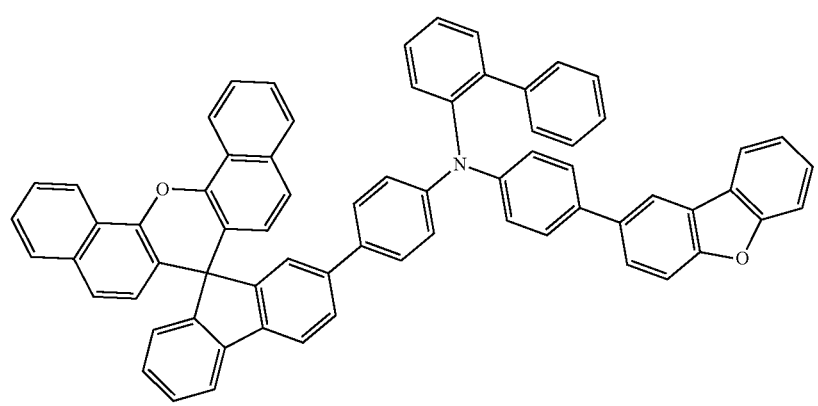

-continued
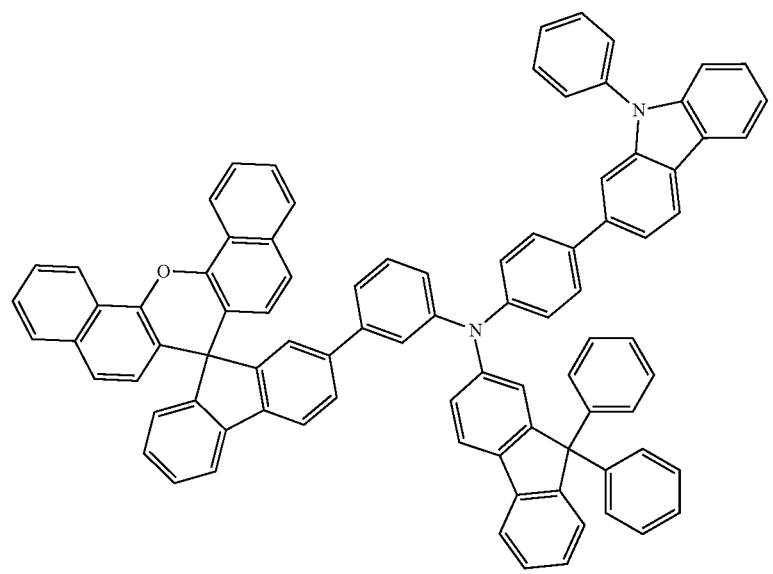
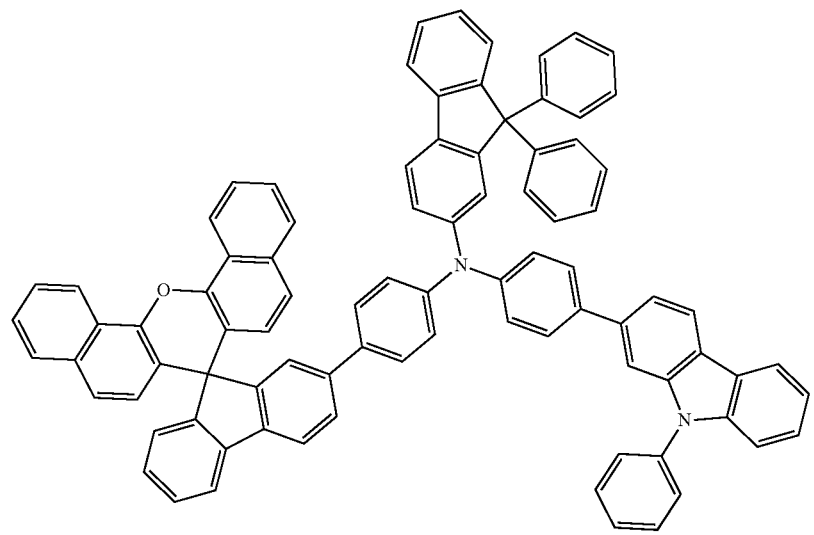
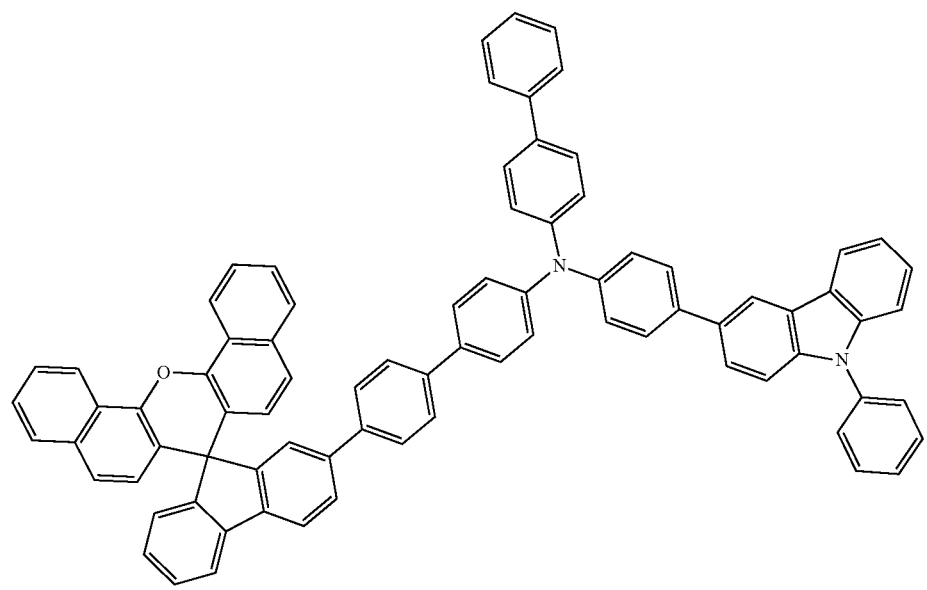

-continued
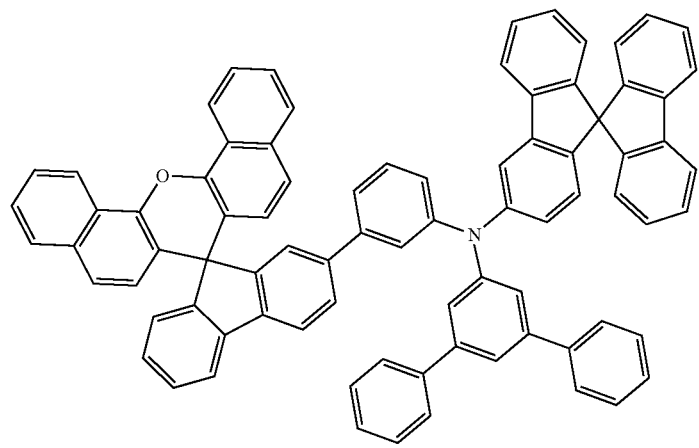
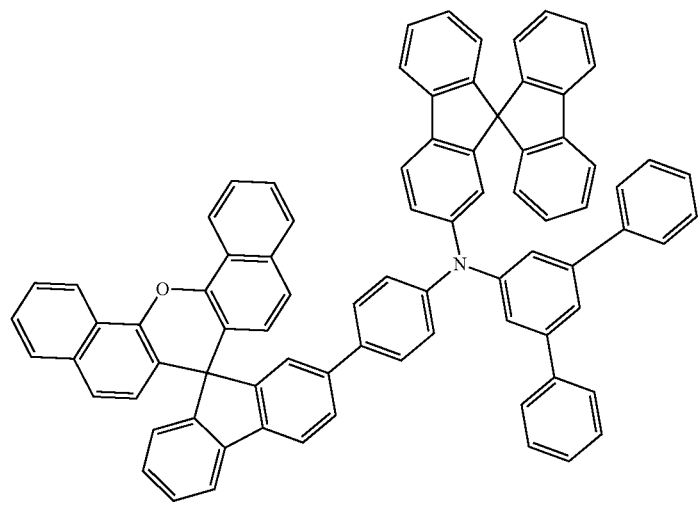
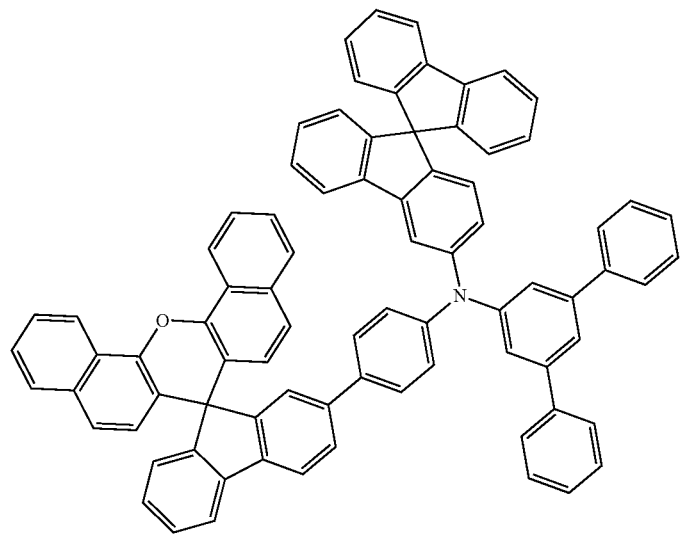

-continued
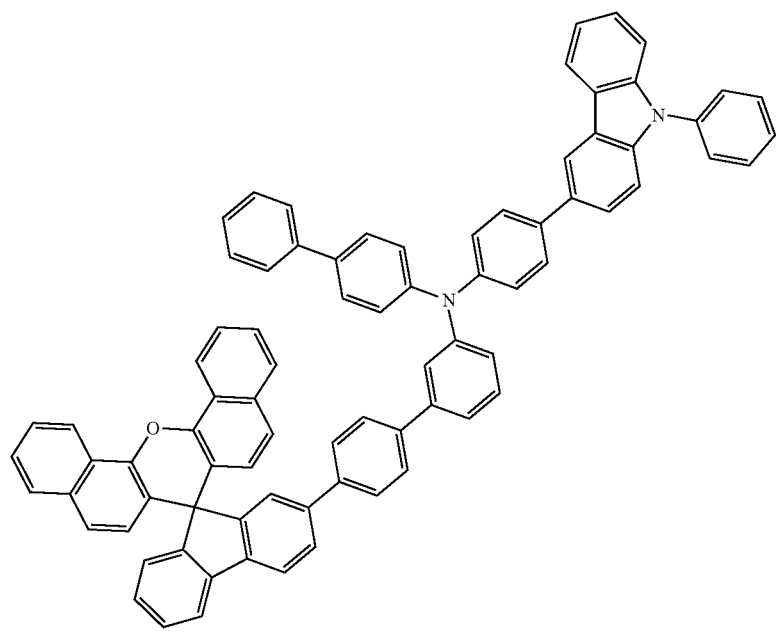
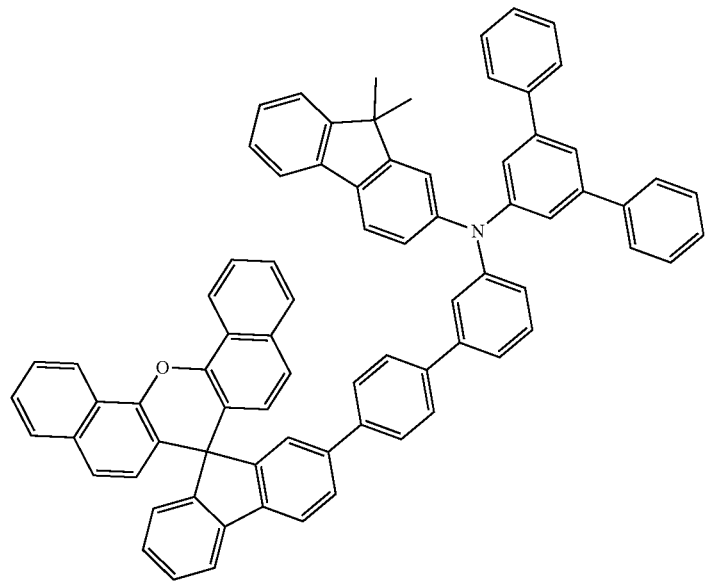
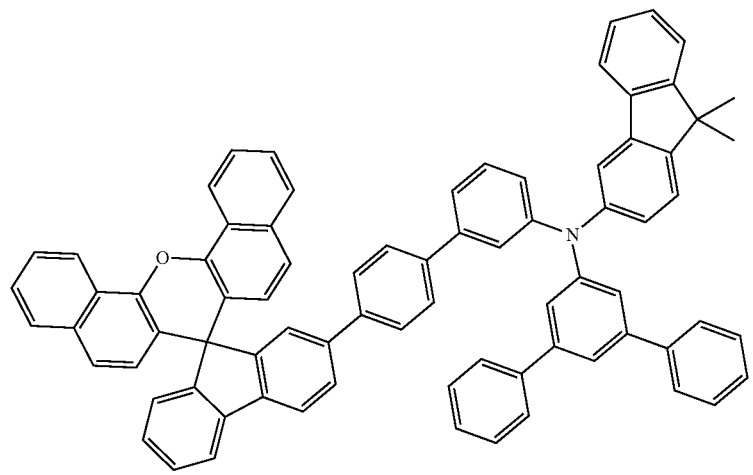

-continued
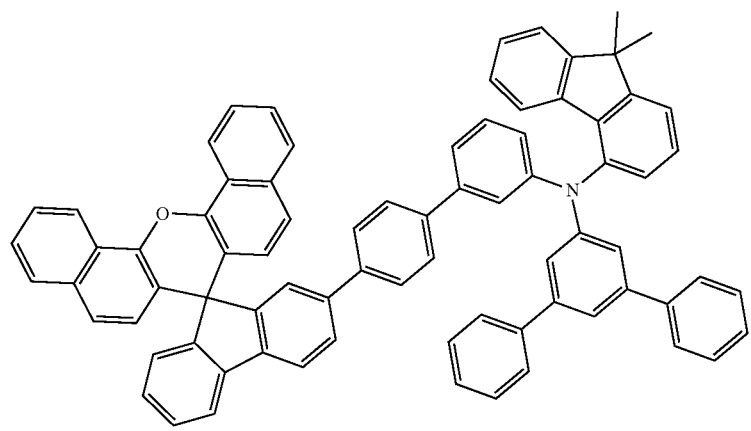
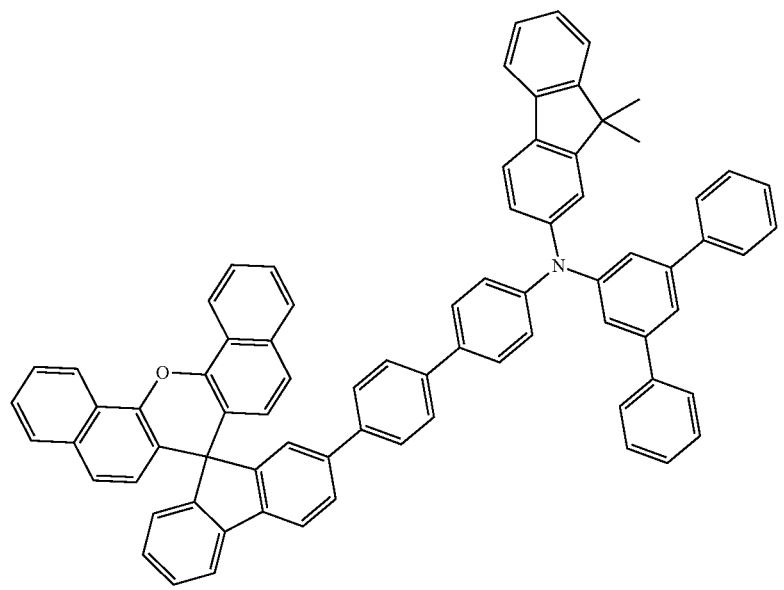
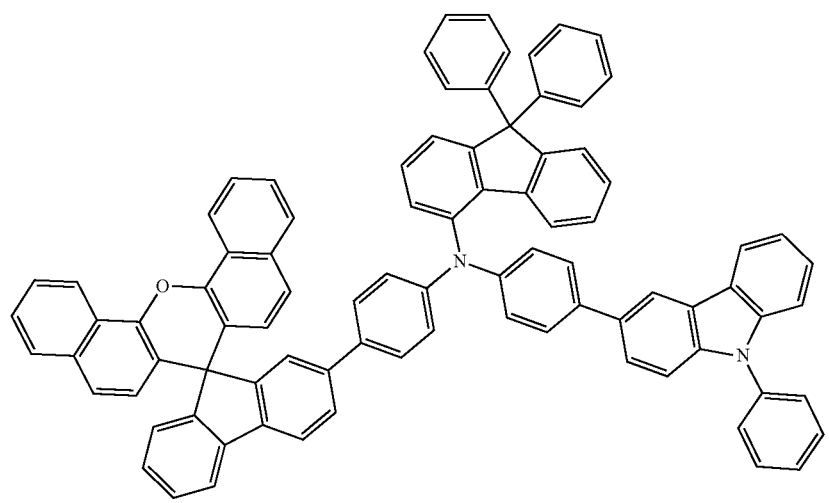

467
468
-continued
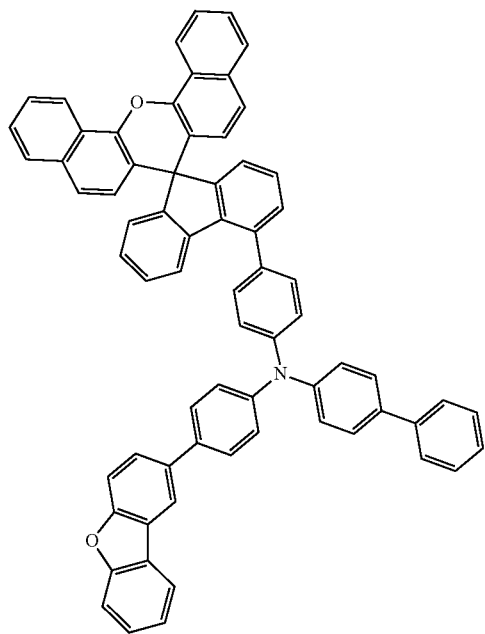
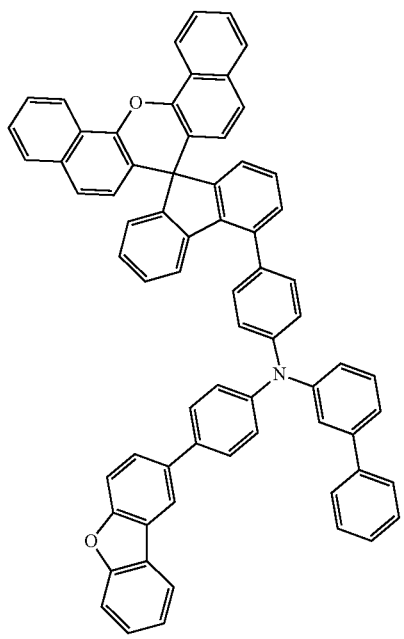
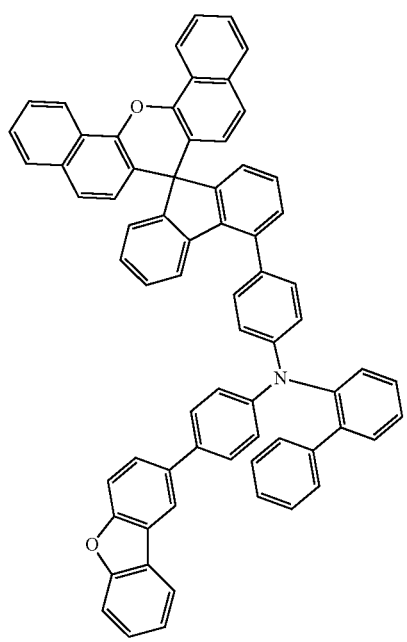

-continued
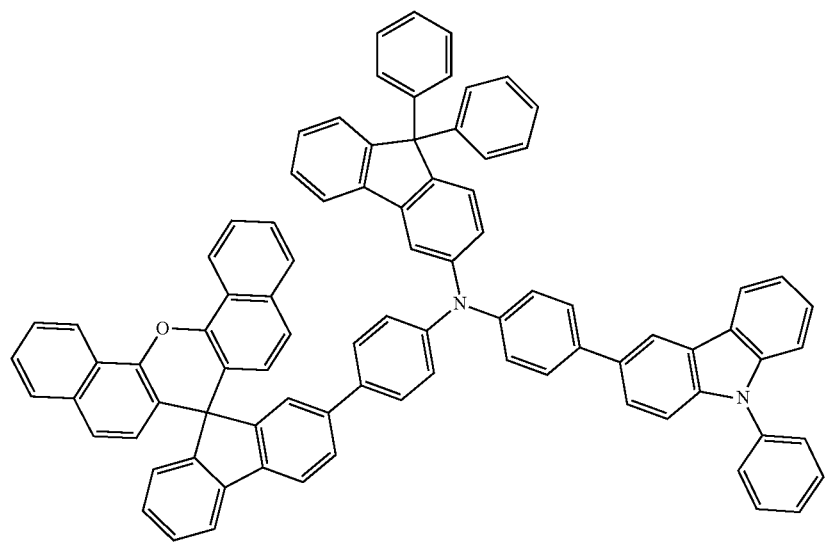
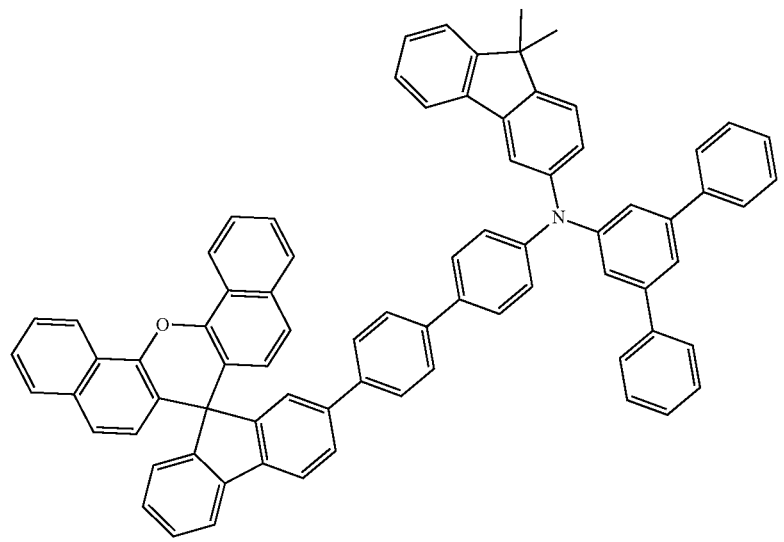
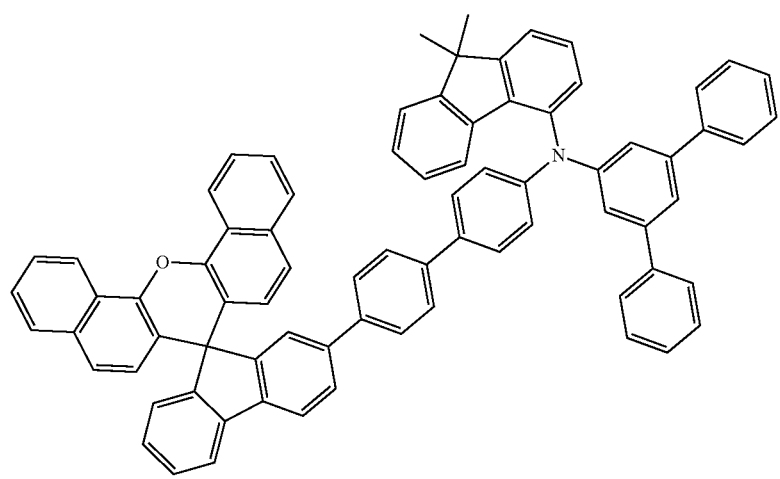

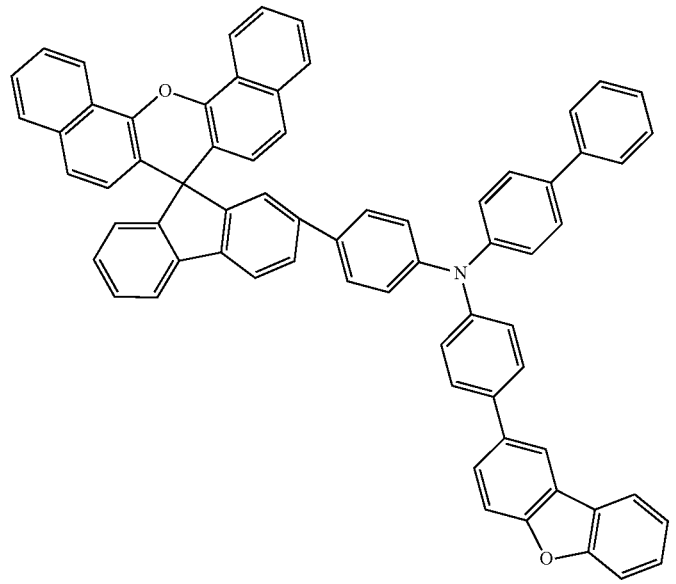
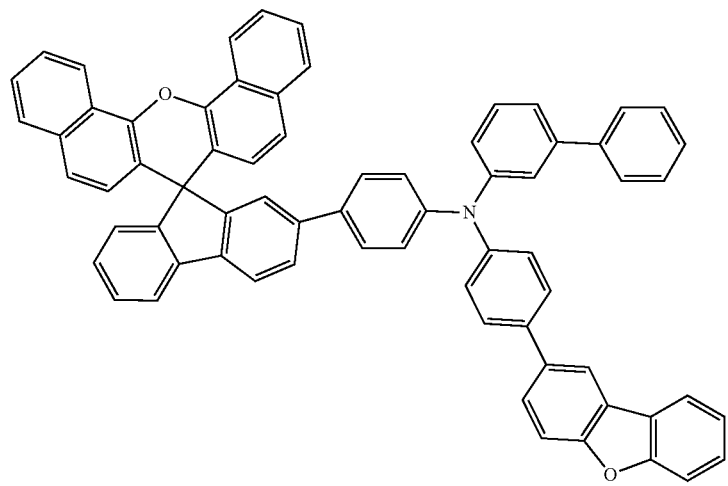
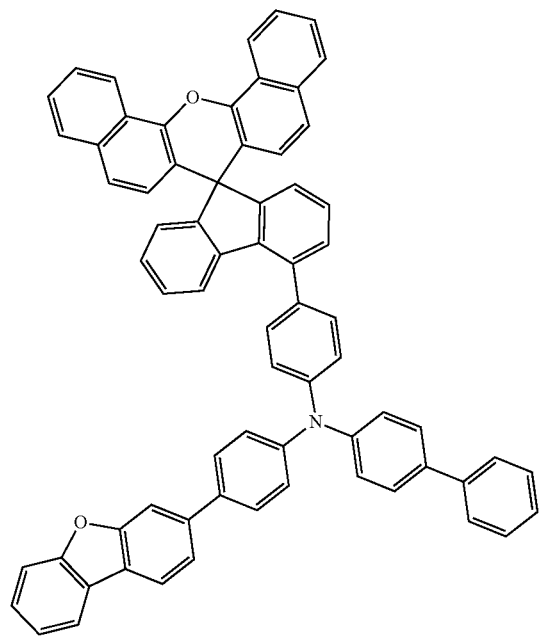

-continued
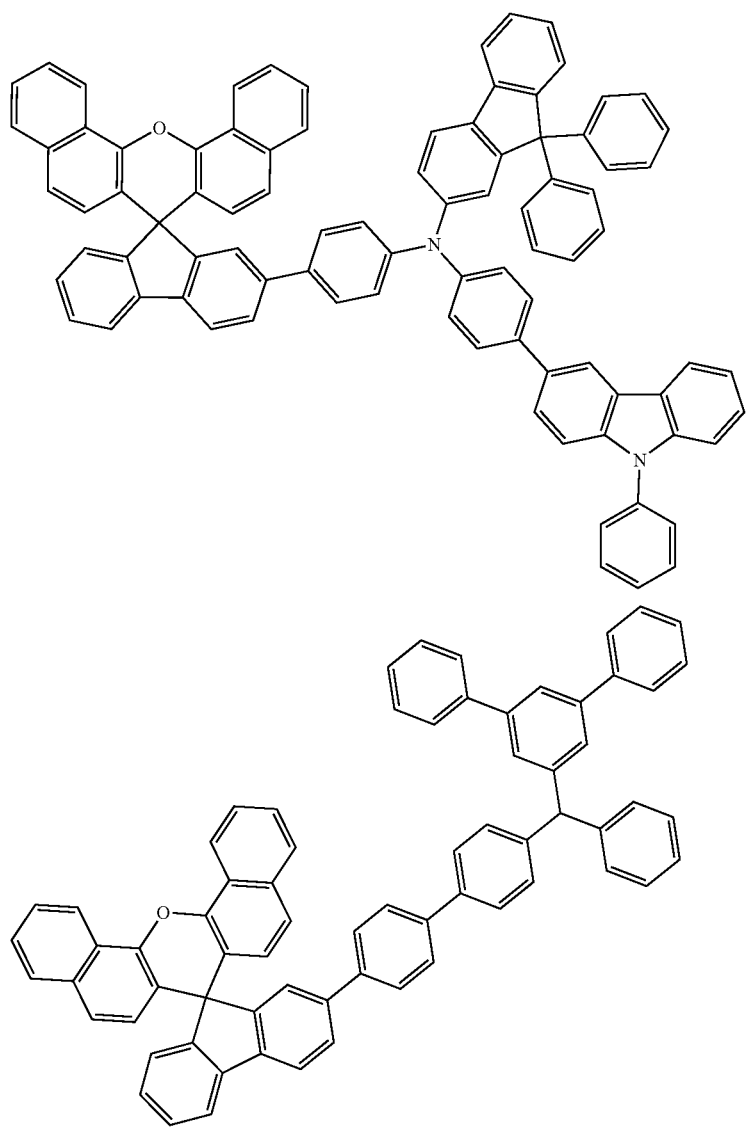
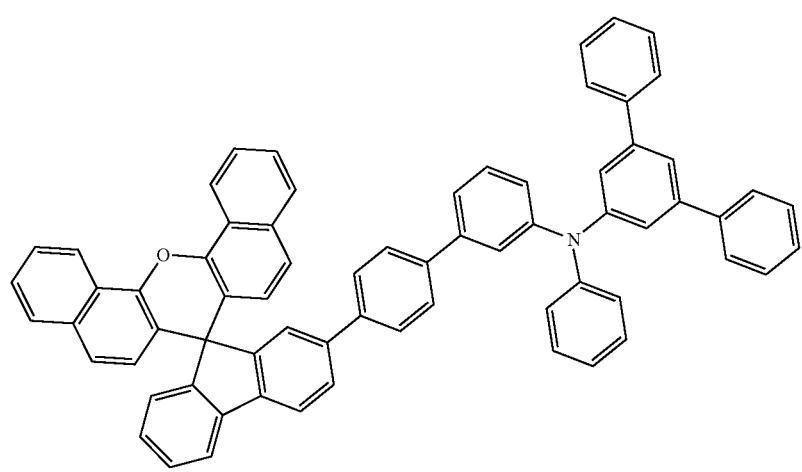

-continued
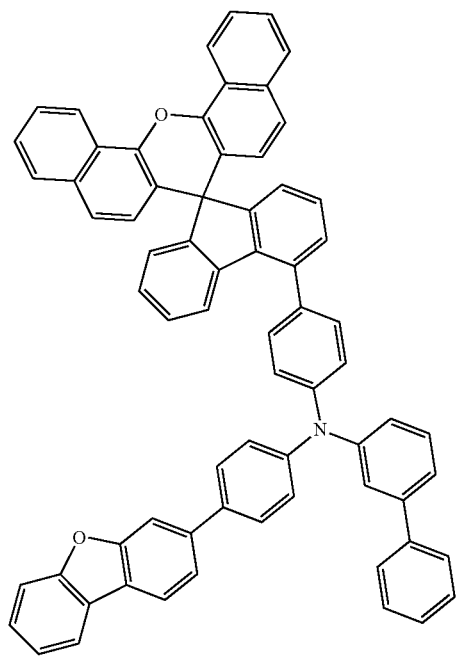
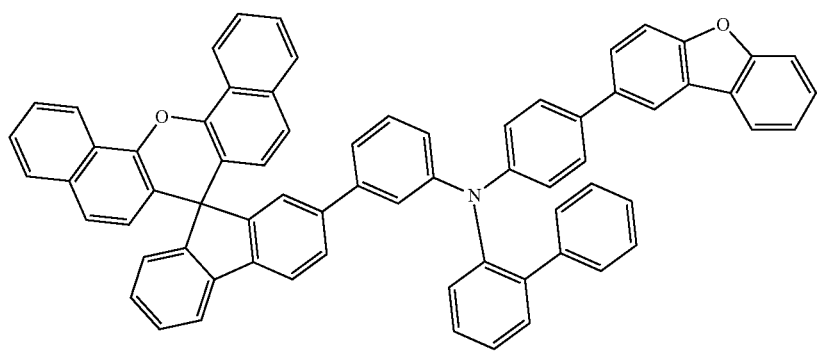
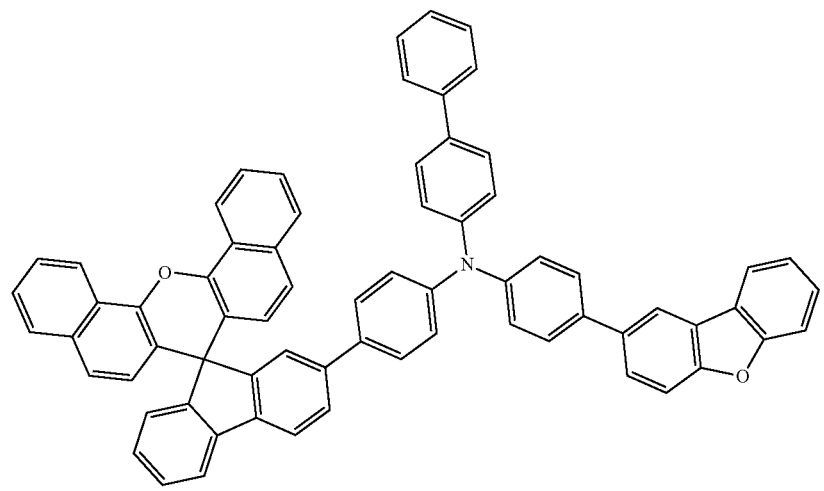

477
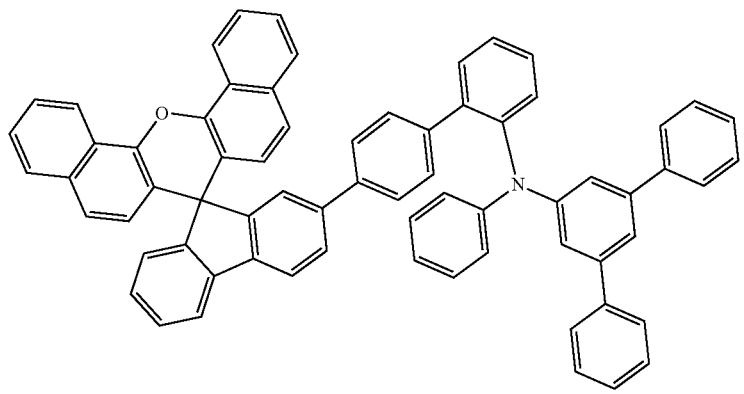
478
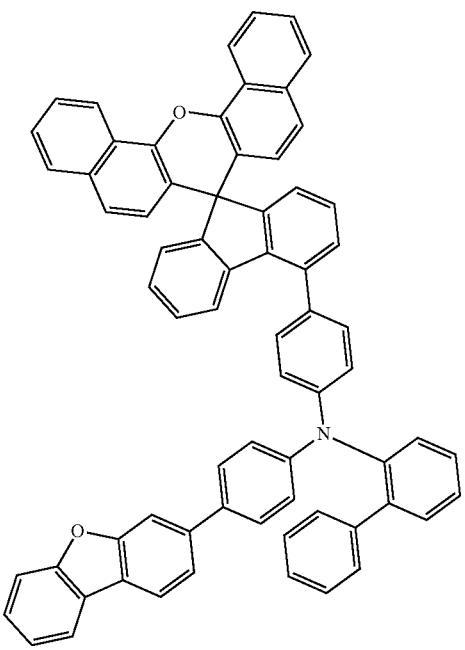
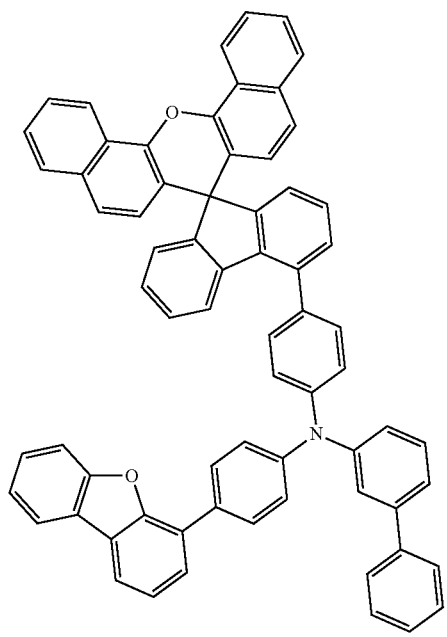
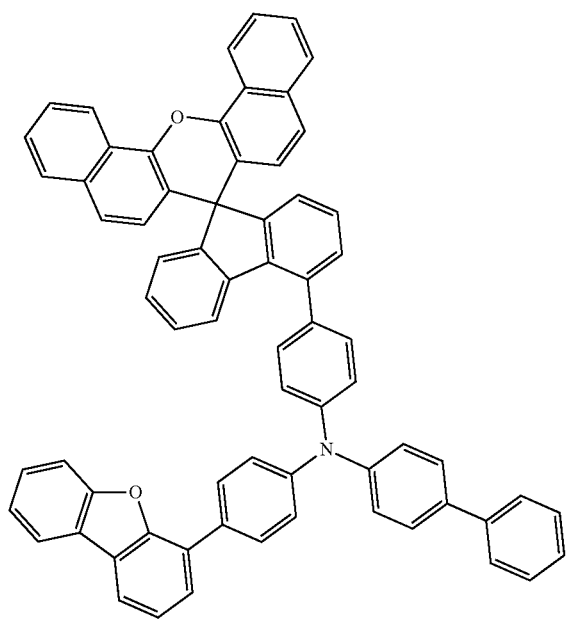

-continued
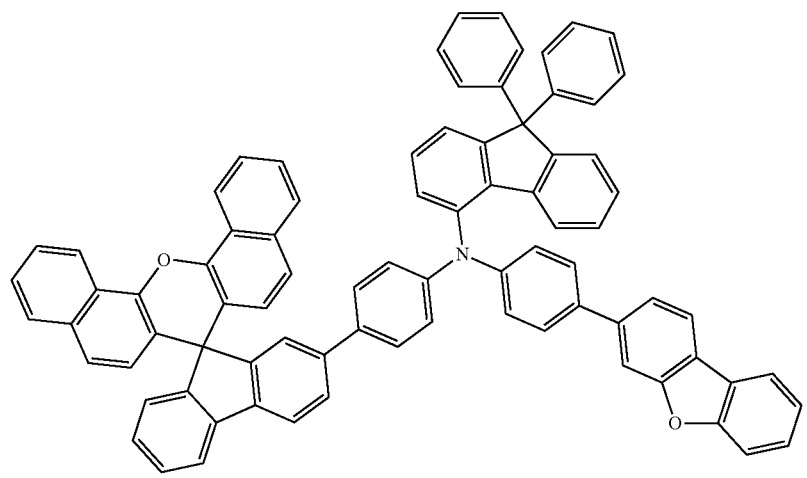
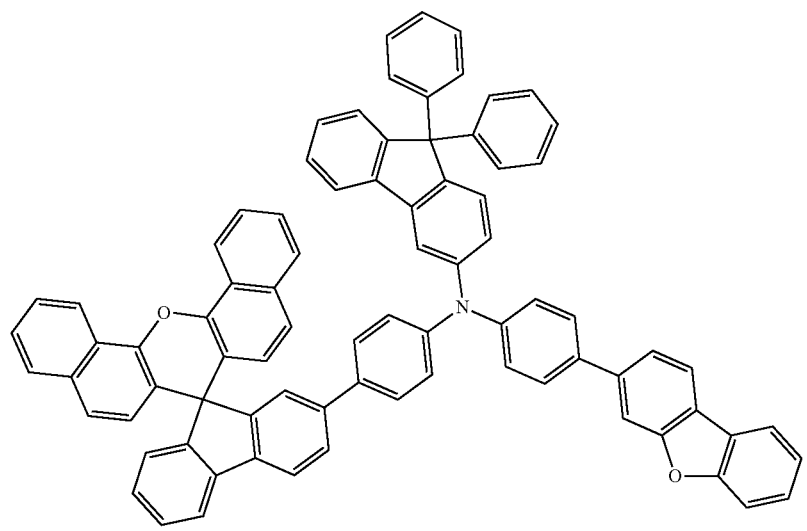
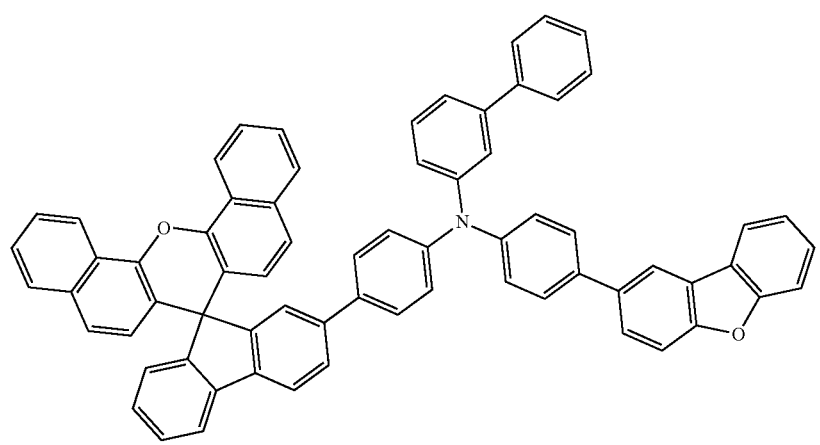

-continued
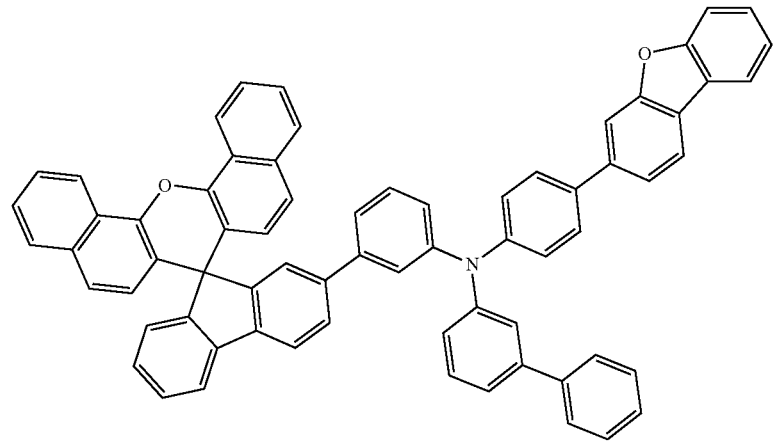
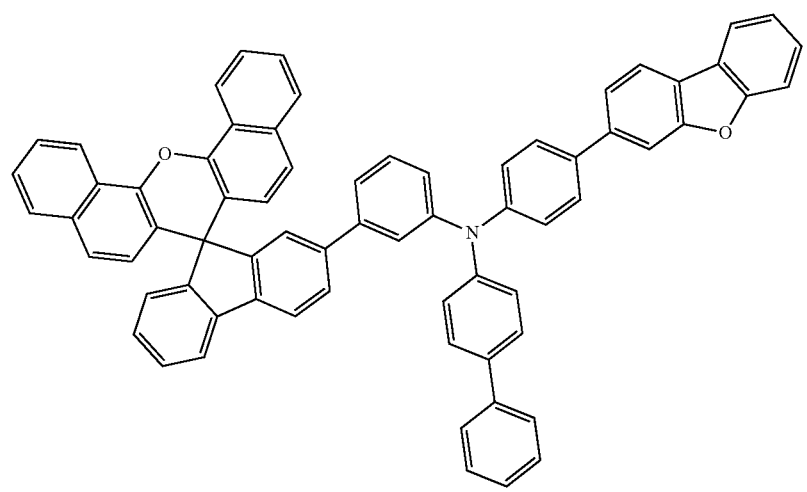
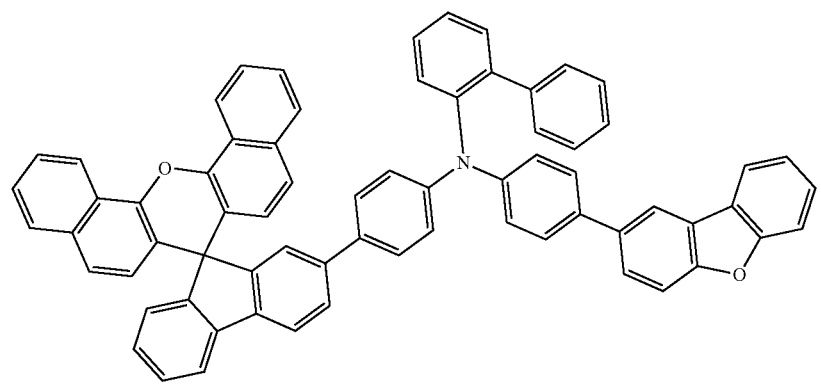

-continued
483
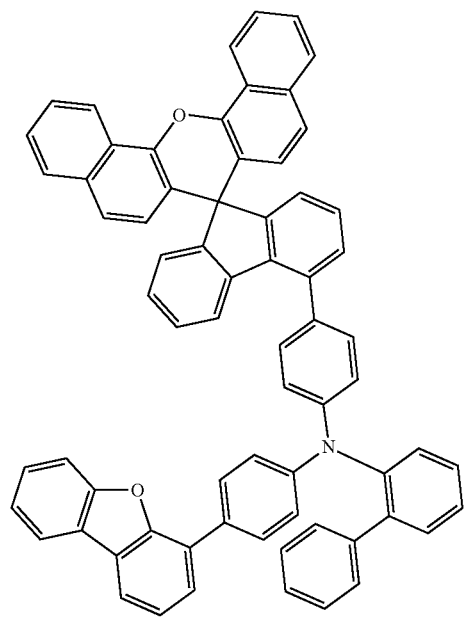
484
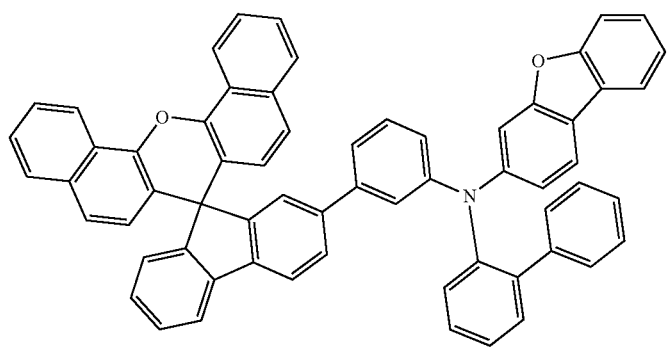
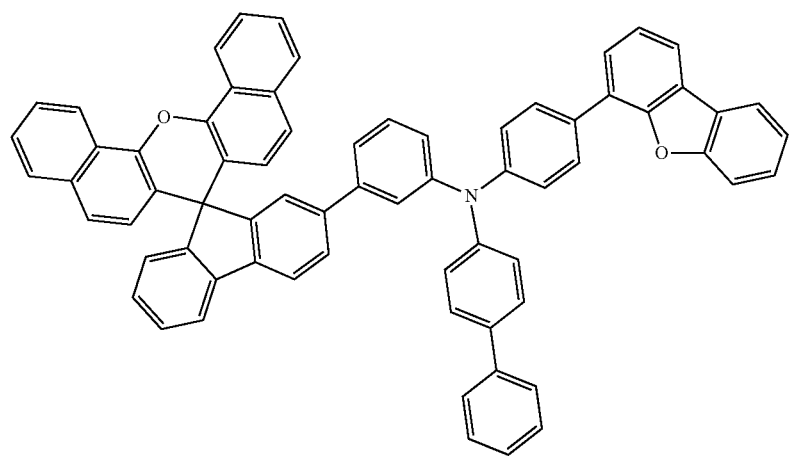
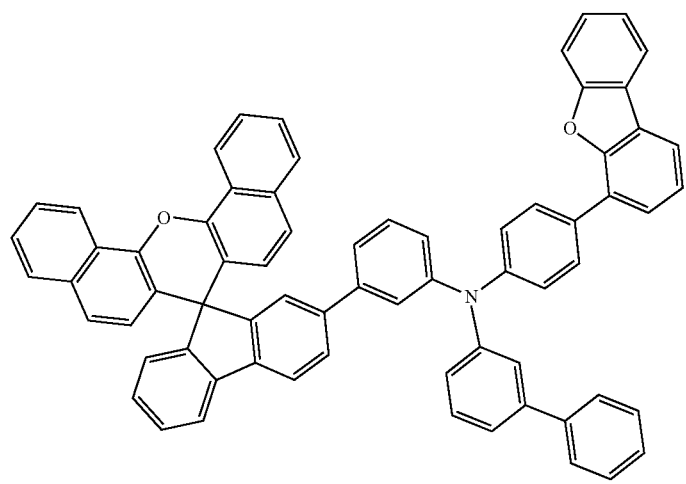

-continued
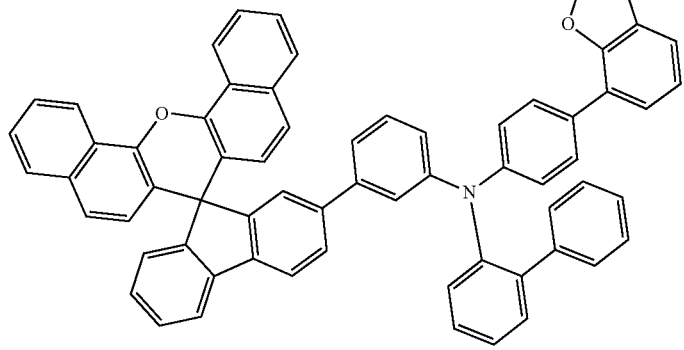
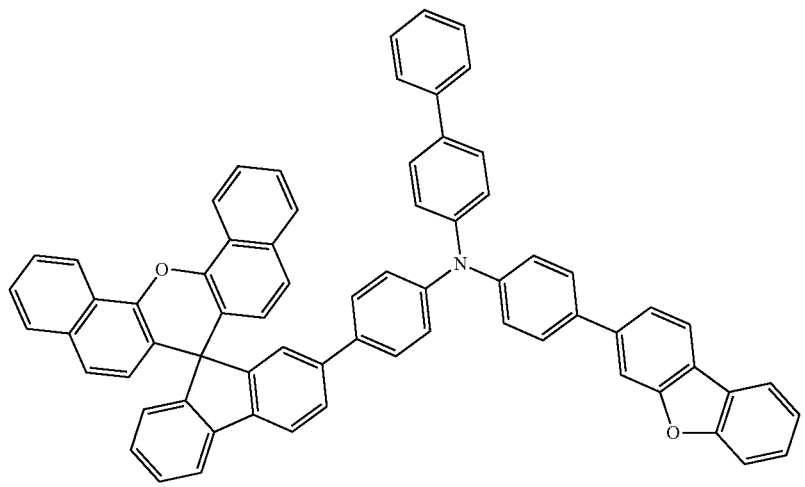
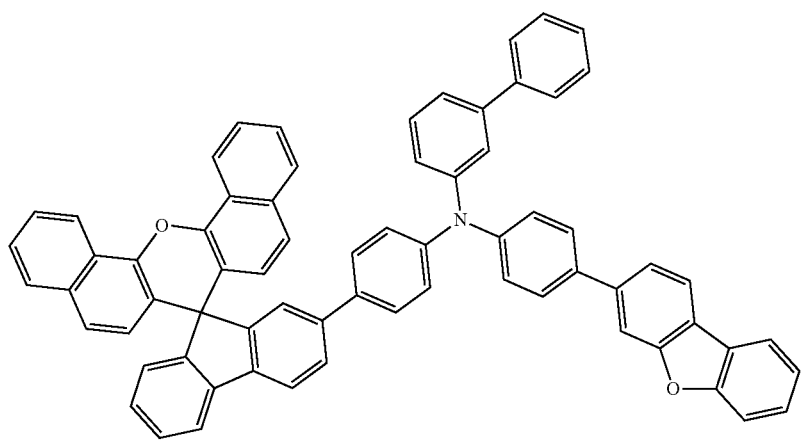

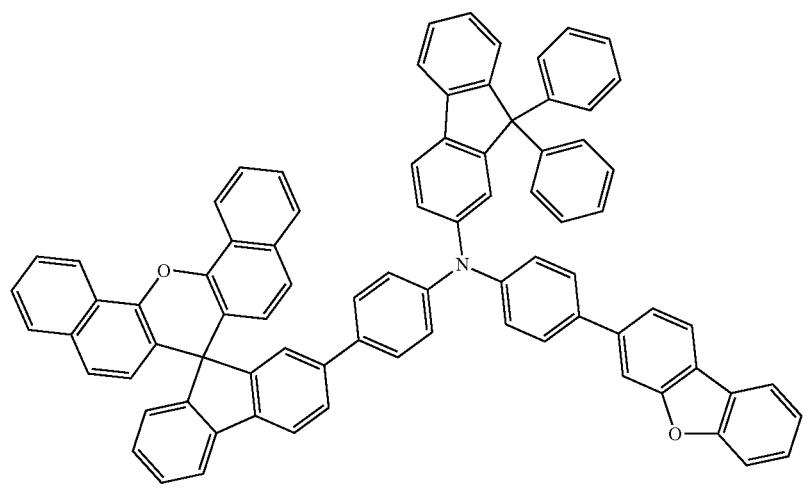
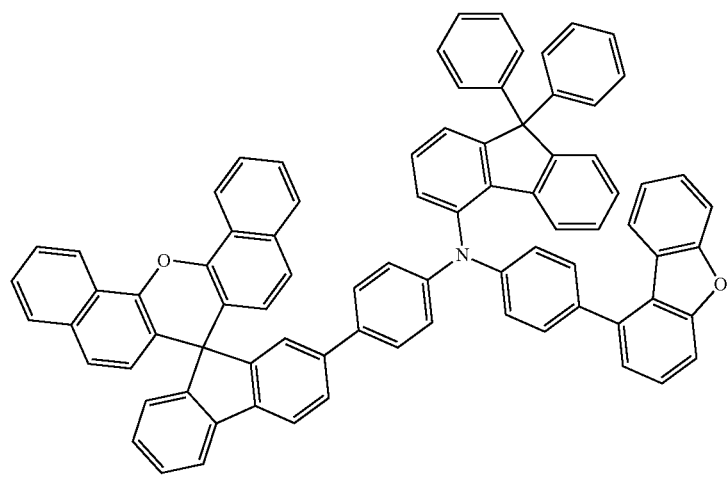
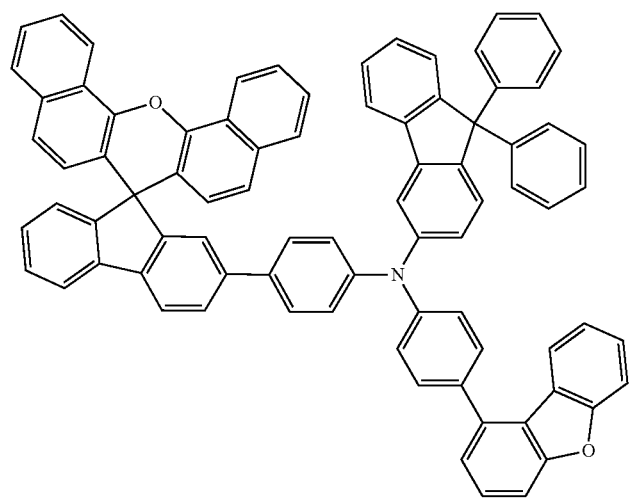

-continued
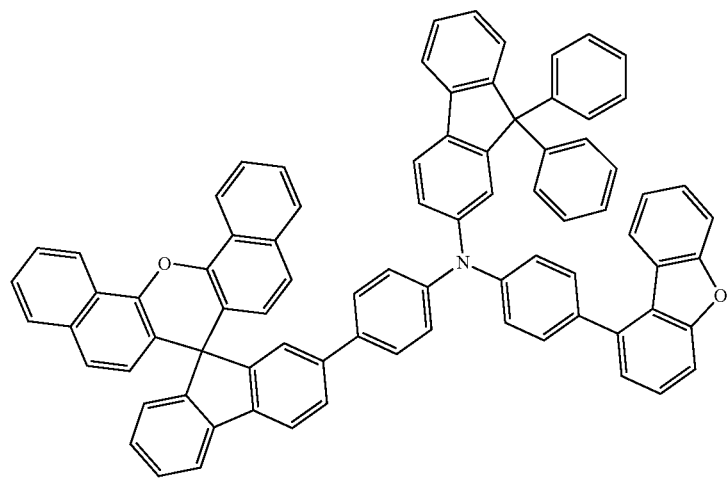
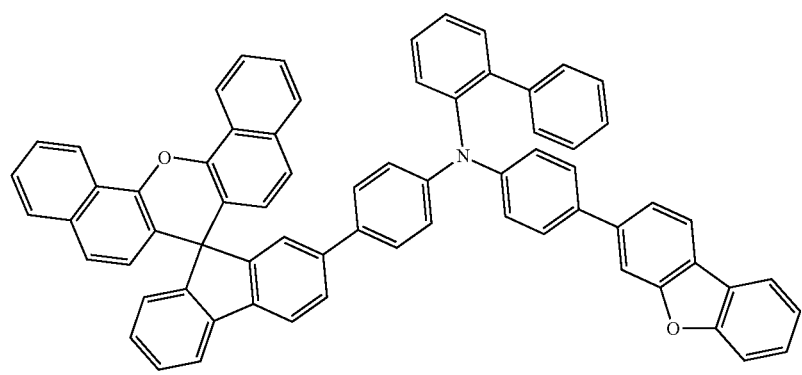
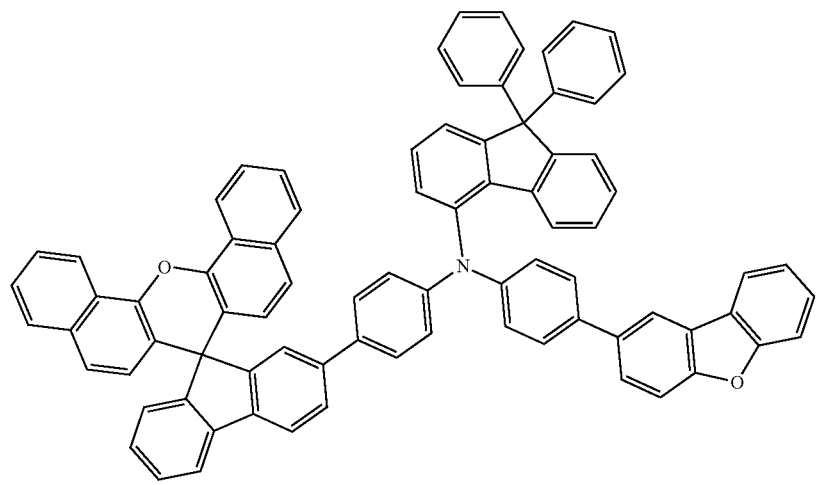

-continued
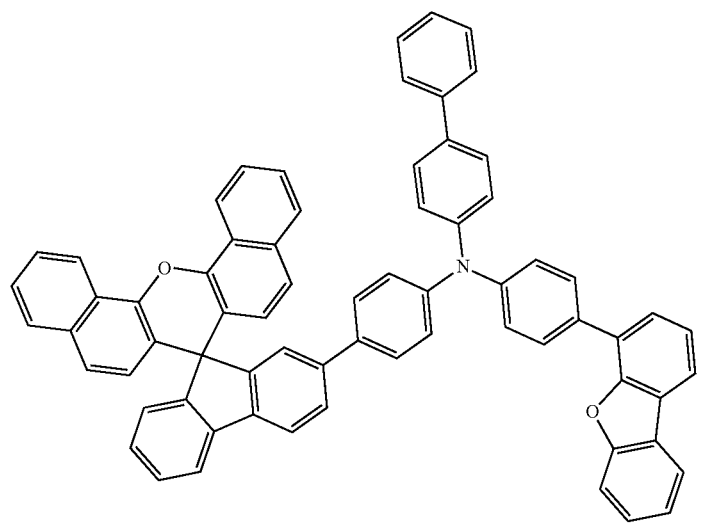
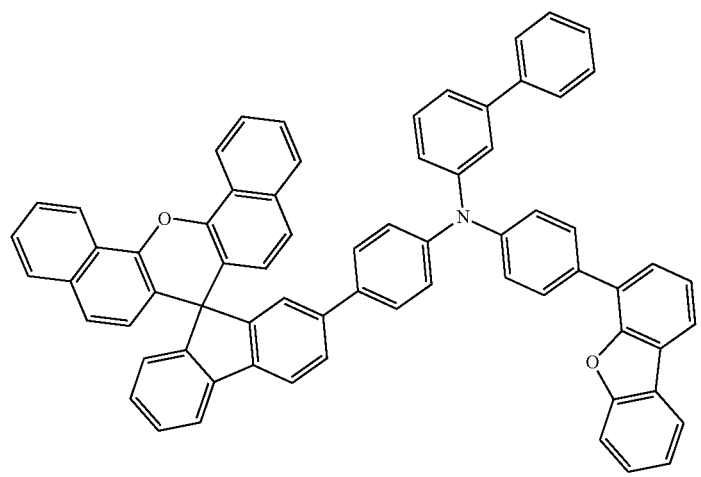
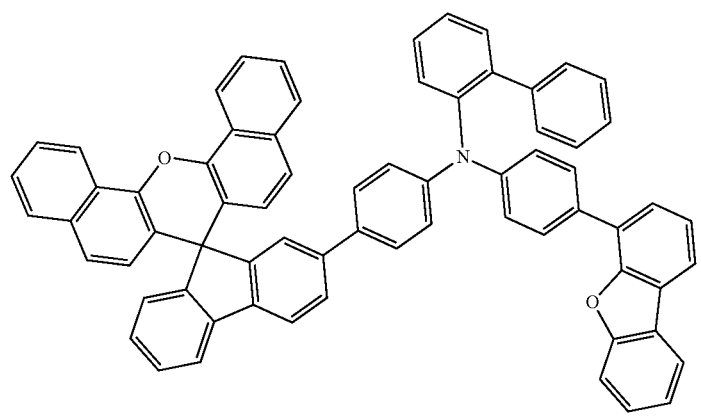

-continued
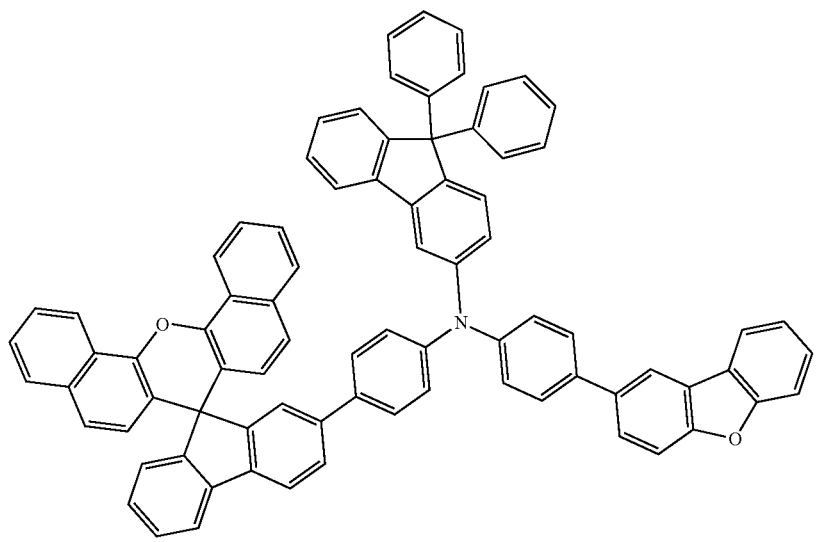
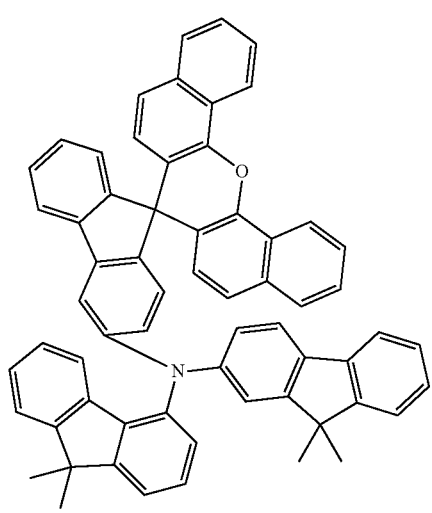
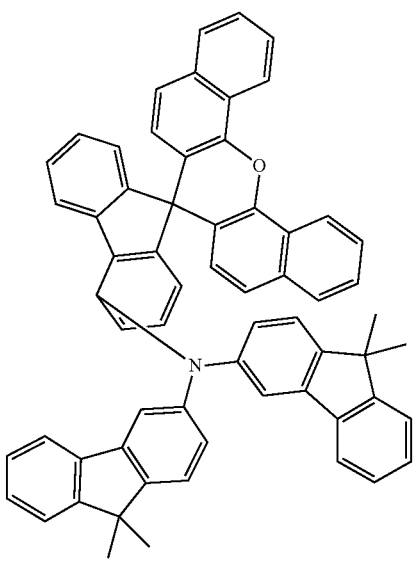
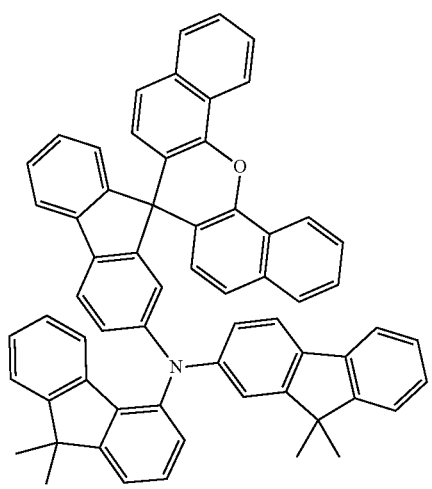
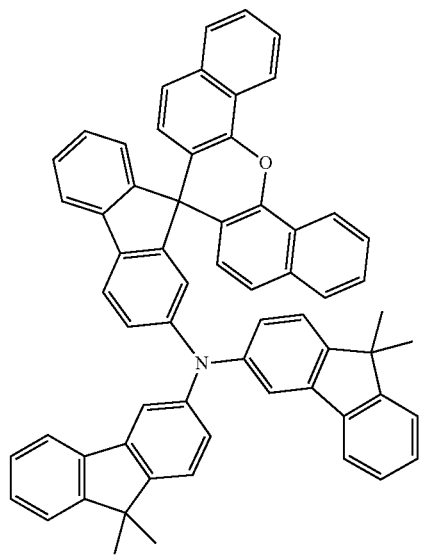

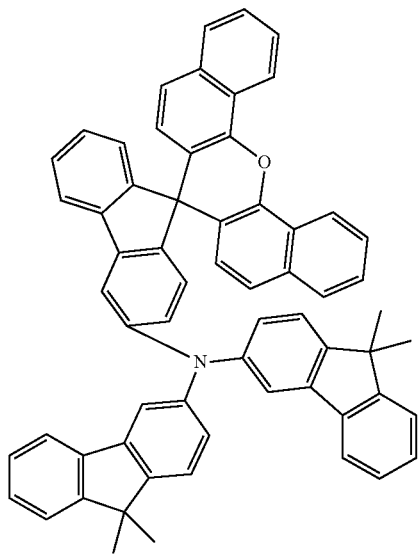

7. An organic light emitting device comprising:
a first electrode;
a second electrode provided to face the first electrode; and
one or more organic material layers provided between the first electrode and the second electrode,
wherein one or more layers of the organic material layers comprise the compound of claim 1.

8. The organic light emitting device of claim 7, wherein the organic material layer is composed of the compound alone or composed of the doped compound.

9. The organic light emitting device of claim 7, wherein the organic material layer is a hole injection layer, a hole transport layer, an electron transport layer, or an electron injection layer.

10. The organic light emitting device of claim 7, wherein the organic material layer is a layer which injects and transports holes simultaneously.

11. The organic light emitting device of claim 7, wherein the organic material layer is a layer which transports and injects electrons simultaneously.

12. The organic light emitting device of claim 7, wherein the organic material layer is a light emitting layer.

* * * * *